US010041947B2

(12) United States Patent
Konthur et al.

(10) Patent No.: US 10,041,947 B2
(45) Date of Patent: Aug. 7, 2018

(54) BIOMARKER FOR THE PREDICTION OF RESPONSIVENESS TO AN ANTI-TUMOUR NECROSIS FACTOR ALPHA (TNF) TREATMENT

(71) Applicant: Max-Planck-Gesellschaft zur Förderung der Wissenschaften e. V., München (DE)

(72) Inventors: Zoltán Konthur, Berlin (DE); Hans Lehrach, Berlin (DE); Karl Skriner, Berlin (DE)

(73) Assignee: MAX-PLANCK-GESELLSCHAFT ZUR FORDERUNG DER WISSENSHAFTEN E.V., Munich (DE)

(*) Notice: Subject to any disclaimer, the term of this patent is extended or adjusted under 35 U.S.C. 154(b) by 304 days.

(21) Appl. No.: 14/730,497

(22) Filed: Jun. 4, 2015

(65) Prior Publication Data
US 2015/0338411 A1 Nov. 26, 2015

Related U.S. Application Data

(62) Division of application No. 12/740,166, filed as application No. PCT/EP2008/064820 on Oct. 31, 2008, now Pat. No. 9,052,312.

(30) Foreign Application Priority Data
Oct. 31, 2007 (EP) ................................. 07119810

(51) Int. Cl.
G01N 33/53 (2006.01)
G01N 33/573 (2006.01)
G01N 33/68 (2006.01)
G01N 33/564 (2006.01)

(52) U.S. Cl.
CPC ......... *G01N 33/573* (2013.01); *G01N 33/564* (2013.01); *G01N 33/68* (2013.01); *G01N 33/6854* (2013.01); *G01N 33/6863* (2013.01); *G01N 2333/47* (2013.01); *G01N 2333/4703* (2013.01); *G01N 2333/705* (2013.01); *G01N 2333/82* (2013.01); *G01N 2333/916* (2013.01); *G01N 2333/9121* (2013.01); *G01N 2333/91171* (2013.01); *G01N 2333/91205* (2013.01); *G01N 2333/99* (2013.01); *G01N 2800/10* (2013.01); *G01N 2800/102* (2013.01); *G01N 2800/52* (2013.01)

(58) Field of Classification Search
None
See application file for complete search history.

(56) References Cited

U.S. PATENT DOCUMENTS

| 4,281,061 A | 7/1981 | Zuk et al. |
|---|---|---|
| 5,977,322 A | 11/1999 | Marks et al. |
| 2003/0224486 A1 | 12/2003 | Carman et al. |
| 2003/0228690 A1 | 12/2003 | Baker et al. |
| 2006/0099582 A1 | 5/2006 | Papadopoulos et al. |
| 2006/0121511 A1 | 6/2006 | Lee et al. |
| 2006/0216707 A1 | 9/2006 | Stuhlmuller et al. |
| 2008/0026485 A1 | 1/2008 | Hueber et al. |
| 2011/0045490 A1 | 2/2011 | Konthur et al. |

FOREIGN PATENT DOCUMENTS

| JP | 2006-133181 A | 5/2005 |
|---|---|---|
| WO | WO 00/55350 | 9/2000 |
| WO | WO 02/066045 A2 | 8/2002 |
| WO | WO 2005/014622 A2 | 2/2005 |
| WO | WO 2005/019258 A2 | 3/2005 |
| WO | WO-2007/039280 A1 | 4/2007 |
| WO | WO 2007/085240 A1 | 8/2007 |
| WO | WO-2007/117611 A2 | 10/2007 |

OTHER PUBLICATIONS

Yanagisawa et al.; "A novel splice variant of mouse interleukin-1-receptor-associated kinase-1 (IRAK-1) activates nuclear factor-κB (NF-κB) and c-Jun N-terminal kinase (JNK)"; Biochem J. 370:159-166 (Mar. 2003).
Notice of Reasons for Rejection with English Translation for Japanese Application No. 2014-004083 dated Sep. 9, 2014.
U.S. Non-final Office Action issued in U.S. Appl. No. 14/318,366 dated Jan. 3, 2017.
USPTO Memorandum from A. H. Hirshfeld, Deputy Commissioner for Patent Examination Policy; "2014 Procedure for Subject Matter Eligibility Analysis of Claims Reciting or Involving Laws of Nature/Natural Principles, Natural Phenomena, and/or Natural Products"; Mar. 4, 2014; 19 pages.
USPTO Publication; "2014 Interim Guidance on Patent Subject Matter Eligibility"; 1-44 (Dec. 16, 2014).
USPTO Publication; "Evaluating Subject Matter Eligibility Under 35 USC § 101: Mar. 2014 Update"; 1-93 (Mar. 19, 2014).
USPTO Publication; "Subject Matter Eligiblity Examples: Life Sciences"; 1-31 (May 2016).
Leuking et al., Molecular & Cellular Proteomics 4: 1382-1390, 2005.
Horn et al., Proteomics 2006, 6, 605-613.

(Continued)

*Primary Examiner* — Zachary S Skelding
(74) *Attorney, Agent, or Firm* — Foley & Lardner LLP

(57) ABSTRACT

The invention refers to a method for diagnosing an individual who is to be subjected to or is being subjected to an anti-tumor necrosis factor alpha (TNFα or TNF) treatment to assess the responsiveness to an anti-TNF treatment which comprises the detection of immunoglobulin(s) against one or more biomarker proteins in a bodily fluid or an excrement of said patient, and sorting the individual into one of two categories based on detection of said immunoglobulin(s), wherein individuals are classified as NON-responder or responder. The invention refers to diagnostic kits comprising said one or more biomarker proteins and the use of these kits for assessing the responsiveness to an anti-TNF treatment of an individual who is to be subjected to or is being subjected to an anti-TNFα treatment.

5 Claims, 126 Drawing Sheets

(56) References Cited

OTHER PUBLICATIONS

Nishimura et al., Ann. Intern. Med. 2007; 146: 797-808.
Verpoort et al., Arthritis & Rheumatism, 54(12), Dec. 2006, 3799-3808.
Sarah Jesse et al., "Summary of Cerebrospinal Fluid Routine Parameters in Neurodegenerative Diseases," J Neurol (2011) 258, 1034-1041.
Ewa Maria Kratz et al.,"Terminal Monosaccharide Screening of Synovial Immunoglobulins G and A for the Early Detection of Rheumatoid Arthritis," Rheumatol Int (2010) 30, 1285-1292.
Yukio Ishiguro et al., "Sensitive Solid Phase Enzyme Immunoassay for Human IgA, Secretory IgA, and Secretory Component," Clinica Chimica Acta (1981), 116, 237-243.
Andrew D. Strand et al., "Gene Expression in Huntington's Disease Skeletal Muscle: A Potential Biomarker," Human Molecular Genetics (2005), 14, 1863-1876.
JM Woof et al., "Structure and Function Relationships in IgA," Immunology (2011), 4, 590-597.
Xueling Wu et al., "Plasma and Salivary IgA Subclasses and IgM in HIV-1-Infected Individuals," J Clin Immunol (2002) 22, 106-115.
Bussow et al., Genomics, Apr. 1, 2000; 65(1), pp. 1-8.
Firestein et al., Arthritis & Rheumatism 46(2), Feb. 2002, pp. 298-308.
Meyer et al., Arthritis Res. Ther. 8(2), 2006; R40.
Written Opinion of the International Searching Authority in International Application No. PCT/EP2008/064820, dated Apr. 30, 2010, pp. 1-15.
Braun-Moscovici et al., "Anti-Cyclic Citrullinated Protein Antibodies as a Predictor of Response to Anti-Tumor Necrosis Factor-α Therapy in Patients with Rheumatoid Arthritis", The Journal of Rheumatology, vol. 33, No. 3 (2006), pp. 497-500.
Hueber et al., "Antigen Microarray Profiling of Autoantibodies in Rheumatoid Arthritis", Arthritis & Rheumatism, vol. 52, No. 9 (2005), pp. 2645-2655.
Krenn et al., "Array technology and proteomics in autoimmune diseases", Pathology Research and Practice, vol. 200, No. 2 (2004), pp. 95-103.
Skriner et al., "Immunomics in Inflammatory Rheumatic Diseases", Annals of the Rheumatic Diseases, vol. 65, No. 1 (2006), pp. A5.
Ho et al., "Tolerizing DNA vaccines for autoimmune arthritis", Autoimmunity, vol. 39, No, 8 (2006), pp. 675-682.
Lequerré et al., "Gene profiling in white blood cells predicts infliximab responsiveness in rheumatoid arthritis", Arthritis Research & Therapy, vol. 8, No. 4 (2006), pp. 1-11.
Bussow, Konrad et al.; "A method for global protein expression and antibody screening on high-density filters of an arrayed cDNA library"; Nucleic Acids Research, 1998, vol. 26, No. 21; Nov. 1998; pp. 5007-5008.
European Patent Office Communication pursuant to Article 94(3) EPC on application 08 843 343.8 dated Nov. 25, 2015; 6 pages.
Japan Patent Office Notice of Reasons for Rejection on application 2014-145938 dated Aug. 4, 2015; with English translation; 8 pages.

Fig. 1

SEQ ID No. 1
RAB11B
>ENSG00000185236|19|protein_coding|ENST00000328024|ENSP00000333547
ATGGGGACCCGGGACGACGAGTACGACTACCTATTCAAAGTGGTGCTCATCGGGGACTCA
GGCGTGGGCAAGAGCAACCTGCTGTCGCGCTTCACCCGCAACGAGTTCAACCTGGAGAGC
AAGAGCACCATCGGCGTGGAGTTCGCCACCCGCAGCATCCAGGTGGACGGCAAGACCATC
AAGGCGCAGATCTGGGACACCGCTGGCCAGGAGCGCTACCGCGCCATCACCTCCGCGTAC
TACCGTGGTGCAGTGGGCGCCCTGCTGGTGTACGACATCGCCAAGCACCTGACCTATGAG
AACGTGGAGCGCTGGCTGAAGGAGCTGCGGGACCACGCAGACAGCAACATCGTCATCATG
CTGGTGGGCAACAAGAGTGACCTGCGCCACCTGCGGGCTGTGCCCACTGACGAGGCCCGC
GCCTTCGCAGAAAAGAACAACTTGTCCTTCATCGAGACCTCAGCCTTGGATTCCACTAAC
GTAGAGGAAGCATTCAAGAACATCCTCACAGAGATCTACCGCATCGTGTCACAGAAACAG
ATCGCAGACCGCGCTGCCCACGACGAGTCCCGGGGAACAACGTGGTGGACATCAGCGTG
CCGCCCACCACGGACGGACAGAAGCCCAACAAGCTGCAGTGCTGCCAGAACCTGTGA

Fig. 2

SEQ ID No. 2
PPP2R1A
>ENSG00000105568|19|protein_coding|ENST00000391791|ENSP00000375668
ATGAGGACGTTCAGCTTCGCCTCAACAGCATCAAGAAGCTGTCCACCATCGCCTTGGCCC
TTGGGGTTGAAAGGACCCGAAGTGAGCTTCTGCCTTTCCTTACAGATACCATCTATGATG
AAGATGAGGTCCTCCTGGCCCTGGCAGAACAGCTGGGAACCTTCACTACCCTGGTGGGAG
GCCCAGAGTACGTGCACTGCCTGCTGCCTCTTCTCCGTCTGCTACCCCGAGTGTCCAGT
GCTGTGAAGGCGGAACTTCGACAGTACTTCCGGAACCTGTGCTCAGATGACACCCCCATG
GTGCGGCGGGCCGCAGCCTCCAAGCTGGGGGAGTTTGCCAAGGTGCTGGAGCTGGACAAC
GTCAAGAGTGAGATCATCCCCATGTTCTCCAACCTGGCCTCTGACGAGCAGGACTCGGTG
CGGCTGCTGGCGGTGGAGGCGTGCGTGAACATCGCCCAGCTTCTGCCCCAGGAGGATCTG
GAGGCCCTGGTGATGCCCACTCTGCGCCAGGCCGCTGAAGACAAGTCCTGGCGCGTCCGC
TACATGGTGGCTGACAAGTTCACAGAGCTCCAGAAAGCAGTGGGGCCTGAGATCACCAAG
ACAGACCTGGTCCCTGCCTTCCAGAACCTGATGAAAGACTGTGAGGCCGAGGTGAGGGCC
GCAGCCTCCCACAAGGTCAAAGAGTTCTGTGAAAACCTCTCAGCTGACTGTCGGGAGAAT
GTGATCATGTCCCAGATCTTGCCCTGCATCAAGGAGCTGGTGTCCGATGCCAACCAACAT
GTCAAGTCTGCCCTGGCCTCAGTCATCATGGGTCTCTCTCCCATCTTGGGCAAAGACAAC
ACCATCGAGCACCTCTTGCCCCTCTTCCTGGCTCAGCTGAAGGATGAGTGCCCTGAGGTA
CGGCTGAACATCATCTCTAACCTGGACTGTGTGAACGAGGTGATTGGCATCCGGCAGCTG
TCCCAGTCCCTGCTCCCTGCCATTGTGGAGCTGGCTGAGGACGCCAAGTGGCGGGTGCGG
CTGGCCATCATTGAGTACATGCCCCTCCTGGCTGGACAGCTGGGAGTGGAGTTCTTTGAT
GAGAAACTTAACTCCTTGTGCATGGCCTGGCTTGTGGATCATGTATATGCCATCCGCGAG
GCAGCCACCAGCAACCTGAAGAAGCTAGTGGAAAAGTTTGGGAAGGAGTGGGCCCATGCC
ACAATCATCCCCAAGGTCTTGGCCATGTCCGGAGACCCCAACTACCTGCACCGCATGACT
ACGCTCTTCTGCATCAATGTGCTGTCTGAGGTCTGTGGGCAGGACATCACCACCAAGCAC
ATGCTACCCACGGTTCTGCGCATGGCTGGGGACCCGGTTGCCAATGTCCGCTTCAATGTG
GCCAAGTCTCTGCAGAAGATAGGGCCCATCCTGGACAACAGCACCTTGCAGAGTGAAGTC
AAGCCCATCCTAGAGAAGCTGACCCAGGACCAGGATGTGGACGTCAAATACTTTGCCCAG
GAGGCTCTGACTGTTCTGTCTCTCGCCTGA

Fig. 3

SEQ ID No. 3
PPP2R1A
>ENSG00000105568|19|protein_coding|ENST00000322088|ENSP00000324804
ATGGCGGCGGCCGACGGCGACGACTCGCTGTACCCCATCGCGGTGCTCATAGACGAACTC
CGCAATGAGGACGTTCAGCTTCGCCTCAACAGCATCAAGAAGCTGTCCACCATCGCCTTG
GCCCTTGGGGTTGAAAGGACCCGAAGTGAGCTTCTGCCTTTCCTTACAGATACCATCTAT
GATGAAGATGAGGTCCTCCTGGCCCTGGCAGAACAGCTGGGAACCTTCACTACCCTGGTG
GGAGGCCCAGAGTACGTGCACTGCCTGCTGCCACCGCTGGAGTCGCTGGCCACAGTGGAG
GAGACAGTGGTGCGGGACAAGGCAGTGGAGTCCTTACGGGCCATCTCACACGAGCACTCG
CCCTCTGACCTGGAGGCGCACTTTGTGCCGCTAGTGAAGCGGCTGGCGGGCGGCGACTGG
TTCACCTCCCGCACCTCGGCCTGCGGCCTCTTCTCCGTCTGCTACCCCGAGTGTCCAGT
GCTGTGAAGGCGGAACTTCGACAGTACTTCCGGAACCTGTGCTCAGATGACACCCCCATG
GTGCGGCGGGCCGCAGCCTCCAAGCTGGGGGAGTTTGCCAAGGTGCTGGAGCTGGACAAC
GTCAAGAGTGAGATCATCCCCATGTTCTCCAACCTGGCCTCTGACGAGCAGGACTCGGTG
CGGCTGCTGGCGGTGGAGGCGTGCGTGAACATCGCCCAGCTTCTGCCCCAGGAGGATCTG
GAGGCCCTGGTGATGCCCACTCTGCGCCAGGCCGCTGAAGACAAGTCCTGGCGCGTCCGC
TACATGGTGGCTGACAAGTTCACAGAGCTCCAGAAAGCAGTGGGGCCTGAGATCACCAAG
ACAGACCTGGTCCCTGCCTTCCAGAACCTGATGAAAGACTGTGAGGCCGAGGTGAGGGCC
GCAGCCTCCCACAAGGTCAAAGAGTTCTGTGAAAACCTCTCAGCTGACTGTCGGGAGAAT
GTGATCATGTCCCAGATCTTGCCCTGCATCAAGGAGCTGGTGTCCGATGCCAACCAACAT
GTCAAGTCTGCCCTGGCCTCAGTCATCATGGGTCTCTCTCCCATCTTGGGCAAAGACAAC
ACCATCGAGCACCTCTTGCCCCTCTTCCTGGCTCAGCTGAAGGATGAGTGCCCTGAGGTA
CGGCTGAACATCATCTCTAACCTGGACTGTGTGAACGAGGTGATTGGCATCCGGCAGCTG
TCCCAGTCCCTGCTCCCTGCCATTGTGGAGCTGGCTGAGGACGCCAAGTGGCGGGTGCGG
CTGGCCATCATTGAGTACATGCCCCTCCTGGCTGGACAGCTGGGAGTGGAGTTCTTTGAT
GAGAAACTTAACTCCTTGTGCATGGCCTGGCTTGTGGATCATGTATATGCCATCCGCGAG
GCAGCCACCAGCAACCTGAAGAAGCTAGTGGAAAAGTTTGGGAAGGAGTGGGCCCATGCC
ACAATCATCCCCAAGGTCTTGGCCATGTCCGGAGACCCCAACTACCTGCACCGCATGACT
ACGCTCTTCTGCATCAATGTGCTGTCTGAGGTCTGTGGGCAGGACATCACCACCAAGCAC
ATGCTACCCACGGTTCTGCGCATGGCTGGGGACCCGGTTGCCAATGTCCGCTTCAATGTG
GCCAAGTCTCTGCAGAAGATAGGGCCCATCCTGGACAACAGCACCTTGCAGAGTGAAGTC
AAGCCCATCCTAGAGAAGCTGACCCAGGACCAGGATGTGGACGTCAAATACTTTGCCCAG
GAGGCTCTGACTGTTCTGTCTCTCGCCTGA

Fig. 4

SEQ ID No. 4
KPNB1
>ENSG00000108424|17|protein_coding|ENST00000290158|ENSP00000290158
ATGGAGCTGATCACCATTCTCGAGAAGACCGTGTCTCCCGATCGGCTGGAGCTGGAAGCG
GCGCAGAAGTTCCTGGAGCGTGCGGCCGTGGAGAACCTGCCCACTTTCCTTGTGGAACTG
TCCAGAGTGCTGGCAAATCCAGGAAACAGTCAGGTTGCCAGAGTTGCAGCTGGTCTACAA
ATCAAGAACTCTTTGACATCTAAAGATCCAGATATCAAGGCACAATATCAGCAGAGGTGG
CTTGCTATTGATGCTAATGCTCGACGAGAAGTCAAGAACTATGTTTTGCAGACATTGGGT
ACAGAAACTTACCGGCCTAGTTCTGCCTCACAGTGTGTGGCTGGTATTGCTTGTGCAGAG
ATCCCAGTAAACCAGTGGCCAGAACTCATTCCTCAGCTGGTGGCCAATGTCACAAACCCC
AACAGCACAGAGCACATGAAGGAGTCGACATTGGAAGCCATCGGTTATATTTGCCAAGAT
ATAGACCCAGAGCAGCTACAAGATAAATCCAATGAGATTCTGACTGCCATAATCCAGGGG
ATGAGGAAAGAAGAGCCTAGTAATAATGTGAAGCTAGCTGCTACGAATGCACTCCTGAAC
TCATTGGAGTTCACCAAAGCAAACTTTGATAAAGAGTCTGAAAGGCACTTTATTATGCAG
GTGGTCTGTGAAGCCACACAGTGTCCAGATACGAGGGTACGAGTGGCTGCTTTACAGAAT
CTGGTGAAGATAATGTCCTTATATTATCAGTACATGGAGACATATATGGGTCCTGCTCTT
TTTGCAATCACAATCGAAGCAATGAAAAGTGACATTGATGAGGTGGCTTTACAAGGGATA
GAATTCTGGTCCAATGTCTGTGATGAGGAAATGGATTTGGCCATTGAAGCTTCAGAGGCA
GCAGAACAAGGACGGCCCCCTGAGCACACCAGCAAGTTTATGCGAAGGGAGCACTACAG
TATCTGGTTCCAATCCTCACACAGACACTAACTAAACAGGACGAAAATGATGATGACGAT
GACTGGAACCCCTGCAAAGCAGCAGGGGTGTGCCTCATGCTTCTGGCCACCTGCTGTGAA
GATGACATTGTCCCACATGTCCTCCCCTTCATTAAAGAACACATCAAGAACCCAGATTGG
CGGTACCGGGATGCAGCAGTGATGGCTTTTGGTTGTATCTTGGAAGGACCAGAGCCCAGT
CAGCTCAAACCACTAGTTATACAGGCTATGCCCACCCTAATAGAATTAATGAAAGACCCC
AGTGTAGTTGTTCGAGATACAGCTGCATGGACTGTAGGCAGAATTTGTGAGCTGCTTCCT
GAAGCTGCCATCAATGATGTCTACTTGGCTCCCCTGCTACAGTGTCTGATTGAGGGTCTC
AGTGCTGAACCCAGAGTGGCTTCAAATGTGTGCTGGGCTTTCTCCAGTCTGGCTGAAGCT
GCTTATGAAGCTGCAGACGTTGCTGATGATCAGGAAGAACCAGCTACTTACTGCTTATCT
TCTTCATTTGAACTCATAGTTCAGAAGCTCCTAGAGACTACAGACAGACCTGATGGACAC
CAGAACAACCTGAGGAGTTCTGCATATGAATCTCTGATGGAAATTGTGAAAAACAGTGCC
AAGGATTGTTATCCTGCTGTCCAGAAAACGACTTTGGTCATCATGGAACGACTGCAACAG
GTTCTTCAGATGGAGTCACATATCCAGAGCACATCCGATAGAATCCAGTTCAATGACCTT
CAGTCTTTACTCTGTGCAACTCTTCAGAATGTTCTTCGGAAAGTGCAACATCAAGATGCT
TTGCAGATCTCTGATGTGGTTATGGCCTCCCTGTTAAGGATGTTCCAAAGCACAGCTGGG
TCTGGGGGAGTACAAGAGGATGCCCTGATGGCAGTTAGCACACTGGTGGAAGTGTTGGGT
GGTGAATTCCTCAAGTACATGGAGGCCTTTAAACCCTTCCTGGGCATTGGATTAAAAAAT
TATGCTGAATACCAGGTTTGTTTGGCAGCTGTGGGCTTAGTGGGAGACTTGTGCCGTGCC
CTGCAATCCAACATCATACCTTTCTGTGACGAGGTGATGCAGCTGCTTCTGGAAAATTTG
GGGAATGAGAACGTCCACAGGTCTGTGAAGCCGCAGATTCTGTCAGTGTTTGGTGATATT
GCCCTTGCTATTGGAGGAGAGTTTAAAAAATACTTAGAGGTTGTATTGAATACTCTTCAG
CAGGCCTCCCAAGCCCAGGTGGACAAGTCAGACTATGACATGGTGGATTATCTGAATGAG
CTAAGGGAAAGCTGCTTGGAAGCCTATACTGGAATCGTCCAGGGATTAAAGGGGGATCAG
GAGAACGTACACCCGGATGTGATGCTGGTACAACCCAGAGTAGAATTTATTCTGTCTTTC
ATTGACCACATTGCTGGAGATGAGGATCACACAGATGGAGTAGTAGCTTGTGCTGCTGGA
CTAATAGGGGACTTATGTACAGCATTTGGGAAGGATGTACTGAAATTAGTAGAAGCTAGG
CCAATGATCCATGAATTGTTAACTGAAGGGCGGAGATCGAAGACTAACAAAGCAAAAACC
CTTGCTACATGGGCAACAAAAGAACTGAGGAAACTGAAGAACCAAGCTTGA

Fig. 5

SEQ ID No. 5
COG4
>ENSG00000103051|16|protein_coding|ENST00000323786|ENSP00000315775
ATGGGGACCAAGATGGCGGACCTTGATTCGCCTCCGAAGCTGTCAGGGGTGCAGCAGCCG
TCTGAGGGGGTGGGAGGTGGCCGCTGCTCCGAAATCTCCGCTGAGCTCATTCGCTCCCTG
ACAGAGCTGCAGGAGCTGGAGGCTGTATACGAACGGCTCTGCGGCGAGGAGAAAGTGGTG
GAGAGAGAGCTGGATGCTCTTTTGGAACAGCAAAACACCATTGAAAGTAAGATGGTCACT
CTCCACCGAATGGGTCCTAATCTGCAGCTGATTGAGGGAGATGCAAAGCAGCTGGCTGGA
ATGATCACCTTTACCTGCAACCTGGCTGAGAATGTGTCCAGCAAAGTTCGTCAGCTTGAC
CTGGCCAAGAACCGCCTCTATCAGGCCATTCAGAGAGCTGATGACATCTTGGACCTGAAG
TTCTGCATGGATGGAGTTCAGACTGCTTTGAGGAGTGAAGATTATGAGCAGGCTGCAGCA
CATACTCATCGCTACTTGTGCCTGGACAAGTCGGTCATTGAGCTCAGCCGACAGGGCAAA
GAGGGGAGCATGATTGATGCCAACCTGAAATTGCTGCAGGAAGCTGAGCAACGTCTCAAA
GCCATTGTGGCAGAGAAGTTTGCCATTGCCACCAAGGAAGGTGATCTGCCCCAGGTGGAG
CGCTTCTTCAAGATCTTCCCACTGCTGGGTTTGCATGAGGAGGGATTAAGAAAGTTCTCG
GAGTACCTTTGCAAGCAGGTGGCCAGTAAAGCTGAGGAGAATCTGCTCATGGTGCTGGGG
ACAGACATGAGTGATCGGAGAGCTGCAGTCATCTTTGCAGATACACTTACTCTTCTGTTT
GAAGGGATTGCCCGCATTGTGGAGACCCACCAGCCAATAGTGGAGACCTATTATGGGCCA
GGGAGACTCTATACCCTGATCAAATATCTGCAGGTGGAATGTGACAGACAGGTGGAGAAG
GTGGTAGACAAGTTCATCAAGCAAAGGGACTACCACCAGCAGTTCCGGCATGTTCAGAAC
AACCTGATGAGAAATTCTACAACAGAAAAAATCGAACCAAGAGAACTGGACCCCATCCTG
ACTGAGGTCACCCTGATGAATGCCCGCAGTGAGCTATACTTACGCTTCCTCAAGAAGAGG
ATTAGCTCTGATTTTGAGGTGGGAGACTCCATGGCCTCAGAGGAAGTAAAGCAAGAGCAC
CAGAAGTGTCTGGACAAACTCCTCAATAACTGCCTTTTGAGCTGTACCATGCAGGAGCTA
ATTGGCTTATATGTTACCATGGAGGAGTACTTCATGAGGGAGACTGTCAATAAGGCTGTG
GCTCTGGACACCTATGAGAAGGGCCAGCTGACATCCAGCATGGTGGATGATGTCTTCTAC
ATTGTTAAGAAGTGCATTGGGCGGGCTCTGTCCAGCTCCAGCATTGACTGTCTCTGTGCC
ATGATCAACCTCGCCACCACAGAGCTGGAGTCTGACTTCAGGGATGTTCTGTGTAATAAG
CTGCGGATGGGCTTTCCTGCCACCACCTTCCAGGACATCCAGCGCGGGGTGACAAGTGCC
GTGAACATCATGCACAGCAGCCTCCAGCAAGGCAAATTTGACACAAAAGGCATCGAGAGT
ACTGACGAGGCGAAGATGTCCTTCCTGGTGACTCTGAACAACGTGGAAGTCTGCAGTGAA
AACATCTCCACTCTGAAGAAGACACTGGAGAGTGACTGCACCAAGCTCTTCAGCCAGGGC
ATTGGAGGGGAGCAGGCCCAGGCCAAGTTTGACAGCTGCCTTTCTGACTTGGCCGCCGTG
TCCAACAAATTCCGAGACCTCTTGCAGGAAGGGCTGACGGAGCTCAACAGCACAGCCATC
AAGCCACAGGTGCAGCCTTGGATCAACAGCTTTTTCTCCGTCTCCCACAACATCGAGGAG
GAAGAATTCAATGACTATGAGGCCAACGACCCTTGGGTACAACAGTTCATCCTTAACCTG
GAGCAGCAAATGGCAGAGTTCAAGGCCAGCCTGTCCCGGTCATCTACGACAGCCTAACC
GGCCTCATGACTAGCCTTGTTGCCGTCGAGTTGGAGAAAGTGGTGCTGAAATCCACCTTT
AACCGGCTGGGTGGTCTGCAGTTTGACAAGGAGCTGAGGTCGCTCATTGCCTACCTTACC
ACGGTGACCACCTGGACCATCCGAGACAAGTTTGCCCGGCTCTCCCAGATGGCCACCATC
CTCAATCTGGAGCGGGTGACCGAGATCCTCGATTACTGGGGACCCAATTCCGGCCCATTG
ACGTGGCGCCTCACCCCTGCTGAAGTGCGCCAGGTGCTGGCCCTGCGGATAGACTTCCGC
AGTGAAGATATCAAGAGGCTGCGCCTGTAG

Fig. 6

SEQ ID No. 6
COG4
>ENSG00000103051|16|protein_coding|ENST00000393612|ENSP00000377236
ATGGCGGACCTTGATTCGCCTCCGAAGCTGTCAGGGGTGCAGCAGCCGTCTGAGGGGGTG
GGAGGTGGCCGCTGCTCCGAAATCTCCGCTGAGCTCATTCGCTCCCTGACAGAGCTGCAG
GAGCTGGAGGCTGTATACGAACGGCTCTGCGGCGAGGAGAAAGTGGTGGAGAGAGAGCTG
GATGCTCTTTTGGAACAGCAAAACACCATTGAAAGTAAGATGGTCACTCTCCACCGAATG
GGTCCTAATCTGCAGCTGATTGAGGGAGATGCAAAGCAGCTGGCTGGAATGATCACCTTT
ACCTGCAACCTGGCTGAGAATGTGTCCAGCAAAGTTCGTCAGCTTGACCTGGCCAAGAAC
CGCCTCTATCAGGCCATTCAGAGAGCTGATGACATCTTGGACCTGAAGTTCTGCATGGAT
GGAGTTCAGACTGCTTTGAGGAGTGAAGATTATGAGCAGGCTGCAGCACATACTCATCGC
TACTTGTGCCTGGACAAGTCGGTCATTGAGCTCAGCCGACAGGGCAAAGAGGGGAGCATG
ATTGATGCCAACCTGAAATTGCTGCAGGAAGCTGAGCAACGTCTCAAAGCCATTGTGGCA
GAGAAGTTTGCCATTGCCACCAAGGAAGGTGATCTGCCCCAGGTGGAGCGCTTCTTCAAG
ATCTTCCCACTGCTGGGTTTGCATGAGGAGGGATTAAGAAAGTTCTCGGAGTACCTTTGC
AAGCAGGTGGCCAGTAAAGCTGAGGAGAATCTGCTCATGGTGCTGGGGACAGACATGAGT
GATCGGAGAGCTGCAGTCATCTTTGCAGATACACTTACTCTTCTGTTTGAAGGGATTGCC
CGCATTGTGGAGACCCACCAGCCAATAGTGGAGACCTATTATGGGCCAGGGAGACTCTAT
ACCCTGATCAAATATCTGCAGGTGGAATGTGACAGACAGGTGGAGAAGGTGGTAGACAAG
TTCATCAAGCAAAGGGACTACCACCAGCAGAACTTTGTTTTTTCCTTCTTTTGA

Fig. 7

SEQ ID No. 7
COG4
>ENSG00000103051|16|protein_coding|ENST00000338984|ENSP00000345047
ATGGCGGACCTTGATTCGCCTCCGAAGCTGTCAGGGGTGCAGCAGCCGTCTGAGGGGGTG
GGAGGTGGCCGCTGCTCCGAAATCTCCGCTGAGCTCATTCGCTCCCTGACAGAGCTGCAG
GAGCTGGAGGCTGTATACGAACGGCTCTGCGGCGAGGAGAAAGTGGTGGAGAGAGAGCTG
GATGCTCTTTTGGAACAGCAAAACACCATTGAAAGTAAGATGGTCACTCTCCACCGAATG
GGTCCTAATCTGCAGCTGATTGAGGGAGATGCAAAGCAGCTGGCTGGAATGATCACCTTT
ACCTGCAACCTGGCTGAGAATGTGTCCAGCAAAGTTCGTCAGCTTGACCTGGCCAAGAAC
CGCCTCTATCAGGCCATTCAGAGAGCTGATGACATCTTGGACCTGAAGTTCTGCATGGAT
GGAGTTCAGACTGCTTTGAGGAGTGAAGATTATGAGCAGGCTGCAGCACATACTCATCGC
TACTTGTGCCTGGACAAGTCGGTCATTGAGCTCAGCCGACAGGGCAAAGAGGGGAGCATG
ATTGATGCCAACCTGAAATTGCTGCAGGAAGCTGAGCAACGTCTCAAAGCCATTGTGGCA
GAGAAGTTTGCCATTGCCACCAAGGAAGGTGATCTGCCCCAGGTGGAGCGCTTCTTCAAG
ATCTTCCCACTGCTGGGTTTGCATGAGGAGGGATTAAGAAAGTTCTCGGAGTACCTTTGC
AAGCAGGTGGCCAGTAAAGCTGAGGAGAATCTGCTCATGGTGCTGGGGACAGACATGAGT
GATCGGAGAGCTGCAGTCATCTTTGCAGATACACTTACTCTTCTGTTTGAAGGGATTGCC
CGCATTGTGGAGACCCACCAGCCAATAGTGGAGACCTATTATGGGCCAGGGAGACTCTAT
ACCCTGATCAAATATCTGCAGGTGGAATGTGACAGACAGGTGGAGAAGGTGGTAGACAAG
TTCATCAAGCAAAGGGACTACCACCAGCAGTTCCGGCATGTTCAGAACAACCTGATGAGA
AATTCTACAACAGAAAAAATCGAACCAAGAGAACTGGACCCCATCCTGACTGAGGTCACC
CTGATGAATGCCCGCAGTGAGCTATACTTACGCTTCCTCAAGAAGAGGATTAGCTCTGAT
TTTGAGGTGGGAGACTCCATGGCCTCAGAGGAAGTAAAGCAAGAGCACCAGAAGTGTCTG
GACAAACTCCTCAATAACTGCCTTTTGAGCTGTACCATGCAGGAGCTAATTGGCTTATAT
GTTACCATGGAGGAGTACTTCATGAGGGAGACTGTCAATAAGGCTGTGGCTCTGGACACC
TATGAGAAGGGCCAGCTGACATCCAGCATGGTGGATGATGTCTTCTACATTGTTAAGAAG
TGCATTGGGCGGGCTCTGTCCAGCTCCAGCATTGACTGTCTCTGTGCCATGATCAACCTC
GCCACCACAGAGCTGGAGTCTGACTTCAGGGATGTTCTGTGTAATAAGCTGCGGATGGGC
TTTCCTGCCACCACCTTCCAGGACATCCAGCGCGGGGTGACAAGTGCCGTGAACATCATG
CACAGCAGCCTCCAGCAAGGCAAATTTGACACAAAAGGCATCGAGAGTACTGACGAGGCG
AAGATGTCCTTCCTGGTGACTCTGAACAACGTGGAAGTCTGCAGTGAAAACATCTCCACT
CTGAAGAAGACACTGGAGAGTGACTGCACCAAGCTCTTCAGCCAGGGCATTGGAGGGGAG
CAGGCCCAGGCCAAGTTTGACAGCTGCCTTTCTGACTTGGCCGCCGTGTCCAACAAATTC
CGAGACCTCTTGCAGGAAGGGCTGACGGAGCTCAACAGCACAGCCATCAAGCCACAGGTG
CAGCCTTGGATCAACAGCTTTTTCTCCGTCTCCCACAACATCGAGGAGGAAGAATTCAAT
GACTATGAGGCCAACGACCCTTGGGTACAACAGTTCATCCTTAACCTGGAGCAGCAAATG
GCAGAGTTCAAGGCCAGCCTGTCCCCGGTCATCTACGACAGCCTAACCGGCCTCATGACT
AGCCTTGTTGCCGTCGAGTTGGAGAAAGTGGTGCTGAAATCCACCTTTAACCGGCTGGGT
GGTCTGCAGTTTGACAAGGAGCTGAGGTCGCTCATTGCCTACCTTACCACGGTGACCACC
TGGACCATCCGAGACAAGTTTGCCCGGCTCTCCCAGATGGCCACCATCCTCAATCTGGAG
CGGGTGACCGAGATCCTCGATTACTGGGGACCCAATTCCGGCCCATTGACGTGGCGCCTC
ACCCCTGCTGAAGTGCGCCAGGTGCTGGCCCTGCGGATAGACTTCCGCAGTGAAGATATC
AAGAGGCTGCGCCTGTAG

Fig. 8

SEQ ID No. 8
COG4
>ENSG00000103051|16|protein_coding|ENST00000219329|ENSP00000219329
ATGGGGACCAAGATGGCGGACCTTGATTCGCCTCCGAAGCTGTCAGGGGTGCAGCAGCCG
TCTGAGGGGGTGGGAGGTGGCCGCTGCTCCGAAATCTCCGCTGAGCTCATTCGCTCCCTG
ACAGAGCTGCAGGAGCTGGAGGCTGTATACGAACGGCTCTGCGGCGAGGAGAAAGTGGTG
GAGAGAGAGCTGGATGCTCTTTTGGAACAGCAAAACACCATTGAAAGTAAGATGGTCACT
CTCCACCGAATGGGTCCTAATCTGCAGCTGATTGAGGCCAACCTGAAATTGCTGCAGGAA
GCTGAGCAACGTCTCAAAGCCATTGTGGCAGAGAAGTTTGCCATTGCCACCAAGGAAGGT
GATCTGCCCCAGGTGGAGCGCTTCTTCAAGATCTTCCCACTGCTGGGTTTGCATGAGGAG
GGATTAAGAAAGTTCTCGGAGTACCTTTGCAAGCAGGTGGCCAGTAAAGCTGAGGAGAAT
CTGCTCATGGTGCTGGGGACAGACATGAGTGATCGGAGAGCTGCAGTCATCTTTGCAGAT
ACACTTACTCTTCTGTTTGAAGGGATTGCCCGCATTGTGGAGACCCACCAGCCAATAGTG
GAGACCTATTATGGGCCAGGGAGACTCTATACCCTGATCAAATATCTGCAGGTGGAATGT
GACAGACAGGTGGAGAAGGTGGTAGACAAGTTCATCAAGCAAAGGGACTACCACCAGCAG
TTCCGGCATGTTCAGAACAACCTGATGAGAAATTCTACAACAGAAAAAATCGAACCAAGA
GAACTGGACCCCATCCTGACTGAGGTCACCCTGATGAATGCCCGCAGTGAGCTATACTTA
CGCTTCCTCAAGAAGAGGATTAGCTCTGATTTTGAGGTGGGAGACTCCATGGCCTCAGAG
GAAGTAAAGCAAGAGCACCAGAAGTGTCTGGACAAACTCCTCAATAACTGCCTTTTGAGC
TGTACCATGCAGGAGCTAATTGGCTTATATGTTACCATGGAGGAGTACTTCATGAGGGAG
ACTGTCAATAAGGCTGTGGCTCTGGACACCTATGAGAAGGGCCAGCTGACATCCAGCATG
GTGGATGATGTCTTCTACATTGTTAAGAAGTGCATTGGGCGGGCTCTGTCCAGCTCCAGC
ATTGACTGTCTCTGTGCCATGATCAACCTCGCCACCACAGAGCTGGAGTCTGACTTCAGG
GATGTTCTGTGTAATAAGCTGCGGATGGGCTTTCCTGCCACCACCTTCCAGGACATCCAG
CGCGGGGTGACAAGTGCCGTGAACATCATGCACAGCAGCCTCCAGCAAGGCAAATTTGAC
ACAAAAGGCATCGAGAGTACTGACGAGGCGAAGATGTCCTTCCTGGTGACTCTGAACAAC
GTGGAAGTCTGCAGTGAAAACATCTCCACTCTGAAGAAGACACTGGAGAGTGACTGCACC
AAGCTCTTCAGCCAGGGCATTGGAGGGGAGCAGGCCCAGGCCAAGTTTGACAGCTGCCTT
TCTGACTTGGCCGCCGTGTCCAACAAATTCCGAGACCTCTTGCAGGAAGGGCTGACGGAG
CTCAACAGCACAGCCATCAAGCCACAGGTGCAGCCTTGGATCAACAGCTTTTTCTCCGTC
TCCCACAACATCGAGGAGGAAGAATTCAATGACTATGAGGCCAACGACCCTTGGGTACAA
CAGTTCATCCTTAACCTGGAGCAGCAAATGGCAGAGTTCAAGGCCAGCCTGTCCCCGGTC
ATCTACGACAGCCTAACCGGCCTCATGACTAGCCTTGTTGCCGTCGAGTTGGAGAAAGTG
GTGCTGAAATCCACCTTTAACCGGCTGGGTGGTCTGCAGTTTGACAAGGAGCTGAGGTCG
CTCATTGCCTACCTTACCACGGTGACCACCTGGACCATCCGAGACAAGTTTGCCCGGCTC
TCCCAGATGGCCACCATCCTCAATCTGGAGCGGGTGACCGAGATCCTCGATTACTGGGGA
CCCAATTCCGGCCCATTGACGTGGCGCCTCACCCCTGCTGAAGTGCGCCAGGTGCTGGCC
CTGCGGATAGACTTCCGCAGTGAAGATATCAAGAGGCTGCGCCTGTAG

Fig. 9

SEQ ID No. 9
FDFT1
>ENSG00000079459|8|protein_coding|ENST00000220584|ENSP00000220584
ATGGAGTTCGTGAAATGCCTTGGCCACCCCGAAGAGTTCTACAACCTGGTGCGCTTCCGG
ATCGGGGGCAAGCGGAAGGTGATGCCCAAGATGGACCAGGACTCGCTCAGCAGCAGCCTG
AAAACTTGCTACAAGTATCTCAATCAGACCAGTCGCAGTTTCGCAGCTGTTATCCAGGCG
CTGGATGGGAAATGCGCAACGCAGTGTGCATATTTTATCTGGTTCTCCGAGCTCTGGAC
ACACTGGAAGATGACATGACCATCAGTGTGGAAAAGAAGGTCCCGCTGTTACACAACTTT
CACTCTTTCCTTTACCAACCAGACTGGCGGTTCATGGAGAGCAAGGAGAAGGATCGCCAG
GTGCTGGAGGACTTCCCAACGATCTCCCTTGAGTTTAGAAATCTGGCTGAGAAATACCAA
ACAGTGATTGCCGACATTTGCCGGAGAATGGGCATTGGGATGGCAGAGTTTTTGGATAAG
CATGTGACCTCTGAACAGGAGTGGGACAAGTACTGCCACTATGTTGCTGGGCTGGTCGGA
ATTGGCCTTTCCCGTCTTTTCTCAGCCTCAGAGTTTGAAGACCCCTTAGTTGGTGAAGAT
ACAGAACGTGCCAACTCTATGGGCCTGTTTTTGCAGAAAACAAACATCATCCGTGACTAT
CTGGAAGACCAGCAAGGAGGAAGAGAGTTCTGGCCTCAAGAGGTTTGGAGCAGGTATGTT
AAGAAGTTAGGGGATTTTGCTAAGCCGGAGAATATTGACTTGGCCGTGCAGTGCCTGAAT
GAACTTATAACCAATGCACTGCACCACATCCCAGATGTCATCACCTACCTTTCGAGACTC
AGAAACCAGAGTGTGTTTAACTTCTGTGCTATTCCACAGGTGATGGCCATTGCCACTTTG
GCTGCCTGTTATAATAACCAGCAGGTGTTCAAAGGGGCAGTGAAGATTCGGAAAGGGCAA
GCAGTGACCCTGATGATGGATGCCACCAATATGCCAGCTGTCAAAGCCATCATATATCAG
TATATGGAAGAGATTTATCATAGAATCCCCGACTCAGACCCATCTTCTAGCAAAACAAGG
CAGATCATCTCCACCATCCGGACGCAGAATCTTCCCAACTGTCAGCTGATTTCCCGAAGC
CACTACTCCCCATCTACCTGTCGTTTGTCATGCTTTTGGCTGCCCTGAGCTGGCAGTAC
CTGACCACTCTCTCCCAGGTAACAGAAGACTATGTTCAGACTGGAGAACACTGA

Fig. 10

SEQ ID No. 10
PECI
>ENSG00000198721|6|protein_coding|ENST00000380125|ENSP00000369468
ATGAGAGCCAGTCAGAAGGACTTTGAAAATTCAATGAATCAAGTGAAACTCTTGAAAAAG
GATCCAGGAAACGAAGTGAAGCTAAAACTCTACGCGCTATATAAGCAGGCCACTGAAGGA
CCTTGTAACATGCCCAAACCAGGTGTATTTGACTTGATCAACAAGGCCAAATGGGACGCA
TGGAATGCCCTTGGCAGCCTGCCCAAGGAAGCTGCCAGGCAGAACTATGTGGATTTGGTG
TCCAGTTTGAGTCCTTCATTGGAATCCTCTAGTCAGGTGGAGCCTGGAACAGACAGGAAA
TCAACTGGGTTTGAAACTCTGGTGGTGACCTCCGAAGATGGCATCACAAAGATCATGTTC
AACCGGCCCAAAAAGAAAAATGCCATAAACACTGAGATGTATCATGAAATTATGCGTGCA
CTTAAAGCTGCCAGCAAGGATGACTCAATCATCACTGTTTTAACAGGAAATGGTGACTAT
TACAGTAGTGGGAATGATCTGACTAACTTCACTGATATTCCCCCTGGTGGAGTAGAGGAG
AAAGCTAAAAATAATGCCGTTTTACTGAGGGAATTTGTGGGCTGTTTTATAGATTTTCCT
AAGCCTCTGATTGCAGTGGTCAATGGTCCAGCTGTGGGCATCTCCGTCACCCTCCTTGGG
CTATTCGATGCCGTGTATGCATCTGACAGGGCAACATTTCATACACCATTTAGTCACCTA
GGCCAAAGTCCGGAAGGATGCTCCTCTTACACTTTTCCGAAGATAATGAGCCCAGCCAAG
GCAACAGAGATGCTTATTTTTGGAAAGAAGTTAACAGCGGGAGAGGCATGTGCTCAAGGA
CTTGTTACTGAAGTTTTCCCTGATAGCACTTTTCAGAAAGAAGTCTGGACCAGGCTGAAG
GCATTTGCAAAGCTTCCCCCAAATGCCTTGAGAATTTCAAAAGAGGTAATCAGGAAAAGA
GAGAGAGAAAAACTACACGCTGTTAATGCTGAAGAATGCAATGTCCTTCAGGGAAGATGG
CTATCAGATGAATGCACAAATGCTGTGGTGAACTTCTTATCCAGAAAATCAAAACTGTGA

Fig. 11

SEQ ID No. 11
PECI
>ENSG00000198721|6|protein_coding|ENST00000380114|ENSP00000369457
ATGTATCATGAAATTATGCGTGCACTTAAAGCTGCCAGCAAGGATGACTCAATCATCACT
GTTTTAACAGGAAATGGTGACTATTACAGTAGTGGGAATGATCTGACTAACTTCACTGAT
ATTCCCCCTGGTGGAGTAGAGGAGAAAGCTAAAAATAATGCCGTTTTACTGAGGGAATTT
GTGGGCTGTTTTATAGATTTTCCTAAGCCTCTGATTGCAGTGGTCAATGGTCCAGCTGTG
GGCATCTCCGTCACCCTCCTTGGGCTATTCGATGCCGTGTATGCATCTGACAGGGCAACA
TTTCATACACCATTTAGTCACCTAGGCCAAAGTCCGGAAGGATGCTCCTCTTACACTTTT
CCGAAGATAATGAGCCCAGCCAAGGCAACAGAGATGCTTATTTTTGGAAAGAAGTTAACA
GCGGGAGAGGCATGTGCTCAAGGACTTGTTACTGAAGTTTTCCCTGATAGCACTTTTCAG
AAAGAAGTCTGGACCAGGCTGAAGGCATTTGCAAAGCTTCCCCCAAATGCCTTGAGAATT
TCAAAAGAGGTAATCAGGAAAAGAGAGAGAGAAAAACTACACGCTGTTAATGCTGAAGAA
TGCAATGTCCTTCAGGGAAGATGGCTATCAGATGAATGCACAAATGCTGTGGTGAACTTC
TTATCCAGAAAATCAAAACTGTGA

Fig. 12

SEQ ID No. 12
PECI
>ENSG00000198721|6|protein_coding|ENST00000380118|ENSP00000369461
ATGGCGATGGCGTACTTGGCTTGGAGACTGGCGCGGCGTTCGTGTCCGAGTTCTCTGCAG
GTCACTAGTTTCCCGGTAGTTCAGCTGCACATGAATAGAACAGCAATGAGAGCCAGTCAG
AAGGACTTTGAAAATTCAATGAATCAAGTGAAACTCTTGAAAAAGGATCCAGGAAACGAA
GTGAAGCTAAAACTCTACGCGCTATATAAGCAGGCCACTGAAGGACCTTGTAACATGCCC
AAACCAGGTGTATTTGACTTGATCAACAAGGCCAAATGGGACGCATGGAATGCCCTTGGC
AGCCTGCCCAAGGAAGCTGCCAGGCAGAACTATGTGGATTTGGTGTCCAGTTTGAGTCCT
TCATTGGAATCCTCTAGTCAGGTGGAGCCTGGAACAGACAGGAAATCAACTGGGTTTGAA
ACTCTGGTGGTGACCTCCGAAGATGGCATCACAAAGATCATGTTCAACCGGCCCAAAAAG
AAAAATGCCATAAACACTGAGATGTATCATGAAATTATGCGTGCACTTAAAGCTGCCAGC
AAGGATGACTCAATCATCACTGTTTTAACAGGAAATGGTGACTATTACAGTAGTGGGAAT
GATCTGACTAACTTCACTGATATTCCCCCTGGTGGAGTAGAGGAGAAAGCTAAAAATAAT
GCCGTTTTACTGAGGGAATTTGTGGGCTGTTTTATAGATTTTCCTAAGCCTCTGATTGCA
GTGGTCAATGGTCCAGCTGTGGGCATCTCCGTCACCCTCCTTGGGCTATTCGATGCCGTG
TATGCATCTGACAGGGCAACATTTCATACACCATTTAGTCACCTAGGCCAAAGTCCGGAA
GGATGCTCCTCTTACACTTTTCCGAAGATAATGAGCCCAGCCAAGGCAACAGAGATGCTT
ATTTTTGGAAGAAGTTAACAGCGGGAGAGGCATGTGCTCAAGGACTTGTTACTGAAGTT
TTCCCTGATAGCACTTTTCAGAAAGAAGTCTGGACCAGGCTGAAGGCATTTGCAAAGCTT
CCCCCAAATGCCTTGAGAATTTCAAAAGAGGTAATCAGGAAAAGAGAGAGAGAAAAACTA
CACGCTGTTAATGCTGAAGAATGCAATGTCCTTCAGGGAAGATGGCTATCAGATGAATGC
ACAAATGCTGTGGTGAACTTCTTATCCAGAAAATCAAAACTGTGA

Fig. 13

SEQ ID No. 13
PECI
>ENSG00000198721|6|protein_coding|ENST00000361538|ENSP00000354737
ATGAATAGAACAGCAATGAGAGCCAGTCAGAAGGACTTTGAAAATTCAATGAATCAAGTG
AAACTCTTGAAAAAGGATCCAGGAAACGAAGTGAAGCTAAAACTCTACGCGCTATATAAG
CAGGCCACTGAAGGACCTTGTAACATGCCCAAACCAGGTGTATTTGACTTGATCAACAAG
GCCAAATGGGACGCATGGAATGCCCTTGGCAGCCTGCCCAAGGAAGCTGCCAGGCAGAAC
TATGTGGATTTGGTGTCCAGTTTGAGTCCTTCATTGGAATCCTCTAGTCAGGTGGAGCCT
GGAACAGACAGGAAATCAACTGGGTTTGAAACTCTGGTGGTGACCTCCGAAGATGGCATC
ACAAAGATCATGTTCAACCGGCCCAAAAAGAAAAATGCCATAAACACTGAGATGTATCAT
GAAATTATGCGTGCACTTAAAGCTGCCAGCAAGGATGACTCAATCATCACTGTTTTAACA
GGAAATGGTGACTATTACAGTAGTGGGAATGATCTGACTAACTTCACTGATATTCCCCCT
GGTGGAGTAGAGGAGAAAGCTAAAAATAATGCCGTTTTACTGAGGGAATTTGTGGGCTGT
TTTATAGATTTTCCTAAGCCTCTGATTGCAGTGGTCAATGGTCCAGCTGTGGGCATCTCC
GTCACCCTCCTTGGGCTATTCGATGCCGTGTATGCATCTGACAGGGCAACATTTCATACA
CCATTTAGTCACCTAGGCCAAAGTCCGGAAGGATGCTCCTCTTACACTTTTCCGAAGATA
ATGAGCCCAGCCAAGGCAACAGAGATGCTTATTTTTGGAAAGAAGTTAACAGCGGGAGAG
GCATGTGCTCAAGGACTTGTTACTGAAGTTTTCCCTGATAGCACTTTTCAGAAAGAAGTC
TGGACCAGGCTGAAGGCATTTGCAAAGCTTCCCCCAAATGCCTTGAGAATTTCAAAAGAG
GTAATCAGGAAAAGAGAGAGAGAAAAACTACACGCTGTTAATGCTGAAGAATGCAATGTC
CTTCAGGGAAGATGGCTATCAGATGAATGCACAAATGCTGTGGTGAACTTCTTATCCAGA
AAATCAAAACTGTGA

Fig. 14

SEQ ID No. 14
PECI
>ENSG00000198721|6|protein_coding|ENST00000380120|ENSP00000369463
ATGTTCAACCGGCCCAAAAAGAAAAATGCCATAAACACTGAGATGTATCATGAAATTATG
CGTGCACTTAAAGCTGCCAGCAAGGATGACTCAATCATCACTGTTTTAACAGGAAATGGT
GACTATTACAGTAGTGGGAATGATCTGACTAACTTCACTGATATTCCCCCTGGTGGAGTA
GAGGAGAAAGCTAAAAATAATGCCGTTTTACTGAGGGAATTTGTGGGCTGTTTTATAGAT
TTTCCTAAGCCTCTGATTGCAGTGGTCAATGGTCCAGCTGTGGGCATCTCCGTCACCCTC
CTTGGGCTATTCGATGCCGTGTATGCATCTGACAGGGCAACATTTCATACACCATTTAGT
CACCTAGGCCAAAGTCCGGAAGGATGCTCCTCTTACACTTTTCCGAAGATAATGAGCCCA
GCCAAGGCAACAGAGATGCTTATTTTTGGAAAGAAGTTAACAGCGGGAGAGGCATGTGCT
CAAGGACTTGTTACTGAAGTTTTCCCTGATAGCACTTTTCAGAAAGAAGTCTGGACCAGG
CTGAAGGCATTTGCAAAGCTTCCCCCAAATGCCTTGAGAATTTCAAAAGAGGTAATCAGG
AAAAGAGAGAGAGAAAAACTACACGCTGTTAATGCTGAAGAATGCAATGTCCTTCAGGA
AGATGGCTATCAGATGAATGCACAAATGCTGTGGTGAACTTCTTATCCAGAAAATCAAAA
CTGTGA

Fig. 15

SEQ ID No. 15
CTNND2
>ENSG00000169862|5|protein_coding|ENST00000359640|ENSP00000352661
ATGTTTGCGAGGAAGCCGCCGGGCGCCGCGCCTTTGGGAGCTATGCCTGTTCCAGACCAG
CCTTCATCAGCCTCAGAGAAGACGAGTTCCCTGAGCCCCGGCTTAAACACCTCCAACGGG
GATGGCTCTGAAACAGAAACCACCTCTGCCATCCTCGCCTCAGTCAAAGAACAGGAATTA
CAGTTTGAAAGGCTGACCCGAGAGCTGGAGGCTGAACGGCAGATCGTAGCCAGCCAGCTG
GAGCGATGCAAGCTCGGATCCGAGACTGGCAGCATGAGCAGCATGAGTTCAGCAGAAGAG
CAGTTTCAGTGGCAGTCACAAGATGGTCAAAAAGATATCGAAGATGAGCTTACAACAGGT
CTCGAGCTGGTGGACTCCTGTATTAGGTCACTACAGGAATCAGGAATACTTGACCCACAG
GATTATTCTACAGGTGAAAGGCCCAGCCTGCTCTCCCAGAGTGCACTTCAGCTCAATTCC
AAACCTGAAGGGTCTTTCCAGTATCCGGCCAGCTACCATAGCAACCAGACCCTGGCCCTG
GGGGAAACCACCCCTTCACAGCTCCCGGCCCGAGGCACACAAGCCCGAGCTACGGGCCAG
AGCTTCAGCCAGGGCACGACCAGCCGCGCCGGCCACCTGGCGGGGCCCGAGCCCGCGCCG
CCGCCGCCGCCGCCGCGGGAGCCGTTCGCGCCCAGCCTGGGCAGCGCCTTCCACCTG
CCCGACGCGCCGCCCGCCGCCGCCGCCGCCGCGCTCTACTACTCCAGCTCCACGCTGCCC
GCGCCGCCGCGCGGGGGCTCCCCGCTGGCCGCGCCCCAGGGCGGTTCGCCCACCAAGCTG
CAGCGCGGCGGCTCGGCCCCGAGGGCGCCACCTACGCCGCGCCGCGCGGCTCCTCGCCC
AAGCAGTCGCCCAGCCGCCTGGCCAAGTCCTACAGCACCAGCTCGCCCATCAACATCGTC
GTGTCCTCGGCCGGCCTGTCCCCGATCCGCGTGACCTCGCCCCCACCGTGCAGTCCACC
ATCTCCTCCTCGCCCATCCACCAGCTGAGCTCCACCATCGGCACGTACGCCACCCTGTCG
CCCACCAAGCGCCTGGTCCACGCGTCCGAGCAGTACAGCAAGCACTCGCAGGAGCTGTAT
GCCACGGCCACCCTCCAGAGGCCGGGCAGCCTGGCAGCTGGTTCCCGAGCCTCATACAGC
AGCCAGCATGGGCACCTGGGCCCAGAGTTGCGGGCCCTGCAGTCCCCAGAACACCACATA
GATCCCATCTATGAAGACCGCGTCTATCAGAAGCCCCCTATGAGGAGTCTCAGCCAGAGC
CAGGGGGACCCTCTGCCGCCAGCACACACCGGCACCTACCGCACGAGCACAGCCCCATCT
TCCCCTGGTGTCGACTCCGTCCCCTTGCAGCGCACAGGCAGCCAGCACGGCCCACAGAAT
GCCGCCGCCGGCCACCTTCCAGAGGGCCAGCTATGCCGCCGGCCCAGCCTCCAATTACGCG
GACCCCTACCGACAGCTGCAGTATTGTCCCTCTGTTGAGTCTCCATACAGCAAATCCGGC
CCTGCTCTCCCGCCTGAAGGCACCTTGGCCAGGTCCCCGTCCATTGATAGCATTCAGAAA
GATCCCAGAGAATTTGGATGGAGAGACCCGGAACTGCCGGAAGTGATTCAGATGTTGCAG
CACCAGTTTCCCTCGGTCCAGTCTAACGCGGCAGCCTACTTGCAACACCTCTGTTTTGGA
GACAACAAAATTAAAGCCGAGATAAGGAGACAAGGAGGCATCCAGCTCCTGGTGGACCTG
TTGGATCATCGGATGACCGAAGTCCACCGTAGTGCCTGTGGAGCTCTGAGAAACCTGGTG
TATGGGAAGGCCAACGATGATAACAAAATTGCCCTGAAAAACTGTGGTGGCATCCCAGCA
CTGGTGAGGTTACTCCGCAAGACGACTGACCTGGAGATCCGGGAGCTGGTCACAGGAGTC
CTTTGGAACCTCTCCTCATGCGATGCACTCAAAATGCCAATCATCCAGGATGCCCTAGCA
GTACTGACCAACGCGGTGATTATCCCCCACTCAGGCTGGAAAATTCGCCTCTTCAGGAT
GATCGGAAAATACAGCTGCATTCATCACAGGTGCTGCGTAACGCCACCGGGTGCCTAAGG
AATGTTAGTTCGGCCGGAGAGGAGGCCCGCAGAAGGATGAGAGAGTGTGATGGGCTTACG
GATGCCTTGCTGTACGTGATCCAGTCTGCGCTGGGGAGCAGTGAGATCGATAGCAAGACC
GTTGAAAACTGTGTGTGCATTTTAAGGAACCTCTCGTACCGGCTGGCGGCAGAAACGTCT
CAGGGACAGCACATGGGCACGACGAGCTGGACGGGCTACTCTGTGGCGAGGCCAATGGC
AAGGATGCTGAGAGCTCTGGGTGCTGGGGCAAGAAGAAGAAGAAAAAGAAATCCCAAGAT
CAGTGGTCAGTATATATCCGAGCCGCTGTCCGAAAAGAGAAAGGCCTGCCCATCCTCGTG
GAGCTGCTCCGAATAGACAATGACCGTGTGGTGTGCGCGGTGGCCACTGCGCTGCGGAAC
ATGGCCTTGGACGTCAGAAATAAGGAGCTCATCGGCAAATACGCCATGCGAGACCTAGTC
CACAGGCTTCCAGGAGGGAACAACAGCAACAACACTGCAAGCAAGGCCATGTCGGATGAC
ACAGTGACAGCTGTCTGCTGCACACTGCACGAAGTGATTACCAAGAACATGGAGAACGCC
AAGGCCTTACGGGATGCCGGTGGCATCGAGAAGTTGGTCGGCATCTCCAAAAGCAAGGA
GATAAACACTCTCCAAAAGTGGTCAAGGCTGCATCTCAGGTCCTCAACAGCATGTGGCAG
TACCGAGATCTGAGGAGTCTCTACAAAAAGGATGGATGGTCACAATACCACTTTGTAGCC
TCGTCTTCAACCATCGAGAGGGACCGGCAAAGGCCCTACTCCTCCTCCCGCACGCCCTCC
ATCTCCCCTGTGCGCGTGTCTCCCAACAACCGCTCAGCAAGTGCCCCAGCTTCACCTCGG
GAAATGATCAGCCTCAAAGAAAGGAAAACAGACTACGAGTGCACCGGCAGCAACGCCACC
TACCACGGAGCTAAAGGCGAACACACTTCCAGGAAAGATGCCATGACAGCTCAAAACACT
GGAATTTCAACTTTGTATAGGAATTCTTATGGTGCGCCCGCTGAAGACATCAAACACAAC
CAGGTTTCAGCACAGCCAGTCCCACAGGAGCCCAGCAGAAAGATTACGAGACCTACCAG
CCATTTCAGAATTCCACAAGAAATTACGATGAGTCCTTCTTCGAGGACCAGGTCCACCAT
CGCCCTCCCGCCAGCGAGTACACCATGCACCTGGGTCTCAAGTCCACCGGCAACTACGTT
GACTTCTACTCAGCTGCCCGTCCCTACAGTGAACTGAACTATGAAACGAGCCACTACCCG
GCCTCCCCCGACTCCTGGGTGTGA

Fig. 16

SEQ ID No. 16
CTNND2
>ENSG00000169862|5|protein_coding|ENST00000304623|ENSP00000307134
ATGTTTGCGAGGAAGCCGCCGGGCGCCGCGCCTTTGGGAGCTATGCCTGTTCCAGACCAG
CCTTCATCAGCCTCAGAGAAGACGAGTTCCCTGAGCCCCGGCTTAAACACCTCCAACGGG
GATGGCTCTGAAACAGAAACCACCTCTGCCATCCTCGCCTCAGTCAAAGAACAGGAATTA
CAGTTTGAAAGGCTGACCCGAGAGCTGGAGGCTGAACGGCAGATCGTAGCCAGCCAGCTG
GAGCGATGCAAGCTCGGATCCGAGACTGGCAGCATGAGCAGCATGAGTTCAGCAGAAGAG
CAGTTTCAGTGGCAGTCACAAGATGGTCAAAAAGATATCGAAGATGAGCTTACAACAGGT
CTCGAGCTGGTGGACTCCTGTATTAGGTCACTACAGGAATCAGGAATACTTGACCCACAG
GATTATTCTACAGGTGAAAGGCCCAGCCTGCTCTCCCAGAGTGCACTTCAGCTCAATTCC
AAACCTGAAGGGTCTTTCCAGTATCCGGCCAGCTACCATAGCAACCAGACCCTGGCCCTG
GGGGAAACCACCCCTTCACAGCTCCCGGCCCGAGGCACACAAGCCCGAGCTACGGGCCAG
AGCTTCAGCCAGGGCACGACCAGCCGCGCCGGGCCACCTGGCGGGGCCCGAGCCCGCGCCG
CCGCCGCCGCCGCCGCCGCGGGAGCCGTTCGCGCCCAGCCTGGGCAGCGCCTTCCACCTG
CCCGACGCCGCCGCCGCCGCCGCCGCCGCGCTCTACTACTCCAGCTCCACGCTGCCC
GCGCCGCCGCGCGGGGGCTCCCCGCTGGCCGCGCCCCAGGGCGGTTCGCCCACCAAGCTG
CAGCGCGGCGGCTCGGCCCCCGAGGGCGCCACCTACGCCGCGCCGCGCGGCTCCTCGCCC
AAGCAGTCGCCCAGCCGCCTGGCCAAGTCCTACAGCACCAGCTCGCCCATCAACATCGTC
GTGTCCTCGGCCGGCCTGTCCCCGATCCGCGTGACCTCGCCCCCACCGTGCAGTCCACC
ATCTCCTCCTCGCCCATCCACCAGCTGAGCTCCACCATCGGCACGTACGCCACCCTGTCG
CCCACCAAGCGCCTGGTCCACGCGTCCGAGCAGTACAGCAAGCACTCGCAGGAGCTGTAT
GCCACGGCCACCCTCCAGAGGCCGGGCAGCCTGGCAGCTGGTTCCGAGCCTCATACAGC
AGCCAGCATGGGCACCTGGGCCCAGAGTTGCGGGCCTGCAGTCCCCAGAACACCACATA
GATCCCATCTATGAAGACCGCGTCTATCAGAAGCCCCTATGAGGAGTCTCAGCCAGAGC
CAGGGGGACCCTCTGCCGCCAGCACACACCGGCACCTACCGCACGAGCACAGCCCCATCT
TCCCCTGGTGTCGACTCCGTCCCCTTGCAGCGCACAGGCAGCCAGCACGGCCCACAGAAT
GCCGCCGCGGCCACCTTCCAGAGGGCCAGCTATGCCGCCGGCCCAGCCTCCAATTACGCG
GACCCCTACGACAGCTGCAGTATTGTCCCTCTGTTGAGTCTCCATACAGCAAATCCGGC
CCTGCTCTCCCGCCTGAAGGCACCTTGGCCAGGTCCCCGTCCATTGATAGCATTCAGAAA
GATCCCAGAGAATTTGGATGGAGAGACCCGGAACTGCCAGGAAGTGATTCAGATGTTGCAG
CACCAGTTTCCCTCGGTCCAGTCTAACGCGGCAGCCTACTTGCAACACCTCTGTTTTGGA
GACAACAAAATTAAAGCCGAGATAAGGAGACAAGGAGGCATCCAGCTCCTGGTGGACCTG
TTGGATCATCGGATGACCGAAGTCCACCGTAGTGCCTGTGGAGCTCTGAGAAACCTGGTG
TATGGGAAGGCCAACGATGATAACAAAATTGCCCTGAAAAACTGTGGTGGCATCCCAGCA
CTGGTGAGGTTACTCCGCAAGACGACTGACCTGGAGATCCGGGAGCTGGTCACAGGAGTC
CTTTGGAACCTCTCCTCATGCGATGCACTCAAAATGCCAATCATCCAGGATGCCCTAGCA
GTACTGACCAACGCGGTGATTATCCCCACTCAGGCTGGGAAAATTCGCCTCTTCAGGAT
GATCGGAAAATACAGCTGCATTCATCACAGGTGCTGCGTAACGCCACCGGGTGCCTAAGG
AATGTTAGTTCGCCGGAGAGGAGGCCCGCAGAAGGATGAGAGAGTGTGATGGGCTTACG
GATGCCTTGCTGTACGTGATCCAGTCTGCGCTGGGGAGCAGTGAGATCGATAGCAAGACC
GTTGAAACTGTGTGTGCATTTTAAGGAACCTCTCGTACCGGCTGGCGGCAGAAACGTCT
CAGGGACAGCACATGGGCACGGACGAGCTGGACGGGCTACTCTGTGGCGAGGCCAATGGC
AAGGATGCTGAGAGCTCTGGGTGCTGGGGCAAGAAGAAGAAGAAAAAGAAATCCCAAGAT
CAGTGGGATGGAGTAGGACCTCTTCCAGACTGTGCTGAACCACCAAAAGGGATCCAGATG
CTGTGGCACCCATCAATAGTCAAACCCTACCTCACACTGCTCTCTGAGTGCTCAAATCCA
GACACGCTGGAAGGGGCGGCAGGCGCCCTGCAGAACTTGGCTGCAGGGAGCTGGAAGTGG
TCAGTATATATCCGAGCCGCTGTCCGAAAAGAGAAAGGCCTGCCCATCCTCGTGGAGCTG
CTCCGAATAGACAATGACCGTGTGGTGCGCGGTGGCCACTGCGCTGCGGAACATGGCC
TTGGACGTCAGAAATAAGGAGCTCATCGGCAAATACGCCATGCGAGACCTAGTCCACAGG
CTTCCAGGAGGGAACAACAGCAACAACACTGCAAGCAAGCCCATGTCGGATGACACAGTG
ACAGCTGTCTGCTGCACACTGCACGAAGTGATTACCAAGAACATGGAGAACGCCAAGGCC
TTACGGGATGCCGGTGGCATCGAGAAGTTGGTCGGCATCTCCAAAAGCAAAGGAGATAAA
CACTCTCCAAAAGTGGTCAAGGCTGCATCTCAGGTCCTCAACAGCATGTGGCAGTACCGA
GATCTGAGGAGTCTCTACAAAAAGGATGGATGGTCACAATACCACTTTGTAGCCTCGTCT
TCAACCATCGAGAGGGACCGGCAAAGGCCCTACTCCTCCTCCCGCACGCCCTCCATCTCC
CCTGTGCGCGTGTCTCCCAACAACCGCTCAGCAAGTGCCCCAGCTTCACCTCGGGAAATG
ATCAGCCTCAAAGAAAGGAAAACAGACTACGAGTGCACCGGCAGCAACGCCACCTACCAC
GGAGCTAAAGGCGAACACACTTCCAGGAAAGATGCCATGACAGCTCAAAACACTGGAATT
TCAACTTTGTATAGGAATTCTTATGGTGCGCCCGCTGAAGACATCAAACACAACCAGGTT
TCAGCACAGCCAGTCCCACAGGAGCCCAGCAGAAAAGATTACGAGACCTACCAGCCATTT
CAGAATTCCACAAGAAATTACGATGAGTCCTTCTTCGAGGACCAGGTCCACCATCGCCCT

```
CCCGCCAGCGAGTACACCATGCACCTGGGTCTCAAGTCCACCGGCAACTACGTTGACTTC
TACTCAGCTGCCCGTCCCTACAGTGAACTGAACTATGAAACGAGCCACTACCCGGCCTCC
CCCGACTCCTGGGTGTGA
```

SEQ ID No. 17
NSMCE1
>ENSG00000169189|16|protein_coding|ENST00000358787|ENSP00000351638
CCGTATCCGCTAGCGCGGTGGGATGCGCTTGGGCTCCCTGTTCGTTCCCACATGCAGGGC
AGCACAAGGAGAATGGGCGTCATGACTGATGTCCACCGGCGCTTCCTCCAGTTGCTGATG
ACCCATGGCGTGCTAGAGGAATGGGACGTGAAGCGCTTGCAGACGCACTGCTACAAGGTC
CATGACCGCAATGCCACCGTAGATAAGTTGGAGGACTTCATCAACAACATTAACAGTGTC
TTGGAGTCCTTGTATATTGAGATAAAGAGAGGAGTCACGGAAGATGATGGGAGACCCATT
TATGCGTTGGTGAATCTTGCTACAACTTCAATTTCCAAAATGGCTACGGATTTTGCAGAG
AATGAACTGGATTTGTTTAGAAAGGCTCTGGAACTGATTATTGACTCAGAAACCTTGCGT
CTTCCACAAACATATTGA

Fig. 18

SEQ ID No. 18
NSMCE1
>ENSG00000169189|16|protein_coding|ENST00000361439|ENSP00000355077
ATGCAGGGCAGCACAAGGAGAATGGGCGTCATGACTGATGTCCACCGGCGCTTCCTCCAG
TTGCTGATGACCCATGGCGTGCTAGAGGAATGGGACGTGAAGCGCTTGCAGACGCACTGC
TACAAGGTCCATGACCGCAATGCCACCGTAGATAAGTTGGAGGACTTCATCAACAACATT
AACAGTGTCTTGGAGTCCTTGTATATTGAGATAAAGAGAGGAGTCACGGAAGATGATGGG
AGACCCATTTATGCGTTGGTGAATCTTGCTACAACTTCAATTTCCAAAATGGCTACGGAT
TTTGCAGAGAATGAACTGGATTTGTTTAGAAAGGCTCTGGAACTGATTATTGACTCAGAA
ACCGGCTTTGCGTCTTCCACAAACATATTGAACCTGGTTGATCAACTTAAAGGCAAGAAG
ATGAGGAAGAAGGAAGCGGAGCAGGTGCTGCAGAAGTTTGTTCAAAACAAGTGGCTGATT
GAGAAGGAAGGGGAGTTCACCCTGCACGGCCGGGCCATCCTGGAGATGGAGCAATACATC
CGGGAGACGTACCCCGACGCGGTGAAGATCTGCAATATCTGTCACAGCCTCCTCATCCAG
GGTCAAAGCTGCGAAACCTGTGGGATCAGGATGCACTTACCCTGCGTGGCCAAGTACTTC
CAGTCGAATGCTGAACCGCGCTGCCCCCACTGCAACGACTACTGGCCCCACGAGATCCCA
AAAGTCTTCGACCCTGAGAAGGAGAGGGAGTCTGGTGTCTTGAAATCGAACAAAAAGTCC
CTGCGGTCCAGGCAGCATTAG

Fig. 19

SEQ ID No. 19
NSMCE1
>ENSG00000169189|16|protein_coding|ENST00000311505|ENSP00000310853
GTCCACCTTGCGACCGTATCCGCTAGCGCGGCCTGGGATGCGCTTGGGCTCCCTGTTCGT
TCCCACATGCAGGGCAGCACAAGGAGAATGGGCGTCATGACTGATGTCCACCGGCGCTTC
CTCCAGTTGCTGATGACCCATGGCGTGCTAGAGGAATGGGACGTGAAGCGCTTGCAGACG
CACTGCTACAAGGTCCATGACCGCAATGCCACCGTAGATAAGTTGGAGGACTTCATCAAC
AACATTAACAGTGTCTTGGAGTCCTTGTATATTGAGATAAAGAGAGGAGTCACGGAAGAT
GATGGGAGACCCATTTATGCGTTGGTGAATCTTGCTACAACTTCAATTTCCAAAATGGCT
ACGGATTTTGCAGAGAATGAACTGGATTTGTTTAGAAAGGCTCTGGAACTGATTATTGAC
TCAGAAACCGGCTTTGCGTCTTCCACAAACATATTGAACCTGGTTGATCAACTTAAAGGC
AAGAAGATGAGGAAGAAGGAAGCGAGGTGCTGCAGAAGTTTGTTCAAAACAAGTGGCTGA

Fig. 20

SEQ ID No. 20
KTELC1
>ENSG00000163389|3|protein_coding|ENST00000295588|ENSP00000295588
ATGGAGTGGTGGGCTAGCTCGCCGCTTCGGCTCTGGCTGCTGTTGTTCCTCCTGCCCTCA
GCGCAGGGCCGCCAGAAGGAGTCAGGTTCAAAATGGAAAGTATTTATTGACCAAATTAAC
AGGTCTTTGGAGAATTACGAACCATGTTCAAGTCAAAACTGCAGCTGCTACCATGGTGTC
ATAGAAGAGGATCTAACTCCTTTCCGAGGAGGCATCTCCAGGAAGATGATGGCAGAGGTA
GTCAGACGGAAGCTAGGGACCCACTATCAGATCACTAAGAACAGACTGTACCGGGAAAAT
GACTGCATGTTCCCCTCAAGGTGTAGTGGTGTTGAGCACTTTATTTTGGAAGTGATCGGG
CGTCTCCCTGACATGGAGATGGTGATCAATGTACGAGATTATCCTCAGGTTCCTAAATGG
ATGGAGCCTGCCATCCCAGTCTTCTCCTTCAGTAAGACATCAGAGTACCATGATATCATG
TATCCTGCTTGGACATTTGGGAAGGGGGACCTGCTGTTTGGCCAATTTATCCTACAGGT
CTTGGACGGTGGGACCTCTTCAGAGAAGATCTGGTAAGGTCAGCAGCACAGTGGCCATGG
AAAAAGAAAAACTCTACAGCATATTTCCGAGGATCAAGGACAAGTCCAGAACGAGATCCT
CTCATTCTTCTGTCTCGGAAAAACCCAAAACTTGTTGATGCAGAATACACCAAAAACCAG
GCCTGGAAATCTATGAAAGATACCTTAGGAAAGCCAGCTGCTAAGGATGTCCATCTTGTG
GATCACTGCAAATACAAGTATCTGTTTAATTTTCGAGGCGTAGCTGCAAGTTTCCGGTTT
AAACACCTCTTCCTGTGTGGCTCACTTGTTTTCCATGTTGGTGATGAGTGGCTAGAATTC
TTCTATCCACAGCTGAAGCCATGGGTTCACTATATCCCAGTCAAAACAGATCTCTCCAAT
GTCCAAGAGCTGTTACAATTTGTAAAAGCAAATGATGATGTAGCTCAAGAGATTGCTGAA
AGGGGAAGCCAGTTTATTAGGAACCATTTGCAGATGGATGACATCACCTGTTACTGGGAG
AACCTCTTGAGTGAATACTCTAAATTCCTGTCTTATAATGTAACGAGAAGGAAAGGTTAT
GATCAAATTATTCCCAAAATGTTGAAAACTGAACTATAG

Fig. 21

SEQ ID No. 21
HS6ST1
>ENSG00000136720|2|protein_coding|ENST00000259241|ENSP00000259241
ATGCGGCGGCGGCGCCGGCGGCAGGACCATGGTTGAGCGCGCCAGCAAGTTCGTGCTG
GTGGTGGCGGGCTCGGTGTGCTTCATGCTCATCTTGTACCAGTACGCGGGCCCAGGACTG
AGCCTGGGCGCGCCCGGCGGCCGCGCGCCGCCCGACGACCTGGACCTGTTCCCCACACCC
GACCCCCACTACGAGAAGAAGTACTACTTCCCGGTCCGCGAGCTGGAGCGCTCGCTGCGC
TTCGACATGAAGGGCGACGACGTGATCGTCTTCCTGCACATCCAGAAGACGGGCGGCACC
ACCTTCGGCCGCCACCTCGTGCAGAACGTACGCCTCGAGGTGCCGTGCGACTGCCGGCCC
GGCCAGAAGAAGTGCACCTGCTACCGGCCCAACCGCCGCGAGACTTGGCTCTTCTCCCGC
TTCTCCACCGGCTGGAGCTGCGGGCTGCACGCCGACTGGACCGAGCTCACCAACTGCGTG
CCCGGCGTGCTGGACCGCCGCGACTCCGCCGCGCTGCGCACGCCCAGGAAGTTCTACTAC
ATCACCCTGCTACGAGACCCCGTGTCCCGCTACCTGAGCGAGTGGCGGCATGTGCAGAGG
GGTGCCACGTGGAAGACGTCGTTGCATATGTGTGATGGGCGCACGCCCACGCCTGAGGAG
CTGCCGCCCTGCTACGAGGGCACGGACTGGTCGGGCTGCACGCTACAGGAGTTCATGGAC
TGCCCGTACAACCTGGCCAACAACCGCCAGGTGCGCATGCTGGCCGACCTGAGCCTGGTG
GGCTGCTACAACCTGTCCTTCATCCCCGAGGGCAAGCGGGCCCAGCTGCTGCTCGAGAGC
GCCAAGAAGAACCTGCGGGGCATGGCCTTCTTCGGCCTGACCGAGTTCCAGCGCAAGACG
CAGTACCTGTTCGAGCGGACGTTCAACCTCAAGTTCATCCGGCCCTTCATGCAGTACAAT
AGCACGCGGCGGGCGGCGTGGAGGTGGATGAAGACACCATCCGGCGCATCGAGGAGCTC
AACGACCTGGACATGCAGCTGTACGACTACGCCAAGGACCTCTTCCAGCAGCGCTACCAG
TACAAGCGGCAGCTGGAGCGCAGGGAGCAGCGCCTGAGGAGCCGCGAGGAGCGTCTGCTG
CACCGGGCCAAGGAGGCACTGCCGCGGGAGGATGCCGACGAGCCGGGCCGCGTGCCCACC
GAGGACTACATGAGCCACATCATTGAGAAGTGGTAG

Fig. 22

SEQ ID No. 22
ARMC6
>ENSG00000105676|19|protein_coding|ENST00000379532|ENSP00000368847
ATGACATCCTGCAGATGCTCAGTGACCTCCAGGAGTCTGTGGCCAGCTCTCGCCCCCAGG
AGGTGTCAGCATACCTCACCCGCTTCTGCGCAGTGCAAACAGGACAAGGCCTGCCGCTTC
CTCGCGGCCCAGAAGGGGGCCTACCCCATCATCTTCACTGCCTGGAAGCTGGCCACTGCA
GGTGACCAGGGCCTTCTGCTCCAGTCCCTCAATGCCCTGTCGGTGCTGACTGATGGACAG
CCAGACCTCCTGGATGCCCAGGGCCTGCAGCTCCTAGTGGCCACGCTGACCCAGAATGCT
GATGAGGCTGACCTGACCTGCTCTGGGATCCGCTGTGTGCGTCACGCTTGCCTGAAACAT
GAACAGAATCGGCAAGACCTGGTGAAAGCTGGCGTGCTGCCTCTGCTGACTGGTGCCATC
ACCCATCATGGCCACCACACTGACGTGGTCAGGGAAGCCTGCTGGGCCCTGCGTGTCATG
ACCTTCGATGACGACATCCGTGTGCCCTTTGGCCATGCCCACAACCATGCCAAGATGATT
GTGCAGGAGAACAAAGGCTTGAAGGTGCTCATCGAAGCCACCAAAGCGTTCCTGGATAAC
CCTGGCATCCTGAGCGAGCTCTGTGGAACCCTGTCCCGCCTGGCCATTCGCAACGAGTTC
TGCCAGGAGGTCGTCGACCTCGGGGGCCTGAGCATTCTGGTGTCCCTGCTAGCCGACTGC
AATGACCACCAGATGAGGGACCAGAGCGGCGTTCAGGAGCTCGTGAAGCAAGTGCTGAGC
ACCCTGCGAGCCATCGCAGGCAACGACGACGTGAAAGATGCTATTGTCCGTGCTGGTGGG
ACGGAGTCCATCGTGGCTGCTATGACCCAGCATCTGACCAGCCCCAGGTGTGTGAGCAG
AGCTGCGCGGCCCTGTGCTTCCTGGCCCTGCGTAAGCCCGACAACAGCCGCATCATCGTG
GAGGGTGGCGGGCTGTGGCAGCACTGCAGGCCATGAAGGCACACCCGCAGAAGGCCGGC
GTGCAGAAACAGGCTTGCATGCTGATCCGAAACCTGGTGGCCCACAGGCCTTCTCGAAGC
CCATCCTGGACCTGGGGCTGAGGCACTCATCATGCAGGCCCGATCTGCCCACCGTGACT
GTGAGGACGTGGCCAAGGCCGCCCTGCGGGACCTGGGTTGTCATGTCGAGCTCCGAGAGC
TGTGGACAGGCCAGAGGGGCAACCTGGCGCCATGACCCCAGGCCCAGTCTGGTGACTCTG
GGTGAGTCGTGTGACTCAGGAATGGGGGTAGATCCATGTCCTCCACTGTCCCCCATTAGT
TCTGTCCCCTTCACAATGAGAAGTGTTTTCTGGCAGGCCCTAGGTAAAGGGTCGGGGGAG
GGGGGAGCCTTGTAG

Fig. 23

SEQ ID No. 23
ARMC6
>ENSG00000105676|19|protein_coding|ENST00000392335|ENSP00000376147
ATGGTCTCCAAGCGCATTGCCCAGGAGACCTTTGATGCAGCTGTGCGCGAGAACATCGAG
GAGTTTGCGATGGGGCCAGAGGAGGCAGTGAAAGAGGCCGTGGAGCAGTTTGAATCGCAA
GGGGTTGATCTGAGCAACATTGTAAAGACGGCACCTAAAGTCTCTGCAGACGGATCCCAG
GAGCCCACACATGACATCCTGCAGATGCTCAGTGACCTCCAGGAGTCTGTGGCCAGCTCT
CGCCCCAGGAGGTGTCAGCATACCTCACCCGCTTCTGCGACCAGTGCAAACAGGACAAG
GCCTGCCGCTTCCTCGCGGCCCAGAAGGGGGCCTACCCCATCATCTTCACTGCCTGGAAG
CTGGCCACTGCAGGTGACCAGGGCCTTCTGCTCCAGTCCCTCAATGCCCTGTCGGTGCTG
ACTGATGGACAGCCAGACCTCCTGGATGCCCAGGGCCTGCAGCTCCTAGTGGCCACGCTG
ACCCAGAATGCTGATGAGGCTGACCTGACCTGCTCTGGGATCCGCTGTGTGCGTCACGCT
TGCCTGAAACATGAACAGAATCGGCAAGACCTGGTGAAAGCTGGCGTGCTGCCTCTGCTG
ACTGGTGCCATCACCCATCATGGCCACCACACTGACGTGGTCAGGGAAGCCTGCTGGGCC
CTGCGTGTCATGACCTTCGATGACGACATCCGTGTGCCCTTTGGCCATGCCCACAACCAT
GCCAAGATGATTGTGCAGGAGAACAAAGGCTTGAAGGTGCTCATCGAAGCCACCAAAGCG
TTCCTGGATAACCCTGGCATCCTGAGCGAGCTCTGTGGAACCCTGTCCCGCCTGGCCATT
CGCAACGAGTTCTGCCAGGAGGTCGTCGACCTCGGGGGCCTGAGCATTCTGGTGTCCCTG
CTAGCCGACTGCAATGACCACCAGATGAGGGACCAGAGCGGCGTTCAGGAGCTCGTGAAG
CAAGTGCTGAGCACCCTGCGAGCCATCGCAGGCAACGACGACGTGAAAGATGCTATTGTC
CGTGCTGGTGGGACGGAGTCCATCGTGGCTGCTATGACCCAGCATCTGACCAGCCCCAG
GTGTGTGAGCAGAGCTGCGCGGCCCTGTGCTTCCTGGCCCTGCGTAAGCCCGACAACAGC
CGCATCATCGTGGAGGGTGGCGGGGCTGTGGCAGCACTGCAGGCCATGAAGGCACACCCG
CAGAAGGCCGGCGTGCAGAAACAGGCTTGCATGCTGATCCGAAACCTGGTGGCCCACGGC
CAGGCCTTCTCGAAGCCCATCCTGGACCTGGGGGCTGAGGCACTCATCATGCAGGCCCGA
TCTGCCCACCGTGACTGTGAGGACGTGGCCAAGGCCGCCCTGCGGGACCTGGGTTGTCAT
GTCGAGCTCCGAGAGCTGTGGACAGGCCAGAGGGGCAACCTGGCGCCATGA

Fig. 24

SEQ ID No. 24
ARMC6
>ENSG00000105676|19|protein_coding|ENST00000392336|ENSP00000376148
ATGAGTGAACGATGTTGCTCTAGATACAGCTCAGGAGCATCTATCGGCTGCACGCCAACA
TCAACACAGGCGAAGATGGTCTCCAAGCGCATTGCCCAGGAGACCTTTGATGCAGCTGTG
CGCGAGAACATCGAGGAGTTTGCGATGGGGCCAGAGGAGGCAGTGAAAGAGGCCGTGGAG
CAGTTTGAATCGCAAGGGGTTGATCTGAGCAACATTGTAAAGACGGCACCTAAAGTCTCT
GCAGACGGATCCCAGGAGCCCACACATGACATCCTGCAGATGCTCAGTGACCTCCAGGAG
TCTGTGGCCAGCTCTCGCCCCAGGAGGTGTCAGCATACCTCACCCGCTTCTGCGACCAG
TGCAAACAGGACAAGGCCTGCCGCTTCCTCGCGGCCCAGAAGGGGGCCTACCCCATCATC
TTCACTGCCTGGAAGCTGGCCACTGCAGGTGACCAGGGCCTTCTGCTCCAGTCCCTCAAT
GCCCTGTCGGTGCTGACTGATGGACAGCCAGACCTCCTGGATGCCCAGGGCCTGCAGCTC
CTAGTGGCCACGCTGACCCAGAATGCTGATGAGGCTGACCTGACCTGCTCTGGGATCCGC
TGTGTGCGTCACGCTTGCCTGAAACATGAACAGAATCGGCAAGACCTGGTGAAAGCTGGC
GTGCTGCCTCTGCTGACTGGTGCCATCACCCATCATGGCCACCACACTGACGTGGTCAGG
GAAGCCTGCTGGGCCCTGCGTGTCATGACCTTCGATGACGACATCCGTGTGCCCTTTGGC
CATGCCCACAACCATGCCAAGATGATTGTGCAGGAGAACAAAGGCTTGAAGGTGCTCATC
GAAGCCACCAAAGCGTTCCTGGATAACCCTGGCATCCTGAGCGAGCTCTGTGGAACCCTG
TCCCGCCTGGCCATTCGCAACGAGTTCTGCCAGGAGGTCGTCGACCTCGGGGGCCTGAGC
ATTCTGGTGTCCCTGCTAGCCGACTGCAATGACCACCAGATGAGGGACCAGAGCGGCGTT
CAGGAGCTCGTGAAGCAAGTGCTGAGCACCCTGCGAGCCATCGCAGGCAACGACGACGTG
AAAGATGCTATTGTCCGTGCTGGTGGGACGGAGTCCATCGTGGCTGCTATGACCCAGCAT
CTGACCAGCCCCCAGGTGTGTGAGCAGAGCTGCGCGGCCCTGTGCTTCCTGGCCCTGCGT
AAGCCCGACAACAGCCGCATCATCGTGGAGGGTGGCGGGGCTGTGGCAGCACTGCAGGCC
ATGAAGGCACACCCGCAGAAGGCCGGCGTGCAGAAACAGGCTTGCATGCTGATCCGAAAC
CTGGTGGCCACGGCCAGGCCTTCTCGAAGCCCATCCTGGACCTGGGGGCTGAGGCACTC
ATCATGCAGGCCCGATCTGCCCACCGTGACTGTGAGGACGTGGCCAAGGCCGCCCTGCGG
GACCTGGGTTGTCATGTCGAGCTCCGAGAGCTGTGGACAGGCCAGAGGGGCAACCTGGCG
CCATGA

Fig. 25

SEQ ID No. 25
ARMC6
>ENSG00000105676|19|protein_coding|ENST00000269932|ENSP00000269932
ATGGTCTCCAAGCGCATTGCCCAGGAGACCTTTGATGCAGCTGTGCGCGAGAACATCGAG
GAGTTTGCGATGGGGCCAGAGGAGGCAGTGAAAGAGGCCGTGGAGCAGTTTGAATCGCAA
GGGGTTGATCTGAGCAACATTGTAAAGACGGCACCTAAAGTCTCTGCAGACGGATCCCAG
GAGCCCACACATGACATCCTGCAGATGCTCAGTGACCTCCAGGAGTCTGTGGCCAGCTCT
CGCCCCAGGAGGTGTCAGCATACCTCACCCGCTTCTGCGACCAGTGCAAACAGGACAAG
GCCTGCCGCTTCCTCGCGGCCCAGAAGGGGGCCTACCCCATCATCTTCACTGCCTGGAAG
CTGGCCACTGCAGGTGACCAGGGCCTTCTGCTCCAGTCCCTCAATGCCCTGTCGGTGCTG
ACTGATGGACAGCCAGACCTCCTGGATGCCCAGGGCCTGCAGCTCCTAGTGGCCACGCTG
ACCCAGAATGCTGATGAGGCTGACCTGACCTGCTCTGGGATCCGCTGTGTGCGTCACGCT
TGCCTGAAACATGAACAGAATCGGCAAGACCTGGTGAAAGCTGGCGTGCTGCCTCTGCTG
ACTGGTGCCATCACCCATCATGGCCACCACACTGACGTGGTCAGGGAAGCCTGCTGGGCC
CTGCGTGTCATGACCTTCGATGACGACATCCGTGTGCCCTTTGGCCATGCCCACAACCAT
GCCAAGATGATTGTGCAGGAGAACAAAGGCTTGAAGGTGCTCATCGAAGCCACCAAAGCG
TTCCTGGATAACCCTGGCATCCTGAGCGAGCTCTGTGGAACCCTGTCCCGCCTGGCCATT
CGCAACGAGTTCTGCCAGGAGGTCGTCGACCTCGGGGGCCTGAGCATTCTGGTGTCCCTG
CTAGCCGACTGCAATGACCACCAGATGAGGGACCAGAGCGGCGTTCAGGAGCTCGTGAAG
CAAGTGCTGAGCACCCTGCGAGCCATCGCAGGCAACGACGACGTGAAAGATGCTATTGTC
CGTGCTGGTGGGACGGAGTCCATCGTGGCTGCTATGACCCAGCATCTGACCAGCCCCCAG
GTGTGTGAGCAGAGCTGCGCGGCCCTGTGCTTCCTGGCCCTGCGTAAGCCCGACAACAGC
CGCATCATCGTGGAGGGTGGCGGGGCTGTGGCAGCACTGCAGGCCATGAAGGCACACCCG
CAGAAGGCCGGCGTGCAGAAACAGGCTTGCATGCTGATCCGAAACCTGGTGGCCCACGGC
CAGGCCTTCTCGAAGCCCATCCTGGACCTGGGGGCTGAGGCACTCATCATGCAGGCCCGA
TCTGCCCACCGTGACTGTGAGGACGTGGCCAAGGCCGCCCTGCGGGACCTGGGTTGTCAT
GTCGAGCTCCGAGAGCTGTGGACAGGCCAGAGGGGCAACCTGGCGCCATGA

Fig. 26

SEQ ID No. 26
TH1L
>ENSG00000101158|20|protein_coding|ENST00000344018|ENSP00000342300
ATGGCGGGGGCCGTGCCGGGCGCCATCATGGACGAGGACTACTACGGGAGCGCGGCCGAG
TGGGGCGACGAGGCTGACGGCGGCCAGCAGGAGGATGATTCTGGAGAAGGAGAGGATGAT
GCGGAGGTTCAGCAAGAATGCCTGCATAAATTTTCCACCCGGGATTATATCATGGAACCC
TCCATCTTCAACACTCTGAAGAGGTATTTTCAGGCAGGAGGGTCTCCAGAGAATGTTATC
CAGCTCTTATCTGAAAACTACACCGCTGTGGCCCAGACTGTGAACCTGCTGGCCGAGTGG
CTCATTCAGACAGGTGTTGAGCCAGTGCAGGTTCAGGAAACTGTGGAAAATCACTTGAAG
AGTTTGCTGATCAAACATTTTGACCCCCGCAAAGCAGATTCTATTTTTACTGAAGAAGGA
GAGACCCCAGCGTGGCTGGAACAGATGATTGCACATACCACGTGGCGGGACCTTTTTTAT
AAACTGGCTGAAGCCCATCCAGACTGTTTGATGCTGAACTTCACCGTTAAGCTTATTTCT
GACGCAGGGTACCAGGGGGAGATCACCAGTGTGTCCACAGCATGCCAGCAGCTAGAAGTG
TTCTCGAGAGTGCTCCGGACCTCTCTAGCTACAATTTTAGATGGAGGAGAAGAAAACCTT
GAAAAAAATCTCCCTGAGTTTGCCAAGATGGTGTGCCACGGGGAGCACACGTACCTGTTT
GCCCAGGCCATGATGTCCGTGCTGGCCCAGGAGGAGCAGGGGGGCTCCGCTGTGCGCAGG
ATCGCCCAGGAAGTGCAGCGCTTTGCCCAGGAGAAAGGTCATGACGCCAGTCAGATCACA
CTAGCCTTGGGCACAGCTGCCTCCTACCCCAGGGCCTGCCAGGCTCTCGGGGCCATGCTG
TCCAAAGGAGCCCTGAACCCTGCTGACATCACCGTCCTGTTCAAGATGTTCACAAGCATG
GACCCTCCTCCGGTTGAACTTATCCGCGTTCCAGCCTTCCTGGACCTGTTCATGCAGTCA
CTCTTTAAACCAGGGGCTCGGATCAACCAGGACCACAAGCACAAATACATCCACATCTTG
GCGTACGCAGCAAGCGTGGTTGAGACCTGGAAGAAGAACAAGCGAGTGAGCATCAATAAA
GATGAGCTGAAGTCAACGTCAAAAGCTGTCGAAACCGTTCACAATTTGTGTTGCAACGAG
AACAAAGGGGCCTCTGAACTAGTGGCAGAATTGAGCACACTTTATCAGTGTATTAGGTTT
CCAGTGGTAGCAATGGGTGTGCTGAAGTGGGTGGATTGGACTGTATCAGAACCAAGGTAC
TTTCAGCTGCAGACTGACCATACCCCTGTCCACCTGGCGTTGCTGGATGAGATCAGCACC
TGCCACCAGCTCCTGCACCCCCAGGTCCTGCAGCTGCTTGTTAAGCTTTTTGAGACTGAG
CACTCCCAGCTGGACGTGATGGAGCAGCTTGAGTTGAAGAAGACACTGCTGGACAGGATG
GTTCACCTGCTGAGTCGAGGTTATGTACTTCCTGTTGTCAGTTACATCCGAAAGTGTCTG
GAGAAGCTGGACACTGACATTTCACTCATTCGCTATTTTGTCACTGAGGTGCTGGACGTC
ATTGCTCCTCCTTATACCTCTGACTTCGTGCAACTTTTCCTCCCCATCCTGGAGAATGAC
AGCATCGCAGGTACCATCAAAACGGAAGGCGAGCATGACCCTGTGACGGAGTTTATAGCT
CACTGCAAATCTAACTTCATCATGGTGAACTAA

Fig. 27

SEQ ID No. 27
PSME1
>ENSG00000092010|14|protein_coding|ENST00000382708|ENSP00000372155
ATGGCCATGCTCAGGGTCCAGCCCGAGGCCCAAGCCAAGGTGGATGTGTTTCGTGAAGAC
CTCTGTACCAAGACAGAGAACCTGCTCGGGAGCTATTTCCCCAAGAAGATTTCTGAGCTG
GATGCATTTTTAAAGGAGCCAGCTCTCAATGAAGCCAACTTGAGCAATCTGAAGGCCCCA
TTGGACATCCCAGTGCCTGATCCAGTCAAGGAGAAAGAGAAAGAGGAGCGGAAGAAACAG
CAGGAGAAGGAAGACAAGGATGAAAAGAAGAAGGGGGAGGATGAAGACAAAGGTCCTCCC
TGTGGCCCAGTGAACTGCAATGAAAAGATCGTGGTCCTTCTGCAGCGCTTGAAGCCTGAG
ATCAAGGATGTCATTGAGCAGCTCAACCTGGTCACCACCTGGTTGCAGCTGCAGATACCT
CGGATTGAGGATGGTAACAATTTTGGAGTGGCTGTCCAGGAGAAGGTGTTTGAGCTGATG
ACCAGCCTCCACACCAAGCTAGAAGGCTTCCACACTCAAATCTCTAAGTATTTCTCTGAG
CGTGGTGATGCAGTGACTAAAGCAGCCAAGCAGCCCCATGTGGGTGATTATCGGCAGCTG
GTGCACGAGCTGGATGAGGCAGAGTACCGGGACATCCGGCTGATGGTCATGGAGATCCGC
AATGCTTATGTGAGGAGGCAAGGGCAGGGCAGGGGTGGGCAGAGGCAGCTTTCCCAGGCC
ACCCACTCCCTGACCCTGCAGGCTAGGGGTTAA

Fig. 28

SEQ ID No. 28
PSME1
>ENSG00000092010|14|protein_coding|ENST00000206451|ENSP00000206451
ATGGCCATGCTCAGGGTCCAGCCCGAGGCCCAAGCCAAGGTGGATGTGTTTCGTGAAGAC
CTCTGTACCAAGACAGAGAACCTGCTCGGGAGCTATTTCCCCAAGAAGATTTCTGAGCTG
GATGCATTTTTAAAGGAGCCAGCTCTCAATGAAGCCAACTTGAGCAATCTGAAGGCCCCA
TTGGACATCCCAGTGCCTGATCCAGTCAAGGAGAAAGAGAAAGAGGAGCGGAAGAAACAG
CAGGAGAAGGAAGACAAGGATGAAAAGAAGAAGGGGGAGGATGAAGACAAAGGTCCTCCC
TGTGGCCCAGTGAACTGCAATGAAAAGATCGTGGTCCTTCTGCAGCGCTTGAAGCCTGAG
ATCAAGGATGTCATTGAGCAGCTCAACCTGGTCACCACCTGGTTGCAGCTGCAGATACCT
CGGATTGAGGATGGTAACAATTTTGGAGTGGCTGTCCAGGAGAAGGTGTTTGAGCTGATG
ACCAGCCTCCACACCAAGCTAGAAGGCTTCCACACTCAAATCTCTAAGTATTTCTCTGAG
CGTGGTGATGCAGTGACTAAAGCAGCCAAGCAGCCCCATGTGGGTGATTATCGGCAGCTG
GTGCACGAGCTGGATGAGGCAGAGTACCGGGACATCCGGCTGATGGTCATGGAGATCCGC
AATGCTTATGCTGTGTTATATGACATCATCCTGAAGAACTTCGAGAAGCTCAAGAAGCCC
AGGGGAGAAACAAAGGGAATGATCTATTGA

Fig. 29

SEQ ID No. 29
GPC1
>ENSG00000063660|2|protein_coding|ENST00000264039|ENSP00000264039
ATGGAGCTCCGGGCCCGAGGCTGGTGGCTGCTATGTGCGGCCGCAGCGCTGGTCGCCTGC
GCCCGCGGGGACCCGGCCAGCAAGAGCCGGAGCTGCGGCGAGGTCCGCCAGATCTACGGA
GCCAAGGGCTTCAGCCTGAGCGACGTGCCCCAGGCGGAGATCTCGGGTGAGCACCTGCGG
ATCTGTCCCCAGGGCTACACCTGCTGCACCAGCGAGATGGAGGAGAACCTGGCCAACCGC
AGCCATGCCGAGCTGGAGACCGCGCTCCGGGACAGCAGCCGCGTCCTGCAGGCCATGCTT
GCCACCCAGCTGCGCAGCTTCGATGACCACTTCCAGCACCTGCTGAACGACTCGGAGCGG
ACGCTGCAGGCCACCTTCCCCGGCGCCTTCGGAGAGCTGTACACGCAGAACGCGAGGGCC
TTCCGGGACCTGTACTCAGAGCTGCGCCTGTACTACCGCGGTGCCAACCTGCACCTGGAG
GAGACGCTGGCCGAGTTCTGGGCCCGCCTGCTCGAGCGCCTCTTCAAGCAGCTGCACCCC
CAGCTGCTGCTGCCTGATGACTACCTGGACTGCCTGGGCAAGCAGGCCGAGGCGCTGCGG
CCCTTCGGGGAGGCCCCGAGAGAGCTGCGCCTGCGGGCCACCCGTGCCTTCGTGGCTGCT
CGCTCCTTTGTGCAGGGCCTGGGCGTGGCCAGCGACGTGGTCCGGAAAGTGGCTCAGGTC
CCCCTGGGCCCGGAGTGCTCGAGAGCTGTCATGAAGCTGGTCTACTGTGCTCACTGCCTG
GGAGTCCCCGGCGCCAGGCCCTGCCCTGACTATTGCCGAAATGTGCTCAAGGGCTGCCTT
GCCAACCAGGCCGACCTGGACGCCGAGTGGAGGAACCTCCTGGACTCCATGGTGCTCATC
ACCGACAAGTTCTGGGGTACATCGGGTGTGGAGAGTGTCATCGGCAGCGTGCACACGTGG
CTGGCGGAGGCCATCAACGCCCTCCAGGACAACAGGGACACGCTCACGGCCAAGGTCATC
CAGGGCTGCGGGAACCCCAAGGTCAACCCCAGGGCCCCGGGCCTGAGGAGAAGCGGCGC
CGGGGCAAGCTGGCCCCGCGGGAGAGGCCACCTTCAGGCACGCTGGAGAAGCTGGTCTCC
GAAGCCAAGGCCCAGCTCCGCGACGTCCAGGACTTCTGGATCAGCCTCCCAGGGACACTG
TGCAGTGAGAAGATGGCCCTGAGCACTGCCAGTGATGACCGCTGCTGGAACGGGATGGCC
AGAGGCCGGTACCTCCCCGAGGTCATGGGTGACGGCCTGGCCAACCAGATCAACAACCCC
GAGGTGGAGGTGGACATCACCAAGCCGGACATGACCATCCGGCAGCAGATCATGCAGCTG
AAGATCATGACCAACCGGCTGCGCAGCGCCTACAACGGCAACGACGTGGACTTCCAGGAC
GCCAGTGACGACGGCAGCGGCTCGGGCAGCGGTGATGGCTGTCTGGATGACCTCTGCAGC
CGGAAGGTCAGCAGGAAGAGCTCCAGCTCCCGGACGCCCTTGACCCATGCCCTCCCAGGC
CTGTCAGAGCAGGAAGGACAGAAGACCTCGGCTGCCAGCTGCCCCAGCCCCCGACCTTC
CTCCTGCCCCTCCTCCTCTTCCTGGCCCTTACAGTAGCCAGGCCCCGGTGGCGGTAA

Fig. 30

SEQ ID No. 30
EDC4
>ENSG00000038358|16|protein_coding|ENST00000041337|ENSP00000041337
ATGGCCTCCTGCGCGAGCATCGACATCGAGGACGCCACGCAGCACCTGCGGGACATCCTC
AAGCTGGACCGGCCCGCGGGCGGCCCCAGTGCAGAGAGCCCACGGCCATCCAGTGCCTAC
AATGGGGACCTCAATGGACTTCTGGTCCCAGACCCGCTCTGCTCAGGTGATAGTACCTCA
GCAAACAAGACTGGTCTTCGGACCATGCCACCCATTAACCTGCAAGAGAAGCAGGTCATC
TGTCTCTCAGGAGATGATAGCTCCACCTGCATTGGGATTTTGGCCAAGGAGGTGGAGATT
GTGGCTAGCAGTGACTCTAGCATTTCAAGCAAGGCCCGGGGAAGCAACAAGGTGAAAATT
CAGCCTGTCGCCAAGTATGACTGGGAACAGAAGTACTACTATGGCAACCTGATTGCTGTG
TCTAACTCCTTCTTGGCCTATGCCATTCGGGCTGCCAACAATGGCTCTGCCATGGTGCGG
GTGATCAGCGTCAGCACTTCGGAGCGGACCTTGCTCAAGGGCTTCACAGGCAGTGTGGCT
GATCTGGCTTTCGCGCACCTCAACTCTCCACAGCTGGCCTGCCTGGATGAGGCAGGCAAC
CTGTTCGTGTGGCGCTTGGCTCTGGTTAATGGCAAAATTCAAGAAGAGATCTTGGTCCAT
ATTCGGCAGCCAGAGGGCACGCCACTGAACCACTTTCGCAGGATCATCTGGTGCCCCTTC
ATCCCTGAGGAGAGCGAAGACTGCTGTGAGGAGAGCAGCCCAACAGTGGCCCTGCTGCAT
GAAGACCGGGCTGAGGTGTGGGACCTGGACATGCTCCGCTCCAGCCACAGTACCTGGCCT
GTGGATGTTAGCCAGATCAAGCAGGGCTTCATTGTGGTAAAAGGTCATAGCACGTGCCTC
AGTGAAGGAGCCCTCTCTCCTGATGGGACTGTGCTGGCTACTGCGAGCCACGATGGCTAT
GTCAAGTTCTGGCAGATCTACATTGAGGGGCAAGATGAGCCAAGGTGTCTGCACGAGTGG
AAACCTCATGATGGGCGGCCCCTCTCCTGCCTCCTGTTCTGTGACAACCATAAGAAACAA
GACCCTGATGTCCCTTTCTGGAGGTTCCTTATTACTGGTGCTGACCAGAACCGAGAGTTA
AAGATGTGGTGTACAGTATCCTGGACCTGCCTGCAGACTATTCGCTTCTCCCCAGATATC
TTCAGCTCAGTGAGTGTGCCCCCTAGCCTCAAGGTTTGCTTGGACCTCTCAGCAGAATAC
CTGATTCTCAGCGATGTGCAACGGAAGGTCCTCTATGTGATGGAGCTGCTGCAAAACCAG
GAGGAGGCCACGCCTGCTTCAGCTCCATCTCGGAGTTCCTGCTCACCCACCCTGTGCTG
AGCTTTGGTATCCAGGTTGTGAGTCGCTGCCGGCTACGGCACACTGAGGTGCTGCCTGCC
GAAGAGGAAAATGACAGCCTGGGTGCTGATGGTACCCATGGAGCCGGTGCCATGGAGTCT
GCGGCCGGTGTGCTCATCAAGCTCTTTTGTGTGCATACTAAGGCACTGCAAGATGTGCAG
ATCCGCTTCCAGCCACAGCTGAACCCTGATGTGGTGGCCCCACTGCCCACCCACACTGCC
CACGAGGACTTCACATTTGGAGAGTCTCGGCCCGAACTGGGCTCTGAGGGCCTGGGGTCA
GCCGCTCACGGCTCCCAGCCTGACCTCCGACGAATCGTGGAGCTGCCTGCACCTGCCGAC
TTCCTCAGTCTGAGCAGTGAGACCAAGCCCAAGTTGATGACACCTGACGCCTTCATGACA
CCTAGCGCCTCCTTGCAGCAGATCACTGCCTCTCCCAGCAGCAGCAGCAGCGGTAGCAGC
AGCAGCAGCAGCAGTAGCAGCAGCTCCCTTACAGCTGTGTCTGCCATGAGCAGCACCTCA
GCTGTGGACCCTCCTTGACCAGGCCACCTGAGGAGCTGACCTTGAGCCCCAAGCTGCAG
CTGGATGGCAGCCTGACAATGAGCAGCAGTGGCAGCCTTCAGGCAAGCCCGCGTGGCCTC
CTGCCTGGCCTGCTCCCAGCCCCAGCTGACAAACTGACTCCCAAGGGGCCGGGCCAGGTG
CCTACTGCCACCTCTGCACTGTCCCTGGAGCTGCAGGAAGTGGAGCCCCTGGGGCTACCC
CAAGCCTCCCCTAGCCGCACTCGTTCCCCTGATGTCATCTCCTCAGCTTCCACTGCCCTG
TCCCAGGACATCCCTGAGATTGCATCTGAGGCCCTGTCCCGTGGTTTTGGCTCCTCTGCA
CCAGAGGGCCTTGAGCCAGACAGTATGGCTTCAGCCGCCTCGGCACTGCACCTGCTGTCC
CCACGGCCCCGGCCAGGGCCCGAGCTCGGCCCCCAGCTCGGGCTTGATGGAGGCCCTGGG
GATGGAGATCGGCATAATACCCCCTCCCTCCTGGAGGCAGCCTTGACCCAGGAGGCCTCG
ACTCCTGACAGTCAGGTTTGGCCCACAGCACCTGACATTACTCGTGAGACCTGCAGCACC
CTGGCAGAAAGCCCCAGGAATGGCCTTCAGGAAAAGCACAAGAGCCTGGCCTTCCACCGA
CCACCTATATCACCTGCTGCAGCAACGTGACAGCCAGGATGCCAGTGCTGAGCAAAGTGAC
CATGATGATGAGGTGGCCAGCCTTGCCTCTGCTTCAGGAGGCTTTGGCACCAAAGTTCCT
GCTCCACGGCTGCCTGCCAAGGACTGGAAGACCAAGGGATCCCCTCGAACCTCACCCAAG
CTCAAGAGGAAAAGCAAGAAGGATGATGGGGATGCAGCCATGGGATCCCGGCTCACAGAG
CACCAGGTGGCAGAGCCCCCTGAGGACTGGCCAGCACTAATTTGGCAACAGCAGAGAGAG
CTGGCAGAGCTGCGGCACAGCCAGGAAGAGCTGCTGCAGCGTCTGTGTACCCAACTCGAA
GGCCTGCAGAGCACAGTCACAGGCCACGTAGAACGTGCCCTTGAGACTCGGCACGAGCAG
GAACAGCGGCGGCTGGAGCGAGCACTGGCTGAGGGGCAGCAGCGGGGAGGGCAGCTGCAG
GAGCAGCTGACACAACAGTTGTCCCAAGCACTGTCGTCAGCTGTAGCTGGGCGGCTAGAG
CGCAGCATACGGGATGAGATCAAGAAGACAGTCCCTCCATGTGTCTCAAGGAGTCTGGAG
CCTATGGCAGGCCAACTGAGCAACTCAGTGGCTACCAAGCTCACAGCTGTGGAGGGCAGC
ATGAAAGAGAACATCTCCAAGCTGCTCAAGTCCAAGAACTTGACTGATGCCATCGCCCGA
GCAGCTGCAGACACATTACAAGGGCCGATGCAGGCTGCCTACCGGGAAGCCTTCCAGAGT
GTGGTGCTGCCGGCCTTTGAGAAGAGCTGCCAGGCCATGTTCCAGCAAATCAATGATAGC
TTCCGGCTGGGGACACAGGAATACTTGCAGCAGCTAGAAAGCCACATGAAGAGCCGGAAG
GCACGGGAACAGGAGGCCAGGGAGCCTGTGCTAGCCCAGCTGCGGGGCCTGGTCAGCACA

```
CTGCAGAGTGCCACTGAGCAGATGCCACCGTGGCCGGCAGTGTTCGTGCTGAGGTGCAGC
ACCAGCTGCATGTGGCTGTGGGCAGCCTGCAGGAGTCCATTTTAG
```

```
SEQ ID No. 31
EDC4
>ENSG00000038358|16|protein_coding|ENST00000358933|ENSP00000351811
ATGGCCTCCTGCGCGAGCATCGACATCGAGGACGCCACGCAGCACCTGCGGGACATCCTC
AAGCTGGACCGGCCCGCGGGCGGCCCCAGTGCAGAGAGCCCACGGCCATCCAGTGCCTAC
AATGGGGACCTCAATGGACTTCTGGTCCCAGACCCGCTCTGCTCAGGTGATAGTACCTCA
GCAAACAAGACTGGTCTTCGGACCATGCCACCCATTAACCTGCAAGAGAAGCAGGTCATC
TGTCTCTCAGGAGATGATAGCTCCACCTGCATTGGGATTTTGGCCAAGGAGGTGGAGATT
GTGGCTAGCAGTGACTCTAGCATTTCAAGCAAGGCCCGGGGAAGCAACAAGGTGAAAATT
CAGCCTGTCGCCAAGTATGACTGGGAACAGAAGTACTACTATGGCAACCTGATTGCTGTG
TCTAACTCCTTCTTGGCCTATGCCATTCGGGCTGCCAACAATGGCTCTGCCATGGTGCGG
GTGATCAGCGTCAGCACTTCGGAGCGGACCTTGCTCAAGGGCTTCACAGGCAGTGTGGCT
GATCTGGCTTTCGCGCACCTCAACTCTCCACAGCTGGCCTGCCTGGATGAGGCAGGCAAC
CTGTTCGTGTGGCGCTTGGCTCTGGTTAATGGCAAAATTCAAGAAGAGATCTTGGTCCAT
ATTCGGCAGCCAGAGGGCACGCCACTGAACCACTTTCGCAGGATCATCTGGTGCCCCTTC
ATCCCTGAGGAGAGCGAAGACTGCTGTGAGGAGAGCAGCCCAACAGTGGCCCTGCTGCAT
GAAGACCGGGCTGAGGTGTGGGACCTGGACATGCTCCGCTCCAGCCACAGTACCTGGCCT
GTGGATGTTAGCCAGATCAAGCAGGGCTTCATTGTGGTAAAAGGTCATAGCACGTGCCTC
AGTGAAGGAGCCCTCTCTCCTGATGGGACTGTGCTGGCTACTGCGAGCCACGATGGCTAT
GTCAAGTTCTGGCAGATCTACATTGAGGGGCAAGATGAGCCAAGGTGTCTGCACGAGTGG
AAACCTCATGATGGGCGGCCCCTCTCCTGCCTCCTGTTCTGTGACAACCATAAGAAACAA
GACCCTGATGTCCCTTTCTGGAGGTTCCTTATTACTGGTGCTGACCAGAACCGAGAGTTA
AAGATGTGGTGTACAGTATCCTGGACCTGCCTGCAGACTATTCGCTTCTCCCCAGATATC
TTCAGCTCAGTGAGTGTGCCCCCTAGCCTCAAGGTTTGCTTGGACCTCTCAGCAGAATAC
CTGATTCTCAGCGATGTGCAACGGAAGGTCCTCTATGTGATGGAGCTGCTGCAAAACCAG
GAGGAGGGCCACGCCTGCTTCAGCTCCATCTCGGAGTTCCTGCTCACCCACCCTGTGCTG
AGCTTTGGTATCCAGGTTGTGAGTCGCTGCCGGCTACGGCACACTGAGGTGCTGCCTGCC
GAAGAGGAAAATGACAGCCTGGGTGCTGATGGTACCCATGGAGCCGGTGCCATGGAGTCT
GCGGCCGGTGTGCTCATCAAGCTCTTTTGTGTGCATACTAAGGCACTGCAAGATGTGCAG
ATCCGCTTCCAGCCACAGCTGAACCCTGATGTGGTGGCCCCACTGCCCACCCACACTGCC
CACGAGGACTTCACATTTGGAGAGTCTCGGCCCGAACTGGGCTCTGAGGGCCTGGGGTCA
GCCGCTCACGGCTCCCAGCCTGACCTCCGACGAATCGTGGAGCTGCCCTGCACCTGCCGAC
TTCCTCAGTCTGAGCAGTGAGACCAAGCCCAAGTTGATGACACCTGACGCCTTCATGACA
CCTAGCGCCTCCTTGCAGCAGATCACTGCCTCTCCCAGCAGCAGCAGCAGCGGTAGCAGC
AGCAGCAGCAGCAGTAGCAGCAGCTCCCTTACAGCTGTGTCTGCCATGAGCAGCACCTCA
GCTGTGGACCCCTCCTTGACCAGGCCACCTGAGGAGCTGACCTTGAGCCCCAAGCTGCAG
CTGGATGGCAGCCTGACAATGAGCAGCAGTGGCAGCCTTCAGGCAAGCCCGCGTGGCCTC
CTGCCTGGCCTGCTCCCAGCCCCAGCTGACAAACTGACTCCCAAGGGGCCGGGCCAGGTG
CCTACTGCCACCTCTGCACTGTCCCTGGAGCTGCAGGAAGTGGAGCCCCTGGGGCTACCC
CAAGCCTCCCCTAGCCGCACTCGTTCCCCTGATGTCATCTCCTCAGCTTCCACTGCCCTG
TCCCAGGACATCCCTGAGATTGCATCTGAGGCCCTGTCCCGTGGTTTTGGCTCCTCTGCA
CCAGAGGGCCTTGAGCCAGACAGTATGGCTTCAGCCGCCTCGGCACTGCACCTGCTGTCC
CCACGGCCCCGGCCAGGGCCCGAGCTCGGCCCCAGCTCGGGCTTGATGGAGGCCCTGGG
GATGGAGATCGGCATAATACCCCCTCCCTCCTGGAGGCAGCCTTGACCCAGGAGGCCTCG
ACTCCTGACAGTCAGGTTTGGCCCACAGCACCTGACATTACTCGTGAGACCTGCAGCACC
CTGGCAGAAAGCCCCAGGAATGGCCTTCAGGAAAAGCACAAGAGCCTGGCCTTCCACCGA
CCACCATATCACCTGCTGCAGCAACGTGACAGCCAGGATGCCAGTGCTGAGCAAAGTGAC
CATGATGATGAGGTGGCCAGCCTTGCCTCTGCTTCAGGAGGCTTTGGCACCAAAGTTCCT
GCTCCACGGCTGCCTGCCAAGGACTGGAAGACCAAGGGATCCCCTCGAACCTCACCCAAG
CTCAAGAGGGAAAAGCAAGAAGGATGATGGGGATGCAGCCATGGGATCCCGGCTCACAGAG
CACCAGGTGGCAGAGCCCCTGAGGACTGGCCAGCACTAATTTGGCAACAGCAGAGAGAG
CTGGCAGAGCTGCGGCACAGCCAGGAAGAGCTGCTGCAGCGTCTGTGTACCCAACTCGAA
GGCCTGCAGAGCACAGTCACAGGCCACGTAGAACGTGCCCTTGAGACTCGGCACGAGCAG
GAACAGCGGCGGCTGGAGCGAGCACTGGCTGAGGGGCAGCAGCGGGGAGGGCAGCTGCAG
GAGCAGCTGACACAACAGTTGTCCCAAGCACTGTCGTCAGCTGTAGCTGGGCGGCTAGAG
CGCAGCATACGGGATGAGATCAAGAAGACAGTCCCTCCATGTGTCTCAAGGAGTCTGGAG
CCTATGGCAGGCCAACTGAGCAACTCAGTGGCTACCAAGCTCACAGCTGTGGAGGGCAGC
ATGAAAGAGAACATCTCCAAGCTGCTCAAGTCCAAGAACTTGACTGATGCCATCGCCCGA
GCAGCTGCAGACACATTACAAGGGCCGATGCAGGCTGCCTACCGGGAAGCCTTCCAGAGT
GTGGTGCTGCCGGCCTTTGAGAAGAGCTGCCAGGCCATGTTCCAGCAAATCAATGATAGC
TTCCGGCTGGGGACACAGGAATACTTGCAGCAGCTAGAAAGCCACATGAAGAGCCGGAAG
GCACGGGAACAGGAGGCCAGGGAGCCTGTGCTAGCCCAGCTGCGGGGCCTGGTCAGCACA
```

```
CTGCAGAGTGCCACTGAGCAGATGGCAGCCACCGTGGCCGGCAGTGTTCGTGCTGAGGTG
CAGCACCAGCTGCATGTGGCTGTGGGCAGCCTGCAGGAGTCCATTTTAGCACAGGTACAG
CGCATCGTTAAGGGTGAGGTGAGTGTGGCGCTCAAGGAGCAGCAGGCCGCCGTCACCTCC
AGCATCATGCAGGCCATGCGCTCAGCTGCTGGCACACCTGTCCCCTCTGCCCACCTTGAC
TGCCAGGCCCAGCAAGCCCATATCCTGCAGCTGCTGCAGCAGGGCCACCTCAATCAGGCC
TTCCAGCAGGCGCTGACAGCTGCTGACCTGAACCTGGTGCTGTATGTGTGTGAAACTGTG
GACCCAGCCCAGGTTTTTGGGCAGCCACCCTGCCCGCTCTCCCAGCCTGTGCTCCTTTCC
CTCATCCAGCAGCTGGCATCTGACCTTGGCACTCGAACTGACCTCAAGCTCAGCTACCTG
GAAGAGGCCGTGATGCACCTGGACCACAGTGACCCCATCACTCGGGACCACATGGGCTCC
GTTATGGCCCAGGTGCGCCAAAAGCTTTTTCAGTTCCTGCAGGCTGAGCCACACAACTCA
CTTGGCAAAGCAGCTCGGCGTCTCAGCCTCATGCTGCATGGCCTCGTGACCCCCAGCCTC
CCTTAG
```

SEQ ID No. 32
PRC1
>ENSG00000198901|15|protein_coding|ENST00000361188|ENSP00000354679
ACGAGGCTTCGCCCCGTGGCGCGGTTTGAAATTTTGCGGGGCTCAACGGCTCGCGGAGCG
GCTACGCGGAGTGACATCGCCGGTGTTTGCGGGTGGTTGTTGCTCTCGGGGCCGTGTGGA
GTAGGTCTGGACCTGGACTCACGGCTGCTTGGAGCGTCCGCCATGAGGAGAAGTGAGGTG
CTGGCGGAGGAGTCCATAGTATGTCTGCAGAAAGCCCTAAATCACCTTCGGGAAATATGG
GAGCTAATTGGGATTCCAGAGGACCAGCGGTTACAAAGAACTGAGGTGGTAAAGAAGCAT
ATCAAGGAACTCCTGGATATGATGATTGCTGAAGAGGAAAGCCTGAAGGAAAGACTCATC
AAAGCATATCCGTCTGTCAGAAAGAGCTGAACACTCTGTGCAGCGAGTTACATGTTGAG
CCATTTCAGGAAGAAGGAGAGACGACCATCTTGCAACTAGAAAAAGATTTGCGCACCCAA
GTGGAATTGATGCGAAAACAGAAAAAGGAGAGAAAACAGGAACTGAAGCTACTTCAAGAG
CAAGATCAAGAACTGTGCGAAATTCTTTGTATGCCCCACTATGATATTGACAGTGCCTCA
GTGCCCAGCTTAGAAGAGCTGAACCAGTTCAGGCAACATGTGACAACTTTGAGGGAAACA
AAGGCTTCTAGGCGTGAGGAGTTTGTCAGTATAAAGAGACAGATCATACTGTGTATGAA
GCATTAGACCACACCCCAGACACAAGCTTTGAAAGAGATGTGGTGTGTGAAGACGAAGAT
GCCTTTTGTTTGTCTTTGGAGAATATTGCAACACTACAAAAGTTGCTACGGCAGCTGGAA
ATGCAGAAATCACAAAATGAAGCAGTGTGTGAGGGGCTGCGTACTCAAATCCGAGAGCTC
TGGGACAGGTTGCAAATACCTGAAGAAGAAAGAGAAGCTGTGGCCACCATTATGTCTGGG
TCAAAGGCCAAGGTCCGGAAAGCGCTGCAATTAGAAGTGGATCGGTTGGAAGAACTGAAA
ATGCAAAACATGAAGAAAGTGATTGAGGCAATTCGAGTGGAGCTGGTTCAGTACTGGGAC
CAGTGCTTTTATAGCCAGGAGCAGAGACAAGCTTTTGCCCCTTTCTGTGCTGAGGACTAC
ACAGAAAGTCTGCTCCAGCTCCACGATGCTGAGATTGTGCGGTTAAAAAACTACTATGAA
GTTCACAAGGAACTCTTTGAAGGTGTCCAGAAGTGGAAGAAACCTGGAGGCTTTTCTTA
GAGTTTGAGAGAAAAGCTTCAGATCCAAATCGATTTACAAACCGAGGAGGAAATCTTCTA
AAAGAAGAAAAACAACGAGCCAAGCTCCAGAAAATGCTGCCCAAGCTGGAAGAAGAGTTG
AAGGCACGAATTGAATTGTGGGAACAGGAACATTCAAAGGCATTTATGGTGAATGGGCAG
AAATTCATGGAGTATGTGGCAGAACAATGGGAGATGCATCGATTGGAGAAAGAGAGAGCC
AAGCAGGAAAGACAACTGAAGAACAAAAAACAGACAGAGACAGAGATGCTGTATGGCAGC
GCTCCTCGAACACCTAGCAAGCGGCGAGGACTGGCTCCCAATACACCGGGCAAAGCACGT
AAGCTGAACACTACCACCATGTCCAATGCTACGGCCAATAGTAGCATTCGGCCTATCTTT
GGAGGGACAGTCTACCACTCCCCCGTGTCTCGACTTCCTCCTTCTGGCAGCAAGCCAGTC
GCTGCTTCCACCTGTTCAGGGAAGAAAACACCCCGTACTGGCAGGCATGGAGCCAACAAG
GAGAACCTGGAGCTCAACGGCAGCATCCTGAGTGGTGGGTACCCTGGCTCGGCCCCCCTC
CAGCGCAACTTCAGCATTAATTCTGTTGCCAGCACCTATTCTGAGTTTGCGCGAGAACTT
TCAAAGGCTTCCAAATCTGATGCTACTTCTGGAATCCTCAATTCAACCAACATCCAGTCC
TGA

Fig. 33

SEQ ID No. 33
PRC1
>ENSG00000198901|15|protein_coding|ENST00000394249|ENSP00000377793
ACGAGGCTTCGCCCCGTGGCGCGGTTTGAAATTTTGCGGGGCTCAACGGCTCGCGGAGCG
GCTACGCGGAGTGACATCGCCGGTGTTTGCGGGTGGTTGTTGCTCTCGGGGCCGTGTGGA
GTAGGTCTGGACCTGGACTCACGGCTGCTTGGAGCGTCCGCCATGAGGAGAAGTGAGGTG
CTGGCGGAGGAGTCCATAGTATGTCTGCAGAAAGCCCTAAATCACCTTCGGGAAATATGG
GAGCTAATTGGGATTCCAGAGGACCAGCGGTTACAAAGAACTGAGGTGGTAAAGAAGCAT
ATCAAGGAACTCCTGGATATGATGATTGCTGAAGAGGAAAGCCTGAAGGAAAGACTCATC
AAAAGCATATCCGTCTGTCAGAAAGAGCTGAACACTCTGTGCAGCGAGTTACATGTTGAG
CCATTTCAGGAAGAAGGAGAGACGACCATCTTGCAACTAGAAAAAGATTTGCGCACCCAA
GTGGAATTGATGCGAAAACAGAAAAAGGAGAGAAAACAGGAACTGAAGCTACTTCAAGAG
CAAGATCAAGAACTGTGCGAAATTCTTTGTATGCCCCACTATGATATTGACAGTGCCTCA
GTGCCCAGCTTAGAAGAGCTGAACCAGTTCAGGCAACATGTGACAACTTTGAGGGAAACA
AAGGCTTCTAGGCGTGAGGAGTTTGTCAGTATAAAGAGACAGATCATACTGTGTATGGAA
GCATTAGACCACACCCCAGACACAAGCTTTGAAAGAGATGTGGTGTGTGAAGACGAAGAT
GCCTTTTGTTTGTCTTTGGAGAATATTGCAACACTACAAAAGTTGCTACGGCAGCTGGAA
ATGCAGAAATCACAAAATGAAGCAGTGTGTGAGGGGCTGCGTACTCAAATCCGAGAGCTC
TGGGACAGGTTGCAAATACCTGAAGAAGAAAGAGAAGCTGTGGCCACCATTATGTCTGGG
TCAAAGGCCAAGGTCCGGAAAGCGCTGCAATTAGAAGTGGATCGGTTGGAAGAACTGAAA
ATGCAAAACATGAAGAAAGTGATTGAGGCAATTCGAGTGGAGCTGGTTCAGTACTGGGAC
CAGTGCTTTTATAGCCAGGAGCAGAGACAAGCTTTTGCCCCTTTCTGTGCTGAGGACTAC
ACAGAAAGTCTGCTCCAGCTCCACGATGCTGAGATTGTGCGGTTAAAAAACTACTATGAA
GTTCACAAGGAACTCTTTGAAGGTGTCCAGAAGTGGGAAGAAACCTGGAGGCTTTTCTTA
GAGTTTGAGAGAAAAGCTTCAGATCCAAATCGATTTACAAACCGAGGAGGAAATCTTCTA
AAAGAAGAAAACAACGAGCCAAGCTCCAGAAAATGCTGCCCAAGCTGGAAGAAGAGTTG
AAGGCACGAATTGAATTGTGGAACAGGAACATTCAAAGGCATTTATGGTGAATGGGCAG
AAATTCATGGAGTATGTGGCAGAACAATGGGAGATGCATCGATTGGAGAAAGAGAGAGCC
AAGCAGGAAAGACAACTGAAGAACAAAAAACAGACAGAGACAGAGATGCTGTATGGCAGC
GCTCCTCGAACACCTAGCAAGCGGCGAGGACTGGCTCCCAATACACCGGGCAAAGCACGT
AAGCTGAACACTACCACCATGTCCAATGCTACGGCCAATAGTAGCATTCGGCCTATCTTT
GGAGGGACAGTCTACCACTCCCCGTGTCTCGACTTCCTCCTTCTGGCAGCAAGCCAGTC
GCTGCTTCCACCTGTTCAGGGAAGAAAACACCCCGTACTGGCAGGCATGGAGCCAACAAG
GAGAACCTGGAGCTCAACGGCAGCATCCTGAGTGGTGGGTACCCTGGCTCGGCCCCCTC
CAGCGCAACTTCAGCATTAATTCTGTTGCCAGCACCTATTCTGAGTTTGCGAAGGATCCG
TCCCTCTCTGACAGTTCCACTGTTGGGCTTCAGCGAGAACTTTCAAAGGCTTCCAAATCT
GATGCTACTTCTGGAATCCTCAATTCAACCAACATCCAGTCCTGA

Fig. 34

SEQ ID No. 34
PRC1
>ENSG00000198901|15|protein_coding|ENST00000361919|ENSP00000354618
ATGAGGAGAAGTGAGGTGCTGGCGGAGGAGTCCATAGTATGTCTGCAGAAAGCCCTAAAT
CACCTTCGGGAAATATGGGAGCTAATTGGGATTCCAGAGGACCAGCGGTTACAAAGAACT
GAGGTGGTAAAGAAGCATATCAAGGAACTCCTGGATATGATGATTGCTGAAGAGGAAAGC
CTGAAGGAAAGACTCATCAAAAGCATATCCGTCTGTCAGAAAGAGCTGAACACTCTGTGC
AGCGAGTTACATGTTGAGCCATTTCAGGAAGAAGGAGAGACGACCATCTTGCAACTAGAA
AAAGATTTGCGCACCCAAGTGGAATTGATGCGAAAACAGAAAAGGAGAGAAACAGGAA
CTGAAGCTACTTCAAGAGCAAGATCAAGAACTGTGCGAAATTCTTTGTATGCCCCACTAT
GATATTGACAGTGCCTCAGTGCCCAGCTTAGAAGAGCTGAACCAGTTCAGGCAACATGTG
ACAACTTTGAGGGAAACAAAGGCTTCTAGGCGTGAGGAGTTTGTCAGTATAAAGAGACAG
ATCATACTGTGTATGGAAGCATTAGACCACACCCCAGCACAAGCTTTGAAAGAGATGTG
GTGTGTGAAGACGAAGATGCCTTTTGTTTGTCTTTGGAGAATATTGCAACACTACAAAAG
TTGCTACGGCAGCTGGAAATGCAGAAATCACAAAATGAAGCAGTGTGTGAGGGGCTGCGT
ACTCAAATCCGAGAGCTCTGGGACAGGTTGCAAATACCTGAAGAAGAAAGAGAAGCTGTG
GCCACCATTATGTCTGGGTCAAAGGCCAAGGTCCGGAAAGCGCTGCAATTAGAAGTGGAT
CGGTTGGAAGAACTGAAAATGCAAAACATGAAGAAAGTGATTGAGGCAATTCGAGTGGAG
CTGGTTCAGTACTGGGACCAGTGCTTTTATAGCCAGGAGCAGAGACAAGCTTTTGCCCCT
TTCTGTGCTGAGGACTACACAGAAAGTCTGCTCCAGCTCCACGATGCTGAGATTGTGCGG
TTAAAAAACTACTATGAAGTTCACAAGGAACTCTTTGAAGGTGTCCAGAAGTGGGAAGAA
ACCTGGAGGCTTTTCTTAGAGTTTGAGAGAAAAGCTTCAGATCCAAATCGATTTACAAAC
CGAGGAGGAAATCTTCTAAAAGAAGAAAAACAACGAGCCAAGCTCCAGAAAATGCTGCCC
AAGCTGGAAGAAGAGTTGAAGGCACGAATTGAATTGTGGGAACAGGAACATTCAAAGGCA
TTTATGGTGAATGGGCAGAAATTCATGGAGTATGTGGCAGAACAATGGGAGATGCATCGA
TTGGAGAAAGAGAGAGCCAAGCAGGAAAGACAACTGAAGAACAAAAAACAGACAGAGACA
GAGATGCTGTATGGCAGCGCTCCTCGAACACCTAGCAAGCGGCGAGGACTGGCTCCCAAT
ACACCGGGCAAAGCACGTAAGCTGAACACTACCACCATGTCCAATGCTACGGCCAATAGT
AGCATTCGGCCTATCTTTGGAGGGACAGTCTACCACTCCCCCGTGTCTCGACTTCCTCCT
TCTGGCAGCAAGCCAGTCGCTGCTTCCACCTGTTCAGGGAAGAAAACACCCCGTACTGGC
AGGCATGGAGCCAACAAGGAGAACCTGGAGCTCAACGGCAGCATCCTGAGTGGTGGGTAC
CCTGGCTCGGCCCCCCTCCAGCGCAACTTCAGCATTAATTCTGTTGCCAGCACCTATTCT
GAGTTTGCGAAGGATCCGTCCCTCTCTGACAGTTCCACTGTTGGGCTTCAGCGAGAACTT
TCAAAGGCTTCCAAATCTGATGCTACTTCTGGAATCCTCAATTCAACCAACATCCAGTCC
TGA

Fig. 35

SEQ ID No. 35
NAT6
>ENSG00000186792|3|protein_coding|ENST00000359051|ENSP00000351946
ATGACCACGCAACTGGGCCCAGCCCTGGTGCTGGGGGTGGCCCTGTGCCTGGGTTGTGGC
CAGCCCCTACCACAGGTCCCTGAACGCCCCTTCTCTGTGCTGTGGAATGTACCCTCAGCA
CACTGTGAGGCCCGCTTTGGTGTGCACCTGCCACTCAATGCTCTGGGCATCATAGCCAAC
CGTGGCCAGCATTTTCACGGTCAGAACATGACCATTTTCTACAAGAACCAACTCGGCCTC
TATCCCTACTTTGGACCCAGGGGCACAGCTCACAATGGGGGCATCCCCCAGGCTTTGCCC
CTTGACCGCCACCTGGCACTGGCTGCCTACCAGATCCACCACAGCCTGAGACCTGGCTTT
GCTGGCCCAGCAGTGCTGGATTGGGAGGAGTGGTGTCCACTCTGGGCTGGGAACTGGGGC
CGCCGCCGAGCTTATCAGGCAGCCTCTTGGGCTTGGGCACAGCAGGTATTCCCTGACCTG
GACCCTCAGGAGCAGCTCTACAAGGCCTATACTGGCTTTGAGCAGGCGGCCCGTGCACTG
ATGGAGGATACGCTGCGGGTGGCCCAGGCACTACGGCCCCATGGACTCTGGGGCTTCTAT
CACTACCCAGCCTGTGGCAATGGCTGGCATAGTATGGCTTCCAACTATACCGGCCGCTGC
CATGCAGCCACCCTTGCCCGCAACACTCAACTGCATTGGCTCTGGGCCGCCTCCAGTGCC
CTCTTCCCCAGCATCTACCTCCCACCCAGGCTGCCACCTGCCCACCACCAGGCCTTTGTC
CGACATCGCCTGGAGGAGGCCTTCCGTGTGGCCCTTGTTGGGCACCGACATCCCCTGCCT
GTCCTGGCCTATGTCCGCCTCACACACCGGAGATCTGGGAGGTTCCTGTCCCAGGAGGAG
TGCTGGCATCTCCATGACTACCTGGTGGACACCTTGGGCCCCTATGTGATCAATGTGACC
AGGGCAGCGATGGCCTGCAGTCACCAGCGGTGCCATGGCCACGGGCGCTGTGCCCGGCGA
GATCCAGGACAGATGGAAGCCTTTCTACACCTGTGGCCAGACGGCAGCCTTGGAGATTGG
AAGTCCTTCAGCTGCCACTGTTACTGGGGCTGGGCTGGCCCCACCTGCCAGGAGCCCAGG
CCTGGGCCTAAAGAAGCAGTATAA

Fig. 36

SEQ ID No. 36
NAT6
>ENSG00000186792|3|protein_coding|ENST00000066014|ENSP00000066014
ATGACCACGCAACTGGGCCCAGCCCTGGTGCTGGGGGTGGCCCTGTGCCTGGGTTGTGGC
CAGCCCCTACCACAGGTCCCTGAACGCCCCTTCTCTGTGCTGTGGAATGTACCCTCAGCA
CACTGTGAGGCCCGCTTTGGTGTGCACCTGCCACTCAATGCTCTGGGCATCATAGCCAAC
CGTGGCCAGCATTTTCACGGTCAGAACATGACCATTTTCTACAAGAACCAACTCGGCCTC
TATCCCTACTTTGGACCCAGGGGCACAGCTCACAATGGGGGCATCCCCCAGGCTTTGCCC
CTTGACCGCCACCTGGCACTGGCTGCCTACCAGATCCACCACAGCCTGAGACCTGGCTTT
GCTGGCCCAGCAGTGCTGGATTGGGAGGAGTGGTGTCCACTCTGGGCTGGGAACTGGGGC
CGCCGCCGAGCTTATCAGGCAGCCTCTTGGGCTTGGGCACAGCAGGTATTCCCTGACCTG
GACCCTCAGGAGCAGCTCTACAAGGCCTATACTGGCTTTGAGCAGGCGGCCCGTGCACTG
ATGGAGGATACGCTGCGGGTGGCCCAGGCACTACGGCCCCATGGACTCTGGGGCTTCTAT
CACTACCCAGCCTGTGGCAATGGCTGGCATAGTATGGCTTCCAACTATACCGGCCGCTGC
CATGCAGCCACCCTTGCCCGCAACACTCAACTGCATTGGCTCTGGGCCGCCTCCAGTGCC
CTCTTCCCCAGCATCTACCTCCCACCCAGGCTGCCACCTGCCCACCACCAGGCCTTTGTC
CGACATCGCCTGGAGGAGGCCTTCCGTGTGGCCCTTGTTGGGCACCGACATCCCCTGCCT
GTCCTGGCCTATGTCCGCCTCACACACCGGAGATCTGGGAGGTTCCTGTCCCAGGATGAC
CTTGTGCAGTCCATTGGTGTGAGTGCAGCACTAGGGGCAGCCGGCGTGGTGCTCTGGGGG
GACCTGAGCCTCTCCAGCTCTGAGGAGGAGTGCTGGCATCTCCATGACTACCTGGTGGAC
ACCTTGGGCCCCTATGTGATCAATGTGACCAGGGCAGCGATGGCCTGCAGTCACCAGCGG
TGCCATGGCCACGGGCGCTGTGCCCGGCGAGATCCAGGACAGATGGAAGCCTTTCTACAC
CTGTGGCCAGACGGCAGCCTTGGAGATTGGAAGTCCTTCAGCTGCCACTGTTACTGGGGC
TGGGCTGGCCCCACCTGCCAGGAGCCCCTGGGCCTAAAGAAGCAGTATAAAGCCAGGGCC
CCTGCCACTGCCTCTTCTTTTCCCTGCTGCCACTTTTCCAGTCCTGGAACTACTCTGTCC
CACTCTTGCTCTATTCAGTTTACAGTCAACCCTCCCAAGCACACACCCCGCTTCCCTTGG
AATCCCTGA

Fig. 37

SEQ ID No. 37
NAT6
>ENSG00000186792|3|protein_coding|ENST00000336307|ENSP00000337425
ATGACCACGCAACTGGGCCCAGCCCTGGTGCTGGGGGTGGCCCTGTGCCTGGGTTGTGGC
CAGCCCCTACCACAGGTCCCTGAACGCCCCTTCTCTGTGCTGTGGAATGTACCCTCAGCA
CACTGTGAGGCCCGCTTTGGTGTGCACCTGCCACTCAATGCTCTGGGCATCATAGCCAAC
CGTGGCCAGCATTTTCACGGTCAGAACATGACCATTTTCTACAAGAACCAACTCGGCCTC
TATCCCTACTTTGGACCCAGGGGCACAGCTCACAATGGGGGCATCCCCCAGGCTTTGCCC
CTTGACCGCCACCTGGCACTGGCTGCCTACCAGATCCACCACAGCCTGAGACCTGGCTTT
GCTGGCCAGCAGTGCTGGATTGGGAGGAGTGGTGTCCACTCTGGGCTGGGAACTGGGGC
CGCCGCCGAGCTTATCAGGCAGCCTCTTGGGCTTGGGCACAGCAGGTATTCCCTGACCTG
GACCCTCAGGAGCAGCTCTACAAGGCCTATACTGGCTTTGAGCAGGCGGCCCGTGCACTG
ATGGAGGATACGCTGCGGGTGGCCCAGGCACTACGGCCCCATGGACTCTGGGGCTTCTAT
CACTACCCAGCCTGTGGCAATGGCTGGCATAGTATGGCTTCCAACTATACCGGCCGCTGC
CATGCAGCCACCCTTGCCCGCAACACTCAACTGCATTGGCTCTGGGCCGCCTCCAGTGCC
CTCTTCCCCAGCATCTACCTCCCACCCAGGCTGCCACCTGCCCACCACCAGGCCTTTGTC
CGACATCGCCTGGAGGAGGCCTTCCGTGTGGCCCTTGTTGGGCACCGACATCCCCTGCCT
GTCCTGGCCTATGTCCGCCTCACACACCGGAGATCTGGGAGGTTCCTGTCCCAGGATGAC
CTTGTGCAGTCCATTGGTGTGAGTGCAGCACTAGGGGCAGCCGGCGTGGTGCTCTGGGGG
GACCTGAGCCTCTCCAGCTCTGAGGAGGAGTGCTGGCATCTCCATGACTACCTGGTGGAC
ACCTTGGGCCCCTATGTGATCAATGTGACCAGGGCAGCGATGGCCTGCAGTCACCAGCGG
TGCCATGGCCACGGGCGCTGTGCCCGGCGAGATCCAGGACAGATGGAAGCCTTTCTACAC
CTGTGGCCAGACGGCAGCCTTGGAGATTGGAAGTCCTTCAGCTGCCACTGTTACTGGGGC
TGGGCTGGCCCCACCTGCCAGGAGCCCAGGCCTGGGCCTAAAGAAGCAGTATAA

Fig. 38

SEQ ID No. 38
EEF1AL3
>ENSG00000185637|9|protein_coding|ENST00000329018|ENSP00000332874
ATGGGAAAGGAAAAGACTCATATCAACATTGTCGTCATTGGACACGTAGATTCGGGCAAG
TCCACCACTACTGGCCATCTGATCTATAAATGCGGTGGCATCGACAAAAGAACCATTGAA
AAATTTGAGAAGGAGGCTGCTGAGATGGGAAAGGGCTCCTTCAAGTATGCCTGGGTCTTG
GATAAACTGAAAGCTGAGCGTGAACGTGGTATCACCATTGATATCTCCTTGTGGAAATTT
GAGACCAGCAAGTACTATGTGACTATCATTGATGCCCCAGGACACAGAGACTTCATCAAA
AACATGATTACAGGGACATCTCAGGCTGACTGTGCTGTCCTGATTGTTGCTGCTGGTGTT
GGTGAATTTGAAGCTGGTATCTCCAAGAATGGGCAGACCCGAGAGCATGCCCTTCTGGCT
TACACACTGGGTGTGAAACAACTAATTGTCGGTGTTAACAAAATGGATTCCACTGAGCCA
CCCTACAGCCAGAAGAGATATGAGGAAATTGTTAAGGAAGTCAGCACTTACATTAAGAAA
ATTGGCTACAACCCCGACACAGTAGCATTTGTGCCAATTTCTGGTTGGAATGGTGACAAC
ATGCTGGAGCCAAGTGCTAACATGCCTTGGTTCAAGGGATGGAAAGTCACCCGTAAGGAT
GGCAATGCCAGTGGAACCACGCTGCTTGAGGCTCTGGACTGCATCCTACCACCAACTCGC
CCAACTGACAAGCCCTTGCGCCTGCCTCTCCAGGATGTCTACAAAATTGGTGGTATTGGT
ACTGTTCCTGTTGGCCGAGTGGAGACTGGTGTTCTCAAACCCGGTATGGTGGTCACCTTT
GCTCCAGTCAACGTTACAACGGAAGTAAAATCTGTCGAAATGCACCATGAAGCTTTGAGT
GAAGCTCTTCCTGGGGACAATGTGGGCTTCAAGGTCAAGAATGTGTCTGTCAAGGATGTT
CGTCGTGGCAACGTTGCTGGTGACAGCAAAAATGACCCACCAATGGAAGCAGCTGGCTTC
ACTGCTCAGGTGATTATCCTGAACCATCCAGGCCAAATAAGCGCCGGCTATGCCCCTGTA
TTGGATTGCCACATGGCTCACATTGCATGCAAGTTTGCTGAGCTGAAGGAAAAGATTGAT
CGCCGTTCTGGTAAAAAGCTGGAAGATGGCCCTAAATTCTTGAAGTCTGGTGATGCTGCC
ATTGTTGATATGGTTCCTGGCAAGCCCATGTGTGTTGAGAGCTTCTCAGACTATCCACCT
TTGGGTCGCTTTGCTGTTCGTGATATGAGACAGACAGTTGCGGTGGGTGTCATCAAAGCA
GTGGACAAGAAGGCTGCTGGAGCTGGCAAGGTCACCAAGTCTGCCCAGAAAGCTCAGAAG
GCTAAATGA

Fig. 39

SEQ ID No. 39
NP_612480.1
>ENSG00000168005|11|protein_coding|ENST00000294244|ENSP00000294244
ATGGCCCTAAAGGCCGAGGGCGCCGCACTCGACTGCTTCGAGGTGACGCTGAAATGCGAG
GAAGGGGAGGACGAGGAGGAGGCCATGGTGGTGGCCGTAATTCCGCGGCCCGAGCCGATG
CTCAGAGTGACCCAACAGGAGAAGACCCCACCGCCTAGACCCAGCCCGCTAGAGGCAGGC
AGTGATGGCTGTGAGGAGCCGAAGCAGCAGGTGTCTTGGGAGCAGGAGTTCCTGGTGGGC
AGCAGCCCAGGAGGCAGCGGGCGGGCACTGTGCATGGTGTGTGGCGCTGAGATCCGGGCA
CCCTCGGCCGACACAGCTCGCTCGCACATCTTGGAGCAGCACCCTCACACCTTGGACCTG
AGCCCTTCTGAGAAGAGCAATATCCTGGAGGCCTGGAGTGAAGGGGTGGCCCTCTTGCAA
GACGTGAGAGCTGAGCAGCCGTCCCCACCCAACTCAGACTCGGGCCAGGATGCCCACCCA
GACCCAGACGCCAACCCAGACGCTGCCAGAATGCCAGCCGAAATCGTCGTTCTCCTTGAC
TCTGAGGATAACCCATCCCTCCCTAAAAGGAGCCGGCCCAGGGGACTCCGCCCCCTCGAG
CTTCCTGCTGTCCCTGCCACAGAGCCAGGAAATAAGAAGCCCCGTGGTCAGAGATGGAAG
GAACCCCCAGGGGAAGAGCCAGTCAGAAAGAAAAGAGGCAGACCTATGACCAAAAACCTG
GACCCTGACCCAGAGCCCCCATCGCCAGACTCGCCCACGGAGACTTTCGCAGCACCAGCC
GAGGTCCGACACTTCACTGACGGCAGCTTCCCCGCCGGCTTCGTCTTGCAGCTCTTCTCC
CACACCCAGCTCAGGGGCCCAGACAGCAAGGACTCACCCAAAGACAGGGAAGTGGCAGAA
GGAGGCCTTCCCCGGGCGGAGAGCCCCTCTCCAGCTCCCCCTCCGGGGCTCCGCGGGACA
CTGGATCTCCAGGTTATCCGCGTGCGGATGGAGGAGCCCCCAGCGGTCAGCCTCCTGCAA
GACTGGTCCAGGCACCCCCAGGGCACCAAGCGTGTGGGAGCAGGTGACACCTCAGACTGG
CCCACAGTTCTGTCAGAATCCAGCACCACTGTGGCAGGGAAGCCGGAAAAAGGGAATGGA
GTGTAA

Fig. 40

SEQ ID No. 40
PLXNA2
>ENSG00000076356|1|protein_coding|ENST00000321063|ENSP00000323194
ATGAGCACACACAGGAGCCGTCTCCTCACCGCCGCCCCTCTCAGCATGGAACAGAGGCGG
CCCTGGCCCCGGCCCTGGAGGTGGACAGCCGCTCTGTGGTCCTGCTCTCAGTGGTCTGG
GTGCTGCTGGCCCCCCCAGCAGCCGGCATGCCTCAGTTCAGCACCTTCCACTCTGAGAAT
CGTGACTGGACCTTCAACCACTTGACCGTCCACCAAGGGACGGGGCCGTCTATGTGGGG
GCCATCAACCGGGTCTATAAGCTGACAGGCAACCTGACCATCCAGGTGGCTCATAAGACA
GGGCCAGAAGAGGACAACAAGTCTTGTTACCCGCCCCTCATCGTGCAGCCCTGCAGCGAA
GTGCTCACCCTCACCAACAATGTCAACAAGCTGCTCATCATTGACTACTCTGAGAACCGC
CTGCTGGCCTGTGGGAGCCTCTACCAGGGGGTCTGCAAGCTGCTGCGGCTGGATGACCTC
TTCATCCTGGTGGAGCCATCCCACAAGAAGGAGCACTACCTGTCCAGTGTCAACAAGACG
GGCACCATGTACGGGGTGATTGTGCGCTCTGAGGGTGAGGATGGCAAGCTCTTCATCGGC
ACGGCTGTGGATGGAAGCAGGATTACTTCCCGACCCTGTCCAGCCGGAAGCTGCCCCGA
GACCCTGAGTCCTCAGCCATGCTCGACTATGAGCTACACAGCGATTTTGTCTCCTCTCTC
ATCAAGATCCCTTCAGACACCCTGGCCCTGGTCTCCCACTTTGACATCTTCTACATCTAC
GGCTTTGCTAGTGGGGGCTTTGTCTACTTTCTCACTGTCCAGCCCGAGACCCCTGAGGGT
GTGGCCATCAACTCCGCTGGAGACCTCTTCTACACCTCACGCATCGTGCGGCTCTGCAAG
GATGACCCCAAGTTCCACTCATACGTGTCCCTGCCCCTTCGGCTGCACCCGGGCCGGGGTG
GAATACCGCCTCCTGCAGGCTGCTTACCTGGCCAAGCCTGGGGACTCACTGGCCCAGGCC
TTCAATATCACCAGCCAGGACGATGTACTCTTTGCCATCTTCTCCAAAGGGCAGAAGCAG
TATCACCACCGCCCGATGACTCTGCCCTGTGTGCCTTCCCTATCCGGGCCATCAACTTG
CAGATCAAGGAGCGCCTGCAGTCCTGCTACCAGGGCGAGGGCAACCTGGAGCTCAACTGG
CTGCTGGGGAAGGACGTCCAGTGCACCAAGGCGCCTGTCCCATCGATGATAACTTCTGT
GGACTGGACATCAACCAGCCCTGGGAGGCTCAACTCCAGTGGAGGGCCTGACCCTGTAC
ACCACCAGCAGGGACCGCATGACCTCTGTGGCCTCCTACGTTTACAACGGCTACAGCGTG
GTTTTTGTGGGGACTAAGAGTGGCAAGCTGAAAAGATTCGGGCCGACGGTCCCCCCCAT
GGTGGGGTCCAGTACGAGATGGTCTCTGTGCTCAAGGACGGAAGCCCCATCCTCCGGGAC
ATGGCCTTCTCCATTGATCAGCGCTACCTGTACGTCATGTCTGAGAGACAGGTCACCAGG
GTCCCCGTGGAGTCATGTGAGCAGTATACGACTTGTGGGGAGTGCCTGAGCTCTGGGGAC
CCTCACTGTGGCTGGTGTGCCCTGCACAACATGTGCTCCCGCAGGGACAAATGCCAACAG
GCCTGGGAACCTAATCGATTTGCTGCCAGCATCAGCCAGTGTGTGAGCCTTGCAGTGCAT
CCCAGCAGCATCTCAGTATCTGAGCACAGCCGGTTGCTTAGCCTGGTAGTGAGTGATGCT
CCTGATCTATCTGCGGGTATCGCCTGTGCCTTTGGGAACCTGACAGAGGTGGAGGGGCAG
GTGTCCGGGAGCCAGGTCATCTGCATCTCACCTGGGCCCAAGGATGTCCCTGTCATCCCG
CTGGATCAAGACTGGTTTGGCTGGAGCTACAGCTGAGGTCCAAGGAGACAGGGAAGATA
TTTGTCAGCACCGAGTTCAAGTTTTACAACTGCAGTGCCCACCAACTGTGCCTGTCCTGT
GTCAACAGCGCCTTCCGCTGCCATTGGTGCAAGTACCGCAACCTCTGCACTCATGACCCC
ACCACCTGCTCCTTCCAGGAGGGCCGGATCAATATTTCAGAGGACTGTCCCCAGCTGGTG
CCCACAGAGGAGATCTTGATTCCAGTCGGGGAGGTAAAGCCAATCACCCTTAAGGCGCGA
AATCTGCCCCAGCCGCAGTCCGGCCAGCGAGGCTATGAGTGTGTCCTCAACATACAAGGA
GCCATCCACCGGGTCCCCGCTCTGCGCTTCAACAGCTCCAGCGTTCAGTGTCAGAACAGC
TCGTACCAGTATGATGGCATGGACATCAGCAATCTGGCCGTGGATTTCGCTGTGGTGTGG
AACGGCAATTTCATCATTGACAACCCTCAGGACCTGAAAGTCCATCTCTACAAGTGTGCA
GCCCAGCGGGAGAGCTGCGGCCTCTGCCTCAAGGCCGACCGGAAGTTTGAGTGTGGCTGG
TGCAGCGGCGAGCGCAGGTGCACCCTCCACCAGCACTGTACCAGCCCTTCCAGCCCCTGG
CTCGACTGGTCCGCCACAATGTCAAGTGCTCCAACCCTCAAATCACCGAGATTTTGACG
GTGTCTGGACGCCGGAAGGAGGGACGCGAGTGACCATCCATGGCGTGAACCTGGGTCTG
GACTTCTCCGAGATCGCCCACCATGTGCAGGTGGCTGGGGTGCCCTGCACGCCCCTCCCA
GGGGAATACATCATCGCTGAGCAGATTGTCTGTGAGATGGGCCATGCCCTCGTGGGAACC
ACCTCCGGCCAGTACGCCTGTGTATTGGCGAGTGTAAGCCAGAGTTCATGACGAAGTCC
CATCAGCAGTACACCTTCGTGAACCCTTCTGTGCTGTCACTCAACCCAATCCGAGGTCCC
GAGTCAGGAGGCACTATGGTGACCATTACCGGCCATTACCTTGGGGCTGGGAGCAGCGTG
GCAGTCTACCTGGGCAACCAGACCTGCGAGTTCTACGGGAGGTCAATGAGTGAGATCGTG
TGTGTCTCACCCCCATCATCCAATGGCCTTGGCCCGGTCCCTGTTTCTGTGAGTGTCGAC
CGAGCCCATGTGGATAGCAACCTGCAGTTTGAGTACATAGATGACCCTCGGGTCCAGCGC
ATCGAGCCAGAGTGGAGCATTGCCAGTGGCCACACACCCCTGACCATCACAGGCTTCAAC
CTGGATGTCATTCAGGAGCCAAGGATCCGAGTCAAATTCAATGGCAAAGAATCTGTCAAT
GTGTGTAAAGTTGTGAACACAACCACCCTCACCTGCCTGGCACCCTCTCTGACCACGGAC
TACCGCCCTGGCCTGGACACTGTGGAACGCCCAGATGAGTTTGGATTTGTCTTTAACAAT
GTCCAATCCTTGCTAATTTACAACGACACCAAGTTTATCTACTACCCCAACCCGACCTTT
GAACTGCTTAGCCCTACTGGAGTCTTGGATCAAAAGCCAGGATCGCCCATCATTCTGAAG

```
GGCAAAAACCTCTGCCCTCCTGCCTCTGGAGGGGCCAAACTCAACTACACTGTGCTCATC
GGAGAGACCCCTTGTGCTGTCACCGTATCTGAGACCCAGCTTCTCTGCGAGCCTCCCAAC
CTCACCGGGCAGCACAAGGTCATGGTTCACGTGGGCGGGATGGTGTTCTCGCCTGGCTCG
GTGAGTGTCATCTCAGACAGCTTGCTGACCCTGCCAGCCATCGTCAGCATCGCGGCCGGC
GGCAGCCTCCTCCTCATCATCGTCATCATCGTCCTCATTGCCTACAAGCGCAAGTCTCGA
GAAAATGACCTCACTCTCAAGCGGCTGCAAATGCAGATGGACAATCTGGAGTCCCGTGTG
GCCTTGGAGTGCAAGGAAGCTTTTGCTGAGCTCCAGACGGATATCAATGAGTTGACCAGT
GACCTGGACCGCTCAGGAATCCCTTACCTGGACTATCGTACCTACGCTATGCGAGTCCTG
TTCCCGGGCATCGAGGACCACCCCGTCCTGCGGGAGCTGGAGGTACAAGGAAACGGGCAG
CAGCACGTGGAGAAGGCCCTGAAGCTCTTTGCCCAGCTCATCAACAACAAGGTGTTCCTG
CTGACCTTCATCCGCACCCTGGAGCTGCAGCGCAGTTTCTCCATGCGCGACCGGGGCAAC
GTGGCTTCGCTCATCATGACCGGCCTGCAGGGCCGCCTGGAATATGCCACTGATGTCCTC
AAGCAGCTGCTCTCTGACCTCATCGATAAGAACCTGGAGAACAAGAACCACCCCAAGCTG
CTACTCCGGAGGACAGAGTCTGTGGCTGAAAAGATGCTGACCAATTGGTTCGCCTTCCTC
CTGCACAAGTTCCTAAAGGAGTGCGCAGGGGAGCCACTCTTCATGCTATACTGTGCCATC
AAGCAGCAGATGGAGAAGGGCCCCATTGATGCCATCACGGGCGAGGCCCGCTACTCCCTG
AGCGAGGACAAGCTCATCCGGCAGCAGATCGAGTACAAGACCCTGATCCTGAACTGCGTC
AACCCTGACAACGAGAACAGTCCAGAGATCCCAGTGAAGGTGTTAAACTGTGACACCATC
ACACAGGTCAAGGAGAAGATTCTTGATGCCGTGTATAAGAATGTGCCCTATTCCCAGCGG
CCGAGGGCAGTGGACATGGACTTGGAGTGGCGCCAAGGCCGGATCGCCCGGGTCGTGCTG
CAAGATGAGGACATCACCACCAAGATTGAGGGTGACTGGAAGCGGCTCAACACACTGATG
CATTATCAGGTGTCAGACAGGTCGGTGGTGGCTCTGGTCCCCAAACAGACCTCCTCCTAC
AACATCCCTGCCTCTGCCAGCATCTCCCGGACGTCCATCAGCAGATACGACTCCTCCTTC
AGGTATACGGGCAGCCCCGACAGCCTGCGGTCCCGGGCCCCGATGATCACCCCAGACCTG
GAAAGTGGGGTCAAGGTGTGGCATCTGGTGAAGAACCATGACCACGGTGACCAGAAGGAG
GGTGACCGGGGCAGCAAGATGGTGTCCGAGATCTACCTGACCCGGCTACTGGCCACCAAG
GGCACCCTGCAGAAGTTTGTGGACGACTTGTTTGAGACCTTGTTCAGCACTGTGCACCGG
GGCAGCGCTCTCCCCCTGGCCATCAAGTACATGTTTGATTTCCTAGATGAGCAGGCAGAC
AGGCACAGCATCCATGACACAGATGTGCGGCACACCTGGAAAAGCAACTGCCTCCCTCTG
CGCTTCTGGGTGAACGTGATTAAGAACCCCCAGTTCGTGTTTGACATCCACAAGGGCAGC
ATCACGGACGCCTGCCTCTCTGTGGTGGCCCAGACCTTCATGGACTCTTGTTCAACGTCA
GAGCACCGGCTGGGCAAGGACTCCCCCTCCAACAAGCTGCTCTATGCCAAGGACATCCCC
AGCTACAAGAGCTGGGTGGAGAGATACTACGCAGACATCGCCAAGCTCCCAGCCATCAGT
GACCAGGACATGAATGCCTACCTCGCCGAGCAGTCCCGCCTGCACGCCGTGGAGTTCAAC
ATGCTGAGTGCCCTCAATGAGATCTACTCCTATGTCAGCAAGTATAGTGAGGAGCTCATC
GGGGCCCTAGAGCAGGATGAGCAGGCACGGCGGCAGCGGCTGGCTTATAAGGTGGAGCAG
CTCATTAATGCCATGTCCATTGAGAGCTGA
```

SEQ ID No. 41
PLXNA2
>ENSG00000076356|1|protein_coding|ENST00000367033|ENSP00000356000
ATGGAACAGAGGCGGCCCTGGCCCCGGGCCCTGGAGGTGGACAGCCGCTCTGTGGTCCTG
CTCTCAGTGGTCTGGGTGCTGCTGGCCCCCCCAGCAGCCGGCATGCCTCAGTTCAGCACC
TTCCACTCTGAGAATCGTGACTGGACCTTCAACCACTTGACCGTCCACCAAGGGACGGGG
GCCGTCTATGTGGGGGCCATCAACCGGGTCTATAAGCTGACAGGCAACCTGACCATCCAG
GTGGCTCATAAGACAGGGCCAGAAGAGGACAACAAGTCTTGTTACCCGCCCCTCATCGTG
CAGCCCTGCAGCGAAGTGCTCACCCTCACCAACAATGTCAACAAGCTGCTCATCATTGAC
TACTCTGAGAACCGCCTGCTGGCCTGTGGAGCCTCTACCAGGGGGTCTGCAAGCTGCTG
CGGCTGGATGACCTCTTCATCCTGGTGGAGCCATCCCACAAGAAGGAGCACTACCTGTCC
AGTGTCAACAAGACGGGCACCATGTACGGGGTGATTGTGCGCTCTGAGGGTGAGGATGGC
AAGCTCTTCATCGGCACGGCTGTGGATGGGAAGCAGGATTACTTCCCGACCCTGTCCAGC
CGGAAGCTGCCCCGAGACCCTGAGTCCTCAGCCATGCTCGACTATGAGCTACACAGCGAT
TTTGTCTCCTCTCTCATCAAGATCCCTTCAGACACCCTGGCCCTGGTCTCCCACTTTGAC
ATCTTCTACATCTACGGCTTTGCTAGTGGGGCTTTGTCTACTTTCTCACTGTCCAGCCC
GAGACCCCTGAGGGTGTGGCCATCAACTCCGCTGGAGACCTCTTCTACACCTCACGCATC
GTGCGGCTCTGCAAGGATGACCCCAAGTTCCACTCATACGTGTCCCTGCCCTTCGGCTGC
ACCCGGGCCGGGGTGGAATACCGCCTCCTGCAGGCTGCTTACCTGGCCAAGCCTGGGGAC
TCACTGGCCCAGGCCTTCAATATCACCAGCCAGGACGATGTACTCTTTGCCATCTTCTCC
AAAGGGCAGAAGCAGTATCACCACCCGCCCGATGACTCTGCCCTGTGTGCCTTCCCTATC
CGGGCCATCAACTTGCAGATCAAGGAGCGCCTGCAGTCCTGCTACCAGGGCGAGGGCAAC
CTGGAGCTCAACTGGCTGCTGGGGAAGGACGTCCAGTGCACCAAGGCGCCTGTCCCCATC
GATGATAACTTCTGTGGACTGGACATCAACCAGCCCCTGGGAGGCTCAACTCCAGTGGAG
GGCCTGACCCTGTACACCACCAGCAGGGACCGCATGACCTCTGTGGCCTCCTACGTTTAC
AACGGCTACAGCGTGGTTTTTGTGGGGACTAAGAGTGGCAAGCTGAAAAAGATTCGGGCC
GACGGTCCCCCCCATGGTGGGGTCCAGTACGAGATGGTCTCTGTGCTCAAGGACGGAAGC
CCCATCCTCCGGGACATGGCCTTCTCCATTGATCAGCGCTACCTGTACGTCATGTCTGAG
AGACAGGTCACCAGGGTCCCCGTGGAGTCATGTGAGCAGTATACGACTTGTGGGGAGTGC
CTGAGCTCTGGGGACCCTCACTGTGGCTGGTGTGCCCTGCACAACATGTGCTCCCGCAGG
GACAAATGCCAACAGGCCTGGGAACCTAATCGATTTGCTGCCAGCATCAGCCAGTGTGTG
AGCCTTGCAGTGCATCCCAGCAGCATCTCAGTATCTGAGCACAGCCGGTTGCTTAGCCTG
GTAGTGAGTGATGCTCCTGATCTATCTGCGGGTATCGCCTGTGCCTTTGGGAACCTGACA
GAGGTGGAGGGCAGGTGTCCGGGAGCCAGGTCATCTGCATCTCACCTGGGCCCAAGGAT
GTCCCTGTCATCCCGCTGGATCAAGACTGGTTTGGGCTGGAGCTACAGCTGAGGTCCAAG
GAGACAGGGAAGATATTTGTCAGCACCGAGTTCAAGTTTTACAACTGCAGTGCCCACCAA
CTGTGCCTGTCCTGTGTCAACAGCGCCTTCCGCTGCCATTGGTGCAAGTACCGCAACCTC
TGCACTCATGACCCCACCACCTGCTCCTTCCAGGAGGGCCGGATCAATATTTCAGAGGAC
TGTCCCCAGCTGGTGCCCACAGAGGAGATCTTGATTCCAGTCGGGGAGGTAAAGCCAATC
ACCCTTAAGGCGCGAAATCTGCCCCAGCCGCAGTCCGGCCAGCGAGGCTATGAGTGTGTC
CTCAACATACAAGGAGCCATCCACCGGGTCCCCGCTCTGCGCTTCAACAGCTCCAGCGTT
CAGTGTCAGAACAGCTCGTACCAGTATGATGGCATGGACATCAGCAATCTGGCCGTGGAT
TTCGCTGTGGTGTGGAACGGCAATTTCATCATTGACAACCCTCAGGACCTGAAAGTCCAT
CTCTACAAGTGTGCAGCCCAGCGGGAGAGCTGCGGCCTCTGCCTCAAGGCCGACCGGAAG
TTTGAGTGTGGCTGGTGCAGCGGCGAGCGCAGTCCACCCTCCACCAGCACTGTACCAGC
CCTTCCAGCCCCTGGCTCGACTGGTCCAGCCACAATGTCAAGTGCTCCAACCCCTCAAATC
ACCGAGATTTTGACGGTGTCTGGACCGCCGGAAGGAGGGACGCGAGTGACCATCCATGGC
GTGAACCTGGGTCTGGACTTCTCCGAGATCGCCCACCATGTGCAGGTGGCTGGGGTGCCC
TGCACGCCCCTCCCAGGGGAATACATCATCGCTGAGCAGATTGTCTGTGAGATGGGCCAT
GCCCTCGTGGGAACCACCTCCGGGCCAGTACGCCTGTGTATTGGCGAGTGTAAGCCAGAG
TTCATGACGAAGTCCCATCAGCAGTACACCTTCGTGAACCCTTCTGTGCTGTCACTCAAC
CCAATCCGAGGTCCCGAGTCAGGAGGCACTATGGTGACCATTACCGGCCATTACCTTGGG
GCTGGGAGCAGCGTGGCAGTCTACCTGGGCAACCAGACCTGCGAGTTCTACGGGAGGTCA
ATGAGTGAGATCGTGTGTGTCTCACCCCCATCATCCAATGGCCTTGGCCCGGTCCCTGTT
TCTGTGAGTGTCGACCGAGCCCATGTGGATAGCAACCTGCAGTTTGAGTACATAGATGAC
CCTCGGGTCCAGCGCATCGAGCCAGAGTGGAGCATTGCCAGTGGCCACACACCCCTGACC
ATCACAGGCTTCAACCTGGATGTCATTCAGGAGCCAAGGATCCGAGTCAAATTCAATGGC
AAAGAATCTGTCAATGTGTGTAAAGTTGTGAACACAACCACCCTCACCTGCCTGGCACCC
TCTCTGACCACGGACTACCGCCCTGGCCTGGACACTGTGGAACGCCCAGATGAGTTTGGA
TTTGTCTTTAACAATGTCCAATCCTTGCTAATTTACAACGACACCAAGTTTATCTACTAC
CCCAACCCGACCTTTGAACTGCTTAGCCCTACTGGAGTCTTGGATCAAAAGCCAGGATCG
CCCATCATTCTGAAGGGCAAAAACCTCTGCCCTCCTGCCTCTGGAGGGGCCAAACTCAAC

```
TACACTGTGCTCATCGGAGAGACCCCTTGTGCTGTCACCGTATCTGAGACCCAGCTTCTC
TGCGAGCCTCCCAACCTCACCGGGCAGCACAAGGTCATGGTTCACGTGGGCGGGATGGTG
TTCTCGCCTGGCTCGGTGAGTGTCATCTCAGACAGCTTGCTGACCCTGCCAGCCATCGTC
AGCATCGCGGCCGGCGGCAGCCTCCTCCTCATCATCGTCATCATCGTCCTCATTGCCTAC
AAGCGCAAGTCTCGAGAAAATGACCTCACTCTCAAGCGGCTGCAAATGCAGATGGACAAT
CTGGAGTCCCGTGTGGCCTTGGAGTGCAAGGAAGCTTTTGCTGAGCTCCAGACGGATATC
AATGAGTTGACCAGTGACCTGGACCGCTCAGGAATCCCTTACCTGGACTATCGTACCTAC
GCTATGCGAGTCCTGTTCCCGGGCATCGAGGACCACCCCGTCCTGCGGGAGCTGGAGGTA
CAAGGAAACGGGCAGCAGCACGTGGAGAAGGCCCTGAAGCTCTTTGCCCAGCTCATCAAC
AACAAGGTGTTCCTGCTGACCTTCATCCGCACCCTGGAGCTGCAGCGCAGTTTCTCCATG
CGCGACCGGGGCAACGTGGCTTCGCTCATCATGACCGGCCTGCAGGGCCGCCTGGAATAT
GCCACTGATGTCCTCAAGCAGCTGCTCTCTGACCTCATCGATAAGAACCTGGAGAACAAG
AACCACCCCAAGCTGCTACTCCGGAGGACAGAGTCTGTGGCTGAAAGATGCTGACCAAT
TGGTTCGCCTTCCTCCTGCACAAGTTCCTAAAGGAGTGCGCAGGGGAGCCACTCTTCATG
CTATACTGTGCCATCAAGCAGCAGATGGAGAAGGGCCCCATTGATGCCATCACGGGCGAG
GCCCGCTACTCCCTGAGCGAGGACAAGCTCATCCGGCAGCAGATCGAGTACAAGACCCTG
ATCCTGAACTGCGTCAACCCTGACAACGAGAACAGTCCAGAGATCCCAGTGAAGGTGTTA
AACTGTGACACCATCACACAGGTCAAGGAGAAGATTCTTGATGCCGTGTATAAGAATGTG
CCCTATTCCCAGCGGCCGAGGGCAGTGGACATGGACTTGGAGTGGCGCCAAGGCCGGATC
GCCCGGGTCGTGCTGCAAGATGAGGACATCACCACCAAGATTGAGGGTGACTGGAAGCGG
CTCAACACACTGATGCATTATCAGGTGTCAGACAGGTCGGTGGTGGCTCTGGTCCCCAAA
CAGACCTCCTCCTACAACATCCCTGCCTCTGCCAGCATCTCCCGGACGTCCATCAGCAGA
TACGACTCCTCCTTCAGGTATACGGGCAGCCCCGACAGCCTGCGGTCCCGGGCCCCGATG
ATCACCCCAGACCTGGAAAGTGGGGTCAAGGTGTGGCATCTGGTGAAGAACCATGACCAC
GGTGACCAGAAGGAGGGTGACCGGGGCAGCAAGATGGTGTCCGAGATCTACCTGACCCGG
CTACTGGCCACCAAGGGCACCCTGCAGAAGTTTGTGGACGACTTGTTTGAGACCTTGTTC
AGCACTGTGCACCGGGGCAGCGCTCTCCCCCTGGCCATCAAGTACATGTTTGATTTCCTA
GATGAGCAGGCAGACAGGCACAGCATCCATGACACAGATGTGCGGCACACCTGGAAAAGC
AACTGCCTCCCTCTGCGCTTCTGGGTGAACGTGATTAAGAACCCCCAGTTCGTGTTTGAC
ATCCACAAGGGCAGCATCACGGACGCCTGCCTCTCTGTGGTGGCCCAGACCTTCATGGAC
TCTTGTTCAACGTCAGAGCACCGGCTGGGCAAGGACTCCCCCTCCAACAAGCTGCTCTAT
GCCAAGGACATCCCCAGCTACAAGAGCTGGGTGGAGAGATACTACGCAGACATCGCCAAG
CTCCCAGCCATCAGTGACCAGGACATGAATGCCTACCTCGCCGAGCAGTCCCGCCTGCAC
GCCGTGGAGTTCAACATGCTGAGTGCCCTCAATGAGATCTACTCCTATGTCAGCAAGTAT
AGTGAGGAGCTCATCGGGGCCCTAGAGCAGGATGAGCAGGCACGGCGGCAGCGGCTGGCT
TATAAGGTGGAGCAGCTCATTAATGCCATGTCCATTGAGAGCTGA
```

SEQ ID No. 42
ELMO2
>ENSG00000062598|20|protein_coding|ENST00000290246|ENSP00000290246
ATGCCACCACCGTCAGACATTGTCAAAGTGGCCATTGAGTGGCCAGGTGCTAACGCCCAG
CTCCTTGAAATCGACCAGAAACGGCCCCTGGCATCCATTATCAAGGAAGTTTGTGATGGG
TGGTCGTTGCCAAACCCAGAGTATTATACCCTCCGTTATGCAGATGGTCCTCAGCTGTAC
ATCACCGAACAGACTCGCAGTGACATTAAGAATGGGACAATCTTACAACTGGCTATCTCC
CCGTCCCGGGCTGCACGCCAGCTGATGGAGAGGACCCAGTCATCCAACATGGAGACCCGG
CTGGATGCCATGAAGGAGCTGGCCAAGCTCTCTGCCGACGTGACTTTCGCTACTGAGTTC
ATCAACATGGATGGCATCATTGTGCTGACAAGGCTCGTGGAAAGTGGAACCAAGCTCTTG
TCCCACTACAGTGAGATGCTGGCATTCACCCTGACTGCCTTCCTAGAGCTCATGGACCAT
GGCATTGTCTCCTGGGACATGGTTTCAATCACCTTTATTAAGCAGATTGCAGGGTATGTG
AGCCAGCCCATGGTGGACGTGTCAATCCTTCAGAGGTCCCTGGCCATCCTGGAGAGCATG
GTCTTGAACAGCCAGAGTCTGTACCAGAAGATAGCCGAGGAAATCACCGTGGGACAGCTC
ATCTCACACCTCCAGGTCTCCAACCAGGAGATTCAGACCTACGCCATTGCACTGATTAAT
GCACTTTTTCTGAAGGCTCCTGAGGACAAACGACAGGATATGGCAAATGCATTTGCACAG
AAGCATCTCCGGTCTATAATCCTGAATCATGTGATCCGAGGGAACCGCCCATCAAAACT
GAGATGGCCCATCAGCTATATGTCCTTCAAGTCCTAACCTTTAACCTTCTGGAAGAAAGG
ATGATGACCAAGATGGACCCCAATGACCAGGCTCAAAGGGACATCATATTTGAACTGAGG
AGGATTGCATTTGACGCAGAGTCTGATCCTAGCAATGCCCCTGGGAGTGGGACCGAAAAA
CGCAAAGCCATGTACACAAAGGACTACAAAATGCTGGGATTTACCAACCACATCAATCCA
GCCATGGACTTTACCCAGACTCCTCCTGGAATGCTGGCCTTGGACAACATGCTGTACTTG
GCTAAAGTCCACCAGGACACCTACATCCGGATTGTCTTGGAGAACAGTAGCCGGGAAGAC
AAACATGAATGCCCCTTTGGCCGCAGTGCCATTGAGCTCACCAAAATGCTCTGTGAAATC
CTGCAGGTTGGGGAACTACCAAATGAAGGACGCAATGACTACCACCCGATGTTCTTTACC
CATGACCGAGCCTTTGAAGAGCTCTTTGGAATCTGCATCCAGCTGTTGAACAAGACCTGG
AAGGAGATGAGGGCAACAGCAGAGGACTTCAACAAGGTTATGCAAGTCGTCCGAGAGCAA
ATCACTCGAGCTTTGCCCTCCAAACCCAACTCTTTGGATCAGTTCAAGAGCAAATTGCGT
AGCCTGAGTTACTCTGAGATTCTACGACTGCGCCAGTCTGAGAGGATGAGTCAGGATGAC
TTCCAGTCCCCGCCAATTGTGGAGCTGAGGGAGAAGATCCAGCCCGAGATCCTTGAGCTG
ATCAAGCAGCAGCGCCTGAACCGGCTCTGTGAGGGCAGCAGCTTCCGAAAGATTGGGAAC
CGCCGAAGGCAAGAACGGTTCTGGTACTGCCGGTTGGCACTGAACCACAAGGTCCTTCAC
TATGGTGACTTGGATGACAACCCACAAGGGGAGGTGACATTTGAATCCCTGCAGGAGAAA
ATTCCTGTTGCAGACATTAAGGCCATTGTCACTGGGAAAGATTGTCCCCACATGAAAGAG
AAAAGTGCTCTGAAACAGAACAAGGAGGTGTTGGAATTGGCCTTCTCCATCCTGTATGAC
CCTGATGAGACCTTAAACTTCATCGCACCTAATAAATATGAGTACTGCATCTGGATTGAT
GGCCTCAGTGCCCTTCTGGGGAAGGACATGTCCAGTGAGCTGACCAAGAGTGACCTGGAC
ACCCTGCTGAGCATGGAGATGAAGCTGCGGCTCCTGGACCTGGAGAACATCCAGATTCCC
GAAGCCCCACCCCCCATCCCCAAGGAGCCCAGCAGCTATGACTTTGTCTATCACTATGGC
TGA

Fig. 43

SEQ ID No. 43
ELMO2
>ENSG00000062598|20|protein_coding|ENST00000396391|ENSP00000379673
ATGCCACCACCGTCAGACATTGTCAAAGTGGCCATTGAGTGGCCAGGTGCTAACGCCCAG
CTCCTTGAAATCGACCAGAAACGGCCCTGGCATCCATTATCAAGGAAGTTTGTGATGGG
TGGTCGTTGCCAAACCCAGAGTATTATACCCTCCGTTATGCAGATGGTCCTCAGCTGTAC
ATCACCGAACAGACTCGCAGTGACATTAAGAATGGGACAATCTTACAACTGGCTATCTCC
CCGTCCCGGCTGCACGCCAGCTGATGGAGAGGACCCAGTCATCCAACATGGAGACCCGG
CTGGATGCCATGAAGGAGCTGGCCAAGCTCTCTGCCGACGTGACTTTCGCTACTGAGTTC
ATCAACATGGATGGCATCATTGTGCTGACAAGGCTCGTGGAAAGTGGAACCAAGCTCTTG
TCCCACTACAGTGAGATGCTGGCATTCACCCTGACTGCCTTCCTAGAGCTCATGGACCAT
GGCATTGTCTCCTGGGACATGGTTTCAATCACCTTTATTAAGCAGATTGCAGGGTATGTG
AGCCAGCCCATGGTGGACGTGTCAATCCTTCAGAGGTCCCTGGCCATCCTGGAGAGCATG
GTCTTGAACAGCCAGAGTCTGTACCAGAAGATAGCCGAGGAAATCACCGTGGGACAGCTC
ATCTCACACCTCCAGGTCTCCAACCAGGAGATTCAGACCTACGCCATTGCACTGATTAAT
GCACTTTTTCTGAAGGCTCCTGAGGACAAACGACAGGATATGGCAAATGCATTTGCACAG
AAGCATCTCCGGTCTATAATCCTGAATCATGTGATCCGAGGGAACCGCCCCATCAAAACT
GAGATGGCCCATCAGCTATATGTCCTTCAAGTCCTAACCTTTAACCTTCTGGAAGAAAGG
ATGATGACCAAGATGGACCCCAATGACCAGGCTCAAAGGGACATCATATTTGAACTGAGG
AGGATTGCATTTGACGCAGAGTCTGATCCTAGCAATGCCCTGGGAGTGGGACCGAAAAA
CGCAAAGCCATGTACACAAAGGACTACAAAATGCTGGGATTTACCAACCACATCAATCCA
GCCATGGACTTTACCCAGACTCCTCCTGGAATGCTGGCCTTGGACAACATGCTGTACTTG
GCTAAAGTCCACCAGGACACCTACATCCGGATTGTCTTGGAGAACAGTAGCCGGGAAGAC
AAACATGAATGCCCCTTTGGCCGCAGTGCCATTGAGCTCACCAAAATGCTCTGTGAAATC
CTGCAGGTTGGGGAACTACCAAATGAAGGACGCAATGACTACCACCCGATGTTCTTTACC
CATGACCGAGCCTTTGAAGAGCTCTTTGGAATCTGCATCCAGCTGTTGAACAAGACCTGG
AAGGAGATGAGGGCAACAGCAGAGGACTTCAACAAGGTTATGCAAGTCGTCCGAGAGCAA
ATCACTCGAGCTTTGCCCTCCAAACCCAACTCTTTGGATCAGTTCAAGAGCAAATTGCGT
AGCCTGAGTTACTCTGAGATTCTACGACTGCGCCAGTCTGAGAGGATGAGTCAGGATGAC
TTCCAGTCCCCGCCAATTGTGGAGCTGAGGGAGAAGATCCAGCCCGAGATCCTTGAGCTG
ATCAAGCAGCAGCGCCTGAACCGGCTCTGTGAGGGCAGCAGCTTCCGAAAGATTGGGAAC
CGCCGAAGGCAAGAACGGTTCTGGTACTGCCGGTTGGCACTGAACCACAAGGTCCTTCAC
TATGGTGACTTGGATGACAACCCACAAGGGGAGGTGACATTTGAATCCCTGCAGGAGAAA
ATTCCTGTTGCAGACATTAAGGCCATTGTCACTGGGAAAGATTGTCCCCACATGAAAGAG
AAAAGTGCTCTGAAACAGAACAAGGAGGTGTTGGAATTGGCCTTCTCCATCCTGTATGAC
CCTGATGAGACCTTAAACTTCATCGCACCTAATAAATATGAGTACTGCATCTGGATTGAT
GGCCTCAGTGCCCTTCTGGGGAAGGACATGTCCAGTGAGCTGACCAAGAGTGACCTGGAC
ACCCTGCTGAGCATGGAGATGAAGCTGCGGCTCCTGGACCTGGAGAACATCCAGATTCCC
GAAGCCCACCCCCCATCCCCAAGGAGCCCAGCAGCTATGACTTTGTCTATCACTATGGC
TGA

Fig. 44

SEQ ID No. 44
ELMO2
>ENSG00000062598|20|protein_coding|ENST00000372176|ENSP00000361249
ATGGAGAGGACCCAGTCATCCAACATGGAGACCCGGCTGGATGCCATGAAGGAGCTGGCC
AAGCTCTCTGCCGACGTGACTTTCGCTACTGAGTTCATCAACATGGATGGCATCATTGTG
CTGACAAGGCTCGTGGAAAGTGGAACCAAGCTCTTGTCCCACTACAGTGAGATGCTGGCA
TTCACCCTGACTGCCTTCCTAGAGCTCATGGACCATGGCATTGTCTCCTGGGACATGGTT
TCAATCACCTTTATTAAGCAGATTGCAGGGTATGTGAGCCAGCCCATGGTGGACGTGTCA
ATCCTTCAGAGGTCCCTGGCCATCCTGGAGAGCATGGTCTTGAACAGCCAGAGTCTGTAC
CAGAAGATAGCCGAGGAAATCACCGTGGGACAGCTCATCTCACACCTCCAGGTCTCCAAC
CAGGAGATTCAGACCTACGCCATTGCACTGATTAATGCACTTTTTCTGAAGGCTCCTGAG
GACAAACGACAGGATATGGCAAATGCATTTGCACAGAAGCATCTCCGGTCTATAATCCTG
AATCATGTGATCCGAGGGAACCGCCCCATCAAAACTGAGATGGCCCATCAGCTATATGTC
CTTCAAGTCCTAACCTTTAACCTTCTGGAAGAAAGGATGATGACCAAGATGGACCCCAAT
GACCAGGCTCAAAGGGACATCATATTTGAACTGAGGAGGATTGCATTTGACGCAGAGTCT
GATCCTAGCAATGCCCCTGGGAGTGGGACCGAAAAACGCAAAGCCATGTACACAAAGGAC
TACAAAATGCTGGGATTTACCAACCACATCAATCCAGCCATGGACTTTACCCAGACTCCT
CCTGGAATGCTGGCCTTGGACAACATGCTGTACTTGGCTAAAGTCCACCAGGACACCTAC
ATCCGGATTGTCTTGGAGAACAGTAGCCGGGAAGACAAACATGAATGCCCCTTTGGCCGC
AGTGCCATTGAGCTCACCAAAATGCTCTGTGAAATCCTGCAGGTTGGGGAACTACCAAAT
GAAGGACGCAATGACTACCACCCGATGTTCTTTACCCATGACCGAGCCTTTGAAGAGCTC
TTTGGAATCTGCATCCAGCTGTTGAACAAGACCTGGAAGGAGATGAGGGCAACAGCAGAG
GACTTCAACAAGGTTATGCAAGTCGTCCGAGAGCAAATCACTCGAGCTTTGCCCTCCAAA
CCCAACTCTTTGGATCAGTTCAAGAGCAAATTGCGTAGCCTGAGTTACTCTGAGATTCTA
CGACTGCGCCAGTCTGAGAGGATGAGTCAGGATGACTTCCAGTCCCCGCCAATTGTGGAG
CTGAGGGAGAAGATCCAGCCCGAGATCCTTGAGCTGATCAAGCAGCAGCGCCTGAACCGG
CTCTGTGAGGGCAGCAGCTTCCGAAAGATTGGGAACCGCCGAAGGCAAGAACGGTTCTGG
TACTGCCGGTTGGCACTGAACCACAAGGTCCTTCACTATGGTGACTTGGATGACAACCCA
CAAGGGGAGGTGACATTTGAATCCCTGCAGGAGAAAATTCCTGTTGCAGACATTAAGGCC
ATTGTCACTGGGAAAGATTGTCCCCACATGAAAGAGAAAGTGCTCTGAAACAGAACAAG
GAGGTGTTGGAATTGGCCTTCTCCATCCTGTATGACCCTGATGAGACCTTAAACTTCATC
GCACCTAATAAATATGAGTACTGCATCTGGATTGATGGCCTCAGTGCCCTTCTGGGGAAG
GACATGTCCAGTGAGCTGACCAAGAGTGACCTGGACACCCTGCTGAGCATGGAGATGAAG
CTGCGGCTCCTGGACCTGGAGAACATCCAGATTCCCGAAGCCCCACCCCCATCCCCAAG
GAGCCCAGCAGCTATGACTTTGTCTATCACTATGGCTGA

Fig. 45

SEQ ID No. 45
ELMO2
>ENSG00000062598|20|protein_coding|ENST00000352077|ENSP00000326172
ATGCCACCACCGTCAGACATTGTCAAAGTGGCCATTGAGTGGCCAGGTGCTAACGCCCAG
CTCCTTGAAATCGACCAGAAACGGCCCCTGGCATCCATTATCAAGGAAGTTTGTGATGGG
TGGTCGTTGCCAAACCCAGAGTATTATACCCTCCGTTATGCAGATGGTCCTCAGCTGTAC
ATCACCGAACAGACTCGCAGTGACATTAAGAATGGGACAATCTTACAACTGGCTATCTCC
CCGTCCCGGGCTGCACGCCAGCTGATGGAGAGGACCCAGTCATCCAACATGGAGACCCGG
CTGGATGCCATGAAGGAGCTGGCCAAGCTCTCTGCCGACGTGACTTTCGCTACTGAGTTC
ATCAACATGGATGGCATCATTGTGCTGACAAGGCTCGTGGAAAGTGGAACCAAGCTCTTG
TCCCATGAGATGCTGGCATTCACCCTGACTGCCTTCCTAGAGCTCATGGACCATGGCATT
GTCTCCTGGGACATGGTTTCAATCACCTTTATTAAGCAGATTGCAGGGTATGTGAGCCAG
CCCATGGTGGACGTGTCAATCCTTCAGAGGTCCCTGGCCATCCTGGAGAGCATGGTCTTG
AACAGCCAGAGTCTGTACCAGAAGATAGCCGAGGAAATCACCGTGGGACAGCTCATCTCA
CACCTCCAGGTCTCCAACCAGGAGATTCAGACCTACGCCATTGCACTGATTAATGCACTT
TTTCTGAAGGCTCCTGAGGACAAACGACAGGATATGGCAAATGCATTTGCACAGAAGCAT
CTCCGGTCTATAATCCTGAATCATGTGATCCGAGGGAACCGCCCCATCAAAACTGAGATG
GCCCATCAGCTATATGTCCTTCAAGTCCTAACCTTTAACCTTCTGGAAGAAAGGATGATG
ACCAAGATGGACCCCAATGACCAGGCTCAAAGGGACATCATATTTGAACTGAGGAGGATT
GCATTTGACGCAGAGTCTGATCCTAGCAATGCCCCTGGGAGTGGGACCGAAAAACGCAAA
GCCATGTACACAAAGGACTACAAAATGCTGGGATTTACCAACCACATCAATCCAGCCATG
GACTTTACCCAGACTCCTCCTGGAATGCTGGCCTTGGACAACATGCTGTACTTGGCTAAA
GTCCACCAGGACACCTACATCCGGATTGTCTTGGAGAACAGTAGCCGGGAAGACAAACAT
GAATGCCCCTTTGGCCGCAGTGCCATTGAGCTCACCAAAAATGCTCTGTGAAATCCTGCAG
GTTGGGGAACTACCAAATGAAGGACGCAATGACTACCACCCGATGTTCTTTACCCATGAC
CGAGCCTTTGAAGAGCTCTTTGGAATCTGCATCCAGCTGTTGAACAAGACCTGGAAGGAG
ATGAGGGCAACAGCAGAGGACTTCAACAAGGTTATGCAAGTCGTCCGAGAGCAAATCACT
CGAGCTTTGCCCTCCAAACCCAACTCTTTGGATCAGTTCAAGAGCAAATTGCGTAGCCTG
AGTTACTCTGAGATTCTACGACTGCGCCAGTCTGAGAGGATGAGTCAGGATGACTTCCAG
TCCCCGCCAATTGTGGAGCTGAGGGAGAAGATCCAGCCCGAGATCCTTGAGCTGATCAAG
CAGCAGCGCCTGAACCGGCTCTGTGAGGGCAGCAGCTTCCGAAAGATTGGGAACCGCCGA
AGGCAAGAACGGTTCTGGTACTGCCGGTTGGCACTGAACCACAAGGTCCTTCACTATGGT
GACTTGGATGACAACCCACAAGGGGAGGTGACATTTGAATCCCTGCAGGAGAAAATTCCT
GTTGCAGACATTAAGGCCATTGTCACTGGGAAAGATTGTCCCCACATGAAAGAGAAAGT
GCTCTGAAACAGAACAAGGAGGTGTTGGAATTGGCCTTCTCCATCCTGTATGACCCTGAT
GAGACCTTAAACTTCATCGCACCTAATAAATATGAGTACTGCATCTGGATTGATGGCCTC
AGTGCCCTTCTGGGGAAGGACATGTCCAGTGAGCTGACCAAGAGTGACCTGGACACCCTG
CTGAGCATGGAGATGAAGCTGCGGCTCCTGGACCTGGAGAACATCCAGATTCCCGAAGCC
CCACCCCCCATCCCCAAGGAGCCCAGCAGCTATGACTTTGTCTATCACTATGGCTGA

Fig. 46

SEQ ID No. 46
NDUFS2
>ENSG00000158864|1|protein_coding|ENST00000367993|ENSP00000356972
ATGGCGGCGCTGAGGGCTTTGTGCGGCTTCCGGGGCGTCGCGGCCCAGGTGCTGCGGCCT
GGGGCTGGAGTCCGATTGCCGATTCAGCCCAGCAGAGGTGTTCGGCAGTGGCAGCCAGAT
GTGGAATGGGCACAGCAGTTTGGGGGAGCTGTTATGTACCCAAGCAAAGAAACAGCCCAC
TGGAAGCCTCCACCTTGGAATGATGTGGACCCTCCAAAGGACACAATTGTGAAGAACATT
ACCCTGAACTTTGGGCCCCAACACCCAGCAGCGCATGGTGTCCTGCGACTAGTGATGGAA
TTGAGTGGGGAGATGGTGCGGAAGTGTGATCCTCACATCGGGCTCCTGCACCGAGGCACT
GAGAAGCTCATTGAATACAAGACCTATCTTCAGGCCCTTCCATACTTTGACCGGCTAGAC
TATGTGTCCATGATGTGTAACGAACAGGCCTATTCTAGCTGTGGAGAAGTTGCTAAAC
ATCCGGCCTCCTCCTCGGGCACAGTGGATCCGAGTGCTGTTTGGAGAAATCACACGTTTG
TTGAACCACATCATGGCTGTGACCACACATGCCCTGGACCTTGGGGCCATGACCCCTTTC
TTCTGGCTGTTTGAAGAAAGGGAGAAGATGTTTGAGTTCTACGAGCGAGTGTCTGGAGCC
CGAATGCATGCTGCTTATATCCGGCCAGGAGGAGTGCACCAGGACCTACCCCTTGGGCTT
ATGGATGACATTTATCAGTTTTCTAAGAACTTCTCTCTTCGGCTTGATGAGTTGGAGGAG
TTGCTGACCAACAATAGGATCTGGCGAAATCGGACAATTGACATTGGGGTTGTAACAGCA
GAAGAAGCACTTAACTATGGTTTTAGTGGAGTGATGCTTCGGGGCTCAGGCATCCAGTGG
GACCTGCGGAAGACCCAGCCCTATGATGTTTACGACCAGGTTGAGTTTGATGTTCCTGTT
GGTTCTCGAGGGGACTGCTATGATAGGTACCTGTGCCGGGTGGAGGAGATGCGCCAGTCC
CTGAGAATTATCGCACAGTGTCTAAACAAGATGCCTCCTGGGGAGATCAAGGTTGATGAT
GCCAAAGTGTCTCCACCTAAGCGAGCAGAGATGAAGACTTCCATGGAGTCACTGATTCAT
CACTTTAAGTTGTATACTGAGGGCTACCAAGTTCCTCCAGGAGCCACATATACTGCCATT
GAGGCTCCCAAGGGAGAGTTTGGGGTGTACCTGGTGTCTGATGGCAGCAGCCGCCCTTAT
CGATGCAAGATCAAGGCTCCTGGTTTTGCCCATCTGGCTGGTTTGGACAAGATGTCTAAG
GGACACATGTTGGCAGATGTCGTTGCCATCATAGGTACCCAAGATATTGTATTTGGAGAA
GTAGATCGGTGA

Fig. 47

SEQ ID No. 47
NDUFS2
>ENSG00000158864|1|protein_coding|ENST00000392179|ENSP00000376018
ATGGCGGCGCTGAGGGCTTTGTGCGGCTTCCGGGGCGTCGCGGCCCAGGTGCTGCGGCCT
GGGGCTGGAGTCCGATTGCCGATTCAGCCCAGCAGAGGTGTTCGGCAGTGGCAGCCAGAT
GTGGAATGGGCACAGCAGTTTGGGGGAGCTGTTATGTACCCAAGCAAAGAAACAGCCCAC
TGGAAGCCTCCACCTTGGAATGATGTGGACCCTCCAAAGGACACAATTGTGAAGAACATT
ACCCTGAACTTTGGGCCCCAACACCCAGCAGCGCATGGTGTCCTGCGACTAGTGATGGAA
TTGAGTGGGGAGATGGTGCGGAAGTGTGATCCTCACATCGGGCTCCTGCACCGAGGCACT
GAGAAGCTCATTGAATACAAGACCTATCTTCAGGCCCTTCCATACTTTGACCGGCTAGAC
TATGTGTCCATGATGTGTAACGAACAGGCCTATTCTCTAGCTGTGGAGAAGTTGCTAAAC
ATCCGGCCTCCTCCTCGGGCACAGTGGATCCGAGTGCTGTTTGGAGAAATCACACGTTTG
TTGAACCACATCATGGCTGTGACCACACATGCCCTGGACCTTGGGGCCATGACCCCTTTC
TTCTGGCTGTTTGAAGAAAGGGAGAAGATGTTTGAGTTCTACGAGCGAGTGTCTGGAGCC
CGAATGCATGCTGCTTATATCCGGCCAGGAGGAGTGCACCAGGACCTACCCCTTGGGCTT
ATGGATGACATTTATCAGTTTTCTAAGAACTTCTCTCTTCGGCTTGATGAGTTGGAGGAG
TTGCTGACCAACAATAGGATCTGGCGAAATCGGACAATTGACATTGGGGTTGTAACAGCA
GAAGAAGCACTTAACTATGGTTTTAGTGGAGTGATGCTTCGGGCTCAGGCATCCAGTGG
GACCTGCGGAAGACCCAGCCCTATGATGTTTACGACCAGGTTGAGTTTGATGTTCCTGTT
GGTTCTCGAGGGGACTGCTATGATAGGTACCTGTGCCGGGTGGAGGAGATGCGCCAGTCC
CTGAGAATTATCGCACAGTGTCTAAACAAGATGCCTCCTGGGGAGATCAAGGTTGATGAT
GCCAAAGTGTCTCCACCTAAGCGAGCAGAGATGAAGACTTCCATGGAGTCACTGATTCAT
CACTTTAAGTTGTATACTGAGGGCTACCAAGTTCCTCCAGGAGCCACATATACTGCCATT
GAGGCTCCCAAGGGAGAGTTTGGGGTGTACCTGGTGTCTGATGGCAGCAGCCGCCCTTAT
CGATGCAAGATCAAGGCTCCTGGTTTTGCCCATCTGGCTGGTTTGGACAAGATGTCTAAG
GGACACATGTTGGCAGATGTCGTTGCCATCATAGGTACCCAAGATATTGTATTTGGAGAA
GTAGATCGGTGA

Fig. 48

SEQ ID No. 48
IRAK1
>ENSG00000184216|X|protein_coding|ENST00000369980|ENSP00000358997
ATGGCCGGGGGGCCGGGCCCGGGGGAGCCCGCAGCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGCCGCCCTGATCGTGCGCGACCAGACCGAGCTGCGGCTGTGCGAG
CGCTCCGGGCAGCGCACGGCCAGCGTCCTGTGGCCCTGGATCAACCGCAACGCCCGTGTG
GCCGACCTCGTGCACATCCTCACGCACCTGCAGCTGCTCCGTGCGCGGGACATCATCACA
GCCTGGCACCCTCCCGCCCCGCTTCCGTCCCCAGGCACCACTGCCCGAGGCCCAGCAGC
ATCCCTGCACCCGCCGAGGCCGAGGCCTGGAGCCCCCGGAAGTTGCCATCCTCAGCCTCC
ACCTTCCTCTCCCCAGCTTTTCCAGGCTCCCAGACCCATTCAGGGCCTGAGCTCGGCCTG
GTCCCAAGCCCTGCTTCCCTGTGGCCTCCACCGCCATCTCCAGCCCCTTCTTCTACCAAG
CCAGGCCCAGAGAGCTCAGTGTCCCTCCTGCAGGGAGCCCGCCCCTTTCCGTTTTGCTGG
CCCCTCTGTGAGATTTCCCGGGGCACCCACAACTTCTCGGAGGAGCTCAAGATCGGGGAG
GGTGGCTTTGGGTGCGTGTACCGGGCGGTGATGAGGAACACGGTGTATGCTGTGAAGAGG
CTGAAGGAGAACGCTGACCTGGAGTGGACTGCAGTGAAGCAGAGCTTCCTGACCGAGGTG
GAGCAGCTGTCCAGGTTTCGTCACCCAAACATTGTGGACTTTGCTGGCTACTGTGCTCAG
AACGGCTTCTACTGCCTGGTGTACGGCTTCCTGCCCAACGGCTCCCTGGAGGACCGTCTC
CACTGCCAGACCCAGGCCTGCCCACCTCTCTCCTGGCCTCAGCGACTGGACATCCTTCTG
GGTACAGCCCGGGCAATTCAGTTTCTACATCAGGACAGCCCCAGCCTCATCCATGGAGAC
ATCAAGAGTTCCAACGTCCTTCTGGATGAGAGGCTGACACCCAAGCTGGGAGACTTTGGC
CTGGCCCGGTTCAGCCGCTTTGCCGGGTCCAGCCCCAGCCAGAGCAGCATGGTGGCCCGG
ACACAGACAGTGCGGGGCACCCTGGCCTACCTGCCCGAGGAGTACATCAAGACGGGAAGG
CTGGCTGTGGACACGGACACCTTCAGCTTTGGGGTGGTAGTGCTAGAGACCTTGGCTGGT
CAGAGGGCTGTGAAGACGCACGGTGCCAGGACCAAGTATCTGAAAGACCTGGTGGAAGAG
GAGGCTGAGGAGGCTGGAGTGGCTTTGAGAAGCACCCAGAGCACACTGCAAGCAGGTCTG
GCTGCAGATGCCTGGGCTGCTCCCATCGCCATGCAGATCTACAAGAAGCACCTGGACCCC
AGGCCCGGGCCCTGCCCACCTGAGCTGGGCCTGGGCCTGGGCCAGCTGGCCTGCTGCTGC
CTGCACCGCCGGGCCAAAAGGAGGCCTCCTATGACCCAGGTGTACGAGAGGCTAGAGAAG
CTGCAGGCAGTGGTGGCGGGGGTGCCCGGGCATTCGGAGGCCGCCAGCTGCATCCCCCCT
TCCCCGCAGGAGAACTCCTACGTGTCCAGCACTGGCAGAGCCCACAGTGGGGCTGCTCCA
TGGCAGCCCCTGGCAGCGCCATCAGGAGCCAGTGCCCAGGCAGCAGAGCAGCTGCAGAGA
GGCCCCAACCAGCCCGTGGAGAGTGACGAGAGCCTAGGCGGCCTCTCTGCTGCCCTGCGC
TCCTGGCACTTGACTCCAAGCTGCCCTCTGGACCCAGCACCCCTCAGGGAGGCCGGCTGT
CCTCAGGGGGACACGGCAGGAGAATCGAGCTGGGGGAGTGGCCCAGGATCCCGGCCCACA
GCCGTGGAAGGACTGGCCCTTGGCAGCTCTGCATCATCGTCGTCAGAGCCACCGCAGATT
ATCATCAACCCTGCCCGACAGAAGATGGTCCAGAAGCTGGCCCTGTACGAGGATGGGGCC
CTGGACAGCCTGCAGCTGCTGTCGTCCAGCTCCCTCCCAGGCTTGGGCCTGGAACAGGAC
AGGCAGGGGCCCGAAGAAAGTGATGAATTTCAGAGCTGA

Fig. 49

SEQ ID No. 49
IRAK1
>ENSG00000184216|X|protein_coding|ENST00000369973|ENSP00000358990
ATGGCCGGGGGCCGGGCCGGGGGAGCCCGCAGCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGTGGGTGGCGGCGGGCTGCCGGGGGGCGGGAGGCGCGCGGGCTC
CTGGCGCCGACGCCTGACGCCCCCGCCCCGCAGCCGCCCTGATCGTGCGCGACCAGACC
GAGCTGCGGCTGTGCGAGCGCTCCGGGCAGCGCACGGCCAGCGTCCTGTGGCCCTGGATC
AACCGCAACGCCCGTGTGGCCGACCTCGTGCACATCCTCACGCACCTGCAGCTGCTCCGT
GCGCGGGACATCATCACAGCCTGGCACCCTCCCGCCCCGCTTCCGTCCCCAGGCACCACT
GCCCCGAGGCCCAGCAGCATCCCTGCACCCGCCGAGGCCGAGGCCTGGAGCCCCCGGAAG
TTGCCATCCTCAGCCTCCACCTTCCTCTCCCCAGCTTTTCCAGGCTCCCAGACCCATTCA
GGGCCTGAGCTCGGCCTGGTCCCAAGCCCTGCTTCCCTGTGGCCTCCACCGCCATCTCCA
GCCCCTTCTTCTACCAAGCCAGGCCCAGAGAGCTCAGTGTCCCTCCTGCAGGGAGCCCGC
CCCTTTCCGTTTTGCTGGCCCCTCTGTGAGATTTCCGGGGCACCCACAACTTCTCGGAG
GAGCTCAAGATCGGGGAGGGTGGCTTTGGGTGCGTGTACCGGGCGGTGATGAGGAACACG
GTGTATGCTGTGAAGAGGCTGAAGGAGAACGCTGACCTGGAGTGGACTGCAGTGAAGCAG
AGCTTCCTGACCGAGGTGGAGCAGCTGTCCAGGTTTCGTCACCCAAACATTGTGGACTTT
GCTGGCTACTGTGCTCAGAACGGCTTCTACTGCCTGGTGTACGGCTTCCTGCCCAACGGC
TCCCTGGAGGACCGTCTCCACTGCCAGACCCAGGCCTGCCCACCTCTCTCCTGGCCTCAG
CGACTGGACATCCTTCTGGGTACAGCCCGGGCAATTCAGTTTCTACATCAGGACAGCCCC
AGCCTCATCCATGGAGACATCAAGAGTTCCAACGTCCTTCTGGATGAGAGGCTGACACCC
AAGCTGGGAGACTTTGGCCTGGCCCGGTTCAGCCGCTTTGCCGGGTCCAGCCCCAGCCAG
AGCAGCATGGTGGCCCGGACACAGACAGTGCGGGGCACCCTGGCCTACCTGCCCGAGGAG
TACATCAAGACGGGAAGGCTGGCTGTGGACACGGACACCTTCAGCTTTGGGGTGGTAGTG
CTAGAGACCTTGGCTGGTCAGAGGGCTGTGAAGACGCACGGTGCCAGGACCAAGTATCTG
AAAGACCTGGTGGAAGAGGAGGCTGAGGAGGCTGGAGTGGCTTTGAGAAGCACCCAGAGC
ACACTGCAAGCAGGTCTGGCTGCAGATGCCTGGGCTGCTCCCATCGCCATGCAGATCTAC
AAGAAGCACCTGGACCCCAGGCCCGGGCCTGCCCACCTGAGCTGGGCCTGGGCCTGGGC
CAGCTGGCCTGCTGCTGCCTGCACCGCCGGGCCAAAAGGAGGCCTCCTATGACCCAGGAG
AACTCCTACGTGTCCAGCACTGGCAGAGCCCACAGTGGGCTGCTCCATGGCAGCCCTG
GCAGCGCCATCAGGAGCCAGTGCCCAGGCAGCAGAGCAGCTGCAGAGAGGCCCCAACCAG
CCCGTGGAGAGTGACGAGAGCCTAGGCGGCCTCTCTGCTGCCCTGCGCTCCTGGCACTTG
ACTCCAAGCTGCCCTCTGGACCCAGCACCCCTCAGGGAGGCCGGCTGTCCTCAGGGGAC
ACGGCAGGAGAATCGAGCTGGGGGAGTGGCCCAGGATCCCGGCCCACAGCCGTGGAAGGA
CTGGCCCTTGGCAGCTCTGCATCATCGTCGTCAGAGCCACCGCAGATTATCATCAACCCT
GCCCGACAGAAGATGGTCCAGAAGCTGGCCCTGTACGAGGATGGGGCCCTGGACAGCCTG
CAGCTGCTGTCGTCCAGCTCCCTCCCAGGCTTGGGCCTGGAACAGGACAGGCAGGGGCCC
GAAGAAAGTGATGAATTTCAGAGCTGA

Fig. 50

SEQ ID No. 50
IRAK1
>ENSG00000184216|X|protein_coding|ENST00000369974|ENSP00000358991
ATGGCCGGGGGGCCGGGCCCGGGGGAGCCCGCAGCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGCCGCCCTGATCGTGCGCGACCAGACCGAGCTGCGGCTGTGCGAG
CGCTCCGGGCAGCGCACGGCCAGCGTCCTGTGGCCCTGGATCAACCGCAACGCCCGTGTG
GCCGACCTCGTGCACATCCTCACGCACCTGCAGCTGCTCCGTGCGCGGGACATCATCACA
GCCTGGCACCCTCCCGCCCCGCTTCCGTCCCAGGCACCACTGCCCCGAGGCCCAGCAGC
ATCCCTGCACCCGCCGAGGCCGAGGCCTGGAGCCCCGGAAGTTGCCATCCTCAGCCTCC
ACCTTCCTCTCCCCAGCTTTTCCAGGCTCCCAGACCCATTCAGGGCCTGAGCTCGGCCTG
GTCCCAAGCCCTGCTTCCCTGTGGCCTCCACCGCCATCTCCAGCCCCTTCTTCTACCAAG
CCAGGCCCAGAGAGCTCAGTGTCCCTCCTGCAGGGAGCCCGCCCCTTTCCGTTTTGCTGG
CCCCTCTGTGAGATTTCCCGGGGCACCCACAACTTCTCGGAGGAGCTCAAGATCGGGGAG
GGTGGCTTTGGGTGCGTGTACCGGGCGGTGATGAGGAACACGGTGTATGCTGTGAAGAGG
CTGAAGGAGAACGCTGACCTGGAGTGGACTGCAGTGAAGCAGAGCTTCCTGACCGAGGTG
GAGCAGCTGTCCAGGTTTCGTCACCCAAACATTGTGGACTTTGCTGGCTACTGTGCTCAG
AACGGCTTCTACTGCCTGGTGTACGGCTTCCTGCCCAACGGCTCCCTGGAGGACCGTCTC
CACTGCCAGACCCAGGCCTGCCCACCTCTCCTGGCCTCAGCGACTGGACATCCTTCTG
GGTACAGCCCGGGCAATTCAGTTTCTACATCAGGACAGCCCCAGCCTCATCCATGGAGAC
ATCAAGAGTTCCAACGTCCTTCTGGATGAGAGGCTGACACCCAAGCTGGGAGACTTTGGC
CTGGCCCGGTTCAGCCGCTTTGCCGGGTCCAGCCCCAGCCAGAGCAGCATGGTGGCCCGG
ACACAGACAGTGCGGGCACCCTGGCCTACCTGCCCGAGGAGTACATCAAGACGGGAAGG
CTGGCTGTGGACACGGACACCTTCAGCTTTGGGGTGGTAGTGCTAGAGACCTTGGCTGGT
CAGAGGGCTGTGAAGACGCACGGTGCCAGGACCAAGTATCTGGTGTACGAGAGGCTAGAG
AAGCTGCAGGCAGTGGTGGCGGGGGTGCCCGGGCATTCGGAGGCCGCCAGCTGCATCCCC
CCTTCCCCGCAGGAGAACTCCTACGTGTCCAGCACTGGCAGAGCCCACAGTGGGGCTGCT
CCATGGCAGCCCCTGGCAGCGCCATCAGGAGCCAGTGCCCAGGCAGCAGAGCAGCTGCAG
AGAGGCCCCAACCAGCCCGTGGAGAGTGACGAGAGCCTAGGCGGCCTCTCTGCTGCCCTG
CGCTCCTGGCACTTGACTCCAAGCTGCCCTCTGGACCCAGCACCCTCAGGGAGGCCGGC
TGTCCTCAGGGGGACACGGCAGGAGAATCGAGCTGGGGGAGTGGCCCAGGATCCCGGCCC
ACAGCCGTGGAAGGACTGGCCCTTGGCAGCTCTGCATCATCGTCGTCAGAGCCACCGCAG
ATTATCATCAACCCTGCCCGACAGAAGATGGTCCAGAAGCTGGCCCTGTACGAGGATGGG
GCCCTGGACAGCCTGCAGCTGCTGTCGTCCAGCTCCCTCCCAGGCTTGGGCCTGGAACAG
GACAGGCAGGGGCCCGAAGAAAGTGATGAATTTCAGAGCTGA

Fig. 51

SEQ ID No. 51
IRAK1
>ENSG00000184216|X|protein_coding|ENST00000393682|ENSP00000377287
ATGGCCGGGGGCCGGGCCGGGGGAGCCCGCAGCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGGTGGGTGGCGGCGGGCTGCCGGGGGGCGGGAGGCGCGCGGGCTC
CTGGCGCCGACGCCTGACGCCCCCGCCCCGCAGCCGCCCTGATCGTGCGCGACCAGACC
GAGCTGCGGCTGTGCGAGCGCTCCGGGCAGCGCACGGCCAGCGTCCTGTGGCCCTGGATC
AACCGCAACGCCCGTGTGGCCGACCTCGTGCACATCCTCACGCACCTGCAGCTGCTCCGT
GCGCGGGACATCATCACAGCCTGGCACCCTCCCGCCCCGCTTCCGTCCCCAGGCACCACT
GCCCCGAGGCCCAGCAGCATCCCTGCACCCGCCGAGGCCGAGGCCTGGAGCCCCCGGAAG
TTGCCATCCTCAGCCTCCACCTTCCTCTCCCCAGCTTTTCCAGGCTCCCAGACCCATTCA
GGGCCTGAGCTCGGCCTGGTCCCAAGCCCTGCTTCCCTGTGGCCTCCACCGCCATCTCCA
GCCCCTTCTTCTACCAAGCCAGGCCCAGAGAGCTCAGTGTCCCTCCTGCAGGGAGCCCGC
CCCTTTCCGTTTTGCTGGCCCCTCTGTGAGATTTCCCGGGGCACCCACAACTTCTCGGAG
GAGCTCAAGATCGGGGAGGGTGGCTTTGGGTGCGTGTACCGGGCGGTGATGAGGAACACG
GTGTATGCTGTGAAGAGGCTGAAGGAGAACGCTGACCTGGAGTGGACTGCAGTGAAGCAG
AGCTTCCTGACCGAGGTGGAGCAGCTGTCCAGGTTTCGTCACCCAAACATTGTGGACTTT
GCTGGCTACTGTGCTCAGAACGGCTTCTACTGCCTGGTGTACGGCTTCCTGCCCAACGGC
TCCCTGGAGGACCGTCTCCACTGCCAGACCCAGGCCTGCCCACCTCTCTCCTGGCCTCAG
CGACTGGACATCCTTCTGGGTACAGCCCGGGCAATTCAGTTTCTACATCAGGACAGCCCC
AGCCTCATCCATGGAGACATCAAGAGTTCCAACGTCCTTCTGGATGAGAGGCTGACACCC
AAGCTGGGAGACTTTGGCCTGGCCCGGTTCAGCCGCTTTGCCGGGTCCAGCCCCAGCCAG
AGCAGCATGGTGGCCCGGACACAGACAGTGCGGGGCACCCTGGCCTACCTGCCCGAGGAG
TACATCAAGACGGGAAGGCTGGCTGTGGACACGGACACCTTCAGCTTTGGGGTGGTAGTG
CTAGAGACCTTGGCTGGTCAGAGGGCTGTGAAGACGCACGGTGCCAGGACCAAGTATCTG
AAAGACCTGGTGGAAGAGGAGGCTGAGGAGGCTGGAGTGGCTTTGAGAAGCACCCAGAGC
ACACTGCAAGCAGGTCTGGCTGCAGATGCCTGGGCTGCTCCCATCGCCATGCAGATCTAC
AAGAAGCACCTGGGCCAGCTGGCCTGCTGCTGCCTGCACCGCCGGGCCAAAAGGAGGCCT
CCTATGACCCAGGAGAACTCCTACGTGTCCAGCACTGGCAGAGCCCACAGTGGGCTGCT
CCATGGCAGCCCCTGGCAGCGCCATCAGGAGCCAGTGCCCAGGCAGCAGAGCAGCTGCAG
AGAGGCCCAACCAGCCCGTGGAGAGTGACGAGAGCCTAGGCGGCCTCTCTGCTGCCCTG
CGCTCCTGGCACTTGACTCCAAGCTGCCCTCTGGACCCAGCACCCCTCAGGGAGGCCGGC
TGTCCTCAGGGGACACGGCAGGAGAATCGAGCTGGGGGAGTGGCCCAGGATCCCGGCCC
ACAGCCGTGGAAGGACTGGCCCTTGGCAGCTCTGCATCATCGTCGTCAGAGCCACCGCAG
ATTATCATCAACCCTGCCCGACAGAAGATGGTCCAGAAGCTGGCCCTGTACGAGGATGGG
GCCCTGGACAGCCTGCAGCTGCTGTCGTCCAGCTCCCTCCCAGGCTTGGGCCTGGAACAG
GACAGGCAGGGGCCCGAAGAAAGTGATGAATTTCAGAGCTGA

Fig. 52

SEQ ID No. 52
IRAK1
>ENSG00000184216|X|protein_coding|ENST00000393687|ENSP00000377291
ATGGCCGGGGGGCCGGGCCCGGGGGAGCCCGCAGCCCCCGGCGCCCAGCACTTCTTGTAC
GAGGTGCCGCCCTGGGTCATGTGCCGCTTCTACAAAGTGATGGACGCCCTGGAGCCCGCC
GACTGGTGCCAGTTCGCCGCCCTGATCGTGCGCGACCAGACCGAGCTGCGGCTGTGCGAG
CGCTCCGGGCAGCGCACGGCCAGCGTCCTGTGGCCCTGGATCAACCGCAACGCCCGTGTG
GCCGACCTCGTGCACATCCTCACGCACCTGCAGCTGCTCCGTGCGCGGGACATCATCACA
GCCTGGCACCCTCCCGCCCCGCTTCCGTCCCCAGGCACCACTGCCCCGAGGCCCAGCAGC
ATCCCTGCACCCGCCGAGGCCGAGGCCTGGAGCCCCGGAAGTTGCCATCCTCAGCCTCC
ACCTTCCTCTCCCCAGCTTTTCCAGGCTCCCAGACCCATTCAGGGCCTGAGCTCGGCCTG
GTCCCAAGCCCTGCTTCCCTGTGGCCTCCACCGCCATCTCCAGCCCCTTCTTCTACCAAG
CCAGGCCCAGAGAGCTCAGTGTCCCTCCTGCAGGGAGCCCGCCCCTTTCCGTTTTGCTGG
CCCCTCTGTGAGATTTCCCGGGGCACCCACAACTTCTCGGAGGAGCTCAAGATCGGGGAG
GGTGGCTTTGGGTGCGTGTACCGGGCGGTGATGAGGAACACGGTGTATGCTGTGAAGAGG
CTGAAGGAGAACGCTGACCTGGAGTGGACTGCAGTGAAGCAGAGCTTCCTGACCGAGGTG
GAGCAGCTGTCCAGGTTTCGTCACCCAAACATTGTGGACTTTGCTGGCTACTGTGCTCAG
AACGGCTTCTACTGCCTGGTGTACGGCTTCCTGCCCAACGGCTCCCTGGAGGACCGTCTC
CACTGCCAGACCCAGGCCTGCCCACCTCTCTCCTGGCCTCAGCGACTGGACATCCTTCTG
GGTACAGCCCGGGCAATTCAGTTTCTACATCAGGACAGCCCCAGCCTCATCCATGGAGAC
ATCAAGAGTTCCAACGTCCTTCTGGATGAGAGGCTGACACCCAAGCTGGGAGACTTTGGC
CTGGCCCGGTTCAGCCGCTTTGCCGGGTCCAGCCCCAGCCAGAGCAGCATGGTGGCCCGG
ACACAGACAGTGCGGGGCACCCTGGCCTACCTGCCCGAGGAGTACATCAAGACGGGAAGG
CTGGCTGTGGACACGGACACCTTCAGCTTTGGGGTGGTAGTGCTAGAGACCTTGGCTGGT
CAGAGGGCTGTGAAGACGCACGGTGCCAGGACCAAGTATCTGAAAGACCTGGTGGAAGAG
GAGGCTGAGGAGGCTGGAGTGGCTTTGAGAAGCACCCAGAGCACACTGCAAGCAGGTCTG
GCTGCAGATGCCTGGGCTGCTCCCATCGCCATGCAGATCTACAAGAAGCACCTGGACCCC
AGGCCCGGGCCCTGCCCACCTGAGCTGGGCCTGGGCCTGGGCCAGCTGGCCTGCTGCTGC
CTGCACCGCCGGGCCAAAAGGAGGCCTCCTATGACCCAGGAGAACTCCTACGTGTCCAGC
ACTGGCAGAGCCCACAGTGGGGCTGCTCCATGGCAGCCCCTGGCAGCGCCATCAGGAGCC
AGTGCCCAGGCAGCAGAGCAGCTGCAGAGAGGCCCCAACCAGCCCGTGGAGAGTGACGAG
AGCCTAGGCGGCCTCTCTGCTGCCCTGCGCTCCTGGCACTTGACTCCAAGCTGCCCTCTG
GACCCAGCACCCCTCAGGGAGGCCGGCTGTCCTCAGGGGACACGGCAGGAGAATCGAGC
TGGGGGAGTGGCCCAGGATCCCGGCCCACAGCCGTGGAAGGACTGGCCCTTGGCAGCTCT
GCATCATCGTCGTCAGAGCCACCGCAGATTATCATCAACCCTGCCCGACAGAAGATGGTC
CAGAAGCTGGCCCTGTACGAGGATGGGGCCCTGGACAGCCTGCAGCTGCTGTCGTCCAGC
TCCCTCCCAGGCTTGGGCCTGGAACAGGACAGGCAGGGGCCCGAAGAAAGTGATGAATTT
CAGAGCTGA

Fig. 53

SEQ ID No. 53
C20orf149
>ENSG00000125534|20|protein_coding|ENST00000370177|ENSP00000359196
ATGGCGGCCATCCCCTCCAGCGGCTCGCTCGTGGCCACCCACGACTACTACCGGCGCCGC
CTGGGTTCCACTTCCAGCAACAGCTCCTGCAGCAGTACCGAGTGCCCCGGGGAAGCCATT
CCCCACCCCCCAGGTGAGTGCAGGATCGCCCCTTTCTCCCCCCGCTCCTCCAGGAGCTGG
CAGCATCAAGACCCCACTTCGCTTCTCTCAGGTCTCCCCAAGGCTGACCCGGGTCATTGG
TGGGCCAGCTTCTTTTTCGGGAAGTCCACCCTCCCGTTCATGGCCACGGTGTTGGAGTCC
GCAGAGCACTCGGAACCTCCCCAGGCCTCCAGCAGCATGACCGCCTGTGGCCTGGCTCGG
GACGCCCCGAGGAAGCAGCCCGGCGGTCAGTCCAGCACAGCCAGCGCTGGGCCCCCGTCC
TGA

Fig. 54

SEQ ID No. 54
C20orf149
>ENSG00000125534|20|protein_coding|ENST00000370178|ENSP00000359197
ATGGCGGCCATCCCCTCCAGCGGCTCGCTCGTGGCCACCCACGACTACTACCGGCGCCGC
CTGGGTTCCACTTCCAGCAACAGCTCCTGCAGCAGTACCGAGTGCCCCGGGGAAGCCATT
CCCCACCCCCAGGTCTCCCCAAGGCTGACCCGGGTCATTGGTGGGCCAGCTTCTTTTTC
GGGAAGTCCACCCTCCCACCCCCCACCCTGTAA

Fig. 55

SEQ ID No. 55
C20orf149
>ENSG00000125534|20|protein_coding|ENST00000370179|ENSP00000359198
ATGGCGGCCATCCCCTCCAGCGGCTCGCTCGTGGCCACCCACGACTACTACCGGCGCCGC
CTGGGTTCCACTTCCAGCAACAGCTCCTGCAGCAGTACCGAGTGCCCCGGGGAAGCCATT
CCCCACCCCCCAGGTCTCCCCAAGGCTGACCCGGGTCATTGGTGGGCCAGCTTCTTTTTC
GGGAAGTCCACCCTCCCGTTCATGGCCACGGTGTTGGAGTCCGCAGAGCACTCGGAACCT
CCCCAGGCCTCCAGCAGCATGACCGCCTGTGGCCTGGCTCGGGACGCCCCGAGGAAGCAG
CCCGGCGGTCAGTCCAGCACAGCCAGCGCTGGGCCCCGTCCTGA

Fig. 56

SEQ ID No. 56
PSCD2L
>ENSG00000105443|19|protein_coding|ENST00000325139|ENSP00000314566
ATGGAGGACGGCGTCTATGAACCCCCAGACCTGACTCCGGAGGAGCGGATGGAGCTGGAG
AACATCCGGCGGCGGAAGCAGGAGCTGCTGGTGGAGATTCAGCGCCTGCGGGAGGAGCTC
AGTGAAGCCATGAGCGAGGTGGAGGGGCTGGAGGCCAATGAGGGCAGTAAGACCTTGCAA
CGGAACCGGAAGATGGCAATGGGCAGGAAGAAGTTCAACATGGACCCCAAGAAGGGGATC
CAGTTCTTGGTGGAGAATGAACTGCTGCAGAACACACCCGAGGAGATCGCCCGCTTCCTG
TACAAGGGCGAGGGGCTGAACAAGACAGCCATCGGGGACTACCTGGGGGAGAGGGAAGAA
CTGAACCTGGCAGTGCTCCATGCTTTTGTGGATCTGCATGAGTTCACCGACCTCAATCTG
GTGCAGGCCCTCAGGCAGTTTCTATGGAGCTTTCGCCTACCCGGAGAGGCCCAGAAAATT
GACCGGATGATGGAGGCCTTCGCCCAGCGATACTGCCTGTGCAACCCTGGGGTTTTCCAG
TCCACAGACACGTGCTATGTGCTGTCCTTCGCCGTCATCATGCTCAACACCAGTCTCCAC
AATCCCAATGTCCGGGACAAGCCGGGCCTGGAGCGCTTTGTGGCCATGAACCGGGGCATC
AACGAGGGCGGGGACCTGCCTGAGGAGCTGCTCAGGAACCTGTACGACAGCATCCGAAAT
GAGCCCTTCAAGATTCCTGAGGATGACGGGAATGACCTGACCCACACCTTCTTCAACCCG
GACCGGGAGGGCTGGCTCCTGAAGCTGGGTAGGGCCGGGTGAAGACGTGGAAGCGGCGC
TGGTTTATCCTCACAGACAACTGCCTCTACTACTTTGAGTACACCACGGACAAGGAGCCC
CGAGGAATCATCCCCCTGGAGAATCTGAGCATCCGAGAGGTGGACGACCCCCGGAAACCG
AACTGCTTTGAACTTTACATCCCCAACAACAAGGGGCAGCTCATCAAAGCCTGCAAAACT
GAGGCGGACGGCCGAGTGGTGGAGGGAAACCACATGGTGTACCGGATCTCGGCCCCCACG
CAGGAGGAGAAGGACGAGTGGATCAAGTCCATCCAGGCGGCTGTGAGTGTGGACCCCTTC
TATGAGATGCTGGCAGCGAGAAGAAGCGGATTTCAGTCAAGAAGAAGCAGGAGCAGCCC
TGA

Fig. 57

SEQ ID No. 57
PSCD2L
>ENSG00000105443|19|protein_coding|ENST00000391881|ENSP00000375753
ATGGAGGACGGCGTCTATGAACCCCAGACCTGACTCCGGAGGAGCGGATGGAGCTGGAG
AACATCCGGCGGCGGAAGCAGGAGCTGCTGGTGGAGATTCAGCGCCTGCGGGAGGAGCTC
AGTGAAGCCATGAGCGAGGTGGAGGGGCTGGAGGCCAATGAGGGCAGTAAGACCTTGCAA
CGGAACCGGAAGATGGCAATGGGCAGGAAGAAGTTCAACATGGACCCCAAGAAGGGGATC
CAGTTCTTGGTGGAGAATGAACTGCTGCAGAACACACCCGAGGAGATCGCCCGCTTCCTG
TACAAGGGCGAGGGGCTGAACAAGACAGCCATCGGGGACTACCTGGGGGAGAGGGAAGAA
CTGAACCTGGCAGTGCTCCATGCTTTTGTGGATCTGCATGAGTTCACCGACCTCAATCTG
GTGCAGGCCCTCAGGCAGTTTCTATGGAGCTTTCGCCTACCCGGAGAGGCCCAGAAAATT
GACCGGATGATGGAGGCCTTCGCCCAGCGATACTGCCTGTGCAACCCTGGGGTTTTCCAG
TCCACAGACACGTGCTATGTGCTGTCCTTCGCCGTCATCATGCTCAACACCAGTCTCCAC
AATCCCAATGTCCGGGACAAGCCGGGCCTGGAGCGCTTTGTGGCCATGAACCGGGGCATC
AACGAGGGCGGGGACCTGCCTGAGGAGCTGCTCAGGAACCTGTACGACAGCATCCGAAAT
GAGCCCTTCAAGATTCCTGAGGATGACGGGAATGACCTGACCCACACCTTCTTCAACCCG
GACCGGGAGGGCTGGCTCCTGAAGCTGGGGGGCCGGGTGAAGACGTGGAAGCGGCGCTGG
TTTATCCTCACAGACAACTGCCTCTACTACTTTGAGTACACCACGGACAAGGAGCCCCGA
GGAATCATCCCCCTGGAGAATCTGAGCATCCGAGAGGTGGACGACCCCCGGAAACCGAAC
TGCTTTGAACTTTACATCCCCAACAACAAGGGGCAGCTCATCAAAGCCTGCAAAACTGAG
GCGGACGGCCGAGTGGTGGAGGGAAACCACATGGTGTACCGGATCTCGGCCCCCACGCAG
GAGGAGAAGGACGAGTGGATCAAGTCCATCCAGGCGGCTGTGAGTGTGGACCCCTTCTAT
GAGATGCTGGCAGCGAGAAAGAAGCGGATTTCAGTCAAGAAGAAGCAGGAGCAGCCCTGA

Fig. 58

SEQ ID No. 58
PPIA
>ENSG00000198618|21|protein_coding|ENST00000358455|ENSP00000351238
ATGGTCAACCCCACCGTGTTCTTCGACATTGCCGTCGACGGCGAGCCCTTGGGCCGCGTC
TCCTTTGAGCTGTTTGCAGACAAGGTCCCAAAGACAGCAGAAAATTTTCGTGCTCTGAGC
ACTGGAGAGAAAGGATTTGGTTATAAGGGTTCCTGCTTTCACAGAATTATTCCAGGGTTT
ATGTGTCAGGGTGGTGACTTCACACGCCATAATGGCACTGGTGGCAAGTCCATCTATGGG
GAGAAATTTGAAGATGAGAACTTCATCCTAAAGCATACAGGTCCTGGCATCTTGTCCATG
GCAAATGCTGGACCCAACACAAATGGATCCCAGTTTTTCATCTGCACTGCCAAGACTGAG
TGGTTGGATGGCAAGCATGTGGTGTTTGGCAAAGTGAAAGAAGGCATGAATATTGTGGAG
GCCATGGAGCGCTTTGGGTCCAGGAATGGCAAGACCAGCAAGAAGATCACCATTGCTGAC
TGTGGACAACTCGAATAA

Fig. 59

SEQ ID No. 59
MGTRDDEYDYLFKVVLIGDSGVGKSNLLSRFTRNEFNLESKSTIGVEFATRSIQVDGKTI
KAQIWDTAGQERYRAITSAYYRGAVGALLVYDIAKHLTYENVERWLKELRDHADSNIVIM
LVGNKSDLRHLRAVPTDEARAFAEKNNLSFIETSALDSTNVEEAFKNILTEIYRIVSQKQ
IADRAAHDESPGNNVVDISVPPTTDGQKPNKLQCCQNL*

Fig. 60

SEQ ID No. 60
MAAADGDDSLYPIAVLIDELRNEDVQLRLNSIKKLSTIALALGVERTRSELLPFLTDTIY
DEDEVLLALAEQLGTFTTLVGGPEYVHCLLPPLESLATVEETVVRDKAVESLRAISHEHS
PSDLEAHFVPLVKRLAGGDWFTSRTSACGLFSVCYPRVSSAVKAELRQYFRNLCSDDTPM
VRRAAASKLGEFAKVLELDNVKSEIIPMFSNLASDEQDSVRLLAVEACVNIAQLLPQEDL
EALVMPTLRQAAEDKSWRVRYMVADKFTELQKAVGPEITKTDLVPAFQNLMKDCEAEVRA
AASHKVKEFCENLSADCRENVIMSQILPCIKELVSDANQHVKSALASVIMGLSPILGKDN
TIEHLLPLFLAQLKDECPEVRLNIISNLDCVNEVIGIRQLSQSLLPAIVELAEDAKWRVR
LAIIEYMPLLAGQLGVEFFDEKLNSLCMAWLVDHVYAIREAATSNLKKLVEKFGKEWAHA
TIIPKVLAMSGDPNYLHRMTTLFCINVLSEVCGQDITTKHMLPTVLRMAGDPVANVRFNV
AKSLQKIGPILDNSTLQSEVKPILEKLTQDQDVDVKYFAQEALTVLSLA*

Fig. 61

SEQ ID No. 61
MRTFSFASTASRSCPPSPWPLGLKGPEVSFCLSLQIPSMMKMRSSWPWQNSWEPSLPWWE
AQSTCTACCLFSVCYPRVSSAVKAELRQYFRNLCSDDTPMVRRAAASKLGEFAKVLELDN
VKSEIIPMFSNLASDEQDSVRLLAVEACVNIAQLLPQEDLEALVMPTLRQAAEDKSWRVR
YMVADKFTELQKAVGPEITKTDLVPAFQNLMKDCEAEVRAAASHKVKEFCENLSADCREN
VIMSQILPCIKELVSDANQHVKSALASVIMGLSPILGKDNTIEHLLPLFLAQLKDECPEV
RLNIISNLDCVNEVIGIRQLSQSLLPAIVELAEDAKWRVRLAIIEYMPLLAGQLGVEFFD
EKLNSLCMAWLVDHVYAIREAATSNLKKLVEKFGKEWAHATIIPKVLAMSGDPNYLHRMT
TLFCINVLSEVCGQDITTKHMLPTVLRMAGDPVANVRFNVAKSLQKIGPILDNSTLQSEV
KPILEKLTQDQDVDVKYFAQEALTVLSLA*

Fig. 62

SEQ ID No. 62
MELITILEKTVSPDRLELEAAQKFLERAAVENLPTFLVELSRVLAMPGNSQVARVAAGLQ
IKNSLTSKDPDIKAQYQQRWLAIDANARREVKNYVLQTLGTETYRPSSASQCVAGIACAE
IPVNQWPELIPQLVANVTNPNSTEHMKESTLEAIGYICQDIDPEQLQDKSNEILTAIIQG
MRKEEPSNNVKLAATNALLNSLEFTKANFDKESERHFIMQVVCEATQCPDTRVRVAALQN
LVKIMSLYYQYMETYMGPALFAITIEAMKSDIDEVALQGIEFWSNVCDEEMDLAIEASEA
AEQGRPPEHTSKFYAKGALQYLVPILTQTLTKQDENDDDDDWNPCKAAGVCLMLLATCCE
DDIVPHVLPFIKEHIKNPDWRYRDAAVMAFGCILEGPEPSQLKPLVIQAMPTLIELMKDP
SVVVRDTAAWTVGRICELLPEAAINDVYLAPLLQCLIEGLSAEPRVASNVCWAFSSLAEA
AYEAADVADDQEEPATYCLSSSFELIVQKLLETTDRPDGHQNNLRSSAYESLMEIVKNSA
KDCYPAVQKTTLVIMERLQQVLQMESHIQSTSDRIQFNDLQSLLCATLQNVLRKVQHQDA
LQISDVVMASLLRMFQSTAGSGGVQEDALMAVSTLVEVLGGEFLKYMEAFKPFLGIGLKN
YAEYQVCLAAVGLVGDLCRALQSNIIPFCDEVMQLLLENLGNENVHRSVKPQILSVFGDI
ALAIGGEFKKYLEVVLNTLQQASQAQVDKSDYDMVDYLNELRESCLEAYTGIVQGLKGDQ
ENVHPDVMLVQPRVEFILSFIDHIAGDEDHTDGVVACAAGLIGDLCTAFGKDVLKLVEAR
PMIHELLTEGRRSKTNKAKTLATWATKELRKLKNQA*

Fig. 64

SEQ ID No. 64
MGTKMADLDSPPKLSGVQQPSEGVGGGRCSEISAELIRSLTELQELEAVYERLCGEEKVV
ERELDALLEQQNTIESKMVTLHRMGPNLQLIEGDAKQLAGMITFTCNLAENVSSKVRQLD
LAKNRLYQAIQRADDILDLKFCMDGVQTALRSEDYEQAAAHTHRYLCLDKSVIELSRQGK
EGSMIDANLKLLQEAEQRLKAIVAEKFAIATKEGDLPQVERFFKIFPLLGLHEEGLRKFS
EYLCKQVASKAEENLLMVLGTDMSDRRAAVIFADTLTLLFEGIARIVETHQPIVETYYGP
GRLYTLIKYLQVECDRQVEKVVDKFIKQRDYHQQFRHVQNNLMRNSTTEKIEPRELDPIL
TEVTLMNARSELYLRFLKKRISSDFEVGDSMASEEVKQEHQKCLDKLLNNCLLSCTMQEL
IGLYVTMEEYFMRETVNKAVALDTYEKGQLTSSMVDDVFYIVKKCIGRALSSSSIDCLCA
MINLATTELESDFRDVLCNKLRMGFPATTFQDIQRGVTSAVNIMHSSLQQGKFDTKGIES
TDEAKMSFLVTLNNVEVCSENISTLKKTLESDCTKLFSQGIGGEQAQAKFDSCLSDLAAV
SNKFRDLLQEGLTELNSTAIKPQVQPWINSFFSVSHNIEEEEFNDYEANDPWVQQFILNL
EQQMAEFKASLSPVIYDSLTGLMTSLVAVELEKVVLKSTFNRLGGLQFDKELRSLIAYLT
TVTTWTIRDKFARLSQMATILNLERVTEILDYWGPNSGPLTWRLTPAEVRQVLALRIDFR
SEDIKRLRL*

Fig. 65

SEQ ID No. 65
MADLDSPPKLSGVQQPSEGVGGGRCSEISAELIRSLTELQELEAVYERLCGEEKVVEREL
DALLEQQNTIESKMVTLHRMGPNLQLIEGDAKQLAGMITFTCNLAENVSSKVRQLDLAKN
RLYQAIQRADDILDLKFCMDGVQTALRSEDYEQAAAHTHRYLCLDKSVIELSRQGKEGSM
IDANLKLLQEAEQRLKAIVAEKFAIATKEGDLPQVERFFKIFPLLGLHEEGLRKFSEYLC
KQVASKAEENLLMVLGTDMSDRRAAVIFADTLTLLFEGIARIVETHQPIVETYYGPGRLY
TLIKYLQVECDRQVEKVVDKFIKQRDYHQQFRHVQNNLMRNSTTEKIEPRELDPILTEVT
LMNARSELYLRFLKKRISSDFEVGDSMASEEVKQEHQKCLDKLLNNCLLSCTMQELIGLY
VTMEEYFMRETVNKAVALDTYEKGQLTSSMVDDVFYIVKKCIGRALSSSSIDCLCAMINL
ATTELESDFRDVLCNKLRMGFPATTFQDIQRGVTSAVNIMHSSLQQGKFDTKGIESTDEA
KMSFLVTLNNVEVCSENISTLKKTLESDCTKLFSQGIGGEQAQAKFDSCLSDLAAVSNKF
RDLLQEGLTELNSTAIKPQVQPWINSFFSVSHNIEEEEFNDYEANDPWVQQFILNLEQQM
AEFKASLSPVIYDSLTGLMTSLVAVELEKVVLKSTFNRLGGLQFDKELRSLIAYLTTVTT
WTIRDKFARLSQMATILNLERVTEILDYWGPNSGPLTWRLTPAEVRQVLALRIDFRSEDI
KRLRL*

Fig. 66

SEQ ID No. 66
MADLDSPPKLSGVQQPSEGVGGGRCSEISAELIRSLTELQELEAVYERLCGEEKVVEREL
DALLEQQNTIESKMVTLHRMGPNLQLIEGDAKQLAGMITFTCNLAENVSSKVRQLDLAKN
RLYQAIQRADDILDLKFCMDGVQTALRSEDYEQAAAHTHRYLCLDKSVIELSRQGKEGSM
IDANLKLLQEAEQRLKAIVAEKFAIATKEGDLPQVERFFKIFPLLGLHEEGLRKFSEYLC
KQVASKAEENLLMVLGTDMSDRRAAVIFADTLTLLFEGIARIVETHQPIVETYYGPGRLY
TLIKYLQVECDRQVEKVVDKFIKQRDYHQQNFVFSFF*

Fig. 67

SEQ ID No. 67
MGTKMADLDSPPKLSGVQQPSEGVGGGRCSEISAELIRSLTELQELEAVYERLCGEEKVV
ERELDALLEQQNTIESKMVTLHRMGPNLQLIEANLKLLQEAEQRLKAIVAEKFAIATKEG
DLPQVERFFKIFPLLGLHEEGLRKFSEYLCKQVASKAEENLLMVLGTDMSDRRAAVIFAD
TLTLLFEGIARIVETHQPIVETYYGPGRLYTLIKYLQVECDRQVEKVVDKFIKQRDYHQQ
FRHVQNNLMRNSTTEKIEPRELDPILTEVTLMNARSELYLRFLKKRISSDFEVGDSMASE
EVKQEHQKCLDKLLNNCLLSCTMQELIGLYVTMEEYFMRETVNKAVALDTYEKGQLTSSM
VDDVFYIVKKCIGRALSSSSIDCLCAMINLATTELESDFRDVLCNKLRMGFPATTFQDIQ
RGVTSAVNIMHSSLQQGKFDTKGIESTDEAKMSFLVTLNNVEVCSENISTLKKTLESDCT
KLFSQGIGGEQAQAKFDSCLSDLAAVSNKFRDLLQEGLTELNSTAIKPQVQPWINSFFSV
SHNIEEEEFNDYEANDPWVQQFILNLEQQMAEFKASLSPVIYDSLTGLMTSLVAVELEKV
VLKSTFNRLGGLQFDKELRSLIAYLTTVTTWTIRDKFARLSQMATILNLERVTEILDYWG
PNSGPLTWRLTPAEVRQVLALRIDFRSEDIKRLRL*

Fig. 68

SEQ ID No. 68
MEFVKCLGHPEEFYNLVRFRIGGKRKVMPKMDQDSLSSSLKTCYKYLNQTSRSFAAVIQA
LDGEMRNAVCIFYLVLRALDTLEDDMTISVEKKVPLLHNFHSFLYQPDWRFMESKEKDRQ
VLEDFPTISLEFRNLAEKYQTVIADICRRMGIGMAEFLDKHVTSEQEWDKYCHYVAGLVG
IGLSRLFSASEFEDPLVGEDTERANSMGLFLQKTNIIRDYLEDQQGGREFWPQEVWSRYV
KKLGDFAKPENIDLAVQCLNELITNALHHIPDVITYLSRLRNQSVFNFCAIPQVMAIATL
AACYNNQQVFKGAVKIRKGQAVTLMMDATNMPAVKAIIYQYMEEIYHRIPDSDPSSSKTR
QIISTIRTQNLPNCQLISRSHYSPIYLSFVMLLAALSWQYLTTLSQVTEDYVQTGEH*

Fig. 69

SEQ ID No. 69
MRASQKDFENSMNQVKLLKKDPGNEVKLKLYALYKQATEGPCNMPKPGVFDLINKAKWDA
WNALGSLPKEAARQNYVDLVSSLSPSLESSSQVEPGTDRKSTGFETLVVTSEDGITKIMF
NRPKKKNAINTEMYHEIMRALKAASKDDSIITVLTGNGDYYSSGNDLTNFTDIPPGGVEE
KAKNNAVLLREFVGCFIDFPKPLIAVVNGPAVGISVTLLGLFDAVYASDRATFHTPFSHL
GQSPEGCSSYTFPKIMSPAKATEMLIFGKKLTAGEACAQGLVTEVFPDSTFQKEVWTRLK
AFAKLPPNALRISKEVIRKREREKLHAVNAEECNVLQGRWLSDECTNAVVNFLSRKSKL*

Fig. 70

SEQ ID No. 70
MYHEIMRALKAASKDDSIITVLTGNGDYYSSGNDLTNFTDIPPGGVEEKAKNNAVLLREF
VGCFIDFPKPLIAVVNGPAVGISVTLLGLFDAVYASDRATFHTPFSHLGQSPEGCSSYTF
PKIMSPAKATEMLIFGKKLTAGEACAQGLVTEVFPDSTFQKEVWTRLKAFAKLPPNALRI
SKEVIRKREREKLHAVNAEECNVLQGRWLSDECTNAVVNFLSRKSKL*

Fig. 71

SEQ ID No. 71
MAMAYLAWRLARRSCPSSLQVTSFPVVQLHMNRTAMRASQKDFENSMNQVKLLKKDPGNE
VKLKLYALYKQATEGPCNMPKPGVFDLINKAKWDAWNALGSLPKEAARQNYVDLVSSLSP
SLESSSQVEPGTDRKSTGFETLVVTSEDGITKIMFNRPKKKNAINTEMYHEIMRALKAAS
KDDSIITVLTGNGDYYSSGNDLTNFTDIPPGGVEEKAKNNAVLLREFVGCFIDFPKPLIA
VVNGPAVGISVTLLGLFDAVYASDRATFHTPFSHLGQSPEGCSSYTFPKIMSPAKATEML
IFGKKLTAGEACAQGLVTEVFPDSTFQKEVWTRLKAFAKLPPNALRISKEVIRKREREKL
HAVNAEECNVLQGRWLSDECTNAVVNFLSRKSKL*

Fig. 72

SEQ ID No. 72
MNRTAMRASQKDFENSMNQVKLLKKDPGNEVKLKLYALYKQATEGPCNMPKPGVFDLINK
AKWDAWNALGSLPKEAARQNYVDLVSSLSPSLESSSQVEPGTDRKSTGFETLVVTSEDGI
TKIMFNRPKKKNAINTEMYHEIMRALKAASKDDSIITVLTGNGDYYSSGNDLTNFTDIPP
GGVEEKAKNNAVLLREFVGCFIDFPKPLIAVVNGPAVGISVTLLGLFDAVYASDRATFHT
PFSHLGQSPEGCSSYTFPKIMSPAKATEMLIFGKKLTAGEACAQGLVTEVFPDSTFQKEV
WTRLKAFAKLPPNALRISKEVIRKREREKLHAVNAEECNVLQGRWLSDECTNAVVNFLSR
KSKL*

Fig. 73

SEQ ID No. 73
MFNRPKKKNAINTEMYHEIMRALKAASKDDSIITVLTGNGDYYSSGNDLTNFTDIPPGGV
EEKAKNNAVLLREFVGCFIDFPKPLIAVVNGPAVGISVTLLGLFDAVYASDRATFHTPFS
HLGQSPEGCSSYTFPKIMSPAKATEMLIFGKKLTAGEACAQGLVTEVFPDSTFQKEVWTR
LKAFAKLPPNALRISKEVIRKREREKLHAVNAEECNVLQGRWLSDECTNAVVNFLSRKSK
L*

Fig. 74

SEQ ID No. 74
MFARKPPGAAPLGAMPVPDQPSSASEKTSSLSPGLNTSNGDGSETETTSAILASVKEQEL
QFERLTRELEAERQIVASQLERCKLGSETGSMSSMSSAEEQFQWQSQDGQKDIEDELTTG
LELVDSCIRSLQESGILDPQDYSTGERPSLLSQSALQLNSKPEGSFQYPASYHSNQTLAL
GETTPSQLPARGTQARATGQSFSQGTTSRAGHLAGPEPAPPPPPPPREPFAPSLGSAFHL
PDAPPAAAAAALYYSSSTLPAPPRGGSPLAAPQGGSPTKLQRGGSAPEGATYAAPRGSSP
KQSPSRLAKSYSTSSPINIVVSSAGLSPIRVTSPPTVQSTISSSPIHQLSSTIGTYATLS
PTKRLVHASEQYSKHSQELYATATLQRPGSLAAGSRASYSSQHGHLGPELRALQSPEHHI
DPIYEDRVYQKPPMRSLSQSQGDPLPPAHTGTYRTSTAPSSPGVDSVPLQRTGSQHGPQN
AAAATFQRASYAAGPASNYADPYRQLQYCPSVESPYSKSGPALPPEGTLARSPSIDSIQK
DPREFGWRDPELPEVIQMLQHQFPSVQSNAAAYLQHLCFGDNKIKAEIRRQGGIQLLVDL
LDHRMTEVHRSACGALRNLVYGKANDDNKIALKNCGGIPALVRLLRKTTDLEIRELVTGV
LWNLSSCDALKMPIIQDALAVLTNAVIIPHSGWENSPLQDDRKIQLHSSQVLRNATGCLR
NVSSAGEEARRRMRECDGLTDALLYVIQSALGSSEIDSKTVENCVCILRNLSYRLAAETS
QGQHMGTDELDGLLCGEANGKDAESSGCWGKKKKKKKSQDQWDGVGPLPDCAEPPKGIQM
LWHPSIVKPYLTLLSECSNPDTLEGAAGALQNLAAGSWKWSVYIRAAVRKEKGLPILVEL
LRIDNDRVVCAVATALRNMALDVRNKELIGKYAMRDLVHRLPGGNNSNNTASKAMSDDTV
TAVCCTLHEVITKNMENAKALRDAGGIEKLVGISKSKGDKHSPKVVKAASQVLNSMWQYR
DLRSLYKKDGWSQYHFVASSSTIERDRQRPYSSSRTPSISPVRVSPNNRSASAPASPREM
ISLKERKTDYECTGSNATYHGAKGEHTSRKDAMTAQNTGISTLYRNSYGAPAEDIKHNQV
SAQPVPQEPSRKDYETYQPFQNSTRNYDESFFEDQVHHRPPASEYTMHLGLKSTGNYVDF
YSAARPYSELNYETSHYPASPDSWV*

Fig. 75

SEQ ID No. 75
MFARKPPGAAPLGAMPVPDQPSSASEKTSSLSPGLNTSNGDGSETETTSAILASVKEQEL
QFERLTRELEAERQIVASQLERCKLGSETGSMSSMSSAEEQFQWQSQDGQKDIEDELTTG
LELVDSCIRSLQESGILDPQDYSTGERPSLLSQSALQLNSKPEGSFQYPASYHSNQTLAL
GETTPSQLPARGTQARATGQSFSQGTTSRAGHLAGPEPAPPPPPPREPFAPSLGSAFHL
PDAPPAAAAAALYYSSSTLPAPPRGGSPLAAPQGGSPTKLQRGGSAPEGATYAAPRGSSP
KQSPSRLAKSYSTSSPINIVVSSAGLSPIRVTSPPTVQSTISSSPIHQLSSTIGTYATLS
PTKRLVHASEQYSKHSQELYATATLQRPGSLAAGSRASYSSQHGHLGPELRALQSPEHHI
DPIYEDRVYQKPPMRSLSQSQGDPLPPAHTGTYRTSTAPSSPGVDSVPLQRTGSQHGPQN
AAAATFQRASYAAGPASNYADPYRQLQYCPSVESPYSKSGPALPPEGTLARSPSIDSIQK
DPREFGWRDPELPEVIQMLQHQFPSVQSNAAAYLQHLCFGDNKIKAEIRRQGGIQLLVDL
LDHRMTEVHRSACGALRNLVYGKANDDNKIALKNCGGIPALVRLLRKTTDLEIRELVTGV
LWNLSSCDALKMPIIQDALAVLTNAVIIPHSGWENSPLQDDRKIQLHSSQVLRNATGCLR
NVSSAGEEARRRMRECDGLTDALLYVIQSALGSSEIDSKTVENCVCILRNLSYRLAAETS
QGQHMGTDELDGLLCGEANGKDAESSGCWGKKKKKKKSQDQWSVYIRAAVRKEKGLPILV
ELLRIDNDRVVCAVATALRNMALDVRNKELIGKYAMRDLVHRLPGGNNSNNTASKAMSDD
TVTAVCCTLHEVITKNMENAKALRDAGGIEKLVGISKSKGDKHSPKVVKAASQVLNSMWQ
YRDLRSLYKKDGWSQYHFVASSSTIERDRQRPYSSSRTPSISPVRVSPNNRSASAPASPR
EMISLKERKTDYECTGSNATYHGAKGEHTSRKDAMTAQNTGISTLYRNSYGAPAEDIKHN
QVSAQPVPQEPSRKDYETYQPFQNSTRNYDESFFEDQVHHRPPASEYTMHLGLKSTGNYV
DFYSAARPYSELNYETSHYPASPDSWV*

Fig. 76

SEQ ID No. 76
MQGSTRRMGVMTDVHRRFLQLLMTHGVLEEWDVKRLQTHCYKVHDRNATVDKLEDFINNI
NSVLESLYIEIKRGVTEDDGRPIYALVNLATTSISKMATDFAENELDLFRKALELIIDSE
TGFASSTNILNLVDQLKGKKMRKKEAEQVLQKFVQNKWLIEKEGEFTLHGRAILEMEQYI
RETYPDAVKTCNICHSLLIQGQSCETCGIRMHLPCVAKYFQSNAEPRCPHCNDYWPHEIP
KVFDPEKERESGVLKSNKKSLRSRQH*

Fig. 77

SEQ ID No. 77
PYPLARWDALGLPVRSHMQGSTRRMGVMTDVHRRFLQLLMTHGVLEEWDVKRLQTHCYKV
HDRNATVDKLEDFINNINSVLESLYIEIKRGVTEDDGRPIYALVNLATTSISKMATDFAE
NELDLFRKALELIIDSETLRLPQTY*

Fig. 78

SEQ ID No. 78
VHLATVSASAAWDALGLPVRSHMQGSTRRMGVMTDVHRRFLQLLMTHGVLEEWDVKRLQT
HCYKVHORNATVDKLEDFINNINSVLESLYIEIKRGVTEDDGRPIYALVNLATTSISKMA
TDFAENELDLFRKALELIIDSETGFASSTNILNLVDQLKGKKMRKKEARCCRSLFKTSG*

Fig. 79

SEQ ID No. 79
MEWWASSPLRLWLLLFLLPSAQGRQKESGSKWKVFIDQINRSLENYEPCSSQNCSCYHGV
IEEDLTPFRGGISRKMMAEVVRRKLGTHYQITKNRLYRENDCMFPSRCSGVEHFILEVIG
RLPDMEMVINVRDYPQVPKWMEPAIPVFSFSKTSEYHDIMYPAWTFWEGGPAVWPIYPTG
LGRWDLFREDLVRSAAQWPWKKKNSTAYFRGSRTSPERDPLILLSRKNPKLVDAEYTKNQ
AWKSMKDTLGKPAAKDVHLVDHCKYKYLFNFRGVAASFRFKHLFLCGSLVFHVGDEWLEF
FYPQLKPWVHYIPVKTDLSNVQELLQFVKANDDVAQEIAERGSQFTRNHLQMDDITCYWE
NLLSEYSKFLSYNVTRRKGYDQIIPKMLKTEL*

Fig. 80

SEQ ID No. 80
MRRRRAGGRTMVERASKFVLVVAGSVCFMLILYQYAGPGLSLGAPGGRAPPDDLDLFPTP
DPHYEKKYYFPVRELERSLRFDMKGDDVIVFLHIQKTGGTTFGRHLVQNVRLEVPCDCRP
GQKKCTCYRPNRRETWLFSRFSTGWSCGLHADWTELTNCVPGVLDRRDSAALRTPRKFYY
ITLLRDPVSRYLSEWRHVQRGATWKTSLHMCDGRTPTPEELPPCYEGTDWSGCTLQEFMD
CPYNLANNRQVRMLADLSLVGCYNLSFIPEGKRAQLLLESAKKNLRGMAFFGLTEFQRKT
QYLFERTFNLKFIRPFMQYNSTRAGGVEVDEDTIRRIEELNDLDMQLYDYAKDLFQQRYQ
YKRQLERREQRLRSREERLLHRAKEALPREDADEPGRVPTEDYMSHIIEKW*

Fig. 81

SEQ ID No. 81
MTSCRCSVTSRSLWPALAPRRCQHTSPASAQCKQDKACRFLAAQKGAYPIIFTAWKLATA
GDQGLLLQSLNALSVLTDGQPDLLDAQGLQLLVATLTQNADEADLTCSGIRCVRHACLKH
EQNRQDLVKAGVLPLLTGAITHHGHHTDVVREACWALRVMTFDDDIRVPFGHAHNHAKMI
VQENKGLKVLIEATKAFLDNPGILSELCGTLSRLAIRNEFCQEVVDLGGLSILVSLLADC
NDHQMRDQSGVQELVKQVLSTLRAIAGNDDVKDAIVRAGGTESIVAAMTQHLTSPQVCEQ
SCAALCFLALRKPDNSRIIVEGGGAVAALQAMKAHPQKAGVQKQACMLIRNLVAHRPSRS
PSWTWGLRHSSCRPDLPTVTVRTWPRPPCGTWVVMSSSESCGQARGATWRHDPRPSLVTL
GESCDSGMGVDPCPPLSPISSVPFTMRSVFWQALGKGSGEGGAL*

Fig. 82

SEQ ID No. 82
MSERCCSRYSSGASIGCTPTSTQAKMVSKRIAQETFDAAVRENIEEFAMGPEEAVKEAVE
QFESQGVDLSNIVKTAPKVSADGSQEPTHDILQMLSDLQESVASSRPQEVSAYLTRFCDQ
CKQDKACRFLAAQKGAYPIIFTAWKLATAGDQGLLLQSLNALSVLTDGQPDLLDAQGLQL
LVATLTQNADEADLTCSGIRCVRHACLKHEQNRQDLVKAGVLPLLTGAITHHGHHTDVVR
EACWALRVMTFDDDIRVPFGHAHNHAKMIVQENKGLKVLIEATKAFLDNPGILSELCGTL
SRLAIRNEFCQEVVDLGGLSILVSLLADCNDHQMRDQSGVQELVKQVLSTLRAIAGNDDV
KDAIVRAGGTESIVAAMTQHLTSPQVCEQSCAALCFLALRKPDNSRIIVEGGGAVAALQA
MKAHPQKAGVQKQACMLIRNLVAHGQAFSKPILDLGAEALIMQARSAHRDCEDVAKAALR
DLGCHVELRELWTGQRGNLAP*

Fig. 83

SEQ ID No. 83
MVSKRIAQETFDAAVRENIEEFAMGPEEAVKEAVEQFESQGVDLSNIVKTAPKVSADGSQ
EPTHDILQMLSDLQESVASSRPQEVSAYLTRFCDQCKQDKACRFLAAQKGAYPIIFTAWK
LATAGDQGLLLQSLNALSVLTDGQPDLLDAQGLQLLVATLTQNADEADLTCSGIRCVRHA
CLKHEQNRQDLVKAGVLPLLTGAITHHGRHTDVVREACWALRVMTFDDDIRVPFGHAHNH
AKMIVQENKGLKVLIEATKAFLDNPGILSELCGTLSRLAIRNEFCQEVVDLGGLSILVSL
LADCNDHQMRDQSGVQELVKQVLSTLRAIAGNDDVKDAIVRAGGTESIVAAMTQHLTSPQ
VCEQSCAALCFLALRKPDNSRIIVEGGGAVAALQAMKAHPQKAGVQKQACMLIRNLVAHG
QAFSKPILDLGAEALIMQARSAHRDCEDVAKAALRDLGCHVELRELWTGQRGNLAP*

Fig. 84

SEQ ID No. 84
MVSKRIAQETFDAAVRENIEEFAMGPEEAVKEAVEQFESQGVDLSNIVKTAPKVSADGSQ
EPTHDILQMLSDLQESVASSRPQEVSAYLTRFCDQCKQDKACRFLAAQKGAYPIIFTAWK
LATAGDQGLLLQSLNALSVLTDGQPDLLDAQGLQLLVATLTQNADEADLTCSGIRCVRHA
CLKHEQNRQDLVKAGVLPLLTGAITHHGHHTDVVREACWALRVMTFDDDIRVPFGHAHNH
AKMIVQENKGLKVLIEATKAFLDNPGILSELCGTLSRLAIRNEFCQEVVDLGGLSILVSL
LADCNDHQMRDQSGVQELVKQVLSTLRAIAGNDDVKDAIVRAGGTESIVAAMTQHLTSPQ
VCEQSCAALCFLALRKPDNSRIIVEGGGAVAALQAMKAHPQKAGVQKQACMLIRNLVAHG
QAFSKPILDLGAEALIMQARSAHRDCEDVAKAALRDLGCHVELRELWTGQRGNLAP*

Fig. 85

SEQ ID No. 85
MAGAVPGAIMDEDYYGSAAEWGDEADGGQQEDDSGEGEDDAEVQQECLHKFSTRDYIMEP
SIFNTLKRYFQAGGSPENVIQLLSENYTAVAQTVNLLAEWLIQTGVEPVQVQETVENHLK
SLLIKHFDPRKADSIFTEEGETPAWLEQMIAHTTWRDLFYKLAEAHPDCLMLNFTVKLIS
DAGYQGEITSVSTACQQLEVFSRVLRTSLATILDGGEENLEKNLPEFAKMVCHGEHTYLF
AQAMMSVLAQEEQGGSAVRRIAQEVQRFAQEKGHDASQITLALGTAASYPRACQALGAML
SKGALNPADITVLFKMFTSMDPPPVELIRVPAFLDLFMQSLFKPGARINQDHKHKYIHIL
AYAASVVETWKKNKRVSINKDELKSTSKAVETVHNLCCNENKGASELVAELSTLYQCIRF
PVVAMGVLKWVDWTVSEPRYFQLQTDHTPVHLALLDEISTCHQLLHPQVLQLLVKLFETE
HSQLDVMEQLELKKTLLDRMVHLLSRGYVLPVVSYIRKCLEKLDTDISLIRYFVTEVLDV
IAPPYTSDFVQLFLPILENDSIAGTIKTEGEHDPVTEFIAHCKSNFIMVN*

Fig. 86

SEQ ID No. 86
MAMLRVQPEAQAKVDVFREDLCTKTENLLGSYFPKKISELDAFLKEPALNEANLSNLKAP
LDIPVPDPVKEKEKEERKKQQEKEDKDEKKKGEDEDKGPPCGPVNCNEKIVVLLQRLKPE
IKDVIEQLNLVTTWLQLQIPRIEDGNNFGVAVQEKVFELMTSLHTKLEGFHTQISKYFSE
RGDAVTKAAKQPHVGDYRQLVHELDEAEYRDIRLMVMEIRNAYVRRQGQGRGGQRQLSQA
THSLTLQARG*

Fig. 87

SEQ ID No. 87
MAMLRVQPEAQAKVDVFREDLCTKTENLLGSYFPKKISELDAFLKEPALNEANLSNLKAP
LDIPVPDPVKEKEKEERKKQQEKEDKDEKKKGEDEDKGPPCGPVNCNEKIVVLLQRLKPE
IKDVIEQLNLVTTWLQLQIPRIEDGNNFGVAVQEKVFELMTSLHTKLEGFHTQISKYFSE
RGDAVTKAAKQPHVGDYRQLVHELDEAEYRDIRLMVMEIRNAYAVLYDIILKNFEKLKKP
RGETKGMIY*

Fig. 88

SEQ ID No. 88
MELRARGWWLLCAAAALVACARGDPASKSRSCGEVRQIYGAKGFSLSDVPQAEISGEHLR
ICPQGYTCCTSEMEENLANRSHAELETALRDSSRVLQAMLATQLRSFDDHFQHLLNDSER
TLQATFPGAFGELYTQNARAFRDLYSELRLYYRGANLHLEETLAEFWARLLERLFKQLHP
QLLLPDDYLDCLGKQAEALRPFGEAPRELRLRATRAFVAARSFVQGLGVASDVVRKVAQV
PLGPECSRAVMKLVYCAHCLGVPGARPCPDYCRNVLKGCLANQADLDAEWRNLLDSMVLI
TDKFWGTSGVESVIGSVHTWLAEAINALQDNRDTLTAKVIQGCGNPKVNPQGPGPEEKRR
RGKLAPRERPPSGTLEKLVSEAKAQLRDVQDFWISLPGTLCSEKMALSTASDDRCWNGMA
RGRYLPEVMGDGLANQINNPEVEVDITKPDMTIRQQIMQLKIMTNRLRSAYNGNDVDFQD
ASDDGSGSGSGDGCLDDLCSRKVSRKSSSSRTPLTHALPGLSEQEGQKTSAASCPQPPTF
LLPLLLFLALTVARPRWR*

Fig. 89

SEQ ID No. 89
MASCASIDIEDATQHLRDILKLDRPAGGPSAESPRPSSAYNGDLNGLLVPDPLCSGDSTS
ANKTGLRTMPPINLQEKQVICLSGDDSSTCIGILAKEVEIVASSDSSISSKARGSNKVKI
QPVAKYDWEQKYYYGNLIAVSNSFLAYAIRAANNGSAMVRVISVSTSERTLLKGFTGSVA
DLAFAHLNSPQLACLDEAGNLFVWRLALVNGKIQEEILVHIRQPEGTPLNHFRRIIWCPF
IPEESEDCCEESSPTVALLHEDRAEVWDLDMLRSSHSTWPVDVSQIKQGFIVVKGHSTCL
SEGALSPDGTVLATASHDGYVKFWQIYIEGQDEPRCLHEWKPHDGRPLSCLLFCDNHKKQ
DPDVPFWRFLITGADQNRELKMWCTVSWTCLQTIRFSPDIFSSVSVPPSLKVCLDLSAEY
LILSDVQRKVLYVMELLQNQEEGHACFSSISEFLLTHPVLSFGIQVVSRCRLRHTEVLPA
EEENDSLGADGTHGAGAMESAAGVLIKLFCVHTKALQDVQIRFQPQLNPDVVAPLPTHTA
HEDFTFGESRPELGSEGLGSAAHGSQPDLRRIVELPAPADFLSLSSETKPKLMTPDAFMT
PSASLQQITASPSSSSGSSSSSSSSSSLTAVSAMSSTSAVDPSLTRPPEELTLSPKLQ
LDGSLTMSSSGSLQASPRGLLPGLLPAPADKLTPKGPGQVPTATSALSLELQEVEPLGLP
QASPSRTRSPDVISSASTALSQDIPEIASEALSRGFGSSAPEGLEPDSMASAASALHLLS
PRPRPGPELGPQLGLDGGPGDGDRHNTPSLLEAALTQEASTPDSQVWPTAPDITRETCST
LAESPRNGLQEKHKSLAFHRPPYHLLQQRDSQDASAEQSDHDDEVASLASASGGFGTKVP
APRLPAKDWKTKGSPRTSPKLKRKSKKDDGDAAMGSRLTEHQVAEPPEDWPALIWQQQRE
LAELRHSQEELLQRLCTQLEGLQSTVTGHVERALETRHEQEQRRLERALAEGQQRGGQLQ
EQLTQQLSQALSSAVAGRLERSIRDEIKKTVPPCVSRSLEPMAGQLSNSVATKLTAVEGS
MKENISKLLKSKNLTDAIARAAADTLQGPMQAAYREAFQSVVLPAFEKSCQAMFQQINDS
FRLGTQEYLQQLESHMKSRKAREQEAREPVLAQLRGLVSTLQSATEQMPPWPAVFVLRCS
TSCMWLWAACRSPF*

Fig. 90

SEQ ID No. 90
MASCASIDIEDATQHLRDILKLDRPAGGPSAESPRPSSAYNGDLNGLLVPDPLCSGDSTS
ANKTGLRTMPPINLQEKQVICLSGDDSSTCIGILAKEVEIVASSDSSISSKARGSNKVKI
QPVAKYDWEQKYYYGNLIAVSNSFLAYAIRAANNGSAMVRVISVSTSERTLLKGFTGSVA
DLAFAHLNSPQLACLDEAGNLFVWRLALVNGKIQEEILVHIRQPEGTPLNHFRRIIWCPF
IPEESEDCCEESSPTVALLHEDRAEVWDLDMLRSSHSTWPVDVSQIKQGFIVVKGHSTCL
SEGALSPDGTVLATASHDGYVKFWQIYIEGQDEPRCLHEWKPHDGRPLSCLLFCDNHKKQ
DPDVPFWRFLITGADQNRELKMWCTVSWTCLQTIRFSPDIFSSVSVPPSLKVCLDLSAEY
LILSDVQRKVLYVMELLQNQEEGHACFSSISEFLLTHPVLSFGIQVVSRCRLRHTEVLPA
EEENDSLGADGTHGAGAMESAAGVLIKLFCVHTKALQDVQIRFQPQLNPDVVAPLPTHTA
HEDFTFGESRPELGSEGLGSAAHGSQPDLRRIVELPAPADFLSLSSETKPKLMTPDAFMT
PSASLQQITASPSSSSSGSSSSSSSSSSLTAVSAMSSTSAVDPSLTRPPEELTLSPKLQ
LDGSLTMSSSGSLQASPRGLLPGLLPAPADKLTPKGPGQVPTATSALSLELQEVEPLGLP
QASPSRTRSPDVISSASTALSQDIPEIASEALSRGFGSSAPEGLEPDSMASAASALHLLS
PRPRPGPELGPQLGLDGGPGDGDRHNTPSLLEAALTQEASTPDSQVWPTAPDITRETCST
LAESPRNGLQEKHKSLAFHRPPYHLLQQRDSQDASAEQSDHDDEVASLASASGGFGTKVP
APRLPAKDWKTKGSPRTSPKLKRKSKKDDGDAAMGSRLTEHQVAEPPEDWPALIWQQQRE
LAELRHSQEELLQRLCTQLEGLQSTVTGHVERALETRHEQEQRRLERALAEGQQRGGQLQ
EQLTQQLSQALSSAVAGRLERSIRDEIKKTVPPCVSRSLEPMAGQLSNSVATKLTAVEGS
MKENISKLLKSKNLTDAIARAAADTLQGPMQAAYREAFQSVVLPAFEKSCQAMFQQINDS
FRLGTQEYLQQLESHMKSRKAREQEAREPVLAQLRGLVSTLQSATEQMAATVAGSVRAEV
QHQLHVAVGSLQESILAQVQRIVKGEVSVALKEQQAAVTSSIMQAMRSAAGTPVPSAHLD
CQAQQAHILQLLQQGHLNQAFQQALTAADLNLVLYVCETVDPAQVFGQPPCPLSQPVLLS
LIQQLASDLGTRTDLKLSYLEEAVMHLDHSDPITRDHMGSVMAQVRQKLFQFLQAEPHNS
LGKAARRLSLMLHGLVTPSLP*

Fig. 91

SEQ ID No. 91
MRRSEVLAEESIVCLQKALNHLREIWELIGIPEDQRLQRTEVVKKHIKELLDMMIAEEES
LKERLIKSISVCQKELNTLCSELHVEPFQEEGETTILQLEKDLRTQVELMRKQKKERKQE
LKLLQEQDQELCEILCMPHYDIDSASVPSLEELNQFRQHVTTLRETKASRREEFVSIKRQ
IILCMEALDHTPDTSFERDVVCEDEDAFCLSLENIATLQKLLRQLEMQKSQNEAVCEGLR
TQIRELWDRLQIPEEEREAVATIMSGSKAKVRKALQLEVDRLEELKMQNMKKVIEAIRVE
LVQYWDQCFYSQEQRQAFAPFCAEDYTESLLQLHDAEIVRLKNYYEVHKELFEGVQKWEE
TWRLFLEFERKASDPNRFTNRGGNLLKEEKQRAKLQKMLPKLEEELKARIELWEQEHSKA
FMVNGQKFMEYVAEQWEMHRLEKERAKQERQLKNKKQTETEMLYGSAPRTPSKRRGLAPN
TPGKARKLNTTTMSNATANSSIRPIFGGTVYHSPVSRLPPSGSKPVAASTCSGKKTPRTG
RHGANKENLELNGSILSGGYPGSAPLQRNFSINSVASTYSEFAKDPSLSDSSTVGLQREL
SKASKSDATSGILNSTNIQS*

Fig. 92

SEQ ID No. 92
TRLRPVARFEILRGSTARGAATRSDIAGVCGWLLLSGPCGVGLDLDSRLLGASAMRRSEV
LAEESIVCLQKALNHLREIWELIGIPEDQRLQRTEVVKKHIKELLDMMIAEEESLKERLI
KSISVCQKELNTLCSELHVEPFQEEGETTILQLEKDLRTQVELMRKQKKERKQELKLLQE
QDQELCEILCMPHYDIDSASVPSLEELNQFRQHVTTLRETKASRREEFVSIKRQIILCME
ALDHTPDTSFERDVVCEDEDAFCLSLENIATLQKLLRQLEMQKSQNEAVCEGLRTQIREL
WDRLQIPEEEREAVATIMSGSKAKVRKALQLEVDRLEELKMQNMKKVIEAIRVELVQYWD
QCFYSQEQRQAFAPFCAEDYTESLLQLHDAEIVRLKNYYEVHKELFEGVQKWEETWRLFL
EFERKASDPNRFTNRGGNLLKEEKQRAKLQKMLPKLEEELKARIELWEQEHSKAFMVNGQ
KFMEYVAEQWEMHRLEKERAKQERQLKNKKQTETEMLYGSAPRTPSKRRGLAPNTPGKAR
KLNTTTMSNATANSSIRPIFGGTVYHSPVSRLPPSGSKPVAASTCSGKKTPRTGRHGANK
ENLELNGSILSGGYPGSAPLQRNFSINSVASTYSEFAKDPSLSDSSTVGLQRELSKASKS
DATSGILNSTNIQS*

Fig. 93

SEQ ID No. 93
TRLRPVARFEILRGSTARGAATRSDIAGVCGWLLLSGPCGVGLDLDSRLLGASAMRRSEV
LAEESIVCLQKALNHLREIWELIGIPEDQRLQRTEVVKKHIKELLDMMIAEEESLKERLI
KSISVCQKELNTLCSELHVEPFQEEGETTILQLEKDLRTQVELMRKQKKERKQELKLLQE
QDQELCEILCMPHYDIDSASVPSLEELNQFRQHVTTLRETKASRREEFVSIKRQIILCME
ALDHTPDTSFERDVVCEDEDAFCLSLENIATLQKLLRQLEMQKSQNEAVCEGLRTQIREL
WDRLQIPEEEREAVATIMSGSKAKVRKALQLEVDRLEELKMQNMKKVIEAIRVELVQYWD
QCFYSQEQRQAFAPFCAEDYTESLLQLHDAEIVRLKNYYEVHKELFEGVQKWEETWRLFL
EFERKASDPNRFTNRGGNLLKEEKQRAKLQKMLPKLEEELKARIELWEQEHSKAFMVNGQ
KFMEYVAEQWEMHRLEKERAKQERQLKNKKQTETEMLYGSAPRTPSKRRGLAPNTPGKAR
KLNTTTMSNATANSSIRPIFGGTVYHSPVSRLPPSGSKPVAASTCSGKKTPRTGRHGANK
ENLELNGSILSGGYPGSAPLQRNFSINSVASTYSEFARELSKASKSDATSGILNSTNIQS
*

Fig. 94

SEQ ID No. 94
MTTQLGPALVLGVALCLGCGQPLPQVPERPFSVLWNVPSAHCEARFGVHLPLNALGIIAN
RGQHFHGQNMTIFYKNQLGLYPYFGPRGTAHNGGIPQALPLDRHLALAAYQIHHSLRPGF
AGPAVLDWEEWCPLWAGNWGRRRAYQAASWAWAQQVFPDLDPQEQLYKAYTGFEQAARAL
MEDTLRVAQALRPHGLWGFYHYPACGNGWHSMASNYTGRCHAATLARNTQLHWLWAASSA
LFPSIYLPPRLPPAHHQAFVRHRLEEAFRVALVGHRHPLPVLAYVRLTHRRSGRFLSQDD
LVQSIGVSAALGAAGVVLWGDLSLSSSEEECWHLHDYLVDTLGPYVINVTRAAMACSHQR
CHGHGRCARRDPGQMEAFLHLWPDGSLGDWKSFSCHCYWGWAGPTCQEPRPGPKEAV*

Fig. 95

SEQ ID No. 95
MTTQLGPALVLGVALCLGCGQPLPQVPERPFSVLWNVPSAHCEARFGVHLPLNALGIIAN
RGQHFHGQNMTIFYKNQLGLYPYFGPRGTAHNGGIPQALPLDRHLALAAYQIHHSLRPGF
AGPAVLDWEEWCPLWAGNWGRRRAYQAASWAWAQQVFPDLDPQEQLYKAYTGFEQAARAL
MEDTLRVAQALRPHGLWGFYHYPACGNGWHSMASNYTGRCHAATLARNTQLHWLWAASSA
LFPSIYLPPRLPPAHHQAFVRHRLEEAFRVALVGHRHPLPVLAYVRLTHRRSGRFLSQDD
LVQSIGVSAALGAAGVVLWGDLSLSSSEEECWHLHDYLVDTLGPYVINVTRAAMACSHQR
CHGHGRCARRDPGQMEAFLHLWPDGSLGDWKSFSCHCYWGWAGPTCQEPLGLKKQYKARA
PATASSFPCCHFSSPGTTLSHSCSIQFTVNPPKHTPRFPWNP*

Fig. 96

SEQ ID No. 96
MTTQLGPALVLGVALCLGCGQPLPQVPERPFSVLWNVPSAHCEARFGVHLPLNALGIIAN
RGQHFHGQNMTIFYKNQLGLYPYFGPRGTAHNGGIPQALPLDRHLALAAYQIHHSLRPGF
AGPAVLDWEEWCPLWAGNWGRRRAYQAASWAWAQQVFPDLDPQEQLYKAYTGFEQAARAL
MEDTLRVAQALRPHGLWGFYHYPACGNGWHSMASNYTGRCHAATLARNTQLHWLWAASSA
LFPSIYLPPRLPPAHHQAFVRHRLEEAFRVALVGHRHPLPVLAYVRLTHRRSGRFLSQEE
CWHLHDYLVDTLGPYVINVTRAAMACSHQRCHGHGRCARRDPGQMEAFLHLWPDGSLGDW
KSFSCHCYWGWAGPTCQEPRPGPKEAV*

Fig. 97

SEQ ID No. 97
MGKEKTHINIVVIGHVDSGKSTTTGHLIYKCGGIDKRTIEKFEKEAAEMGKGSFKYAWVL
DKLKAERERGITIDISLWKFETSKYYVTIIDAPGHRDFIKNMITGTSQADCAVLIVAAGV
GEFEAGISKNGQTREHALLAYTLGVKQLIVGVNKMDSTEPPYSQKRYEEIVKEVSTYIKK
IGYNPDTVAFVPISGWNGDNMLEPSANMPWFKGWKVTRKDGNASGTTLLEALDCILPPTR
PTDKPLRLPLQDVYKIGGIGTVPVGRVETGVLKPGMVVTFAPVNVTTEVKSVEMHHEALS
EALPGDNVGFKVKNVSVKDVRRGNVAGDSKNDPPMEAAGFTAQVIILNHPGQISAGYAPV
LDCHMAHIACKFAELKEKIDRRSGKKLEDGPKFLKSGDAAIVDMVPGKPMCVESFSDYPP
LGRFAVRDMRQTVAVGVIKAVDKKAAGAGKVTKSAQKAQKAK*

Fig. 98

SEQ ID No. 98
MALKAEGAALDCFEVTLKCEEGEDEEEAMVVAVIPRPEPMLRVTQQEKTPPPRPSPLEAG
SDGCEEPKQQVSWEQEFLVGSSPGGSGRALCMVCGAEIRAPSADTARSHILEQHPHTLDL
SPSEKSNILEAWSEGVALLQDVRAEQPSPPNSDSGQDAHPDPDANPDAARMPAEIVVLLD
SEDNPSLPKRSRPRGLRPLELPAVPATEPGNKKPRGQRWKEPPGEEPVRKKRGRPMTKNL
DPDPEPPSPDSPTETFAAPAEVRHFTDGSFPAGFVLQLFSHTQLRGPDSKDSPKDREVAE
GGLPRAESPSPAPPPGLRGTLDLQVIRVRMEEPPAVSLLQDWSRHPQGTKRVGAGDTSDW
PTVLSESSTTVAGKPEKGNGV*

Fig. 99

SEQ ID No. 99
MSTHRSRLLTAAPLSMEQRRPWPRALEVDSRSVVLLSVVWVLLAPPAAGMPQFSTFHSEN
RDWTFNHLTVHQGTGAVYVGAINRVYKLTGNLTIQVAHKTGPEEDNKSCYPPLIVQPCSE
VLTLTNNVNKLLIIDYSENRLLACGSLYQGVCKLLRLDDLFILVEPSHKKEHYLSSVNKT
GTMYGVIVRSEGEDGKLFIGTAVDGKQDYFPTLSSRKLPRDPESSAMLDYELHSDFVSSL
IKIPSDTLALVSHFDIFYIYGFASGGFVYFLTVQPETPEGVAINSAGDLFYTSRIVRLCK
DDPKFHSYVSLPFGCTRAGVEYRLLQAAYLAKPGDSLAQAFNITSQDDVLFAIFSKGQKQ
YHHPPDDSALCAFPIRAINLQIKERLQSCYQGEGNLELNWLLGKDVQCTKAPVPIDDNFC
GLDINQPLGGSTPVEGLTLYTTSRDRMTSVASYVYNGYSVVFVGTKSGKLKKIRADGPPH
GGVQYEMVSVLKDGSPILRDMAFSIDQRYLYVMSERQVTRVPVESCEQYTTCGECLSSGD
PHCGWCALHNMCSRRDKCQQAWEPNRFAASISQCVSLAVHPSSISVSEHSRLLSLVVSDA
PDLSAGIACAFGNLTEVEGQVSGSQVICISPGPKDVPVIPLDQDWFGLELQLRSKETGKI
FVSTEFKFYNCSAHQLCLSCVNSAFRCHWCKYRNLCTHDPTTCSFQEGRINISEDCPQLV
PTEEILIPVGEVKPITLKARNLPQPQSGQRGYECVLNIQGAIHRVPALRFNSSSVQCQNS
SYQYDGMDISNLAVDFAVVWNGNFIIDNPQDLKVHLYKCAAQRESCGLCLKADRKFECGW
CSGERRCTLHQHCTSPSSPWLDWSSHNVKCSNPQITEILTVSGPPEGGTRVTIHGVNLGL
DFSEIAHHVQVAGVPCTPLPGEYIIAEQIVCEMGHALVGTTSGPVRLCIGECKPEFMTKS
HQQYTFVNPSVLSLNPIRGPESGGTMVTITGHYLGAGSSVAVYLGNQTCEFYGRSMSEIV
CVSPPSSNGLGPVPVSVSVDRAHVDSNLQFEYIDDPRVQRIEPEWSIASGHTPLTITGFN
LDVIQEPRIRVKFNGKESVNVCKVVNTTTLTCLAPSLTTDYRPGLDTVERPDEFGFVFNN
VQSLLIYNDTKFIYYPNPTFELLSPTGVLDQKPGSPIILKGKNLCPPASGGAKLNYTVLI
GETPCAVTVSETQLLCEPPNLTGQHKVMVHVGGMVFSPGSVSVISDSLLTLPAIVSIAAG
GSLLLIIVIIVLIAYKRKSRENDLTLKRLQMQMDNLESRVALECKEAFAELQTDINELTS
DLDRSGIPYLDYRTYAMRVLFPGIEDHPVLRELEVQGNGQQHVEKALKLFAQLINNKVFL
LTFIRTLELQRSFSMRDRGNVASLIMTGLQGRLEYATDVLKQLLSDLIDKNLENKNHPKL
LLRRTESVAEKMLTNWFAFLLHKFLKECAGEPLFMLYCAIKQMEKGPIDAITGEARYSL
SEDKLIRQQIEYKTLILNCVNPDNENSPEIPVKVLNCDTITQVKEKILDAVYKNVPYSQR
PRAVDMDLEWRQGRIARVVLQDEDITTKIEGDWKRLNTLMHYQVSDRSVVALVPKQTSSY
NIPASASISRTSISRYDSSFRYTGSPDSLRSRAPMITPDLESGVKVWHLVKNHDHGDQKE
GDRGSKMVSEIYLTRLLATKGTLQKFVDDLFETLFSTVHRGSALPLAIKYMFDFLDEQAD
RHSIHDTDVRHTWKSNCLPLRFWVNVIKNPQFVFDIHKGSITDACLSVVAQTFMDSCSTS
EHRLGKDSPSNKLLYAKDIPSYKSWVERYYADIAKLPAISDQDMNAYLAEQSRLHAVEFN
MLSALNEIYSYVSKYSEELIGALEQDEQARRQRLAYKVEQLINAMSIES*

Fig. 100

SEQ ID No. 100
MEQRRPWPRALEVDSRSVVLLSVVWVLLAPPAAGMPQFSTFHSENRDWTFNHLTVHQGTG
AVYVGAINRVYKLTGNLTIQVAHKTGPEEDNKSCYPPLIVQPCSEVLTLTNNVNKLLIID
YSENRLLACGSLYQGVCKLLRLDDLFILVEPSHKKEHYLSSVNKTGTMYGVIVRSEGEDG
KLFIGTAVDGKQDYFPTLSSRKLPRDPESSAMLDYELHSDFVSSLIKIPSDTLALVSHFD
IFYIYGFASGGFVYFLTVQPETPEGVAINSAGDLFYTSRIVRLCKDDPKFHSYVSLPFGC
TRAGVEYRLLQAAYLAKPGDSLAQAFNITSQDDVLFAIFSKGQKQYHHPPDDSALCAFPI
RAINLQIKERLQSCYQGEGNLELNWLLGKDVQCTKAPVPIDDNFCGLDINQPLGGSTPVE
GLTLYTTSRDRMTSVASYVYNGYSVVFVGTKSGKLKKIRADGPPHGGVQYEMVSVLKDGS
PILRDMAFSIDQRYLYVMSERQVTRVPVESCEQYTTCGECLSSGDPHCGWCALHNMCSRR
DKCQQAWEPNRFAASISQCVSLAVHPSSISVSEHSRLLSLVVSDAPDLSAGIACAFGNLT
EVEGQVSGSQVICISPGPKDVPVIPLDQDWFGLELQLRSKETGKIFVSTEFKFYNCSAHQ
LCLSCVNSAFRCHWCKYRNLCTHDPTTCSFQEGRINISEDCPQLVPTEEILIPVGEVKPI
TLKARNLPQPQSGQRGYECVLNIQGAIHRVPALRFNSSSVQCQNSSYQYDGMDISNLAVD
FAVVWNGNFIIDNPQDLKVHLYKCAAQRESCGLCLKADRKFECGWCSGERRCTLHQHCTS
PSSPWLDWSSHNVKCSNPQITEILTVSGPPEGGTRVTIHGVNLGLDFSEIAHHVQVAGVP
CTPLPGEYIIAEQIVCEMGHALVGTTSGPVRLCIGECKPEFMTKSHQQYTFVNPSVLSLN
PIRGPESGGTMVTITGHYLGAGSSVAVYLGNQTCEFYGRSMSEIVCVSPPSSNGLGPVPV
SVSVDRAHVDSNLQFEYIDDPRVQRIEPEWSIASGHTPLTITGFNLDVIQEPRIRVKFNG
KESVNVCKVVNTTTLTCLAPSLTTDYRPGLDTVERPDEFGFVFNNVQSLLIYNDTKFIYY
PNPTFELLSPTGVLDQKPGSPIILKGKNLCPPASGGAKLNYTVLIGETPCAVTVSETQLL
CEPPNLTGQHKVMVHVGGMVFSPGSVSVISDSLLTLPAIVSIAAGGSLLLIIVIIVLIAY
KRKSRENDLTLKRLQMQMDNLESRVALECKEAFAELQTDINELTSDLDRSGIPYLDYRTY
AMRVLFPGIEDHPVLRELEVQGNGQQHVEKALKLFAQLINNKVFLLTFIRTLELQRSFSM
RDRGNVASLIMTGLQGRLEYATDVLKQLLSDLIDKNLENKNHPKLLLRRTESVAEKMLTN
WFAFLLHKFLKECAGEPLFMLYCAIKQQMEKGPIDAITGEARYSLSEDKLIRQQIEYKTL
ILNCVNPDNENSPEIPVKVLNCDTITQVKEKILDAVYKNVPYSQRPRAVDMDLEWRQGRI
ARVVLQDEDITTKIEGDWKRLNTLMHYQVSDRSVVALVPKQTSSYNIPASASISRTSISR
YDSSFRYTGSPDSLRSRAPMITPDLESGVKVWHLVKNHDHGDQKEGDRGSKMVSEIYLTR
LLATKGTLQKFVDDLFETLFSTVHRGSALPLAIKYMFDFLDEQADRHSIHDTDVRHTWKS
NCLPLRFWVNVIKNPQFVFDIHKGSITDACLSVVAQTFMDSCSTSEHRLGKDSPSNKLLY
AKDIPSYKSWVERYYADIAKLPAISDQDMNAYLAEQSRLHAVEFNMLSALNEIYSYVSKY
SEELIGALEQDEQARRQRLAYKVEQLINAMSIES*

Fig. 101

SEQ ID No. 101
MPPPSDIVKVAIEWPGANAQLLEIDQKRPLASIIKEVCDGWSLPNPEYYTLRYADGPQLY
ITEQTRSDIKNGTILQLAISPSRAARQLMERTQSSNMETRLDAMKELAKLSADVTFATEF
INMDGIIVLTRLVESGTKLLSHYSEMLAFTLTAFLELMDHGIVSWDMVSITFIKQIAGYV
SQPMVDVSILQRSLAILESMVLNSQSLYQKIAEEITVGQLISHLQVSNQEIQTYAIALIN
ALFLKAPEDKRQDMANAFAQKHLRSIILNHVIRGNRPIKTEMAHQLYVLQVLTFNLLEER
MMTKMDPNDQAQRDIIFELRRIAFDAESDPSNAPGSGTEKRKAMYTKDYKMLGFTNHINP
AMDFTQTPPGMLALDNMLYLAKVHQDTYIRIVLENSSREDKHECPFGRSAIELTKMLCEI
LQVGELPNEGRNDYHPMFFTHDRAFEELFGICIQLLNKTWKEMRATAEDFNKVMQVVREQ
ITRALPSKPNSLDQFKSKLRSLSYSEILRLRQSERMSQDDFQSPPIVELREKIQPEILEL
IKQQRLNRLCEGSSFRKIGNRRRQERFWYCRLALNHKVLHYGDLDDNPQGEVTFESLQEK
IPVADIKAIVTGKDCPHMKEKSALKQNKEVLELAFSILYDPDETLNFIAPNKYEYCIWID
GLSALLGKDMSSELTKSDLDTLLSMEMKLRLLDLENIQIPEAPPPIPKEPSSYDFVYHYG
*

Fig. 102

SEQ ID No. 102
MPPPSDIVKVAIEWPGANAQLLEIDQKRPLASIIKEVCDGWSLPNPEYYTLRYADGPQLY
ITEQTRSDIKNGTILQLAISPSRAARQLMERTQSSNMETRLDAMKELAKLSADVTFATEF
INMDGIIVLTRLVESGTKLLSHYSEMLAFTLTAFLELMDHGIVSWDMVSITFIKQIAGYV
SQPMVDVSILQRSLAILESMVLNSQSLYQKIAEEITVGQLISHLQVSNQEIQTYAIALIN
ALFLKAPEDKRQDMANAFAQKHLRSIILNHVIRGNRPIKTEMAHQLYVLQVLTFNLLEER
MMTKMDPNDQAQRDIIFELRRIAFDAESDPSNAPGSGTEKRKAMYTKDYKMLGFTNHINP
AMDFTQTPPGMLALDNMLYLAKVHQDTYIRIVLENSSREDKHECPFGRSAIELTKMLCEI
LQVGELPNEGRNDYHPMFFTHDRAFEELFGICIQLLNKTWKEMRATAEDFNKVMQVVREQ
ITRALPSKPNSLDQFKSKLRSLSYSEILRLRQSERMSQDDFQSPPIVELREKIQPEILEL
IKQQRLNRLCEGSSFRKIGNRRRQERFWYCRLALNHKVLHYGDLDDNPQGEVTFESLQEK
IPVADIKAIVTGKDCPHMKEKSALKQNKEVLELAFSILYDPDETLNFIAPNKYEYCIWID
GLSALLGKDMSSELTKSDLDTLLSMEMKLRLLDLENIQIPEAPPPIPKEPSSYDFVYHYG
*

Fig. 103

SEQ ID No. 103
MPPPSDIVKVAIEWPGANAQLLEIDQKRPLASIIKEVCDGWSLPNPEYYTLRYADGPQLY
ITEQTRSDIKNGTILQLAISPSRAARQLMERTQSSNMETRLDAMKELAKLSADVTFATEF
INMDGIIVLTRLVESGTKLLSHEMLAFTLTAFLELMDHGIVSWDMVSITFIKQIAGYVSQ
PMVDVSILQRSLAILESMVLNSQSLYQKIAEEITVGQLISHLQVSNQEIQTYAIALINAL
FLKAPEDKRQDMANAFAQKHLRSIILNHVIRGNRPIKTEMAHQLYVLQVLTFNLLEERMM
TKMDPNDQAQRDIIFELRRIAFDAESDPSNAPGSGTEKRKAMYTKDYKMLGFTNHINPAM
DFTQTPPGMLALDNMLYLAKVHQDTYIRIVLENSSREDKHECPFGRSAIELTKMLCEILQ
VGELPNEGRNDYHPMFFTHDRAFEELFGICIQLLNKTWKEMRATAEDFNKVMQVVREQIT
RALPSKPNSLDQFKSKLRSLSYSEILRLRQSERMSQDDFQSPPIVELREKIQPEILELIK
QQRLNRLCEGSSFRKIGNRRRQERFWYCRLALNHKVLHYGDLDDNPQGEVTFESLQEKIP
VADIKAIVTGKDCPHMKEKSALKQNKEVLELAFSILYDPDETLNFIAPNKYEYCIWIDGL
SALLGKDMSSELTKSDLDTLLSMEMKLRLLDLENIQIPEAPPPIPKEPSSYDFVYHYG*

Fig. 104

SEQ ID No. 104
MERTQSSNMETRLDAMKELAKLSADVTFATEFINMDGIIVLTRLVESGTKLLSHYSEMLA
FTLTAFLELMDHGIVSWDMVSITFIKQIAGYVSQPMVDVSILQRSLAILESMVLNSQSLY
QKIAEEITVGQLISHLQVSNQEIQTYAIALINALFLKAPEDKRQDMANAFAQKHLRSIIL
NHVIRGNRPIKTEMAHQLYVLQVLTFNLLEERMMTKMDPNDQAQRDIIFELRRIAFDAES
DPSNAPGSGTEKRKAMYTKDYKMLGFTNHINPAMDFTQTPPGMLALDNMLYLAKVHQDTY
IRIVLENSSREDKHECPFGRSAIELTKMLCEILQVGELPNEGRNDYHPMFFTHDRAFEEL
FGICIQLLNKTWKEMRATAEDFNKVMQVVREQITRALPSKPNSLDQFKSKLRSLSYSEIL
RLRQSERMSQDDFQSPPIVELREKIQPEILELIKQQRLNRLCEGSSFRKIGNRRRQERFW
YCRLALNHKVLHYGDLDDNPQGEVTFESLQEKIPVADIKAIVTGKDCPHMKEKSALKQNK
EVLELAFSILYDPDETLNFIAPNKYEYCIWIDGLSALLGKDMSSELTKSDLDTLLSMEMK
LRLLDLENIQIPEAPPPIPKEPSSYDFVYHYG*

Fig. 105

SEQ ID No. 105
  MAALRALCGFRGVAAQVLRPGAGVRLPIQPSRGVRQWQPDVEWAQQFGGAVMYPSKETAH
WKPPPWNDVDPPKDTIVKNITLNFGPQHPAAHGVLRLVMELSGEMVRKCDPHIGLLHRGT
EKLIEYKTYLQALPYFDRLDYVSMMCNEQAYSLAVEKLLNIRPPPRAQWIRVLFGEITRL
LNHIMAVTTHALDLGAMTPFFWLFEEREKMFEFYERVSGARMHAAYIRPGGVHQDLPLGL
MDDIYQFSKNFSLRLDELEELLTNNRIWRNRTIDIGVVTAEEALNYGFSGVMLRGSGIQW
DLRKTQPYDVYDQVEFDVPVGSRGDCYDRYLCRVEEMRQSLRIIAQCLNKMPPGEIKVDD
AKVSPPKRAEMKTSMESLIHHFKLYTEGYQVPPGATYTAIEAPKGEFGVYLVSDGSSRPY
RCKIKAPGFAHLAGLDKMSKGHMLADVVAIIGTQDIVFGEVDR*

Fig. 106

SEQ ID No. 106
MAALRALCGFRGVAAQVLRPGAGVRLPIQPSRGVRQWQPDVEWAQQFGGAVMYPSKETAH
WKPPPWNDVDPPKDTIVKNITLNFGPQHPAAHGVLRLVMELSGEMVRKCDPHIGLLHRGT
EKLIEYKTYLQALPYFDRLDYVSMMCNEQAYSLAVEKLLNIRPPPRAQWIRVLFGEITRL
LNHIMAVTTHALDLGAMTPFFWLFEEREKMFEFYERVSGARMHAAYIRPGGVHQDLPLGL
MDDIYQFSKNFSLRLDELEELLTNNRIWRNRTIDIGVVTAEEALNYGFSGVMLRGSGIQW
DLRKTQPYDVYDQVEFDVPVGSRGDCYDRYLCRVEEMRQSLRIIAQCLNKMPPGEIKVDD
AKVSPPKRAEMKTSMESLIHHFKLYTEGYQVPPGATYTAIEAPKGEFGVYLVSDGSSRPY
RCKIKAPGFAHLAGLDKMSKGHMLADVVAIIGTQDIVFGEVDR*

Fig. 107

SEQ ID No. 107
MAGGPGPGEPAAPGAQHFLYEVPPWVMCRFYKVMDALEPADWCQFGGWRRAAGGREARGL
LAPTPDAPRPAAALIVRDQTELRLCERSGQRTASVLWPWINRNARVADLVHILTHLQLLR
ARDIITAWHPPAPLPSPGTTAPRPSSIPAPAEAEAWSPRKLPSSASTFLSPAFPGSQTHS
GPELGLVPSPASLWPPPPSPAPSSTKPGPESSVSLLQGARPFPFCWPLCEISRGTHNFSE
ELKIGEGGFGCVYRAVMRNTVYAVKRLKENADLEWTAVKQSFLTEVEQLSRFRHPNIVDF
AGYCAQNGFYCLVYGFLPNGSLEDRLHCQTQACPPLSWPQRLDILLGTARAIQFLHQDSP
SLIHGDIKSSNVLLDERLTPKLGDFGLARFSRFAGSSPSQSSMVARTQTVRGTLAYLPEE
YIKTGRLAVDTDTFSFGVVVLETLAGQRAVKTHGARTKYLKDLVEEEAEEAGVALRSTQS
TLQAGLAADAWAAPIAMQIYKKHLGQLACCCLHRRAKRRPPMTQENSYVSSTGRAHSGAA
PWQPLAAPSGASAQAAEQLQRGPNQPVESDESLGGLSAALRSWHLTPSCPLDPAPLREAG
CPQGDTAGESSWGSGPGSRPTAVEGLALGSSASSSEPPQIIINPARQKMVQKLALYEDG
ALDSLQLLSSSSLPGLGLEQDRQGPEESDEFQS*

Fig. 108

SEQ ID No. 108
MAGGPGPGEPAAPGAQHFLYEVPPWVMCRFYKVMDALEPADWCQFAALIVRDQTELRLCE
RSGQRTASVLWPWINRNARVADLVHILTHLQLLRARDIITAWHPPAPLPSPGTTAPRPSS
IPAPAEAEAWSPRKLPSSASTFLSPAFPGSQTHSGPELGLVPSPASLWPPPPSPAPSSTK
PGPESSVSLLQGARPFPFCWPLCEISRGTHNFSEELKIGEGGFGCVYRAVMRNTVYAVKR
LKENADLEWTAVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLDERLTPKLGDFG
LARFSRFAGSSPSQSSMVARTQTVRGTLAYLPEEYIKTGRLAVDTDTFSFGVVVLETLAG
QRAVKTHGARTKYLKDLVEEEAEEAGVALRSTQSTLQAGLAADAWAAPIAMQIYKKHLDP
RPGPCPPELGLGLGQLACCCLHRRAKRRPPMTQVYERLEKLQAVVAGVPGHSEAASCIPP
SPQENSYVSSTGRAHSGAAPWQPLAAPSGASAQAAEQLQRGPNQPVESDESLGGLSAALR
SWHLTPSCPLDPAPLREAGCPQGDTAGESSWGSGPGSRPTAVEGLALGSSASSSSEPPQI
IINPARQKMVQKLALYEDGALDSLQLLSSSSLPGLGLEQDRQGPEESDEFQS*

Fig. 109

SEQ ID No. 109
MAGGPGPGEPAAPGAQHFLYEVPPWVMCRFYKVMDALEPADWCQFAALIVRDQTELRLCE
RSGQRTASVLWPWINRMARVADLVHILTHLQLLRARDIITAWHPPAPLPSPGTTAPRPSS
IPAPAEAEAWSPRKLPSSASTFLSPAFPGSQTHSGPELGLVPSPASLWPPPPSPAPSSTK
PGPESSVSLLQGARPFPFCWPLCEISRGTHNFSEELKIGEGGFGCVYRAVMRNTVYAVKR
LKENADLEWTAVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLDERLTPKLGDFG
LARFSRFAGSSPSQSSMVARTQTVRGTLAYLPEEYIKTGRLAVDTDTFSFGVVVLETLAG
QRAVKTHGARTKYLKDLVEEEAEEAGVALRSTQSTLQAGLAADAWAAPIAMQIYKKHLDP
RPGPCPPELGLGLGQLACCCLHRRAKRRPPMTQENSYVSSTGRAHSGAAPWQPLAAPSGA
SAQAAEQLQRGPNQPVESDESLGGLSAALRSWHLTPSCPLDPAPLREAGCPQGDTAGESS
WGSGPGSRPTAVEGLALGSSASSSSEPPQIIINPARQKMVQKLALYEDGALDSLQLLSSS
SLPGLGLEQDRQGPEESDEFQS*

Fig. 110

SEQ ID No. 110
MAGGPGPGEPAAPGAQHFLYEVPPWVMCRFYKVMDALEPADWCQFAALIVRDQTELRLCE
RSGQRTASVLWPWINRNARVADLVHILTHLQLLRARDIITAWHPPAPLPSPGTTAPRPSS
IPAPAEAEAWSPRKLPSSASTFLSPAFPGSQTHSGPELGLVPSPASLWPPPPSPAPSSTK
PGPESSVSLLQGARPFPFCWPLCEISRGTHNFSEELKIGEGGFGCVYRAVMRNTVYAVKR
LKENADLEWTAVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLDERLTPKLGDFG
LARFSRFAGSSPSQSSMVARTQTVRGTLAYLPEEYIKTGRLAVDTDTFSFGVVVLETLAG
QRAVKTHGARTKYLVYERLEKLQAVVAGVPGHSEAASCIPPSPQENSYVSSTGRAHSGAA
PWQPLAAPSGASAQAAEQLQRGPNQPVESDESLGGLSAALRSWHLTPSCPLDPAPLREAG
CPQGDTAGESSWGSGPGSRPTAVEGLALGSSASSSSEPPQIIINPARQKMVQKLALYEDG
ALDSLQLLSSSSLPGLGLEQDRQGPEESDEFQS*

Fig. 111

SEQ ID No. 111
MAGGPGPGEPAAPGAQHFLYEVPPWVMCRFYKVMDALEPADWCQFGGWRRAAGGREARGL
LAPTPDAPRPAAALIVRDQTELRLCERSGQRTASVLWPWINRNARVADLVHILTHLQLLR
ARDIITAWHPPAPLPSPGTTAPRPSSIPAPAEAEAWSPRKLPSSASTFLSPAFPGSQTHS
GPELGLVPSPASLWPPPPSPAPSSTKPGPESSVSLLQGARPFPFCWPLCEISRGTHNFSE
ELKIGEGGFGCVYRAVMRNTVYAVKRLKENADLEWTAVKQSFLTEVEQLSRFRHPNIVDF
AGYCAQNGFYCLVYGFLPNGSLEDRLHCQTQACPPLSWPQRLDILLGTARAIQFLHQDSP
SLIHGDIKSSNVLLDERLTPKLGDFGLARFSRFAGSSPSQSSMVARTQTVRGTLAYLPEE
YIKTGRLAVDTDTFSFGVVVLETLAGQRAVKTHGARTKYLKDLVEEEAEEAGVALRSTQS
TLQAGLAADAWAAPIAMQIYKKHLDPRPGPCPPELGLGLGQLACCCLHRRAKRRPPMTQE
NSYVSSTGRAHSGAAPWQPLAAPSGASAQAAEQLQRGPNQPVESDESLGGLSAALRSWHL
TPSCPLDPAPLREAGCPQGDTAGESSWGSGPGSRPTAVEGLALGSSASSSSEPPQIIINP
ARQKMVQKLALYEDGALDSLQLLSSSSLPGLGLEQDRQGPEESDEFQS*

Fig. 112

SEQ ID No. 112
MAAIPSSGSLVATHDYYRRRLGSTSSNSSCSSTECPGEAIPHPPGECRIAPFSPRSSRSW
QHQDPTSLLSGLPKADPGHWWASFFFGKSTLPFMATVLESAEHSEPPQASSSMTACGLAR
DAPRKQPGGQSSTASAGPPS*

Fig. 113

SEQ ID No. 113
MAAIPSSGSLVATHDYYRRRLGSTSSNSSCSSTECPGEAIPHPPGLPKADPGHWWASFFF
GKSTLPPPTL*

Fig. 114

SEQ ID No. 114
MAAIPSSGSLVATHDYYRRRLGSTSSNSSCSSTECPGEAIPHPPGLPKADPGHWWASFFF
GKSTLPFMATVLESAEHSEPPQASSSMTACGLARDAPRKQPGGQSSTASAGPPS*

Fig. 115

SEQ ID No. 115
MEDGVYEPPDLTPEERMELENIRRRKQELLVEIQRLREELSEAMSEVEGLEANEGSKTLQ
RNRKMAMGRKKFNMDPKKGIQFLVENELLQNTPEEIARFLYKGEGLNKTAIGDYLGEREE
LNLAVLHAFVDLHEFTDLNLVQALRQFLWSFRLPGEAQKIDRMMEAFAQRYCLCNPGVFQ
STDTCYVLSFAVIMLNTSLHNPNVRDKPGLERFVAMNRGINEGGDLPEELLRNLYDSIRN
EPFKIPEDDGNDLTHTFFNPDREGWLLKLGRGRVKTWKRRWFILTDNCLYYFEYTTDKEP
RGIIPLENLSIREVDDPRKPNCFELYIPNNKGQLIKACKTEADGRVVEGNHMVYRISAPT
QEEKDEWIKSIQAAVSVDPFYEMLAARKKRISVKKKQEQP*

Fig. 116

SEQ ID No. 116
MEDGVYEPPDLTPEERMELENIRRRKQELLVEIQRLREELSEAMSEVEGLEANEGSKTLQ
RNRKMAMGRKKFNMDPKKGIQFLVENELLQNTPEEIARFLYKGEGLNKTAIGDYLGEREE
LNLAVLHAFVDLHEFTDLNLVQALRQFLWSFRLPGEAQKIDRMMEAFAQRYCLCNPGVFQ
STDTCYVLSFAVIMLNTSLHNPNVRDKPGLERFVAMNRGINEGGDLPEELLRNLYDSIRN
EPFKIPEDDGNDLTHTFFNPDREGWLLKLGGRVKTWKRRWFILTDNCLYYFEYTTDKEPR
GIIPLENLSIREVDDPRKPNCFELYIPNNKGQLIKACKTEADGRVVEGNHMVYRISAPTQ
EEKDEWIKSIQAAVSVDPFYEMLAARKKRISVKKKQEQP*

Fig. 117

SEQ ID No. 117
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLE*

Fig. 118

SEQ ID No. 118
TAEEEASSEACAGPATRSPGWGDPGISHRDCCRRKAEWGTAESR*

Fig. 119

SEQ ID No. 119
EAELPDRGGAAVQVSSPKHCGLCWLLCSERLLLPGVRLPAQRLPGGPSPLPDPGLPTSLL
ASATGHPSGYSPGNSVSTSGQPQPHPWRHQEFQRPSG*

Fig. 120

SEQ ID 120
LRGLAPPSPPPVIVRRGPRGVAAQIPPASKLKHGGHPLQRLARGHPRLLPAPPGFHFQQQ
LLQQYRVPRGSHSPPPRSPQG*

Fig. 121

SEQ ID No. 121
APWPSAPVPATRDRAPRPARGRRPDPTSQQAKAWRPSPPAARSWPPTTTTGAAWVPLPAT
APAAVPSAPGKPFPTPQVSPRLTRVIGGPASFSGSPPSRSWPRCWSPQSTRNLPRPPAA*

Fig. 122

SEQ ID No. 122
WTCSPHPTPTTRRSTTSRSASWSARCAST*

BIOMARKER FOR THE PREDICTION OF RESPONSIVENESS TO AN ANTI-TUMOUR NECROSIS FACTOR ALPHA (TNF) TREATMENT

CROSS-REFERENCE TO RELATED APPLICATIONS

This application is a divisional of U.S. application Ser. No. 12/740,166, filed Oct. 22, 2010; which is a national stage entry of International Application No. PCT/EP2008/064820, filed Oct. 31 2008; which claims priority to European Application No. 07119810.5 filed Oct. 31, 2007; the contents of all of which are herein incorporated by reference in their entirety.

The instant application contains a Sequence Listing which has been submitted in ASCII format via EFS-WEB and is hereby incorporated by reference in its entirety. Said ASCII copy, created on Aug. 13, 2015, is named sequence.txt and is 413 KB.

The invention refers to a method for diagnosing an individual who is to be subjected to or is being subjected to an anti-tumour necrosis factor alpha (TNFα or TNF) treatment to assess the responsiveness to an anti-TNF treatment which comprises the detection of immunoglobulin(s) against one or more biomarker proteins in a bodily fluid or an excrement of said patient, and sorting the individual into one of two categories based on detection of said immunoglobulin(s), wherein individuals are classified as NON-responder or responder. The invention refers to diagnostic kits comprising said one or more biomarker proteins and the use of these kits for assessing the responsiveness to an anti-TNF treatment of an individual who is to be subjected to or is being subjected to an anti-TNFα treatment.

BACKGROUND

Rheumatic diseases are the most common chronic inflammatory disorders. In Germany alone, one million patients suffer from immunologically mediated rheumatic diseases including rheumatoid arthritis (RA), spondyloarthropathies (SpA) and systemic autoimmune diseases like systemic lupus erythematosus (SLE), while additional five million individuals have osteoarthritis (OA), a primarily degenerative joint disease, which, however, in its active phases is also dominated by inflammatory processes. Rheumatoid arthritis leads to severe pain, loss of function and serious impairment of the quality of life. Besides these deleterious consequences for the individual patient, there is a striking socio-economic impact leading to direct and indirect costs of about 20 billion Euros in Germany per year. The demographic development clearly indicates that rheumatic diseases will dramatically increase over the next decades and will be equal in importance to cardiovascular diseases and cancer. Already now, rheumatic disorders dominate the number of patient visits in the General Practitioner's office and are the leading cause of absence from work and premature invalidity. In recognition of the tremendous impact of arthritic and bone diseases, the World Health Organization has announced the current decade as the "Decade of Bone and Joint Diseases".

A range of therapies for rheumatoid arthritis is available based on standard disease-modifying antirheumatic drugs (DMARDs), such as Methotrexate (MTX) and on biologicals, such as TNF inhibitors/antagonists. Chronically elevated levels of TNF have been implicated as a pathogenic component in rheumatoid arthritis. TNF inhibitors are biologicals which bind to soluble and cell membrane-associated form of TNFα and neutralise the proinflammatory effect of TNFα by preventing the binding of TNFα to the TNF-RI/II cell-surface receptors. TNFa-inhibiting biological agents comprise e.g. therapeutic antibodies (Adalimumab® & Infliximab®) and soluble receptor constructs (Etanercept®). These biologicals are currently used to treat active rheumatoid arthritis, all of which effectively reduce the signs and symptoms of the disease and inhibit radiographic joint damage progression. Currently ~10% of patients in Germany, but up to 30% in Scandinavian countries are treated with TNF-α inhibitors and the numbers are continuously growing. Anti-TNF-α antibodies (Adalimumab®; Humira) account for 90% of all biologicals in current use of rheumatoid arthritis therapy.

However, only 70% of rheumatoid arthritis patients benefit from a treatment with anti-TNFα, while 30% (~10.000 patients in Germany in 2006) remain non-responders. An anti-TNFα therapy costs currently ~20.000 € in Germany and hence, the costs of unsuccessful therapies account for 200 Mio €/year in Germany alone.

Next to rheumatoid arthritis, chronically elevated levels of TNF have been implicated as a pathogenic component in a number of other disease states—primarily autoimmune conditions—such as psoriasis, psoriatic arthritis, ankylosing spondylitis, Crohn's disease, ulcerative colitis, etc.

Currently, there are no biomarkers available, which can predict the outcome of a treatment with anti-TNF agents (e.g. TNF antagonists/inhibitors) prior treatment. Only reduction of all isotype levels of rheumatoid factors during and after treatment is associated with a positive response and outcome of the treatment (van Laar J M. Nat Clin Pract Rheumatol. 2007 October; 3(10):544-5. PMID: 17726429). However, high level of IgA rheumatoid factor in sera of patients with rheumatoid arthritis has been suggested to identify a subgroup of patients at risk of a poor clinical response to treatment with anti-TNFα antibodies (Bobbio-Pallavicini F. et al Ann Rheum Dis. 2007 March; 66(3):302-7. PMID: 17079248; Bobbio-Pallavicini F. et al Ann N Y Acad Sci. 2007 August; 1109:287-95. PMID: 17785317; van Laar J M. Nat Clin Pract Rheumatol. 2007 October; 3(10): 544-5. PMID: 17726429). The nature of anti-CCP antibodies suggested as a predictor for therapy efficacy is controversial (Braun-Moscovici Y et al. J Rheumatol. 2006 March; 33(3):497-500. PMID: 16511906; Bobbio-Pallavicini F et al. Ann N Y Acad Sci. 2007 August; 1109:287-95. PMID: 17785317; van Laar J M. Nat Clin Pract Rheumatol. 2007 October; 3(10):544-5. PMID: 17726429).

Thus, there is a need in the art for markers, which can predict the outcome of an anti-TNFα therapy prior to and during treatment. There is a need for stratification of patients who are to be subjected to or are being subjected to an anti-TNFα treatment and distinguishing between anti-TNFα treatment responder and Non-responder patients.

Subject of the present invention is a method for diagnosing an individual who is to be subjected to or is being subjected to an anti-TNFα treatment to assess the responsiveness to an anti-TNF treatment prior, during and/or after anti-TNFα treatment which comprises:

a. Detection of immunoglobulin(s) against one or more biomarker proteins in a bodily fluid or excrement of said patient, wherein the one or more biomarker is indicative for the responsiveness to an anti-TNF treatment prior, during and after anti-TNFα treatment.

b. Sorting the individual into responder or NON-responder based on detection of said immunoglobulin(s).

Thus, the invention provides for the first time marker which can predict the outcome of an anti-TNFα treatment prior to treatment in addition to during and/or after treatment. Anti-TNFalpha treatment may be conducted by administration of TNF inhibitors, e.g. TNF antagonists. These markers are not related to IgA rheumatoid factor. The marker according to the present invention can either be indicative of responder or of NON-responder as will be outlined below in detail. It is preferred that the responsiveness is assessed prior to treatment.

Subject of the present invention is a method for diagnosing an individual who is to be subjected to or is being subjected to an anti-TNFα treatment to assess the responsiveness to an anti-TNF treatment which comprises:

Detection of immunoglobulin(s) against one or more biomarker proteins in a bodily fluid or an excrement of said patient, wherein a biomarker protein is an expression product encoded by a gene selected from the group comprising RAB11B, PPP2R1A, KPNB1, COG4 and FDFT1, wherein an individual positive for at least one of said immunoglobulin(s) is classified as NON-responder.

In a preferred embodiment of the above-identified method the individual is sorted into one of two categories based on detection of said immunoglobulin(s), wherein an individual positive for at least one of said immunoglobulin(s) is classified as NON-responder and, wherein an individual negative for any of said detected immunoglobulin(s) is classified as responder.

In a preferred embodiment of the inventive method at least two of the biomarker proteins of the protein marker group are detected wherein a biomarker protein is an expression product encoded by a gene selected from the group comprising RAB11B, PPP2R1A, KPNB1, COG4 and FDFT1 (Protein Set 1=RAB11B, PPP2R1A, KPNB1, COG4 and FDFT1). In another preferred embodiment of the inventive method at least expression products encoded by genes RAB11B, PPP2R1A, KPNB1, COG4 and FDFT1 are detected. In another preferred embodiment only expression products encoded by genes RAB11B, PPP2R1A, KPNB1, COG4 and FDFT1 are detected. In another preferred embodiment each and only the expression products encoded by genes RAB11B, PPP2R1A, KPNB1, COG4 and FDFT1 are detected.

In another preferred embodiment of the method for diagnosing an individual who is to be subjected to or is being subjected to an anti-TNFα treatment according to the invention the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4 (Protein Set 2) and at least one of the proteins of the entire group 1 and 2 (Protein Set 1 and 2) is detected. In a preferred embodiment of the invention at least one protein from Protein Set 1 is detected and additionally at least one of Protein Set 2 is detected. In another preferred embodiment at least two of the proteins of Protein Set 1 and additionally at least one of Protein Set 2 are detected. In another preferred embodiment Protein Set 1 and Protein Set 2 are detected.

In another preferred embodiment additionally to the above cited combinations of marker proteins a protein of Protein Set 3 is detected: the Protein Set 3 comprises the expression products encoded by genes PRC1, NAT6, EEF1AL3, NP_612480.1, PLXNA2, ELMO2 and NDUFS2.

In another preferred embodiment of the invention at least two marker proteins are selected from the group comprising the marker from protein sets 1, 2 and 3 for the method for diagnosing an individual who is to be subjected to or is being subjected to an anti-TNFα treatment to assess the responsiveness to an anti-TNF treatment prior, during and/or after anti-TNFα treatment. This means in this embodiment at least two marker are selected from the group comprising RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

In another preferred embodiment at least three marker proteins are selected, more preferably four or five protein marker.

According to the present invention biomarker proteins of the present invention may be peptides, protein fragments, full length or splice variants or synthetically modified derivatives or post-translationally modified versions of the proteins encoded by aforementioned genes. Preferably, said protein fragments have a length of more than nine amino acids, more preferably at least twelve or more than twelve amino acids. Modification of proteins may be but are not limited to deimination, deamidation and/or transglutamination. Additionally, they can be artificial polypeptides being expression products derived from incorrect reading frames within the gene. An examples for such an expression product derived from incorrect reading frames within the gene is shown in FIG. 122 which is a protein sequence derived from an incorrect reading frame of the gene HS6SP1. Another example is shown in FIG. 121 which is a protein sequence derived from an incorrect reading frame of the gene C20orf149. Yet another example is shown in FIG. 119 which is a protein sequence derived from an incorrect reading frame of the gene IRAK1.

This means when for example IRAK1 is mentioned in the context of the present application it may concern the peptides, protein fragments, full length or splice variants or synthetically modified derivatives and/or post-translationally modified versions of IRAK1 and/or a protein sequence derived from an incorrect reading frame of the gene IRAK1.

A biomarker protein encompasses also variants thereof, such as peptides, protein fragments, artificial polypeptides, full length or splice variants, synthetically modified derivatives or post-translationally modified versions of the proteins encoded by aforementioned genes which are characterized in that these variants exhibit essentially the same ability to be recognized by the respective immunoglobulin as the biomarker proteins that are subject of the invention.

In particular, according to the present inventions biomarker proteins are encompassed wherein the sequences involved in binding to the respective immunoglobulin exhibit at least 80%, preferred at least 90%, more preferred at least 95% degree of sequence identity on the amino acid level to the sequences involved in binding of the biomarker proteins defined in SEQ ID No.s 59-122 as well as peptides, protein fragments, full length or splice variants, synthetically modified derivatives or post-translationally modified versions thereof exhibiting the same ability.

In context of the present invention a DNA sequence of a gene is defined by comprising all exons of a gene necessary to represent the protein coding sequence (CDS) or all splice variants thereof, as well as the exons representing the 5' untranslated region (UTR) and the 3' UTR.

According to the present invention all DNA sequences are encompassed which encode the before-mentioned biomarker proteins.

In particular, according to the present inventions furthermore DNA sequences are encompassed which exhibit referred to the sequence encoding a stretch which is involved in the binding region at least 80%, preferred at least 90%, more preferred at least 95% degree of sequence identity on the nucleic acid level to the DNA sequences encoding a stretch which is involved in the binding region defined in SEQ ID No.s 1-58 as well as fragments thereof encoding the biomarkers according to the present invention.

The before mentioned definitions for biomarker proteins and for genes encoding said biomarker proteins apply to every single embodiment of this inventions, any specific method, kit etc.

The determination of percent identity between two sequences is accomplished using the mathematical algorithm of Karlin and Altschul (1993) Proc. Natl. Acad. Sci. USA 90: 5873-5877. Such an algorithm is incorporated into the BLASTN and BLASTP programs of Altschul et al. (1990) J. Mol. Biol. 215: 403-410. BLAST nucleotide searches may be performed with the BLASTN program, score=100, word length=12, to obtain nucleotide sequences homologous to variant polypeptide encoding nucleic acids. BLAST protein searches are performed with the BLASTP program, score=50, wordlength=3, to obtain amino acid sequences homologous to the variant polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

The immunoglobulin(s) to be detected may be selected from IgA, IgD, IgG and IgM. In a preferred embodiment the immunoglobulin(s) to be detected is IgA or IgG. In the most preferred embodiment the immunoglobulin is IgA. The immunoglobulin(s) to be detected is not related to IgA rheumatoid factor.

In another preferred embodiment subsets of biomarker proteins may be used to assess the responsiveness to an anti-TNF treatment prior, during and/or after anti-TNFα treatment.

The respective set of proteins can not only predict responsiveness before, but also during treatment. Thus, a diagnostic assay based on one or more protein of the set will help the clinician in treatment decisions and the identification of anti-TNF therapy responders and non-responders a priory.

The bodily fluid and/or excrement from the individual to be assessed may be selected from a group comprising: blood, saliva, tears, synovial and spinal fluid, plasma, urine and stool.

An individual who is to be subjected to or is being subjected to an anti-TNFα treatment may suffer autoimmune conditions such as Crohn's disease, ulcerative colitis, psoriasis, psoriatic arthritis, ankylosing spondylitis, spondyloarthropathies, rheumatoid arthritis etc.

The method of the invention is especially suited for individuals suffering from rheumatoid arthritis.

Subject of the present invention is furthermore a kit for diagnosing an individual who is to be subjected to or is being subjected to an anti-TNFα treatment to assess the responsiveness to an anti-TNF treatment which comprises one or more biomarker proteins, wherein a biomarker protein is an expression product encoded by a gene selected from the group comprising RAB11B, PPP2R1A, KPNB1, COG4 and FDFT1. In a preferred embodiment the kit comprises at least those proteins encoded by a gene selected from the group comprising RAB11B, PPP2R1A, KPNB1, COG4 and FDFT1.

In a preferred embodiment of the inventive kit at least two of the biomarker proteins of the protein marker group are detected wherein a biomarker protein is an expression product encoded by a gene selected from the group comprising RAB11B, PPP2R1A, KPNB1, COG4 and FDFT1 (Protein Set 1=RAB11B, PPP2R1A, KPNB1, COG4 and FDFT1). In another preferred embodiment of the inventive kit at least one expression product encoded by genes RAB11B, PPP2R1A, KPNB1, COG4 and FDFT1 are detected. In another preferred embodiment only expression products encoded by genes RAB11B, PPP2R1A, KPNB1, COG4 and FDFT1 are detected. In another preferred embodiment each and only the expression products encoded by genes RAB11B, PPP2R1A, KPNB1, COG4 and FDFT1 are detected.

In another preferred embodiment of the kit for diagnosing an individual who is to be subjected to or is being subjected to an anti-TNFα treatment according to the invention the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4 (Protein Set 2) and at least one of the proteins of the entire group 1 and 2 (Protein Set 1 and 2) is detected. In a preferred embodiment of the invention at least one protein from Protein Set 1 is detected and additionally at least one of Protein Set 2 is detected. In another preferred embodiment at least two of the proteins of Protein Set 1 and additionally at least one of Protein Set 2 are detected. In another preferred embodiment Protein Set 1 and Protein Set 2 are detected.

In another preferred embodiment additionally to the above cited combinations of marker proteins a protein of Protein Set 3 is detected: the Protein Set 3 comprises the expression products encoded by genes PRC1, NAT6, EEF1AL3, NP_612480.1, PLXNA2, ELMO2 and NDUFS2.

In another preferred embodiment of the kit the biomarker protein group additionally comprises at least one expression product encoded by genes PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

Another preferred embodiment of the invention is a kit for diagnosing an individual who is to be subjected to or is being subjected to an anti-TNFα treatment to assess the responsiveness to an anti-TNF treatment which comprises at least two biomarker proteins, wherein a biomarker protein is an expression product encoded by a gene selected from the group comprising RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

As outlined above subject of the present invention is a method, wherein markers are detected and used to identify non-responder. A further embodiment of the present invention is the provision of marker(s), wherein the detection of those marker(s) is indicative for responder.

Thus, subject of the present invention is further a method for diagnosing an individual who is to be subjected to or is being subjected to an anti-TNFα treatment to assess the responsiveness to an anti-TNF treatment which comprises:
Detection of immunoglobulin(s) against one or more biomarker proteins in a bodily fluid or excrement of said patient, wherein a biomarker protein is an artificial peptides deduced from an expression product in an incorrect reading frame of a gene selected from the group comprising IRAK1 and C20orf149, wherein an individual positive for at least one of said immunoglobulin(s) is classified as responder.

In a preferred embodiment of the above-identified method the individual is sorted into one of two categories based on detection of said immunoglobulin(s), wherein an individual positive for at least one of said immunoglobulin(s) is classified as responder and, wherein an individual negative for any of said detected immunoglobulin(s) is classified as NON-responder.

In a preferred embodiment of the present invention the method for diagnosing an individual who is to be subjected to or is being subjected to an anti-TNFα treatment the biomarker protein group additionally comprises at least one other expression product encoded by a gene selected from a group comprising PSCD2L and PPIA.

In another preferred embodiment all members of the biomarker group are detected, the group comprising either artificial peptides deduced from an expression product in an incorrect reading frame of a gene or the expression products encoded by the following genes IRAK1 and C20orf149 as well as PSCD2L and PPIA.

The immunoglobulin(s) to be detected may be selected from IgA, IgD, IgG and IgM. In a preferred embodiment the immunoglobulin(s) to be detected is IgA or IgG. In the most preferred embodiment the immunoglobulin is IgG. The immunoglobulin(s) to be detected is not related to IgA rheumatoid factor.

Subject of the method of the present invention is a method for diagnosing an individual who is to be subjected to or is being subjected to an anti-TNFα treatment, wherein the immunoglobulin(s) is IgA and/or IgG. IgG is especially preferred in the context of a method for diagnosing an individual who is to be subjected to or is being subjected to an anti-TNFα treatment to assess the responsiveness to an anti-TNF treatment, wherein an individual positive for at least one of before said immunoglobulin(s) is classified as responder.

The respective set of proteins can not only predict responsiveness before, but also during treatment. Thus, a diagnostic assay based on one or more protein of the set will help the clinician in treatment decisions and the identification of anti-TNF therapy responders and non-responders a priory.

The bodily fluid and/or excrement from the individual to be assessed may be selected from a group comprising: blood, saliva, tears, synovial and spinal fluid, plasma, urine and stool.

An individual who is to be subjected to or is being subjected to an anti-TNFα treatment may suffer autoimmune conditions such as Crohn's disease, ulcerative colitis, psoriasis, psoriatic arthritis, ankylosing spondylitis, spondyloarthropathies, rheumatoid arthritis etc.

The method of the invention is especially suited for individuals suffering from rheumatoid arthritis.

Subject of the present invention is also a kit for diagnosing an individual who is to be subjected to or is being subjected to an anti-TNFα treatment to assess the responsiveness to an anti-TNF treatment which comprises one or more biomarker proteins, wherein a biomarker protein is an artificial peptides deduced from an expression product in an incorrect reading frame of a gene selected from the group comprising IRAK1 and C20orf149.

In a preferred embodiment of the present invention the kit for diagnosing an individual who is to be subjected to or is being subjected to an anti-TNFα treatment the biomarker protein group additionally comprises at least one other expression product encoded by a gene selected from a group comprising PSCD2L and PPIA.

In another preferred embodiment all members of the biomarker group are detected, the group comprising either artificial peptides deduced from an expression product in an incorrect reading frame of a gene or the expression products encoded by the following genes IRAK1 and C20orf149 as well as PSCD2L and PPIA.

In another embodiment of the invention the kit and the method according to the present invention may additionally comprise one or more known diagnostic markers e.g. for autoimmune disorders. In a preferred embodiment the kit may also comprise other known diagnostic markers for rheumatoid arthritis.

The proteins, protein sets/kits may be conducted in different assay types known to a person skilled in the art.

The immunoglobulins to be detected are in or isolated from body fluids and excrements, such as blood, saliva, tears, synovial and spinal fluid, plasma, urine and stool, etc.

The diagnostic assay can be of any type applied in the field of diagnostics, including but not restricted to assays methods based on
enzymatic reactions
luminescence
fluorescence
radiochemicals The preferred detection methods comprise strip tests, radioimmunoassay, chemiluminescence- and fluorescence-immunoassay, Immunoblot assay, Enzyme-linked immunoassay (ELISA), Luminex-based bead arrays, and protein microarray assay.

The assay types can further be microtitre plate-based, chip-based, bead-based, wherein the biomarker proteins can be attached to the surface or in solution.

The assays can be homogenous or heterogeneous assays, sandwich assays, competitive and non-competitive assays (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134).

TNFα treatment is conducted by administration of a TNF inhibitor to an individual in need thereof. TNF inhibitors are biologicals which bind to soluble and cell membrane-associated form of TNFα and neutralise the proinflammatory effect of TNF by preventing the binding of TNFα to the TNF-RI/II cell-surface receptors. The TNF inhibitors can be anti-TNFα antibodies or receptor molecules but also of other types. The essential of a TNF inhibitor according to the present invention is the ability to capture TNF before it binds to the TNF receptor on the cells.

Subject to the present invention is also the use of the biomarker proteins and/or protein sets and the kits comprising these biomarker proteins and/or protein sets according to the present invention for assessing the responsiveness to an anti-TNFα treatment of an individual who is to be subjected to or is being subjected to an anti-TNFα treatment.

FIGURE DESCRIPTION

FIG. 1 shows SEQ ID No. 1 which is a DNA sequence of the gene RAB11B (Table 1, No. 1)

FIG. 2 shows SEQ ID No. 2 which is a DNA sequence of the gene PPP2R1A (Table 1, No. 2)

FIG. 3 shows SEQ ID No. 3 which is a DNA sequence of the gene PPP2R1A (Table 1, No. 2)

FIG. 4 shows SEQ ID No. 4 which is a DNA sequence of the gene KPNB1 (Table 1, No. 3)

FIG. 5 shows SEQ ID No. 5 which is a DNA sequence of the gene COG4 (Table 1, No. 4)

FIG. 6 shows SEQ ID No. 6 which is a DNA sequence of the gene COG4 (Table 1, No. 4)

FIG. 7 shows SEQ ID No. 7 which is a DNA sequence of the gene COG4 (Table 1, No. 4)

FIG. 8 shows SEQ ID No. 8 which is a DNA sequence of the gene COG4 (Table 1, No. 4)

FIG. 9 shows SEQ ID No. 9 which is a DNA sequence of the gene FDFT1 (Table 1, No. 5)

FIG. 10 shows SEQ ID No. 10 which is a DNA sequence of the gene PECI (Table 1, No. 6)

FIG. 11 shows SEQ ID No. 11 which is a DNA sequence of the gene PECI (Table 1, No. 6)

FIG. 12 shows SEQ ID No. 12 which is a DNA sequence of the gene PECI (Table 1, No. 6)

FIG. 13 shows SEQ ID No. 13 which is a DNA sequence of the gene PECI (Table 1, No. 6)

FIG. 14 shows SEQ ID No. 14 which is a DNA sequence of the gene PECI (Table 1, No. 6)

FIG. 15 shows SEQ ID No. 15 which is a DNA sequence of the gene CTNND2 (Table 1, No. 7)

FIG. 16 shows SEQ ID No. 16 which is a DNA sequence of the gene CTNND2 (Table 1, No. 7)

FIG. 17 shows SEQ ID No. 17 which is a DNA sequence of the gene NSMCE1 (Table 1, No. 8)

FIG. 18 shows SEQ ID No. 18 which is a DNA sequence of the gene NSMCE1 (Table 1, No. 8)

FIG. 19 shows SEQ ID No. 19 which is a DNA sequence of the gene NSMCE1 (Table 1, No. 8)

FIG. 20 shows SEQ ID No. 20 which is a DNA sequence of the gene KTELC1 (Table 1, No. 9)

FIG. 21 shows SEQ ID No. 21 which is a DNA sequence of the gene HS6ST1 (Table 1, No. 10)

FIG. 22 shows SEQ ID No. 22 which is a DNA sequence of the gene ARMC6 (Table 1, No. 11)

FIG. 23 shows SEQ ID No. 23 which is a DNA sequence of the gene ARMC6 (Table 1, No. 11)

FIG. 24 shows SEQ ID No. 24 which is a DNA sequence of the gene ARMC6 (Table 1, No. 11)

FIG. 25 shows SEQ ID No. 25 which is a DNA sequence of the gene ARMC6 (Table 1, No. 11)

FIG. 26 shows SEQ ID No. 26 which is a DNA sequence of the gene TH1L (Table 1, No. 12)

FIG. 27 shows SEQ ID No. 27 which is a DNA sequence of the gene PSME1 (Table 1, No. 13)

FIG. 28 shows SEQ ID No. 28 which is a DNA sequence of the gene PSME1 (Table 1, No. 13)

FIG. 29 shows SEQ ID No. 29 which is a DNA sequence of the gene GPC1 (Table 1, No. 14)

FIG. 30 shows SEQ ID No. 30 which is a DNA sequence of the gene EDC4 (Table 1, No. 15)

FIG. 31 shows SEQ ID No. 31 which is a DNA sequence of the gene EDC4 (Table 1, No. 15)

FIG. 32 shows SEQ ID No. 32 which is a DNA sequence of the gene PRC1 (Table 1, No. 16)

FIG. 33 shows SEQ ID No. 33 which is a DNA sequence of the gene PRC1 (Table 1, No. 16)

FIG. 34 shows SEQ ID No. 34 which is a DNA sequence of the gene PRC1 (Table 1, No. 16)

FIG. 35 shows SEQ ID No. 35 which is a DNA sequence of the gene NAT6 (Table 1, No. 17)

FIG. 36 shows SEQ ID No. 36 which is a DNA sequence of the gene NAT6 (Table 1, No. 17)

FIG. 37 shows SEQ ID No. 37 which is a DNA sequence of the gene NAT6 (Table 1, No. 17)

FIG. 38 shows SEQ ID No. 38 which is a DNA sequence of the gene EEF1AL3 (Table 1, No. 18)

FIG. 39 shows SEQ ID No. 39 which is a DNA sequence of the gene NP_612480.1 (Table 1, No. 19)

FIG. 40 shows SEQ ID No. 40 which is a DNA sequence of the gene PLXNA2 (Table 1, No. 20)

FIG. 41 shows SEQ ID No. 41 which is a DNA sequence of the gene PLXNA2 (Table 1, No. 20)

FIG. 42 shows SEQ ID No. 42 which is a DNA sequence of the gene ELMO2 (Table 1, No. 21)

FIG. 43 shows SEQ ID No. 43 which is a DNA sequence of the gene ELMO2 (Table 1, No. 21)

FIG. 44 shows SEQ ID No. 44 which is a DNA sequence of the gene ELMO2 (Table 1, No. 21)

FIG. 45 shows SEQ ID No. 45 which is a DNA sequence of the gene ELMO2 (Table 1, No. 21)

FIG. 46 shows SEQ ID No. 46 which is a DNA sequence of the gene NDUFS2 (Table 1, No. 22)

FIG. 47 shows SEQ ID No. 47 which is a DNA sequence of the gene NDUFS2 (Table 1, No. 22)

FIG. 48 shows SEQ ID No. 48 which is a DNA sequence of the gene IRAK1 (Table 1, No. 23)

FIG. 49 shows SEQ ID No. 49 which is a DNA sequence of the gene IRAK1 (Table 1, No. 23)

FIG. 50 shows SEQ ID No. 50 which is a DNA sequence of the gene IRAK1 (Table 1, No. 23)

FIG. 51 shows SEQ ID No. 51 which is a DNA sequence of the gene IRAK1 (Table 1, No. 23)

FIG. 52 shows SEQ ID No. 52 which is a DNA sequence of the gene IRAK1 (Table 1, No. 23)

FIG. 53 shows SEQ ID No. 53 which is a DNA sequence of the gene C20orf149 (Table 1, No. 24)

FIG. 54 shows SEQ ID No. 54 which is a DNA sequence of the gene C20orf149 (Table 1, No. 24)

FIG. 55 shows SEQ ID No. 55 which is a DNA sequence of the gene C20orf149 (Table 1, No. 24)

FIG. 56 shows SEQ ID No. 56 which is a DNA sequence of the gene PCSD2L (Table 1, No. 25)

FIG. 57 shows SEQ ID No. 57 which is a DNA sequence of the gene PCSD2L (Table 1, No. 25)

FIG. 58 shows SEQ ID No. 58 which is a DNA sequence of the gene PPIA (Table 1, No. 26)

FIG. 59 shows SEQ ID No. 59 which is a Protein sequence of the gene RAB11B (Table 1, No. 1)

FIG. 60 shows SEQ ID No. 60 which is a Protein sequence of the gene PPP2R1A (Table 1, No. 2)

FIG. 61 shows SEQ ID No. 61 which is a Protein sequence of the gene PPP2R1A (Table 1, No. 2)

FIG. 62 shows SEQ ID No. 62 which is a Protein sequence of the gene KPNB1 (Table 1, No. 3)

FIG. 64 shows SEQ ID No. 64 which is a Protein sequence of the gene COG4 (Table 1, No. 4)

FIG. 65 shows SEQ ID No. 65 which is a Protein sequence of the gene COG4 (Table 1, No. 4)

FIG. 66 shows SEQ ID No. 66 which is a Protein sequence of the gene COG4 (Table 1, No. 4)

FIG. 67 shows SEQ ID No. 67 which is a Protein sequence of the gene COG4 (Table 1, No. 4)

FIG. 68 shows SEQ ID No. 68 which is a Protein sequence of the gene FDFT1 (Table 1, No. 5)

FIG. 69 shows SEQ ID No. 69 which is a Protein sequence of the gene PECI (Table 1, No. 6)

FIG. 70 shows SEQ ID No. 70 which is a Protein sequence of the gene PECI (Table 1, No. 6)

FIG. 71 shows SEQ ID No. 71 which is a Protein sequence of the gene PECI (Table 1, No. 6)

FIG. 72 shows SEQ ID No. 72 which is a Protein sequence of the gene PECI (Table 1, No. 6)

FIG. 73 shows SEQ ID No. 73 which is a Protein sequence of the gene PECI (Table 1, No. 6)

FIG. 74 shows SEQ ID No. 74 which is a Protein sequence of the gene CTNND2 (Table 1, No. 7)

FIG. 75 shows SEQ ID No. 75 which is a Protein sequence of the gene CTNND2 (Table 1, No. 7)

FIG. 76 shows SEQ ID No. 76 which is a Protein sequence of the gene NSMCE1 (Table 1, No. 8)

FIG. 77 shows SEQ ID No. 77 which is a Protein sequence of the gene NSMCE1 (Table 1, No. 8)

FIG. 78 shows SEQ ID No. 78 which is a Protein sequence of the gene NSMCE1 (Table 1, No. 8)

FIG. 79 shows SEQ ID No. 79 which is a Protein sequence of the gene KTELC1 (Table 1, No. 9)

FIG. 80 shows SEQ ID No. 80 which is a Protein sequence of the gene HS6ST1 (Table 1, No. 10)

FIG. 81 shows SEQ ID No. 81 which is a Protein sequence of the gene ARMC6 (Table 1, No. 11)

FIG. 82 shows SEQ ID No. 82 which is a Protein sequence of the gene ARMC6 (Table 1, No. 11)

FIG. 83 shows SEQ ID No. 83 which is a Protein sequence of the gene ARMC6 (Table 1, No. 11)

FIG. 84 shows SEQ ID No. 84 which is a Protein sequence of the gene ARMC6 (Table 1, No. 11)

FIG. 85 shows SEQ ID No. 85 which is a Protein sequence of the gene TH1L (Table 1, No. 12)

FIG. 86 shows SEQ ID No. 86 which is a Protein sequence of the gene PSME1 (Table 1, No. 13)

FIG. 87 shows SEQ ID No. 87 which is a Protein sequence of the gene PSME1 (Table 1, No. 13)

FIG. 88 shows SEQ ID No. 88 which is a Protein sequence of the gene GPC1 (Table 1, No. 14)

FIG. 89 shows SEQ ID No. 89 which is a Protein sequence of the gene EDC4 (Table 1, No. 15)

FIG. 90 shows SEQ ID No. 90 which is a Protein sequence of the gene EDC4 (Table 1, No. 15)

FIG. 91 shows SEQ ID No. 91 which is a Protein sequence of the gene PRC1 (Table 1, No. 16)

FIG. 92 shows SEQ ID No. 92 which is a Protein sequence of the gene PRC1 (Table 1, No. 16)

FIG. 93 shows SEQ ID No. 93 which is a Protein sequence of the gene PRC1 (Table 1, No. 16)

FIG. 94 shows SEQ ID No. 94 which is a Protein sequence of the gene NAT6 (Table 1, No. 17)

FIG. 95 shows SEQ ID No. 95 which is a Protein sequence of the gene NAT6 (Table 1, No. 17)

FIG. 96 shows SEQ ID No. 96 which is a Protein sequence of the gene NAT6 (Table 1, No. 17)

FIG. 97 shows SEQ ID No. 97 which is a Protein sequence of the gene EEF1AL3 (Table 1, No. 18)

FIG. 98 shows SEQ ID No. 98 which is a Protein sequence of the gene NP_612480.1 (Table 1, No. 19)

FIG. 99 shows SEQ ID No. 99 which is a Protein sequence of the gene PLXNA2 (Table 1, No. 20)

FIG. 100 shows SEQ ID No. 100 which is a Protein sequence of the gene PLXNA2 (Table 1, No. 20)

FIG. 101 shows SEQ ID No. 101 which is a Protein sequence of the gene ELMO2 (Table 1, No. 21)

FIG. 102 shows SEQ ID No. 102 which is a Protein sequence of the gene ELMO2 (Table 1, No. 21)

FIG. 103 shows SEQ ID No. 103 which is a Protein sequence of the gene ELMO2 (Table 1, No. 21)

FIG. 104 shows SEQ ID No. 104 which is a Protein sequence of the gene ELMO2 (Table 1, No. 21)

FIG. 105 shows SEQ ID No. 105 which is a Protein sequence of the gene NDUFS2 (Table 1, No. 22)

FIG. 106 shows SEQ ID No. 106 which is a Protein sequence of the gene NDUFS2 (Table 1, No. 22)

FIG. 107 shows SEQ ID No. 107 which is a Protein sequence of the gene IRAK1 (Table 1, No. 23)

FIG. 108 shows SEQ ID No. 108 which is a Protein sequence of the gene IRAK1 (Table 1, No. 23)

FIG. 109 shows SEQ ID No. 109 which is a Protein sequence of the gene IRAK1 (Table 1, No. 23)

FIG. 110 shows SEQ ID No. 110 which is a Protein sequence of the gene IRAK1 (Table 1, No. 23)

FIG. 111 shows SEQ ID No. 111 which is a Protein sequence of the gene IRAK1 (Table 1, No. 23)

FIG. 112 shows SEQ ID No. 112 which is a Protein sequence of the gene C20orf149 (Table 1, No. 24)

FIG. 113 shows SEQ ID No. 113 which is a Protein sequence of the gene C20orf149 (Table 1, No. 24)

FIG. 114 shows SEQ ID No. 114 which is a Protein sequence of the gene C20orf149 (Table 1, No. 24)

FIG. 115 shows SEQ ID No. 115 which is a Protein sequence of the gene PCSD2L (Table 1, No. 25)

FIG. 116 shows SEQ ID No. 116 which is a Protein sequence of the gene PCSD2L (Table 1, No. 25)

FIG. 117 shows SEQ ID No. 117 which is a Protein sequence of the gene PPIA (Table 1, No. 26)

FIG. 118 shows SEQ ID No. 118 which is a Protein sequence derived from an incorrect reading frame of the gene HS6ST1 (Table 1, No. 10)

FIG. 119 shows SEQ ID No. 119 which is a Protein sequence derived from an incorrect reading frame of the gene IRAK1 (Table 1, No. 23)

FIG. 120 shows SEQ ID No. 120 which is a Protein sequence derived from an incorrect reading frame of the gene C20orf149 (Table 1, No. 24)

FIG. 121 shows SEQ ID No. 121 which is a Protein sequence derived from an incorrect reading frame of the gene C20orf149 (Table 1, No. 24)

FIG. 122 shows SEQ ID No. 122 which is a Protein sequence derived from an incorrect reading frame of the gene HS6ST1 (Table 1, No. 10)

The invention also relates to the following items:

Item 1:

A method for diagnosing an individual who is to be subjected to or is being subjected to an anti-TNFα treatment to assess the responsiveness to an anti-TNF treatment prior to anti-TNFα treatment which comprises:
(a) Detection of immunoglobulin(s) against one or more biomarker proteins in a bodily fluid or an excrement of said patient, wherein the one or more biomarker is indicative for the responsiveness to an anti-TNF treatment prior to anti-TNFα treatment,
(b) Sorting the individual into responder or NON-responder based on detection of said immunoglobulin(s).

Item 2:

A method for diagnosing an individual who is to be subjected to or is being subjected to an anti-TNFα treatment to assess the responsiveness to an anti-TNF treatment prior, during and/or after anti-TNFα treatment which comprises:
(a) Detection of immunoglobulin(s) against at least two biomarker proteins in a bodily fluid or an excrement of said patient, wherein the at least two biomarker are indicative for the responsiveness to an anti-TNF treatment prior to anti-TNFα treatment,
(b) Sorting the individual into responder or NON-responder based on detection of said immunoglobulin(s).
wherein the at least two biomarker proteins are selected from the group comprising RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

Item 3:

A method for diagnosing an individual who is to be subjected to or is being subjected to an anti-TNFα treatment to assess the responsiveness to an anti-TNF treatment which comprises:

Detection of immunoglobulin(s) against one or more biomarker proteins in a bodily fluid or an excrement of said patient, wherein a biomarker protein is an expression product encoded by a gene selected from the group comprising RAB11B, PPP2R1A, KPNB1, COG4 and FDFT1, wherein an individual positive for at least one of said immunoglobulin(s) is classified as NON-Responder.

Item 4:

A method for diagnosing an individual who is to be subjected to or is being subjected to an anti-TNFα treatment according to item 1 to 3, wherein the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

Item 5:

A method for diagnosing an individual who is to be subjected to or is being subjected to an anti-TNFα treatment according to any of items 1 to 4, wherein the immunoglobulin(s) is IgA and/or IgG.

Item 6:

A method for diagnosing an individual who is to be subjected to or is being subjected to an anti-TNFα treatment according any of items 1 to 5, wherein the bodily fluid and/or excrement may be selected from a group comprising: blood, saliva, tears, synovial and spinal fluid, plasma, urine and stool.

Item 7:

A method for diagnosing an individual who is to be subjected to or is being subjected to an anti-TNFα treatment according any of items 1 to 6, wherein the individual suffers from rheumatoid arthritis.

Item 8:

A kit for diagnosing an individual who is to be subjected to or is being subjected to an anti-TNFα treatment to assess the responsiveness to an anti-TNF treatment which comprises one or more biomarker proteins, wherein a biomarker protein is an expression product encoded by a gene selected from the group comprising RAB11B, PPP2R1A, KPNB1, COG4 and FDFT1.

Item 9:

A kit according to item 8 wherein the biomarker protein group additionally comprises at least one other expression product encoded by a gene selected from the group comprising PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

Item 10

A kit for diagnosing an individual who is to be subjected to or is being subjected to an anti-TNFα treatment to assess the responsiveness to an anti-TNF treatment which comprises at least two biomarker proteins, wherein a biomarker protein is an expression product encoded by a gene selected from the group comprising RAB11B, PPP2R1A, KPNB1, COG4, FDFT1, PECI, CTNND2, NSMCE1, KTELC1, HS6ST1, ARMC6, TH1L, PSME1, GPC1, EDC4, PRC1, NAT6, EEF1AL3, NP_612480.1, PLXNA2, ELMO2 and NDUFS2.

Item 11:

A method for diagnosing an individual who is to be subjected to or is being subjected to an anti-TNFα treatment to assess the responsiveness to an anti-TNF treatment which comprises: Detection of immunoglobulin(s) against one or more biomarker proteins in a bodily fluid or an excrement of said patient, wherein a biomarker protein is an artificial peptide deduced from an expression product in an incorrect reading frame of a gene selected from the group comprising IRAK1 and C20orf149, wherein an individual positive for at least one of said immunoglobulin(s) is classified as responder.

Item 12:

A method for diagnosing an individual who is to be subjected to or is being subjected to an anti-TNFα treatment according to item 11, wherein the biomarker protein group additionally comprises at least one other expression product encoded by a gene selected from the group comprising PSCD2L and PPIA.

Item 13:

A method for diagnosing an individual who is to be subjected to or is being subjected to an anti-TNFα treatment according to any of items 11 to 12, wherein the immunoglobulin(s) is IgA and/or IgG.

Item 14:

A method for diagnosing an individual who is to be subjected to or is being subjected to an anti-TNFα treatment according any of items 11 to 13, wherein the bodily fluid and/or excrement may be selected from a group comprising: blood, saliva, tears, synovial and spinal fluid, plasma, urine and stool.

Item 15:

A method for diagnosing an individual who is to be subjected to or is being subjected to an anti-TNFα treatment according any of items 11 to 14, wherein the individual suffers from rheumatoid arthritis.

Item 16:

A kit for diagnosing an individual who is to be subjected to or is being subjected to an anti-TNFα treatment to assess the responsiveness to an anti-TNF treatment which comprises one or more biomarker proteins, wherein a biomarker protein is an artificial peptide deduced from an expression product in an incorrect reading frame of a gene selected from the group comprising IRAK1 and C20orf149.

Item 17:

A kit according to items 8 to 10, wherein the biomarker protein group additionally comprises at least one other expression product encoded by a gene selected from the group comprising PSCD2L and PPIA.

Item 18:

The use of a kit according to any of items 8 to 10, 16 and 17 for assessing the responsiveness to an anti-TNFα treatment of an individual who is to be subjected to or is being subjected to an anti-TNFα treatment.

EXAMPLES

The set of proteins which are subject of the present invention have been found by conducting serum screening experiments on protein macroarrays. The protein macroarrays consist of >38.000 individual *E. coli* clones expressing human gene fragments cloned from a foetal brain cDNA library. These fragments can be full length proteins and fragments thereof, as well as artificial peptides resulting from translation products in the incorrect reading frame. The technology for screening was developed at the MPI for Molecular Genetics and constitutes prior art; Büssow K, et al. Nucleic Acids Res. 1998 Nov. 1; 26(21):5007-8. PMID: 9776767; Büssow K, et al. Genomics 2000 Apr. 1; 65(1):1-8. PMID: 10777659) and has been applied since then in multiple scientific publications (e.g. Horn S, et al. Proteomics. 2006 January; 6(2):605-13. PMID: 16419013; Lueking A, et al. Mol Cell Proteomics. 2005 September; 4(9):1382-90. PMID: 15939964). The only amendment to the method described in the original paper is the incubation with patient serum and the use of specific secondary antibodies directed against different immunoglobulin isotypes such as IgG, IgA, IgM and IgD as described beneath:

Patient serum was diluted 1:40 in blocking buffer (3% Milk powder/TBST) and incubated overnight at room temperature, kept in slow motion on an orbital shaker. After incubation filters are washed 3×20 min. in TBST, followed by a second incubation for 1 h at room temperature with anti human IgG or anti human IgA secondary antibody (mouse) conjugated with alkaline phosphatase, 1:1000 in blocking buffer. Positive signals on the macroarray (PVDF filter) were recorded as described and correlated to the original *E. coli* clones stored in 384-well microtitre plates. *E. coli* clones corresponding with the signals on the macroarray were sequenced to obtain information of the insert, and hence the gene fragment of which the translation product is recognised by the patient sera. These fragments can be full length proteins and fragments thereof, as well as artificial peptides resulting from out-of frame-translation products.

The protein macroarrays were screened with pools of anti-TNFα treatment (Adalimumab®; Humira) responder and non-responder patient sera before and after therapy. Responder and non-responder patients were categorised according to the clinical response evaluated after 1 year (or at drop-out) in accordance with the European League Against Rheumatism criteria using the modified disease activity score that includes 28 joints (DAS 28). The DAS28 score and the European League Against Rheumatism (EULAR) response criteria are widely used to record disease activity and therapeutic response in patients with RA (Van Gestel A M et al. Arthritis Rheum 1996; 39:34-40. PMID:

The DAS28 was developed and validated for patients with RA, and in addition to disease activity it also reflects the patient's satisfaction with reasonable accuracy. This composite index comprises 4 items, namely, swollen joint count (SJC), tender joint count (TJC), a visual analog scale (VAS) of the patient's assessment of general health (GH), and erythrocyte sedimentation rate (ESR; first hour), which are also part of the American College of Rheumatology (ACR) response criteria.

Description of the used patient sera:

DAS28 values from 2 RA patient cohorts comprising 3 patients each were compared and sera of these patients before and after therapy were used for screening the protein macroarrays. RA cohort 1 (RA1) consisted of therapy responder patients and the RA cohort 2 (RA2) consisted of of age- and sex-matched patients seen during the same period who were therapy non-responders. Item weighting, factor loading, and internal consistency were assessed by factor analysis, principal component analysis, and calculation of Cronbach's alpha. The range of DAS 28 scores in the responder group initially before treatment was from 4.4-6 with a mean value of 4.83 and in the non responder group 4.1-8.6 with a mean value 6.2. Responder had a mean change of 2.36 during therapy while there was no mean change in the DAS28 in the non responder group.

Table 1 (consisting of Table 1 A and Table 1 B) shows a summary list of genes of which the expression products represent biomarker proteins and artificial peptides resulting from translation products in the incorrect reading frame found to be predictive for responsiveness to anti-TNFα antibody treatment (Adalimumab; Humira) of the patient groups described above having been subjected to an anti-TNFα treatment.

TABLE 1A

List of candidate genes encoding a biomarker set detected by immunoglobulins of TNF inhibitor therapy NON-RESPONDER patients

| No. | Importance | frame offset | ENSEMBL gene identifier | HGNC gene symbol | gene description and alternative identifiers |
|---|---|---|---|---|---|
| 1 | 1: High | 0 | ENSG00000185236 | RAB11B | Ras-related protein Rab-11B (GTP-binding protein YPT3). [Source: Uniprot/SWISSPROT; Acc: Q15907] |
| 2 | 1: High | 0 | ENSG00000105568 | PPP2R1A | Serine/threonine-protein phosphatase 2A 65 kDa regulatory subunit A alpha isoform (PP2A, subunit A, PR65-alpha isoform) (PP2A, subunit A, R1-alpha isoform) (Medium tumor antigen-associated 61 kDa protein). [Source: Uniprot/SWISSPROT; Acc: P30153] |
| 3 | 1: High | 0 | ENSG00000108424 | KPNB1 | Importin beta-1 subunit (Karyopherin beta-1 subunit) (Nuclear factor P97) (Importin 90). [Source: Uniprot/SWISSPROT; Acc: Q14974] |
| 4 | 1: High | 0 | ENSG00000103051 | COG4 | Conserved oligomeric Golgi complex component 4. [Source: Uniprot/SWISSPROT; Acc: Q9H9E3] |
| 5 | 1: High | 0 | ENSG00000079459 | FDFT1 | Squalene synthetase (EC 2.5.1.21) (SQS) (SS) (Farnesyl-diphosphate farnesyltransferase) (FPP: FPP farnesyltransferase). [Source: Uniprot/SWISSPROT; Acc: P37268] |
| 6 | 2: Medium | 0 | ENSG00000198721 | PECI | Peroxisomal 3,2-trans-enoyl-CoA isomerase (EC 5.3.3.8) (Dodecenoyl-CoA isomerase) (Delta(3), delta(2)-enoyl-CoA isomerase) (D3,D2-enoyl-CoA isomerase) (DBI-related protein 1) (DRS-1) (Hepatocellular carcinoma-associated antigen 88) (Renal carcinoma antige |
| 7 | 2: Medium | 0 | ENSG00000169862 | CTNND2 | Catenin delta-2 (Delta-catenin) (Neural plakophilin-related ARM-repeat protein) (NPRAP) (Neurojungin) (GT24). [Source: Uniprot/SWISSPROT; Acc: Q9UQB3] chromosome_NCBI36: 5: 11024952-11957110: −1 |
| 8 | 2: Medium | 0 | ENSG00000169189 | NSMCE1 | non-SMC element 1 homolog [Source: RefSeq_peptide; Acc: NP_659547] chromosome_NCBI36: 16: 27143817-27187586: −1 |
| 9 | 2: Medium | 0 | ENSG00000163389 | KTELC1 | KTEL motif-containing protein 1 precursor (CAP10-like 46 kDa protein) (Myelodysplastic syndromes relative protein). [Source: Uniprot/SWISSPROT; Acc: Q8NBL1] |
| 10 | 2: Medium | −1 | ENSG00000136720 | HS6ST1 | Heparan-sulfate 6-O-sulfotransferase 1 (EC 2.8.2.—) (HS6ST-1). [Source: Uniprot/SWISSPROT; Acc: O60243] |

TABLE 1A-continued

List of candidate genes encoding a biomarker set detected by immunoglobulins of TNF inhibitor therapy NON-RESPONDER patients

| No. | Importance | frame offset | ENSEMBL gene identifier | HGNC gene symbol | gene description and alternative identifiers |
|---|---|---|---|---|---|
| 11 | 2: Medium | 0 | ENSG00000105676 | ARMC6 | Armadillo repeat-containing protein 6. [Source: Uniprot/SWISSPROT; Acc: Q6NXE6] chromosome_NCBI36: 19: 19005538-19029985: 1 |
| 12 | 2: Medium | 0 | ENSG00000101158 | TH1L | Negative elongation factor C/D (NELF-C/D) (TH1-like protein). [Source: Uniprot/SWISSPROT; Acc: Q8IXH7] |
| 13 | 2: Medium | 0 | ENSG00000092010 | PSME1 | Proteasome activator complex subunit 1 (Proteasome activator 28-alpha subunit) (PA28alpha) (PA28a) (Activator of multicatalytic protease subunit 1) (11S regulator complex subunit alpha) (REG-alpha) (Interferon gamma up-regulated I-5111 protein) (IGUP I-51 |
| 14 | 2: Medium | 0 | ENSG00000063660 | GPC1 | Glypican-1 precursor. [Source: Uniprot/SWISSPROT; Acc: P35052] |
| 15 | 2: Medium | 0 | ENSG00000038358 | EDC4 | autoantigen RCD8 [Source: RefSeq_peptide; Acc: NP_055144] chromosome_NCBI36: 16: 66464500-66475906: 1 |
| 16 | 3: Low | 0 | ENSG00000198901 | PRC1 | Protein regulator of cytokinesis 1. [Source: Uniprot/SWISSPROT; Acc: O43663] chromosome_NCBI36: 15: 89310279-89338808: −1 |
| 17 | 3: Low | 0 | ENSG00000186792 | NAT6 | Hyaluronidase-3 precursor (EC 3.2.1.35) (Hyal-3) (Hyaluronoglucosaminidase-3) (LUCA-3). [Source: Uniprot/SWISSPROT; Acc: O43820] chromosome_NCBI36: 3: 50300178-50311903: −1 |
| 18 | 3: Low | 0 | ENSG00000185637 | EEF1AL3 | Eukaryotic translation elongation factor 1 alpha 1 (Fragment). [Source: Uniprot/SPTREMBL; Acc: Q5JR01] chromosome_NCBI36: 9: 134884631-134886374: 1 |
| 19 | 3: Low | 0 | ENSG00000168005 | NP_612480.1 | chromosome_NCBI36: 11: 63337436-63351727: 1 |
| 20 | 3: Low | 0 | ENSG00000076356 | PLXNA2 | Plexin-A2 precursor (Semaphorin receptor OCT). [Source: Uniprot/SWISSPROT; Acc: O75051] chromosome_NCBI36: 1: 206262210-206484288: −1 |
| 21 | 3: Low | 0 | ENSG00000062598 | ELMO2 | Engulfment and cell motility protein 2 (CED-12 homolog A) (hCED-12A). [Source: Uniprot/SWISSPROT; Acc: Q96JJ3] chromosome_NCBI36: 20: 44428096-44468678: −1 |
| 22 | 3: Low | 0 | ENSG00000158864 | NDUFS2 | NADH-ubiquinone oxidoreductase 49 kDa subunit, mitochondrial precursor (EC 1.6.5.3) (EC 1.6.99.3) (Complex I-49KD) (CI-49KD). [Source: Uniprot/SWISSPROT; Acc: O75306] |

TABLE 1B

List of candidate genes encoding a biomarker set detected by immunoglobulins of TNF inhibitor therapy RESPONDER patients

| No. | Importance | frame offset | ENSEMBL gene identifier | HGNC gene symbol | gene description and alternative identifiers |
|---|---|---|---|---|---|
| 23 | 1: High | −1 | ENSG00000184216 | IRAK1 | Interleukin-1 receptor-associated kinase 1 (EC 2.7.11.1) (IRAK-1). [Source: Uniprot/SWISSPROT; Acc: P51617] |
| 24 | 1: High | −1 | ENSG00000125534 | C20orf149 | UPF0362 protein C20orf149. [Source: Uniprot/SWISSPROT; Acc: Q9H3Y8] |
| 25 | 2: Medium | 0 | ENSG00000105443 | PSCD2L | Cytohesin-2 (ARF nucleotide-binding site opener) (ARNO protein) (ARF exchange factor). [Source: Uniprot/SWISSPROT; Acc: Q99418] chromosome_NCBI36: 19: 53664424-53674457: 1 |
| 26 | 3: Low | 0 | ENSG00000198618 | PPIA | Peptidyl-prolyl cis-trans isomerase A (EC 5.2.1.8) (PPIase A) (Rotamase A) (Cyclophilin A) (Cyclosporin A-binding protein). [Source: Uniprot/SWISSPROT; Acc: P62937] chromosome_NCBI36: 21: 19151917-19152651: 1 |

What is claimed is:

1. A method for diagnosing whether an individual suffering from rheumatoid arthritis will be responsive to an anti-TNFα treatment, comprising:
   (i) obtaining a biological sample from the individual;
   (ii) providing a surface comprising one or more biomarker proteins attached to said surface, wherein the biomarker protein(s) comprises one or more sequences selected from the group consisting of SEQ ID NO:119, SEQ ID NO:120 and SEQ ID NO:121
   (iii) incubating said surface with said biological sample;
   (iv) washing the product of step (iii) and incubating with an antibody that binds an IgG isotype, wherein the presence of IgG isotype immunoglobulin(s) that bind to one or more of said biomarker proteins classifies the individual as a responder to anti-TNFα treatment.

2. The method according to claim 1, wherein the biomarkers attached to said surface comprise at least one expression product encoded by a gene selected from the group consisting of PSCD2L and PPIA, wherein the expression product comprises a sequence selected from the group consisting of SEQ ID NO:115, SEQ ID NO:116, and SEQ ID NO:117.

3. The method according to claim 1, wherein the surface is part of an immunoassay.

4. The method according to claim 1, wherein the surface is part of a composition selected from the group consisting of a strip test, a radioimmunoassay, a chemiluminescence immunoassay, a fluorescence immunoassay, a immunoblot assay, an Enzyme-linked Immunoassay (ELISA), a Luminex-based bead arrays, and a protein microarray assay.

5. The method according to claim 1, wherein the biological sample is selected from the group consisting of blood, saliva, tears, synovial and spinal fluid, plasma, urine and stool.

* * * * *

```
                        SEQUENCE LISTING

<160> NUMBER OF SEQ ID NOS: 122

<210> SEQ ID NO 1
<211> LENGTH: 657
<212> TYPE: DNA
<213> ORGANISM: Human

<400> SEQUENCE: 1
atggggaccc gggacgacga gtacgactac ctattcaaag tggtgctcat cggggactca      60
ggcgtgggca agagcaacct gctgtcgcgc ttcacccgca acgagttcaa cctggagagc     120
aagagcacca tcggcgtgga gttcgccacc cgcagcatcc aggtggacgg caagaccatc     180
```

```
aaggcgcaga tctgggacac cgctggccag gagcgctacc gcgccatcac ctccgcgtac      240
taccgtggtg cagtgggcgc cctgctggtg tacgacatcg ccaagcacct gacctatgag      300
aacgtggagc gctggctgaa ggagctgcgg gaccacgcag acagcaacat cgtcatcatg      360
ctggtgggca acaagagtga cctgcgccac ctgcgggctg tgcccactga cgaggcccgc      420
gccttcgcag aaaagaacaa cttgtccttc atcgagacct cagccttgga ttccactaac      480
gtagaggaag cattcaagaa catcctcaca gagatctacc gcatcgtgtc acagaaacag      540
atcgcagacc gcgctgccca cgacgagtcc ccggggaaca acgtggtgga catcagcgtg      600
ccgcccacca cggacggaca gaagcccaac aagctgcagt gctgccagaa cctgtga        657

<210> SEQ ID NO 2
<211> LENGTH: 1530
<212> TYPE: DNA
<213> ORGANISM: Human

<400> SEQUENCE: 2
atgaggacgt tcagcttcgc ctcaacagca tcaagaagct gtccaccatc gccttggccc       60
ttggggttga aggacccga agtgagcttc tgcctttcct tacagatacc atctatgatg      120
aagatgaggt cctcctggcc ctggcagaac agctgggaac cttcactacc ctggtgggag      180
gcccagagta cgtgcactgc ctgctgcctc ttctccgtct gctaccccg agtgtccagt       240 gctgtgaagg cggaacttcg acagtacttc cggaacctgt gctcagatga caccccccatg     300 gtgcggcggg ccgcagcctc caagctgggg gagtttgcca aggtgctgga gctggacaac      360
gtcaagagtg agatcatccc catgttctcc aacctggcct ctgacgagca ggactcggtg      420
cggctgctgg cggtggaggc gtgcgtgaac atcgcccagc ttctgcccca ggaggatctg      480
gaggccctgg tgatgcccac tctgcgccag gccgctgaag acaagtcctg gcgcgtccgc      540
tacatggtgg ctgacaagtt cacagagctc cagaaagcag tggggcctga gatcaccaag      600
acagacctgg tccctgcctt ccagaacctg atgaaagact gtgaggccga ggtgagggcc      660
gcagcctccc acaaggtcaa agagttctgt gaaaacctct cagctgactg tcgggagaat      720
gtgatcatgt cccagatctt gccctgcatc aaggagctgg tgtccgatgc aaccaacat       780 gtcaagtctg ccctggcctc agtcatcatg ggtctctctc ccatcttggg caaagacaac      840
accatcgagc cctcttgcc cctcttcctg gctcagctga aggatgagtg ccctgaggta       900
cggctgaaca tcatctctaa cctggactgt gtgaacgagg tgattggcat ccggcagctg      960
tcccagtccc tgctccctgc cattgtggag ctggctgagg acgccaagtg gcgggtgcgg     1020
ctggccatca ttgagtacat gcccctcctg gctggacagc tgggagtgga gttctttgat     1080
gagaaactta actccttgtg catggcctgg cttgtggatc atgtatatgc catccgcgag     1140
gcagccacca gcaacctgaa gaagctagtg gaaaagtttg ggaaggagtg ggcccatgcc     1200
acaatcatcc ccaaggtctt ggccatgtcc ggagacccca actacctgca ccgcatgact     1260
acgctcttct gcatcaatgt gctgtctgag gtctgtgggc aggacatcac caccaagcac     1320
atgctaccca cggttctgcg catggctggg gacccggttg ccaatgtccg cttcaatgtg     1380
gccaagtctc tgcagaagat agggcccatc ctggacaaca gcaccttgca gagtgaagtc     1440
aagcccatcc tagagaagct gacccaggac caggatgtgg acgtcaaata ctttgcccag     1500
gaggctctga ctgttctgtc tctcgcctga                                     1530

<210> SEQ ID NO 3
<211> LENGTH: 1770
```

<212> TYPE: DNA
<213> ORGANISM: Human

<400> SEQUENCE: 3

```
atggcggcgg ccgacggcga cgactcgctg taccccatcg cggtgctcat agacgaactc      60
cgcaatgagg acgttcagct tcgcctcaac agcatcaaga agctgtccac catcgccttg     120
gcccttgggg ttgaaaggac ccgaagtgag cttctgcctt tccttacaga taccatctat     180
gatgaagatg aggtcctcct ggccctggca aacagctgg gaaccttcac taccctggtg      240
ggaggcccag agtacgtgca ctgcctgctg ccaccgctgg agtcgctggc cacagtggag     300
gagacagtgg tgcgggacaa ggcagtgag tccttacggg ccatctcaca cgagcactcg      360
ccctctgacc tggaggcgca ctttgtgccg ctagtgaagc ggctggcggg cggcgactgg     420
ttcacctccc gcacctcggc ctgcggcctc ttctccgtct gctaccccg agtgtccagt      480
gctgtgaagg cggaacttcg acagtacttc cggaacctgt gctcagatga cacccccatg     540
gtgcggcggg ccgcagcctc caagctgggg gagtttgcca aggtgctgga gctggacaac     600
gtcaagagtg agatcatccc catgttctcc aacctggcct ctgacgagca ggactcggtg     660
cggctgctgg cggtggaggc gtgcgtgaac atcgcccagc ttctgcccca ggaggatctg     720
gaggccctgg tgatgcccac tctgcgccag ccgctgaag acaagtcctg gcgcgtccgc      780
tacatggtgg ctgacaagtt cacagagctc cagaaagcag tggggcctga gatcaccaag     840
acagacctgg tccctgcctt ccagaacctg atgaaagact gtgaggccga ggtgagggcc     900
gcagcctccc acaaggtcaa agagttctgt gaaaacctct cagctgactg tcgggagaat     960
gtgatcatgt cccagatctt gccctgcatc aaggagctgg tgtccgatgc caaccaacat    1020
gtcaagtctg ccctggcctc agtcatcatg ggtctctctc ccatcttggg caaagacaac    1080
accatcgagc acctcttgcc cctcttcctg gctcagctga aggatgagtg ccctgaggta    1140
cggctgaaca tcatctctaa cctggactgt gtgaacgagg tgattggcat ccggcagctg    1200
tcccagtccc tgctccctgc cattgtggag ctggctgagg acgccaagtg gcgggtgcgg    1260
ctggccatca ttgagtacat gccccttcctg gctggacagc tgggagtgga gttctttgat    1320
gagaaactta actccttgtg catggcctgg cttgtggatc atgtatatgc catccgcgag    1380
gcagccacca gcaacctgaa gaagctagtg aaaagtttg ggaaggagtg ggcccatgcc     1440
acaatcatcc ccaaggtctt ggccatgtcc ggagacccca actacctgca ccgcatgact    1500
acgctcttct gcatcaatgt gctgtctgag gtctgtgggc aggacatcac caccaagcac    1560
atgctaccca cggttctgcg catggctggg gacccggttg ccaatgtccg cttcaatgtg    1620
gccaagtctc tgcagaagat agggcccatc ctggacaaca gcaccttgca gagtgaagtc    1680
aagcccatcc tagagaagct gacccaggac caggatgtgg acgtcaaata ctttgcccag    1740
gaggctctga ctgttctgtc tctcgcctga                                    1770
```

<210> SEQ ID NO 4
<211> LENGTH: 2631
<212> TYPE: DNA
<213> ORGANISM: Human

<400> SEQUENCE: 4

```
atggagctga tcaccattct cgagaagacc gtgtctcccg atcggctgga gctggaagcg      60
gcgcagaagt tcctggagcg tgcggccgtg agaacctgc ccactttcct tgtggaactg      120
tccagagtgc tggcaaatcc aggaaacagt caggttgcca gagttgcagc tggtctacaa     180
```

```
atcaagaact ctttgacatc taaagatcca gatatcaagg cacaatatca gcagaggtgg      240
cttgctattg atgctaatgc tcgacgagaa gtcaagaact atgttttgca gacattgggt      300
acagaaactt accggcctag ttctgcctca cagtgtgtgg ctggtattgc ttgtgcagag      360
atcccagtaa accagtggcc agaactcatt cctcagctgg tggccaatgt cacaaacccc      420
aacagcacag agcacatgaa ggagtcgaca ttggaagcca tcggttatat ttgccaagat      480
atagacccag agcagctaca agataaatcc aatgagattc tgactgccat aatccagggg      540
atgaggaaag aagagcctag taataatgtg aagctagctg ctacgaatgc actcctgaac      600
tcattggagt tcaccaaagc aaactttgat aaagagtctg aaaggcactt tattatgcag      660
gtggtctgtg aagccacaca gtgtccagat acgagggtac gagtggctgc tttacagaat      720
ctggtgaaga taatgtcctt atattatcag tacatggaga catatatggg tcctgctctt      780
tttgcaatca caatcgaagc aatgaaaagt gacattgatg aggtggcttt acaagggata      840
gaattctggt ccaatgtctg tgatgaggaa atggatttgg ccattgaagc ttcagaggca      900
gcagaacaag gacggccccc tgagcacacc agcaagtttt atgcgaaggg agcactacag      960
tatctggttc caatcctcac acagacacta actaaacagg acgaaaatga tgatgacgat     1020
gactggaacc cctgcaaagc agcaggggtg tgcctcatgc ttctggccac ctgctgtgaa     1080
gatgacattg tcccacatgt cctcccctctc attaaagaac acatcaagaa cccagattgg     1140
cggtaccggg atgcagcagt gatggctttt ggttgtatct tggaaggacc agagcccagt     1200
cagctcaaac cactagttat acaggctatg cccaccctaa tagaattaat gaaagacccc     1260
agtgtagttc ttcgagatac agctgcatgg actgtaggca gaatttgtga gctgcttcct     1320
gaagctgcca tcaatgatgt ctacttggct cccctgctac agtgtctgat tgagggtctc     1380
agtgctgaac cagagtggc ttcaaatgtg tgctgggctt tctccagtct ggctgaagct     1440
gcttatgaag ctgcagacgt tgctgatgat caggaagaac cagctactta ctgcttatct     1500
tcttcatttg aactcatagt tcagaagctc ctagagacta cagacagacc tgatggacac     1560
cagaacaacc tgaggagttc tgcatatgaa tctctgatgg aaattgtgaa aaacagtgcc     1620
aaggattgtt atcctgctgt ccagaaaacg actttggtca tcatggaacg actgcaacag     1680
gttcttcaga tggagtcaca tatccagagc acatccgata gaatccagtt caatgacctt     1740
cagtctttac tctgtgcaac tcttcagaat gttcttcgga aagtgcaaca tcaagatgct     1800
ttgcagatct ctgatgtggt tatggcctcc ctgttaagga tgttccaaag cacagctggg     1860
tctgggggag tacaagagga tgccctgatg gcagttagca cactggtgga agtgtttggt     1920
ggtgaattcc tcaagtacat ggaggccttt aaacccttcc tgggcattgg attaaaaaat     1980
tatgctgaat accaggtttg tttggcagct gtgggcttag tgggagactt gtgccgtgcc     2040
ctgcaatcca acatcatacc tttctgtgac gaggtgatgc agctgcttct ggaaaatttg     2100
gggaatgaga acgtccacag gtctgtgaag ccgcagattc tgtcagtgtt tggtgatatt     2160
gcccttgcta ttggaggaga gtttaaaaaa tacttagagg ttgtattgaa tactcttcag     2220
caggcctccc aagcccaggt ggacaagtca gactatgaca tggtggatta tctgaatgag     2280
ctaagggaaa gctgcttgga agcctatact ggaatcgtcc agggattaaa ggggatcag      2340 gagaacgtac acccggatgt gatgctggta caacccagag tagaatttat tctgtctttc     2400
attgaccaca ttgctggaga tgaggatcac acagatggag tagtagcttg tgctgctgga     2460 ctaataggggg acttatgtac agcatttggg aaggatgtac tgaaattagt agaagctagg     2520
ccaatgatcc atgaattgtt aactgaaggg cggagatcga agactaacaa agcaaaaacc     2580
```

```
cttgctacat gggcaacaaa agaactgagg aaactgaaga accaagcttg a            2631
```

<210> SEQ ID NO 5
<211> LENGTH: 2370
<212> TYPE: DNA
<213> ORGANISM: Human

<400> SEQUENCE: 5

```
atggggacca agatggcgga ccttgattcg cctccgaagc tgtcagggt gcagcagccg      60
tctgagggg tgggaggtgg ccgctgctcc gaaatctccg ctgagctcat tcgctccctg     120
acagagctgc aggagctgga ggctgtatac aacggctct gcggcgagga aaagtggtg     180
gagagagagc tggatgctct tttggaacag caaaacacca ttgaaagtaa gatggtcact     240
ctccaccgaa tgggtcctaa tctgcagctg attgagggag atgcaaagca gctggctgga     300
atgatcacct ttacctgcaa cctggctgag aatgtgtcca gcaaagttcg tcagcttgac     360
ctggccaaga accgcctcta tcaggccatt cagagagctg atgacatctt ggacctgaag     420
ttctgcatgg atggagttca gactgctttg aggagtgaag attatgagca ggctgcagca     480
catactcatc gctacttgtg cctggacaag tcggtcattg agctcagccg acagggcaaa     540
gaggggagca tgattgatgc caacctgaaa ttgctgcagg aagctgagca acgtctcaaa     600
gccattgtgg cagagaagtt tgccattgcc accaaggaag tgatctgcc ccaggtggag     660
cgcttcttca agatcttccc actgctgggt ttgcatgagg agggattaag aaagttctcg     720
gagtaccttt gcaagcaggt ggccagtaaa gctgaggaga tctgctcat ggtgctgggg     780
acagacatga gtgatcggag agctgcagtc atctttgcag atacacttac tcttctgttt     840
gaagggattg cccgcattgt ggagacccac cagccaatag tggagaccta ttatgggcca     900
gggagactct ataccctgat caaatatctg caggtggaat gtgacagaca ggtggagaag     960
gtggtagaca agttcatcaa gcaaagggac taccaccagc agttccggca tgttcagaac    1020
aacctgatga gaaattctac aacagaaaaa atcgaaccaa gagaactgga ccccatcctg    1080
actgaggtca ccctgatgaa tgcccgcagt gagctatact tacgcttcct caagaagagg    1140
attagctctg attttgaggt gggagactcc atggcctcag aggaagtaaa gcaagagcac    1200
cagaagtgtc tggacaaaact cctcaataac tgccttttga gctgtaccat gcaggagcta    1260
attggcttat atgttaccat ggaggagtac ttcatgaggg agactgtcaa taaggctgtg    1320
gctctggaca cctatgagaa gggccagctg acatccagca tggtggatga tgtcttctac    1380
attgttaaga agtgcattgg gcgggctctg tccagctcca gcattgactg tctctgtgcc    1440
atgatcaacc tcgccaccac agagctggag tctgacttca gggatgttct gtgtaataag    1500
ctgcggatgg gctttcctgc caccaccttc aggacatcc agcgcgggt gacaagtgcc    1560
gtgaacatca tgcacagcag cctccagcaa ggcaaatttg acacaaaagg catcgagagt    1620
actgacgagg cgaagatgtc cttcctggtg actctgaaca acgtggaagt ctgcagtgaa    1680
aacatctcca ctctgaagaa gacactggag agtgactgca ccaagctctt cagccagggc    1740
attggagggg agcaggccca ggccaagttt gacagctgcc tttctgactt ggccgccgtg    1800
tccaacaaat tccgagacct cttgcaggaa gggctgacga gctcaacag cacagccatc    1860
aagccacagg tgcagccttg gatcaacagc ttttttctccg tctcccacaa catcgaggag    1920
gaagaattca atgactatga ggccaacgac ccttgggtac aacagttcat ccttaacctg    1980
gagcagcaaa tggcagagtt caaggccagc ctgtccccgg tcatctacga cagcctaacc    2040
```

| | |
|---|---:|
| ggcctcatga ctagccttgt tgccgtcgag ttggagaaag tggtgctgaa atccaccttt | 2100 |
| aaccggctgg gtggtctgca gtttgacaag gagctgaggt cgctcattgc ctaccttacc | 2160 |
| acggtgacca cctggaccat ccgagacaag tttgcccggc tctcccagat ggccaccatc | 2220 |
| ctcaatctgg agcgggtgac cgagatcctc gattactggg acccaattc cggcccattg | 2280 |
| acgtggcgcc tcacccctgc tgaagtgcgc caggtgctgg ccctgcggat agacttccgc | 2340 |
| agtgaagata tcaagaggct gcgcctgtag | 2370 |

<210> SEQ ID NO 6
<211> LENGTH: 1014
<212> TYPE: DNA
<213> ORGANISM: Human

<400> SEQUENCE: 6

| | |
|---|---:|
| atggcggacc ttgattcgcc tccgaagctg tcaggggtgc agcagccgtc tgaggggtg | 60 |
| ggaggtggcc gctgctccga aatctccgct gagctcattc gctccctgac agagctgcag | 120 |
| gagctggagg ctgtatacga acggctctgc ggcgaggaga agtggtgga gagagagctg | 180 |
| gatgctcttt tggaacagca aaacaccatt gaaagtaaga tggtcactct ccaccgaatg | 240 |
| ggtcctaatc tgcagctgat tgaggagat gcaaagcagc tggctggaat gatcaccttt | 300 |
| acctgcaacc tggctgagaa tgtgtccagc aaagttcgtc agcttgacct ggccaagaac | 360 |
| cgcctctatc aggccattca gagagctgat gacatcttgg acctgaagtt ctgcatggat | 420 |
| ggagttcaga ctgctttgag gagtgaagat tatgagcagg ctgcagcaca tactcatcgc | 480 |
| tacttgtgcc tggacaagtc ggtcattgag ctcagccgac agggcaaaga ggggagcatg | 540 |
| attgatgcca acctgaaatt gctgcaggaa gctgagcaac gtctcaaagc cattgtggca | 600 |
| gagaagtttg ccattgccac caaggaaggt gatctgcccc aggtggagcg cttcttcaag | 660 |
| atcttcccac tgctgggttt gcatgaggag ggattaagaa agttctcgga gtacctttgc | 720 |
| aagcaggtgg ccagtaaagc tgaggagaat ctgctcatgg tgctggggac agacatgagt | 780 |
| gatcggagag ctgcagtcat cttttgcaga tacacttactc ttctgtttga agggattgcc | 840 |
| cgcattgtgg agacccacca gccaatagtg gagacctatt atgggccagg agactctat | 900 |
| accctgatca aatatctgca ggtggaatgt gacagacagg tggagaaggt ggtagacaag | 960 |
| ttcatcaagc aaagggacta ccaccagcag aactttgttt tttccttctt ttga | 1014 |

<210> SEQ ID NO 7
<211> LENGTH: 2358
<212> TYPE: DNA
<213> ORGANISM: Human

<400> SEQUENCE: 7

| | |
|---|---:|
| atggcggacc ttgattcgcc tccgaagctg tcaggggtgc agcagccgtc tgaggggtg | 60 |
| ggaggtggcc gctgctccga aatctccgct gagctcattc gctccctgac agagctgcag | 120 |
| gagctggagg ctgtatacga acggctctgc ggcgaggaga agtggtgga gagagagctg | 180 |
| gatgctcttt tggaacagca aaacaccatt gaaagtaaga tggtcactct ccaccgaatg | 240 |
| ggtcctaatc tgcagctgat tgaggagat gcaaagcagc tggctggaat gatcaccttt | 300 |
| acctgcaacc tggctgagaa tgtgtccagc aaagttcgtc agcttgacct ggccaagaac | 360 |
| cgcctctatc aggccattca gagagctgat gacatcttgg acctgaagtt ctgcatggat | 420 |
| ggagttcaga ctgctttgag gagtgaagat tatgagcagg ctgcagcaca tactcatcgc | 480 |
| tacttgtgcc tggacaagtc ggtcattgag ctcagccgac agggcaaaga ggggagcatg | 540 |

-continued

```
attgatgcca acctgaaatt gctgcaggaa gctgagcaac gtctcaaagc cattgtggca      600
gagaagtttg ccattgccac caaggaaggt gatctgcccc aggtggagcg cttcttcaag      660
atcttcccac tgctgggttt gcatgaggag ggattaagaa agttctcgga gtacctttgc      720
aagcaggtgg ccagtaaagc tgaggagaat ctgctcatgg tgctggggac agacatgagt      780
gatcggagag ctgcagtcat cttttgcagat acacttactc ttctgtttga agggattgcc     840
cgcattgtgg agacccacca gccaatagtg gagacctatt atgggccagg agactctat       900 accctgatca aatatctgca ggtggaatgt gacagacagg tggagaaggt ggtagacaag      960
ttcatcaagc aaagggacta ccaccagcag ttccggcatg ttcagaacaa cctgatgaga     1020
aattctacaa cagaaaaaat cgaaccaaga gaactggacc ccatcctgac tgaggtcacc     1080
ctgatgaatg cccgcagtga gctatactta cgcttcctca agaagaggat tagctctgat    1140
tttgaggtgg gagactccat ggcctcagag gaagtaaagc aagagcacca gaagtgtctg     1200
gacaaactcc tcaataactg cctttttgagc tgtaccatgc aggagctaat tggcttatat    1260
gttaccatgg aggagtactt catgagggag actgtcaata aggctgtggc tctggacacc    1320
tatgagaagg ccagctgac atccagcatg gtggatgatg tcttctacat tgttaagaag     1380
tgcattgggc gggctctgtc cagctccagc attgactgtc tctgtgccat gatcaacctc    1440
gccaccacag agctggagtc tgacttcagg gatgttctgt gtaataagct gcggatgggc    1500
tttcctgcca ccaccttcca ggacatccag cgcggggtga caagtgccgt gaacatcatg    1560
cacagcagcc tccagcaagg caaatttgac acaaaaggca tcgagagtac tgacgaggcg    1620
aagatgtcct tcctggtgac tctgaacaac gtggaagtct gcagtgaaaa catctccact    1680
ctgaagaaga cactggagag tgactgcacc aagctcttca gccagggcat tggaggggag    1740
caggcccagg ccaagtttga cagctgcctt tctgacttgg ccgccgtgtc caacaaattc    1800
cgagacctct gcaggaagg gctgacggag ctcaacagca cagccatcaa gccacaggtg    1860
cagccttgga tcaacagctt tttctccgtc tcccacaaca tcgaggagga agaattcaat    1920
gactatgagg ccaacgaccc ttgggtacaa cagttcatcc ttaacctgga gcagcaaatg    1980
gcagagttca aggccagcct gtccccggtc atctacgaca gcctaaccgg cctcatgact   2040
agccttgttg ccgtcgagtt ggagaaagtg gtgctgaaat ccacctttaa ccggctgggt    2100
ggtctgcagt ttgacaagga gctgaggtcg ctcattgcct accttaccac ggtgaccacc    2160
tggaccatcc gagacaagtt tgcccggctc tcccagatgg ccaccatcct caatctggag    2220
cgggtgaccg agatcctcga ttactgggga cccaattccg gcccattgac gtggcgcctc    2280 accccctgctg aagtgcgcca ggtgctggcc ctgcggatag acttccgcag tgaagatatc    2340
aagaggctgc gcctgtag                                                   2358
```

<210> SEQ ID NO 8
<211> LENGTH: 2088
<212> TYPE: DNA
<213> ORGANISM: Human

<400> SEQUENCE: 8

```
atggggacca agatggcgga ccttgattcg cctccgaagc tgtcaggggt gcagcagccg       60
tctgaggggg tgggaggtgg ccgctgctcc gaaatctccg ctgagctcat tcgctccctg      120
acagagctgc aggagctgga ggctgtatac gaacggctct gcggcgagga gaaagtggtg      180
gagagagagc tggatgctct tttggaacag caaaacacca ttgaaagtaa gatggtcact     240
```

```
ctccaccgaa tgggtcctaa tctgcagctg attgaggcca acctgaaatt gctgcaggaa    300
gctgagcaac gtctcaaagc cattgtggca gagaagtttg ccattgccac caaggaaggt    360
gatctgcccc aggtggagcg cttcttcaag atcttccac tgctgggttt gcatgaggag     420
ggattaagaa agttctcgga gtacctttgc aagcaggtgg ccagtaaagc tgaggagaat    480
ctgctcatgg tgctggggac agacatgagt gatcggagag ctgcagtcat ctttgcagat    540
acacttactc ttctgtttga agggattgcc cgcattgtgg agacccacca gccaatagtg    600
gagacctatt atgggccagg gagactctat accctgatca aatatctgca ggtggaatgt    660
gacagacagg tggagaaggt ggtagacaag ttcatcaagc aaagggacta ccaccagcag    720
ttccggcatg ttcagaacaa cctgatgaga aattctacaa cagaaaaaat cgaaccaaga    780
gaactggacc ccatcctgac tgaggtcacc ctgatgaatg cccgcagtga gctatactta    840
cgcttcctca agaagaggat tagctctgat tttgaggtgg gagactccat ggcctcagag    900
gaagtaaagc aagagcacca gaagtgtctg acaaactcc tcaataactg ccttttgagc     960
tgtaccatgc aggagctaat tggcttatat gttaccatgg aggagtactt catgagggag   1020
actgtcaata aggctgtggc tctggacacc tatgagaagg ccagctgac atccagcatg    1080 gtggatgatg tcttctacat tgttaagaag tgcattgggc gggctctgtc cagctccagc   1140
attgactgtc tctgtgccat gatcaacctc gccaccacag agctggagtc tgacttcagg   1200
gatgttctgt gtaataagct gcggatgggc tttcctgcca ccaccttcca ggacatccag   1260
cgcggggtga caagtgccgt gaacatcatg cacagcagcc tccagcaagg caaatttgac   1320
acaaaaggca tcgagagtac tgacgaggcg aagatgtcct tcctggtgac tctgaacaac   1380
gtggaagtct gcagtgaaaa catctccact ctgaagaaga cactggagag tgactgcacc   1440
aagctcttca gccagggcat tggagggag caggcccagg ccaagtttga cagctgcctt    1500
tctgacttgg ccgccgtgtc caacaaattc cgagacctct tgcaggaagg gctgacggag   1560
ctcaacagca cagccatcaa gccacaggtg cagccttgga tcaacagctt tttctccgtc   1620
tcccacaaca tcgaggagga agaattcaat gactatgagg ccaacgaccc ttgggtacaa   1680
cagttcatcc ttaacctgga gcagcaaatg gcagagttca aggccagcct gtccccggtc   1740
atctacgaca gcctaaccgg cctcatgact agccttgttg ccgtcgagtt ggagaaagtg   1800
gtgctgaaat ccacctttaa ccggctgggt ggtctgcagt ttgacaagga gctgaggtcg   1860
ctcattgcct accttaccac ggtgaccacc tggaccatcc gagacaagtt tgcccggctc   1920
tcccagatgg ccaccatcct caatctggag cgggtgaccg agatcctcga ttactgggga   1980
cccaattccg gcccattgac gtggcgcctc accctgctg aagtgcgcca ggtgctggcc     2040
ctgcggatag acttccgcag tgaagatatc aagaggctgc gcctgtag                  2088
```

<210> SEQ ID NO 9
<211> LENGTH: 1254
<212> TYPE: DNA
<213> ORGANISM: Human

<400> SEQUENCE: 9

```
atggagttcg tgaaatgcct tggccacccc gaagagttct acaacctggt gcgcttccgg     60
atcgggggca gcggaaggt gatgcccaag atggaccagg actcgctcag cagcagcctg    120
aaaacttgct acaagtatct caatcagacc agtcgcagtt tcgcagctgt tatccaggcg    180
ctggatgggg aaatgcgcaa cgcagtgtgc atattttatc tggttctccg agctctggac    240
acactggaag atgacatgac catcagtgtg gaaaagaagg tcccgctgtt acacaacttt    300
```

-continued

```
cactctttcc tttaccaacc agactggcgg ttcatggaga gcaaggagaa ggatcgccag      360
gtgctggagg acttcccaac gatctccctt gagtttagaa atctggctga aaataccaa      420 acagtgattg ccgacatttg ccggagaatg ggcattggga tggcagagtt tttggataag      480
catgtgacct ctgaacagga gtgggacaag tactgccact atgttgctgg gctggtcgga      540
attggccttt cccgtctttt ctcagcctca gagtttgaag accccttagt tggtgaagat      600
acagaacgtg ccaactctat gggcctgttt ttgcagaaaa caaacatcat ccgtgactat      660
ctggaagacc agcaaggagg aagagagttc tggcctcaag aggtttggag caggtatgtt      720
aagaagttag gggattttgc taagccggag aatattgact tggccgtgca gtgcctgaat      780
gaacttataa ccaatgcact gcaccacatc ccagatgtca tcacctacct ttcgagactc      840
agaaaccaga gtgtgtttaa cttctgtgct attccacagg tgatggccat tgccactttg      900 gctgctgtt ataataacca gcaggtgttc aaaggggcag tgaagattcg gaaagggcaa      960
gcagtgaccc tgatgatgga tgccaccaat atgccagctg tcaaagccat catatatcag     1020
tatatggaag agatttatca tagaatcccc gactcagacc catcttctag caaaacaagg     1080
cagatcatct ccaccatccg gacgcagaat cttcccaact gtcagctgat tcccgaagc     1140 cactactccc ccatctacct gtcgtttgtc atgcttttgg ctgccctgag ctggcagtac     1200
ctgaccactc tctcccaggt aacagaagac tatgttcaga ctggagaaca ctga           1254
```

<210> SEQ ID NO 10
<211> LENGTH: 1080
<212> TYPE: DNA
<213> ORGANISM: Human

<400> SEQUENCE: 10

```
atgagagcca gtcagaagga cttttgaaaat tcaatgaatc aagtgaaact cttgaaaaag       60
gatccaggaa acgaagtgaa gctaaaactc tacgcgctat ataagcaggc cactgaagga      120
ccttgtaaca tgcccaaacc aggtgtattt gacttgatca acaaggccaa atgggacgca      180
tggaatgccc ttggcagcct gcccaaggaa gctgccaggc agaactatgt ggatttggtg      240
tccagtttga gtccttcatt ggaatcctct agtcaggtgg agcctggaac agacaggaaa      300
tcaactgggt ttgaaactct ggtggtgacc tccgaagatg gcatcacaaa gatcatgttc      360
aaccggccca aaagaaaaa tgccataaac actgagatgt atcatgaaat tatgcgtgca      420
cttaaagctg ccagcaagga tgactcaatc atcactgttt taacaggaaa tggtgactat      480
tacagtagtg ggaatgatct gactaacttc actgatattc ccctggtgg agtagaggag      540 aaagctaaaa ataatgccgt tttactgagg gaatttgtgg gctgttttat agattttcct      600
aagcctctga ttgcagtggt caatggtcca gctgtgggca tctccgtcac cctccttggg      660
ctattcgatg ccgtgtatgc atctgacagg gcaacatttc ataccccatt tagtcaccta      720
ggccaaagtc cggaaggatg ctcctcttac acttttccga agataatgag cccagccaag      780
gcaacagaga tgcttatttt tggaaagaag ttaacagcgg gagaggcatg tgctcaagga      840
cttgttactg aagtttttccc tgatagcact tttcagaaag aagtctggac caggctgaag      900
gcatttgcaa gcttccccc aaatgccttg agaatttcaa aagaggtaat caggaaaaga      960
gagagagaaa aactacacgc tgttaatgct gaagaatgca atgtccttca gggaagatgg     1020
ctatcagatg aatgcacaaa tgctgtggtg aacttcttat ccagaaaatc aaaactgtga     1080
```

<210> SEQ ID NO 11

<211> LENGTH: 684
<212> TYPE: DNA
<213> ORGANISM: Human

<400> SEQUENCE: 11

```
atgtatcatg aaattatgcg tgcacttaaa gctgccagca aggatgactc aatcatcact        60
gttttaacag gaaatggtga ctattacagt agtgggaatg atctgactaa cttcactgat       120 attcccctg gtggagtaga ggagaaagct aaaaataatg ccgtttact gagggaattt         180 gtgggctgtt ttatagattt tcctaagcct ctgattgcag tggtcaatgg tccagctgtg       240
ggcatctccg tcaccctcct tgggctattc gatgccgtgt atgcatctga cagggcaaca       300
tttcatacac catttagtca cctaggccaa agtccggaag gatgctcctc ttacactttt       360
ccgaagataa tgagcccagc caaggcaaca gagatgctta ttttggaaa gaagttaaca        420 gcgggagagg catgtgctca aggacttgtt actgaagttt tccctgatag cacttttcag       480
aaagaagtct ggaccaggct gaaggcattt gcaaagcttc ccccaaatgc cttgagaatt       540
tcaaaagagg taatcaggaa aagagagaga gaaaaactac acgctgttaa tgctgaagaa       600
tgcaatgtcc ttcagggaag atggctatca gatgaatgca caaatgctgt ggtgaacttc       660
ttatccagaa aatcaaaact gtga                                             684
```

<210> SEQ ID NO 12
<211> LENGTH: 1185
<212> TYPE: DNA
<213> ORGANISM: Human

<400> SEQUENCE: 12

```
atggcgatgg cgtacttggc ttggagactg gcgcggcgtt cgtgtccgag ttctctgcag        60
gtcactagtt tcccggtagt tcagctgcac atgaatagaa cagcaatgag agccagtcag       120
aaggactttg aaaattcaat gaatcaagtg aaactcttga aaaaggatcc aggaaacgaa       180
gtgaagctaa aactctacgc gctatataag caggccactg aaggaccttg taacatgccc       240
aaaccaggtg tatttgactt gatcaacaag gccaatggg acgcatggaa tgcccttggc       300
agcctgccca aggaagctgc caggcagaac tatgtggatt tggtgtccag tttgagtcct       360
tcattggaat cctctagtca ggtggagcct ggaacagaca ggaaatcaac tgggtttgaa       420
actctggtgg tgacctccga agatggcatc acaaagatca tgttcaaccg gcccaaaaag       480
aaaaatgcca taaacactga gatgtatcat gaaattatgc gtgcacttaa agctgccagc       540
aaggatgact caatcatcac tgttttaaca ggaaatggtg actattacag tagtgggaat       600
gatctgacta acttcactga tattcccct ggtggagtag aggagaaagc taaaaataat        660
gccgttttac tgagggaatt tgtgggctgt tttatagatt ttcctaagcc tctgattgca       720
gtggtcaatg gtccagctgt gggcatctcc gtcaccctcc ttgggctatt cgatgccgtg       780
tatgcatctg acagggcaac atttcataca ccatttagtc acctaggcca aagtccggaa       840
ggatgctcct cttacacttt tccgaagata atgagcccag ccaaggcaac agagatgctt       900 attttggaa gaagttaac agcgggagag gcatgtgctc aaggacttgt tactgaagtt         960
ttccctgata gcacttttca gaaagaagtc tggaccaggc tgaaggcatt tgcaaagctt      1020
cccccaaatg ccttgagaat ttcaaaagag gtaatcagga aagagagag agaaaaacta      1080 cacgctgtta atgctgaaga atgcaatgtc cttcagggaa gatggctatc agatgaatgc      1140
acaaatgctg tggtgaactt cttatccaga aaatcaaaac tgtga                     1185
```

```
<210> SEQ ID NO 13
<211> LENGTH: 1095
<212> TYPE: DNA
<213> ORGANISM: Human

<400> SEQUENCE: 13
atgaatagaa cagcaatgag agccagtcag aaggactttg aaaattcaat gaatcaagtg      60
aaactcttga aaaaggatcc aggaaacgaa gtgaagctaa aactctacgc gctatataag     120
caggccactg aaggaccttg taacatgccc aaaccaggtg tatttgactt gatcaacaag     180
gccaaatggg acgcatggaa tgcccttggc agcctgccca aggaagctgc caggcagaac     240
tatgtggatt tggtgtccag tttgagtcct tcattggaat cctctagtca ggtggagcct     300
ggaacagaca ggaaatcaac tgggtttgaa actctggtgg tgacctccga agatggcatc     360
acaaagatca tgttcaaccg gcccaaaaag aaaaatgcca taaacactga gatgtatcat     420
gaaattatgc gtgcacttaa agctgccagc aaggatgact caatcatcac tgttttaaca     480
ggaaatggtg actattacag tagtgggaat gatctgacta acttcactga tattcccccct     540 ggtggagtag aggagaaagc taaaaataat gccgttttac tgagggaatt tgtgggctgt     600 ttttatagatt ttcctaagcc tctgattgca gtggtcaatg gtccagctgt gggcatctcc     660
gtcaccctcc ttgggctatt cgatgccgtg tatgcatctg acagggcaac atttcataca     720
ccatttagtc acctaggcca aagtccggaa ggatgctcct cttacacttt tccgaagata     780
atgagcccag ccaaggcaac agagatgctt attttttggaa agaagttaac agcgggagag     840
gcatgtgctc aaggacttgt tactgaagtt ttccctgata gcactttttca gaaagaagtc     900 tggaccaggc tgaaggcatt tgcaaagctt cccccaaatg ccttgagaat ttcaaaagag     960
gtaatcagga aaagagagag agaaaaacta cacgctgtta atgctgaaga atgcaatgtc    1020
cttcagggaa gatggctatc agatgaatgc acaaatgctg tggtgaactt cttatccaga    1080
aaatcaaaac tgtga                                                     1095

<210> SEQ ID NO 14
<211> LENGTH: 726
<212> TYPE: DNA
<213> ORGANISM: Human

<400> SEQUENCE: 14
atgttcaacc ggcccaaaaa gaaaaatgcc ataaacactg agatgtatca tgaaattatg      60
cgtgcactta agctgccag caaggatgac tcaatcatca ctgttttaac aggaaatggt     120
gactattaca gtagtgggaa tgatctgact aacttcactg atattccccc tggtggagta     180
gaggagaaag ctaaaaataa tgccgtttta ctgagggaat tgtgggctg ttttatagat     240 tttcctaagc ctctgattgc agtggtcaat ggtccagctg tgggcatctc cgtcaccctc     300
cttgggctat cgatgccgt gtatgcatct gacagggcaa catttcatac accatttagt     360
cacctaggcc aaagtccgga aggatgctcc tcttacactt tccgaagat aatgagccca     420 gccaaggcaa cagagatgct tattttttgga aagaagttaa cagcgggaga ggcatgtgct     480
caaggacttg ttactgaagt tttccctgat agcacttttc agaaagaagt ctggaccagg     540
ctgaaggcat ttgcaaagct tcccccaaat gccttgagaa tttcaaaaga ggtaatcagg     600
aaaagagaga gagaaaaact acacgctgtt aatgctgaag aatgcaatgt ccttcaggga     660
agatggctat cagatgaatg cacaaatgct gtggtgaact tcttatccag aaaatcaaaa     720
ctgtga                                                                726
```

<210> SEQ ID NO 15
<211> LENGTH: 3504
<212> TYPE: DNA
<213> ORGANISM: Human

<400> SEQUENCE: 15

| | | | | | | |
|---|---|---|---|---|---|---|
| atgtttgcga | ggaagccgcc | gggcgccgcg | cctttgggag | ctatgcctgt | tccagaccag | 60 |
| ccttcatcag | cctcagagaa | gacgagttcc | ctgagcccg | gcttaaacac | ctccaacggg | 120 |
| gatggctctg | aaacagaaac | cacctctgcc | atcctcgcct | cagtcaaaga | acaggaatta | 180 |
| cagtttgaaa | ggctgacccg | agagctggag | gctgaacggc | agatcgtagc | cagccagctg | 240 |
| gagcgatgca | agctcggatc | cgagactggc | agcatgagca | gcatgagttc | agcagaagag | 300 |
| cagtttcagt | ggcagtcaca | agatggtcaa | aaagatatcg | aagatgagct | acaacaggt | 360 |
| ctcgagctgg | tggactcctg | tattaggtca | ctacaggaat | caggaatact | tgacccacag | 420 |
| gattattcta | caggtgaaag | gcccagcctg | ctctcccaga | gtgcacttca | gctcaattcc | 480 |
| aaacctgaag | ggtctttcca | gtatccggcc | agctaccata | gcaaccagac | cctggccctg | 540 |
| ggggaaacca | ccccttcaca | gctcccggcc | cgaggcacac | aagcccgagc | tacgggccag | 600 |
| agcttcagcc | agggcacgac | cagcgcgcc | ggccacctgg | cggggcccga | gcccgcgccg | 660 |
| ccgccgccgc | cgccgccgcg | ggagccgttc | gcgcccagcc | tgggcagcgc | cttccacctg | 720 |
| cccgacgcgc | cgcccgccgc | cgccgccgcc | gcgctctact | actccagctc | cacgctgccc | 780 |
| gcgccgccgc | gcggggggctc | cccgctggcc | gcgcccaggg | gcggttcgcc | caccaagctg | 840 |
| cagcgcggcg | gctcggcccc | cgagggcgcc | acctacgccg | cgccgcgcgg | ctcctcgccc | 900 |
| aagcagtcgc | ccagccgcct | ggccaagtcc | tacagcacca | gctcgcccat | caacatcgtc | 960 |
| gtgtcctcgg | ccgcctgtc | cccgatccgc | gtgacctcgc | ccccaccgt | gcagtccacc | 1020 |
| atctcctcct | cgcccatcca | ccagctgagc | tccaccatcg | gcacgtacgc | caccctgtcg | 1080 |
| cccaccaagc | gcctggtcca | gcgtccgag | cagtacagca | agcactcgca | ggagctgtat | 1140 |
| gccacggcca | ccctccagag | gccgggcagc | ctggcagctg | gttcccgagc | ctcatacagc | 1200 |
| agccagcatg | ggcacctggg | cccagagttg | cgggccctgc | agtccccaga | acaccacata | 1260 |
| gatcccatct | atgaagaccg | cgtctatcag | aagcccccta | tgaggagtct | cagccagagc | 1320 |
| caggggggacc | ctctgccgcc | agcacacacc | ggcacctacc | gcacgagcac | agccccatct | 1380 |
| tccctggtg | tcgactccgt | cccttgcag | cgcacaggca | gccagcacgg | cccacagaat | 1440 |
| gccgccgcgg | ccaccttcca | gagggccagc | tatgccgccg | gccagcctc | caattacgcg | 1500 |
| gaccctacc | gacagctgca | gtattgtccc | tctgttgagt | ctccatacag | caaatccggc | 1560 |
| cctgctctcc | cgcctgaagg | caccttggcc | aggtccccgt | ccattgatag | cattcagaaa | 1620 |
| gatcccagag | aatttggatg | gagagacccg | gaactgccgg | aagtgattca | gatgttgcag | 1680 |
| caccagtttc | cctcggtcca | gtctaacgcg | gcagcctact | gcaacacct | ctgttttgga | 1740 |
| gacaacaaaa | ttaaagccga | gataaggaga | caaggaggca | tccagctcct | ggtggacctg | 1800 |
| ttggatcatc | ggatgaccga | agtccaccgt | agtgcctgtg | gagctctgag | aaacctggtg | 1860 |
| tatgggaagg | ccaacgatga | taacaaaatt | gccctgaaaa | actgtggtgg | catcccagca | 1920 |
| ctggtgaggt | tactccgcaa | gacgactgac | ctggagatcc | gggagctggt | cacaggagtc | 1980 |
| ctttggaacc | tctcctcatg | cgatgcactc | aaaatgccaa | tcatccagga | tgccctagca | 2040 |
| gtactgacca | acgcggtgat | tatccccac | tcaggctggg | aaaattcgcc | tcttcaggat | 2100 |
| gatcggaaaa | tacagctgca | ttcatcacag | gtgctgcgta | acgccaccgg | gtgcctaagg | 2160 |

```
aatgttagtt cggccggaga ggaggcccgc agaaggatga gagagtgtga tgggcttacg    2220
gatgccttgc tgtacgtgat ccagtctgcg ctggggagca gtgagatcga tagcaagacc    2280
gttgaaaact gtgtgtgcat tttaaggaac ctctcgtacc ggctggcggc agaaacgtct    2340
cagggacagc acatgggcac ggacgagctg acgggctac tctgtggcga ggccaatggc    2400
aaggatgctg agagctctgg gtgctggggc aagaagaaga agaaaaagaa atcccaagat    2460
cagtggtcag tatatatccg agccgctgtc cgaaaagaga aaggcctgcc catcctcgtg    2520
gagctgctcc gaatagacaa tgaccgtgtg gtgtgcgcgg tggccactgc gctgcggaac    2580
atggccttgg acgtcagaaa taaggagctc atcggcaaat acgccatgcg agacctagtc    2640
cacaggcttc caggagggaa caacagcaac aacactgcaa gcaaggccat gtcggatgac    2700
acagtgacag ctgtctgctg cacactgcac gaagtgatta ccaagaacat ggagaacgcc    2760
aaggccttac gggatgccgg tggcatcgag aagttggtcg gcatctccaa aagcaaagga    2820
gataaacact ctccaaaagt ggtcaaggct gcatctcagg tcctcaacag catgtggcag    2880
taccgagatc tgaggagtct ctacaaaaag gatggatggt cacaatacca ctttgtagcc    2940
tcgtcttcaa ccatcgagag ggaccggcaa aggccctact cctcctcccg cacgccctcc    3000
atctcccctg tgcgcgtgtc tcccaacaac cgctcagcaa gtgccccagc ttcacctcgg    3060
gaaatgatca gcctcaaaga aaggaaaaca gactacgagt gcaccggcag caacgccacc    3120
taccacggag ctaaaggcga acacacttcc aggaaagatg ccatgacagc tcaaaacact    3180
ggaatttcaa ctttgtatag gaattcttat ggtgcgcccg ctgaagacat caaacacaac    3240
caggtttcag cacagccagt cccacaggag cccagcagaa aagattacga gacctaccag    3300
ccatttcaga attccacaag aaattacgat gagtccttct tcgaggacca ggtccaccat    3360
cgccctcccg ccagcgagta caccatgcac ctgggtctca gtccaccgg caactacgtt    3420 gacttctact cagctgcccg tccctacagt gaactgaact atgaaacgag ccactacccg    3480
gcctcccccg actcctgggt gtga                                           3504
```

<210> SEQ ID NO 16
<211> LENGTH: 3678
<212> TYPE: DNA
<213> ORGANISM: Human

<400> SEQUENCE: 16

```
atgtttgcga ggaagccgcc gggcgccgcg cctttgggag ctatgcctgt tccagaccag      60
ccttcatcag cctcagagaa gacgagttcc ctgagcccg gcttaaacac ctccaacggg     120
gatggctctg aaacagaaac cacctctgcc atcctcgcct cagtcaaaga acaggaatta     180
cagtttgaaa ggctgacccg agagctggag gctgaacggc agatcgtagc cagccagctg     240
gagcgatgca agctcggatc cgagactggc agcatgagca gcatgagttc agcagaagag     300
cagtttcagt ggcagtcaca agatggtcaa aaagatatcg aagatgagct acaacaggt     360 ctcgagctgg tggactcctg tattaggtca ctacaggaat caggaatact tgacccacag     420
gattattcta caggtgaaag gcccagcctg ctctcccaga gtgcacttca gctcaattcc     480
aaacctgaag ggtctttcca gtatccggcc agctaccata gcaaccagac cctgccctg     540 ggggaaacca cccttcaca gctcccggcc cgaggcacac aagcccgagc tacgggccag     600
agcttcagcc agggcacgac cagccgcgcc ggccacctgg cggggcccga gcccgcgccg     660
ccgccgccgc cgccgccgcg ggagccgttc gcgcccagcc tgggcagcgc cttccacctg     720
```

```
cccgacgcgc cgcccgccgc cgccgccgcc gcgctctact actccagctc cacgctgccc   780
gcgccgccgc gcggggctc cccgctggcc gcgcccagg gcggttcgcc caccaagctg     840
cagcgcggcg gctcggcccc cgagggcgcc acctacgccg cgccgcgcgg ctcctcgccc   900
aagcagtcgc ccagccgcct ggccaagtcc tacagcacca gctcgcccat caacatcgtc   960
gtgtcctcgg ccggcctgtc cccgatccgc gtgacctcgc cccccaccgt gcagtccacc  1020
atctcctcct cgcccatcca ccagctgagc tccaccatcg gcacgtacgc caccctgtcg  1080
cccaccaagc gcctggtcca cgcgtccgag cagtacagca agcactcgca ggagctgtat  1140
gccacggcca ccctccagag gccgggcagc ctggcagctg gttcccgagc tcatacagc   1200
agccagcatg ggcacctggg cccagagttg cgggccctgc agtccccaga acaccacata  1260
gatcccatct atgaagaccg cgtctatcag aagccccta tgaggagtct cagccagagc   1320
caggggggacc ctctgccgcc agcacacacc ggcacctacc gcacgagcac agccccatct 1380
tccccctggtg tcgactccgt ccccttgcag cgcacaggca gccagcacgg cccacagaat 1440
gccgccgcgg ccaccttcca gagggccagc tatgccgccg gccagcctc caattacgcg  1500
gaccctacc gacagctgca gtattgtccc tctgttgagt ctccatacag caaatccggc   1560
cctgctctcc cgcctgaagg caccttggcc aggtccccgt ccattgatag cattcagaaa  1620
gatcccagag aatttggatg gagagacccg gaactgccgg aagtgattca gatgttgcag  1680
caccagttttc cctcggtcca gtctaacgcg gcagcctact gcaacaccct ctgttttgga 1740
gacaacaaaa ttaaagccga gataaggaga caaggaggca tccagctcct ggtggacctg  1800
ttggatcatc ggatgaccga agtccaccgt agtgcctgtg gagctctgag aaacctggtg   1860
tatgggaagg ccaacgatga taacaaaatt gccctgaaaa actgtggtgg catcccagca   1920
ctggtgaggt tactccgcaa gacgactgac ctggagatcc gggagctggt cacaggagtc   1980
cttttggaacc tctcctcatg cgatgcactc aaaatgccaa tcatccagga tgccctagca  2040
gtactgacca acgcggtgat tatcccccac tcaggctggg aaaattcgcc tcttcaggat   2100
gatcggaaaa tacagctgca ttcatcacag gtgctgcgta acgccaccgg gtgcctaagg   2160
aatgttagtt cggccggaga ggaggcccgc agaaggatga gagagtgtga tgggcttacg   2220
gatgccttgc tgtacgtgat ccagtctgcg ctggggagca gtgagatcga tagcaagacc   2280
gttgaaaact gtgtgtgcat tttaaggaac ctctcgtacc ggctggcggc agaaacgtct   2340
cagggacagc acatgggcac ggacgagctg gacgggctac tctgtggcga ggccaatggc   2400
aaggatgctg agagctctgg gtgctgggc aagaagaaga agaaaaagaa atcccaagat   2460
cagtgggatg gagtaggacc tcttccagac tgtgctgaac caccaaaagg gatccagatg   2520
ctgtggcacc catcaatagt caaaccctac ctcacactgc tctctgagtg ctcaaatcca   2580
gacacgctgg aaggggcggc aggcgccctg cagaacttgg ctgcagggag ctggaagtgg   2640
tcagtatata tccgagccgc tgtccgaaaa gagaaaggcc tgcccatcct cgtggagctg   2700
ctccgaatag acaatgaccg tgtggtgtgc gcggtggcca ctgcgctgcg aacatggcc   2760
ttggacgtca gaaataagga gctcatcggc aaatacgcca tgcgagacct agtccacagg   2820
cttccaggag gcaacaacag caacaacact gcaagcaagg ccatgtcgga tgacacagtg   2880
acagctgtct gctgcacact gcacgaagtg attaccaaga acatggagaa cgccaaggcc   2940
ttacgggat ccggtggcat cgagaagttg gtcggcatct ccaaaagcaa aggagataaa   3000
cactctccaa aagtggtcaa ggctgcatct caggtcctca acagcatgtg gcagtaccga   3060
gatctgagga gtctctacaa aaaggatgga tggtcacaat accactttgt agcctcgtct   3120
```

```
tcaaccatcg agagggaccg gcaaaggccc tactcctcct cccgcacgcc ctccatctcc    3180
cctgtgcgcg tgtctcccaa caaccgctca gcaagtgccc cagcttcacc tcgggaaatg    3240
atcagcctca aagaaaggaa aacagactac gagtgcaccg gcagcaacgc cacctaccac    3300
ggagctaaag gcgaacacac ttccaggaaa gatgccatga cagctcaaaa cactggaatt    3360
tcaactttgt ataggaattc ttatggtgcg cccgctgaag acatcaaaca caaccaggtt    3420
tcagcacagc cagtcccaca ggagcccagc agaaaagatt acgagaccta ccagccattt    3480
cagaattcca caagaaatta cgatgagtcc ttcttcgagg accaggtcca ccatcgccct    3540
cccgccagcg agtacaccat gcacctgggt ctcaagtcca ccgcaacta cgttgacttc    3600 tactcagctg cccgtcccta cagtgaactg aactatgaaa cgagccacta cccggcctcc    3660
cccgactcct gggtgtga                                                   3678

<210> SEQ ID NO 17
<211> LENGTH: 438
<212> TYPE: DNA
<213> ORGANISM: Human

<400> SEQUENCE: 17
ccgtatccgc tagcgcggtg ggatgcgctt gggctccctg ttcgttccca catgcagggc      60
agcacaagga gaatgggcgt catgactgat gtccaccggc gcttcctcca gttgctgatg     120
acccatggcg tgctagagga atgggacgtg aagcgcttgc agacgcactg ctacaaggtc     180
catgaccgca atgccaccgt agataagttg gaggacttca tcaacaacat taacagtgtc     240
ttggagtcct tgtatattga gataaagaga ggagtcacgg aagatgatgg gagacccatt     300
tatgcgttgg tgaatcttgc tacaacttca atttccaaaa tggctacgga ttttgcagag     360
aatgaactgg atttgtttag aaaggctctg gaactgatta ttgactcaga aaccttgcgt     420
cttccacaaa catattga                                                  438

<210> SEQ ID NO 18
<211> LENGTH: 801
<212> TYPE: DNA
<213> ORGANISM: Human

<400> SEQUENCE: 18
atgcagggca gcacaaggag aatgggcgtc atgactgatg tccaccggcg cttcctccag     60
ttgctgatga cccatggcgt gctagaggaa tgggacgtga agcgcttgca gacgcactgc    120
tacaaggtcc atgaccgcaa tgccaccgta gataagttgg aggacttcat caacaacatt    180
aacagtgtct tggagtcctt gtatattgag ataaagagag gagtcacgga agatgatggg    240
agacccattt atgcgttggt gaatcttgct acaacttcaa tttccaaaat ggctacggat    300
tttgcagaga atgaactgga tttgtttaga aaggctctgg aactgattat tgactcagaa    360
accggctttg cgtcttccac aaacatattg aacctggttg atcaacttaa aggcaagaag    420
atgaggaaga aggaagcgga gcaggtgctg cagaagtttg ttcaaaacaa gtggctgatt    480
gagaaggaag gggagttcac cctgcacggc cgggccatcc tggagatgga gcaatacatc    540
cgggagacgt accccgacgc ggtgaagatc tgcaatatct gtcacagcct cctcatccag    600
ggtcaaagct gcgaaacctg tgggatcagg atgcacttac cctgcgtggc caagtacttc    660
cagtcgaatg ctgaaccgcg ctgccccac tgcaacgact actggcccca cgagatccca    720
aaagtcttcg accctgagaa ggagagggag tctggtgtct tgaaatcgaa caaaaagtcc    780
```
ctgcggtcca ggcagcatta g                                              801

<210> SEQ ID NO 19
<211> LENGTH: 540
<212> TYPE: DNA
<213> ORGANISM: Human

<400> SEQUENCE: 19
gtccaccttg cgaccgtatc cgctagcgcg gcctgggatg cgcttgggct ccctgttcgt    60
tcccacatgc agggcagcac aaggagaatg ggcgtcatga ctgatgtcca ccggcgcttc   120
ctccagttgc tgatgaccca tggcgtgcta gaggaatggg acgtgaagcg cttgcagacg   180
cactgctaca aggtccatga ccgcaatgcc accgtagata agttggagga cttcatcaac   240
aacattaaca gtgtcttgga gtccttgtat attgagataa agagaggagt cacggaagat   300
gatgggagac ccatttatgc gttggtgaat cttgctacaa cttcaatttc caaaatggct   360
acggattttg cagagaatga actggatttg tttagaaagg ctctggaact gattattgac   420
tcagaaaccg gctttgcgtc ttccacaaac atattgaacc tggttgatca acttaaaggc   480
aagaagatga ggaagaagga agcgaggtgc tgcagaagtt tgttcaaaac aagtggctga   540

<210> SEQ ID NO 20
<211> LENGTH: 1179
<212> TYPE: DNA
<213> ORGANISM: Human

<400> SEQUENCE: 20
atggagtggt gggctagctc gccgcttcgg ctctggctgc tgttgttcct cctgccctca    60
gcgcagggcc gccagaagga gtcaggttca aaatggaaag tatttattga ccaaattaac   120
aggtctttgg agaattacga accatgttca agtcaaaact gcagctgcta ccatggtgtc   180
atagaagagg atctaactcc tttccgagga ggcatctcca ggaagatgat ggcagaggta   240
gtcagacgga agctagggac ccactatcag atcactaaga acagactgta ccgggaaaat   300
gactgcatgt tcccctcaag gtgtagtggt gttgagcact ttatttttgga agtgatcggg   360
cgtctccctg acatggagat ggtgatcaat gtacgagatt atcctcaggt tcctaaatgg   420
atggagcctg ccatcccagt cttctccttc agtaagacat cagagtacca tgatatcatg   480
tatcctgctt ggacattttg ggaaggggga cctgctgttt ggccaattta tcctacaggt   540
cttggacggt gggacctctt cagagaagat ctggtaaggt cagcagcaca gtggccatgg   600
aaaaagaaaa actctacagc atatttccga ggatcaagga caagtccaga acgagatcct   660
ctcattcttc tgtctcggaa aaacccaaaa cttgttgatg cagaatacac caaaaaccag   720
gcctggaaat ctatgaaaga taccttagga aagccagctg ctaaggatgt ccatcttgtg   780
gatcactgca atacaagta tctgttttaat tttcgaggcg tagctgcaag tttccggttt   840
aaacacctct tcctgtgtgg ctcacttgtt ttccatgttg gtgatgagtg gctagaattc   900
ttctatccac agctgaagcc atgggttcac tatatcccag tcaaaacaga tctctccaat   960
gtccaagagc tgttacaatt tgtaaaagca atgatgatg tagctcaaga gattgctgaa  1020
agggaagcc agtttattag gaaccatttg cagatggatg acatcacctg ttactgggag  1080
aacctcttga gtgaatactc taaattcctg tcttataatg taacgagaag gaaaggttat  1140
gatcaaatta ttcccaaaat gttgaaaact gaactatag                         1179

<210> SEQ ID NO 21
<211> LENGTH: 1236

<212> TYPE: DNA
<213> ORGANISM: Human

<400> SEQUENCE: 21

| | | | | | |
|---|---|---|---|---|---|
| atgcggcggc | ggcgcgccgg | cggcaggacc | atggttgagc | gcgccagcaa | gttcgtgctg | 60 |
| gtggtggcgg | gctcggtgtg | cttcatgctc | atcttgtacc | agtacgcggg | cccaggactg | 120 |
| agcctgggcg | cgcccggcgg | ccgcgcgccg | cccgacgacc | tggacctgtt | ccccacaccc | 180 |
| gacccccact | acgagaagaa | gtactacttc | ccggtccgcg | agctggagcg | ctcgctgcgc | 240 |
| ttcgacatga | agggcgacga | cgtgatcgtc | ttcctgcaca | tccagaagac | gggcggcacc | 300 |
| accttcggcc | gccacctcgt | gcagaacgta | cgcctcgagg | tgccgtgcga | ctgccggccc | 360 |
| ggccagaaga | agtgcacctg | ctaccggccc | aaccgcgcg | agacttggct | cttctcccgc | 420 |
| ttctccaccg | gctggagctg | cgggctgcac | gccgactgga | ccgagctcac | caactgcgtg | 480 |
| cccggcgtgc | tggaccgccg | cgactccgcc | gcgctgcgca | cgcccaggaa | gttctactac | 540 |
| atcaccctgc | tacgagaccc | cgtgtcccgc | tacctgagcg | agtggcggca | tgtgcagagg | 600 |
| ggtgccacgt | ggaagacgtc | gttgcatatg | tgtgatgggc | gcacgccac | gcctgaggag | 660 |
| ctgccgccct | gctacgaggg | cacggactgg | tcgggctgca | cgctacagga | gttcatggac | 720 |
| tgcccgtaca | acctggccaa | caaccgccag | gtgcgcatgc | tggccgacct | gagcctggtg | 780 |
| ggctgctaca | acctgtcctt | catccccgag | ggcaagcggg | cccagctgct | gctcgagagc | 840 |
| gccaagaaga | acctgcgggg | catggccttc | ttcggcctga | ccgagttcca | gcgcaagacg | 900 |
| cagtacctgt | cgagcggac | gttcaacctc | aagttcatcc | ggcccttcat | gcagtacaat | 960 |
| agcacgcggg | cgggcggcgt | ggaggtggat | gaagacacca | tccggcgcat | cgaggagctc | 1020 |
| aacgacctgg | acatgcagct | gtacgactac | gccaaggacc | tcttccagca | gcgctaccag | 1080 |
| tacaagcggc | agctggagcg | cagggagcag | cgcctgagga | gccgcgagga | gcgtctgctg | 1140 |
| caccgggcca | aggaggcact | gccgcgggag | gatgccgacg | agccgggccg | cgtgcccacc | 1200 |
| gaggactaca | tgagccacat | cattgagaag | tggtag | | | 1236 |

<210> SEQ ID NO 22
<211> LENGTH: 1395
<212> TYPE: DNA
<213> ORGANISM: Human

<400> SEQUENCE: 22

| | | | | | |
|---|---|---|---|---|---|
| atgacatcct | gcagatgctc | agtgacctcc | aggagtctgt | ggccagctct | cgccccagg | 60 |
| aggtgtcagc | atacctcacc | cgcttctgcg | cagtgcaaac | aggacaaggc | ctgccgcttc | 120 |
| ctcgcggccc | agaagggggc | ctaccccatc | atcttcactg | cctggaagct | ggccactgca | 180 |
| ggtgaccagg | gccttctgct | ccagtccctc | aatgccctgt | cggtgctgac | tgatggacag | 240 |
| ccagacctcc | tggatgccca | gggcctgcag | ctcctagtgg | ccacgctgac | ccagaatgct | 300 |
| gatgaggctg | acctgacctg | ctctgggatc | cgctgtgtgc | gtcacgcttg | cctgaaacat | 360 |
| gaacagaatc | ggcaagacct | ggtgaaagct | ggcgtgctgc | ctctgctgac | tggtgccatc | 420 |
| acccatcatg | ccaccacac | tgacgtggtc | agggaagcct | gctgggccct | gcgtgtcatg | 480 |
| accttcgatg | acgacatccg | tgtgcccttt | ggccatgccc | acaaccatgc | caagatgatt | 540 |
| gtgcaggaga | acaaaggctt | gaaggtgctc | atcgaagcca | ccaaagcgtt | cctggataac | 600 |
| cctggcatcc | tgagcgagct | ctgtggaacc | ctgtcccgcc | tggccattcg | caacgagttc | 660 |
| tgccaggagg | tcgtcgacct | cgggggcctg | agcattctgg | tgtccctgct | agccgactgc | 720 |

```
aatgaccacc agatgaggga ccagagcggc gttcaggagc tcgtgaagca agtgctgagc      780
accctgcgag ccatcgcagg caacgacgac gtgaaagatg ctattgtccg tgctggtggg      840
acggagtcca tcgtggctgc tatgacccag catctgacca gcccccaggt gtgtgagcag      900
agctgcgcgg ccctgtgctt cctggccctg cgtaagcccg acaacagccg catcatcgtg      960
gagggtggcg gggctgtggc agcactgcag gccatgaagg cacacccgca gaaggccggc     1020
gtgcagaaac aggcttgcat gctgatccga aacctggtgg cccacaggcc ttctcgaagc     1080
ccatcctgga cctgggggct gaggcactca tcatgcaggc ccgatctgcc caccgtgact     1140
gtgaggacgt ggccaaggcc gccctgcggg acctgggttg tcatgtcgag ctccgagagc     1200
tgtggacagg ccagaggggc aacctggcgc catgacccca ggcccagtct ggtgactctg     1260
ggtgagtcgt gtgactcagg aatgggggta gatccatgtc ctccactgtc ccccattagt     1320
tctgtcccct tcacaatgag aagtgttttc tggcaggccc taggtaaagg gtcgggggag     1380
gggggagcct tgtag                                                      1395

<210> SEQ ID NO 23
<211> LENGTH: 1431
<212> TYPE: DNA
<213> ORGANISM: Human

<400> SEQUENCE: 23
atggtctcca agcgcattgc ccaggagacc tttgatgcag ctgtgcgcga gaacatcgag       60
gagtttgcga tggggccaga ggaggcagtg aaagaggccg tggagcagtt tgaatcgcaa      120
ggggttgatc tgagcaacat tgtaaagacg gcacctaaag tctctgcaga cggatcccag      180
gagcccacac atgacatcct gcagatgctc agtgacctcc aggagtctgt ggccagctct      240
cgcccccagt aggtgtcagc atacctcacc cgcttctgcg accagtgcaa acaggacaag      300
gcctgccgct tcctcgcggc ccagaagggg gcctacccca tcatcttcac tgcctggaag      360
ctggccactg caggtgacca gggccttctg ctccagtccc tcaatgccct gtcggtgctg      420
actgatggac agccagacct cctggatgcc cagggcctgc agctcctagt ggccacgctg      480
acccagaatg ctgatgaggc tgacctgacc tgctctggga tccgctgtgt gcgtcacgct      540
tgcctgaaac atgaacagaa tcggcaagac ctggtgaaag ctggcgtgct gcctctgctg      600
actggtgcca tcacccatca tggccaccac actgacgtgg tcaggaagc ctgctgggcc      660 ctgcgtgtca tgaccttcga tgacgacatc cgtgtgccct ttggccatgc ccacaaccat      720
gccaagatga ttgtgcagga gaacaaaggc ttgaaggtgc tcatcgaagc caccaaagcg      780
ttcctggata accctggcat cctgagcgag ctctgtggaa ccctgtcccg cctggccatt      840
cgcaacgagt tctgccagga ggtcgtcgac ctcggggggcc tgagcattct ggtgtccctg      900
ctagccgact gcaatgacca ccagatgagg gaccagagcg gcgttcagga gctcgtgaag      960
caagtgctga gcaccctgcg agccatcgca ggcaacgacg acgtgaaaga tgctattgtc     1020
cgtgctggtg ggacggagtc catcgtggct gctatgaccc agcatctgac cagccccag      1080 gtgtgtgagc agagctgcgc ggccctgtgc ttcctggccc tgcgtaagcc cgacaacagc     1140
cgcatcatcg tggagggtgg cggggctgtg gcagcactgc aggccatgaa ggcacacccg     1200
cagaaggccg gcgtgcagaa acaggcttgc atgctgatcc gaaacctggt ggcccacggc     1260
caggccttct cgaagcccat cctggacctg ggggctgagg cactcatcat gcaggcccga     1320
tctgcccacc gtgactgtga ggacgtggcc aaggccgccc tgcgggacct gggttgtcat     1380
gtcgagctcc gagagctgtg gacaggccag aggggcaacc tggcgccatg a              1431
```

<210> SEQ ID NO 24
<211> LENGTH: 1506
<212> TYPE: DNA
<213> ORGANISM: Human

<400> SEQUENCE: 24

| | | | | | |
|---|---|---|---|---|---|
| atgagtgaac | gatgttgctc | tagatacagc | tcaggagcat | ctatcggctg | cacgccaaca | 60 |
| tcaacacagg | cgaagatggt | ctccaagcgc | attgcccagg | agacctttga | tgcagctgtg | 120 |
| cgcgagaaca | tcgaggagtt | tgcgatgggg | ccagaggagg | cagtgaaaga | ggccgtggag | 180 |
| cagtttgaat | cgcaaggggt | tgatctgagc | aacattgtaa | agacggcacc | taaagtctct | 240 |
| gcagacggat | cccaggagcc | cacacatgac | atcctgcaga | tgctcagtga | cctccaggag | 300 |
| tctgtggcca | gctctcgccc | caggaggtg | tcagcatacc | tcacccgctt | ctgcgaccag | 360 |
| tgcaaacagg | acaaggcctg | ccgcttcctc | gcggcccaga | aggggccta | ccccatcatc | 420 |
| ttcactgcct | ggaagctggc | cactgcaggt | gaccagggcc | ttctgctcca | gtccctcaat | 480 |
| gccctgtcgg | tgctgactga | tggacagcca | gacctcctgg | atgcccaggg | cctgcagctc | 540 |
| ctagtggcca | cgctgaccca | gaatgctgat | gaggctgacc | tgacctgctc | tgggatccgc | 600 |
| tgtgtgcgtc | acgcttgcct | gaaacatgaa | cagaatcggc | aagacctggt | gaaagctggc | 660 |
| gtgctgcctc | tgctgactgg | tgccatcacc | catcatggcc | accacactga | cgtggtcagg | 720 |
| gaagcctgct | gggccctgcg | tgtcatgacc | ttcgatgacg | acatccgtgt | gcccttggc | 780 |
| catgcccaca | accatgccaa | gatgattgtg | caggagaaca | aaggcttgaa | ggtgctcatc | 840 |
| gaagccacca | agcgttcct | ggataaccct | ggcatcctga | gcgagctctg | tggaaccctg | 900 |
| tcccgcctgg | ccattcgcaa | cgagttctgc | caggaggtcg | tcgacctcgg | ggcctgagc | 960 |
| attctggtgt | ccctgctagc | cgactgcaat | gaccaccaga | tgagggacca | gagcggcgtt | 1020 |
| caggagctcg | tgaagcaagt | gctgagcacc | ctgcgagcca | tcgcaggcaa | cgacgacgtg | 1080 |
| aaagatgcta | ttgtccgtgc | tggtgggacg | gagtccatcg | tggctgctat | gacccagcat | 1140 |
| ctgaccagcc | cccaggtgtg | tgagcagagc | tgcgcggccc | tgtgcttcct | ggccctgcgt | 1200 |
| aagcccgaca | acagccgcat | catcgtggag | ggtggcgggg | ctgtggcagc | actgcaggcc | 1260 |
| atgaaggcac | acccgcagaa | ggccggcgtg | cagaaacagg | cttgcatgct | gatccgaaac | 1320 |
| ctggtggccc | acgccaggc | cttctcgaag | cccatcctgg | acctggggc | tgaggcactc | 1380 |
| atcatgcagg | cccgatctgc | ccaccgtgac | tgtgaggacg | tggccaaggc | cgccctgcgg | 1440 |
| gacctggggtt | gtcatgtcga | gctccgagag | ctgtggacag | ccagaggg | caacctggcg | 1500 |
| ccatga | | | | | 1506 |

<210> SEQ ID NO 25
<211> LENGTH: 1431
<212> TYPE: DNA
<213> ORGANISM: Human

<400> SEQUENCE: 25

| | | | | | |
|---|---|---|---|---|---|
| atggtctcca | agcgcattgc | ccaggagacc | tttgatgcag | ctgtgcgcga | gaacatcgag | 60 |
| gagtttgcga | tggggccaga | ggaggcagtg | aaagaggcc | tggagcagtt | tgaatcgcaa | 120 |
| ggggttgatc | tgagcaacat | tgtaaagacg | gcacctaaag | tctctgcaga | cggatcccag | 180 |
| gagcccacac | atgacatcct | gcagatgctc | agtgacctcc | aggagtctgt | ggccagctct | 240 |
| cgcccccagg | aggtgtcagc | atacctcacc | cgcttctgcg | accagtgcaa | acaggacaag | 300 |

```
gcctgccgct tcctcgcggc ccagaagggg gcctacccca tcatcttcac tgcctggaag    360
ctggccactg caggtgacca gggccttctg ctccagtccc tcaatgccct gtcggtgctg    420
actgatggac agccagacct cctggatgcc cagggcctgc agctcctagt ggccacgctg    480
acccagaatg ctgatgaggc tgacctgacc tgctctggga tccgctgtgt gcgtcacgct    540
tgcctgaaac atgaacagaa tcggcaagac ctggtgaaag ctggcgtgct gcctctgctg    600
actggtgcca tcacccatca tggccaccac actgacgtgg tcagggaagc ctgctgggcc    660
ctgcgtgtca tgaccttcga tgacgacatc cgtgtgccct ttggccatgc ccacaaccat    720
gccaagatga ttgtgcagga gaacaaaggc ttgaaggtgc tcatcgaagc caccaaagcg    780
ttcctggata accctggcat cctgagcgag ctctgtggaa ccctgtcccg cctggccatt    840
cgcaacgagt ctgccagga ggtcgtcgac ctcgggggcc tgagcattct ggtgtccctg    900
ctagccgact gcaatgacca ccagatgagg gaccagagcg gcgttcagga gctcgtgaag    960
caagtgctga gcaccctgcg agccatcgca ggcaacgacg acgtgaaaga tgctattgtc    1020
cgtgctggtg ggacggagtc catcgtggct gctatgaccc agcatctgac cagccccag   1080 gtgtgtgagc agagctgcgc ggccctgtgc ttcctggccc tgcgtaagcc cgacaacagc   1140
cgcatcatcg tggagggtgg cggggctgtg gcagcactgc aggccatgaa ggcacacccg   1200
cagaaggccg gcgtgcagaa acaggcttgc atgctgatcc gaaacctggt ggcccacggc   1260
caggccttct cgaagcccat cctggacctg ggggctgagg cactcatcat gcaggcccga   1320
tctgcccacc gtgactgtga ggacgtggcc aaggccgccc tgcgggacct gggttgtcat   1380
gtcgagctcc gagagctgtg gacaggccag aggggcaacc tggcgccatg a           1431
```

<210> SEQ ID NO 26
<211> LENGTH: 1773
<212> TYPE: DNA
<213> ORGANISM: Human

<400> SEQUENCE: 26

```
atggcgggg ccgtgccggg cgccatcatg acgaggact actacgggag cgcggccgag     60
tggggcgacg aggctgacgg cggccagcag gaggatgatt ctggagaagg agaggatgat    120
gcggaggttc agcaagaatg cctgcataaa ttttccaccc gggattatat catggaaccc    180
tccatcttca acactctgaa gaggtatttt caggcaggag ggtctccaga gaatgttatc    240
cagctcttat ctgaaaacta caccgctgtg gcccagactg tgaacctgct ggccgagtgg    300
ctcattcaga caggtgttga gccagtgcag gttcaggaaa ctgtggaaaa tcacttgaag    360
agtttgctga tcaaacattt tgacccccgc aaagcagatt ctattttac tgaagaagga    420 gagaccccag cgtggctgga acagatgatt gcacatacca cgtggcggga ccttttttat   480
aaactggctg aagcccatcc agactgtttg atgctgaact tcaccgttaa gcttattct    540 gacgcagggt accaggggga gatcaccagt gtgtccacag catgccagca gctagaagtg    600
ttctcgagag tgctccggac ctctctagct acaattttag atggaggaga agaaaacctt    660
gaaaaaaatc tccctgagtt tgccaagatg gtgtgccacg gggagcacac gtacctgttt    720
gcccaggcca tgatgtccgt gctggcccag gaggagcagg ggggctccgc tgtgcgcagg    780
atcgcccagg aagtgcagcg cttttgccag agaaaggtc atgacgccag tcagatcaca    840
ctagccttgg gcacagctgc ctcctacccc agggcctgcc aggctctcgg ggccatgctg    900
tccaaaggag ccctgaaccc tgctgacatc accgtcctgt tcaagatgtt cacaagcatg    960
gaccctcctc cggttgaact tatccgcgtt ccagccttcc tggacctgtt catgcagtca   1020
```

```
ctctttaaac cagggctcg gatcaaccag gaccacaagc acaaatacat ccacatcttg    1080
gcgtacgcag caagcgtggt tgagacctgg aagaagaaca agcgagtgag catcaataaa   1140
gatgagctga agtcaacgtc aaaagctgtc gaaaccgttc acaatttgtg ttgcaacgag   1200
aacaaagggg cctctgaact agtggcagaa ttgagcacac tttatcagtg tattaggttt   1260
ccagtggtag caatgggtgt gctgaagtgg gtggattgga ctgtatcaga accaaggtac   1320
tttcagctgc agactgacca taccctgtc cacctggcgt tgctggatga gatcagcacc     1380
tgccaccagc tcctgcaccc ccaggtcctg cagctgcttg ttaagctttt tgagactgag   1440
cactcccagc tggacgtgat ggagcagctt gagttgaaga agacactgct ggacaggatg   1500
gttcacctgc tgagtcgagg ttatgtactt cctgttgtca gttacatccg aaagtgtctg   1560
gagaagctgg acactgacat ttcactcatt cgctattttg tcactgaggt gctggacgtc   1620
attgctcctc cttataccctc tgacttcgtg caacttttcc tccccatcct ggagaatgac   1680
agcatcgcag gtaccatcaa aacggaaggc gagcatgacc ctgtgacgga gtttatagct   1740
cactgcaaat ctaacttcat catggtgaac taa                                 1773
```

<210> SEQ ID NO 27
<211> LENGTH: 753
<212> TYPE: DNA
<213> ORGANISM: Human

<400> SEQUENCE: 27

```
atggccatgc tcagggtcca gcccgaggcc caagccaagg tggatgtgtt tcgtgaagac     60
ctctgtacca agacagagaa cctgctcggg agctatttcc ccaagaagat ttctgagctg    120
gatgcatttt taaggagcc agctctcaat gaagccaact tgagcaatct gaaggcccca    180
ttggacatcc cagtgcctga tccagtcaag gagaaagaga aagaggagcg gaagaaacag   240
caggagaagg aagacaagga tgaaaagaag aaggggagg atgaagacaa aggtcctccc    300
tgtggcccag tgaactgcaa tgaaaagatc gtggtccttc tgcagcgctt gaagcctgag   360
atcaaggatg tcattgagca gctcaacctg gtcaccacct ggttgcagct gcagatacct   420
cggattgagg atggtaacaa ttttggagtg gctgtccagg agaaggtgtt tgagctgatg   480
accagcctcc acaccaagct agaaggcttc cacactcaaa tctctaagta tttctctgag   540
cgtggtgatg cagtgactaa agcagccaag cagccccatg tgggtgatta tcggcagctg   600
gtgcacgagc tggatgaggc agagtaccgg gacatccggc tgatggtcat ggagatccgc   660
aatgcttatg tgaggaggca agggcagggc aggggtgggc agaggcagct ttcccaggcc   720
acccactccc tgaccctgca ggctaggggt taa                                 753
```

<210> SEQ ID NO 28
<211> LENGTH: 750
<212> TYPE: DNA
<213> ORGANISM: Human

<400> SEQUENCE: 28

```
atggccatgc tcagggtcca gcccgaggcc caagccaagg tggatgtgtt tcgtgaagac     60
ctctgtacca agacagagaa cctgctcggg agctatttcc ccaagaagat ttctgagctg    120
gatgcatttt taaggagcc agctctcaat gaagccaact tgagcaatct gaaggcccca    180
ttggacatcc cagtgcctga tccagtcaag gagaaagaga aagaggagcg gaagaaacag   240
caggagaagg aagacaagga tgaaaagaag aaggggagg atgaagacaa aggtcctccc    300
```

| | |
|---|---|
| tgtggcccag tgaactgcaa tgaaaagatc gtggtccttc tgcagcgctt gaagcctgag | 360 |
| atcaaggatg tcattgagca gctcaacctg gtcaccacct ggttgcagct gcagatacct | 420 |
| cggattgagg atggtaacaa ttttggagtg gctgtccagg agaaggtgtt tgagctgatg | 480 |
| accagcctcc acaccaagct agaaggcttc cacactcaaa tctctaagta tttctctgag | 540 |
| cgtggtgatg cagtgactaa agcagccaag cagccccatg tgggtgatta tcggcagctg | 600 |
| gtgcacgagc tggatgaggc agagtaccgg gacatccggc tgatggtcat ggagatccgc | 660 |
| aatgcttatg ctgtgttata tgacatcatc ctgaagaact tcgagaagct caagaagccc | 720 |
| aggggagaaa caaagggaat gatctattga | 750 |

<210> SEQ ID NO 29
<211> LENGTH: 1677
<212> TYPE: DNA
<213> ORGANISM: Human

<400> SEQUENCE: 29

| | |
|---|---|
| atggagctcc gggcccgagg ctggtggctg ctatgtgcgg ccgcagcgct ggtcgcctgc | 60 |
| gcccgcgggg acccggccag caagagccgg agctgcggcg aggtccgcca gatctacgga | 120 |
| gccaagggct tcagcctgag cgacgtgccc caggcggaga tctcgggtga gcacctgcgg | 180 |
| atctgtcccc agggctacac ctgctgcacc agcgagatgg aggagaacct ggccaaccgc | 240 |
| agccatgcca gctggagac cgcgctccgg gacagcagcc gcgtcctgca ggccatgctt | 300 |
| gccacccagc tgcgcagctt cgatgaccac ttccagcacc tgctgaacga ctcggagcgg | 360 |
| acgctgcagg ccaccttccc cggcgccttc ggagagctgt acacgcagaa cgcgagggcc | 420 |
| ttccgggacc tgtactcaga gctgcgcctg tactaccgcg gtgccaacct gcacctggag | 480 |
| gagacgctgg ccgagttctg ggcccgcctg ctcgagcgcc tcttcaagca gctgcacccc | 540 |
| cagctgctgc tgcctgatga ctacctggac tgcctgggca gcaggccga ggcgctgcgg | 600 |
| cccttcgggg aggccccgag agagctgcgc ctgcgggcca ccgtgccctt cgtggctgct | 660 |
| cgctcctttg tgcagggcct gggcgtggcc agcgacgtgg tccggaaagt ggctcaggtc | 720 |
| cccctggggc cggagtgctc gagagctgtc atgaagctgg tctactgtgc tcactgcctg | 780 |
| ggagtccccg gcgccaggcc ctgccctgac tattgccgaa atgtgctcaa gggctgcctt | 840 |
| gccaaccagg ccgacctgga cgccgagtgg aggaacctcc tggactccat ggtgctcatc | 900 |
| accgacaagt ctggggtac atcgggtgtg agagtgtca tcggcagcgt gcacacgtgg | 960 |
| ctggcggagg ccatcaacgc cctccaggac aacaggaca cgctcacggc caaggtcatc | 1020 |
| cagggctgcg ggaaccccaa ggtcaacccc cagggccccg gcctgaggga agcggcgc | 1080 |
| cggggcaagc tggccccgcg ggagaggcca ccttcaggca cgctggagaa gctggtctcc | 1140 |
| gaagccaagg cccagctccg cgacgtccag gacttctgga tcagcctccc agggacactg | 1200 |
| tgcagtgaga agatggccct gagcactgcc agtgatgacc gctgctggaa cgggatggcc | 1260 |
| agaggccggt acctccccga ggtcatgggt gacggcctgg ccaaccagat caacaacccc | 1320 |
| gaggtggagg tggacatcac caagccggac atgaccatcc ggcagcagat catgcagctg | 1380 |
| aagatcatga ccaaccggct gcgcagcgcc tacaacggca acgacgtgga cttccaggac | 1440 |
| gccagtgacg acggcagcgg ctcgggcagc ggtgatggct gtctggatga cctctgcagc | 1500 |
| cggaaggtca gcaggaagag ctccagctcc cggacgccct tgaccatgc cctcccaggc | 1560 |
| ctgtcagagc aggaaggaca gaagacctcg gctgccagct gccccagcc cccgaccttc | 1620 |
| ctcctgcccc tcctcctctt cctggccctt acagtagcca ggccccggtg gcggtaa | 1677 |

<210> SEQ ID NO 30
<211> LENGTH: 3645
<212> TYPE: DNA
<213> ORGANISM: Human

<400> SEQUENCE: 30

| | | | | | |
|---|---|---|---|---|---|
| atggcctcct | gcgcgagcat | cgacatcgag | gacgccacgc | agcacctgcg | ggacatcctc | 60 |
| aagctggacc | ggcccgcggg | cggccccagt | gcagagagcc | cacggccatc | cagtgcctac | 120 |
| aatggggacc | tcaatggact | tctggtccca | gacccgctct | gctcaggtga | tagtacctca | 180 |
| gcaaacaaga | ctggtcttcg | gaccatgcca | cccattaacc | tgcaagagaa | gcaggtcatc | 240 |
| tgtctctcag | gagatgatag | ctccacctgc | attgggattt | ggccaaggga | ggtggagatt | 300 |
| gtggctagca | gtgactctag | catttcaagc | aaggcccggg | gaagcaacaa | ggtgaaaatt | 360 |
| cagcctgtcg | ccaagtatga | ctgggaacag | aagtactact | atggcaacct | gattgctgtg | 420 |
| tctaactcct | tcttggccta | tgccattcgg | gctgccaaca | atggctctgc | catggtgcgg | 480 |
| gtgatcagcg | tcagcacttc | ggagcggacc | ttgctcaagg | gcttcacagg | cagtgtggct | 540 |
| gatctggctt | tcgcgcacct | caactctcca | cagctggcct | gcctggatga | ggcaggcaac | 600 |
| ctgttcgtgt | ggcgcttggc | tctggttaat | ggcaaaattc | aagaagagat | cttggtccat | 660 |
| attcggcagc | cagagggcac | gccactgaac | cactttcgca | ggatcatctg | gtgcccttc | 720 |
| atccctgagg | agagcgaaga | ctgctgtgag | gagagcagcc | caacagtggc | cctgctgcat | 780 |
| gaagaccggg | ctgaggtgtg | ggaccctgac | atgctccgct | ccagccacag | tacctggcct | 840 |
| gtggatgtta | gccagatcaa | gcagggcttc | attgtggtaa | aaggtcatag | cacgtgcctc | 900 |
| agtgaaggag | ccctctctcc | tgatgggact | gtgctggcta | ctgcgagcca | cgatggctat | 960 |
| gtcaagttct | ggcagatcta | cattgagggg | caagatgagc | caaggtgtct | gcacgagtgg | 1020 |
| aaacctcatg | atgggcggcc | cctctcctgc | tcctgttct | gtgacaacca | taagaaacaa | 1080 |
| gaccctgatg | tcccttttctg | gaggttcctt | attactggtg | ctgaccagaa | ccgagagtta | 1140 |
| aagatgtggt | gtacagtatc | ctggacctgc | ctgcagacta | ttcgcttctc | cccagatatc | 1200 |
| ttcagctcag | tgagtgtgcc | ccctagcctc | aaggtttgct | tggacctctc | agcagaatac | 1260 |
| ctgattctca | gcgatgtgca | acggaaggtc | ctctatgtga | tggagctgct | gcaaaaccag | 1320 |
| gaggagggcc | acgcctgctt | cagctccatc | tcggagttcc | tgctcaccca | ccctgtgctg | 1380 |
| agctttggta | tccaggttgt | gagtcgctgc | cggctacggc | acactgaggt | gctgcctgcc | 1440 |
| gaagaggaaa | atgacagcct | gggtgctgat | ggtacccatg | gagccggtgc | catggagtct | 1500 |
| gcggccggtg | tgctcatcaa | gctcttttgt | gtgcatacta | aggcactgca | agatgtgcag | 1560 |
| atccgcttcc | agccacagct | gaaccctgat | gtggtggccc | cactgcccac | ccacactgcc | 1620 |
| cacgaggact | tcacatttgg | agagtctcgg | cccgaactgg | ctctgagggg | cctggggtca | 1680 |
| gccgctcacg | gctcccagcc | tgacctccga | cgaatcgtgg | agctgcctgc | acctgccgac | 1740 |
| ttcctcagtc | tgagcagtga | gaccaagccc | aagttgatga | cacctgacgc | cttcatgaca | 1800 |
| cctagcgcct | ccttgcagca | gatcactgcc | tctcccagca | gcagcagcag | cggtagcagc | 1860 |
| agcagcagca | gcagtagcag | cagctccctt | acagctgtgt | ctgccatgag | cagcacctca | 1920 |
| gctgtggacc | cctccttgac | caggccacct | gaggagctga | ccttgagccc | caagctgcag | 1980 |
| ctggatggca | gctgacaat | gagcagcagt | ggcagccttc | aggcaagccc | gcgtggcctc | 2040 |
| ctgcctggcc | tgctcccagc | cccagctgac | aaactgactc | caaggggcc | gggccaggtg | 2100 |

-continued

```
cctactgcca cctctgcact gtccctggag ctgcaggaag tggagcccct ggggctaccc     2160
caagcctccc ctagccgcac tcgttcccct gatgtcatct cctcagcttc cactgccctg     2220
tcccaggaca tccctgagat tgcatctgag gccctgtccc gtggttttgg ctcctctgca     2280
ccagagggcc ttgagccaga cagtatggct tcagccgcct cggcactgca cctgctgtcc     2340
ccacggcccc ggccagggcc cgagctcggc ccccagctcg ggcttgatgg aggccctggg     2400
gatggagatc ggcataatac cccctccctc ctggaggcag ccttgaccca ggaggcctcg     2460
actcctgaca gtcaggtttg gcccacagca cctgacatta tcgtgagac ctgcagcacc      2520 ctggcagaaa gccccaggaa tggccttcag gaaaagcaca gagcctggc cttccaccga      2580 ccaccatatc acctgctgca gcaacgtgac agccaggatg ccagtgctga gcaaagtgac     2640
catgatgatg aggtggccag ccttgcctct gcttcaggag ctttggcac caaagttcct      2700 gctccacggc tgcctgccaa ggactggaag accaagggat cccctcgaac ctcacccaag     2760
ctcaagagga aaagcaagaa ggatgatggg gatgcagcca tgggatcccg gctcacagag     2820
caccaggtgg cagagccccc tgaggactgg ccagcactaa tttggcaaca gcagagagag     2880
ctggcagagc tgcggcacag ccaggaagag ctgctgcagc gtctgtgtac ccaactcgaa     2940
ggcctgcaga gcacagtcac aggccacgta aacgtgcccc ttgagactcg gcacgagcag     3000
gaacagcggc ggctggagcg agcactggct gaggggcagc agcggggagg gcagctgcag     3060
gagcagctga cacaacagtt gtcccaagca ctgtcgtcag ctgtagctgg gcggctagag     3120
cgcagcatac gggatgagat caagaagaca gtccctccat gtgtctcaag gagtctggag     3180
cctatggcag ccaactgag caactcagtg gctaccaagc tcacagctgt ggagggcagc     3240
atgaaagaga acatctccaa gctgctcaag tccaagaact tgactgatgc catcgcccga     3300
gcagctgcag acacattaca agggccgatg caggctgcct accgggaagc cttccagagt     3360
gtggtgctgc cggcctttga aagagctgc caggccatgt tccagcaaat caatgatagc      3420
ttccggctgg ggacacagga atacttgcag cagctagaaa gccacatgaa gagccggaag     3480
gcacgggaac aggaggccag ggagcctgtg ctagcccagc tgcggggcct ggtcagcaca     3540
ctgcagagtg ccactgagca gatgccaccg tggccggcag tgttcgtgct gaggtgcagc     3600
accagctgca tgtggctgtg ggcagcctgc aggagtccat tttag                    3645
```

<210> SEQ ID NO 31
<211> LENGTH: 4206
<212> TYPE: DNA
<213> ORGANISM: Human

<400> SEQUENCE: 31

```
atggcctcct gcgcgagcat cgacatcgag gacgccacgc agcacctgcg ggacatcctc      60
aagctggacc ggcccgcggg cggccccagt gcagagagcc cacggccatc cagtgcctac     120
aatggggacc tcaatggact tctggtccca gacccgctct gctcaggtga tagtacctca     180
gcaaacaaga ctggtcttcg gaccatgcca cccattaacc tgcaagagaa gcaggtcatc     240
tgtctctcag gagatgatag ctccacctgc attgggattt tggccaagga ggtggagatt     300
gtggctagca gtgactctag catttcaagc aaggcccggg gaagcaacaa ggtgaaaatt     360
cagcctgtcg ccaagtatga ctgggaacag aagtactact atggcaacct gattgctgtg     420
tctaactcct tcttggccta tgccattcgg gctgccaaca atggctctgc catggtgcgg     480
gtgatcagcg tcagcacttc ggagcggacc ttgctcaagg gcttcacagg cagtgtggct     540
gatctggctt tcgcgcacct caactctcca cagctggcct gcctggatga ggcaggcaac     600
```

```
ctgttcgtgt ggcgcttggc tctggttaat ggcaaaattc aagaagagat cttggtccat      660
attcggcagc cagagggcac gccactgaac cactttcgca ggatcatctg gtgcccttc       720 atccctgagg agagcgaaga ctgctgtgag gagagcagcc caacagtggc cctgctgcat      780
gaagaccggg ctgaggtgtg ggacctggac atgctccgct ccagccacag tacctggcct      840
gtggatgtta gccagatcaa gcagggcttc attgtggtaa aaggtcatag cacgtgcctc     900
agtgaaggag ccctctctcc tgatgggact gtgctggcta ctgcgagcca cgatggctat      960
gtcaagttct ggcagatcta cattgagggg caagatgagc caaggtgtct gcacgagtgg     1020
aaacctcatg atgggcggcc cctctcctgc ctcctgttct gtgacaacca taagaaacaa     1080
gaccctgatg tccctttctg gaggttcctt attactggtg ctgaccagaa ccgagagtta     1140
aagatgtggt gtacagtatc ctggacctgc ctgcagacta ttcgcttctc cccagatatc     1200
ttcagctcag tgagtgtgcc ccctagcctc aaggtttgct tggacctctc agcagaatac     1260
ctgattctca gcgatgtgca acggaaggtc ctctatgtga tggagctgct gcaaaaccag     1320
gaggagggcc acgcctgctt cagctccatc tcggagttcc tgctcaccca ccctgtgctg     1380
agctttggta tccaggttgt gagtcgctgc cggctacggc acactgaggt gctgcctgcc     1440
gaagaggaaa atgacagcct gggtgctgat ggtacccatg gagccggtgc catggagtct     1500
gcggccggtg tgctcatcaa gctcttttgt gtgcatacta aggcactgca agatgtgcag     1560
atccgcttcc agccacagct gaaccctgat gtggtggccc actgcccac ccacactgcc      1620 cacgaggact tcacatttgg agagtctcgg cccgaactgg gctctgaggg cctggggtca     1680
gccgctcacg gctcccagcc tgacctccga cgaatcgtgg agctgcctgc acctgccgac     1740
ttcctcagtc tgagcagtga gaccaagccc aagttgatga cacctgacgc cttcatgaca     1800
cctagcgcct ccttgcagca gatcactgcc tctcccagca gcagcagcag cggtagcagc     1860
agcagcagca gcagtagcag cagctcccct tacagctgtgt ctgccatgag cagcacctca     1920
gctgtggacc cctccttgac caggccacct gaggagctga ccttgagccc caagctgcag     1980
ctggatggca gcctgacaat gagcagcagt ggcagccttc aggcaagccc gcgtggcctc     2040
ctgcctggcc tgctcccagc cccagctgac aaactgactc caaggggcc gggccaggtg      2100 cctactgcca cctctgcact gtccctggag ctgcaggaag tggagcccct ggggctaccc     2160
caagcctccc ctagccgcac tcgttcccct gatgtcatct cctcagcttc cactgccctg     2220
tcccaggaca tccctgagat tgcatctgag gccctgtccc gtggttttgg ctcctctgca     2280
ccagagggcc ttgagccaga cagtatggct tcagccgcct cggcactgca cctgctgtcc     2340
ccacggcccc ggccagggcc cgagctcggc ccccagctcg ggcttgatgg aggccctggg     2400
gatggagatc ggcataatac cccctccctc ctggaggcag ccttgaccca ggaggcctcg     2460
actcctgaca gtcaggtttg gcccacagca cctgacatta tcgtgagac ctgcagcacc      2520 ctggcagaaa gccccaggaa tggccttcag gaaaagcaca agagcctggc cttccaccga     2580
ccaccatatc acctgctgca gcaacgtgac agccaggatg ccagtgctga gcaaagtgac     2640
catgatgatg aggtggccag ccttgcctct gcttcaggag gctttggcac caaagttcct     2700
gctccacggc tgcctgccaa ggactggaag accaaggat cccctcgaac ctcacccaag       2760
ctcaagagga aaagcaagaa ggatgatggg gatgcagcca tgggatcccg gctcacagag     2820
caccaggtgg cagagccccc tgaggactgg ccagcactaa tttggcaaca gcagagagag     2880
ctggcagagc tgcggcacag ccaggaagag ctgctgcagc gtctgtgtac ccaactcgaa     2940
```

```
ggcctgcaga gcacagtcac aggccacgta gaacgtgccc ttgagactcg gcacgagcag    3000
gaacagcggc ggctggagcg agcactggct gaggggcagc agcggggagg gcagctgcag    3060
gagcagctga cacaacagtt gtcccaagca ctgtcgtcag ctgtagctgg gcggctagag    3120
cgcagcatac gggatgagat caagaagaca gtccctccat gtgtctcaag gagtctggag    3180
cctatggcag gccaactgag caactcagtg gctaccaagc tcacagctgt ggagggcagc    3240
atgaaagaga acatctccaa gctgctcaag tccaagaact tgactgatgc catcgcccga    3300
gcagctgcag acacattaca agggccgatg caggctgcct accgggaagc cttccagagt    3360
gtggtgctgc cggcctttga aaagagctgc caggccatgt tccagcaaat caatgatagc    3420
ttccggctgg ggacacagga atacttgcag cagctagaaa gccacatgaa gagccggaag    3480
gcacgggaac aggaggccag ggagcctgtg ctagcccagc tgcggggcct ggtcagcaca    3540
ctgcagagtg ccactgagca gatggcagcc accgtggccg gcagtgttcg tgctgaggtg    3600
cagcaccagc tgcatgtggc tgtgggcagc ctgcaggagt ccattttagc acaggtacag    3660
cgcatcgtta agggtgaggt gagtgtgccg ctcaaggagc agcaggccgc cgtcacctcc    3720
agcatcatgc aggccatgcg ctcagctgct ggcacacctg tcccctctgc ccaccttgac    3780
tgccaggccc agcaagccca tatcctgcag ctgctgcagc agggccacct caatcaggcc    3840
ttccagcagg cgctgacagc tgctgacctg aacctggtgc tgtatgtgtg tgaaactgtg    3900
gacccagccc aggttttttgg gcagccaccc tgcccgctct cccagcctgt gctccttttcc    3960 ctcatccagc agctggcatc tgaccttggc actcgaactg acctcaagct cagctacctg    4020
gaagaggccg tgatgcacct ggaccacagt gaccccatca ctcgggacca catgggctcc    4080
gttatggccc aggtgcgcca aaagcttttt cagttcctgc aggctgagcc acacaactca    4140
cttggcaaag cagctcggcg tctcagcctc atgctgcatg gcctcgtgac ccccagcctc    4200
ccttag                                                              4206

<210> SEQ ID NO 32
<211> LENGTH: 1983
<212> TYPE: DNA
<213> ORGANISM: Human

<400> SEQUENCE: 32
acgaggcttc gccccgtggc gcggtttgaa attttgcggg gctcaacggc tcgcggagcg      60
gctacgcgga gtgacatcgc cggtgtttgc gggtggttgt tgctctcggg gccgtgtgga     120
gtaggtctgg acctggactc acggctgctt ggagcgtccg ccatgaggag aagtgaggtg     180
ctggcggagg agtccatagt atgtctgcag aaagccctaa atcaccttcg ggaaatatgg     240
gagctaattg ggattccaga ggaccagcgg ttacaaagaa ctgaggtggt aaagaagcat     300
atcaaggaac tcctggatat gatgattgct gaagaggaaa gcctgaagga aagactcatc     360
aaaagcatat ccgtctgtca gaaagagctg aacactctgt gcagcgagtt acatgttgag     420
ccatttcagg aagaaggaga gacgaccatc ttgcaactag aaaaagattt gcgcacccaa     480
gtggaattga tgcgaaaaca gaaaaaggag agaaaacagg aactgaagct acttcaagag     540
caagatcaag aactgtgcga aattcttttgt atgccccact atgatattga cagtgcctca     600
gtgcccagct tagaagagct gaaccagttc aggcaacatg tgacaacttt gagggaaaca     660
aaggcttcta ggcgtgagga gtttgtcagt ataaagagac agatcatact gtgtatggaa     720
gcattagacc acaccccaga cacaagcttt gaaagagatg tggtgtgtga agacgaagat     780
gccttttgtt tgtctttgga gaatattgca acactacaaa agttgctacg gcagctggaa     840
```

-continued

```
atgcagaaat cacaaaatga agcagtgtgt gaggggctgc gtactcaaat ccgagagctc      900
tgggacaggt tgcaaatacc tgaagaagaa agagaagctg tggccaccat tatgtctggg      960
tcaaaggcca aggtccggaa agcgctgcaa ttagaagtgg atcggttgga agaactgaaa     1020
atgcaaaaca tgaagaaagt gattgaggca attcgagtgg agctggttca gtactgggac     1080
cagtgctttt atagccagga gcagagacaa gcttttgccc ctttctgtgc tgaggactac     1140
acagaaagtc tgctccagct ccacgatgct gagattgtgc ggttaaaaaa ctactatgaa     1200
gttcacaagg aactctttga aggtgtccag aagtgggaag aaacctggag cttttcttta     1260
gagtttgaga gaaaagcttc agatccaaat cgatttacaa accgaggagg aaatcttcta     1320
aaagaagaaa acaacgagc caagctccag aaaatgctgc ccaagctgga agaagagttg     1380
aaggcacgaa ttgaattgtg gaacaggaa cattcaaagg catttatggt gaatgggcag     1440
aaattcatgg agtatgtggc agaacaatgg gagatgcatc gattggagaa agagagagcc     1500
aagcaggaaa gacaactgaa gaacaaaaaa cagacagaga cagagatgct gtatggcagc     1560
gctcctcgaa cacctagcaa gcggcgagga ctggctccca atacaccggg caaagcacgt     1620
aagctgaaca ctaccaccat gtccaatgct acggccaata gtagcattcg gcctatcttt     1680
ggagggacag tctaccactc ccccgtgtct cgacttcctc cttctggcag caagccagtc     1740
gctgcttcca cctgttcagg gaagaaaaca ccccgtactg gcaggcatgg agccaacaag     1800
gagaacctgg agctcaacgg cagcatcctg agtggtgggt accctggctc ggccccctc     1860 cagcgcaact tcagcattaa ttctgttgcc agcacctatt ctgagtttgc gcagaaactt     1920
tcaaaggctt ccaaatctga tgctacttct ggaatcctca attcaaccaa catccagtcc     1980
tga                                                                  1983
```

<210> SEQ ID NO 33
<211> LENGTH: 2025
<212> TYPE: DNA
<213> ORGANISM: Human

<400> SEQUENCE: 33

```
acgaggcttc gccccgtggc gcggtttgaa attttgcggg gctcaacggc tcgcggagcg       60
gctacgcgga gtgacatcgc cggtgtttgc gggtggttgt tgctctcggg gccgtgtgga      120
gtaggtctgg acctggactc acggctgctt ggagcgtccg ccatgaggag aagtgaggtg      180
ctggcggagg agtccatagt atgtctgcag aaagccctaa atcaccttcg ggaaatatgg      240
gagctaattg ggattccaga ggaccagcgg ttacaaagaa ctgaggtggt aaagaagcat      300
atcaaggaac tcctggatat gatgattgct gaagaggaaa gcctgaagga aagactcatc      360
aaaagcatat ccgtctgtca gaaagagctg aacactctgt gcagcgagtt acatgttgag      420
ccatttcagg aagaaggaga gacgaccatc ttgcaactag aaaaagattt gcgcacccaa      480
gtggaattga tgcgaaaaca gaaaaggag agaaaacagg aactgaagct acttcaagag      540
caagatcaag aactgtgcga aattctttgt atgccccact atgatattga cagtgcctca      600
gtgcccagct tagaagagct gaaccagttc aggcaacatg tgacaacttt gagggaaaca      660
aaggcttcta ggcgtgagga gtttgtcagt ataaagagac agatcatact gtgtatggaa      720
gcattagacc acaccccaga cacaagcttt gaaagagatg tggtgtgtga agacgaagat      780
gccttttgtt tgtctcttgga gaatattgca acactacaaa agttgctacg gcagctggaa      840
atgcagaaat cacaaaatga agcagtgtgt gaggggctgc gtactcaaat ccgagagctc      900
```

-continued

```
tgggacaggt tgcaaatacc tgaagaagaa agagaagctg tggccaccat tatgtctggg      960
tcaaaggcca aggtccggaa agcgctgcaa ttagaagtgg atcggttgga agaactgaaa     1020
atgcaaaaca tgaagaaagt gattgaggca attcgagtgg agctggttca gtactgggac    1080
cagtgctttt atagccagga gcagagacaa gcttttgccc ctttctgtgc tgaggactac    1140
acagaaagtc tgctccagct ccacgatgct gagattgtgc ggttaaaaaa ctactatgaa    1200
gttcacaagg aactctttga aggtgtccag aagtgggaag aaacctggag gcttttctta    1260
gagtttgaga gaaaagcttc agatccaaat cgatttacaa accgaggagg aaatcttcta    1320
aaagaagaaa acaacgagc caagctccag aaaatgctgc ccaagctgga agaagagttg     1380
aaggcacgaa ttgaattgtg ggaacaggaa cattcaaagg catttatggt gaatgggcag    1440
aaattcatgg agtatgtggc agaacaatgg gagatgcatc gattggagaa agagagagcc    1500
aagcaggaaa gacaactgaa gaacaaaaaa cagacagaga cagagatgct gtatggcagc    1560
gctcctcgaa cacctagcaa gcggcgagga ctggctccca ataccggg caaagcacgt     1620 aagctgaaca ctaccaccat gtccaatgct acggccaata gtagcattcg gcctatcttt    1680
ggagggacag tctaccactc ccccgtgtct cgacttcctc cttctggcag caagccagtc    1740
gctgcttcca cctgttcagg gaagaaaaca ccccgtactg gcaggcatgg agccaacaag    1800
gagaacctgg agctcaacgg cagcatcctg agtggtgggt accctggctc ggccccctc    1860 cagcgcaact tcagcattaa ttctgttgcc agcacctatt ctgagtttgc gaaggatccg    1920
tccctctctg acagttccac tgttgggctt cagcgagaac tttcaaaggc ttccaaatct    1980
gatgctactt ctggaatcct caattcaacc aacatccagt cctga                    2025
```

<210> SEQ ID NO 34
<211> LENGTH: 1863
<212> TYPE: DNA
<213> ORGANISM: Human

<400> SEQUENCE: 34

```
atgaggagaa gtgaggtgct ggcggaggag tccatagtat gtctgcagaa agccctaaat      60 cacccttcggg aaatatggga gctaattggg attccagagg accagcggtt acaaagaact    120
gaggtggtaa agaagcatat caaggaactc ctggatatga tgattgctga agaggaaagc    180
ctgaaggaaa gactcatcaa aagcatatcc gtctgtcaga aagagctgaa cactctgtgc    240
agcgagttac atgttgagcc atttcaggaa gaaggagaga cgaccatctt gcaactagaa    300
aaagatttgc gcacccaagt ggaattgatg cgaaaacaga aaaggagag aaaacaggaa     360 ctgaagctac ttcaagagca agatcaagaa ctgtgcgaaa ttctttgtat gccccactat    420
gatattgaca gtgcctcagt gcccagctta aagagctga accagttcag caacatgtg      480 acaactttga gggaaacaaa ggcttctagg cgtgaggagt ttgtcagtat aaagagacag    540
atcatactgt gtatggaagc attagaccac accccagaca caagctttga agagatgtg     600 gtgtgtgaag acgaagatgc cttttgtttg tctttggaga atattgcaac actacaaaag    660
ttgctacggc agctggaaat gcagaaatca caaaatgaag cagtgtgtga ggggctgcgt    720
actcaaatcc gagagctctg gacaggttca caaatacctg aagaagaag agaagctgtg     780 gccaccatta tgtctgggtc aaaggccaag gtccggaaag cgctgcaatt agaagtggat    840
cggttggaag aactgaaaat gcaaaacatg aagaaagtga ttgaggcaat tcgagtggag    900
ctggttcagt actgggacca gtgcttttat agccaggagc agagacaagc ttttgcccct    960
ttctgtgctg aggactacac agaaagtctg ctccagctcc acgatgctga gattgtgcgg   1020
```

```
ttaaaaaact actatgaagt tcacaaggaa ctctttgaag gtgtccagaa gtgggaagaa    1080
acctggaggc ttttcttaga gtttgagaga aaagcttcag atccaaatcg atttacaaac    1140
cgaggaggaa atcttctaaa agaagaaaaa caacgagcca agctccagaa aatgctgccc    1200
aagctggaag aagagttgaa ggcacgaatt gaattgtggg aacaggaaca ttcaaaggca    1260
tttatggtga atgggcagaa attcatggag tatgtggcag aacaatggga gatgcatcga    1320
ttggagaaag agagagccaa gcaggaaaga caactgaaga acaaaaaaca gacagagaca    1380
gagatgctgt atggcagcgc tcctcgaaca cctagcaagc ggcgaggact ggctcccaat    1440
acaccgggca agcacgtaa gctgaacact accaccatgt ccaatgctac ggccaatagt     1500
agcattcggc ctatctttgg agggacagtc taccactccc ccgtgtctcg acttcctcct    1560
tctggcagca agccagtcgc tgcttccacc tgttcaggga agaaaacacc ccgtactggc    1620
aggcatggag ccaacaagga gaacctggag ctcaacggca gcatcctgag tggtgggtac    1680
cctggctcgg ccccccctcca gcgcaacttc agcattaatt ctgttgccag cacctattct    1740
gagtttgcga aggatccgtc cctctctgac agttccactg ttgggcttca gcgagaactt    1800
tcaaaggctt ccaaatctga tgctacttct ggaatcctca attcaaccaa catccagtcc    1860
tga                                                                   1863

<210> SEQ ID NO 35
<211> LENGTH: 1164
<212> TYPE: DNA
<213> ORGANISM: Human

<400> SEQUENCE: 35
atgaccacgc aactgggccc agccctggtg ctggggtgg ccctgtgcct gggttgtggc       60
cagcccctac acaggtccc tgaacgcccc ttctctgtgc tgtggaatgt accctcagca     120
cactgtgagg cccgcttgg tgtgcacctg ccactcaatg ctctgggcat catagccaac     180
cgtggccagc attttcacgg tcagaacatg accattttct acaagaacca actcggcctc     240
tatccctact ttggacccag ggcacagct cacaatgggg gcatccccca ggctttgccc       300
cttgaccgcc acctggcact ggctgcctac cagatccacc acagcctgag acctggcttt     360
gctggcccag cagtgctgga ttgggaggag tggtgtccac tctgggctgg gaactggggc    420
cgccgccgag cttatcaggc agcctcttgg gcttgggcac agcaggtatt ccctgacctg     480
gaccctcagg agcagctcta caaggcctat actggctttg agcaggcggc ccgtgcactg    540
atggaggata cgctgcgggt ggcccaggca ctacggcccc atggactctg ggcttctat      600
cactacccag cctgtggcaa tggctggcat agtatggctt ccaactatac cggccgctgc     660
catgcagcca cccttgcccg caacactcaa ctgcattggc tctgggccgc ctccagtgcc     720
ctcttcccca gcatctacct cccacccagg ctgccacctg cccaccacca ggcctttgtc     780
cgacatcgcc tggaggaggc cttccgtgtg gccttgttg gcaccgaca tcccctgcct       840
gtcctggcct atgtccgcct cacacaccgg agatctggga ggttcctgtc ccaggaggag    900
tgctggcatc tccatgacta cctggtggac accttgggcc ctatgtgat caatgtgacc       960
agggcagcga tggcctgcag tcaccagcgg tgccatggca cgggcgctg tgcccggcga    1020
gatccaggac agatggaagc ctttctacac ctgtggccag acggcagcct ggagattgg     1080
aagtccttca gctgccactg ttactggggc tgggctggcc ccacctgcca ggagcccagg    1140
cctgggccta agaagcagt ataa                                              1164
```

<210> SEQ ID NO 36
<211> LENGTH: 1389
<212> TYPE: DNA
<213> ORGANISM: Human

<400> SEQUENCE: 36

| | | | | | |
|---|---|---|---|---|---|
| atgaccacgc | aactgggccc | agccctggtg | ctggggggtgg | ccctgtgcct | gggttgtggc | 60 |
| cagcccctac | acaggtccc | tgaacgcccc | ttctctgtgc | tgtggaatgt | accctcagca | 120 |
| cactgtgagg | cccgctttgg | tgtgcacctg | ccactcaatg | ctctgggcat | catagccaac | 180 |
| cgtggccagc | attttcacgg | tcagaacatg | accattttct | acaagaacca | actcggcctc | 240 |
| tatccctact | ttggacccag | gggcacagct | cacaatgggg | gcatccccca | ggctttgccc | 300 |
| cttgaccgcc | acctggcact | ggctgcctac | cagatccacc | acagcctgag | acctggcttt | 360 |
| gctggcccag | cagtgctgga | ttgggaggag | tggtgtccac | tctgggctgg | aactggggc | 420 |
| cgccgccgag | cttatcaggc | agcctcttgg | gcttgggcac | agcaggtatt | ccctgacctg | 480 |
| gaccctcagg | agcagctcta | caaggcctat | actggctttg | agcaggcggc | ccgtgcactg | 540 |
| atggaggata | cgctgcgggt | ggcccaggca | ctacggcccc | atggactctg | ggcttctat | 600 |
| cactaccag | cctgtggcaa | tggctggcat | agtatggctt | ccaactatac | cggccgctgc | 660 |
| catgcagcca | cccttgcccg | caacactcaa | ctgcattggc | tctgggccgc | ctccagtgcc | 720 |
| ctcttcccca | gcatctacct | cccacccagg | ctgccacctg | cccaccacca | ggcctttgtc | 780 |
| cgacatcgcc | tggaggaggc | cttccgtgtg | gccctgttg | ggcaccgaca | tcccctgcct | 840 |
| gtcctggcct | atgtccgcct | cacacaccgg | agatctggga | ggttcctgtc | ccaggatgac | 900 |
| cttgtgcagt | ccattggtgt | gagtgcagca | ctaggggcag | ccggcgtggt | gctctggggg | 960 |
| gacctgagcc | tctccagctc | tgaggaggag | tgctggcatc | tccatgacta | cctggtggac | 1020 |
| accttgggcc | cctatgtgat | caatgtgacc | agggcagcga | tggcctgcag | tcaccagcgg | 1080 |
| tgccatggcc | acgggcgctg | tgcccggcga | gatccaggac | agatggaagc | ctttctacac | 1140 |
| ctgtggccag | acggcagcct | ggagattgg | aagtccttca | gctgccactg | ttactggggc | 1200 |
| tgggctggcc | ccacctgcca | ggagcccctg | ggcctaaaga | agcagtataa | agccagggcc | 1260 |
| cctgccactg | cctcttcttt | tccctgctgc | cacttttcca | gtcctggaac | tactctgtcc | 1320 |
| cactcttgct | ctattcagtt | tacagtcaac | cctcccaagc | acacacccg | cttcccttgg | 1380 |
| aatccctga | | | | | 1389 |

<210> SEQ ID NO 37
<211> LENGTH: 1254
<212> TYPE: DNA
<213> ORGANISM: Human

<400> SEQUENCE: 37

| | | | | | |
|---|---|---|---|---|---|
| atgaccacgc | aactgggccc | agccctggtg | ctggggggtgg | ccctgtgcct | gggttgtggc | 60 |
| cagcccctac | acaggtccc | tgaacgcccc | ttctctgtgc | tgtggaatgt | accctcagca | 120 |
| cactgtgagg | cccgctttgg | tgtgcacctg | ccactcaatg | ctctgggcat | catagccaac | 180 |
| cgtggccagc | attttcacgg | tcagaacatg | accattttct | acaagaacca | actcggcctc | 240 |
| tatccctact | ttggacccag | gggcacagct | cacaatgggg | gcatccccca | ggctttgccc | 300 |
| cttgaccgcc | acctggcact | ggctgcctac | cagatccacc | acagcctgag | acctggcttt | 360 |
| gctggcccag | cagtgctgga | ttgggaggag | tggtgtccac | tctgggctgg | aactggggc | 420 |
| cgccgccgag | cttatcaggc | agcctcttgg | gcttgggcac | agcaggtatt | ccctgacctg | 480 |

```
gaccctcagg agcagctcta caaggcctat actggctttg agcaggcggc ccgtgcactg        540
atggaggata cgctgcgggt ggcccaggca ctacggcccc atggactctg gggcttctat        600
cactacccag cctgtggcaa tggctggcat agtatggctt ccaactatac cggccgctgc        660
catgcagcca cccttgcccg caacactcaa ctgcattggc tctgggccgc ctccagtgcc        720
ctcttcccca gcatctacct cccacccagg ctgccacctg cccaccacca ggcctttgtc        780
cgacatcgcc tggaggaggc cttccgtgtg cccttgttg gcaccgaca tccctgcct           840 gtcctggcct atgtccgcct cacacaccgg agatctggga ggttcctgtc ccaggatgac        900
cttgtgcagt ccattggtgt gagtgcagca ctagggcag ccggcgtggt gctctggggg         960
gacctgagcc tctccagctc tgaggaggag tgctggcatc tccatgacta cctggtggac       1020
accttgggcc cctatgtgat caatgtgacc agggcagcga tggcctgcag tcaccagcgg       1080
tgccatggcc acgggcgctg tgcccggcga gatccaggac agatggaagc ctttctacac       1140
ctgtggccag acgcagcct ggagattgg aagtccttca gctgccactg ttactggggc        1200
tgggctggcc ccacctgcca ggagcccagg cctgggccta agaagcagt ataa             1254
```

<210> SEQ ID NO 38
<211> LENGTH: 1389
<212> TYPE: DNA
<213> ORGANISM: Human

<400> SEQUENCE: 38

```
atgggaaagg aaaagactca tatcaacatt gtcgtcattg acacgtaga ttcgggcaag         60 tccaccacta ctggccatct gatctataaa tgcggtggca tcgacaaaag aaccattgaa       120
aaatttgaga aggaggctgc tgagatggga aagggctcct tcaagtatgc ctgggtcttg       180
gataaactga agctgagcg tgaacgtggt atcaccattg atatctcctt gtggaaattt       240
gagaccagca agtactatgt gactatcatt gatgccccag acacagaga cttcatcaaa       300 aacatgatta caggggacatc tcaggctgac tgtgctgtcc tgattgttgc tgctggtgtt      360
ggtgaatttg aagctggtat ctccaagaat gggcagaccc gagagcatgc ccttctggct      420
tacacactgg gtgtgaaaca actaattgtc ggtgttaaca aaatggattc cactgagcca      480
ccctacagcc agaagagata tgaggaaatt gttaaggaag tcagcactta cattaagaaa      540
attggctaca ccccgacac agtagcattt gtgccaattt ctggttggaa tggtgacaac       600
atgctggagc aagtgctaa catgccttgg ttcaagggat ggaaagtcac ccgtaaggat      660
ggcaatgcca gtgaaccac gctgcttgag gctctggact gcatcctacc accaactcgc       720
ccaactgaca gcccttgcg cctgcctctc caggatgtct acaaaattgg tggtattggt       780
actgttcctg ttggccgagt ggagactggt gttctcaaac ccgtatggt ggtcacctt        840 gctccagtca acgttacaac ggaagtaaaa tctgtcgaaa tgcaccatga gctttgagt       900 gaagctcttc ctggggacaa tgtgggcttc aaggtcaaga atgtgtctgt caaggatgtt      960
cgtcgtggca acgttgctgg tgacagcaaa aatgacccac caatggaagc agctggcttc     1020
actgctcagg tgattatcct gaaccatcca ggccaaataa gcgccggcta tgcccctgta      1080
ttggattgcc acatggctca cattgcatgc aagtttgctg agctgaagga aaagattgat      1140
cgccgttctg gtaaaaagct ggaagatggc cctaaattct tgaagtctgg tgatgctgcc      1200
attgttgata tggttcctgg caagcccatg tgtgttgaga gcttctcaga ctatccacct      1260
ttgggtcgct ttgctgttcg tgatatgaga cagacagttg cggtgggtgt catcaaagca      1320
```

```
gtggacaaga aggctgctgg agctggcaag gtcaccaagt ctgcccagaa agctcagaag    1380
gctaaatga                                                           1389
```

<210> SEQ ID NO 39
<211> LENGTH: 1146
<212> TYPE: DNA
<213> ORGANISM: Human

<400> SEQUENCE: 39

```
atggccctaa aggccgaggg cgccgcactc gactgcttcg aggtgacgct gaaatgcgag     60 gaagggagg acgaggagga ggccatggtg gtggccgtaa ttccgcggcc cgagccgatg    120
ctcagagtga cccaacagga aagaccccca ccgcctagac ccagcccgct agaggcaggc    180
agtgatggct gtgaggagcc gaagcagcag gtgtcttggg agcaggagtt cctggtgggc    240
agcagcccag gaggcagcgg gcgggcactg tgcatggtgt gtggcgctga gatccgggca    300
ccctcggccg acacagctcg ctcgcacatc ttggagcagc accctcacac cttggacctg    360 agccttctg agaagagcaa tatcctggag gcctggagtg aaggggtggc cctcttgcaa    420
gacgtgagag ctgagcagcc gtccccaccc aactcagact cgggccagga tgcccaccca    480
gacccagacg ccaacccaga cgctgccaga atgccagccg aaatcgtcgt tctccttgac    540
tctgaggata acccatccct ccctaaaagg agccggccca ggggactccg cccccctcgag    600 cttcctgctg tccctgccac agagccagga aataagaagc ccgtggtca gagatggaag    660 gaaccccag gggaagagcc agtcagaaag aaaagaggca gacctatgac caaaaacctg    720
gaccctgacc cagagccccc atcgccgac tcgcccacgg agactttcgc agcaccagcc    780
gaggtccgac acttcactga cggcagcttc cccgccggct tcgtcttgca gctcttctcc    840
cacacccagc tcaggggccc agacagcaag gactcaccca agacaggga agtggcagaa    900 ggaggccttc cccgggcgga gagccctct ccagctcccc ctccggggct ccgcgggaca    960
ctggatctcc aggttatccg cgtgcggatg gaggagcccc cagcggtcag cctcctgcaa   1020
gactggtcca ggcacccca gggcaccaag cgtgtgggag caggtgacac ctcagactgg   1080
cccacagttc tgtcagaatc cagcaccact gtggcaggga gccggaaaaa agggaatgga   1140
gtgtaa                                                             1146
```

<210> SEQ ID NO 40
<211> LENGTH: 5730
<212> TYPE: DNA
<213> ORGANISM: Human

<400> SEQUENCE: 40

```
atgagcacac acaggagccg tctcctcacc gccgccctc tcagcatgga acagaggcgg     60
ccctggcccc gggccctgga ggtggacagc cgctctgtgg tcctgctctc agtggtctgg    120
gtgctgctgg ccccccagc agccggcatg cctcagttca gcaccttcca ctctgagaat    180
cgtgactgga ccttcaacca cttgaccgtc accaaggga cggggccgt ctatgtgggg    240 gccatcaacc gggtctataa gctgacaggc aacctgacca tccaggtggc tcataagaca    300
gggccagaag aggacaacaa gtcttgttac ccgcccctca tcgtgcagcc tgcagcgaa    360 gtgctcaccc tcaccaacaa tgtcaacaag ctgctcatca ttgactactc tgagaaccgc    420
ctgctggcct gtgggagcct ctaccagggg gtctgcaagc tgctgcggct ggatgacctc    480
ttcatcctgg tggagccatc ccacaagaag gagcactacc tgtccagtgt caacaagacg    540
ggcaccatgt acggggtgat tgtgcgctct gagggtgagg atggcaagct cttcatcggc    600
```

```
acggctgtgg atgggaagca ggattacttc ccgaccctgt ccagccggaa gctgccccga    660
gaccctgagt cctcagccat gctcgactat gagctacaca gcgattttgt ctcctctctc    720
atcaagatcc cttcagacac cctggccctg tctcccact  ttgacatctt ctacatctac    780
ggctttgcta gtgggggctt tgtctacttt ctcactgtcc agcccgagac ccctgagggt    840
gtggccatca actccgctgg agacctcttc tacacctcac gcatcgtgcg gctctgcaag    900
gatgacccca agttccactc atacgtgtcc ctgcccttcg gctgcacccg gccggggtg    960 gaataccgcc tcctgcaggc tgcttacctg gccaagcctg ggactcact  ggcccaggcc   1020 ttcaatatca ccagccagga cgatgtactc tttgccatct tctccaaagg gcagaagcag   1080
tatcaccacc cgcccgatga ctctgccctg tgtgccttcc ctatccgggc catcaacttg   1140
cagatcaagg agcgcctgca gtcctgctac cagggcgagg gcaacctgga gctcaactgg   1200
ctgctgggga aggacgtcca gtgcaccaag gcgcctgtcc ccatcgatga taacttctgt   1260 ggactgtgaca tcaaccagcc cctgggaggc tcaactccag tggagggcct gaccctgtac   1320
accaccagca gggaccgcat gacctctgtg gcctcctacg tttacaacgg ctacagcgtg   1380 gttttttgtgg ggactaagag tggcaagctg aaaaagattc gggccgacgg tcccccccat   1440
ggtggggtcc agtacgagat ggtctctgtg ctcaaggacg aagcccccat cctccgggac   1500
atggccttct ccattgatca gcgctacctg tacgtcatgt ctgagagaca ggtcaccagg   1560
gtccccgtgg agtcatgtga gcagtatacg acttgtgggg agtgcctgag ctctggggac   1620
cctcactgtg gctggtgtgc cctgcacaac atgtgctccc gcagggacaa atgccaacag   1680
gcctgggaac ctaatcgatt tgctgccagc atcagccagt gtgtgagcct tgcagtgcat   1740
cccagcagca tctcagtatc tgagcacagc cggttgctta gcctggtagt gagtgatgct   1800
cctgatctat ctgcgggtat cgcctgtgcc tttgggaacc tgacagaggt ggaggggcag   1860
gtgtccggga gccaggtcat ctgcatctca cctgggccca aggatgtccc tgtcatcccg   1920
ctggatcaag actggttttgg gctggagcta cagctgaggt ccaaggagac agggaagata   1980
tttgtcagca ccgagttcaa gttttacaac tgcagtgccc accaactgtg cctgtcctgt   2040
gtcaacagcg ccttccgctg ccattggtgc aagtaccgca acctctgcac tcatgacccc   2100
accacctgct ccttccagga gggccggatc aatatttcag aggactgtcc ccagctggtg   2160
cccacagagg agatcttgat tccagtcggg gaggtaaagc caataccct  taaggcgcga   2220 aatctgcccc agccgcagtc cggccagcga ggctatgagt gtgtcctcaa catacaagga   2280
gccatccacc gggtccccgc tctgcgcttc aacagctcca cgttcagtg  tcagaacagc   2340 tcgtaccagt atgatggcat ggacatcagc aatctggccg tggatttcgc tgtggtgtgg   2400
aacggcaatt tcatcattga caaccctcag gacctgaaag tccatctcta caagtgtgca   2460
gcccagcggg agagctgcgg cctctgcctc aaggccgacc ggaagtttga gtgtggctgg   2520
tgcagcggcg agcgcaggtg cacctccac  cagcactgta ccagcccttc cagccctggg   2580
ctcgactggt ccagccacaa tgtcaagtgc tccaaccctc aaatcaccga gattttgacg   2640
gtgtctggac cgccggaagg agggacgcga gtgaccatcc atggcgtgaa cctgggtctg   2700
gacttctccg agatcgccca ccatgtgcag gtggctgggg tgcccctgca gccccctccca   2760 ggggaataca tcatcgctga gcagattgtc tgtgagatgg ccatgcccct cgtgggaacc   2820
acctccgggc agtacgcct  gtgtattggc gagtgtaagc agagttcat  gacgaagtcc   2880 catcagcagt acaccttcgt gaaccccttct gtgctgtcac tcaacccaat ccgaggtccc   2940
```

```
gagtcaggag gcactatggt gaccattacc ggccattacc ttggggctgg gagcagcgtg    3000
gcagtctacc tgggcaacca gacctgcgag ttctacggga ggtcaatgag tgagatcgtg    3060
tgtgtctcac ccccatcatc caatggcctt ggcccggtcc ctgtttctgt gagtgtcgac    3120
cgagcccatg tggatagcaa cctgcagttt gagtacatag atgaccctcg ggtccagcgc    3180
atcgagccag agtggagcat tgccagtggc cacacacccc tgaccatcac aggcttcaac    3240
ctggatgtca ttcaggagcc aaggatccga gtcaaattca atggcaaaga atctgtcaat    3300
gtgtgtaaag ttgtgaacac aaccaccctc acctgcctgg caccctctct gaccacggac    3360
taccgccctg gcctggacac tgtggaacgc ccagatgagt ttggatttgt ctttaacaat    3420
gtccaatcct tgctaattta caacgacacc aagtttatct actaccccaa cccgaccttt    3480
gaactgctta gccctactgg agtcttggat caaaagccag gatcgcccat cattctgaag    3540
ggcaaaaacc tctgccctcc tgcctctgga ggggccaaac tcaactacac tgtgctcatc    3600
ggagagaccc cttgtgctgt caccgtatct gagacccagc ttctctgcga gcctcccaac    3660
ctcaccgggc agcacaaggt catggttcac gtgggcggga tggtgttctc gcctggctcg    3720
gtgagtgtca tctcagacag cttgctgacc ctgccagcca tcgtcagcat cgcggccggc    3780
ggcagcctcc tcctcatcat cgtcatcatc gtcctcattg cctacaagcg caagtctcga    3840
gaaaatgacc tcactctcaa gcggctgcaa atgcagatgg acaatctgga gtcccgtgtg    3900
gccttggagt gcaaggaagc ttttgctgag ctccagacgg atatcaatga gttgaccagt    3960
gacctggacc gctcaggaat cccttacctg gactatcgta cctacgctat gcgagtcctg    4020
ttcccgggca tcgaggacca ccccgtcctg cgggagctgg aggtacaagg aaacgggcag    4080
cagcacgtgg agaaggccct gaagctcttt gcccagctca tcaacaacaa ggtgttcctg    4140
ctgaccttca tccgcaccct ggagctgcag cgcagtttct ccatgcgcga ccggggcaac    4200
gtggcttcgc tcatcatgac cggcctgcag ggccgcctgg aatatgccac tgatgtcctc    4260
aagcagctgc tctctgacct catcgataag aacctggaga acaagaacca ccccaagctg    4320
ctactccgga ggacagagtc tgtggctgaa aagatgctga ccaattggtt cgccttcctc    4380
ctgcacaagt tcctaaagga gtgcgcaggg gagccactct tcatgctata ctgtgccatc    4440
aagcagcaga tggagaaggg ccccattgat gccatcacgg gcgaggcccg ctactccctg    4500
agcgaggaca agctcatccg gcagcagatc gagtacaaga ccctgatcct gaactgcgtc    4560
aaccctgaca acgagaacag tccagagatc ccagtgaagg tgttaaactg tgacaccatc    4620
acacaggtca aggagaagat tcttgatgcc gtgtataaga atgtgccctg ttcccagcgg    4680
ccgagggcag tggacatgga cttggagtgg cgccaaggcc ggatcgcccg ggtcgtgctg    4740
caagatgagg acatcaccac caagattgag ggtgactgga gcggctcaa cacactgatg    4800 cattatcagg tgtcagacag gtcggtggtg gctctggtcc ccaaacagac ctcctcctac    4860
aacatccctg cctctgccag catctcccgg acgtccatca gcagatacga ctcctccttc    4920
aggtatacgg gcagccccga cagcctgcgg tcccgggccc cgatgatcac cccagacctg    4980
gaaagtgggg tcaaggtgtg gcatctggtg aagaaccatg accacggtga ccagaaggag    5040
ggtgaccggg gcagcaagat ggtgtccgag atctacctga cccggctact ggccaccaag    5100
ggcacccctg agaagtttgt ggacgacttg tttgagacct tgttcagcac tgtgcaccgg    5160
ggcagcgctc tcccctggc catcaagtac atgtttgatt tcctagatga gcaggcagac    5220
aggcacagca tccatgacac agatgtgcgg cacacctgga aaagcaactg cctccctctg    5280
cgcttctggg tgaacgtgat taagaacccc cagttcgtgt ttgacatcca caagggcagc    5340
```

| | |
|---|---|
| atcacggacg cctgcctctc tgtggtggcc cagaccttca tggactcttg ttcaacgtca | 5400 |
| gagcaccggc tgggcaagga ctccccctcc aacaagctgc tctatgccaa ggacatcccc | 5460 |
| agctacaaga gctgggtgga gagatactac gcagacatcg ccaagctccc agccatcagt | 5520 |
| gaccaggaca tgaatgccta cctcgccgag cagtcccgcc tgcacgccgt ggagttcaac | 5580 |
| atgctgagtg ccctcaatga gatctactcc tatgtcagca agtatagtga ggagctcatc | 5640 |
| ggggccctag agcaggatga gcaggcacgg cggcagcggc tggcttataa ggtggagcag | 5700 |
| ctcattaatg ccatgtccat tgagagctga | 5730 |

<210> SEQ ID NO 41
<211> LENGTH: 5685
<212> TYPE: DNA
<213> ORGANISM: Human

<400> SEQUENCE: 41

| | |
|---|---|
| atggaacaga ggcggccctg gccccgggcc ctggaggtgg acagccgctc tgtggtcctg | 60 |
| ctctcagtgg tctgggtgct gctggccccc ccagcagccg gcatgcctca gttcagcacc | 120 |
| ttccactctg agaatcgtga ctggaccttc aaccacttga ccgtccacca agggacgggg | 180 |
| gccgtctatg tgggggccat caaccgggtc tataagctga caggcaacct gaccatccag | 240 |
| gtggctcata agacagggcc agaagaggac aacaagtctt gttacccgcc cctcatcgtg | 300 |
| cagccctgca gcgaagtgct caccctcacc aacaatgtca acaagctgct catcattgac | 360 |
| tactctgaga accgcctgct ggcctgtggg agcctctacc aggggtctg caagctgctg | 420 |
| cggctggatg acctcttcat cctggtggag ccatcccaca gaaggagca ctacctgtcc | 480 |
| agtgtcaaca gacgggcac catgtacggg gtgattgtgc gctctgaggg tgaggatggc | 540 |
| aagctcttca tcggcacggc tgtggatggg aagcaggatt acttcccgac cctgtccagc | 600 |
| cggaagctgc cccgagaccc tgagtcctca gccatgctcg actatgagct acacagcgat | 660 |
| tttgtctcct ctctcatcaa gatcccttca gacacccctgg ccctggtctc ccactttgac | 720 |
| atcttctaca tctacggctt tgctagtggg ggctttgtct actttctcac tgtccagccc | 780 |
| gagacccctg agggtgtggc catcaactcc gctggagacc tcttctacac ctcacgcatc | 840 |
| gtgcggctct gcaaggatga ccccaagttc cactcatacg tgtccctgcc cttcggctgc | 900 |
| acccgggccg gggtggaata ccgcctcctg caggctgctt acctggccaa gcctggggac | 960 |
| tcactggccc aggccttcaa tatcaccagc caggacgatg tactctttgc catcttctcc | 1020 |
| aaagggcaga agcagtatca ccacccgccc gatgactctg ccctgtgtgc cttccctatc | 1080 |
| cgggccatca acttgcagat caaggagcgc ctgcagtcct gctaccaggg cgagggcaac | 1140 |
| ctggagctca actggctgct ggggaaggac gtccagtgca ccaaggcgcc tgtccccatc | 1200 |
| gatgataact tctgtggact ggacatcaac cagccctgg aggctcaac tccagtggag | 1260 |
| ggcctgaccc tgtacaccac cagcagggac cgcatgacct ctgtggcctc ctacgtttac | 1320 |
| aacggctaca gcgtggtttt tgtggggact aagagtggca agctgaaaaa gattcgggcc | 1380 |
| gacggtcccc cccatggtgg ggtccagtac gagatggtct ctgtgctcaa ggacggaagc | 1440 |
| cccatcctcc gggacatggc cttctccatt gatcagcgct acctgtacgt catgtctgag | 1500 |
| agacaggtca ccagggtccc cgtggagtca tgtgagcagt atacgacttg tgggagtgc | 1560 |
| ctgagctctg ggaccctca ctgtggctgg tgtccctgc acaacatgtg ctcccgcagg | 1620 |
| gacaaatgcc aacaggcctg ggaacctaat cgatttgctg ccagcatcag ccagtgtgtg | 1680 |

```
agccttgcag tgcatcccag cagcatctca gtatctgagc acagccggtt gcttagcctg    1740
gtagtgagtg atgctcctga tctatctgcg ggtatcgcct gtgcctttgg gaacctgaca    1800
gaggtggagg ggcaggtgtc cgggagccag gtcatctgca tctcacctgg gcccaaggat    1860
gtccctgtca tcccgctgga tcaagactgg tttgggctgg agctacagct gaggtccaag    1920
gagacaggga agatatttgt cagcaccgag ttcaagtttt acaactgcag tgcccaccaa    1980
ctgtgcctgt cctgtgtcaa cagcgccttc cgctgccatt ggtgcaagta ccgcaacctc    2040
tgcactcatg accccaccac ctgctccttc caggagggcc ggatcaatat ttcagaggac    2100
tgtccccagc tggtgcccac agaggagatc ttgattccag tcggggaggt aaagccaatc    2160
acccttaagg cgcgaaatct gccccagccg cagtccggcc agcgaggcta tgagtgtgtc    2220
ctcaacatac aaggagccat ccaccgggtc cccgctctgc gcttcaacag ctccagcgtt    2280
cagtgtcaga acagctcgta ccagtatgat ggcatggaca tcagcaatct ggccgtggat    2340
ttcgctgtgg tgtggaacgg caatttcatc attgacaacc tcaggacct gaaagtccat    2400 ctctacaagt gtgcagccca gcgggagagc tgcggcctct gcctcaaggc cgaccggaag    2460
tttgagtgtg gctggtgcag cggcgagcgc aggtgcaccc tccaccagca ctgtaccagc    2520
ccttccagcc cctggctcga ctggtccagc cacaatgtca agtgctccaa ccctcaaatc    2580
accgagattt tgacggtgtc tggaccgccg gaaggaggga cgcgagtgac catccatggc    2640
gtgaacctgg gtctggactt ctccgagatc gcccaccatg tgcaggtggc tggggtgccc    2700
tgcacgcccc tcccagggga atacatcatc gctgagcaga ttgtctgtga gatgggccat    2760
gccctcgtgg gaaccacctc cgggccagta cgcctgtgta ttggcgagtg taagccagag    2820
ttcatgacga agtcccatca gcagtacacc ttcgtgaacc cttctgtgct gtcactcaac    2880
ccaatccgag gtcccgagtc aggaggcact atggtgacca ttaccggcca ttaccttggg    2940
gctgggagca gcgtggcagt ctacctgggc aaccagacct gcgagttcta cgggaggtca    3000
atgagtgaga tcgtgtgtgt ctcaccccca tcatccaatg gccttggccc ggtccctgtt    3060
tctgtgagtg tcgaccgagc ccatgtggat agcaacctgc agtttgagta catagatgac    3120
cctcgggtcc agcgcatcga gccagagtgg agcattgcca gtggccacac accctgacc    3180 atcacaggct tcaacctgga tgtcattcag gagccaagga tccgagtcaa attcaatggc    3240
aaagaatctg tcaatgtgtg taaagttgtg aacacaacca ccctcacctg cctggcaccc    3300
tctctgacca cggactaccg ccctggcctg gacactgtgg aacgcccaga tgagtttgga    3360
tttgtcttta caatgtcca atccttgcta atttacaacg acaccaagtt tatctactac    3420
cccaacccga cctttgaact gcttagccct actggagtct tggatcaaaa gccaggatcg    3480
cccatcattc tgaagggcaa aaacctctgc cctcctgcct ctggagggc caaactcaac    3540 tacactgtgc tcatcggaga taccccttgt gctgtcaccg tatctgagac ccagcttctc    3600
tgcgagcctc ccaacctcac cgggcagcac aaggtcatgg ttcacgtggg cgggatggtg    3660
ttctcgcctg gctcggtgag tgtcatctca gacagcttgc tgaccctgcc agccatcgtc    3720
agcatcgcgg ccggcggcag cctcctcctc atcatcgtca tcatcgtcct cattgcctac    3780
aagcgcaagt ctcgagaaaa tgacctcact ctcaagcggc tgcaaatgca gatggacaat    3840
ctggagtccc gtgtggcctt ggagtgcaag gaagcttttg ctgagctcca gacggatatc    3900
aatgagttga ccagtgacct ggaccgctca ggaatccctt acctggacta tcgtacctac    3960
gctatgcgag tcctgttccc gggcatcgag gaccaccccg tcctgcggga gctgaggta    4020 caaggaaacg ggcagcagca cgtggagaag gccctgaagc tctttgccca gctcatcaac    4080
```

```
aacaaggtgt tcctgctgac cttcatccgc accctggagc tgcagcgcag tttctccatg    4140
cgcgaccggg gcaacgtggc ttcgctcatc atgaccggcc tgcagggccg cctggaatat    4200
gccactgatg tcctcaagca gctgctctct gacctcatcg ataagaacct ggagaacaag    4260
aaccacccca gctgctact  ccggaggaca gagtctgtgg ctgaaaagat gctgaccaat    4320
tggttcgcct tcctcctgca caagttccta aaggagtgcg caggggagcc actcttcatg    4380
ctatactgtg ccatcaagca gcagatggag aagggcccca ttgatgccat cacgggcgag    4440
gcccgctact ccctgagcga ggacaagctc atccggcagc agatcgagta caagaccctg    4500
atcctgaact gcgtcaaccc tgacaacgag aacagtccag agatcccagt gaaggtgtta    4560
aactgtgaca ccatcacaca ggtcaaggag aagattcttg atgccgtgta taagaatgtg    4620
ccctattccc agcggccgag ggcagtggac atggacttgg agtggcgcca aggccggatc    4680
gcccgggtcg tgctgcaaga tgaggacatc accaccaaga ttgagggtga ctggaagcgg    4740
ctcaacacac tgatgcatta tcaggtgtca gacaggtcgg tggtggctct ggtcccaaa    4800 cagacctcct cctacaacat ccctgcctct gccagcatct cccggacgtc catcagcaga    4860
tacgactcct ccttcaggta tacgggcagc cccgacagcc tgcggtcccg gcccccgatg    4920
atcaccccag acctggaaag tggggtcaag gtgtggcatc tggtgaagaa ccatgaccac    4980
ggtgaccaga aggagggtga ccggggcagc aagatggtgt ccgagatcta cctgacccgg    5040
ctactggcca ccaagggcac cctgcagaag tttgtggacg acttgtttga daccttgttc    5100
agcactgtgc accggggcag cgctctcccc ctggccatca gtacatgtt  tgatttccta    5160 gatgagcagg cagacaggca cagcatccat gacacagatg tgcggcacac ctggaaaagc    5220
aactgcctcc ctctgcgctt ctgggtgaac gtgattaaga accccagtt  cgtgtttgac    5280 atccacaagg gcagcatcac ggacgcctgc ctctctgtgg tggcccagac cttcatggac    5340
tcttgttcaa cgtcagagca ccggctgggc aaggactccc cctccaacaa gctgctctat    5400
gccaaggaca tccccagcta caagagctgg gtggagagat actacgcaga catcgccaag    5460
ctcccagcca tcagtgacca ggacatgaat gcctacctcg ccgagcagtc ccgcctgcac    5520
gccgtggagt tcaacatgct gagtgccctc aatgagatct actcctatgt cagcaagtat    5580
agtgaggagc tcatcggggc cctagagcag gatgagcagg cacggcggca gcggctggct    5640
tataaggtgg agcagctcat taatgccatg tccattgaga gctga                   5685

<210> SEQ ID NO 42
<211> LENGTH: 2163
<212> TYPE: DNA
<213> ORGANISM: Human

<400> SEQUENCE: 42
atgccaccac cgtcagacat tgtcaaagtg gccattgagt ggccaggtgc taacgcccag      60
ctccttgaaa tcgaccagaa acggcccctg gcatccatta tcaaggaagt ttgtgatggg     120
tggtcgttgc caaacccaga gtattatacc ctccgttatg cagatggtcc tcagctgtac     180
atcaccgaac agactcgcag tgacattaag aatgggacaa tcttacaact ggctatctcc     240
ccgtcccggg ctgcacgcca gctgatggag aggacccagt catccaacat ggagacccgg     300
ctggatgcca tgaaggagct ggccaagctc tctgccgacg tgactttcgc tactgagttc     360
atcaacatgg atggcatcat tgtgctgaca aggctcgtgg aaagtggaac caagctcttg     420
tcccactaca gtgagatgct ggcattcacc ctgactgcct tcctagagct catggaccat     480
```

```
ggcattgtct cctgggacat ggtttcaatc acctttatta agcagattgc agggtatgtg      540
agccagccca tggtggacgt gtcaatcctt cagaggtccc tggccatcct ggagagcatg      600
gtcttgaaca gccagagtct gtaccagaag atagccgagg aaatcaccgt gggacagctc      660
atctcacacc tccaggtctc caaccaggag attcagacct acgccattgc actgattaat      720 gcacttttc tgaaggctcc tgaggacaaa cgacaggata tggcaaatgc atttgcacag      780
aagcatctcc ggtctataat cctgaatcat gtgatccgag ggaaccgccc catcaaaact      840
gagatggccc atcagctata tgtccttcaa gtcctaacct ttaaccttct ggaagaaagg      900
atgatgacca agatggaccc caatgaccag gctcaaaggg acatcatatt tgaactgagg      960
aggattgcat ttgacgcaga gtctgatcct agcaatgccc ctgggagtgg gaccgaaaaa     1020
cgcaaagcca tgtacacaaa ggactacaaa atgctgggat ttaccaacca catcaatcca     1080
gccatggact ttacccagac tcctcctgga atgctggcct tggacaacat gctgtacttg     1140
gctaaagtcc accaggacac ctacatccgg attgtcttgg agaacagtag ccgggaagac     1200
aaacatgaat gccccttttgg ccgcagtgcc attgagctca ccaaaatgct ctgtgaaatc     1260
ctgcaggttg ggaactacc aaatgaagga cgcaatgact accacccgat gttctttacc     1320
catgaccgag ccttttgaaga gctctttgga atctgcatcc agctgttgaa caagacctgg     1380
aaggagatga gggcaacagc agaggacttc aacaaggtta tgcaagtcgt ccgagagcaa     1440
atcactcgag ctttgccctc caaacccaac tctttggatc agttcaagag caaattgcgt     1500
agcctgagtt actctgagat tctacgactg cgccagtctg agaggatgag tcaggatgac     1560
ttccagtccc cgccaattgt ggagctgagg gagaagatcc agcccgagat ccttgagctg     1620
atcaagcagc agcgcctgaa ccggctctgt gagggcagca gcttccgaaa gattgggaac     1680
cgccgaaggc aagaacggtt ctggtactgc cggttggcac tgaaccacaa ggtccttcac     1740
tatggtgact ggatgacaa cccacaaggg gaggtgacat ttgaatccct gcaggagaaa     1800
attcctgttg cagacattaa ggccattgtc actgggaaag attgtcccca catgaaagag     1860
aaaagtgctc tgaaacagaa caaggaggtg ttggaattgg ccttctccat cctgtatgac     1920
cctgatgaga ccttaaactt catcgcacct aataaatatg agtactgcat ctggattgat     1980
ggcctcagtg cccttctggg gaaggacatg tccagtgagc tgaccaagag tgacctggac     2040
accctgctga gcatggagat gaagctgcgg ctccctggacc tggagaacat ccagattccc     2100
gaagccccac cccccatccc caaggagccc agcagctatg actttgtcta tcactatggc     2160
tga                                                                    2163

<210> SEQ ID NO 43
<211> LENGTH: 2163
<212> TYPE: DNA
<213> ORGANISM: Human

<400> SEQUENCE: 43
atgccaccac cgtcagacat tgtcaaagtg gccattgagt ggccaggtgc taacgcccag       60
ctccttgaaa tcgaccagaa acggcccctg gcatccatta tcaaggaagt ttgtgatggg      120
tggtcgttgc caaacccaga gtattatacc ctccgttatg cagatggtcc tcagctgtac      180
atcaccgaac agactcgcag tgacattaag aatgggacaa tcttacaact ggctatctcc      240
ccgtcccggg ctgcacgcca gctgatggag aggacccagt catccaacat ggagacccgg      300
ctggatgcca tgaaggagct ggccaagctc tctgccgacg tgactttcgc tactgagttc      360
atcaacatgg atggcatcat tgtgctgaca aggctcgtgg aaagtggaac caagctcttg      420
```

```
tcccactaca gtgagatgct ggcattcacc ctgactgcct tcctagagct catggaccat      480
ggcattgtct cctgggacat ggtttcaatc acctttatta agcagattgc agggtatgtg      540
agccagccca tggtggacgt gtcaatcctt cagaggtccc tggccatcct ggagagcatg      600
gtcttgaaca gccagagtct gtaccagaag atagccgagg aaatcaccgt gggacagctc      660
atctcacacc tccaggtctc caaccaggag attcagacct acgccattgc actgattaat      720 gcacttttc tgaaggctcc tgaggacaaa cgacaggata tggcaaatgc atttgcacag      780
aagcatctcc ggtctataat cctgaatcat gtgatccgag ggaaccgccc catcaaaact      840
gagatggccc atcagctata tgtccttcaa gtcctaacct taaccttct ggaagaaagg       900 atgatgacca agatggaccc caatgaccag gctcaaaggg acatcatatt tgaactgagg      960
aggattgcat ttgacgcaga gtctgatcct agcaatgccc ctgggagtgg gaccgaaaaa     1020
cgcaaagcca tgtacacaaa ggactacaaa atgctgggat taccaaccca catcaatcca     1080
gccatggact ttacccagac tcctcctgga atgctgcct tggacaacat gctgtacttg       1140
gctaaagtcc accaggacac ctacatccgg attgtcttgg agaacagtag ccgggaagac     1200
aaacatgaat gcccctttgg ccgcagtgcc attgagctca ccaaaatgct ctgtgaaatc     1260
ctgcaggttg ggaactacc aaatgaagga cgcaatgact accacccgat gttctttacc       1320
catgaccgag cctttgaaga gctctttgga atctgcatcc agctgttgaa caagacctgg     1380
aaggagatga gggcaacagc agaggacttc aacaaggtta tgcaagtcgt ccgagagcaa     1440
atcactcgag ctttgccctc caaacccaac tctttggatc agttcaagag caaattgcgt     1500
agcctgagtt actctgagat tctacgactg cgccagtctg agaggatgag tcaggatgac     1560
ttccagtccc cgccaattgt ggagctgagg gagaagatcc agcccgagat ccttgagctg     1620
atcaagcagc agcgcctgaa ccggctctgt gagggcagca gcttccgaaa gattgggaac     1680
cgccgaaggc aagaacggtt ctggtactgc cggttggcac tgaaccacaa ggtccttcac     1740
tatggtgact tggatgacaa cccacaaggg gaggtgcat ttgaatccct gcaggagaaa      1800
attcctgttg cagacattaa ggccattgtc actgggaaag attgtcccca catgaaagag     1860
aaaagtgctc tgaaacagaa caaggaggtg ttggaattgg ccttctccat cctgtatgac     1920
cctgatgaga ccttaaactt catcgcacct aataaatatg agtactgcat ctggattgat      1980
ggcctcagtg cccttctggg gaaggacatg tccagtgagc tgaccaagag tgacctggac     2040
accctgctga gcatggagat gaagctgcgg ctcctggacc tggagaacat ccagattccc     2100
gaagccccac cccccatccc caaggagccc agcagctatg actttgtcta tcactatggc     2160
tga                                                                    2163
```

<210> SEQ ID NO 44
<211> LENGTH: 1899
<212> TYPE: DNA
<213> ORGANISM: Human

<400> SEQUENCE: 44

```
atggagagga cccagtcatc caacatggag acccggctgg atgccatgaa ggagctggcc       60
aagctctctg ccgacgtgac tttcgctact gagttcatca acatggatgg catcattgtg      120
ctgacaaggc tcgtggaaag tggaaccaag ctcttgtccc actacagtga gatgctggca     180
ttcaccctga ctgccttcct agagctcatg gaccatggca ttgtctcctg ggacatggtt     240 tcaatcaccct ttattaagca gattgcaggg tatgtgagcc agcccatggt ggacgtgtca    300
```

| | |
|---|---|
| atccttcaga ggtccctggc catcctggag agcatggtct tgaacagcca gagtctgtac | 360 |
| cagaagatag ccgaggaaat caccgtggga cagctcatct cacacctcca ggtctccaac | 420 |
| caggagattc agacctacgc cattgcactg attaatgcac tttttctgaa ggctcctgag | 480 |
| gacaaacgac aggatatggc aaatgcattt gcacagaagc atctccggtc tataatcctg | 540 |
| aatcatgtga tccgagggaa ccgccccatc aaaactgaga tggcccatca gctatatgtc | 600 |
| cttcaagtcc taacctttaa ccttctggaa gaaggatga tgaccaagat ggaccccaat | 660 |
| gaccaggctc aaagggacat catatttgaa ctgaggagga ttgcatttga cgcagagtct | 720 |
| gatcctagca atgccctgg gagtgggacc gaaaaacgca aagccatgta cacaaaggac | 780 |
| tacaaaatgc tgggatttac caaccacatc aatccagcca tggactttac ccagactcct | 840 |
| cctggaatgc tggccttgga caacatgctg tacttggcta aagtccacca ggacacctac | 900 |
| atccggattg tcttggagaa cagtagccgg aagacaaac atgaatgccc ctttggccgc | 960 |
| agtgccattg agctcaccaa aatgctctgt gaaatcctgc aggttgggga actaccaaat | 1020 |
| gaaggacgca atgactacca cccgatgttc tttacccatg accgagcctt tgaagagctc | 1080 |
| tttggaatct gcatccagct gttgaacaag acctggaagg agatgagggc aacagcagag | 1140 |
| gacttcaaca aggttatgca agtcgtccga gagcaaatca ctcgagcttt gccctccaaa | 1200 |
| cccaactctt tggatcagtt caagagcaaa ttgcgtagcc tgagttactc tgagattcta | 1260 |
| cgactgcgcc agtctgagag gatgagtcag atgacttcc agtccccgcc aattgtggag | 1320 |
| ctgagggaga agatccagcc cgagatcctt gagctgatca gcagcagcg cctgaaccgg | 1380 |
| ctctgtgagg gcagcagctt ccgaaagatt gggaaccgcc gaaggcaaga acggttctgg | 1440 |
| tactgccggt tggcactgaa ccacaaggtc cttcactatg gtgacttgga tgacaaccca | 1500 |
| caaggggagg tgacatttga atccctgcag gagaaaattc ctgttgcaga cattaaggcc | 1560 |
| attgtcactg ggaaagattg tccccacatg aaagagaaaa gtgctctgaa acagaacaag | 1620 |
| gaggtgttgg aattggcctt ctccatcctg tatgaccctg atgagacctt aaacttcatc | 1680 |
| gcacctaata aatatgagta ctgcatctgg attgatggcc tcagtgccct tctggggaag | 1740 |
| gacatgtcca gtgagctgac caagagtgac ctggacaccc tgctgagcat ggagatgaag | 1800 |
| ctgcggctcc tggacctgga aacatccag attcccgaag ccccacccc catccccaag | 1860 |
| gagcccagca gctatgactt tgtctatcac tatggctga | 1899 |

<210> SEQ ID NO 45
<211> LENGTH: 2157
<212> TYPE: DNA
<213> ORGANISM: Human

<400> SEQUENCE: 45

| | |
|---|---|
| atgccaccac cgtcagacat tgtcaaagtg gccattgagt ggccaggtgc taacgcccag | 60 |
| ctccttgaaa tcgaccagaa acggcccctg gcatccatta tcaaggaagt ttgtgatggg | 120 |
| tggtcgttgc caaacccaga gtattatacc ctccgttatg cagatggtcc tcagctgtac | 180 |
| atcaccgaac agactcgcag tgacattaag aatgggacaa tcttacaact ggctatctcc | 240 |
| ccgtcccggg ctgcacgcca gctgatggag aggacccagt catccaacat ggagacccgg | 300 |
| ctggatgcca tgaaggagct ggccaagctc tctgccgacg tgactttcgc tactgagttc | 360 |
| atcaacatgg atggcatcat tgtgctgaca aggctcgtgg aaagtggaac caagctcttg | 420 |
| tcccatgaga tgctggcatt caccctgact gccttcctag agctcatgga ccatggcatt | 480 |
| gtctcctggg acatggtttc aatcaccttt attaagcaga ttgcagggta tgtgagccag | 540 |

| | | | |
|---|---|---|---|
| cccatggtgg | acgtgtcaat | ccttcagagg tccctggcca tcctggagag catggtcttg | 600 |
| aacagccaga | gtctgtacca | gaagatagcc gaggaaatca ccgtgggaca gctcatctca | 660 |
| cacctccagg | tctccaacca | ggagattcag acctacgcca ttgcactgat taatgcactt | 720 |
| tttctgaagg | ctcctgagga | caaacgacag gatatgcaa atgcatttgc acagaagcat | 780 |
| ctccggtcta | taatcctgaa | tcatgtgatc cgagggaacc gccccatcaa aactgagatg | 840 |
| gcccatcagc | tatatgtcct | tcaagtccta acctttaacc ttctggaaga aggatgatg | 900 |
| accaagatgg | accccaatga | ccaggctcaa aggacatca tatttgaact gaggaggatt | 960 |
| gcatttgacg | cagagtctga | tcctagcaat gcccctggga gtgggaccga aaaacgcaaa | 1020 |
| gccatgtaca | caaggacta | caaaatgctg ggatttacca accacatcaa tccagccatg | 1080 |
| gactttaccc | agactcctcc | tggaatgctg gccttgaca acatgctgta cttggctaaa | 1140 |
| gtccaccagg | acacctacat | ccggattgtc ttggagaaca gtagccggga agacaaacat | 1200 |
| gaatgcccct | ttggccgcag | tgccattgag ctcaccaaaa tgctctgtga atcctgcag | 1260 |
| gttggggaac | taccaaatga | aggacgcaat gactaccacc cgatgttctt tacccatgac | 1320 |
| cgagcctttg | aagagctctt | tggaatctgc atccagctgt tgaacaagac ctggaaggag | 1380 |
| atgagggcaa | cagcagagga | cttcaacaag gttatgcaag tcgtccgaga gcaaatcact | 1440 |
| cgagctttgc | cctccaaacc | caactctttg gatcagttca agagcaaatt gcgtagcctg | 1500 |
| agttactctg | agattctacg | actgcgccag tctgagagga tgagtcagga tgacttccag | 1560 |
| tccccgccaa | ttgtgggagct | gagggagaag atccagcccg agatccttga gctgatcaag | 1620 |
| cagcagcgcc | tgaaccggct | ctgtgagggc agcagcttcc gaaagattgg gaaccgccga | 1680 |
| aggcaagaac | ggttctggta | ctgccggttg gcactgaacc acaaggtcct tcactatggt | 1740 |
| gacttggatg | acaacccaca | aggggaggtg acatttgaat ccctgcagga gaaaattcct | 1800 |
| gttgcagaca | ttaaggccat | tgtcactggg aaagattgtc cccacatgaa agagaaaagt | 1860 |
| gctctgaaac | agaacaagga | ggtgttggaa ttggccttct ccatcctgta tgaccctgat | 1920 |
| gagaccttaa | acttcatcgc | acctaataaa tatgagtact gcatctggat tgatggcctc | 1980 |
| agtgcccttc | tggggaagga | catgtccagt gagctgacca gagtgacct ggacaccctg | 2040 |
| ctgagcatgg | agatgaagct | gcggctcctg gacctggaga acatccagat tcccgaagcc | 2100 |
| ccaccccca | tccccaagga | gcccagcagc tatgactttg tctatcacta tggctga | 2157 |

<210> SEQ ID NO 46
<211> LENGTH: 1392
<212> TYPE: DNA
<213> ORGANISM: Human

<400> SEQUENCE: 46

| | | | |
|---|---|---|---|
| atggcggcgc | tgagggcttt | gtgcggcttc cggggcgtcg cggcccaggt gctgcggcct | 60 |
| ggggctggag | tccgattgcc | gattcagccc agcagaggtg ttcggcagtg cagccagat | 120 |
| gtggaatggg | cacagcagtt | tggggagct gttatgtacc caagcaaaga aacagcccac | 180 |
| tggaagcctc | caccttggaa | tgatgtggac cctccaaagg acacaattgt gaagaacatt | 240 |
| accctgaact | tgggcccca | acacccagca gcgcatggtg tcctgcgact agtgatggaa | 300 |
| ttgagtgggg | agatggtgcg | gaagtgtgat cctcacatcg ggctcctgca ccgaggcact | 360 |
| gagaagctca | ttgaatacaa | gacctatctt caggcccttc catactttga ccggctagac | 420 |
| tatgtgtcca | tgatgtgtaa | cgaacaggcc tattctctag ctgtgggagaa gttgctaaac | 480 |

```
atccggcctc ctcctcgggc acagtggatc cgagtgctgt ttggagaaat cacacgtttg    540
ttgaaccaca tcatggctgt gaccacacat gccctggacc ttggggccat gaccccttc     600
ttctggctgt ttgaagaaag ggagaagatg tttgagttct acgagcgagt gtctggagcc    660
cgaatgcatg ctgcttatat ccggccagga ggagtgcacc aggacctacc ccttgggctt    720
atggatgaca tttatcagtt ttctaagaac ttctctcttc ggcttgatga gttggaggag    780
ttgctgacca acaataggat ctggcgaaat cggacaattg acattggggt tgtaacagca    840
gaagaagcac ttaactatgg ttttagtgga gtgatgcttc ggggctcagg catccagtgg    900
gacctgcgga agacccagcc ctatgatgtt tacgaccagg ttgagtttga tgttcctgtt    960
ggttctcgag gggactgcta tgataggtac ctgtgccggg tggaggagat gcgccagtcc   1020
ctgagaatta tcgcacagtg tctaaacaag atgcctcctg gggagatcaa ggttgatgat   1080
gccaaagtgt ctccacctaa gcgagcagag atgaagactt ccatggagtc actgattcat   1140
cactttaagt tgtatactga gggctaccaa gttcctccag gagccacata tactgccatt   1200
gaggctccca agggagagtt tggggtgtac ctggtgtctg atggcagcag ccgcccttat   1260
cgatgcaaga tcaaggctcc tggttttgcc catctggctg gtttggacaa gatgtctaag   1320
ggacacatgt tggcagatgt cgttgccatc ataggtaccc aagatattgt atttggagaa   1380
gtagatcggt ga                                                       1392
```

<210> SEQ ID NO 47
<211> LENGTH: 1392
<212> TYPE: DNA
<213> ORGANISM: Human

<400> SEQUENCE: 47

```
atggcggcgc tgagggcttt gtgcggcttc cggggcgtcg cggcccaggt gctgcggcct     60
ggggctggag tccgattgcc gattcagccc agcagaggtg ttcggcagtg cagccagat    120
gtggaatggg cacagcagtt tgggggagct gttatgtacc caagcaaaga aacagcccac   180
tggaagcctc caccttggaa tgatgtggac cctccaaagg acacaattgt gaagaacatt   240
accctgaact tgggccccca acacccagca gcgcatggtg tcctgcgact agtgatggaa   300
ttgagtgggg agatggtgcg gaagtgtgat cctcacatcg ggctcctgca ccgaggcact   360
gagaagctca ttgaatacaa gacctatctt caggcccttc catactttga ccggctagac   420
tatgtgtcca tgatgtgtaa cgaacaggcc tattctctag ctgtggagaa gttgctaaac   480
atccggcctc ctcctcgggc acagtggatc cgagtgctgt ttggagaaat cacacgtttg    540
ttgaaccaca tcatggctgt gaccacacat gccctggacc ttggggccat gaccccttc     600
ttctggctgt ttgaagaaag ggagaagatg tttgagttct acgagcgagt gtctggagcc    660
cgaatgcatg ctgcttatat ccggccagga ggagtgcacc aggacctacc ccttgggctt    720
atggatgaca tttatcagtt ttctaagaac ttctctcttc ggcttgatga gttggaggag    780
ttgctgacca acaataggat ctggcgaaat cggacaattg acattggggt tgtaacagca    840
gaagaagcac ttaactatgg ttttagtgga gtgatgcttc ggggctcagg catccagtgg    900
gacctgcgga agacccagcc ctatgatgtt tacgaccagg ttgagtttga tgttcctgtt    960
ggttctcgag gggactgcta tgataggtac ctgtgccggg tggaggagat gcgccagtcc   1020
ctgagaatta tcgcacagtg tctaaacaag atgcctcctg gggagatcaa ggttgatgat   1080
gccaaagtgt ctccacctaa gcgagcagag atgaagactt ccatggagtc actgattcat   1140
cactttaagt tgtatactga gggctaccaa gttcctccag gagccacata tactgccatt   1200
```

```
gaggctccca agggagagtt tggggtgtac ctggtgtctg atggcagcag ccgcccttat      1260
cgatgcaaga tcaaggctcc tggttttgcc catctggctg gtttggacaa gatgtctaag      1320
ggacacatgt tggcagatgt cgttgccatc ataggtaccc aagatattgt atttggagaa      1380
gtagatcggt ga                                                          1392

<210> SEQ ID NO 48
<211> LENGTH: 2139
<212> TYPE: DNA
<213> ORGANISM: Human

<400> SEQUENCE: 48
atggccgggg ggccgggccc gggggagccc gcagcccccg gcgcccagca cttcttgtac        60
gaggtgccgc cctgggtcat gtgccgcttc tacaaagtga tggacgccct ggagcccgcc       120
gactggtgcc agttcgccgc cctgatcgtg cgcgaccaga ccgagctgcg gctgtgcgag       180
cgctccggga gcgcacggc cagcgtcctg tggccctgga tcaaccgcaa cgcccgtgtg        240
gccgacctcg tgcacatcct cacgcacctg cagctgctcc gtgcgcggga catcatcaca       300
gcctggcacc ctcccgcccc gcttccgtcc ccaggcacca ctgccccgag gcccagcagc       360
atccctgcac ccgccgaggc cgaggcctgg agccccggga agttgccatc ctcagcctcc       420
accttcctct cccagctttt ccaggctccc agacccatt cagggcctga gctcggcctg        480
gtcccaagcc ctgcttccct gtggcctcca ccgccatctc cagcccctcc ttctaccaag       540
ccaggcccag agagctcagt gtccctcctg caggagcccg cccctttcc gttttgctgg        600 cccctctgtg agatttcccg gggcacccac aacttctcgg aggagctcaa gatcggggag       660
ggtggctttg gtgcgtgta ccgggcggtg atgaggaaca cggtgtatgc tgtgaagagg       720
ctgaaggaga acgctgacct ggagtggact gcagtgaagc agagcttcct gaccgaggtg       780
gagcagctgt ccaggtttcg tcacccaaac attgtggact tgctggctcta ctgtgctcag      840 aacggcttct actgcctggt gtacggcttc ctgcccaacg ctccctggga ggaccgtctc       900
cactgccaga cccaggcctg cccacctctc tcctggcctc agcgactgga catccttctg       960
ggtacagccc gggcaattca gtttctacat caggacagcc ccagcctcat ccatggagac      1020
atcaagagtt ccaacgtcct tctggatgag aggctgacac ccaagctggg agactttggc      1080
ctggcccggt tcagccgctt tgccgggtcc agccccagcc agagcagcat ggtggcccgg      1140
acacagacag tgcggggcac cctggcctac ctgcccgagg agtacatcaa gacgggaagg      1200
ctggctgtgg acacggacac cttcagcttt gggtggtag tgctagagac cttggctggt      1260
cagagggctg tgaagacgca cggtgccagg accaagtatc tgaaagacct ggtggaagag      1320
gaggctgagg aggctggagt ggcttttgaga agcacccaga gcacactgca agcaggtctg      1380
gctgcagatg cctgggctgc tcccatcgcc atgcagatct acaagaagca cctggacccc      1440
aggcccgggc cctgcccacc tgagctgggc ctgggcctgg ccagctggc tgctgctgc       1500 ctgcaccgcc gggccaaaag gaggcctcct atgacccagg tgtacgagag ctagagaag      1560 ctgcaggcag tggtggcggg ggtgcccggg cattcggagg ccgccagctg catccccct       1620 tccccgcagg agaactccta cgtgtccagc actggcagag cccacagtgg ggctgctcca      1680
tggcagcccc tggcagcgcc atcaggagcc agtgcccagg cagcagagca gctgcagaga      1740
ggccccaacc agcccgtgga gagtgacgag agcctaggcg cctctctgc tgccctgcgc      1800 tcctggcact tgactccaag ctgccctctg gacccagcac ccctcaggga ggccggctgt      1860
```

```
cctcagggg  acacggcagg  agaatcgagc  tggggggagtg  gcccaggatc  ccggcccaca    1920
gccgtggaag  gactggccct  tggcagctct  gcatcatcgt  cgtcagagcc  accgcagatt    1980
atcatcaacc  ctgcccgaca  aagatggtc   cagaagctgg  ccctgtacga  ggatggggcc    2040
ctggacagcc  tgcagctgct  gtcgtccagc  tccctcccag  gcttgggcct  ggaacaggac    2100
aggcaggggc  ccgaagaaag  tgatgaattt  cagagctga                             2139

<210> SEQ ID NO 49
<211> LENGTH: 2127
<212> TYPE: DNA
<213> ORGANISM: Human

<400> SEQUENCE: 49
atggccgggg  ggccgggccc  gggggagccc  gcagcccccg  gcgcccagca  cttcttgtac      60
gaggtgccgc  cctgggtcat  gtgccgcttc  tacaaagtga  tggacgccct  ggagcccgcc    120
gactggtgcc  agttcggtgg  gtggcggcgg  gctgccgggg  ggcgggaggc  gcgcgggctc    180
ctggcgccga  cgcctgacgc  ccccccgccc  gcagccgccc  tgatcgtgcg  cgaccagacc    240
gagctgcggc  tgtgcgagcg  ctccgggcag  cgcacggcca  gcgtcctgtg  gccctggatc    300
aaccgcaacg  cccgtgtggc  cgacctcgtg  cacatcctca  cgcacctgca  gctgctccgt    360
gcgcgggaca  tcatcacagc  ctggcaccct  cccgccccgc  ttccgtcccc  aggcaccact    420
gccccgaggc  ccagcagcat  ccctgcaccc  gccgaggccg  aggcctggag  cccccggaag    480
ttgccatcct  cagcctccac  cttcctctcc  ccagcttttc  caggctccca  gacccattca    540
gggcctgagc  tcggcctggt  cccaagccct  gcttccctgt  ggcctccacc  gccatctcca    600
gccccttctt  ctaccaagcc  aggcccagag  agctcagtgt  ccctcctgca  gggagcccgc    660 cccttttccgt  tttgctggcc  cctctgtgag  atttcccggg  gcacccacaa  cttctcggag    720
gagctcaaga  tcggggaggg  tggctttggg  tgcgtgtacc  gggcggtgat  gaggaacacg    780
gtgtatgctg  tgaagaggct  gaaggagaac  gctgacctgg  agtggactgc  agtgaagcag    840
agcttcctga  ccgaggtgga  gcagctgtcc  aggtttcgtc  acccaaacat  tgtggacttt    900
gctggctact  gtgctcagaa  cggcttctac  tgcctggtgt  acggcttcct  gcccaacggc    960
tccctggagg  accgtctcca  ctgccagacc  caggcctgcc  cacctctctc  ctggcctcag   1020
cgactggaca  tccttctggg  tacagcccgg  gcaattcagt  ttctacatca  ggacagcccc   1080
agcctcatcc  atggagacat  caagagttcc  aacgtccttc  tggatgagag  gctgacaccc   1140
aagctgggag  actttggcct  ggcccggttc  agccgctttg  ccgggtccag  ccccagccag   1200
agcagcatgg  tggcccggac  acagacagtg  cggggcaccc  tggcctacct  gcccgaggag   1260
tacatcaaga  cgggaaggct  ggctgtggac  acggacacct  tcagctttgg  ggtggtagtg   1320
ctagagacct  tggctggtca  gagggctgtg  aagacgcacg  gtgccaggac  caagtatctg   1380
aaagacctgg  tggaagagga  ggctgaggag  gctggagtgg  ctttgagaag  cacccagagc   1440
acactgcaag  caggtctggc  tgcagatgcc  tgggctgctc  ccatcgccat  gcagatctac   1500
aagaagcacc  tggaccccag  gcccgggccc  tgcccacctg  agctgggcct  gggcctgggc   1560
cagctggcct  gctgctgcct  gcaccgccgg  gccaaaagga  ggcctcctat  gacccaggag   1620
aactcctacg  tgtccagcac  tggcagagcc  cacagtgggg  ctgctccatg  gcagcccctg   1680
gcagcgccat  caggagccag  tgccaggca  gcagagcagc  tgcagagagg  ccccaaccag   1740
cccgtggaga  gtgacgagag  cctaggcggc  ctctctgctg  ccctgcgctc  ctggcacttg   1800
actccaagct  gccctctgga  cccagcaccc  ctcagggagg  ccggctgtcc  tcaggggac   1860
```

```
acggcaggag aatcgagctg ggggagtggc ccaggatccc ggcccacagc cgtggaagga    1920
ctggcccttg gcagctctgc atcatcgtcg tcagagccac cgcagattat catcaaccct    1980
gcccgacaga agatggtcca gaagctggcc ctgtacgagg atggggccct ggacagcctg    2040
cagctgctgt cgtccagctc cctcccaggc ttgggcctgg aacaggacag gcaggggccc    2100
gaagaaagtg atgaatttca gagctga                                        2127

<210> SEQ ID NO 50
<211> LENGTH: 1902
<212> TYPE: DNA
<213> ORGANISM: Human

<400> SEQUENCE: 50
atggccgggg ggccgggccc ggggagccc gcagccccg cgcccagca cttcttgtac       60 gaggtgccgc cctgggtcat gtgccgcttc tacaaagtga tggacgccct ggagcccgcc   120
gactggtgcc agttcgccgc cctgatcgtg cgcgaccaga ccgagctgcg gctgtgcgag   180
cgctccgggc agcgcacggc cagcgtcctg tggccctgga tcaaccgcaa cgcccgtgtg   240
gccgacctcg tgcacatcct cacgcacctg cagctgctcc gtgcgcggga catcatcaca   300
gcctggcacc ctcccgcccc gcttccgtcc ccaggcacca ctgccccgag gcccagcagc   360
atccctgcac ccgccgaggc cgaggcctgg agccccgga agttgccatc ctcagcctcc    420
accttcctct ccccagcttt tccaggctcc cagacccatt cagggcctga gctcggcctg    480
gtcccaagcc ctgcttccct gtggcctcca ccgccatctc cagccccttc ttctaccaag   540
ccaggcccag agagctcagt gtccctcctg cagggagccc gccccttttcc gttttgctgg   600 ccctctgtg agatttcccg ggcacccac aacttctcgg aggagctcaa gatcggggag    660
ggtggctttg ggtgcgtgta ccgggcggtg atgaggaaca cggtgtatgc tgtgaagagg    720
ctgaaggaga cgctgacct ggagtggact gcagtgaagc agagcttcct gaccgaggtg    780
gagcagctgt ccaggtttcg tcacccaaac attgtggact ttgctggcta ctgtgctcag    840
aacggcttct actgcctggt gtacggcttc ctgcccaacg ctccctgga ggaccgtctc    900 cactgccaga cccaggcctg cccacctctc tcctggcctc agcgactgga catccttctg    960
ggtacagccc gggcaattca gtttctacat caggacagcc ccagcctcat ccatggagac   1020
atcaagagtt ccaacgtcct tctggatgag aggctgacac ccaagctggg agactttggc   1080
ctggcccggt tcagccgctt tgccgggtcc agcccagcc agagcagcat ggtggcccgg   1140
acacagacag tgcggggcac cctggcctac ctgcccgagg agtacatcaa gacgggaagg   1200
ctggctgtgg acacggacac cttcagcttt gggtggtag tgctagagac cttggctggt   1260
cagagggctg tgaagacgca cggtgccagg accaagtatc tggtgtacga gaggctagag   1320
aagctgcagg cagtggtggc gggggtgccc gggcattcgg aggccgccag ctgcatcccc    1380
ccttccccgc aggagaactc ctacgtgtcc agcactggca gagcccacag tggggctgct   1440
ccatggcagc ccctggcagc gccatcagga gccagtgccc aggcagcaga gcagctgcag   1500
agaggcccca accagcccgt ggagagtgac gagagcctag gcggcctctc tgctgccctg    1560
cgctcctggc acttgactcc aagctgccct ctggacccag cacccctcag ggaggccggc   1620
tgtcctcagg gggacacggc aggagaatcg agctggggga gtggcccagg atcccggccc   1680
acagccgtgg aaggactggc ccttggcagc tctgcatcat cgtcgtcaga gccaccgcag   1740
attatcatca accctgcccg acagaagatg gtccagaagc tggccctgta cgaggatggg   1800
```

| | |
|---|---|
| gccctggaca gcctgcagct gctgtcgtcc agctccctcc caggcttggg cctggaacag | 1860 |
| gacaggcagg ggcccgaaga aagtgatgaa tttcagagct ga | 1902 |

<210> SEQ ID NO 51
<211> LENGTH: 2082
<212> TYPE: DNA
<213> ORGANISM: Human

<400> SEQUENCE: 51

| | |
|---|---|
| atggccgggg ggccgggccc gggggagccc gcagccccg gcgcccagca cttcttgtac | 60 |
| gaggtgccgc cctgggtcat gtgccgcttc tacaaagtga tggacgccct ggagcccgcc | 120 |
| gactggtgcc agttcggtgg gtggcggcgg gctgccgggg ggcgggaggc gcgcgggctc | 180 |
| ctggcgccga cgcctgacgc cccccgcccc gcagccgccc tgatcgtgcg cgaccagacc | 240 |
| gagctgcggc tgtgcgagcg ctccgggcag cgcacggcca cgtcctgtg ccctggatc | 300 |
| aaccgcaacg cccgtgtggc cgacctcgtg cacatcctca cgcacctgca gctgctccgt | 360 |
| gcgcgggaca tcatcacagc ctggcaccct cccgccccgc ttccgtcccc aggcaccact | 420 |
| gccccgaggc ccagcagcat ccctgcaccc gccgaggccg aggcctggag ccccggaag | 480 |
| ttgccatcct cagcctccac cttcctctcc ccagcttttc caggctccca gacccattca | 540 |
| gggcctgagc tcggcctggt cccaagccct gcttccctgt ggcctccacc gccatctcca | 600 |
| gccccttctt ctaccaagcc aggcccagag agctcagtgt ccctcctgca gggagcccgc | 660 |
| cccttccgt tttgctggcc cctctgtgag atttcccggg gcacccacaa cttctcggag | 720 |
| gagctcaaga tcggggaggg tggctttggg tgcgtgtacc gggcggtgat gaggaacacg | 780 |
| gtgtatgctg tgaagaggct gaaggagaac gctgacctgg agtggactgc agtgaagcag | 840 |
| agcttcctga ccgaggtgga gcagctgtcc aggtttcgtc acccaaacat tgtggacttt | 900 |
| gctggctact gtgctcagaa cggcttctac tgcctggtgt acggcttcct gcccaacggc | 960 |
| tccctggagg accgtctcca ctgccagacc caggcctgcc cacctctctc ctggcctcag | 1020 |
| cgactggaca tccttctggg tacagcccgg gcaattcagt ttctacatca ggacagcccc | 1080 |
| agcctcatcc atggagacat caagagttcc aacgtccttc tggatgagag gctgacaccc | 1140 |
| aagctgggag actttggcct ggcccggttc agccgctttg ccgggtccag ccccagccag | 1200 |
| agcagcatgt ggcccggac acagacagtg cggggcaccc tggcctacct gcccgaggag | 1260 |
| tacatcaaga cgggaaggct ggctgtggac acggacacct tcagctttgg ggtggtagtg | 1320 |
| ctagagacct tggctggtca gagggctgtg aagacgcacg tgccaggac caagtatctg | 1380 |
| aaagacctgg tggaagagga ggctgaggag gctggagtgg ctttgagaag cacccagagc | 1440 |
| acactgcaag caggtctggc tgcagatgcc tgggctgctc ccatcgccat gcagatctac | 1500 |
| aagaagcacc tgggccagct ggcctgctgc tgcctgcacc gccgggccaa aaggaggcct | 1560 |
| cctatgaccc aggagaactc ctacgtgtcc agcactggca gagcccacag tggggctgct | 1620 |
| ccatggcagc ccctggcagc gccatcagga gccagtgccc aggcagcaga gcagctgcag | 1680 |
| agaggcccca accagcccgt ggagagtgac gagagcctag cggcctctc tgctgccctg | 1740 |
| cgctcctggc acttgactcc aagctgccct ctggacccag cacccctcag ggaggccggc | 1800 |
| tgtcctcagg gggacacggc aggagaatcg agctggggga gtggcccagg atcccggccc | 1860 |
| acagccgtgg aaggactggc ccttggcagc tctgcatcat cgtcgtcaga gccaccgcag | 1920 |
| attatcatca accctgcccg acagaagatg gtccagaagc tggcccctgta cgaggatggg | 1980 |
| gccctggaca gcctgcagct gctgtcgtcc agctccctcc caggcttggg cctggaacag | 2040 |

```
gacaggcagg ggcccgaaga aagtgatgaa tttcagagct ga            2082
```

<210> SEQ ID NO 52
<211> LENGTH: 2049
<212> TYPE: DNA
<213> ORGANISM: Human

<400> SEQUENCE: 52

```
atggccgggg ggccgggccc ggggagccc gcagccccg gcgcccagca cttcttgtac      60
gaggtgccgc cctgggtcat gtgccgcttc tacaaagtga tggacgccct ggagcccgcc    120
gactggtgcc agttcgccgc cctgatcgtg cgcgaccaga ccgagctgcg gctgtgcgag    180
cgctccgggc agcgcacggc cagcgtcctg tggccctgga tcaaccgcaa cgcccgtgtg    240
gccgacctcg tgcacatcct cacgcacctg cagctgctcc gtgcgcggga catcatcaca    300
gcctggcacc ctcccgcccc gcttccgtcc ccaggcacca ctgccccgag gcccagcagc    360
atccctgcac ccgccgaggc cgaggcctgg agccccgga agttgccatc ctcagcctcc    420
accttcctct ccccagcttt tccaggctcc cagacccatt cagggcctga gctcggcctg    480
gtcccaagcc ctgcttccct gtggcctcca ccgccatctc cagcccttc ttctaccaag    540
ccaggcccag agagctcagt gtccctcctg cagggagccc gcccctttcc gttttgctgg    600
cccctctgtg agatttcccg gggcacccac aacttctcgg aggagctcaa gatcggggag    660
ggtggctttg ggtgcgtgta ccgggcggtg atgaggaaca cggtgtatgc tgtgaagagg    720
ctgaaggaga cgctgacct ggagtggact gcagtgaagc agagcttcct gaccgaggtg    780
gagcagctgt ccaggtttcg tcacccaaac attgtggact ttgctggcta ctgtgctcag    840
aacggcttct actgcctggt gtacggcttc tgcccaacg gctccctgga ggaccgtctc    900
cactgccaga cccaggcctg cccacctctc tcctggcctc agcgactgga catccttctg    960
ggtacagccc gggcaattca gtttctacat caggacagcc ccagcctcat ccatggagac   1020
atcaagagtt ccaacgtcct tctggatgag aggctgacac ccaagctggg agactttggc   1080
ctggcccggt tcagccgctt tgccgggtcc agccccagcc agagcagcat ggtggcccgg   1140
acacagacag tgcggggcac cctggcctac ctgcccgagg agtacatcaa gacgggaagg   1200
ctggctgtgg acacggacac cttcagcttt gggtggtag tgctagagac cttggctggt   1260
cagagggctg tgaagacgca cggtgccagg accaagtatc tgaaagacct ggtggaagag   1320
gaggctgagg aggctggagt ggctttgaga agcacccaga gcacactgca agcaggtctg   1380
gctgcagatg cctgggctgc tcccatcgcc atgcagatct acaagaagca cctgaccccc   1440
aggcccgggc cctgcccacc tgagctgggc ctgggcctgg ccagctggc tgctgctgc    1500
ctgcaccgcc gggccaaaag gaggcctcct atgacccagg agaactccta cgtgtccagc   1560
actggcagag cccacagtgg ggctgctcca tggcagcccc tggcagcgcc atcaggagcc   1620
agtgcccagc agcagagca gctgcagaga ggcccaacc agcccgtgga gagtgacgag   1680
agcctaggcg gcctctctgc tgccctgcgc tcctggcact tgactccaag ctgccctctg   1740
gacccagcac ccctcaggga ggccggctgt cctcaggggg acacggcagg agaatcgagc   1800
tgggggagtg gcccaggatc ccggcccaca gccgtggaag gactggccct tggcagctct   1860
gcatcatcgt cgtcagagcc accgcagatt atcatcaacc tgcccgaca gaagatggtc   1920
cagaagctgg ccctgtacga ggatgggcc ctggacagcc tgcagctgct gtcgtccagc   1980
tcctcccag gcttgggcct ggaacaggac aggcaggggc ccgaagaaag tgatgaattt   2040
``` cagagctga                                                             2049

<210> SEQ ID NO 53
<211> LENGTH: 423
<212> TYPE: DNA
<213> ORGANISM: Human

<400> SEQUENCE: 53
atggcggcca tcccctccag cggctcgctc gtggccaccc acgactacta ccggcgccgc      60
ctgggttcca cttccagcaa cagctcctgc agcagtaccg agtgccccgg ggaagccatt     120
ccccaccccc caggtgagtg caggatcgcc cctttctccc ccgctcctc caggagctgg     180 cagcatcaag accccacttc gcttctctca ggtctcccca aggctgaccc gggtcattgg     240
tgggccagct tcttttttcgg gaagtccacc ctcccgttca tggccacggt gttggagtcc     300
gcagagcact cggaacctcc ccaggcctcc agcagcatga ccgcctgtgg cctggctcgg     360
gacgccccga ggaagcagcc cggcggtcag tccagcacag ccagcgctgg gccccgtcc     420 tga                                                                    423

<210> SEQ ID NO 54
<211> LENGTH: 213
<212> TYPE: DNA
<213> ORGANISM: Human

<400> SEQUENCE: 54
atggcggcca tcccctccag cggctcgctc gtggccaccc acgactacta ccggcgccgc      60
ctgggttcca cttccagcaa cagctcctgc agcagtaccg agtgccccgg ggaagccatt     120
ccccaccccc caggtctccc caaggctgac ccgggtcatt ggtgggccag cttcttttttc     180 gggaagtcca ccctcccacc ccccaccctg taa                                   213

<210> SEQ ID NO 55
<211> LENGTH: 345
<212> TYPE: DNA
<213> ORGANISM: Human

<400> SEQUENCE: 55
atggcggcca tcccctccag cggctcgctc gtggccaccc acgactacta ccggcgccgc      60
ctgggttcca cttccagcaa cagctcctgc agcagtaccg agtgccccgg ggaagccatt     120
ccccaccccc caggtctccc caaggctgac ccgggtcatt ggtgggccag cttcttttttc     180 gggaagtcca ccctcccgtt catggccacg gtgttggagt ccgcagagca ctcggaacct     240
ccccaggcct ccagcagcat gaccgcctgt ggcctggctc gggacgcccc gaggaagcag     300
cccggcggtc agtccagcac agccagcgct gggccccgt cctga                      345

<210> SEQ ID NO 56
<211> LENGTH: 1203
<212> TYPE: DNA
<213> ORGANISM: Human

<400> SEQUENCE: 56
atggaggacg gcgtctatga acccccagac ctgactccgg aggagcggat ggagctggag      60
aacatccggc ggcggaagca ggagctgctg gtggagattc agcgcctgcg ggaggagctc     120
agtgaagcca tgagcgaggt ggaggggctg gaggccaatg agggcagtaa gaccttgcaa     180
cggaaccgga gatggcaat gggcaggaag aagttcaaca tggaccccaa gaggggatc      240 cagttcttgg tggagaatga actgctgcag aacacacccg aggagatcgc ccgcttcctg     300

-continued

```
tacaagggcg aggggctgaa caagacagcc atcggggact acctggggga gagggaagaa    360
ctgaacctgg cagtgctcca tgcttttgtg gatctgcatg agttcaccga cctcaatctg    420
gtgcaggccc tcaggcagtt tctatggagc tttcgcctac ccggagaggc cagaaaatt     480 gaccggatga tggaggcctt cgcccagcga tactgcctgt gcaaccctgg ggttttccag    540
tccacagaca cgtgctatgt gctgtccttc gccgtcatca tgctcaacac cagtctccac    600
aatcccaatg tccgggacaa gccgggcctg agcgctttg tggccatgaa ccggggcatc     660
aacgagggcg ggacctgcc tgaggagctg ctcaggaacc tgtacgacag catccgaaat     720
gagcccttca agattcctga ggatgacggg aatgacctga cccacacctt cttcaacccg    780
gaccgggagg gctggctcct gaagctgggt aggggccggg tgaagacgtg gaagcggcgc    840
tggtttatcc tcacagacaa ctgcctctac tactttgagt acaccacgga caaggagccc    900
cgaggaatca tcccctgga gaatctgagc atccgagagg tggacgaccc ccggaaaccg     960
aactgctttg aactttacat ccccaacaac aaggggcagc tcatcaaagc ctgcaaaact   1020
gaggcggacg gccgagtggt ggagggaaac cacatggtgt accggatctc ggcccccacg   1080
caggaggaga aggacgagtg gatcaagtcc atccaggcgg ctgtgagtgt ggacccttc    1140 tatgagatgc tggcagcgag aaagaagcgg atttcagtca gaagaagca ggagcagccc   1200 tga                                                                  1203
```

<210> SEQ ID NO 57
<211> LENGTH: 1200
<212> TYPE: DNA
<213> ORGANISM: Human

<400> SEQUENCE: 57

```
atggaggacg gcgtctatga accccagac ctgactccgg aggagcggat ggagctggag     60
aacatccggc ggcggaagca ggagctgctg gtggagattc agcgcctgcg ggaggagctc   120
agtgaagcca tgagcgaggt ggaggggctg gaggccaatg agggcagtaa gaccttgcaa   180
cggaaccgga agatggcaat gggcaggaag aagttcaaca tggaccccaa gaaggggatc    240
cagttcttgg tggagaatga actgctgcag aacacacccg aggagatcgc ccgcttcctg   300
tacaagggcg aggggctgaa caagacagcc atcggggact acctggggga gagggaagaa   360
ctgaacctgg cagtgctcca tgcttttgtg gatctgcatg agttcaccga cctcaatctg   420
gtgcaggccc tcaggcagtt tctatggagc tttcgcctac ccggagaggc cagaaaatt    480 gaccggatga tggaggcctt cgcccagcga tactgcctgt gcaaccctgg ggttttccag   540
tccacagaca cgtgctatgt gctgtccttc gccgtcatca tgctcaacac cagtctccac   600
aatcccaatg tccgggacaa gccgggcctg agcgctttg tggccatgaa ccggggcatc    660
aacgagggcg ggacctgcc tgaggagctg ctcaggaacc tgtacgacag catccgaaat    720
gagcccttca agattcctga ggatgacggg aatgacctga cccacacctt cttcaacccg   780
gaccgggagg gctggctcct gaagctgggg ggccgggtga agacgtggaa gcggcgctgg   840
tttatcctca cagacaactg cctctactac tttgagtaca ccacggacaa ggagccccga   900
ggaatcatcc ccctgagaa tctgagcatc cgagaggtg acgaccccg gaaaccgaac      960 tgctttgaac tttacatccc caacaacaag gggcagctca tcaaagcctg caaaactgag  1020
gcggacggcc gagtggtgga gggaaaccac atggtgtacc ggatctcggc ccccacgcag  1080
gaggagaagg acgagtggat caagtccatc caggcggctg tgagtgtgga ccccttctat  1140
```
gagatgctgg cagcgagaaa gaagcggatt tcagtcaaga agaagcagga gcagccctga   1200

<210> SEQ ID NO 58
<211> LENGTH: 498
<212> TYPE: DNA
<213> ORGANISM: Human

<400> SEQUENCE: 58
atggtcaacc ccaccgtgtt cttcgacatt gccgtcgacg gcgagccctt gggccgcgtc    60
tcctttgagc tgtttgcaga caaggtccca agacagcag aaaattttcg tgctctgagc    120
actggagaga aaggatttgg ttataagggt tcctgctttc acagaattat tccaggttt    180 atgtgtcagg gtggtgactt cacacgccat aatggcactg gtggcaagtc catctatggg    240
gagaaatttg aagatgagaa cttcatccta aagcatacag gtcctggcat cttgtccatg    300
gcaaatgctg gacccaacac aaatggatcc cagttttttca tctgcactgc caagactgag    360
tggttggatg gcaagcatgt ggtgtttggc aaagtgaaag aaggcatgaa tattgtggag    420
gccatggagc gctttgggtc caggaatggc aagaccagca gaagatcac cattgctgac    480 tgtggacaac tcgaataa                                                498

<210> SEQ ID NO 59
<211> LENGTH: 218
<212> TYPE: PRT
<213> ORGANISM: Human

<400> SEQUENCE: 59

Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Asn Leu Ser Phe Ile Glu Thr Ser Ala Leu Asp Ser Thr Asn
145                 150                 155                 160

Val Glu Glu Ala Phe Lys Asn Ile Leu Thr Glu Ile Tyr Arg Ile Val
                165                 170                 175

Ser Gln Lys Gln Ile Ala Asp Arg Ala Ala His Asp Glu Ser Pro Gly
            180                 185                 190

Asn Asn Val Val Asp Ile Ser Val Pro Pro Thr Thr Asp Gly Gln Lys
        195                 200                 205

Pro Asn Lys Leu Gln Cys Cys Gln Asn Leu
    210                 215

```
<210> SEQ ID NO 60
<211> LENGTH: 589
<212> TYPE: PRT
<213> ORGANISM: Human

<400> SEQUENCE: 60

Met Ala Ala Asp Gly Asp Asp Ser Leu Tyr Pro Ile Ala Val Leu
1               5                   10                  15

Ile Asp Glu Leu Arg Asn Glu Asp Val Gln Leu Arg Leu Asn Ser Ile
            20                  25                  30

Lys Lys Leu Ser Thr Ile Ala Leu Ala Leu Gly Val Glu Arg Thr Arg
        35                  40                  45

Ser Glu Leu Leu Pro Phe Leu Thr Asp Thr Ile Tyr Asp Glu Asp Glu
    50                  55                  60

Val Leu Leu Ala Leu Ala Glu Gln Leu Gly Thr Phe Thr Thr Leu Val
65                  70                  75                  80

Gly Gly Pro Glu Tyr Val His Cys Leu Leu Pro Pro Leu Glu Ser Leu
                85                  90                  95

Ala Thr Val Glu Glu Thr Val Val Arg Asp Lys Ala Val Glu Ser Leu
            100                 105                 110

Arg Ala Ile Ser His Glu His Ser Pro Ser Asp Leu Glu Ala His Phe
        115                 120                 125

Val Pro Leu Val Lys Arg Leu Ala Gly Gly Asp Trp Phe Thr Ser Arg
    130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ala Ser Lys Leu Gly Glu Phe
            180                 185                 190

Ala Lys Val Leu Glu Leu Asp Asn Val Lys Ser Glu Ile Ile Pro Met
        195                 200                 205

Phe Ser Asn Leu Ala Ser Asp Glu Gln Asp Ser Val Arg Leu Leu Ala
    210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255

Trp Arg Val Arg Tyr Met Val Ala Asp Lys Phe Thr Glu Leu Gln Lys
            260                 265                 270

Ala Val Gly Pro Glu Ile Thr Lys Thr Asp Leu Val Pro Ala Phe Gln
        275                 280                 285

Asn Leu Met Lys Asp Cys Glu Ala Glu Val Arg Ala Ala Ala Ser His
    290                 295                 300

Lys Val Lys Glu Phe Cys Glu Asn Leu Ser Ala Asp Cys Arg Glu Asn
305                 310                 315                 320

Val Ile Met Ser Gln Ile Leu Pro Cys Ile Lys Glu Leu Val Ser Asp
                325                 330                 335

Ala Asn Gln His Val Lys Ser Ala Leu Ala Ser Val Ile Met Gly Leu
            340                 345                 350

Ser Pro Ile Leu Gly Lys Asp Asn Thr Ile Glu His Leu Leu Pro Leu
        355                 360                 365

Phe Leu Ala Gln Leu Lys Asp Glu Cys Pro Glu Val Arg Leu Asn Ile
    370                 375                 380
```

```
Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
            405                 410                 415

Trp Arg Val Arg Leu Ala Ile Ile Glu Tyr Met Pro Leu Leu Ala Gly
                420                 425                 430

Gln Leu Gly Val Glu Phe Phe Asp Glu Lys Leu Asn Ser Leu Cys Met
            435                 440                 445

Ala Trp Leu Val Asp His Val Tyr Ala Ile Arg Glu Ala Ala Thr Ser
450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
                500                 505                 510

Gly Gln Asp Ile Thr Thr Lys His Met Leu Pro Thr Val Leu Arg Met
            515                 520                 525

Ala Gly Asp Pro Val Ala Asn Val Arg Phe Asn Val Ala Lys Ser Leu
            530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
                565                 570                 575

Tyr Phe Ala Gln Glu Ala Leu Thr Val Leu Ser Leu Ala
                580                 585

<210> SEQ ID NO 61
<211> LENGTH: 509
<212> TYPE: PRT
<213> ORGANISM: Human

<400> SEQUENCE: 61

Met Arg Thr Phe Ser Phe Ala Ser Thr Ala Ser Arg Ser Cys Pro Pro
1               5                   10                  15

Ser Pro Trp Pro Leu Gly Leu Lys Gly Pro Glu Val Ser Phe Cys Leu
                20                  25                  30

Ser Leu Gln Ile Pro Ser Met Met Lys Met Arg Ser Ser Trp Pro Trp
            35                  40                  45

Gln Asn Ser Trp Glu Pro Ser Leu Pro Trp Trp Glu Ala Gln Ser Thr
        50                  55                  60

Cys Thr Ala Cys Cys Leu Phe Ser Val Cys Tyr Pro Arg Val Ser Ser
65                  70                  75                  80

Ala Val Lys Ala Glu Leu Arg Gln Tyr Phe Arg Asn Leu Cys Ser Asp
                85                  90                  95

Asp Thr Pro Met Val Arg Arg Ala Ala Ala Ser Lys Leu Gly Glu Phe
                100                 105                 110

Ala Lys Val Leu Glu Leu Asp Asn Val Lys Ser Glu Ile Ile Pro Met
            115                 120                 125

Phe Ser Asn Leu Ala Ser Asp Glu Gln Asp Ser Val Arg Leu Leu Ala
        130                 135                 140

Val Glu Ala Cys Val Asn Ile Ala Gln Leu Leu Pro Gln Glu Asp Leu
145                 150                 155                 160

Glu Ala Leu Val Met Pro Thr Leu Arg Gln Ala Ala Glu Asp Lys Ser
                165                 170                 175
```

```
Trp Arg Val Arg Tyr Met Val Ala Asp Lys Phe Thr Glu Leu Gln Lys
            180                 185                 190

Ala Val Gly Pro Glu Ile Thr Lys Thr Asp Leu Val Pro Ala Phe Gln
            195                 200                 205

Asn Leu Met Lys Asp Cys Glu Ala Glu Val Arg Ala Ala Ser His
            210                 215                 220

Lys Val Lys Glu Phe Cys Glu Asn Leu Ser Ala Asp Cys Arg Glu Asn
225                 230                 235                 240

Val Ile Met Ser Gln Ile Leu Pro Cys Ile Lys Glu Leu Val Ser Asp
                245                 250                 255

Ala Asn Gln His Val Lys Ser Ala Leu Ala Ser Val Ile Met Gly Leu
            260                 265                 270

Ser Pro Ile Leu Gly Lys Asp Asn Thr Ile Glu His Leu Leu Pro Leu
            275                 280                 285

Phe Leu Ala Gln Leu Lys Asp Glu Cys Pro Glu Val Arg Leu Asn Ile
            290                 295                 300

Ile Ser Asn Leu Asp Cys Val Asn Glu Val Ile Gly Ile Arg Gln Leu
305                 310                 315                 320

Ser Gln Ser Leu Leu Pro Ala Ile Val Glu Leu Ala Glu Asp Ala Lys
                325                 330                 335

Trp Arg Val Arg Leu Ala Ile Ile Glu Tyr Met Pro Leu Leu Ala Gly
            340                 345                 350

Gln Leu Gly Val Glu Phe Phe Asp Glu Lys Leu Asn Ser Leu Cys Met
            355                 360                 365

Ala Trp Leu Val Asp His Val Tyr Ala Ile Arg Glu Ala Ala Thr Ser
            370                 375                 380

Asn Leu Lys Lys Leu Val Glu Lys Phe Gly Lys Glu Trp Ala His Ala
385                 390                 395                 400

Thr Ile Ile Pro Lys Val Leu Ala Met Ser Gly Asp Pro Asn Tyr Leu
                405                 410                 415

His Arg Met Thr Thr Leu Phe Cys Ile Asn Val Leu Ser Glu Val Cys
            420                 425                 430

Gly Gln Asp Ile Thr Thr Lys His Met Leu Pro Thr Val Leu Arg Met
            435                 440                 445

Ala Gly Asp Pro Val Ala Asn Val Arg Phe Asn Val Ala Lys Ser Leu
            450                 455                 460

Gln Lys Ile Gly Pro Ile Leu Asp Asn Ser Thr Leu Gln Ser Glu Val
465                 470                 475                 480

Lys Pro Ile Leu Glu Lys Leu Thr Gln Asp Gln Asp Val Asp Val Lys
                485                 490                 495

Tyr Phe Ala Gln Glu Ala Leu Thr Val Leu Ser Leu Ala
            500                 505

<210> SEQ ID NO 62
<211> LENGTH: 876
<212> TYPE: PRT
<213> ORGANISM: Human

<400> SEQUENCE: 62

Met Glu Leu Ile Thr Ile Leu Glu Lys Thr Val Ser Pro Asp Arg Leu
1               5                   10                  15

Glu Leu Glu Ala Ala Gln Lys Phe Leu Glu Arg Ala Ala Val Glu Asn
            20                  25                  30

Leu Pro Thr Phe Leu Val Glu Leu Ser Arg Val Leu Ala Asn Pro Gly
```

```
            35                  40                  45
Asn Ser Gln Val Ala Arg Val Ala Ala Gly Leu Gln Ile Lys Asn Ser
 50                  55                  60

Leu Thr Ser Lys Asp Pro Asp Ile Lys Ala Gln Tyr Gln Gln Arg Trp
 65                  70                  75                  80

Leu Ala Ile Asp Ala Asn Ala Arg Arg Glu Val Lys Asn Tyr Val Leu
                 85                  90                  95

Gln Thr Leu Gly Thr Glu Thr Tyr Arg Pro Ser Ser Ala Ser Gln Cys
                100                 105                 110

Val Ala Gly Ile Ala Cys Ala Glu Ile Pro Val Asn Gln Trp Pro Glu
                115                 120                 125

Leu Ile Pro Gln Leu Val Ala Asn Val Thr Asn Pro Asn Ser Thr Glu
130                 135                 140

His Met Lys Glu Ser Thr Leu Glu Ala Ile Gly Tyr Ile Cys Gln Asp
145                 150                 155                 160

Ile Asp Pro Glu Gln Leu Gln Asp Lys Ser Asn Glu Ile Leu Thr Ala
                165                 170                 175

Ile Ile Gln Gly Met Arg Lys Glu Pro Ser Asn Asn Val Lys Leu
                180                 185                 190

Ala Ala Thr Asn Ala Leu Leu Asn Ser Leu Glu Phe Thr Lys Ala Asn
                195                 200                 205

Phe Asp Lys Glu Ser Glu Arg His Phe Ile Met Gln Val Val Cys Glu
210                 215                 220

Ala Thr Gln Cys Pro Asp Thr Arg Val Arg Val Ala Ala Leu Gln Asn
225                 230                 235                 240

Leu Val Lys Ile Met Ser Leu Tyr Tyr Gln Tyr Met Glu Thr Tyr Met
                245                 250                 255

Gly Pro Ala Leu Phe Ala Ile Thr Ile Glu Ala Met Lys Ser Asp Ile
                260                 265                 270

Asp Glu Val Ala Leu Gln Gly Ile Glu Phe Trp Ser Asn Val Cys Asp
                275                 280                 285

Glu Glu Met Asp Leu Ala Ile Glu Ala Ser Glu Ala Ala Glu Gln Gly
                290                 295                 300

Arg Pro Pro Glu His Thr Ser Lys Phe Tyr Ala Lys Gly Ala Leu Gln
305                 310                 315                 320

Tyr Leu Val Pro Ile Leu Thr Gln Thr Leu Thr Lys Gln Asp Glu Asn
                325                 330                 335

Asp Asp Asp Asp Asp Trp Asn Pro Cys Lys Ala Ala Gly Val Cys Leu
                340                 345                 350

Met Leu Leu Ala Thr Cys Cys Glu Asp Asp Ile Val Pro His Val Leu
                355                 360                 365

Pro Phe Ile Lys Glu His Ile Lys Asn Pro Asp Trp Arg Tyr Arg Asp
                370                 375                 380

Ala Ala Val Met Ala Phe Gly Cys Ile Leu Glu Gly Pro Glu Pro Ser
385                 390                 395                 400

Gln Leu Lys Pro Leu Val Ile Gln Ala Met Pro Thr Leu Ile Glu Leu
                405                 410                 415

Met Lys Asp Pro Ser Val Val Val Arg Asp Thr Ala Ala Trp Thr Val
                420                 425                 430

Gly Arg Ile Cys Glu Leu Leu Pro Glu Ala Ala Ile Asn Asp Val Tyr
                435                 440                 445

Leu Ala Pro Leu Leu Gln Cys Leu Ile Glu Gly Leu Ser Ala Glu Pro
450                 455                 460
```

-continued

```
Arg Val Ala Ser Asn Val Cys Trp Ala Phe Ser Ser Leu Ala Glu Ala
465                 470                 475                 480

Ala Tyr Glu Ala Ala Asp Val Ala Asp Asp Gln Glu Pro Ala Thr
            485                 490                 495

Tyr Cys Leu Ser Ser Ser Phe Glu Leu Ile Val Gln Lys Leu Leu Glu
                500                 505                 510

Thr Thr Asp Arg Pro Asp Gly His Gln Asn Asn Leu Arg Ser Ser Ala
            515                 520                 525

Tyr Glu Ser Leu Met Glu Ile Val Lys Asn Ser Ala Lys Asp Cys Tyr
        530                 535                 540

Pro Ala Val Gln Lys Thr Thr Leu Val Ile Met Glu Arg Leu Gln Gln
545                 550                 555                 560

Val Leu Gln Met Glu Ser His Ile Gln Ser Thr Ser Asp Arg Ile Gln
                565                 570                 575

Phe Asn Asp Leu Gln Ser Leu Leu Cys Ala Thr Leu Gln Asn Val Leu
            580                 585                 590

Arg Lys Val Gln His Gln Asp Ala Leu Gln Ile Ser Asp Val Val Met
        595                 600                 605

Ala Ser Leu Leu Arg Met Phe Gln Ser Thr Ala Gly Ser Gly Gly Val
610                 615                 620

Gln Glu Asp Ala Leu Met Ala Val Ser Thr Leu Val Glu Val Leu Gly
625                 630                 635                 640

Gly Glu Phe Leu Lys Tyr Met Glu Ala Phe Lys Pro Phe Leu Gly Ile
                645                 650                 655

Gly Leu Lys Asn Tyr Ala Glu Tyr Gln Val Cys Leu Ala Ala Val Gly
            660                 665                 670

Leu Val Gly Asp Leu Cys Arg Ala Leu Gln Ser Asn Ile Ile Pro Phe
        675                 680                 685

Cys Asp Glu Val Met Gln Leu Leu Leu Glu Asn Leu Gly Asn Glu Asn
690                 695                 700

Val His Arg Ser Val Lys Pro Gln Ile Leu Ser Val Phe Gly Asp Ile
705                 710                 715                 720

Ala Leu Ala Ile Gly Gly Glu Phe Lys Lys Tyr Leu Glu Val Val Leu
                725                 730                 735

Asn Thr Leu Gln Gln Ala Ser Gln Ala Gln Val Asp Lys Ser Asp Tyr
            740                 745                 750

Asp Met Val Asp Tyr Leu Asn Glu Leu Arg Glu Ser Cys Leu Glu Ala
        755                 760                 765

Tyr Thr Gly Ile Val Gln Gly Leu Lys Gly Asp Gln Glu Asn Val His
770                 775                 780

Pro Asp Val Met Leu Val Gln Pro Arg Val Glu Phe Ile Leu Ser Phe
785                 790                 795                 800

Ile Asp His Ile Ala Gly Asp Glu Asp His Thr Asp Gly Val Val Ala
                805                 810                 815

Cys Ala Ala Gly Leu Ile Gly Asp Leu Cys Thr Ala Phe Gly Lys Asp
            820                 825                 830

Val Leu Lys Leu Val Glu Ala Arg Pro Met Ile His Glu Leu Leu Thr
        835                 840                 845

Glu Gly Arg Arg Ser Lys Thr Asn Lys Ala Lys Thr Leu Ala Thr Trp
850                 855                 860

Ala Thr Lys Glu Leu Arg Lys Leu Lys Asn Gln Ala
865                 870                 875
```

<210> SEQ ID NO 63

<400> SEQUENCE: 63

000

<210> SEQ ID NO 64
<211> LENGTH: 789
<212> TYPE: PRT
<213> ORGANISM: Human

<400> SEQUENCE: 64

```
Met Gly Thr Lys Met Ala Asp Leu Asp Ser Pro Pro Lys Leu Ser Gly
1               5                   10                  15

Val Gln Gln Pro Ser Glu Gly Val Gly Gly Arg Cys Ser Glu Ile
            20                  25                  30

Ser Ala Glu Leu Ile Arg Ser Leu Thr Glu Leu Gln Glu Leu Glu Ala
        35                  40                  45

Val Tyr Glu Arg Leu Cys Gly Glu Lys Val Val Glu Arg Glu Leu
    50                  55                  60

Asp Ala Leu Leu Glu Gln Gln Asn Thr Ile Glu Ser Lys Met Val Thr
65                  70                  75                  80

Leu His Arg Met Gly Pro Asn Leu Gln Leu Ile Glu Gly Asp Ala Lys
                85                  90                  95

Gln Leu Ala Gly Met Ile Thr Phe Thr Cys Asn Leu Ala Glu Asn Val
            100                 105                 110

Ser Ser Lys Val Arg Gln Leu Asp Leu Ala Lys Asn Arg Leu Tyr Gln
        115                 120                 125

Ala Ile Gln Arg Ala Asp Asp Ile Leu Asp Leu Lys Phe Cys Met Asp
    130                 135                 140

Gly Val Gln Thr Ala Leu Arg Ser Glu Asp Tyr Glu Gln Ala Ala Ala
145                 150                 155                 160

His Thr His Arg Tyr Leu Cys Leu Asp Lys Ser Val Ile Glu Leu Ser
                165                 170                 175

Arg Gln Gly Lys Glu Gly Ser Met Ile Asp Ala Asn Leu Lys Leu Leu
            180                 185                 190

Gln Glu Ala Glu Gln Arg Leu Lys Ala Ile Val Ala Glu Lys Phe Ala
        195                 200                 205

Ile Ala Thr Lys Glu Gly Asp Leu Pro Gln Val Glu Arg Phe Phe Lys
    210                 215                 220

Ile Phe Pro Leu Leu Gly Leu His Glu Gly Leu Arg Lys Phe Ser
225                 230                 235                 240

Glu Tyr Leu Cys Lys Gln Val Ala Ser Lys Ala Glu Glu Asn Leu Leu
                245                 250                 255

Met Val Leu Gly Thr Asp Met Ser Asp Arg Arg Ala Ala Val Ile Phe
            260                 265                 270

Ala Asp Thr Leu Thr Leu Leu Phe Glu Gly Ile Ala Arg Ile Val Glu
        275                 280                 285

Thr His Gln Pro Ile Val Glu Thr Tyr Tyr Gly Pro Gly Arg Leu Tyr
    290                 295                 300

Thr Leu Ile Lys Tyr Leu Gln Val Glu Cys Asp Arg Gln Val Glu Lys
305                 310                 315                 320

Val Val Asp Lys Phe Ile Lys Gln Arg Asp Tyr His Gln Gln Phe Arg
                325                 330                 335

His Val Gln Asn Asn Leu Met Arg Asn Ser Thr Thr Glu Lys Ile Glu
```

```
                340             345             350
    Pro Arg Glu Leu Asp Pro Ile Leu Thr Glu Val Thr Leu Met Asn Ala
                355             360             365
    Arg Ser Glu Leu Tyr Leu Arg Phe Leu Lys Lys Arg Ile Ser Ser Asp
                370             375             380
    Phe Glu Val Gly Asp Ser Met Ala Ser Glu Glu Val Lys Gln Glu His
    385             390             395             400
    Gln Lys Cys Leu Asp Lys Leu Leu Asn Asn Cys Leu Leu Ser Cys Thr
                405             410             415
    Met Gln Glu Leu Ile Gly Leu Tyr Val Thr Met Glu Glu Tyr Phe Met
                420             425             430
    Arg Glu Thr Val Asn Lys Ala Val Ala Leu Asp Thr Tyr Glu Lys Gly
                435             440             445
    Gln Leu Thr Ser Ser Met Val Asp Asp Val Phe Tyr Ile Val Lys Lys
                450             455             460
    Cys Ile Gly Arg Ala Leu Ser Ser Ser Ile Asp Cys Leu Cys Ala
    465             470             475             480
    Met Ile Asn Leu Ala Thr Thr Glu Leu Glu Ser Asp Phe Arg Asp Val
                485             490             495
    Leu Cys Asn Lys Leu Arg Met Gly Phe Pro Ala Thr Thr Phe Gln Asp
                500             505             510
    Ile Gln Arg Gly Val Thr Ser Ala Val Asn Ile Met His Ser Ser Leu
                515             520             525
    Gln Gln Gly Lys Phe Asp Thr Lys Gly Ile Glu Ser Thr Asp Glu Ala
                530             535             540
    Lys Met Ser Phe Leu Val Thr Leu Asn Asn Val Glu Val Cys Ser Glu
    545             550             555             560
    Asn Ile Ser Thr Leu Lys Lys Thr Leu Glu Ser Asp Cys Thr Lys Leu
                565             570             575
    Phe Ser Gln Gly Ile Gly Gly Glu Gln Ala Gln Ala Lys Phe Asp Ser
                580             585             590
    Cys Leu Ser Asp Leu Ala Ala Val Ser Asn Lys Phe Arg Asp Leu Leu
                595             600             605
    Gln Glu Gly Leu Thr Glu Leu Asn Ser Thr Ala Ile Lys Pro Gln Val
                610             615             620
    Gln Pro Trp Ile Asn Ser Phe Ser Val Ser His Asn Ile Glu Glu
    625             630             635             640
    Glu Glu Phe Asn Asp Tyr Glu Ala Asn Asp Pro Trp Val Gln Gln Phe
                645             650             655
    Ile Leu Asn Leu Glu Gln Gln Met Ala Glu Phe Lys Ala Ser Leu Ser
                660             665             670
    Pro Val Ile Tyr Asp Ser Leu Thr Gly Leu Met Thr Ser Leu Val Ala
                675             680             685
    Val Glu Leu Glu Lys Val Val Leu Lys Ser Thr Phe Asn Arg Leu Gly
                690             695             700
    Gly Leu Gln Phe Asp Lys Glu Leu Arg Ser Leu Ile Ala Tyr Leu Thr
    705             710             715             720
    Thr Val Thr Thr Trp Thr Ile Arg Asp Lys Phe Ala Arg Leu Ser Gln
                725             730             735
    Met Ala Thr Ile Leu Asn Leu Glu Arg Val Thr Glu Ile Leu Asp Tyr
                740             745             750
    Trp Gly Pro Asn Ser Gly Pro Leu Thr Trp Arg Leu Thr Pro Ala Glu
                755             760             765
```

```
Val Arg Gln Val Leu Ala Leu Arg Ile Asp Phe Arg Ser Glu Asp Ile
            770                 775                 780

Lys Arg Leu Arg Leu
785

<210> SEQ ID NO 65
<211> LENGTH: 785
<212> TYPE: PRT
<213> ORGANISM: Human

<400> SEQUENCE: 65

Met Ala Asp Leu Asp Ser Pro Pro Lys Leu Ser Gly Val Gln Gln Pro
  1               5                  10                  15

Ser Glu Gly Val Gly Gly Gly Arg Cys Ser Glu Ile Ser Ala Glu Leu
             20                  25                  30

Ile Arg Ser Leu Thr Glu Leu Gln Glu Leu Glu Ala Val Tyr Glu Arg
         35                  40                  45

Leu Cys Gly Glu Glu Lys Val Val Glu Arg Glu Leu Asp Ala Leu Leu
     50                  55                  60

Glu Gln Gln Asn Thr Ile Glu Ser Lys Met Val Thr Leu His Arg Met
 65                  70                  75                  80

Gly Pro Asn Leu Gln Leu Ile Glu Gly Asp Ala Lys Gln Leu Ala Gly
                 85                  90                  95

Met Ile Thr Phe Thr Cys Asn Leu Ala Glu Asn Val Ser Ser Lys Val
            100                 105                 110

Arg Gln Leu Asp Leu Ala Lys Asn Arg Leu Tyr Gln Ala Ile Gln Arg
        115                 120                 125

Ala Asp Asp Ile Leu Asp Leu Lys Phe Cys Met Asp Gly Val Gln Thr
    130                 135                 140

Ala Leu Arg Ser Glu Asp Tyr Glu Gln Ala Ala His Thr His Arg
145                 150                 155                 160

Tyr Leu Cys Leu Asp Lys Ser Val Ile Glu Leu Ser Arg Gln Gly Lys
                165                 170                 175

Glu Gly Ser Met Ile Asp Ala Asn Leu Lys Leu Leu Gln Glu Ala Glu
            180                 185                 190

Gln Arg Leu Lys Ala Ile Val Ala Glu Lys Phe Ala Ile Ala Thr Lys
        195                 200                 205

Glu Gly Asp Leu Pro Gln Val Glu Arg Phe Phe Lys Ile Phe Pro Leu
    210                 215                 220

Leu Gly Leu His Glu Glu Gly Leu Arg Lys Phe Ser Glu Tyr Leu Cys
225                 230                 235                 240

Lys Gln Val Ala Ser Lys Ala Glu Glu Asn Leu Leu Met Val Leu Gly
                245                 250                 255

Thr Asp Met Ser Asp Arg Arg Ala Ala Val Ile Phe Ala Asp Thr Leu
            260                 265                 270

Thr Leu Leu Phe Glu Gly Ile Ala Arg Ile Val Glu Thr His Gln Pro
        275                 280                 285

Ile Val Glu Thr Tyr Tyr Gly Pro Gly Arg Leu Tyr Thr Leu Ile Lys
    290                 295                 300

Tyr Leu Gln Val Glu Cys Asp Arg Gln Val Lys Val Asp Lys
305                 310                 315                 320

Phe Ile Lys Gln Arg Asp Tyr His Gln Phe Arg His Val Gln Asn
                325                 330                 335

Asn Leu Met Arg Asn Ser Thr Thr Glu Lys Ile Glu Pro Arg Glu Leu
```

```
                340               345               350
Asp Pro Ile Leu Thr Glu Val Thr Leu Met Asn Ala Arg Ser Glu Leu
                355               360               365
Tyr Leu Arg Phe Leu Lys Lys Arg Ile Ser Ser Asp Phe Glu Val Gly
        370               375               380
Asp Ser Met Ala Ser Glu Val Lys Gln Glu His Gln Lys Cys Leu
385               390               395               400
Asp Lys Leu Leu Asn Asn Cys Leu Leu Ser Cys Thr Met Gln Glu Leu
                405               410               415
Ile Gly Leu Tyr Val Thr Met Glu Glu Tyr Phe Met Arg Glu Thr Val
            420               425               430
Asn Lys Ala Val Ala Leu Asp Thr Tyr Glu Lys Gly Gln Leu Thr Ser
            435               440               445
Ser Met Val Asp Val Phe Tyr Ile Val Lys Lys Cys Ile Gly Arg
        450               455               460
Ala Leu Ser Ser Ser Ile Asp Cys Leu Cys Ala Met Ile Asn Leu
465               470               475               480
Ala Thr Thr Glu Leu Glu Ser Asp Phe Arg Asp Val Leu Cys Asn Lys
                485               490               495
Leu Arg Met Gly Phe Pro Ala Thr Thr Phe Gln Asp Ile Gln Arg Gly
            500               505               510
Val Thr Ser Ala Val Asn Ile Met His Ser Ser Leu Gln Gln Gly Lys
            515               520               525
Phe Asp Thr Lys Gly Ile Glu Ser Thr Asp Glu Ala Lys Met Ser Phe
        530               535               540
Leu Val Thr Leu Asn Asn Val Glu Val Cys Ser Glu Asn Ile Ser Thr
545               550               555               560
Leu Lys Lys Thr Leu Glu Ser Asp Cys Thr Lys Leu Phe Ser Gln Gly
                565               570               575
Ile Gly Gly Glu Gln Ala Gln Ala Lys Phe Asp Ser Cys Leu Ser Asp
            580               585               590
Leu Ala Ala Val Ser Asn Lys Phe Arg Asp Leu Leu Gln Glu Gly Leu
            595               600               605
Thr Glu Leu Asn Ser Thr Ala Ile Lys Pro Gln Val Gln Pro Trp Ile
        610               615               620
Asn Ser Phe Phe Ser Val Ser His Asn Ile Glu Glu Glu Phe Asn
625               630               635               640
Asp Tyr Glu Ala Asn Asp Pro Trp Val Gln Gln Phe Ile Leu Asn Leu
                645               650               655
Glu Gln Gln Met Ala Glu Phe Lys Ala Ser Leu Ser Pro Val Ile Tyr
                660               665               670
Asp Ser Leu Thr Gly Leu Met Thr Ser Leu Val Ala Val Glu Leu Glu
            675               680               685
Lys Val Val Leu Lys Ser Thr Phe Asn Arg Leu Gly Gly Leu Gln Phe
            690               695               700
Asp Lys Glu Leu Arg Ser Leu Ile Ala Tyr Leu Thr Thr Val Thr Thr
705               710               715               720
Trp Thr Ile Arg Asp Lys Phe Ala Arg Leu Ser Gln Met Ala Thr Ile
                725               730               735
Leu Asn Leu Glu Arg Val Thr Glu Ile Leu Asp Tyr Trp Gly Pro Asn
                740               745               750
Ser Gly Pro Leu Thr Trp Arg Leu Thr Pro Ala Glu Val Arg Gln Val
            755               760               765
```

```
Leu Ala Leu Arg Ile Asp Phe Arg Ser Glu Asp Ile Lys Arg Leu Arg
        770                 775                 780
Leu
785
```

<210> SEQ ID NO 66
<211> LENGTH: 337
<212> TYPE: PRT
<213> ORGANISM: Human

<400> SEQUENCE: 66

```
Met Ala Asp Leu Asp Ser Pro Pro Lys Leu Ser Gly Val Gln Gln Pro
1               5                   10                  15

Ser Glu Gly Val Gly Gly Gly Arg Cys Ser Glu Ile Ser Ala Glu Leu
                20                  25                  30

Ile Arg Ser Leu Thr Glu Leu Gln Glu Leu Glu Ala Val Tyr Glu Arg
            35                  40                  45

Leu Cys Gly Glu Glu Lys Val Val Glu Arg Glu Leu Asp Ala Leu Leu
        50                  55                  60

Glu Gln Gln Asn Thr Ile Glu Ser Lys Met Val Thr Leu His Arg Met
65                  70                  75                  80

Gly Pro Asn Leu Gln Leu Ile Glu Gly Asp Ala Lys Gln Leu Ala Gly
                85                  90                  95

Met Ile Thr Phe Thr Cys Asn Leu Ala Glu Asn Val Ser Ser Lys Val
            100                 105                 110

Arg Gln Leu Asp Leu Ala Lys Asn Arg Leu Tyr Gln Ala Ile Gln Arg
        115                 120                 125

Ala Asp Asp Ile Leu Asp Leu Lys Phe Cys Met Asp Gly Val Gln Thr
    130                 135                 140

Ala Leu Arg Ser Glu Asp Tyr Glu Gln Ala Ala His Thr His Arg
145                 150                 155                 160

Tyr Leu Cys Leu Asp Lys Ser Val Ile Glu Leu Ser Arg Gln Gly Lys
                165                 170                 175

Glu Gly Ser Met Ile Asp Ala Asn Leu Lys Leu Leu Gln Glu Ala Glu
            180                 185                 190

Gln Arg Leu Lys Ala Ile Val Ala Glu Lys Phe Ala Ile Ala Thr Lys
        195                 200                 205

Glu Gly Asp Leu Pro Gln Val Glu Arg Phe Phe Lys Ile Phe Pro Leu
    210                 215                 220

Leu Gly Leu His Glu Glu Gly Leu Arg Lys Phe Ser Glu Tyr Leu Cys
225                 230                 235                 240

Lys Gln Val Ala Ser Lys Ala Glu Glu Asn Leu Leu Met Val Leu Gly
                245                 250                 255

Thr Asp Met Ser Asp Arg Arg Ala Ala Val Ile Phe Ala Asp Thr Leu
            260                 265                 270

Thr Leu Leu Phe Glu Gly Ile Ala Arg Ile Val Glu Thr His Gln Pro
        275                 280                 285

Ile Val Glu Thr Tyr Tyr Gly Pro Gly Arg Leu Tyr Thr Leu Ile Lys
    290                 295                 300

Tyr Leu Gln Val Glu Cys Asp Arg Gln Val Lys Val Val Asp Lys
305                 310                 315                 320

Phe Ile Lys Gln Arg Asp Tyr His Gln Asn Phe Val Phe Ser Phe
                325                 330                 335

Phe
```

-continued

<210> SEQ ID NO 67
<211> LENGTH: 695
<212> TYPE: PRT
<213> ORGANISM: Human

<400> SEQUENCE: 67

Met Gly Thr Lys Met Ala Asp Leu Asp Ser Pro Lys Leu Ser Gly
1               5                   10                  15

Val Gln Gln Pro Ser Glu Gly Val Gly Gly Arg Cys Ser Glu Ile
                20                  25                  30

Ser Ala Glu Leu Ile Arg Ser Leu Thr Glu Leu Gln Glu Leu Glu Ala
            35                  40                  45

Val Tyr Glu Arg Leu Cys Gly Glu Lys Val Val Glu Arg Glu Leu
        50                  55                  60

Asp Ala Leu Leu Glu Gln Gln Asn Thr Ile Glu Ser Lys Met Val Thr
65                  70                  75                  80

Leu His Arg Met Gly Pro Asn Leu Gln Leu Ile Glu Ala Asn Leu Lys
                85                  90                  95

Leu Leu Gln Glu Ala Glu Gln Arg Leu Lys Ala Ile Val Ala Glu Lys
                100                 105                 110

Phe Ala Ile Ala Thr Lys Glu Gly Asp Leu Pro Gln Val Glu Arg Phe
            115                 120                 125

Phe Lys Ile Phe Pro Leu Leu Gly Leu His Glu Gly Leu Arg Lys
            130                 135                 140

Phe Ser Glu Tyr Leu Cys Lys Gln Val Ala Ser Lys Ala Glu Glu Asn
145                 150                 155                 160

Leu Leu Met Val Leu Gly Thr Asp Met Ser Asp Arg Arg Ala Ala Val
                165                 170                 175

Ile Phe Ala Asp Thr Leu Thr Leu Leu Phe Glu Gly Ile Ala Arg Ile
            180                 185                 190

Val Glu Thr His Gln Pro Ile Val Glu Thr Tyr Tyr Gly Pro Gly Arg
            195                 200                 205

Leu Tyr Thr Leu Ile Lys Tyr Leu Gln Val Glu Cys Asp Arg Gln Val
        210                 215                 220

Glu Lys Val Val Asp Lys Phe Ile Lys Gln Arg Asp Tyr His Gln Gln
225                 230                 235                 240

Phe Arg His Val Gln Asn Asn Leu Met Arg Asn Ser Thr Thr Glu Lys
                245                 250                 255

Ile Glu Pro Arg Glu Leu Asp Pro Ile Leu Thr Glu Val Thr Leu Met
            260                 265                 270

Asn Ala Arg Ser Glu Leu Tyr Leu Arg Phe Leu Lys Lys Arg Ile Ser
            275                 280                 285

Ser Asp Phe Glu Val Gly Asp Ser Met Ala Ser Glu Glu Val Lys Gln
290                 295                 300

Glu His Gln Lys Cys Leu Asp Lys Leu Leu Asn Asn Cys Leu Leu Ser
305                 310                 315                 320

Cys Thr Met Gln Glu Leu Ile Gly Leu Tyr Val Thr Met Glu Glu Tyr
                325                 330                 335

Phe Met Arg Glu Thr Val Asn Lys Ala Val Ala Leu Asp Thr Tyr Glu
                340                 345                 350

Lys Gly Gln Leu Thr Ser Ser Met Val Asp Asp Val Phe Tyr Ile Val
            355                 360                 365

Lys Lys Cys Ile Gly Arg Ala Leu Ser Ser Ser Ser Ile Asp Cys Leu

```
                 370                 375                 380
Cys Ala Met Ile Asn Leu Ala Thr Thr Glu Leu Glu Ser Asp Phe Arg
385                 390                 395                 400

Asp Val Leu Cys Asn Lys Leu Arg Met Gly Phe Pro Ala Thr Thr Phe
                405                 410                 415

Gln Asp Ile Gln Arg Gly Val Thr Ser Ala Val Asn Ile Met His Ser
            420                 425                 430

Ser Leu Gln Gln Gly Lys Phe Asp Thr Lys Gly Ile Glu Ser Thr Asp
        435                 440                 445

Glu Ala Lys Met Ser Phe Leu Val Thr Leu Asn Asn Val Glu Val Cys
    450                 455                 460

Ser Glu Asn Ile Ser Thr Leu Lys Lys Thr Leu Glu Ser Asp Cys Thr
465                 470                 475                 480

Lys Leu Phe Ser Gln Gly Ile Gly Gly Glu Gln Ala Gln Ala Lys Phe
                485                 490                 495

Asp Ser Cys Leu Ser Asp Leu Ala Ala Val Ser Asn Lys Phe Arg Asp
            500                 505                 510

Leu Leu Gln Glu Gly Leu Thr Glu Leu Asn Ser Thr Ala Ile Lys Pro
        515                 520                 525

Gln Val Gln Pro Trp Ile Asn Ser Phe Ser Val Ser His Asn Ile
    530                 535                 540

Glu Glu Glu Glu Phe Asn Asp Tyr Glu Ala Asn Asp Pro Trp Val Gln
545                 550                 555                 560

Gln Phe Ile Leu Asn Leu Glu Gln Gln Met Ala Glu Phe Lys Ala Ser
                565                 570                 575

Leu Ser Pro Val Ile Tyr Asp Ser Leu Thr Gly Leu Met Thr Ser Leu
            580                 585                 590

Val Ala Val Glu Leu Glu Lys Val Val Leu Lys Ser Thr Phe Asn Arg
        595                 600                 605

Leu Gly Gly Leu Gln Phe Asp Lys Glu Leu Arg Ser Leu Ile Ala Tyr
    610                 615                 620

Leu Thr Thr Val Thr Thr Trp Thr Ile Arg Asp Lys Phe Ala Arg Leu
625                 630                 635                 640

Ser Gln Met Ala Thr Ile Leu Asn Leu Glu Arg Val Thr Glu Ile Leu
                645                 650                 655

Asp Tyr Trp Gly Pro Asn Ser Gly Pro Leu Thr Trp Arg Leu Thr Pro
            660                 665                 670

Ala Glu Val Arg Gln Val Leu Ala Leu Arg Ile Asp Phe Arg Ser Glu
        675                 680                 685

Asp Ile Lys Arg Leu Arg Leu
    690                 695

<210> SEQ ID NO 68
<211> LENGTH: 417
<212> TYPE: PRT
<213> ORGANISM: Human

<400> SEQUENCE: 68

Met Glu Phe Val Lys Cys Leu Gly His Pro Glu Glu Phe Tyr Asn Leu
1               5                   10                  15

Val Arg Phe Arg Ile Gly Gly Lys Arg Lys Val Met Pro Lys Met Asp
                20                  25                  30

Gln Asp Ser Leu Ser Ser Ser Leu Lys Thr Cys Tyr Lys Tyr Leu Asn
            35                  40                  45
```

```
Gln Thr Ser Arg Ser Phe Ala Val Ile Gln Ala Leu Asp Gly Glu
 50                  55                  60

Met Arg Asn Ala Val Cys Ile Phe Tyr Leu Val Leu Arg Ala Leu Asp
 65                  70                  75                  80

Thr Leu Glu Asp Asp Met Thr Ile Ser Val Glu Lys Lys Val Pro Leu
                 85                  90                  95

Leu His Asn Phe His Ser Phe Leu Tyr Gln Pro Asp Trp Arg Phe Met
                100                 105                 110

Glu Ser Lys Glu Lys Asp Arg Gln Val Leu Glu Asp Phe Pro Thr Ile
            115                 120                 125

Ser Leu Glu Phe Arg Asn Leu Ala Glu Lys Tyr Gln Thr Val Ile Ala
130                 135                 140

Asp Ile Cys Arg Arg Met Gly Ile Gly Met Ala Glu Phe Leu Asp Lys
145                 150                 155                 160

His Val Thr Ser Glu Gln Glu Trp Asp Lys Tyr Cys His Tyr Val Ala
                165                 170                 175

Gly Leu Val Gly Ile Gly Leu Ser Arg Leu Phe Ser Ala Ser Glu Phe
            180                 185                 190

Glu Asp Pro Leu Val Gly Glu Asp Thr Glu Arg Ala Asn Ser Met Gly
            195                 200                 205

Leu Phe Leu Gln Lys Thr Asn Ile Ile Arg Asp Tyr Leu Glu Asp Gln
210                 215                 220

Gln Gly Gly Arg Glu Phe Trp Pro Gln Glu Val Trp Ser Arg Tyr Val
225                 230                 235                 240

Lys Lys Leu Gly Asp Phe Ala Lys Pro Glu Asn Ile Asp Leu Ala Val
                245                 250                 255

Gln Cys Leu Asn Glu Leu Ile Thr Asn Ala Leu His His Ile Pro Asp
            260                 265                 270

Val Ile Thr Tyr Leu Ser Arg Leu Arg Asn Gln Ser Val Phe Asn Phe
            275                 280                 285

Cys Ala Ile Pro Gln Val Met Ala Ile Ala Thr Leu Ala Ala Cys Tyr
            290                 295                 300

Asn Asn Gln Gln Val Phe Lys Gly Ala Val Lys Ile Arg Lys Gly Gln
305                 310                 315                 320

Ala Val Thr Leu Met Met Asp Ala Thr Asn Met Pro Ala Val Lys Ala
                325                 330                 335

Ile Ile Tyr Gln Tyr Met Glu Glu Ile Tyr His Arg Ile Pro Asp Ser
            340                 345                 350

Asp Pro Ser Ser Lys Thr Arg Gln Ile Ile Ser Thr Ile Arg Thr
            355                 360                 365

Gln Asn Leu Pro Asn Cys Gln Leu Ile Ser Arg Ser His Tyr Ser Pro
370                 375                 380

Ile Tyr Leu Ser Phe Val Met Leu Leu Ala Ala Leu Ser Trp Gln Tyr
385                 390                 395                 400

Leu Thr Thr Leu Ser Gln Val Thr Glu Asp Tyr Val Gln Thr Gly Glu
                405                 410                 415

His

<210> SEQ ID NO 69
<211> LENGTH: 359
<212> TYPE: PRT
<213> ORGANISM: Human

<400> SEQUENCE: 69
```

Met Arg Ala Ser Gln Lys Asp Phe Glu Asn Ser Met Asn Gln Val Lys
1               5                   10                  15

Leu Leu Lys Lys Asp Pro Gly Asn Glu Val Lys Leu Lys Leu Tyr Ala
            20                  25                  30

Leu Tyr Lys Gln Ala Thr Glu Gly Pro Cys Asn Met Pro Lys Pro Gly
        35                  40                  45

Val Phe Asp Leu Ile Asn Lys Ala Lys Trp Asp Ala Trp Asn Ala Leu
    50                  55                  60

Gly Ser Leu Pro Lys Glu Ala Ala Arg Gln Asn Tyr Val Asp Leu Val
65                  70                  75                  80

Ser Ser Leu Ser Pro Ser Leu Glu Ser Ser Gln Val Glu Pro Gly
                85                  90                  95

Thr Asp Arg Lys Ser Thr Gly Phe Glu Thr Leu Val Val Thr Ser Glu
                100                 105                 110

Asp Gly Ile Thr Lys Ile Met Phe Asn Arg Pro Lys Lys Lys Asn Ala
            115                 120                 125

Ile Asn Thr Glu Met Tyr His Glu Ile Met Arg Ala Leu Lys Ala Ala
        130                 135                 140

Ser Lys Asp Asp Ser Ile Ile Thr Val Leu Thr Gly Asn Gly Asp Tyr
145                 150                 155                 160

Tyr Ser Ser Gly Asn Asp Leu Thr Asn Phe Thr Asp Ile Pro Pro Gly
                165                 170                 175

Gly Val Glu Glu Lys Ala Lys Asn Asn Ala Val Leu Leu Arg Glu Phe
            180                 185                 190

Val Gly Cys Phe Ile Asp Phe Pro Lys Pro Leu Ile Ala Val Val Asn
        195                 200                 205

Gly Pro Ala Val Gly Ile Ser Val Thr Leu Leu Gly Leu Phe Asp Ala
210                 215                 220

Val Tyr Ala Ser Asp Arg Ala Thr Phe His Thr Pro Phe Ser His Leu
225                 230                 235                 240

Gly Gln Ser Pro Glu Gly Cys Ser Ser Tyr Thr Phe Pro Lys Ile Met
                245                 250                 255

Ser Pro Ala Lys Ala Thr Glu Met Leu Ile Phe Gly Lys Lys Leu Thr
            260                 265                 270

Ala Gly Glu Ala Cys Ala Gln Gly Leu Val Thr Glu Val Phe Pro Asp
        275                 280                 285

Ser Thr Phe Gln Lys Glu Val Trp Thr Arg Leu Lys Ala Phe Ala Lys
        290                 295                 300

Leu Pro Pro Asn Ala Leu Arg Ile Ser Lys Glu Val Ile Arg Lys Arg
305                 310                 315                 320

Glu Arg Glu Lys Leu His Ala Val Asn Ala Glu Glu Cys Asn Val Leu
                325                 330                 335

Gln Gly Arg Trp Leu Ser Asp Glu Cys Thr Asn Ala Val Val Asn Phe
            340                 345                 350

Leu Ser Arg Lys Ser Lys Leu
        355

<210> SEQ ID NO 70
<211> LENGTH: 227
<212> TYPE: PRT
<213> ORGANISM: Human

<400> SEQUENCE: 70

Met Tyr His Glu Ile Met Arg Ala Leu Lys Ala Ala Ser Lys Asp Asp
1               5                   10                  15

```
Ser Ile Ile Thr Val Leu Thr Gly Asn Gly Asp Tyr Tyr Ser Ser Gly
            20                  25                  30

Asn Asp Leu Thr Asn Phe Thr Asp Ile Pro Pro Gly Gly Val Glu Glu
            35                  40                  45

Lys Ala Lys Asn Asn Ala Val Leu Leu Arg Glu Phe Val Gly Cys Phe
 50                      55                  60

Ile Asp Phe Pro Lys Pro Leu Ile Ala Val Val Asn Gly Pro Ala Val
 65                  70                  75                  80

Gly Ile Ser Val Thr Leu Leu Gly Leu Phe Asp Ala Val Tyr Ala Ser
                    85                  90                  95

Asp Arg Ala Thr Phe His Thr Pro Phe Ser His Leu Gly Gln Ser Pro
                100                 105                 110

Glu Gly Cys Ser Ser Tyr Thr Phe Pro Lys Ile Met Ser Pro Ala Lys
                115                 120                 125

Ala Thr Glu Met Leu Ile Phe Gly Lys Lys Leu Thr Ala Gly Glu Ala
130                 135                 140

Cys Ala Gln Gly Leu Val Thr Glu Val Phe Pro Asp Ser Thr Phe Gln
145                 150                 155                 160

Lys Glu Val Trp Thr Arg Leu Lys Ala Phe Ala Lys Leu Pro Pro Asn
                165                 170                 175

Ala Leu Arg Ile Ser Lys Glu Val Ile Arg Lys Arg Glu Arg Glu Lys
                180                 185                 190

Leu His Ala Val Asn Ala Glu Glu Cys Asn Val Leu Gln Gly Arg Trp
            195                 200                 205

Leu Ser Asp Glu Cys Thr Asn Ala Val Val Asn Phe Leu Ser Arg Lys
            210                 215                 220

Ser Lys Leu
225

<210> SEQ ID NO 71
<211> LENGTH: 394
<212> TYPE: PRT
<213> ORGANISM: Human

<400> SEQUENCE: 71

Met Ala Met Ala Tyr Leu Ala Trp Arg Leu Ala Arg Arg Ser Cys Pro
 1                5                  10                  15

Ser Ser Leu Gln Val Thr Ser Phe Pro Val Val Gln Leu His Met Asn
            20                  25                  30

Arg Thr Ala Met Arg Ala Ser Gln Lys Asp Phe Glu Asn Ser Met Asn
            35                  40                  45

Gln Val Lys Leu Leu Lys Lys Asp Pro Gly Asn Glu Val Lys Leu Lys
 50                  55                  60

Leu Tyr Ala Leu Tyr Lys Gln Ala Thr Glu Gly Pro Cys Asn Met Pro
 65                  70                  75                  80

Lys Pro Gly Val Phe Asp Leu Ile Asn Lys Ala Lys Trp Asp Ala Trp
                    85                  90                  95

Asn Ala Leu Gly Ser Leu Pro Lys Glu Ala Ala Arg Gln Asn Tyr Val
                100                 105                 110

Asp Leu Val Ser Ser Leu Ser Pro Ser Leu Glu Ser Ser Gln Val
                115                 120                 125

Glu Pro Gly Thr Asp Arg Lys Ser Thr Gly Phe Glu Thr Leu Val Val
130                 135                 140

Thr Ser Glu Asp Gly Ile Thr Lys Ile Met Phe Asn Arg Pro Lys Lys
```

```
               145                 150                 155                 160
        Lys Asn Ala Ile Asn Thr Glu Met Tyr His Glu Ile Met Arg Ala Leu
                            165                 170                 175

Lys Ala Ala Ser Lys Asp Asp Ser Ile Ile Thr Val Leu Thr Gly Asn
                        180                 185                 190

Gly Asp Tyr Tyr Ser Ser Gly Asn Asp Leu Thr Asn Phe Thr Asp Ile
                    195                 200                 205

Pro Pro Gly Gly Val Glu Glu Lys Ala Lys Asn Asn Ala Val Leu Leu
                210                 215                 220

Arg Glu Phe Val Gly Cys Phe Ile Asp Phe Pro Lys Pro Leu Ile Ala
        225                 230                 235                 240

Val Val Asn Gly Pro Ala Val Gly Ile Ser Val Thr Leu Leu Gly Leu
                            245                 250                 255

Phe Asp Ala Val Tyr Ala Ser Asp Arg Ala Thr Phe His Thr Pro Phe
                        260                 265                 270

Ser His Leu Gly Gln Ser Pro Glu Gly Cys Ser Ser Tyr Thr Phe Pro
                    275                 280                 285

Lys Ile Met Ser Pro Ala Lys Ala Thr Glu Met Leu Ile Phe Gly Lys
                290                 295                 300

Lys Leu Thr Ala Gly Glu Ala Cys Ala Gln Gly Leu Val Thr Glu Val
        305                 310                 315                 320

Phe Pro Asp Ser Thr Phe Gln Lys Glu Val Trp Thr Arg Leu Lys Ala
                            325                 330                 335

Phe Ala Lys Leu Pro Pro Asn Ala Leu Arg Ile Ser Lys Glu Val Ile
                        340                 345                 350

Arg Lys Arg Glu Arg Glu Lys Leu His Ala Val Asn Ala Glu Glu Cys
                    355                 360                 365

Asn Val Leu Gln Gly Arg Trp Leu Ser Asp Glu Cys Thr Asn Ala Val
                370                 375                 380

Val Asn Phe Leu Ser Arg Lys Ser Lys Leu
        385                 390

<210> SEQ ID NO 72
        <211> LENGTH: 364
        <212> TYPE: PRT
        <213> ORGANISM: Human

<400> SEQUENCE: 72

Met Asn Arg Thr Ala Met Arg Ala Ser Gln Lys Asp Phe Glu Asn Ser
        1               5                   10                  15

Met Asn Gln Val Lys Leu Leu Lys Lys Asp Pro Gly Asn Glu Val Lys
                        20                  25                  30

Leu Lys Leu Tyr Ala Leu Tyr Lys Gln Ala Thr Glu Gly Pro Cys Asn
                    35                  40                  45

Met Pro Lys Pro Gly Val Phe Asp Leu Ile Asn Lys Ala Lys Trp Asp
                50                  55                  60

Ala Trp Asn Ala Leu Gly Ser Leu Pro Lys Glu Ala Ala Arg Gln Asn
        65                  70                  75                  80

Tyr Val Asp Leu Val Ser Ser Leu Ser Pro Ser Leu Glu Ser Ser Ser
                        85                  90                  95

Gln Val Glu Pro Gly Thr Asp Arg Lys Ser Thr Gly Phe Glu Thr Leu
                    100                 105                 110

Val Val Thr Ser Glu Asp Gly Ile Thr Lys Ile Met Phe Asn Arg Pro
                115                 120                 125
```

Lys Lys Lys Asn Ala Ile Asn Thr Glu Met Tyr His Glu Ile Met Arg
            130                 135                 140

Ala Leu Lys Ala Ala Ser Lys Asp Asp Ser Ile Ile Thr Val Leu Thr
145                 150                 155                 160

Gly Asn Gly Asp Tyr Tyr Ser Ser Gly Asn Asp Leu Thr Asn Phe Thr
                165                 170                 175

Asp Ile Pro Pro Gly Gly Val Glu Glu Lys Ala Lys Asn Asn Ala Val
            180                 185                 190

Leu Leu Arg Glu Phe Val Gly Cys Phe Ile Asp Phe Pro Lys Pro Leu
                195                 200                 205

Ile Ala Val Val Asn Gly Pro Ala Val Gly Ile Ser Val Thr Leu Leu
210                 215                 220

Gly Leu Phe Asp Ala Val Tyr Ala Ser Asp Arg Ala Thr Phe His Thr
225                 230                 235                 240

Pro Phe Ser His Leu Gly Gln Ser Pro Glu Gly Cys Ser Ser Tyr Thr
                245                 250                 255

Phe Pro Lys Ile Met Ser Pro Ala Lys Ala Thr Glu Met Leu Ile Phe
            260                 265                 270

Gly Lys Lys Leu Thr Ala Gly Glu Ala Cys Ala Gln Gly Leu Val Thr
                275                 280                 285

Glu Val Phe Pro Asp Ser Thr Phe Gln Lys Glu Val Trp Thr Arg Leu
290                 295                 300

Lys Ala Phe Ala Lys Leu Pro Pro Asn Ala Leu Arg Ile Ser Lys Glu
305                 310                 315                 320

Val Ile Arg Lys Arg Glu Arg Glu Lys Leu His Ala Val Asn Ala Glu
                325                 330                 335

Glu Cys Asn Val Leu Gln Gly Arg Trp Leu Ser Asp Glu Cys Thr Asn
            340                 345                 350

Ala Val Val Asn Phe Leu Ser Arg Lys Ser Lys Leu
            355                 360

<210> SEQ ID NO 73
<211> LENGTH: 241
<212> TYPE: PRT
<213> ORGANISM: Human

<400> SEQUENCE: 73

Met Phe Asn Arg Pro Lys Lys Lys Asn Ala Ile Asn Thr Glu Met Tyr
1               5                   10                  15

His Glu Ile Met Arg Ala Leu Lys Ala Ala Ser Lys Asp Asp Ser Ile
            20                  25                  30

Ile Thr Val Leu Thr Gly Asn Gly Asp Tyr Tyr Ser Ser Gly Asn Asp
        35                  40                  45

Leu Thr Asn Phe Thr Asp Ile Pro Pro Gly Gly Val Glu Glu Lys Ala
    50                  55                  60

Lys Asn Asn Ala Val Leu Leu Arg Glu Phe Val Gly Cys Phe Ile Asp
65                  70                  75                  80

Phe Pro Lys Pro Leu Ile Ala Val Val Asn Gly Pro Ala Val Gly Ile
                85                  90                  95

Ser Val Thr Leu Leu Gly Leu Phe Asp Ala Val Tyr Ala Ser Asp Arg
            100                 105                 110

Ala Thr Phe His Thr Pro Phe Ser His Leu Gly Gln Ser Pro Glu Gly
        115                 120                 125

Cys Ser Ser Tyr Thr Phe Pro Lys Ile Met Ser Pro Ala Lys Ala Thr
    130                 135                 140

```
Glu Met Leu Ile Phe Gly Lys Lys Leu Thr Ala Gly Glu Ala Cys Ala
145                 150                 155                 160

Gln Gly Leu Val Thr Glu Val Phe Pro Asp Ser Thr Phe Gln Lys Glu
                165                 170                 175

Val Trp Thr Arg Leu Lys Ala Phe Ala Lys Leu Pro Pro Asn Ala Leu
            180                 185                 190

Arg Ile Ser Lys Glu Val Ile Arg Lys Arg Glu Arg Glu Lys Leu His
        195                 200                 205

Ala Val Asn Ala Glu Glu Cys Asn Val Leu Gln Gly Arg Trp Leu Ser
    210                 215                 220

Asp Glu Cys Thr Asn Ala Val Val Asn Phe Leu Ser Arg Lys Ser Lys
225                 230                 235                 240

Leu

<210> SEQ ID NO 74
<211> LENGTH: 1225
<212> TYPE: PRT
<213> ORGANISM: Human

<400> SEQUENCE: 74

Met Phe Ala Arg Lys Pro Pro Gly Ala Ala Pro Leu Gly Ala Met Pro
1               5                   10                  15

Val Pro Asp Gln Pro Ser Ser Ala Ser Glu Lys Thr Ser Ser Leu Ser
                20                  25                  30

Pro Gly Leu Asn Thr Ser Asn Gly Asp Gly Ser Glu Thr Glu Thr Thr
            35                  40                  45

Ser Ala Ile Leu Ala Ser Val Lys Glu Gln Glu Leu Gln Phe Glu Arg
    50                  55                  60

Leu Thr Arg Glu Leu Glu Ala Glu Arg Gln Ile Val Ala Ser Gln Leu
65                  70                  75                  80

Glu Arg Cys Lys Leu Gly Ser Glu Thr Gly Ser Met Ser Ser Met Ser
                85                  90                  95

Ser Ala Glu Glu Gln Phe Gln Trp Gln Ser Gln Asp Gly Gln Lys Asp
                100                 105                 110

Ile Glu Asp Glu Leu Thr Thr Gly Leu Glu Leu Val Asp Ser Cys Ile
            115                 120                 125

Arg Ser Leu Gln Glu Ser Gly Ile Leu Asp Pro Gln Asp Tyr Ser Thr
        130                 135                 140

Gly Glu Arg Pro Ser Leu Leu Ser Gln Ser Ala Leu Gln Leu Asn Ser
145                 150                 155                 160

Lys Pro Glu Gly Ser Phe Gln Tyr Pro Ala Ser Tyr His Ser Asn Gln
                165                 170                 175

Thr Leu Ala Leu Gly Glu Thr Thr Pro Ser Gln Leu Pro Ala Arg Gly
            180                 185                 190

Thr Gln Ala Arg Ala Thr Gly Gln Ser Phe Ser Gln Gly Thr Thr Ser
        195                 200                 205

Arg Ala Gly His Leu Ala Gly Pro Glu Pro Ala Pro Pro Pro Pro Pro
    210                 215                 220

Pro Pro Arg Glu Pro Phe Ala Pro Ser Leu Gly Ser Ala Phe His Leu
225                 230                 235                 240

Pro Asp Ala Pro Pro Ala Ala Ala Ala Ala Leu Tyr Tyr Ser Ser
                245                 250                 255

Ser Thr Leu Pro Ala Pro Pro Arg Gly Gly Ser Pro Leu Ala Ala Pro
            260                 265                 270
```

-continued

Gln Gly Gly Ser Pro Thr Lys Leu Gln Arg Gly Gly Ser Ala Pro Glu
            275                 280                 285

Gly Ala Thr Tyr Ala Ala Pro Arg Gly Ser Ser Pro Lys Gln Ser Pro
        290                 295                 300

Ser Arg Leu Ala Lys Ser Tyr Ser Thr Ser Ser Pro Ile Asn Ile Val
305                 310                 315                 320

Val Ser Ser Ala Gly Leu Ser Pro Ile Arg Val Thr Ser Pro Pro Thr
                325                 330                 335

Val Gln Ser Thr Ile Ser Ser Pro Ile His Gln Leu Ser Ser Thr
            340                 345                 350

Ile Gly Thr Tyr Ala Thr Leu Ser Pro Thr Lys Arg Leu Val His Ala
                355                 360                 365

Ser Glu Gln Tyr Ser Lys His Ser Gln Glu Leu Tyr Ala Thr Ala Thr
    370                 375                 380

Leu Gln Arg Pro Gly Ser Leu Ala Ala Gly Ser Arg Ala Ser Tyr Ser
385                 390                 395                 400

Ser Gln His Gly His Leu Gly Pro Glu Leu Arg Ala Leu Gln Ser Pro
                405                 410                 415

Glu His His Ile Asp Pro Ile Tyr Glu Asp Arg Val Tyr Gln Lys Pro
                420                 425                 430

Pro Met Arg Ser Leu Ser Gln Ser Gln Gly Asp Pro Leu Pro Pro Ala
            435                 440                 445

His Thr Gly Thr Tyr Arg Thr Ser Thr Ala Pro Ser Ser Pro Gly Val
    450                 455                 460

Asp Ser Val Pro Leu Gln Arg Thr Gly Ser Gln His Gly Pro Gln Asn
465                 470                 475                 480

Ala Ala Ala Ala Thr Phe Gln Arg Ala Ser Tyr Ala Ala Gly Pro Ala
                485                 490                 495

Ser Asn Tyr Ala Asp Pro Tyr Arg Gln Leu Gln Tyr Cys Pro Ser Val
                500                 505                 510

Glu Ser Pro Tyr Ser Lys Ser Gly Pro Ala Leu Pro Pro Glu Gly Thr
    515                 520                 525

Leu Ala Arg Ser Pro Ser Ile Asp Ser Ile Gln Lys Asp Pro Arg Glu
            530                 535                 540

Phe Gly Trp Arg Asp Pro Glu Leu Pro Glu Val Ile Gln Met Leu Gln
545                 550                 555                 560

His Gln Phe Pro Ser Val Gln Ser Asn Ala Ala Ala Tyr Leu Gln His
                565                 570                 575

Leu Cys Phe Gly Asp Asn Lys Ile Lys Ala Glu Ile Arg Arg Gln Gly
                580                 585                 590

Gly Ile Gln Leu Leu Val Asp Leu Leu Asp His Arg Met Thr Glu Val
        595                 600                 605

His Arg Ser Ala Cys Gly Ala Leu Arg Asn Leu Val Tyr Gly Lys Ala
    610                 615                 620

Asn Asp Asp Asn Lys Ile Ala Leu Lys Asn Cys Gly Gly Ile Pro Ala
625                 630                 635                 640

Leu Val Arg Leu Leu Arg Lys Thr Thr Asp Leu Glu Ile Arg Glu Leu
                645                 650                 655

Val Thr Gly Val Leu Trp Asn Leu Ser Ser Cys Asp Ala Leu Lys Met
                660                 665                 670

Pro Ile Ile Gln Asp Ala Leu Ala Val Leu Thr Asn Ala Val Ile Ile
            675                 680                 685

```
Pro His Ser Gly Trp Glu Asn Ser Pro Leu Gln Asp Asp Arg Lys Ile
690                 695                 700
Gln Leu His Ser Ser Gln Val Leu Arg Asn Ala Thr Gly Cys Leu Arg
705                 710                 715                 720
Asn Val Ser Ser Ala Gly Glu Glu Ala Arg Arg Arg Met Arg Glu Cys
                725                 730                 735
Asp Gly Leu Thr Asp Ala Leu Leu Tyr Val Ile Gln Ser Ala Leu Gly
                740                 745                 750
Ser Ser Glu Ile Asp Ser Lys Thr Val Glu Asn Cys Val Cys Ile Leu
            755                 760                 765
Arg Asn Leu Ser Tyr Arg Leu Ala Ala Glu Thr Ser Gln Gly Gln His
770                 775                 780
Met Gly Thr Asp Glu Leu Asp Gly Leu Leu Cys Gly Glu Ala Asn Gly
785                 790                 795                 800
Lys Asp Ala Glu Ser Ser Gly Cys Trp Gly Lys Lys Lys Lys Lys Lys
                805                 810                 815
Lys Ser Gln Asp Gln Trp Asp Gly Val Gly Pro Leu Pro Asp Cys Ala
                820                 825                 830
Glu Pro Pro Lys Gly Ile Gln Met Leu Trp His Pro Ser Ile Val Lys
            835                 840                 845
Pro Tyr Leu Thr Leu Leu Ser Glu Cys Ser Asn Pro Asp Thr Leu Glu
850                 855                 860
Gly Ala Ala Gly Ala Leu Gln Asn Leu Ala Ala Gly Ser Trp Lys Trp
865                 870                 875                 880
Ser Val Tyr Ile Arg Ala Ala Val Arg Lys Glu Lys Gly Leu Pro Ile
                885                 890                 895
Leu Val Glu Leu Leu Arg Ile Asp Asn Asp Arg Val Val Cys Ala Val
                900                 905                 910
Ala Thr Ala Leu Arg Asn Met Ala Leu Asp Val Arg Asn Lys Glu Leu
            915                 920                 925
Ile Gly Lys Tyr Ala Met Arg Asp Leu Val His Arg Leu Pro Gly Gly
930                 935                 940
Asn Asn Ser Asn Asn Thr Ala Ser Lys Ala Met Ser Asp Asp Thr Val
945                 950                 955                 960
Thr Ala Val Cys Cys Thr Leu His Glu Val Ile Thr Lys Asn Met Glu
                965                 970                 975
Asn Ala Lys Ala Leu Arg Asp Ala Gly Gly Ile Glu Lys Leu Val Gly
                980                 985                 990
Ile Ser Lys Ser Lys Gly Asp Lys His Ser Pro Lys Val Val Lys Ala
            995                 1000                1005
Ala Ser Gln Val Leu Asn Ser Met Trp Gln Tyr Arg Asp Leu Arg
    1010                1015                1020
Ser Leu Tyr Lys Lys Asp Gly Trp Ser Gln Tyr His Phe Val Ala
    1025                1030                1035
Ser Ser Ser Thr Ile Glu Arg Asp Arg Gln Arg Pro Tyr Ser Ser
    1040                1045                1050
Ser Arg Thr Pro Ser Ile Ser Pro Val Arg Val Ser Pro Asn Asn
    1055                1060                1065
Arg Ser Ala Ser Ala Pro Ala Ser Pro Arg Glu Met Ile Ser Leu
    1070                1075                1080
Lys Glu Arg Lys Thr Asp Tyr Glu Cys Thr Gly Ser Asn Ala Thr
    1085                1090                1095
Tyr His Gly Ala Lys Gly Glu His Thr Ser Arg Lys Asp Ala Met
```

```
              1100                1105                1110
Thr Ala Gln Asn Thr Gly Ile Ser Thr Leu Tyr Arg Asn Ser Tyr
    1115                1120                1125

Gly Ala Pro Ala Glu Asp Ile Lys His Asn Gln Val Ser Ala Gln
    1130                1135                1140

Pro Val Pro Gln Glu Pro Ser Arg Lys Asp Tyr Glu Thr Tyr Gln
    1145                1150                1155

Pro Phe Gln Asn Ser Thr Arg Asn Tyr Asp Glu Ser Phe Phe Glu
    1160                1165                1170

Asp Gln Val His His Arg Pro Pro Ala Ser Glu Tyr Thr Met His
    1175                1180                1185

Leu Gly Leu Lys Ser Thr Gly Asn Tyr Val Asp Phe Tyr Ser Ala
    1190                1195                1200

Ala Arg Pro Tyr Ser Glu Leu Asn Tyr Glu Thr Ser His Tyr Pro
    1205                1210                1215

Ala Ser Pro Asp Ser Trp Val
    1220                1225

<210> SEQ ID NO 75
<211> LENGTH: 1167
<212> TYPE: PRT
<213> ORGANISM: Human

<400> SEQUENCE: 75

Met Phe Ala Arg Lys Pro Pro Gly Ala Ala Pro Leu Gly Ala Met Pro
1               5                   10                  15

Val Pro Asp Gln Pro Ser Ser Ala Ser Glu Lys Thr Ser Ser Leu Ser
            20                  25                  30

Pro Gly Leu Asn Thr Ser Asn Gly Asp Gly Ser Glu Thr Glu Thr Thr
        35                  40                  45

Ser Ala Ile Leu Ala Ser Val Lys Glu Gln Glu Leu Gln Phe Glu Arg
    50                  55                  60

Leu Thr Arg Glu Leu Glu Ala Glu Arg Gln Ile Val Ala Ser Gln Leu
65                  70                  75                  80

Glu Arg Cys Lys Leu Gly Ser Glu Thr Gly Ser Met Ser Ser Met Ser
                85                  90                  95

Ser Ala Glu Glu Gln Phe Gln Trp Gln Ser Gln Asp Gly Gln Lys Asp
            100                 105                 110

Ile Glu Asp Glu Leu Thr Thr Gly Leu Glu Leu Val Asp Ser Cys Ile
        115                 120                 125

Arg Ser Leu Gln Glu Ser Gly Ile Leu Asp Pro Gln Asp Tyr Ser Thr
    130                 135                 140

Gly Glu Arg Pro Ser Leu Leu Ser Gln Ser Ala Leu Gln Leu Asn Ser
145                 150                 155                 160

Lys Pro Glu Gly Ser Phe Gln Tyr Pro Ala Ser Tyr His Ser Asn Gln
                165                 170                 175

Thr Leu Ala Leu Gly Glu Thr Thr Pro Ser Gln Leu Pro Ala Arg Gly
            180                 185                 190

Thr Gln Ala Arg Ala Thr Gly Gln Ser Phe Ser Gln Gly Thr Thr Ser
        195                 200                 205

Arg Ala Gly His Leu Ala Gly Pro Glu Pro Ala Pro Pro Pro Pro
    210                 215                 220

Pro Pro Arg Glu Pro Phe Ala Pro Ser Leu Gly Ser Ala Phe His Leu
225                 230                 235                 240
```

```
Pro Asp Ala Pro Pro Ala Ala Ala Ala Ala Leu Tyr Tyr Ser Ser
            245                 250                 255

Ser Thr Leu Pro Ala Pro Pro Arg Gly Gly Ser Pro Leu Ala Ala Pro
        260                 265                 270

Gln Gly Gly Ser Pro Thr Lys Leu Gln Arg Gly Gly Ser Ala Pro Glu
    275                 280                 285

Gly Ala Thr Tyr Ala Ala Pro Arg Gly Ser Ser Pro Lys Gln Ser Pro
290                 295                 300

Ser Arg Leu Ala Lys Ser Tyr Ser Thr Ser Ser Pro Ile Asn Ile Val
305                 310                 315                 320

Val Ser Ser Ala Gly Leu Ser Pro Ile Arg Val Thr Ser Pro Pro Thr
                325                 330                 335

Val Gln Ser Thr Ile Ser Ser Ser Pro Ile His Gln Leu Ser Ser Thr
            340                 345                 350

Ile Gly Thr Tyr Ala Thr Leu Ser Pro Thr Lys Arg Leu Val His Ala
        355                 360                 365

Ser Glu Gln Tyr Ser Lys His Ser Gln Glu Leu Tyr Ala Thr Ala Thr
    370                 375                 380

Leu Gln Arg Pro Gly Ser Leu Ala Ala Gly Ser Arg Ala Ser Tyr Ser
385                 390                 395                 400

Ser Gln His Gly His Leu Gly Pro Glu Leu Arg Ala Leu Gln Ser Pro
                405                 410                 415

Glu His His Ile Asp Pro Ile Tyr Glu Asp Arg Val Tyr Gln Lys Pro
            420                 425                 430

Pro Met Arg Ser Leu Ser Gln Ser Gln Gly Asp Pro Leu Pro Pro Ala
        435                 440                 445

His Thr Gly Thr Tyr Arg Thr Ser Thr Ala Pro Ser Ser Pro Gly Val
    450                 455                 460

Asp Ser Val Pro Leu Gln Arg Thr Gly Ser Gln His Gly Pro Gln Asn
465                 470                 475                 480

Ala Ala Ala Ala Thr Phe Gln Arg Ala Ser Tyr Ala Ala Gly Pro Ala
                485                 490                 495

Ser Asn Tyr Ala Asp Pro Tyr Arg Gln Leu Gln Tyr Cys Pro Ser Val
            500                 505                 510

Glu Ser Pro Tyr Ser Lys Ser Gly Pro Ala Leu Pro Pro Glu Gly Thr
        515                 520                 525

Leu Ala Arg Ser Pro Ser Ile Asp Ser Ile Gln Lys Asp Pro Arg Glu
    530                 535                 540

Phe Gly Trp Arg Asp Pro Glu Leu Pro Glu Val Ile Gln Met Leu Gln
545                 550                 555                 560

His Gln Phe Pro Ser Val Gln Ser Asn Ala Ala Ala Tyr Leu Gln His
                565                 570                 575

Leu Cys Phe Gly Asp Asn Lys Ile Lys Ala Glu Ile Arg Arg Gln Gly
            580                 585                 590

Gly Ile Gln Leu Leu Val Asp Leu Leu Asp His Arg Met Thr Glu Val
        595                 600                 605

His Arg Ser Ala Cys Gly Ala Leu Arg Asn Leu Val Tyr Gly Lys Ala
    610                 615                 620

Asn Asp Asp Asn Lys Ile Ala Leu Lys Asn Cys Gly Gly Ile Pro Ala
625                 630                 635                 640

Leu Val Arg Leu Leu Arg Lys Thr Thr Asp Leu Glu Ile Arg Glu Leu
                645                 650                 655

Val Thr Gly Val Leu Trp Asn Leu Ser Ser Cys Asp Ala Leu Lys Met
```

-continued

```
                660             665                 670
Pro Ile Ile Gln Asp Ala Leu Ala Val Leu Thr Asn Ala Val Ile Ile
            675             680             685
Pro His Ser Gly Trp Glu Asn Ser Pro Leu Gln Asp Asp Arg Lys Ile
            690             695             700
Gln Leu His Ser Ser Gln Val Leu Arg Asn Ala Thr Gly Cys Leu Arg
705             710             715             720
Asn Val Ser Ser Ala Gly Glu Glu Ala Arg Arg Arg Met Arg Glu Cys
            725             730             735
Asp Gly Leu Thr Asp Ala Leu Leu Tyr Val Ile Gln Ser Ala Leu Gly
            740             745             750
Ser Ser Glu Ile Asp Ser Lys Thr Val Glu Asn Cys Val Cys Ile Leu
            755             760             765
Arg Asn Leu Ser Tyr Arg Leu Ala Ala Glu Thr Ser Gln Gly Gln His
            770             775             780
Met Gly Thr Asp Glu Leu Asp Gly Leu Leu Cys Gly Glu Ala Asn Gly
785             790             795             800
Lys Asp Ala Glu Ser Ser Gly Cys Trp Gly Lys Lys Lys Lys Lys Lys
            805             810             815
Lys Ser Gln Asp Gln Trp Ser Val Tyr Ile Arg Ala Ala Val Arg Lys
            820             825             830
Glu Lys Gly Leu Pro Ile Leu Val Glu Leu Leu Arg Ile Asp Asn Asp
            835             840             845
Arg Val Val Cys Ala Val Ala Thr Ala Leu Arg Asn Met Ala Leu Asp
            850             855             860
Val Arg Asn Lys Glu Leu Ile Gly Lys Tyr Ala Met Arg Asp Leu Val
865             870             875             880
His Arg Leu Pro Gly Gly Asn Asn Ser Asn Asn Thr Ala Ser Lys Ala
            885             890             895
Met Ser Asp Asp Thr Val Thr Ala Val Cys Cys Thr Leu His Glu Val
            900             905             910
Ile Thr Lys Asn Met Glu Asn Ala Lys Ala Leu Arg Asp Ala Gly Gly
            915             920             925
Ile Glu Lys Leu Val Gly Ile Ser Lys Ser Lys Gly Asp Lys His Ser
            930             935             940
Pro Lys Val Val Lys Ala Ala Ser Gln Val Leu Asn Ser Met Trp Gln
945             950             955             960
Tyr Arg Asp Leu Arg Ser Leu Tyr Lys Lys Asp Gly Trp Ser Gln Tyr
            965             970             975
His Phe Val Ala Ser Ser Ser Thr Ile Glu Arg Asp Arg Gln Arg Pro
            980             985             990
Tyr Ser Ser Ser Arg Thr Pro Ser Ile Ser Pro Val Arg Val Ser Pro
            995             1000            1005
Asn Asn Arg Ser Ala Ser Ala Pro Ala Ser Pro Arg Glu Met Ile
            1010            1015            1020
Ser Leu Lys Glu Arg Lys Thr Asp Tyr Glu Cys Thr Gly Ser Asn
            1025            1030            1035
Ala Thr Tyr His Gly Ala Lys Gly Glu His Thr Ser Arg Lys Asp
            1040            1045            1050
Ala Met Thr Ala Gln Asn Thr Gly Ile Ser Thr Leu Tyr Arg Asn
            1055            1060            1065
Ser Tyr Gly Ala Pro Ala Glu Asp Ile Lys His Asn Gln Val Ser
            1070            1075            1080
```

```
Ala Gln Pro Val Pro Gln Glu Pro Ser Arg Lys Asp Tyr Glu Thr
    1085            1090                1095

Tyr Gln Pro Phe Gln Asn Ser Thr Arg Asn Tyr Asp Glu Ser Phe
    1100            1105                1110

Phe Glu Asp Gln Val His His Arg Pro Pro Ala Ser Glu Tyr Thr
    1115            1120                1125

Met His Leu Gly Leu Lys Ser Thr Gly Asn Tyr Val Asp Phe Tyr
    1130            1135                1140

Ser Ala Ala Arg Pro Tyr Ser Glu Leu Asn Tyr Glu Thr Ser His
    1145            1150                1155

Tyr Pro Ala Ser Pro Asp Ser Trp Val
    1160            1165

<210> SEQ ID NO 76
<211> LENGTH: 266
<212> TYPE: PRT
<213> ORGANISM: Human

<400> SEQUENCE: 76

Met Gln Gly Ser Thr Arg Arg Met Gly Val Met Thr Asp Val His Arg
1               5                   10                  15

Arg Phe Leu Gln Leu Leu Met Thr His Gly Val Leu Glu Glu Trp Asp
                20                  25                  30

Val Lys Arg Leu Gln Thr His Cys Tyr Lys Val His Asp Arg Asn Ala
            35                  40                  45

Thr Val Asp Lys Leu Glu Asp Phe Ile Asn Asn Ile Asn Ser Val Leu
        50                  55                  60

Glu Ser Leu Tyr Ile Glu Ile Lys Arg Gly Val Thr Glu Asp Asp Gly
65                  70                  75                  80

Arg Pro Ile Tyr Ala Leu Val Asn Leu Ala Thr Thr Ser Ile Ser Lys
                85                  90                  95

Met Ala Thr Asp Phe Ala Glu Asn Glu Leu Asp Leu Phe Arg Lys Ala
            100                 105                 110

Leu Glu Leu Ile Ile Asp Ser Glu Thr Gly Phe Ala Ser Ser Thr Asn
        115                 120                 125

Ile Leu Asn Leu Val Asp Gln Leu Lys Gly Lys Lys Met Arg Lys Lys
    130                 135                 140

Glu Ala Glu Gln Val Leu Gln Lys Phe Val Gln Asn Lys Trp Leu Ile
145                 150                 155                 160

Glu Lys Glu Gly Glu Phe Thr Leu His Gly Arg Ala Ile Leu Glu Met
                165                 170                 175

Glu Gln Tyr Ile Arg Glu Thr Tyr Pro Asp Ala Val Lys Ile Cys Asn
            180                 185                 190

Ile Cys His Ser Leu Leu Ile Gln Gly Gln Ser Cys Glu Thr Cys Gly
        195                 200                 205

Ile Arg Met His Leu Pro Cys Val Ala Lys Tyr Phe Gln Ser Asn Ala
    210                 215                 220

Glu Pro Arg Cys Pro His Cys Asn Asp Tyr Trp Pro His Glu Ile Pro
225                 230                 235                 240

Lys Val Phe Asp Pro Glu Lys Glu Arg Glu Ser Gly Val Leu Lys Ser
                245                 250                 255

Asn Lys Lys Ser Leu Arg Ser Arg Gln His
            260                 265
```

```
<210> SEQ ID NO 77
<211> LENGTH: 145
<212> TYPE: PRT
<213> ORGANISM: Human

<400> SEQUENCE: 77

Pro Tyr Pro Leu Ala Arg Trp Asp Ala Leu Gly Leu Pro Val Arg Ser
1               5                   10                  15

His Met Gln Gly Ser Thr Arg Arg Met Gly Val Met Thr Asp Val His
            20                  25                  30

Arg Arg Phe Leu Gln Leu Leu Met Thr His Gly Val Leu Glu Glu Trp
        35                  40                  45

Asp Val Lys Arg Leu Gln Thr His Cys Tyr Lys Val His Asp Arg Asn
    50                  55                  60

Ala Thr Val Asp Lys Leu Glu Asp Phe Ile Asn Asn Ile Asn Ser Val
65                  70                  75                  80

Leu Glu Ser Leu Tyr Ile Glu Ile Lys Arg Gly Val Thr Glu Asp Asp
                85                  90                  95

Gly Arg Pro Ile Tyr Ala Leu Val Asn Leu Ala Thr Thr Ser Ile Ser
            100                 105                 110

Lys Met Ala Thr Asp Phe Ala Glu Asn Glu Leu Asp Leu Phe Arg Lys
        115                 120                 125

Ala Leu Glu Leu Ile Ile Asp Ser Glu Thr Leu Arg Leu Pro Gln Thr
    130                 135                 140

Tyr
145

<210> SEQ ID NO 78
<211> LENGTH: 179
<212> TYPE: PRT
<213> ORGANISM: Human

<400> SEQUENCE: 78

Val His Leu Ala Thr Val Ser Ala Ser Ala Ala Trp Asp Ala Leu Gly
1               5                   10                  15

Leu Pro Val Arg Ser His Met Gln Gly Ser Thr Arg Arg Met Gly Val
            20                  25                  30

Met Thr Asp Val His Arg Arg Phe Leu Gln Leu Leu Met Thr His Gly
        35                  40                  45

Val Leu Glu Glu Trp Asp Val Lys Arg Leu Gln Thr His Cys Tyr Lys
    50                  55                  60

Val His Asp Arg Asn Ala Thr Val Asp Lys Leu Glu Asp Phe Ile Asn
65                  70                  75                  80

Asn Ile Asn Ser Val Leu Glu Ser Leu Tyr Ile Glu Ile Lys Arg Gly
                85                  90                  95

Val Thr Glu Asp Asp Gly Arg Pro Ile Tyr Ala Leu Val Asn Leu Ala
            100                 105                 110

Thr Thr Ser Ile Ser Lys Met Ala Thr Asp Phe Ala Glu Asn Glu Leu
        115                 120                 125

Asp Leu Phe Arg Lys Ala Leu Glu Leu Ile Ile Asp Ser Glu Thr Gly
    130                 135                 140

Phe Ala Ser Ser Thr Asn Ile Leu Asn Leu Val Asp Gln Leu Lys Gly
145                 150                 155                 160

Lys Lys Met Arg Lys Lys Glu Ala Arg Cys Cys Arg Ser Leu Phe Lys
                165                 170                 175

Thr Ser Gly
```

<210> SEQ ID NO 79
<211> LENGTH: 392
<212> TYPE: PRT
<213> ORGANISM: Human

<400> SEQUENCE: 79

```
Met Glu Trp Trp Ala Ser Ser Pro Arg Leu Trp Leu Leu Leu Phe
1               5                   10                  15

Leu Leu Pro Ser Ala Gln Gly Arg Gln Lys Glu Ser Gly Ser Lys Trp
                20                  25                  30

Lys Val Phe Ile Asp Gln Ile Asn Arg Ser Leu Glu Asn Tyr Glu Pro
            35                  40                  45

Cys Ser Ser Gln Asn Cys Ser Cys Tyr His Gly Val Ile Glu Glu Asp
        50                  55                  60

Leu Thr Pro Phe Arg Gly Gly Ile Ser Arg Lys Met Met Ala Glu Val
65                  70                  75                  80

Val Arg Arg Lys Leu Gly Thr His Tyr Gln Ile Thr Lys Asn Arg Leu
                85                  90                  95

Tyr Arg Glu Asn Asp Cys Met Phe Pro Ser Arg Cys Ser Gly Val Glu
            100                 105                 110

His Phe Ile Leu Glu Val Ile Gly Arg Leu Pro Asp Met Glu Met Val
        115                 120                 125

Ile Asn Val Arg Asp Tyr Pro Gln Val Pro Lys Trp Met Glu Pro Ala
130                 135                 140

Ile Pro Val Phe Ser Phe Ser Lys Thr Ser Glu Tyr His Asp Ile Met
145                 150                 155                 160

Tyr Pro Ala Trp Thr Phe Trp Glu Gly Gly Pro Ala Val Trp Pro Ile
                165                 170                 175

Tyr Pro Thr Gly Leu Gly Arg Trp Asp Leu Phe Arg Glu Asp Leu Val
            180                 185                 190

Arg Ser Ala Ala Gln Trp Pro Trp Lys Lys Asn Ser Thr Ala Tyr
        195                 200                 205

Phe Arg Gly Ser Arg Thr Ser Pro Glu Arg Asp Pro Leu Ile Leu Leu
    210                 215                 220

Ser Arg Lys Asn Pro Lys Leu Val Asp Ala Glu Tyr Thr Lys Asn Gln
225                 230                 235                 240

Ala Trp Lys Ser Met Lys Asp Thr Leu Gly Lys Pro Ala Ala Lys Asp
                245                 250                 255

Val His Leu Val Asp His Cys Lys Tyr Lys Tyr Leu Phe Asn Phe Arg
            260                 265                 270

Gly Val Ala Ala Ser Phe Arg Phe Lys His Leu Phe Leu Cys Gly Ser
        275                 280                 285

Leu Val Phe His Val Gly Asp Glu Trp Leu Glu Phe Phe Tyr Pro Gln
    290                 295                 300

Leu Lys Pro Trp Val His Tyr Ile Pro Val Lys Thr Asp Leu Ser Asn
305                 310                 315                 320

Val Gln Glu Leu Leu Gln Phe Val Lys Ala Asn Asp Asp Val Ala Gln
                325                 330                 335

Glu Ile Ala Glu Arg Gly Ser Gln Phe Ile Arg Asn His Leu Gln Met
            340                 345                 350

Asp Asp Ile Thr Cys Tyr Trp Glu Asn Leu Leu Ser Glu Tyr Ser Lys
        355                 360                 365

Phe Leu Ser Tyr Asn Val Thr Arg Arg Lys Gly Tyr Asp Gln Ile Ile
```

```
              370                 375                 380
Pro Lys Met Leu Lys Thr Glu Leu
385                 390

<210> SEQ ID NO 80
<211> LENGTH: 411
<212> TYPE: PRT
<213> ORGANISM: Human

<400> SEQUENCE: 80

Met Arg Arg Arg Arg Ala Gly Gly Arg Thr Met Val Glu Arg Ala Ser
1               5                   10                  15

Lys Phe Val Leu Val Val Ala Gly Ser Val Cys Phe Met Leu Ile Leu
            20                  25                  30

Tyr Gln Tyr Ala Gly Pro Gly Leu Ser Leu Gly Ala Pro Gly Gly Arg
        35                  40                  45

Ala Pro Pro Asp Asp Leu Asp Leu Phe Pro Thr Pro Asp Pro His Tyr
    50                  55                  60

Glu Lys Lys Tyr Tyr Phe Pro Val Arg Glu Leu Glu Arg Ser Leu Arg
65                  70                  75                  80

Phe Asp Met Lys Gly Asp Asp Val Ile Val Phe Leu His Ile Gln Lys
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
        115                 120                 125

Arg Pro Asn Arg Arg Glu Thr Trp Leu Phe Ser Arg Phe Ser Thr Gly
    130                 135                 140

Trp Ser Cys Gly Leu His Ala Asp Trp Thr Glu Leu Thr Asn Cys Val
145                 150                 155                 160

Pro Gly Val Leu Asp Arg Arg Asp Ser Ala Ala Leu Arg Thr Pro Arg
                165                 170                 175

Lys Phe Tyr Tyr Ile Thr Leu Leu Arg Asp Pro Val Ser Arg Tyr Leu
            180                 185                 190

Ser Glu Trp Arg His Val Gln Arg Gly Ala Thr Trp Lys Thr Ser Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                245                 250                 255

Leu Ser Leu Val Gly Cys Tyr Asn Leu Ser Phe Ile Pro Glu Gly Lys
            260                 265                 270

Arg Ala Gln Leu Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Asp Glu Asp Thr Ile Arg Arg
                325                 330                 335

Ile Glu Glu Leu Asn Asp Leu Asp Met Gln Leu Tyr Asp Tyr Ala Lys
            340                 345                 350
```

```
Asp Leu Phe Gln Gln Arg Tyr Gln Tyr Lys Arg Gln Leu Glu Arg Arg
            355                 360                 365

Glu Gln Arg Leu Arg Ser Arg Glu Glu Arg Leu Leu His Arg Ala Lys
        370                 375                 380

Glu Ala Leu Pro Arg Glu Asp Ala Asp Glu Pro Gly Arg Val Pro Thr
385                 390                 395                 400

Glu Asp Tyr Met Ser His Ile Ile Glu Lys Trp
                405                 410

<210> SEQ ID NO 81
<211> LENGTH: 464
<212> TYPE: PRT
<213> ORGANISM: Human

<400> SEQUENCE: 81

Met Thr Ser Cys Arg Cys Ser Val Thr Ser Arg Ser Leu Trp Pro Ala
1               5                   10                  15

Leu Ala Pro Arg Arg Cys Gln His Thr Ser Pro Ala Ser Ala Gln Cys
            20                  25                  30

Lys Gln Asp Lys Ala Cys Arg Phe Leu Ala Ala Gln Lys Gly Ala Tyr
        35                  40                  45

Pro Ile Ile Phe Thr Ala Trp Lys Leu Ala Thr Ala Gly Asp Gln Gly
    50                  55                  60

Leu Leu Leu Gln Ser Leu Asn Ala Leu Ser Val Leu Thr Asp Gly Gln
65                  70                  75                  80

Pro Asp Leu Leu Asp Ala Gln Gly Leu Gln Leu Leu Val Ala Thr Leu
                85                  90                  95

Thr Gln Asn Ala Asp Glu Ala Asp Leu Thr Cys Ser Gly Ile Arg Cys
            100                 105                 110

Val Arg His Ala Cys Leu Lys His Glu Gln Asn Arg Gln Asp Leu Val
        115                 120                 125

Lys Ala Gly Val Leu Pro Leu Leu Thr Gly Ala Ile Thr His His Gly
    130                 135                 140

His His Thr Asp Val Val Arg Glu Ala Cys Trp Ala Leu Arg Val Met
145                 150                 155                 160

Thr Phe Asp Asp Asp Ile Arg Val Pro Phe Gly His Ala His Asn His
                165                 170                 175

Ala Lys Met Ile Val Gln Glu Asn Lys Gly Leu Lys Val Leu Ile Glu
            180                 185                 190

Ala Thr Lys Ala Phe Leu Asp Asn Pro Gly Ile Leu Ser Glu Leu Cys
        195                 200                 205

Gly Thr Leu Ser Arg Leu Ala Ile Arg Asn Glu Phe Cys Gln Glu Val
    210                 215                 220

Val Asp Leu Gly Gly Leu Ser Ile Leu Val Ser Leu Leu Ala Asp Cys
225                 230                 235                 240

Asn Asp His Gln Met Arg Asp Gln Ser Gly Val Gln Glu Leu Val Lys
                245                 250                 255

Gln Val Leu Ser Thr Leu Arg Ala Ile Ala Gly Asn Asp Asp Val Lys
            260                 265                 270

Asp Ala Ile Val Arg Ala Gly Gly Thr Glu Ser Ile Val Ala Ala Met
        275                 280                 285

Thr Gln His Leu Thr Ser Pro Gln Val Cys Glu Gln Ser Cys Ala Ala
    290                 295                 300

Leu Cys Phe Leu Ala Leu Arg Lys Pro Asp Asn Ser Arg Ile Ile Val
305                 310                 315                 320
```

```
Glu Gly Gly Gly Ala Ala Leu Gln Ala Met Lys Ala His Pro
            325                 330                 335

Gln Lys Ala Gly Val Gln Lys Gln Ala Cys Met Leu Ile Arg Asn Leu
            340                 345                 350

Val Ala His Arg Pro Ser Arg Ser Pro Ser Trp Thr Trp Gly Leu Arg
            355                 360                 365

His Ser Ser Cys Arg Pro Asp Leu Pro Thr Val Thr Val Arg Thr Trp
            370                 375                 380

Pro Arg Pro Pro Cys Gly Thr Trp Val Val Met Ser Ser Ser Glu Ser
385                 390                 395                 400

Cys Gly Gln Ala Arg Gly Ala Thr Trp Arg His Asp Pro Arg Pro Ser
            405                 410                 415

Leu Val Thr Leu Gly Glu Ser Cys Asp Ser Gly Met Gly Val Asp Pro
            420                 425                 430

Cys Pro Pro Leu Ser Pro Ile Ser Ser Val Pro Phe Thr Met Arg Ser
            435                 440                 445

Val Phe Trp Gln Ala Leu Gly Lys Gly Ser Gly Glu Gly Gly Ala Leu
            450                 455                 460

<210> SEQ ID NO 82
<211> LENGTH: 501
<212> TYPE: PRT
<213> ORGANISM: Human

<400> SEQUENCE: 82

Met Ser Glu Arg Cys Cys Ser Arg Tyr Ser Ser Gly Ala Ser Ile Gly
1               5                   10                  15

Cys Thr Pro Thr Ser Thr Gln Ala Lys Met Val Ser Lys Arg Ile Ala
            20                  25                  30

Gln Glu Thr Phe Asp Ala Ala Val Arg Glu Asn Ile Glu Glu Phe Ala
            35                  40                  45

Met Gly Pro Glu Glu Ala Val Lys Glu Ala Val Glu Gln Phe Glu Ser
        50                  55                  60

Gln Gly Val Asp Leu Ser Asn Ile Val Lys Thr Ala Pro Lys Val Ser
65                  70                  75                  80

Ala Asp Gly Ser Gln Glu Pro Thr His Asp Ile Leu Gln Met Leu Ser
                85                  90                  95

Asp Leu Gln Glu Ser Val Ala Ser Ser Arg Pro Gln Glu Val Ser Ala
            100                 105                 110

Tyr Leu Thr Arg Phe Cys Asp Gln Cys Lys Gln Asp Lys Ala Cys Arg
            115                 120                 125

Phe Leu Ala Ala Gln Lys Gly Ala Tyr Pro Ile Ile Phe Thr Ala Trp
        130                 135                 140

Lys Leu Ala Thr Ala Gly Asp Gln Gly Leu Leu Gln Ser Leu Asn
145                 150                 155                 160

Ala Leu Ser Val Leu Thr Asp Gly Gln Pro Asp Leu Leu Asp Ala Gln
                165                 170                 175

Gly Leu Gln Leu Leu Val Ala Thr Leu Thr Gln Asn Ala Asp Glu Ala
            180                 185                 190

Asp Leu Thr Cys Ser Gly Ile Arg Cys Val Arg His Ala Cys Leu Lys
            195                 200                 205

His Glu Gln Asn Arg Gln Asp Leu Val Lys Ala Gly Val Leu Pro Leu
        210                 215                 220

Leu Thr Gly Ala Ile Thr His His Gly His His Thr Asp Val Val Arg
```

```
                225                 230                 235                 240
        Glu Ala Cys Trp Ala Leu Arg Val Met Thr Phe Asp Asp Ile Arg
                            245                 250                 255

Val Pro Phe Gly His Ala His Asn His Ala Lys Met Ile Val Gln Glu
                        260                 265                 270

Asn Lys Gly Leu Lys Val Leu Ile Glu Ala Thr Lys Ala Phe Leu Asp
                        275                 280                 285

Asn Pro Gly Ile Leu Ser Glu Leu Cys Gly Thr Leu Ser Arg Leu Ala
                        290                 295                 300

Ile Arg Asn Glu Phe Cys Gln Glu Val Val Asp Leu Gly Gly Leu Ser
        305                 310                 315                 320

Ile Leu Val Ser Leu Leu Ala Asp Cys Asn Asp His Gln Met Arg Asp
                        325                 330                 335

Gln Ser Gly Val Gln Glu Leu Val Lys Gln Val Leu Ser Thr Leu Arg
                        340                 345                 350

Ala Ile Ala Gly Asn Asp Asp Val Lys Asp Ala Ile Val Arg Ala Gly
                        355                 360                 365

Gly Thr Glu Ser Ile Val Ala Ala Met Thr Gln His Leu Thr Ser Pro
                    370                 375                 380

Gln Val Cys Glu Gln Ser Cys Ala Ala Leu Cys Phe Leu Ala Leu Arg
        385                 390                 395                 400

Lys Pro Asp Asn Ser Arg Ile Ile Val Glu Gly Gly Ala Val Ala
                        405                 410                 415

Ala Leu Gln Ala Met Lys Ala His Pro Gln Lys Ala Gly Val Gln Lys
                        420                 425                 430

Gln Ala Cys Met Leu Ile Arg Asn Leu Val Ala His Gly Gln Ala Phe
                        435                 440                 445

Ser Lys Pro Ile Leu Asp Leu Gly Ala Glu Ala Leu Ile Met Gln Ala
                        450                 455                 460

Arg Ser Ala His Arg Asp Cys Glu Asp Val Ala Lys Ala Ala Leu Arg
        465                 470                 475                 480

Asp Leu Gly Cys His Val Glu Leu Arg Glu Leu Trp Thr Gly Gln Arg
                        485                 490                 495

Gly Asn Leu Ala Pro
                        500

<210> SEQ ID NO 83
<211> LENGTH: 476
<212> TYPE: PRT
<213> ORGANISM: Human

<400> SEQUENCE: 83

Met Val Ser Lys Arg Ile Ala Gln Glu Thr Phe Asp Ala Ala Val Arg
1               5                   10                  15

Glu Asn Ile Glu Glu Phe Ala Met Gly Pro Glu Glu Ala Val Lys Glu
                20                  25                  30

Ala Val Glu Gln Phe Glu Ser Gln Gly Val Asp Leu Ser Asn Ile Val
            35                  40                  45

Lys Thr Ala Pro Lys Val Ser Ala Asp Gly Ser Gln Glu Pro Thr His
        50                  55                  60

Asp Ile Leu Gln Met Leu Ser Asp Leu Gln Glu Ser Val Ala Ser Ser
65                  70                  75                  80

Arg Pro Gln Glu Val Ser Ala Tyr Leu Thr Arg Phe Cys Asp Gln Cys
                85                  90                  95
```

Lys Gln Asp Lys Ala Cys Arg Phe Leu Ala Ala Gln Lys Gly Ala Tyr
            100                 105                 110

Pro Ile Ile Phe Thr Ala Trp Lys Leu Ala Thr Ala Gly Asp Gln Gly
        115                 120                 125

Leu Leu Leu Gln Ser Leu Asn Ala Leu Ser Val Leu Thr Asp Gly Gln
    130                 135                 140

Pro Asp Leu Leu Asp Ala Gln Gly Leu Gln Leu Leu Val Ala Thr Leu
145                 150                 155                 160

Thr Gln Asn Ala Asp Glu Ala Asp Leu Thr Cys Ser Gly Ile Arg Cys
                165                 170                 175

Val Arg His Ala Cys Leu Lys His Glu Gln Asn Arg Gln Asp Leu Val
            180                 185                 190

Lys Ala Gly Val Leu Pro Leu Leu Thr Gly Ala Ile Thr His His Gly
        195                 200                 205

His His Thr Asp Val Val Arg Glu Ala Cys Trp Ala Leu Arg Val Met
    210                 215                 220

Thr Phe Asp Asp Ile Arg Val Pro Phe Gly His Ala His Asn His
225                 230                 235                 240

Ala Lys Met Ile Val Gln Glu Asn Lys Gly Leu Lys Val Leu Ile Glu
                245                 250                 255

Ala Thr Lys Ala Phe Leu Asp Asn Pro Gly Ile Leu Ser Glu Leu Cys
            260                 265                 270

Gly Thr Leu Ser Arg Leu Ala Ile Arg Asn Glu Phe Cys Gln Glu Val
        275                 280                 285

Val Asp Leu Gly Gly Leu Ser Ile Leu Val Ser Leu Leu Ala Asp Cys
    290                 295                 300

Asn Asp His Gln Met Arg Asp Gln Ser Gly Val Gln Glu Leu Val Lys
305                 310                 315                 320

Gln Val Leu Ser Thr Leu Arg Ala Ile Ala Gly Asn Asp Asp Val Lys
                325                 330                 335

Asp Ala Ile Val Arg Ala Gly Gly Thr Glu Ser Ile Val Ala Ala Met
            340                 345                 350

Thr Gln His Leu Thr Ser Pro Gln Val Cys Glu Gln Ser Cys Ala Ala
        355                 360                 365

Leu Cys Phe Leu Ala Leu Arg Lys Pro Asp Asn Ser Arg Ile Ile Val
    370                 375                 380

Glu Gly Gly Gly Ala Val Ala Ala Leu Gln Ala Met Lys Ala His Pro
385                 390                 395                 400

Gln Lys Ala Gly Val Gln Lys Gln Ala Cys Met Leu Ile Arg Asn Leu
                405                 410                 415

Val Ala His Gly Gln Ala Phe Ser Lys Pro Ile Leu Asp Leu Gly Ala
            420                 425                 430

Glu Ala Leu Ile Met Gln Ala Arg Ser Ala His Arg Asp Cys Glu Asp
        435                 440                 445

Val Ala Lys Ala Ala Leu Arg Asp Leu Gly Cys His Val Glu Leu Arg
    450                 455                 460

Glu Leu Trp Thr Gly Gln Arg Gly Asn Leu Ala Pro
465                 470                 475

<210> SEQ ID NO 84
<211> LENGTH: 476
<212> TYPE: PRT
<213> ORGANISM: Human

<400> SEQUENCE: 84

```
Met Val Ser Lys Arg Ile Ala Gln Glu Thr Phe Asp Ala Val Arg
1               5                   10                  15

Glu Asn Ile Glu Glu Phe Ala Met Gly Pro Glu Ala Val Lys Glu
            20                  25                  30

Ala Val Glu Gln Phe Glu Ser Gln Gly Val Asp Leu Ser Asn Ile Val
        35                  40                  45

Lys Thr Ala Pro Lys Val Ser Ala Asp Gly Ser Gln Glu Pro Thr His
    50                  55                  60

Asp Ile Leu Gln Met Leu Ser Asp Leu Gln Glu Ser Val Ala Ser Ser
65                  70                  75                  80

Arg Pro Gln Glu Val Ser Ala Tyr Leu Thr Arg Phe Cys Asp Gln Cys
                85                  90                  95

Lys Gln Asp Lys Ala Cys Arg Phe Leu Ala Ala Gln Lys Gly Ala Tyr
            100                 105                 110

Pro Ile Ile Phe Thr Ala Trp Lys Leu Ala Thr Ala Gly Asp Gln Gly
        115                 120                 125

Leu Leu Leu Gln Ser Leu Asn Ala Leu Ser Val Leu Thr Asp Gly Gln
    130                 135                 140

Pro Asp Leu Leu Asp Ala Gln Gly Leu Gln Leu Leu Val Ala Thr Leu
145                 150                 155                 160

Thr Gln Asn Ala Asp Glu Ala Asp Leu Thr Cys Ser Gly Ile Arg Cys
                165                 170                 175

Val Arg His Ala Cys Leu Lys His Glu Gln Asn Arg Gln Asp Leu Val
            180                 185                 190

Lys Ala Gly Val Leu Pro Leu Leu Thr Gly Ala Ile Thr His His Gly
        195                 200                 205

His His Thr Asp Val Val Arg Glu Ala Cys Trp Ala Leu Arg Val Met
    210                 215                 220

Thr Phe Asp Asp Asp Ile Arg Val Pro Phe Gly His Ala His Asn His
225                 230                 235                 240

Ala Lys Met Ile Val Gln Glu Asn Lys Gly Leu Lys Val Leu Ile Glu
                245                 250                 255

Ala Thr Lys Ala Phe Leu Asp Asn Pro Gly Ile Leu Ser Glu Leu Cys
            260                 265                 270

Gly Thr Leu Ser Arg Leu Ala Ile Arg Asn Glu Phe Cys Gln Glu Val
        275                 280                 285

Val Asp Leu Gly Gly Leu Ser Ile Leu Val Ser Leu Leu Ala Asp Cys
    290                 295                 300

Asn Asp His Gln Met Arg Asp Gln Ser Gly Val Gln Glu Leu Val Lys
305                 310                 315                 320

Gln Val Leu Ser Thr Leu Arg Ala Ile Ala Gly Asn Asp Asp Val Lys
                325                 330                 335

Asp Ala Ile Val Arg Ala Gly Gly Thr Glu Ser Ile Val Ala Ala Met
            340                 345                 350

Thr Gln His Leu Thr Ser Pro Gln Val Cys Glu Gln Ser Cys Ala Ala
        355                 360                 365

Leu Cys Phe Leu Ala Leu Arg Lys Pro Asp Asn Ser Arg Ile Ile Val
    370                 375                 380

Glu Gly Gly Gly Ala Val Ala Ala Leu Gln Ala Met Lys Ala His Pro
385                 390                 395                 400

Gln Lys Ala Gly Val Gln Lys Gln Ala Cys Met Leu Ile Arg Asn Leu
                405                 410                 415
```

```
Val Ala His Gly Gln Ala Phe Ser Lys Pro Ile Leu Asp Leu Gly Ala
            420                 425                 430

Glu Ala Leu Ile Met Gln Ala Arg Ser Ala His Arg Asp Cys Glu Asp
        435                 440                 445

Val Ala Lys Ala Ala Leu Arg Asp Leu Gly Cys His Val Glu Leu Arg
450                 455                 460

Glu Leu Trp Thr Gly Gln Arg Gly Asn Leu Ala Pro
465                 470                 475

<210> SEQ ID NO 85
<211> LENGTH: 590
<212> TYPE: PRT
<213> ORGANISM: Human

<400> SEQUENCE: 85

Met Ala Gly Ala Val Pro Gly Ala Ile Met Asp Glu Asp Tyr Tyr Gly
1               5                   10                  15

Ser Ala Ala Glu Trp Gly Asp Glu Ala Asp Gly Gly Gln Gln Glu Asp
            20                  25                  30

Asp Ser Gly Glu Gly Glu Asp Ala Glu Val Gln Gln Glu Cys Leu
        35                  40                  45

His Lys Phe Ser Thr Arg Asp Tyr Ile Met Glu Pro Ser Ile Phe Asn
    50                  55                  60

Thr Leu Lys Arg Tyr Phe Gln Ala Gly Gly Ser Pro Glu Asn Val Ile
65                  70                  75                  80

Gln Leu Leu Ser Glu Asn Tyr Thr Ala Val Ala Gln Thr Val Asn Leu
                85                  90                  95

Leu Ala Glu Trp Leu Ile Gln Thr Gly Val Glu Pro Val Gln Val Gln
            100                 105                 110

Glu Thr Val Glu Asn His Leu Lys Ser Leu Leu Ile Lys His Phe Asp
        115                 120                 125

Pro Arg Lys Ala Asp Ser Ile Phe Thr Glu Glu Gly Glu Thr Pro Ala
    130                 135                 140

Trp Leu Glu Gln Met Ile Ala His Thr Thr Trp Arg Asp Leu Phe Tyr
145                 150                 155                 160

Lys Leu Ala Glu Ala His Pro Asp Cys Leu Met Leu Asn Phe Thr Val
                165                 170                 175

Lys Leu Ile Ser Asp Ala Gly Tyr Gln Gly Glu Ile Thr Ser Val Ser
            180                 185                 190

Thr Ala Cys Gln Gln Leu Glu Val Phe Ser Arg Val Leu Arg Thr Ser
        195                 200                 205

Leu Ala Thr Ile Leu Asp Gly Gly Glu Glu Asn Leu Glu Lys Asn Leu
    210                 215                 220

Pro Glu Phe Ala Lys Met Val Cys His Gly His Thr Tyr Leu Phe
225                 230                 235                 240

Ala Gln Ala Met Met Ser Val Leu Ala Gln Glu Glu Gln Gly Gly Ser
                245                 250                 255

Ala Val Arg Arg Ile Ala Gln Glu Val Gln Arg Phe Ala Gln Glu Lys
            260                 265                 270

Gly His Asp Ala Ser Gln Ile Thr Leu Ala Leu Gly Thr Ala Ala Ser
        275                 280                 285

Tyr Pro Arg Ala Cys Gln Ala Leu Gly Ala Met Leu Ser Lys Gly Ala
    290                 295                 300

Leu Asn Pro Ala Asp Ile Thr Val Leu Phe Lys Met Phe Thr Ser Met
305                 310                 315                 320
```

```
Asp Pro Pro Val Glu Leu Ile Arg Val Pro Ala Phe Leu Asp Leu
            325                 330                 335

Phe Met Gln Ser Leu Phe Lys Pro Gly Ala Arg Ile Asn Gln Asp His
            340                 345                 350

Lys His Lys Tyr Ile His Ile Leu Ala Tyr Ala Ala Ser Val Val Glu
            355                 360                 365

Thr Trp Lys Lys Asn Lys Arg Val Ser Ile Asn Lys Asp Glu Leu Lys
            370                 375                 380

Ser Thr Ser Lys Ala Val Glu Thr Val His Asn Leu Cys Cys Asn Glu
385                 390                 395                 400

Asn Lys Gly Ala Ser Glu Leu Val Ala Glu Leu Ser Thr Leu Tyr Gln
            405                 410                 415

Cys Ile Arg Phe Pro Val Val Ala Met Gly Val Leu Lys Trp Val Asp
            420                 425                 430

Trp Thr Val Ser Glu Pro Arg Tyr Phe Gln Leu Gln Thr Asp His Thr
            435                 440                 445

Pro Val His Leu Ala Leu Leu Asp Glu Ile Ser Thr Cys His Gln Leu
            450                 455                 460

Leu His Pro Gln Val Leu Gln Leu Leu Val Lys Leu Phe Glu Thr Glu
465                 470                 475                 480

His Ser Gln Leu Asp Val Met Glu Gln Leu Glu Leu Lys Lys Thr Leu
            485                 490                 495

Leu Asp Arg Met Val His Leu Ser Arg Gly Tyr Val Leu Pro Val
            500                 505                 510

Val Ser Tyr Ile Arg Lys Cys Leu Glu Lys Leu Asp Thr Asp Ile Ser
            515                 520                 525

Leu Ile Arg Tyr Phe Val Thr Glu Val Leu Asp Val Ile Ala Pro Pro
            530                 535                 540

Tyr Thr Ser Asp Phe Val Gln Leu Phe Leu Pro Ile Leu Glu Asn Asp
545                 550                 555                 560

Ser Ile Ala Gly Thr Ile Lys Thr Glu Gly Glu His Asp Pro Val Thr
            565                 570                 575

Glu Phe Ile Ala His Cys Lys Ser Asn Phe Ile Met Val Asn
            580                 585                 590

<210> SEQ ID NO 86
<211> LENGTH: 250
<212> TYPE: PRT
<213> ORGANISM: Human

<400> SEQUENCE: 86

Met Ala Met Leu Arg Val Gln Pro Glu Ala Gln Ala Lys Val Asp Val
1               5                   10                  15

Phe Arg Glu Asp Leu Cys Thr Lys Thr Glu Asn Leu Leu Gly Ser Tyr
            20                  25                  30

Phe Pro Lys Lys Ile Ser Glu Leu Asp Ala Phe Leu Lys Glu Pro Ala
            35                  40                  45

Leu Asn Glu Ala Asn Leu Ser Asn Leu Lys Ala Pro Leu Asp Ile Pro
        50                  55                  60

Val Pro Asp Pro Val Lys Glu Lys Glu Lys Glu Arg Lys Lys Gln
65                  70                  75                  80

Gln Glu Lys Glu Asp Lys Asp Glu Lys Lys Gly Glu Asp Glu Asp
            85                  90                  95

Lys Gly Pro Pro Cys Gly Pro Val Asn Cys Asn Glu Lys Ile Val Val
```

```
                100                 105                 110
Leu Leu Gln Arg Leu Lys Pro Glu Ile Lys Asp Val Ile Glu Gln Leu
            115                 120                 125

Asn Leu Val Thr Thr Trp Leu Gln Leu Gln Ile Pro Arg Ile Glu Asp
        130                 135                 140

Gly Asn Asn Phe Gly Val Ala Val Gln Glu Lys Val Phe Glu Leu Met
145                 150                 155                 160

Thr Ser Leu His Thr Lys Leu Glu Gly Phe His Thr Gln Ile Ser Lys
                165                 170                 175

Tyr Phe Ser Glu Arg Gly Asp Ala Val Thr Lys Ala Ala Lys Gln Pro
            180                 185                 190

His Val Gly Asp Tyr Arg Gln Leu Val His Glu Leu Asp Glu Ala Glu
        195                 200                 205

Tyr Arg Asp Ile Arg Leu Met Val Met Glu Ile Arg Asn Ala Tyr Val
    210                 215                 220

Arg Arg Gln Gly Gln Gly Arg Gly Gln Arg Gln Leu Ser Gln Ala
225                 230                 235                 240

Thr His Ser Leu Thr Leu Gln Ala Arg Gly
                245                 250

<210> SEQ ID NO 87
<211> LENGTH: 249
<212> TYPE: PRT
<213> ORGANISM: Human

<400> SEQUENCE: 87

Met Ala Met Leu Arg Val Gln Pro Glu Ala Gln Ala Lys Val Asp Val
1               5                   10                  15

Phe Arg Glu Asp Leu Cys Thr Lys Thr Glu Asn Leu Leu Gly Ser Tyr
            20                  25                  30

Phe Pro Lys Lys Ile Ser Glu Leu Asp Ala Phe Leu Lys Glu Pro Ala
        35                  40                  45

Leu Asn Glu Ala Asn Leu Ser Asn Leu Lys Ala Pro Leu Asp Ile Pro
    50                  55                  60

Val Pro Asp Pro Val Lys Glu Lys Glu Lys Glu Glu Arg Lys Lys Gln
65                  70                  75                  80

Gln Glu Lys Glu Asp Lys Asp Glu Lys Lys Gly Glu Asp Glu Asp
                85                  90                  95

Lys Gly Pro Pro Cys Gly Pro Val Asn Cys Asn Glu Lys Ile Val Val
            100                 105                 110

Leu Leu Gln Arg Leu Lys Pro Glu Ile Lys Asp Val Ile Glu Gln Leu
            115                 120                 125

Asn Leu Val Thr Thr Trp Leu Gln Leu Gln Ile Pro Arg Ile Glu Asp
        130                 135                 140

Gly Asn Asn Phe Gly Val Ala Val Gln Glu Lys Val Phe Glu Leu Met
145                 150                 155                 160

Thr Ser Leu His Thr Lys Leu Glu Gly Phe His Thr Gln Ile Ser Lys
                165                 170                 175

Tyr Phe Ser Glu Arg Gly Asp Ala Val Thr Lys Ala Ala Lys Gln Pro
            180                 185                 190

His Val Gly Asp Tyr Arg Gln Leu Val His Glu Leu Asp Glu Ala Glu
        195                 200                 205

Tyr Arg Asp Ile Arg Leu Met Val Met Glu Ile Arg Asn Ala Tyr Ala
    210                 215                 220
```

```
Val Leu Tyr Asp Ile Ile Leu Lys Asn Phe Glu Lys Leu Lys Lys Pro
225                 230                 235                 240

Arg Gly Glu Thr Lys Gly Met Ile Tyr
                245

<210> SEQ ID NO 88
<211> LENGTH: 558
<212> TYPE: PRT
<213> ORGANISM: Human

<400> SEQUENCE: 88

Met Glu Leu Arg Ala Arg Gly Trp Trp Leu Leu Cys Ala Ala Ala Ala
1               5                   10                  15

Leu Val Ala Cys Ala Arg Gly Asp Pro Ala Ser Lys Ser Arg Ser Cys
            20                  25                  30

Gly Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
    50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
    130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Glu Ala Pro Arg Glu
        195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
                245                 250                 255

Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
        275                 280                 285

Glu Trp Arg Asn Leu Leu Asp Ser Met Val Leu Ile Thr Asp Lys Phe
    290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350
```

```
Pro Gly Pro Glu Glu Lys Arg Arg Gly Lys Leu Ala Pro Arg Glu
        355                 360                 365

Arg Pro Pro Ser Gly Thr Leu Glu Lys Leu Val Ser Glu Ala Lys Ala
    370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Asp Arg Cys Trp
                405                 410                 415

Asn Gly Met Ala Arg Gly Arg Tyr Leu Pro Glu Val Met Gly Asp Gly
                420                 425                 430

Leu Ala Asn Gln Ile Asn Asn Pro Glu Val Glu Val Asp Ile Thr Lys
            435                 440                 445

Pro Asp Met Thr Ile Arg Gln Gln Ile Met Gln Leu Lys Ile Met Thr
        450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Asp Gly Cys Leu Asp
                485                 490                 495

Asp Leu Cys Ser Arg Lys Val Ser Arg Lys Ser Ser Ser Arg Thr
                500                 505                 510

Pro Leu Thr His Ala Leu Pro Gly Leu Ser Glu Gln Glu Gly Gln Lys
            515                 520                 525

Thr Ser Ala Ala Ser Cys Pro Gln Pro Pro Thr Phe Leu Leu Pro Leu
    530                 535                 540

Leu Leu Phe Leu Ala Leu Thr Val Ala Arg Pro Arg Trp Arg
545                 550                 555

<210> SEQ ID NO 89
<211> LENGTH: 1214
<212> TYPE: PRT
<213> ORGANISM: Human

<400> SEQUENCE: 89

Met Ala Ser Cys Ala Ser Ile Asp Ile Glu Asp Ala Thr Gln His Leu
1               5                   10                  15

Arg Asp Ile Leu Lys Leu Asp Arg Pro Ala Gly Gly Pro Ser Ala Glu
            20                  25                  30

Ser Pro Arg Pro Ser Ser Ala Tyr Asn Gly Asp Leu Asn Gly Leu Leu
        35                  40                  45

Val Pro Asp Pro Leu Cys Ser Gly Asp Ser Thr Ser Ala Asn Lys Thr
    50                  55                  60

Gly Leu Arg Thr Met Pro Pro Ile Asn Leu Gln Glu Lys Gln Val Ile
65                  70                  75                  80

Cys Leu Ser Gly Asp Asp Ser Ser Thr Cys Ile Gly Ile Leu Ala Lys
                85                  90                  95

Glu Val Glu Ile Val Ala Ser Ser Asp Ser Ser Ile Ser Ser Lys Ala
            100                 105                 110

Arg Gly Ser Asn Lys Val Lys Ile Gln Pro Val Ala Lys Tyr Asp Trp
        115                 120                 125

Glu Gln Lys Tyr Tyr Tyr Gly Asn Leu Ile Ala Val Ser Asn Ser Phe
    130                 135                 140

Leu Ala Tyr Ala Ile Arg Ala Ala Asn Asn Gly Ser Ala Met Val Arg
145                 150                 155                 160

Val Ile Ser Val Ser Thr Ser Glu Arg Thr Leu Leu Lys Gly Phe Thr
```

-continued

```
                165                 170                 175
Gly Ser Val Ala Asp Leu Ala Phe Ala His Leu Asn Ser Pro Gln Leu
            180                 185                 190
Ala Cys Leu Asp Glu Ala Gly Asn Leu Phe Val Trp Arg Leu Ala Leu
            195                 200                 205
Val Asn Gly Lys Ile Gln Glu Ile Leu Val His Ile Arg Gln Pro
            210                 215                 220
Glu Gly Thr Pro Leu Asn His Phe Arg Arg Ile Ile Trp Cys Pro Phe
225                 230                 235                 240
Ile Pro Glu Glu Ser Glu Asp Cys Cys Glu Ser Ser Pro Thr Val
                245                 250                 255
Ala Leu Leu His Glu Asp Arg Ala Glu Val Trp Asp Leu Asp Met Leu
            260                 265                 270
Arg Ser Ser His Ser Thr Trp Pro Val Asp Val Ser Gln Ile Lys Gln
            275                 280                 285
Gly Phe Ile Val Val Lys Gly His Ser Thr Cys Leu Ser Glu Gly Ala
            290                 295                 300
Leu Ser Pro Asp Gly Thr Val Leu Ala Thr Ala Ser His Asp Gly Tyr
305                 310                 315                 320
Val Lys Phe Trp Gln Ile Tyr Ile Glu Gly Gln Asp Glu Pro Arg Cys
            325                 330                 335
Leu His Glu Trp Lys Pro His Asp Gly Arg Pro Leu Ser Cys Leu Leu
            340                 345                 350
Phe Cys Asp Asn His Lys Lys Gln Asp Pro Asp Val Pro Phe Trp Arg
            355                 360                 365
Phe Leu Ile Thr Gly Ala Asp Gln Asn Arg Glu Leu Lys Met Trp Cys
            370                 375                 380
Thr Val Ser Trp Thr Cys Leu Gln Thr Ile Arg Phe Ser Pro Asp Ile
385                 390                 395                 400
Phe Ser Ser Val Ser Val Pro Pro Ser Leu Lys Val Cys Leu Asp Leu
            405                 410                 415
Ser Ala Glu Tyr Leu Ile Leu Ser Asp Val Gln Arg Lys Val Leu Tyr
            420                 425                 430
Val Met Glu Leu Leu Gln Asn Gln Glu Glu Gly His Ala Cys Phe Ser
            435                 440                 445
Ser Ile Ser Glu Phe Leu Leu Thr His Pro Val Leu Ser Phe Gly Ile
            450                 455                 460
Gln Val Val Ser Arg Cys Arg Leu Arg His Thr Glu Val Leu Pro Ala
465                 470                 475                 480
Glu Glu Glu Asn Asp Ser Leu Gly Ala Asp Gly Thr His Gly Ala Gly
            485                 490                 495
Ala Met Glu Ser Ala Ala Gly Val Leu Ile Lys Leu Phe Cys Val His
            500                 505                 510
Thr Lys Ala Leu Gln Asp Val Gln Ile Arg Phe Gln Pro Gln Leu Asn
            515                 520                 525
Pro Asp Val Val Ala Pro Leu Pro Thr His Thr Ala His Glu Asp Phe
            530                 535                 540
Thr Phe Gly Glu Ser Arg Pro Glu Leu Gly Ser Glu Gly Leu Gly Ser
545                 550                 555                 560
Ala Ala His Gly Ser Gln Pro Asp Leu Arg Arg Ile Val Glu Leu Pro
            565                 570                 575
Ala Pro Ala Asp Phe Leu Ser Leu Ser Ser Glu Thr Lys Pro Lys Leu
            580                 585                 590
```

```
Met Thr Pro Asp Ala Phe Met Thr Pro Ser Ala Ser Leu Gln Gln Ile
            595                 600                 605

Thr Ala Ser Pro Ser Ser Ser Ser Gly Ser Ser Ser Ser Ser Ser Ser
    610                 615                 620

Ser Ser Ser Ser Ser Leu Thr Ala Val Ser Ala Met Ser Ser Thr Ser
625                 630                 635                 640

Ala Val Asp Pro Ser Leu Thr Arg Pro Glu Glu Leu Thr Leu Ser
                645                 650                 655

Pro Lys Leu Gln Leu Asp Gly Ser Leu Thr Met Ser Ser Gly Ser
            660                 665                 670

Leu Gln Ala Ser Pro Arg Gly Leu Leu Pro Gly Leu Leu Pro Ala Pro
            675                 680                 685

Ala Asp Lys Leu Thr Pro Lys Gly Pro Gly Gln Val Pro Thr Ala Thr
            690                 695                 700

Ser Ala Leu Ser Leu Glu Leu Gln Glu Val Glu Pro Leu Gly Leu Pro
705                 710                 715                 720

Gln Ala Ser Pro Ser Arg Thr Arg Ser Pro Asp Val Ile Ser Ser Ala
                725                 730                 735

Ser Thr Ala Leu Ser Gln Asp Ile Pro Glu Ile Ala Ser Glu Ala Leu
            740                 745                 750

Ser Arg Gly Phe Gly Ser Ser Ala Pro Glu Gly Leu Glu Pro Asp Ser
            755                 760                 765

Met Ala Ser Ala Ala Ser Ala Leu His Leu Leu Ser Pro Arg Pro Arg
770                 775                 780

Pro Gly Pro Glu Leu Gly Pro Gln Leu Gly Leu Asp Gly Gly Pro Gly
785                 790                 795                 800

Asp Gly Asp Arg His Asn Thr Pro Ser Leu Leu Glu Ala Ala Leu Thr
                805                 810                 815

Gln Glu Ala Ser Thr Pro Asp Ser Gln Val Trp Pro Thr Ala Pro Asp
            820                 825                 830

Ile Thr Arg Glu Thr Cys Ser Thr Leu Ala Glu Ser Pro Arg Asn Gly
            835                 840                 845

Leu Gln Glu Lys His Lys Ser Leu Ala Phe His Arg Pro Pro Tyr His
            850                 855                 860

Leu Leu Gln Gln Arg Asp Ser Gln Asp Ala Ser Ala Glu Gln Ser Asp
865                 870                 875                 880

His Asp Asp Glu Val Ala Ser Leu Ala Ser Ala Ser Gly Gly Phe Gly
                885                 890                 895

Thr Lys Val Pro Ala Pro Arg Leu Pro Ala Lys Asp Trp Lys Thr Lys
            900                 905                 910

Gly Ser Pro Arg Thr Ser Pro Lys Leu Lys Arg Lys Ser Lys Lys Asp
            915                 920                 925

Asp Gly Asp Ala Ala Met Gly Ser Arg Leu Thr Glu His Gln Val Ala
    930                 935                 940

Glu Pro Pro Glu Asp Trp Pro Ala Leu Ile Trp Gln Gln Gln Arg Glu
945                 950                 955                 960

Leu Ala Glu Leu Arg His Ser Gln Glu Glu Leu Leu Gln Arg Leu Cys
                965                 970                 975

Thr Gln Leu Glu Gly Leu Gln Ser Thr Val Thr Gly His Val Glu Arg
            980                 985                 990

Ala Leu Glu Thr Arg His Glu Gln  Glu Gln Arg Arg Leu  Glu Arg Ala
            995                 1000                1005
```

-continued

```
Leu Ala Glu Gly Gln Gln Arg Gly Gly Gln Leu Gln Glu Gln Leu
    1010                1015                1020

Thr Gln Gln Leu Ser Gln Ala Leu Ser Ser Ala Val Ala Gly Arg
    1025                1030                1035

Leu Glu Arg Ser Ile Arg Asp Glu Ile Lys Lys Thr Val Pro Pro
    1040                1045                1050

Cys Val Ser Arg Ser Leu Glu Pro Met Ala Gly Gln Leu Ser Asn
    1055                1060                1065

Ser Val Ala Thr Lys Leu Thr Ala Val Glu Gly Ser Met Lys Glu
    1070                1075                1080

Asn Ile Ser Lys Leu Leu Lys Ser Lys Asn Leu Thr Asp Ala Ile
    1085                1090                1095

Ala Arg Ala Ala Ala Asp Thr Leu Gln Gly Pro Met Gln Ala Ala
    1100                1105                1110

Tyr Arg Glu Ala Phe Gln Ser Val Val Leu Pro Ala Phe Glu Lys
    1115                1120                1125

Ser Cys Gln Ala Met Phe Gln Gln Ile Asn Asp Ser Phe Arg Leu
    1130                1135                1140

Gly Thr Gln Glu Tyr Leu Gln Leu Glu Ser His Met Lys Ser
    1145                1150                1155

Arg Lys Ala Arg Glu Gln Glu Ala Arg Glu Pro Val Leu Ala Gln
    1160                1165                1170

Leu Arg Gly Leu Val Ser Thr Leu Gln Ser Ala Thr Glu Gln Met
    1175                1180                1185

Pro Pro Trp Pro Ala Val Phe Val Leu Arg Cys Ser Thr Ser Cys
    1190                1195                1200

Met Trp Leu Trp Ala Ala Cys Arg Ser Pro Phe
    1205                1210

<210> SEQ ID NO 90
<211> LENGTH: 1401
<212> TYPE: PRT
<213> ORGANISM: Human

<400> SEQUENCE: 90

Met Ala Ser Cys Ala Ser Ile Asp Ile Glu Asp Ala Thr Gln His Leu
1               5                   10                  15

Arg Asp Ile Leu Lys Leu Asp Arg Pro Ala Gly Gly Pro Ser Ala Glu
                20                  25                  30

Ser Pro Arg Pro Ser Ser Ala Tyr Asn Gly Asp Leu Asn Gly Leu Leu
            35                  40                  45

Val Pro Asp Pro Leu Cys Ser Gly Asp Ser Thr Ser Ala Asn Lys Thr
        50                  55                  60

Gly Leu Arg Thr Met Pro Pro Ile Asn Leu Gln Glu Lys Gln Val Ile
65                  70                  75                  80

Cys Leu Ser Gly Asp Asp Ser Ser Thr Cys Ile Gly Ile Leu Ala Lys
                85                  90                  95

Glu Val Glu Ile Val Ala Ser Ser Asp Ser Ser Ile Ser Ser Lys Ala
                100                 105                 110

Arg Gly Ser Asn Lys Val Lys Ile Gln Pro Val Ala Lys Tyr Asp Trp
            115                 120                 125

Glu Gln Lys Tyr Tyr Tyr Gly Asn Leu Ile Ala Val Ser Asn Ser Phe
        130                 135                 140

Leu Ala Tyr Ala Ile Arg Ala Ala Asn Asn Gly Ser Ala Met Val Arg
145                 150                 155                 160
```

```
Val Ile Ser Val Ser Thr Ser Glu Arg Thr Leu Leu Lys Gly Phe Thr
                165                 170                 175

Gly Ser Val Ala Asp Leu Ala Phe Ala His Leu Asn Ser Pro Gln Leu
            180                 185                 190

Ala Cys Leu Asp Glu Ala Gly Asn Leu Phe Val Trp Arg Leu Ala Leu
        195                 200                 205

Val Asn Gly Lys Ile Gln Glu Ile Leu Val His Ile Arg Gln Pro
    210                 215                 220

Glu Gly Thr Pro Leu Asn His Phe Arg Arg Ile Ile Trp Cys Pro Phe
225                 230                 235                 240

Ile Pro Glu Glu Ser Glu Asp Cys Cys Glu Glu Ser Ser Pro Thr Val
                245                 250                 255

Ala Leu Leu His Glu Asp Arg Ala Glu Val Trp Asp Leu Asp Met Leu
            260                 265                 270

Arg Ser Ser His Ser Thr Trp Pro Val Asp Val Ser Gln Ile Lys Gln
        275                 280                 285

Gly Phe Ile Val Val Lys Gly His Ser Thr Cys Leu Ser Glu Gly Ala
    290                 295                 300

Leu Ser Pro Asp Gly Thr Val Leu Ala Thr Ala Ser His Asp Gly Tyr
305                 310                 315                 320

Val Lys Phe Trp Gln Ile Tyr Ile Glu Gly Gln Asp Glu Pro Arg Cys
                325                 330                 335

Leu His Glu Trp Lys Pro His Asp Gly Arg Pro Leu Ser Cys Leu Leu
            340                 345                 350

Phe Cys Asp Asn His Lys Lys Gln Asp Pro Asp Val Pro Phe Trp Arg
        355                 360                 365

Phe Leu Ile Thr Gly Ala Asp Gln Asn Arg Glu Leu Lys Met Trp Cys
    370                 375                 380

Thr Val Ser Trp Thr Cys Leu Gln Thr Ile Arg Phe Ser Pro Asp Ile
385                 390                 395                 400

Phe Ser Ser Val Ser Val Pro Pro Ser Leu Lys Val Cys Leu Asp Leu
                405                 410                 415

Ser Ala Glu Tyr Leu Ile Leu Ser Asp Val Gln Arg Lys Val Leu Tyr
            420                 425                 430

Val Met Glu Leu Leu Gln Asn Gln Glu Glu Gly His Ala Cys Phe Ser
        435                 440                 445

Ser Ile Ser Glu Phe Leu Leu Thr His Pro Val Leu Ser Phe Gly Ile
    450                 455                 460

Gln Val Val Ser Arg Cys Arg Leu Arg His Thr Glu Val Leu Pro Ala
465                 470                 475                 480

Glu Glu Glu Asn Asp Ser Leu Gly Ala Asp Gly Thr His Gly Ala Gly
                485                 490                 495

Ala Met Glu Ser Ala Ala Gly Val Leu Ile Lys Leu Phe Cys Val His
            500                 505                 510

Thr Lys Ala Leu Gln Asp Val Gln Ile Arg Phe Gln Pro Gln Leu Asn
        515                 520                 525

Pro Asp Val Val Ala Pro Leu Pro Thr His Thr Ala His Glu Asp Phe
    530                 535                 540

Thr Phe Gly Glu Ser Arg Pro Glu Leu Gly Ser Glu Gly Leu Gly Ser
545                 550                 555                 560

Ala Ala His Gly Ser Gln Pro Asp Leu Arg Arg Ile Val Glu Leu Pro
                565                 570                 575
```

```
Ala Pro Ala Asp Phe Leu Ser Leu Ser Ser Glu Thr Lys Pro Lys Leu
            580                 585                 590

Met Thr Pro Asp Ala Phe Met Thr Pro Ser Ala Ser Leu Gln Gln Ile
        595                 600                 605

Thr Ala Ser Pro Ser Ser Ser Ser Gly Ser Ser Ser Ser Ser
    610                 615                 620

Ser Ser Ser Ser Ser Leu Thr Ala Val Ser Ala Met Ser Ser Thr Ser
625                 630                 635                 640

Ala Val Asp Pro Ser Leu Thr Arg Pro Glu Glu Leu Thr Leu Ser
                645                 650                 655

Pro Lys Leu Gln Leu Asp Gly Ser Leu Thr Met Ser Ser Ser Gly Ser
            660                 665                 670

Leu Gln Ala Ser Pro Arg Gly Leu Leu Pro Gly Leu Leu Pro Ala Pro
        675                 680                 685

Ala Asp Lys Leu Thr Pro Lys Gly Pro Gly Gln Val Pro Thr Ala Thr
    690                 695                 700

Ser Ala Leu Ser Leu Glu Leu Gln Glu Val Glu Pro Leu Gly Leu Pro
705                 710                 715                 720

Gln Ala Ser Pro Ser Arg Thr Arg Ser Pro Asp Val Ile Ser Ser Ala
                725                 730                 735

Ser Thr Ala Leu Ser Gln Asp Ile Pro Glu Ile Ala Ser Glu Ala Leu
            740                 745                 750

Ser Arg Gly Phe Gly Ser Ser Ala Pro Glu Gly Leu Glu Pro Asp Ser
        755                 760                 765

Met Ala Ser Ala Ala Ser Ala Leu His Leu Leu Ser Pro Arg Pro Arg
    770                 775                 780

Pro Gly Pro Glu Leu Gly Pro Gln Leu Gly Leu Asp Gly Gly Pro Gly
785                 790                 795                 800

Asp Gly Asp Arg His Asn Thr Pro Ser Leu Leu Glu Ala Ala Leu Thr
                805                 810                 815

Gln Glu Ala Ser Thr Pro Asp Ser Gln Val Trp Pro Thr Ala Pro Asp
            820                 825                 830

Ile Thr Arg Glu Thr Cys Ser Thr Leu Ala Glu Ser Pro Arg Asn Gly
        835                 840                 845

Leu Gln Glu Lys His Lys Ser Leu Ala Phe His Arg Pro Pro Tyr His
    850                 855                 860

Leu Leu Gln Gln Arg Asp Ser Gln Asp Ala Ser Ala Glu Gln Ser Asp
865                 870                 875                 880

His Asp Asp Glu Val Ala Ser Leu Ala Ser Ala Ser Gly Gly Phe Gly
                885                 890                 895

Thr Lys Val Pro Ala Pro Arg Leu Pro Ala Lys Asp Trp Lys Thr Lys
            900                 905                 910

Gly Ser Pro Arg Thr Ser Pro Lys Leu Lys Arg Lys Ser Lys Lys Asp
        915                 920                 925

Asp Gly Asp Ala Ala Met Gly Ser Arg Leu Thr Glu His Gln Val Ala
    930                 935                 940

Glu Pro Pro Glu Asp Trp Pro Ala Leu Ile Trp Gln Gln Arg Glu
945                 950                 955                 960

Leu Ala Glu Leu Arg His Ser Gln Glu Glu Leu Leu Gln Arg Leu Cys
                965                 970                 975

Thr Gln Leu Glu Gly Leu Gln Ser Thr Val Thr Gly His Val Glu Arg
            980                 985                 990

Ala Leu Glu Thr Arg His Glu Gln  Glu Gln Arg Arg Leu  Glu Arg Ala
```

```
              995                 1000                1005
Leu Ala Glu Gly Gln Gln Arg Gly Gly Gln Leu Gln Glu Gln Leu
    1010                1015                1020

Thr Gln Gln Leu Ser Gln Ala Leu Ser Ser Ala Val Ala Gly Arg
    1025                1030                1035

Leu Glu Arg Ser Ile Arg Asp Glu Ile Lys Lys Thr Val Pro Pro
    1040                1045                1050

Cys Val Ser Arg Ser Leu Glu Pro Met Ala Gly Gln Leu Ser Asn
    1055                1060                1065

Ser Val Ala Thr Lys Leu Thr Ala Val Glu Gly Ser Met Lys Glu
    1070                1075                1080

Asn Ile Ser Lys Leu Leu Lys Ser Lys Asn Leu Thr Asp Ala Ile
    1085                1090                1095

Ala Arg Ala Ala Ala Asp Thr Leu Gln Gly Pro Met Gln Ala Ala
    1100                1105                1110

Tyr Arg Glu Ala Phe Gln Ser Val Val Leu Pro Ala Phe Glu Lys
    1115                1120                1125

Ser Cys Gln Ala Met Phe Gln Gln Ile Asn Asp Ser Phe Arg Leu
    1130                1135                1140

Gly Thr Gln Glu Tyr Leu Gln Gln Leu Glu Ser His Met Lys Ser
    1145                1150                1155

Arg Lys Ala Arg Glu Gln Glu Ala Arg Glu Pro Val Leu Ala Gln
    1160                1165                1170

Leu Arg Gly Leu Val Ser Thr Leu Gln Ser Ala Thr Glu Gln Met
    1175                1180                1185

Ala Ala Thr Val Ala Gly Ser Val Arg Ala Glu Val Gln His Gln
    1190                1195                1200

Leu His Val Ala Val Gly Ser Leu Gln Glu Ser Ile Leu Ala Gln
    1205                1210                1215

Val Gln Arg Ile Val Lys Gly Glu Val Ser Val Ala Leu Lys Glu
    1220                1225                1230

Gln Gln Ala Ala Val Thr Ser Ser Ile Met Gln Ala Met Arg Ser
    1235                1240                1245

Ala Ala Gly Thr Pro Val Pro Ser Ala His Leu Asp Cys Gln Ala
    1250                1255                1260

Gln Gln Ala His Ile Leu Gln Leu Leu Gln Gln Gly His Leu Asn
    1265                1270                1275

Gln Ala Phe Gln Gln Ala Leu Thr Ala Ala Asp Leu Asn Leu Val
    1280                1285                1290

Leu Tyr Val Cys Glu Thr Val Asp Pro Ala Gln Val Phe Gly Gln
    1295                1300                1305

Pro Pro Cys Pro Leu Ser Gln Pro Val Leu Leu Ser Leu Ile Gln
    1310                1315                1320

Gln Leu Ala Ser Asp Leu Gly Thr Arg Thr Asp Leu Lys Leu Ser
    1325                1330                1335

Tyr Leu Glu Glu Ala Val Met His Leu Asp His Ser Asp Pro Ile
    1340                1345                1350

Thr Arg Asp His Met Gly Ser Val Met Ala Gln Val Arg Gln Lys
    1355                1360                1365

Leu Phe Gln Phe Leu Gln Ala Glu Pro His Asn Ser Leu Gly Lys
    1370                1375                1380

Ala Ala Arg Arg Leu Ser Leu Met Leu His Gly Leu Val Thr Pro
    1385                1390                1395
```

Ser Leu Pro
        1400

<210> SEQ ID NO 91
<211> LENGTH: 620
<212> TYPE: PRT
<213> ORGANISM: Human

<400> SEQUENCE: 91

Met Arg Arg Ser Glu Val Leu Ala Glu Glu Ser Ile Val Cys Leu Gln
1               5                   10                  15

Lys Ala Leu Asn His Leu Arg Glu Ile Trp Glu Leu Ile Gly Ile Pro
            20                  25                  30

Glu Asp Gln Arg Leu Gln Arg Thr Glu Val Val Lys Lys His Ile Lys
        35                  40                  45

Glu Leu Leu Asp Met Met Ile Ala Glu Glu Ser Leu Lys Glu Arg
    50                  55                  60

Leu Ile Lys Ser Ile Ser Val Cys Gln Lys Glu Leu Asn Thr Leu Cys
65                  70                  75                  80

Ser Glu Leu His Val Glu Pro Phe Gln Glu Glu Gly Glu Thr Thr Ile
                85                  90                  95

Leu Gln Leu Glu Lys Asp Leu Arg Thr Gln Val Glu Leu Met Arg Lys
            100                 105                 110

Gln Lys Lys Glu Arg Lys Gln Glu Leu Lys Leu Leu Gln Glu Gln Asp
        115                 120                 125

Gln Glu Leu Cys Glu Ile Leu Cys Met Pro His Tyr Asp Ile Asp Ser
    130                 135                 140

Ala Ser Val Pro Ser Leu Glu Glu Leu Asn Gln Phe Arg Gln His Val
145                 150                 155                 160

Thr Thr Leu Arg Glu Thr Lys Ala Ser Arg Arg Glu Glu Phe Val Ser
                165                 170                 175

Ile Lys Arg Gln Ile Ile Leu Cys Met Glu Ala Leu Asp His Thr Pro
            180                 185                 190

Asp Thr Ser Phe Glu Arg Asp Val Val Cys Glu Asp Glu Asp Ala Phe
        195                 200                 205

Cys Leu Ser Leu Glu Asn Ile Ala Thr Leu Gln Lys Leu Leu Arg Gln
    210                 215                 220

Leu Glu Met Gln Lys Ser Gln Asn Glu Ala Val Cys Glu Gly Leu Arg
225                 230                 235                 240

Thr Gln Ile Arg Glu Leu Trp Asp Arg Leu Gln Ile Pro Glu Glu Glu
                245                 250                 255

Arg Glu Ala Val Ala Thr Ile Met Ser Gly Ser Lys Ala Lys Val Arg
            260                 265                 270

Lys Ala Leu Gln Leu Glu Val Asp Arg Leu Glu Glu Leu Lys Met Gln
        275                 280                 285

Asn Met Lys Lys Val Ile Glu Ala Ile Arg Val Glu Leu Val Gln Tyr
    290                 295                 300

Trp Asp Gln Cys Phe Tyr Ser Gln Glu Gln Arg Gln Ala Phe Ala Pro
305                 310                 315                 320

Phe Cys Ala Glu Asp Tyr Thr Glu Ser Leu Leu Gln Leu His Asp Ala
                325                 330                 335

Glu Ile Val Arg Leu Lys Asn Tyr Tyr Glu Val His Lys Glu Leu Phe
            340                 345                 350

Glu Gly Val Gln Lys Trp Glu Glu Thr Trp Arg Leu Phe Leu Glu Phe

```
                355                 360                 365
Glu Arg Lys Ala Ser Asp Pro Asn Arg Phe Thr Asn Arg Gly Gly Asn
370                 375                 380
Leu Leu Lys Glu Glu Lys Gln Arg Ala Lys Leu Gln Lys Met Leu Pro
385                 390                 395                 400
Lys Leu Glu Glu Leu Lys Ala Arg Ile Glu Leu Trp Glu Gln Glu
                405                 410                 415
His Ser Lys Ala Phe Met Val Asn Gly Gln Lys Phe Met Glu Tyr Val
                420                 425                 430
Ala Glu Gln Trp Glu Met His Arg Leu Glu Lys Glu Arg Ala Lys Gln
                435                 440                 445
Glu Arg Gln Leu Lys Asn Lys Lys Gln Thr Glu Thr Glu Met Leu Tyr
        450                 455                 460
Gly Ser Ala Pro Arg Thr Pro Ser Lys Arg Gly Leu Ala Pro Asn
465                 470                 475                 480
Thr Pro Gly Lys Ala Arg Lys Leu Asn Thr Thr Thr Met Ser Asn Ala
                485                 490                 495
Thr Ala Asn Ser Ser Ile Arg Pro Ile Phe Gly Gly Thr Val Tyr His
                500                 505                 510
Ser Pro Val Ser Arg Leu Pro Pro Ser Gly Ser Lys Pro Val Ala Ala
                515                 520                 525
Ser Thr Cys Ser Gly Lys Lys Thr Pro Arg Thr Gly Arg His Gly Ala
        530                 535                 540
Asn Lys Glu Asn Leu Glu Leu Asn Gly Ser Ile Leu Ser Gly Gly Tyr
545                 550                 555                 560
Pro Gly Ser Ala Pro Leu Gln Arg Asn Phe Ser Ile Asn Ser Val Ala
                565                 570                 575
Ser Thr Tyr Ser Glu Phe Ala Lys Asp Pro Ser Leu Ser Asp Ser Ser
                580                 585                 590
Thr Val Gly Leu Gln Arg Glu Leu Ser Lys Ala Ser Lys Ser Asp Ala
                595                 600                 605
Thr Ser Gly Ile Leu Asn Ser Thr Asn Ile Gln Ser
        610                 615                 620

<210> SEQ ID NO 92
<211> LENGTH: 674
<212> TYPE: PRT
<213> ORGANISM: Human

<400> SEQUENCE: 92

Thr Arg Leu Arg Pro Val Ala Arg Phe Glu Ile Leu Arg Gly Ser Thr
1               5                  10                  15
Ala Arg Gly Ala Ala Thr Arg Ser Asp Ile Ala Gly Val Cys Gly Trp
                20                  25                  30
Leu Leu Leu Ser Gly Pro Cys Gly Val Gly Leu Asp Leu Asp Ser Arg
            35                  40                  45
Leu Leu Gly Ala Ser Ala Met Arg Arg Ser Glu Val Leu Ala Glu Glu
        50                  55                  60
Ser Ile Val Cys Leu Gln Lys Ala Leu Asn His Leu Arg Glu Ile Trp
65                  70                  75                  80
Glu Leu Ile Gly Ile Pro Glu Asp Gln Arg Leu Gln Arg Thr Glu Val
                85                  90                  95
Val Lys Lys His Ile Lys Glu Leu Leu Asp Met Met Ile Ala Glu Glu
                100                 105                 110
```

-continued

Glu Ser Leu Lys Glu Arg Leu Ile Lys Ser Ile Ser Val Cys Gln Lys
            115                 120                 125

Glu Leu Asn Thr Leu Cys Ser Glu Leu His Val Glu Pro Phe Gln Glu
            130                 135                 140

Glu Gly Glu Thr Thr Ile Leu Gln Leu Glu Lys Asp Leu Arg Thr Gln
145                 150                 155                 160

Val Glu Leu Met Arg Lys Gln Lys Glu Arg Lys Gln Glu Leu Lys
                165                 170                 175

Leu Leu Gln Glu Gln Asp Gln Glu Leu Cys Glu Ile Leu Cys Met Pro
            180                 185                 190

His Tyr Asp Ile Asp Ser Ala Ser Val Pro Ser Leu Glu Glu Leu Asn
            195                 200                 205

Gln Phe Arg Gln His Val Thr Thr Leu Arg Glu Thr Lys Ala Ser Arg
            210                 215                 220

Arg Glu Glu Phe Val Ser Ile Lys Arg Gln Ile Ile Leu Cys Met Glu
225                 230                 235                 240

Ala Leu Asp His Thr Pro Asp Thr Ser Phe Glu Arg Asp Val Val Cys
            245                 250                 255

Glu Asp Glu Asp Ala Phe Cys Leu Ser Leu Glu Asn Ile Ala Thr Leu
            260                 265                 270

Gln Lys Leu Leu Arg Gln Leu Glu Met Gln Lys Ser Gln Asn Glu Ala
            275                 280                 285

Val Cys Glu Gly Leu Arg Thr Gln Ile Arg Glu Leu Trp Asp Arg Leu
            290                 295                 300

Gln Ile Pro Glu Glu Glu Arg Glu Ala Val Ala Thr Ile Met Ser Gly
305                 310                 315                 320

Ser Lys Ala Lys Val Arg Lys Ala Leu Gln Leu Glu Val Asp Arg Leu
            325                 330                 335

Glu Glu Leu Lys Met Gln Asn Met Lys Lys Val Ile Glu Ala Ile Arg
            340                 345                 350

Val Glu Leu Val Gln Tyr Trp Asp Gln Cys Phe Tyr Ser Gln Glu Gln
            355                 360                 365

Arg Gln Ala Phe Ala Pro Phe Cys Ala Glu Asp Tyr Thr Glu Ser Leu
            370                 375                 380

Leu Gln Leu His Asp Ala Glu Ile Val Arg Leu Lys Asn Tyr Tyr Glu
385                 390                 395                 400

Val His Lys Glu Leu Phe Glu Gly Val Gln Lys Trp Glu Glu Thr Trp
                405                 410                 415

Arg Leu Phe Leu Glu Phe Glu Arg Lys Ala Ser Asp Pro Asn Arg Phe
            420                 425                 430

Thr Asn Arg Gly Gly Asn Leu Leu Lys Glu Glu Lys Gln Arg Ala Lys
            435                 440                 445

Leu Gln Lys Met Leu Pro Lys Leu Glu Glu Glu Leu Lys Ala Arg Ile
            450                 455                 460

Glu Leu Trp Glu Gln Glu His Ser Lys Ala Phe Met Val Asn Gly Gln
465                 470                 475                 480

Lys Phe Met Glu Tyr Val Ala Glu Gln Trp Glu Met His Arg Leu Glu
                485                 490                 495

Lys Glu Arg Ala Lys Gln Glu Arg Gln Leu Lys Asn Lys Lys Gln Thr
            500                 505                 510

Glu Thr Glu Met Leu Tyr Gly Ser Ala Pro Arg Thr Pro Ser Lys Arg
            515                 520                 525

Arg Gly Leu Ala Pro Asn Thr Pro Gly Lys Ala Arg Lys Leu Asn Thr

```
                530             535             540
Thr Thr Met Ser Asn Ala Thr Asn Ser Ser Ile Arg Pro Ile Phe
545                 550             555                 560

Gly Gly Thr Val Tyr His Ser Pro Val Ser Arg Leu Pro Pro Ser Gly
            565                 570             575

Ser Lys Pro Val Ala Ala Ser Thr Cys Ser Gly Lys Lys Thr Pro Arg
            580                 585             590

Thr Gly Arg His Gly Ala Asn Lys Glu Asn Leu Glu Leu Asn Gly Ser
            595                 600             605

Ile Leu Ser Gly Gly Tyr Pro Gly Ser Ala Pro Leu Gln Arg Asn Phe
            610             615             620

Ser Ile Asn Ser Val Ala Ser Thr Tyr Ser Glu Phe Ala Lys Asp Pro
625                 630             635                 640

Ser Leu Ser Asp Ser Ser Thr Val Gly Leu Gln Arg Glu Leu Ser Lys
                645             650             655

Ala Ser Lys Ser Asp Ala Thr Ser Gly Ile Leu Asn Ser Thr Asn Ile
            660             665             670

Gln Ser
```

<210> SEQ ID NO 93
<211> LENGTH: 660
<212> TYPE: PRT
<213> ORGANISM: Human

<400> SEQUENCE: 93

```
Thr Arg Leu Arg Pro Val Ala Arg Phe Glu Ile Leu Arg Gly Ser Thr
1               5                   10                  15

Ala Arg Gly Ala Ala Thr Arg Ser Asp Ile Ala Gly Val Cys Gly Trp
            20                  25                  30

Leu Leu Leu Ser Gly Pro Cys Gly Val Gly Leu Asp Leu Asp Ser Arg
        35                  40                  45

Leu Leu Gly Ala Ser Ala Met Arg Arg Ser Glu Val Leu Ala Glu Glu
    50                  55                  60

Ser Ile Val Cys Leu Gln Lys Ala Leu Asn His Leu Arg Glu Ile Trp
65                  70                  75                  80

Glu Leu Ile Gly Ile Pro Glu Asp Gln Arg Leu Gln Arg Thr Glu Val
                85                  90                  95

Val Lys Lys His Ile Lys Glu Leu Leu Asp Met Met Ile Ala Glu Glu
            100                 105                 110

Glu Ser Leu Lys Glu Arg Leu Ile Lys Ser Ile Ser Val Cys Gln Lys
        115                 120                 125

Glu Leu Asn Thr Leu Cys Ser Glu Leu His Val Glu Pro Phe Gln Glu
    130                 135                 140

Glu Gly Glu Thr Thr Ile Leu Gln Leu Glu Lys Asp Leu Arg Thr Gln
145                 150                 155                 160

Val Glu Leu Met Arg Lys Gln Lys Glu Arg Lys Gln Glu Leu Lys
                165                 170                 175

Leu Leu Gln Glu Gln Asp Gln Glu Leu Cys Glu Ile Leu Cys Met Pro
            180                 185                 190

His Tyr Asp Ile Asp Ser Ala Ser Val Pro Ser Leu Glu Leu Asn
        195                 200                 205

Gln Phe Arg Gln His Val Thr Thr Leu Arg Glu Thr Lys Ala Ser Arg
    210                 215                 220

Arg Glu Glu Phe Val Ser Ile Lys Arg Gln Ile Ile Leu Cys Met Glu
```

```
                225                 230                 235                 240
Ala Leu Asp His Thr Pro Asp Thr Ser Phe Glu Arg Asp Val Val Cys
                    245                 250                 255
Glu Asp Glu Asp Ala Phe Cys Leu Ser Leu Glu Asn Ile Ala Thr Leu
                    260                 265                 270
Gln Lys Leu Leu Arg Gln Leu Glu Met Gln Lys Ser Gln Asn Glu Ala
                    275                 280                 285
Val Cys Glu Gly Leu Arg Thr Gln Ile Arg Glu Leu Trp Asp Arg Leu
                    290                 295                 300
Gln Ile Pro Glu Glu Glu Arg Glu Ala Val Ala Thr Ile Met Ser Gly
305                 310                 315                 320
Ser Lys Ala Lys Val Arg Lys Ala Leu Gln Leu Glu Val Asp Arg Leu
                    325                 330                 335
Glu Glu Leu Lys Met Gln Asn Met Lys Lys Val Ile Glu Ala Ile Arg
                    340                 345                 350
Val Glu Leu Val Gln Tyr Trp Asp Gln Cys Phe Tyr Ser Gln Glu Gln
                    355                 360                 365
Arg Gln Ala Phe Ala Pro Phe Cys Ala Glu Asp Tyr Thr Glu Ser Leu
                    370                 375                 380
Leu Gln Leu His Asp Ala Glu Ile Val Arg Leu Lys Asn Tyr Tyr Glu
385                 390                 395                 400
Val His Lys Glu Leu Phe Glu Gly Val Gln Lys Trp Glu Glu Thr Trp
                    405                 410                 415
Arg Leu Phe Leu Glu Phe Glu Arg Lys Ala Ser Asp Pro Asn Arg Phe
                    420                 425                 430
Thr Asn Arg Gly Gly Asn Leu Leu Lys Glu Lys Gln Arg Ala Lys
                    435                 440                 445
Leu Gln Lys Met Leu Pro Lys Leu Glu Glu Glu Leu Lys Ala Arg Ile
                    450                 455                 460
Glu Leu Trp Glu Gln Glu His Ser Lys Ala Phe Met Val Asn Gly Gln
465                 470                 475                 480
Lys Phe Met Glu Tyr Val Ala Glu Gln Trp Glu Met His Arg Leu Glu
                    485                 490                 495
Lys Glu Arg Ala Lys Gln Glu Arg Gln Leu Lys Asn Lys Lys Gln Thr
                    500                 505                 510
Glu Thr Glu Met Leu Tyr Gly Ser Ala Pro Arg Thr Pro Ser Lys Arg
                    515                 520                 525
Arg Gly Leu Ala Pro Asn Thr Pro Gly Lys Ala Arg Lys Leu Asn Thr
                    530                 535                 540
Thr Thr Met Ser Asn Ala Thr Ala Asn Ser Ser Ile Arg Pro Ile Phe
545                 550                 555                 560
Gly Gly Thr Val Tyr His Ser Pro Val Ser Arg Leu Pro Pro Ser Gly
                    565                 570                 575
Ser Lys Pro Val Ala Ala Ser Thr Cys Ser Gly Lys Lys Thr Pro Arg
                    580                 585                 590
Thr Gly Arg His Gly Ala Asn Lys Glu Asn Leu Glu Leu Asn Gly Ser
                    595                 600                 605
Ile Leu Ser Gly Gly Tyr Pro Gly Ser Ala Pro Leu Gln Arg Asn Phe
                    610                 615                 620
Ser Ile Asn Ser Val Ala Ser Thr Tyr Ser Glu Phe Ala Arg Glu Leu
625                 630                 635                 640
Ser Lys Ala Ser Lys Ser Asp Ala Thr Ser Gly Ile Leu Asn Ser Thr
                    645                 650                 655
```

Asn Ile Gln Ser
            660

<210> SEQ ID NO 94
<211> LENGTH: 417
<212> TYPE: PRT
<213> ORGANISM: Human

<400> SEQUENCE: 94

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
    130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Asp Leu Val Gln Ser
    290                 295                 300

Ile Gly Val Ser Ala Ala Leu Gly Ala Ala Gly Val Val Leu Trp Gly
305                 310                 315                 320

Asp Leu Ser Leu Ser Ser Glu Glu Glu Cys Trp His Leu His Asp
                325                 330                 335

Tyr Leu Val Asp Thr Leu Gly Pro Tyr Val Ile Asn Val Thr Arg Ala
            340                 345                 350

Ala Met Ala Cys Ser His Gln Arg Cys His Gly His Gly Arg Cys Ala

```
                    355                 360                 365
Arg Arg Asp Pro Gly Gln Met Glu Ala Phe Leu His Leu Trp Pro Asp
    370                 375                 380
Gly Ser Leu Gly Asp Trp Lys Ser Phe Ser Cys His Cys Tyr Trp Gly
385                 390                 395                 400
Trp Ala Gly Pro Thr Cys Gln Glu Pro Arg Pro Gly Pro Lys Glu Ala
                    405                 410                 415
Val

<210> SEQ ID NO 95
<211> LENGTH: 462
<212> TYPE: PRT
<213> ORGANISM: Human

<400> SEQUENCE: 95

Met Thr Thr Gln Leu Gly Pro Ala Leu Val Leu Gly Val Ala Leu Cys
1               5                   10                  15
Leu Gly Cys Gly Gln Pro Leu Pro Gln Val Pro Glu Arg Pro Phe Ser
                20                  25                  30
Val Leu Trp Asn Val Pro Ser Ala His Cys Glu Ala Arg Phe Gly Val
            35                  40                  45
His Leu Pro Leu Asn Ala Leu Gly Ile Ile Ala Asn Arg Gly Gln His
        50                  55                  60
Phe His Gly Gln Asn Met Thr Ile Phe Tyr Lys Asn Gln Leu Gly Leu
65                  70                  75                  80
Tyr Pro Tyr Phe Gly Pro Arg Gly Thr Ala His Asn Gly Gly Ile Pro
                85                  90                  95
Gln Ala Leu Pro Leu Asp Arg His Leu Ala Leu Ala Ala Tyr Gln Ile
                100                 105                 110
His His Ser Leu Arg Pro Gly Phe Ala Gly Pro Ala Val Leu Asp Trp
            115                 120                 125
Glu Glu Trp Cys Pro Leu Trp Ala Gly Asn Trp Gly Arg Arg Arg Ala
        130                 135                 140
Tyr Gln Ala Ala Ser Trp Ala Trp Ala Gln Gln Val Phe Pro Asp Leu
145                 150                 155                 160
Asp Pro Gln Glu Gln Leu Tyr Lys Ala Tyr Thr Gly Phe Glu Gln Ala
                165                 170                 175
Ala Arg Ala Leu Met Glu Asp Thr Leu Arg Val Ala Gln Ala Leu Arg
                180                 185                 190
Pro His Gly Leu Trp Gly Phe Tyr His Tyr Pro Ala Cys Gly Asn Gly
            195                 200                 205
Trp His Ser Met Ala Ser Asn Tyr Thr Gly Arg Cys His Ala Ala Thr
        210                 215                 220
Leu Ala Arg Asn Thr Gln Leu His Trp Leu Trp Ala Ala Ser Ser Ala
225                 230                 235                 240
Leu Phe Pro Ser Ile Tyr Leu Pro Pro Arg Leu Pro Pro Ala His His
                245                 250                 255
Gln Ala Phe Val Arg His Arg Leu Glu Glu Ala Phe Arg Val Ala Leu
                260                 265                 270
Val Gly His Arg His Pro Leu Pro Val Leu Ala Tyr Val Arg Leu Thr
            275                 280                 285
His Arg Arg Ser Gly Arg Phe Leu Ser Gln Asp Asp Leu Val Gln Ser
        290                 295                 300
Ile Gly Val Ser Ala Ala Leu Gly Ala Ala Gly Val Val Leu Trp Gly
```

```
                    305                 310                 315                 320
Asp Leu Ser Leu Ser Ser Glu Glu Glu Cys Trp His Leu His Asp
                325                 330                 335

Tyr Leu Val Asp Thr Leu Gly Pro Tyr Val Ile Asn Val Thr Arg Ala
                340                 345                 350

Ala Met Ala Cys Ser His Gln Arg Cys His Gly His Gly Arg Cys Ala
                355                 360                 365

Arg Arg Asp Pro Gly Gln Met Glu Ala Phe Leu His Leu Trp Pro Asp
    370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Leu Gly Leu Lys Lys Gln Tyr
                405                 410                 415

Lys Ala Arg Ala Pro Ala Thr Ala Ser Ser Phe Pro Cys Cys His Phe
                420                 425                 430

Ser Ser Pro Gly Thr Thr Leu Ser His Ser Cys Ser Ile Gln Phe Thr
                435                 440                 445

Val Asn Pro Pro Lys His Thr Pro Arg Phe Pro Trp Asn Pro
    450                 455                 460

<210> SEQ ID NO 96
<211> LENGTH: 387
<212> TYPE: PRT
<213> ORGANISM: Human

<400> SEQUENCE: 96

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
                20                  25                  30

Val Leu Trp Asn Val Pro Ser Ala His Cys Glu Ala Arg Phe Gly Val
            35                  40                  45

His Leu Pro Leu Asn Ala Leu Gly Ile Ile Ala Asn Arg Gly Gln His
        50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
                100                 105                 110

His His Ser Leu Arg Pro Gly Phe Ala Gly Pro Ala Val Leu Asp Trp
            115                 120                 125

Glu Glu Trp Cys Pro Leu Trp Ala Gly Asn Trp Gly Arg Arg Arg Ala
        130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220
```

-continued

```
Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
        275                 280                 285

His Arg Arg Ser Gly Arg Phe Leu Ser Gln Glu Glu Cys Trp His Leu
    290                 295                 300

His Asp Tyr Leu Val Asp Thr Leu Gly Pro Tyr Val Ile Asn Val Thr
305                 310                 315                 320

Arg Ala Ala Met Ala Cys Ser His Gln Arg Cys His Gly His Gly Arg
                325                 330                 335

Cys Ala Arg Arg Asp Pro Gly Gln Met Glu Ala Phe Leu His Leu Trp
                340                 345                 350

Pro Asp Gly Ser Leu Gly Asp Trp Lys Ser Phe Ser Cys His Cys Tyr
            355                 360                 365

Trp Gly Trp Ala Gly Pro Thr Cys Gln Glu Pro Arg Pro Gly Pro Lys
370                 375                 380

Glu Ala Val
385

<210> SEQ ID NO 97
<211> LENGTH: 462
<212> TYPE: PRT
<213> ORGANISM: Human

<400> SEQUENCE: 97

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205
```

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
                260                 265                 270

Lys Pro Gly Met Val Val Thr Phe Ala Pro Val Asn Val Thr Thr Glu
            275                 280                 285

Val Lys Ser Val Glu Met His His Glu Ala Leu Ser Glu Ala Leu Pro
290                 295                 300

Gly Asp Asn Val Gly Phe Lys Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
                340                 345                 350

Ile Ser Ala Gly Tyr Ala Pro Val Leu Asp Cys His Met Ala His Ile
            355                 360                 365

Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
                420                 425                 430

Val Ala Val Gly Val Ile Lys Ala Val Asp Lys Lys Ala Ala Gly Ala
            435                 440                 445

Gly Lys Val Thr Lys Ser Ala Gln Lys Ala Gln Lys Ala Lys
    450                 455                 460

<210> SEQ ID NO 98
<211> LENGTH: 381
<212> TYPE: PRT
<213> ORGANISM: Human

<400> SEQUENCE: 98

Met Ala Leu Lys Ala Glu Gly Ala Ala Leu Asp Cys Phe Glu Val Thr
1               5                   10                  15

Leu Lys Cys Glu Glu Gly Glu Asp Glu Glu Ala Met Val Val Ala
                20                  25                  30

Val Ile Pro Arg Pro Glu Pro Met Leu Arg Val Thr Gln Gln Glu Lys
            35                  40                  45

Thr Pro Pro Pro Arg Pro Ser Pro Leu Glu Ala Gly Ser Asp Gly Cys
50                  55                  60

Glu Glu Pro Lys Gln Gln Val Ser Trp Glu Gly Glu Phe Leu Val Gly
65                  70                  75                  80

Ser Ser Pro Gly Gly Ser Gly Arg Ala Leu Cys Met Val Cys Gly Ala
                85                  90                  95

Glu Ile Arg Ala Pro Ser Ala Asp Thr Ala Arg Ser His Ile Leu Glu
                100                 105                 110

Gln His Pro His Thr Leu Asp Leu Ser Pro Ser Glu Lys Ser Asn Ile

```
            115                 120                 125
Leu Glu Ala Trp Ser Glu Gly Val Ala Leu Leu Gln Asp Val Arg Ala
        130                 135                 140

Glu Gln Pro Ser Pro Pro Asn Ser Asp Ser Gly Gln Asp Ala His Pro
145                 150                 155                 160

Asp Pro Asp Ala Asn Pro Asp Ala Ala Arg Met Pro Ala Glu Ile Val
                165                 170                 175

Val Leu Leu Asp Ser Glu Asp Asn Pro Ser Leu Pro Lys Arg Ser Arg
            180                 185                 190

Pro Arg Gly Leu Arg Pro Leu Glu Leu Pro Ala Val Pro Ala Thr Glu
        195                 200                 205

Pro Gly Asn Lys Lys Pro Arg Gly Gln Arg Trp Lys Glu Pro Pro Gly
210                 215                 220

Glu Glu Pro Val Arg Lys Arg Gly Arg Pro Met Thr Lys Asn Leu
225                 230                 235                 240

Asp Pro Asp Pro Glu Pro Pro Ser Pro Asp Ser Pro Thr Glu Thr Phe
                245                 250                 255

Ala Ala Pro Ala Glu Val Arg His Phe Thr Asp Gly Ser Phe Pro Ala
            260                 265                 270

Gly Phe Val Leu Gln Leu Phe Ser His Thr Gln Leu Arg Gly Pro Asp
        275                 280                 285

Ser Lys Asp Ser Pro Lys Asp Arg Glu Val Ala Glu Gly Gly Leu Pro
290                 295                 300

Arg Ala Glu Ser Pro Ser Pro Ala Pro Pro Gly Leu Arg Gly Thr
305                 310                 315                 320

Leu Asp Leu Gln Val Ile Arg Val Arg Met Glu Glu Pro Pro Ala Val
                325                 330                 335

Ser Leu Leu Gln Asp Trp Ser Arg His Pro Gln Gly Thr Lys Arg Val
            340                 345                 350

Gly Ala Gly Asp Thr Ser Asp Trp Pro Thr Val Leu Ser Glu Ser Ser
        355                 360                 365

Thr Thr Val Ala Gly Lys Pro Glu Lys Gly Asn Gly Val
370                 375                 380

<210> SEQ ID NO 99
<211> LENGTH: 1909
<212> TYPE: PRT
<213> ORGANISM: Human

<400> SEQUENCE: 99

Met Ser Thr His Arg Ser Arg Leu Leu Thr Ala Ala Pro Leu Ser Met
1               5                   10                  15

Glu Gln Arg Arg Pro Trp Pro Arg Ala Leu Glu Val Asp Ser Arg Ser
            20                  25                  30

Val Val Leu Leu Ser Val Val Trp Val Leu Leu Ala Pro Pro Ala Ala
        35                  40                  45

Gly Met Pro Gln Phe Ser Thr Phe His Ser Glu Asn Arg Asp Trp Thr
    50                  55                  60

Phe Asn His Leu Thr Val His Gln Gly Thr Gly Ala Val Tyr Val Gly
65                  70                  75                  80

Ala Ile Asn Arg Val Tyr Lys Leu Thr Gly Asn Leu Thr Ile Gln Val
                85                  90                  95

Ala His Lys Thr Gly Pro Glu Glu Asp Asn Lys Ser Cys Tyr Pro Pro
            100                 105                 110
```

```
Leu Ile Val Gln Pro Cys Ser Glu Val Leu Thr Leu Thr Asn Asn Val
        115                 120                 125

Asn Lys Leu Leu Ile Ile Asp Tyr Ser Glu Asn Arg Leu Leu Ala Cys
130                 135                 140

Gly Ser Leu Tyr Gln Gly Val Cys Lys Leu Leu Arg Leu Asp Asp Leu
145                 150                 155                 160

Phe Ile Leu Val Glu Pro Ser His Lys Lys Glu His Tyr Leu Ser Ser
                165                 170                 175

Val Asn Lys Thr Gly Thr Met Tyr Gly Val Ile Val Arg Ser Glu Gly
            180                 185                 190

Glu Asp Gly Lys Leu Phe Ile Gly Thr Ala Val Asp Gly Lys Gln Asp
        195                 200                 205

Tyr Phe Pro Thr Leu Ser Ser Arg Lys Leu Pro Arg Asp Pro Glu Ser
    210                 215                 220

Ser Ala Met Leu Asp Tyr Glu Leu His Ser Asp Phe Val Ser Ser Leu
225                 230                 235                 240

Ile Lys Ile Pro Ser Asp Thr Leu Ala Leu Val Ser His Phe Asp Ile
                245                 250                 255

Phe Tyr Ile Tyr Gly Phe Ala Ser Gly Gly Phe Val Tyr Phe Leu Thr
            260                 265                 270

Val Gln Pro Glu Thr Pro Glu Gly Val Ala Ile Asn Ser Ala Gly Asp
        275                 280                 285

Leu Phe Tyr Thr Ser Arg Ile Val Arg Leu Cys Lys Asp Asp Pro Lys
    290                 295                 300

Phe His Ser Tyr Val Ser Leu Pro Phe Gly Cys Thr Arg Ala Gly Val
305                 310                 315                 320

Glu Tyr Arg Leu Leu Gln Ala Ala Tyr Leu Ala Lys Pro Gly Asp Ser
                325                 330                 335

Leu Ala Gln Ala Phe Asn Ile Thr Ser Gln Asp Asp Val Leu Phe Ala
            340                 345                 350

Ile Phe Ser Lys Gly Gln Lys Gln Tyr His His Pro Pro Asp Asp Ser
        355                 360                 365

Ala Leu Cys Ala Phe Pro Ile Arg Ala Ile Asn Leu Gln Ile Lys Glu
    370                 375                 380

Arg Leu Gln Ser Cys Tyr Gln Gly Glu Gly Asn Leu Glu Leu Asn Trp
385                 390                 395                 400

Leu Leu Gly Lys Asp Val Gln Cys Thr Lys Ala Pro Val Pro Ile Asp
                405                 410                 415

Asp Asn Phe Cys Gly Leu Asp Ile Asn Gln Pro Leu Gly Gly Ser Thr
            420                 425                 430

Pro Val Glu Gly Leu Thr Leu Tyr Thr Thr Ser Arg Asp Arg Met Thr
        435                 440                 445

Ser Val Ala Ser Tyr Val Tyr Asn Gly Tyr Ser Val Val Phe Val Gly
    450                 455                 460

Thr Lys Ser Gly Lys Leu Lys Lys Ile Arg Ala Asp Gly Pro Pro His
465                 470                 475                 480

Gly Gly Val Gln Tyr Glu Met Val Ser Val Leu Lys Asp Gly Ser Pro
                485                 490                 495

Ile Leu Arg Asp Met Ala Phe Ser Ile Asp Gln Arg Tyr Leu Tyr Val
            500                 505                 510

Met Ser Glu Arg Gln Val Thr Arg Val Pro Val Glu Ser Cys Glu Gln
        515                 520                 525

Tyr Thr Thr Cys Gly Glu Cys Leu Ser Ser Gly Asp Pro His Cys Gly
```

```
              530                 535                 540
Trp Cys Ala Leu His Asn Met Cys Ser Arg Arg Asp Lys Cys Gln Gln
545                 550                 555                 560

Ala Trp Glu Pro Asn Arg Phe Ala Ala Ser Ile Ser Gln Cys Val Ser
                    565                 570                 575

Leu Ala Val His Pro Ser Ser Ile Ser Val Ser Glu His Ser Arg Leu
                580                 585                 590

Leu Ser Leu Val Val Ser Asp Ala Pro Asp Leu Ser Ala Gly Ile Ala
            595                 600                 605

Cys Ala Phe Gly Asn Leu Thr Glu Val Glu Gly Gln Val Ser Gly Ser
        610                 615                 620

Gln Val Ile Cys Ile Ser Pro Gly Pro Lys Asp Val Pro Val Ile Pro
625                 630                 635                 640

Leu Asp Gln Asp Trp Phe Gly Leu Glu Leu Gln Leu Arg Ser Lys Glu
                    645                 650                 655

Thr Gly Lys Ile Phe Val Ser Thr Glu Phe Lys Phe Tyr Asn Cys Ser
                660                 665                 670

Ala His Gln Leu Cys Leu Ser Cys Val Asn Ser Ala Phe Arg Cys His
            675                 680                 685

Trp Cys Lys Tyr Arg Asn Leu Cys Thr His Asp Pro Thr Thr Cys Ser
        690                 695                 700

Phe Gln Glu Gly Arg Ile Asn Ile Ser Glu Asp Cys Pro Gln Leu Val
705                 710                 715                 720

Pro Thr Glu Glu Ile Leu Ile Pro Val Gly Glu Val Lys Pro Ile Thr
                    725                 730                 735

Leu Lys Ala Arg Asn Leu Pro Gln Pro Gln Ser Gly Gln Arg Gly Tyr
                740                 745                 750

Glu Cys Val Leu Asn Ile Gln Gly Ala Ile His Arg Val Pro Ala Leu
            755                 760                 765

Arg Phe Asn Ser Ser Ser Val Gln Cys Gln Asn Ser Ser Tyr Gln Tyr
        770                 775                 780

Asp Gly Met Asp Ile Ser Asn Leu Ala Val Asp Phe Ala Val Val Trp
785                 790                 795                 800

Asn Gly Asn Phe Ile Ile Asp Asn Pro Gln Asp Leu Lys Val His Leu
                    805                 810                 815

Tyr Lys Cys Ala Ala Gln Arg Glu Ser Cys Gly Leu Cys Leu Lys Ala
                820                 825                 830

Asp Arg Lys Phe Glu Cys Gly Trp Cys Ser Gly Glu Arg Arg Cys Thr
            835                 840                 845

Leu His Gln His Cys Thr Ser Pro Ser Ser Pro Trp Leu Asp Trp Ser
        850                 855                 860

Ser His Asn Val Lys Cys Ser Asn Pro Gln Ile Thr Glu Ile Leu Thr
865                 870                 875                 880

Val Ser Gly Pro Pro Glu Gly Gly Thr Arg Val Thr Ile His Gly Val
                    885                 890                 895

Asn Leu Gly Leu Asp Phe Ser Glu Ile Ala His His Val Gln Val Ala
                900                 905                 910

Gly Val Pro Cys Thr Pro Leu Pro Gly Glu Tyr Ile Ile Ala Glu Gln
            915                 920                 925

Ile Val Cys Glu Met Gly His Ala Leu Val Gly Thr Thr Ser Gly Pro
        930                 935                 940

Val Arg Leu Cys Ile Gly Glu Cys Lys Pro Glu Phe Met Thr Lys Ser
945                 950                 955                 960
```

-continued

```
His Gln Gln Tyr Thr Phe Val Asn Pro Ser Val Leu Ser Leu Asn Pro
                965                 970                 975
Ile Arg Gly Pro Glu Ser Gly Gly Thr Met Val Thr Ile Thr Gly His
            980                 985                 990
Tyr Leu Gly Ala Gly Ser Ser Val Ala Val Tyr Leu Gly Asn Gln Thr
        995                1000                1005
Cys Glu Phe Tyr Gly Arg Ser Met Ser Glu Ile Val Cys Val Ser
   1010                1015                1020
Pro Pro Ser Ser Asn Gly Leu Gly Pro Val Pro Val Ser Val Ser
   1025                1030                1035
Val Asp Arg Ala His Val Asp Ser Asn Leu Gln Phe Glu Tyr Ile
   1040                1045                1050
Asp Asp Pro Arg Val Gln Arg Ile Glu Pro Glu Trp Ser Ile Ala
   1055                1060                1065
Ser Gly His Thr Pro Leu Thr Ile Thr Gly Phe Asn Leu Asp Val
   1070                1075                1080
Ile Gln Glu Pro Arg Ile Arg Val Lys Phe Asn Gly Lys Glu Ser
   1085                1090                1095
Val Asn Val Cys Lys Val Val Asn Thr Thr Thr Leu Thr Cys Leu
   1100                1105                1110
Ala Pro Ser Leu Thr Thr Asp Tyr Arg Pro Gly Leu Asp Thr Val
   1115                1120                1125
Glu Arg Pro Asp Glu Phe Gly Phe Val Phe Asn Asn Val Gln Ser
   1130                1135                1140
Leu Leu Ile Tyr Asn Asp Thr Lys Phe Ile Tyr Tyr Pro Asn Pro
   1145                1150                1155
Thr Phe Glu Leu Leu Ser Pro Thr Gly Val Leu Asp Gln Lys Pro
   1160                1165                1170
Gly Ser Pro Ile Ile Leu Lys Gly Lys Asn Leu Cys Pro Pro Ala
   1175                1180                1185
Ser Gly Gly Ala Lys Leu Asn Tyr Thr Val Leu Ile Gly Glu Thr
   1190                1195                1200
Pro Cys Ala Val Thr Val Ser Glu Thr Gln Leu Leu Cys Glu Pro
   1205                1210                1215
Pro Asn Leu Thr Gly Gln His Lys Val Met Val His Val Gly Gly
   1220                1225                1230
Met Val Phe Ser Pro Gly Ser Val Ser Val Ile Ser Asp Ser Leu
   1235                1240                1245
Leu Thr Leu Pro Ala Ile Val Ser Ile Ala Ala Gly Gly Ser Leu
   1250                1255                1260
Leu Leu Ile Ile Val Ile Ile Val Leu Ile Ala Tyr Lys Arg Lys
   1265                1270                1275
Ser Arg Glu Asn Asp Leu Thr Leu Lys Arg Leu Gln Met Gln Met
   1280                1285                1290
Asp Asn Leu Glu Ser Arg Val Ala Leu Glu Cys Lys Glu Ala Phe
   1295                1300                1305
Ala Glu Leu Gln Thr Asp Ile Asn Glu Leu Thr Ser Asp Leu Asp
   1310                1315                1320
Arg Ser Gly Ile Pro Tyr Leu Asp Tyr Arg Thr Tyr Ala Met Arg
   1325                1330                1335
Val Leu Phe Pro Gly Ile Glu Asp His Pro Val Leu Arg Glu Leu
   1340                1345                1350
```

| | | | | | | | | | | | |
|---|---|---|---|---|---|---|---|---|---|---|---|
| Glu | Val | Gln | Gly | Asn | Gly | Gln | Gln | His | Val | Glu | Lys | Ala | Leu | Lys |
| | 1355 | | | | 1360 | | | | | 1365 | | | | |
| Leu | Phe | Ala | Gln | Leu | Ile | Asn | Asn | Lys | Val | Phe | Leu | Leu | Thr | Phe |
| | 1370 | | | | 1375 | | | | | 1380 | | | | |
| Ile | Arg | Thr | Leu | Glu | Leu | Gln | Arg | Ser | Phe | Ser | Met | Arg | Asp | Arg |
| | 1385 | | | | 1390 | | | | | 1395 | | | | |
| Gly | Asn | Val | Ala | Ser | Leu | Ile | Met | Thr | Gly | Leu | Gln | Gly | Arg | Leu |
| | 1400 | | | | 1405 | | | | | 1410 | | | | |
| Glu | Tyr | Ala | Thr | Asp | Val | Leu | Lys | Gln | Leu | Leu | Ser | Asp | Leu | Ile |
| | 1415 | | | | 1420 | | | | | 1425 | | | | |
| Asp | Lys | Asn | Leu | Glu | Asn | Lys | Asn | His | Pro | Lys | Leu | Leu | Leu | Arg |
| | 1430 | | | | 1435 | | | | | 1440 | | | | |
| Arg | Thr | Glu | Ser | Val | Ala | Glu | Lys | Met | Leu | Thr | Asn | Trp | Phe | Ala |
| | 1445 | | | | 1450 | | | | | 1455 | | | | |
| Phe | Leu | Leu | His | Lys | Phe | Leu | Lys | Glu | Cys | Ala | Gly | Glu | Pro | Leu |
| | 1460 | | | | 1465 | | | | | 1470 | | | | |
| Phe | Met | Leu | Tyr | Cys | Ala | Ile | Lys | Gln | Gln | Met | Glu | Lys | Gly | Pro |
| | 1475 | | | | 1480 | | | | | 1485 | | | | |
| Ile | Asp | Ala | Ile | Thr | Gly | Glu | Ala | Arg | Tyr | Ser | Leu | Ser | Glu | Asp |
| | 1490 | | | | 1495 | | | | | 1500 | | | | |
| Lys | Leu | Ile | Arg | Gln | Gln | Ile | Glu | Tyr | Lys | Thr | Leu | Ile | Leu | Asn |
| | 1505 | | | | 1510 | | | | | 1515 | | | | |
| Cys | Val | Asn | Pro | Asp | Asn | Glu | Asn | Ser | Pro | Glu | Ile | Pro | Val | Lys |
| | 1520 | | | | 1525 | | | | | 1530 | | | | |
| Val | Leu | Asn | Cys | Asp | Thr | Ile | Thr | Gln | Val | Lys | Glu | Lys | Ile | Leu |
| | 1535 | | | | 1540 | | | | | 1545 | | | | |
| Asp | Ala | Val | Tyr | Lys | Asn | Val | Pro | Tyr | Ser | Gln | Arg | Pro | Arg | Ala |
| | 1550 | | | | 1555 | | | | | 1560 | | | | |
| Val | Asp | Met | Asp | Leu | Glu | Trp | Arg | Gln | Gly | Arg | Ile | Ala | Arg | Val |
| | 1565 | | | | 1570 | | | | | 1575 | | | | |
| Val | Leu | Gln | Asp | Glu | Asp | Ile | Thr | Thr | Lys | Ile | Glu | Gly | Asp | Trp |
| | 1580 | | | | 1585 | | | | | 1590 | | | | |
| Lys | Arg | Leu | Asn | Thr | Leu | Met | His | Tyr | Gln | Val | Ser | Asp | Arg | Ser |
| | 1595 | | | | 1600 | | | | | 1605 | | | | |
| Val | Val | Ala | Leu | Val | Pro | Lys | Gln | Thr | Ser | Ser | Tyr | Asn | Ile | Pro |
| | 1610 | | | | 1615 | | | | | 1620 | | | | |
| Ala | Ser | Ala | Ser | Ile | Ser | Arg | Thr | Ser | Ile | Ser | Arg | Tyr | Asp | Ser |
| | 1625 | | | | 1630 | | | | | 1635 | | | | |
| Ser | Phe | Arg | Tyr | Thr | Gly | Ser | Pro | Asp | Ser | Leu | Arg | Ser | Arg | Ala |
| | 1640 | | | | 1645 | | | | | 1650 | | | | |
| Pro | Met | Ile | Thr | Pro | Asp | Leu | Glu | Ser | Gly | Val | Lys | Val | Trp | His |
| | 1655 | | | | 1660 | | | | | 1665 | | | | |
| Leu | Val | Lys | Asn | His | Asp | His | Gly | Asp | Gln | Lys | Glu | Gly | Asp | Arg |
| | 1670 | | | | 1675 | | | | | 1680 | | | | |
| Gly | Ser | Lys | Met | Val | Ser | Glu | Ile | Tyr | Leu | Thr | Arg | Leu | Leu | Ala |
| | 1685 | | | | 1690 | | | | | 1695 | | | | |
| Thr | Lys | Gly | Thr | Leu | Gln | Lys | Phe | Val | Asp | Asp | Leu | Phe | Glu | Thr |
| | 1700 | | | | 1705 | | | | | 1710 | | | | |
| Leu | Phe | Ser | Thr | Val | His | Arg | Gly | Ser | Ala | Leu | Pro | Leu | Ala | Ile |
| | 1715 | | | | 1720 | | | | | 1725 | | | | |
| Lys | Tyr | Met | Phe | Asp | Phe | Leu | Asp | Glu | Gln | Ala | Asp | Arg | His | Ser |
| | 1730 | | | | 1735 | | | | | 1740 | | | | |
| Ile | His | Asp | Thr | Asp | Val | Arg | His | Thr | Trp | Lys | Ser | Asn | Cys | Leu |

-continued

```
                1745                1750                1755

Pro Leu Arg Phe Trp Val Asn Val Ile Lys Asn Pro Gln Phe Val
       1760                1765                1770

Phe Asp Ile His Lys Gly Ser Ile Thr Asp Ala Cys Leu Ser Val
   1775                1780                1785

Val Ala Gln Thr Phe Met Asp Ser Cys Ser Thr Ser Glu His Arg
       1790                1795                1800

Leu Gly Lys Asp Ser Pro Ser Asn Lys Leu Leu Tyr Ala Lys Asp
   1805                1810                1815

Ile Pro Ser Tyr Lys Ser Trp Val Glu Arg Tyr Ala Asp Ile
       1820                1825                1830

Ala Lys Leu Pro Ala Ile Ser Asp Gln Asp Met Asn Ala Tyr Leu
   1835                1840                1845

Ala Glu Gln Ser Arg Leu His Ala Val Glu Phe Asn Met Leu Ser
       1850                1855                1860

Ala Leu Asn Glu Ile Tyr Ser Tyr Val Ser Lys Tyr Ser Glu Glu
   1865                1870                1875

Leu Ile Gly Ala Leu Glu Gln Asp Glu Gln Ala Arg Arg Gln Arg
       1880                1885                1890

Leu Ala Tyr Lys Val Glu Gln Leu Ile Asn Ala Met Ser Ile Glu
   1895                1900                1905

Ser

<210> SEQ ID NO 100
<211> LENGTH: 1894
<212> TYPE: PRT
<213> ORGANISM: Human

<400> SEQUENCE: 100

Met Glu Gln Arg Arg Pro Trp Pro Arg Ala Leu Glu Val Asp Ser Arg
1               5                  10                  15

Ser Val Val Leu Leu Ser Val Val Trp Val Leu Leu Ala Pro Pro Ala
            20                  25                  30

Ala Gly Met Pro Gln Phe Ser Thr Phe His Ser Glu Asn Arg Asp Trp
        35                  40                  45

Thr Phe Asn His Leu Thr Val His Gln Gly Thr Gly Ala Val Tyr Val
    50                  55                  60

Gly Ala Ile Asn Arg Val Tyr Lys Leu Thr Gly Asn Leu Thr Ile Gln
65                  70                  75                  80

Val Ala His Lys Thr Gly Pro Glu Glu Asp Asn Lys Ser Cys Tyr Pro
                85                  90                  95

Pro Leu Ile Val Gln Pro Cys Ser Glu Val Leu Thr Leu Thr Asn Asn
            100                 105                 110

Val Asn Lys Leu Leu Ile Ile Asp Tyr Ser Glu Asn Arg Leu Leu Ala
        115                 120                 125

Cys Gly Ser Leu Tyr Gln Gly Val Cys Lys Leu Arg Leu Asp Asp
    130                 135                 140

Leu Phe Ile Leu Val Glu Pro Ser His Lys Lys Glu His Tyr Leu Ser
145                 150                 155                 160

Ser Val Asn Lys Thr Gly Thr Met Tyr Gly Val Ile Val Arg Ser Glu
                165                 170                 175

Gly Glu Asp Gly Lys Leu Phe Ile Gly Thr Ala Val Asp Gly Lys Gln
            180                 185                 190

Asp Tyr Phe Pro Thr Leu Ser Ser Arg Lys Leu Pro Arg Asp Pro Glu
```

```
            195                 200                 205
Ser Ser Ala Met Leu Asp Tyr Glu Leu His Ser Asp Phe Val Ser Ser
    210                 215                 220
Leu Ile Lys Ile Pro Ser Asp Thr Leu Ala Leu Val Ser His Phe Asp
225                 230                 235                 240
Ile Phe Tyr Ile Tyr Gly Phe Ala Ser Gly Gly Phe Val Tyr Phe Leu
                245                 250                 255
Thr Val Gln Pro Glu Thr Pro Glu Gly Val Ala Ile Asn Ser Ala Gly
                260                 265                 270
Asp Leu Phe Tyr Thr Ser Arg Ile Val Arg Leu Cys Lys Asp Asp Pro
                275                 280                 285
Lys Phe His Ser Tyr Val Ser Leu Pro Phe Gly Cys Thr Arg Ala Gly
                290                 295                 300
Val Glu Tyr Arg Leu Leu Gln Ala Ala Tyr Leu Ala Lys Pro Gly Asp
305                 310                 315                 320
Ser Leu Ala Gln Ala Phe Asn Ile Thr Ser Gln Asp Asp Val Leu Phe
                325                 330                 335
Ala Ile Phe Ser Lys Gly Gln Lys Gln Tyr His His Pro Pro Asp Asp
                340                 345                 350
Ser Ala Leu Cys Ala Phe Pro Ile Arg Ala Ile Asn Leu Gln Ile Lys
                355                 360                 365
Glu Arg Leu Gln Ser Cys Tyr Gln Gly Glu Gly Asn Leu Glu Leu Asn
                370                 375                 380
Trp Leu Leu Gly Lys Asp Val Gln Cys Thr Lys Ala Pro Val Pro Ile
385                 390                 395                 400
Asp Asp Asn Phe Cys Gly Leu Asp Ile Asn Gln Pro Leu Gly Gly Ser
                405                 410                 415
Thr Pro Val Glu Gly Leu Thr Leu Tyr Thr Thr Ser Arg Asp Arg Met
                420                 425                 430
Thr Ser Val Ala Ser Tyr Val Tyr Asn Gly Tyr Ser Val Val Phe Val
                435                 440                 445
Gly Thr Lys Ser Gly Lys Leu Lys Lys Ile Arg Ala Asp Gly Pro Pro
450                 455                 460
His Gly Gly Val Gln Tyr Glu Met Val Ser Val Leu Lys Asp Gly Ser
465                 470                 475                 480
Pro Ile Leu Arg Asp Met Ala Phe Ser Ile Asp Gln Arg Tyr Leu Tyr
                485                 490                 495
Val Met Ser Glu Arg Gln Val Thr Arg Val Pro Val Glu Ser Cys Glu
                500                 505                 510
Gln Tyr Thr Thr Cys Gly Glu Cys Leu Ser Ser Gly Asp Pro His Cys
                515                 520                 525
Gly Trp Cys Ala Leu His Asn Met Cys Ser Arg Arg Asp Lys Cys Gln
                530                 535                 540
Gln Ala Trp Glu Pro Asn Arg Phe Ala Ala Ser Ile Ser Gln Cys Val
545                 550                 555                 560
Ser Leu Ala Val His Pro Ser Ser Ile Ser Val Ser Glu His Ser Arg
                565                 570                 575
Leu Leu Ser Leu Val Val Ser Asp Ala Pro Asp Leu Ser Ala Gly Ile
                580                 585                 590
Ala Cys Ala Phe Gly Asn Leu Thr Glu Val Glu Gly Gln Val Ser Gly
                595                 600                 605
Ser Gln Val Ile Cys Ile Ser Pro Gly Pro Lys Asp Val Pro Val Ile
610                 615                 620
```

-continued

```
Pro Leu Asp Gln Asp Trp Phe Gly Leu Glu Leu Gln Leu Arg Ser Lys
625                 630                 635                 640

Glu Thr Gly Lys Ile Phe Val Ser Thr Glu Phe Lys Phe Tyr Asn Cys
                645                 650                 655

Ser Ala His Gln Leu Cys Leu Ser Cys Val Asn Ser Ala Phe Arg Cys
            660                 665                 670

His Trp Cys Lys Tyr Arg Asn Leu Cys Thr His Asp Pro Thr Thr Cys
        675                 680                 685

Ser Phe Gln Glu Gly Arg Ile Asn Ile Ser Glu Asp Cys Pro Gln Leu
690                 695                 700

Val Pro Thr Glu Glu Ile Leu Ile Pro Val Gly Glu Val Lys Pro Ile
705                 710                 715                 720

Thr Leu Lys Ala Arg Asn Leu Pro Gln Pro Gln Ser Gly Gln Arg Gly
                725                 730                 735

Tyr Glu Cys Val Leu Asn Ile Gln Gly Ala Ile His Arg Val Pro Ala
            740                 745                 750

Leu Arg Phe Asn Ser Ser Val Gln Cys Gln Asn Ser Ser Tyr Gln
        755                 760                 765

Tyr Asp Gly Met Asp Ile Ser Asn Leu Ala Val Asp Phe Ala Val Val
770                 775                 780

Trp Asn Gly Asn Phe Ile Ile Asp Asn Pro Gln Asp Leu Lys Val His
785                 790                 795                 800

Leu Tyr Lys Cys Ala Ala Gln Arg Glu Ser Cys Gly Leu Cys Leu Lys
                805                 810                 815

Ala Asp Arg Lys Phe Glu Cys Gly Trp Cys Ser Gly Glu Arg Arg Cys
            820                 825                 830

Thr Leu His Gln His Cys Thr Ser Pro Ser Ser Pro Trp Leu Asp Trp
        835                 840                 845

Ser Ser His Asn Val Lys Cys Ser Asn Pro Gln Ile Thr Glu Ile Leu
850                 855                 860

Thr Val Ser Gly Pro Pro Glu Gly Gly Thr Arg Val Thr Ile His Gly
865                 870                 875                 880

Val Asn Leu Gly Leu Asp Phe Ser Glu Ile Ala His His Val Gln Val
                885                 890                 895

Ala Gly Val Pro Cys Thr Pro Leu Pro Gly Glu Tyr Ile Ile Ala Glu
            900                 905                 910

Gln Ile Val Cys Glu Met Gly His Ala Leu Val Gly Thr Thr Ser Gly
        915                 920                 925

Pro Val Arg Leu Cys Ile Gly Glu Cys Lys Pro Glu Phe Met Thr Lys
930                 935                 940

Ser His Gln Gln Tyr Thr Phe Val Asn Pro Ser Val Leu Ser Leu Asn
945                 950                 955                 960

Pro Ile Arg Gly Pro Glu Ser Gly Gly Thr Met Val Thr Ile Thr Gly
                965                 970                 975

His Tyr Leu Gly Ala Gly Ser Ser Val Ala Val Tyr Leu Gly Asn Gln
            980                 985                 990

Thr Cys Glu Phe Tyr Gly Arg Ser  Met Ser Glu Ile Val  Cys Val Ser
        995                 1000                1005

Pro Pro  Ser Ser Asn Gly Leu  Gly Pro Val Pro Val  Ser Val Ser
    1010                1015                1020

Val Asp  Arg Ala His Val Asp  Ser Asn Leu Gln Phe  Glu Tyr Ile
    1025                1030                1035
```

```
Asp Asp Pro Arg Val Gln Arg Ile Glu Pro Glu Trp Ser Ile Ala
    1040                1045                1050

Ser Gly His Thr Pro Leu Thr Ile Thr Gly Phe Asn Leu Asp Val
    1055                1060                1065

Ile Gln Glu Pro Arg Ile Arg Val Lys Phe Asn Gly Lys Glu Ser
    1070                1075                1080

Val Asn Val Cys Lys Val Val Asn Thr Thr Leu Thr Cys Leu
    1085                1090                1095

Ala Pro Ser Leu Thr Thr Asp Tyr Arg Pro Gly Leu Asp Thr Val
    1100                1105                1110

Glu Arg Pro Asp Glu Phe Gly Phe Val Phe Asn Asn Val Gln Ser
    1115                1120                1125

Leu Leu Ile Tyr Asn Asp Thr Lys Phe Ile Tyr Tyr Pro Asn Pro
    1130                1135                1140

Thr Phe Glu Leu Leu Ser Pro Thr Gly Val Leu Asp Gln Lys Pro
    1145                1150                1155

Gly Ser Pro Ile Ile Leu Lys Gly Lys Asn Leu Cys Pro Pro Ala
    1160                1165                1170

Ser Gly Gly Ala Lys Leu Asn Tyr Thr Val Leu Ile Gly Glu Thr
    1175                1180                1185

Pro Cys Ala Val Thr Val Ser Glu Thr Gln Leu Leu Cys Glu Pro
    1190                1195                1200

Pro Asn Leu Thr Gly Gln His Lys Val Met Val His Val Gly Gly
    1205                1210                1215

Met Val Phe Ser Pro Gly Ser Val Ser Val Ile Ser Asp Ser Leu
    1220                1225                1230

Leu Thr Leu Pro Ala Ile Val Ser Ile Ala Ala Gly Gly Ser Leu
    1235                1240                1245

Leu Leu Ile Ile Val Ile Ile Val Leu Ile Ala Tyr Lys Arg Lys
    1250                1255                1260

Ser Arg Glu Asn Asp Leu Thr Leu Lys Arg Leu Gln Met Gln Met
    1265                1270                1275

Asp Asn Leu Glu Ser Arg Val Ala Leu Glu Cys Lys Glu Ala Phe
    1280                1285                1290

Ala Glu Leu Gln Thr Asp Ile Asn Glu Leu Thr Ser Asp Leu Asp
    1295                1300                1305

Arg Ser Gly Ile Pro Tyr Leu Asp Tyr Arg Thr Tyr Ala Met Arg
    1310                1315                1320

Val Leu Phe Pro Gly Ile Glu Asp His Pro Val Leu Arg Glu Leu
    1325                1330                1335

Glu Val Gln Gly Asn Gly Gln Gln His Val Glu Lys Ala Leu Lys
    1340                1345                1350

Leu Phe Ala Gln Leu Ile Asn Asn Lys Val Phe Leu Leu Thr Phe
    1355                1360                1365

Ile Arg Thr Leu Glu Leu Gln Arg Ser Phe Ser Met Arg Asp Arg
    1370                1375                1380

Gly Asn Val Ala Ser Leu Ile Met Thr Gly Leu Gln Gly Arg Leu
    1385                1390                1395

Glu Tyr Ala Thr Asp Val Leu Lys Gln Leu Leu Ser Asp Leu Ile
    1400                1405                1410

Asp Lys Asn Leu Glu Asn Lys Asn His Pro Lys Leu Leu Leu Arg
    1415                1420                1425

Arg Thr Glu Ser Val Ala Glu Lys Met Leu Thr Asn Trp Phe Ala
```

```
            1430              1435              1440
Phe Leu Leu His Lys Phe Leu Lys Glu Cys Ala Gly Glu Pro Leu
    1445              1450              1455
Phe Met Leu Tyr Cys Ala Ile Lys Gln Gln Met Glu Lys Gly Pro
    1460              1465              1470
Ile Asp Ala Ile Thr Gly Glu Ala Arg Tyr Ser Leu Ser Glu Asp
    1475              1480              1485
Lys Leu Ile Arg Gln Gln Ile Glu Tyr Lys Thr Leu Ile Leu Asn
    1490              1495              1500
Cys Val Asn Pro Asp Asn Glu Asn Ser Pro Glu Ile Pro Val Lys
    1505              1510              1515
Val Leu Asn Cys Asp Thr Ile Thr Gln Val Lys Glu Lys Ile Leu
    1520              1525              1530
Asp Ala Val Tyr Lys Asn Val Pro Tyr Ser Gln Arg Pro Arg Ala
    1535              1540              1545
Val Asp Met Asp Leu Glu Trp Arg Gln Gly Arg Ile Ala Arg Val
    1550              1555              1560
Val Leu Gln Asp Glu Asp Ile Thr Thr Lys Ile Glu Gly Asp Trp
    1565              1570              1575
Lys Arg Leu Asn Thr Leu Met His Tyr Gln Val Ser Asp Arg Ser
    1580              1585              1590
Val Val Ala Leu Val Pro Lys Gln Thr Ser Ser Tyr Asn Ile Pro
    1595              1600              1605
Ala Ser Ala Ser Ile Ser Arg Thr Ser Ile Ser Arg Tyr Asp Ser
    1610              1615              1620
Ser Phe Arg Tyr Thr Gly Ser Pro Asp Ser Leu Arg Ser Arg Ala
    1625              1630              1635
Pro Met Ile Thr Pro Asp Leu Glu Ser Gly Val Lys Val Trp His
    1640              1645              1650
Leu Val Lys Asn His Asp His Gly Asp Gln Lys Glu Gly Asp Arg
    1655              1660              1665
Gly Ser Lys Met Val Ser Glu Ile Tyr Leu Thr Arg Leu Leu Ala
    1670              1675              1680
Thr Lys Gly Thr Leu Gln Lys Phe Val Asp Asp Leu Phe Glu Thr
    1685              1690              1695
Leu Phe Ser Thr Val His Arg Gly Ser Ala Leu Pro Leu Ala Ile
    1700              1705              1710
Lys Tyr Met Phe Asp Phe Leu Asp Glu Gln Ala Asp Arg His Ser
    1715              1720              1725
Ile His Asp Thr Asp Val Arg His Thr Trp Lys Ser Asn Cys Leu
    1730              1735              1740
Pro Leu Arg Phe Trp Val Asn Val Ile Lys Asn Pro Gln Phe Val
    1745              1750              1755
Phe Asp Ile His Lys Gly Ser Ile Thr Asp Ala Cys Leu Ser Val
    1760              1765              1770
Val Ala Gln Thr Phe Met Asp Ser Cys Ser Thr Ser Glu His Arg
    1775              1780              1785
Leu Gly Lys Asp Ser Pro Ser Asn Lys Leu Leu Tyr Ala Lys Asp
    1790              1795              1800
Ile Pro Ser Tyr Lys Ser Trp Val Glu Arg Tyr Tyr Ala Asp Ile
    1805              1810              1815
Ala Lys Leu Pro Ala Ile Ser Asp Gln Asp Met Asn Ala Tyr Leu
    1820              1825              1830
```

```
Ala Glu Gln Ser Arg Leu His Ala Val Glu Phe Asn Met Leu Ser
    1835              1840              1845

Ala Leu Asn Glu Ile Tyr Ser Tyr Val Ser Lys Tyr Ser Glu Glu
    1850              1855              1860

Leu Ile Gly Ala Leu Glu Gln Asp Glu Gln Ala Arg Arg Gln Arg
    1865              1870              1875

Leu Ala Tyr Lys Val Glu Gln Leu Ile Asn Ala Met Ser Ile Glu
    1880              1885              1890

Ser

<210> SEQ ID NO 101
<211> LENGTH: 720
<212> TYPE: PRT
<213> ORGANISM: Human

<400> SEQUENCE: 101

Met Pro Pro Pro Ser Asp Ile Val Lys Val Ala Ile Glu Trp Pro Gly
1               5                   10                  15

Ala Asn Ala Gln Leu Leu Glu Ile Asp Gln Lys Arg Pro Leu Ala Ser
                20                  25                  30

Ile Ile Lys Glu Val Cys Asp Gly Trp Ser Leu Pro Asn Pro Glu Tyr
            35                  40                  45

Tyr Thr Leu Arg Tyr Ala Asp Gly Pro Gln Leu Tyr Ile Thr Glu Gln
    50                  55                  60

Thr Arg Ser Asp Ile Lys Asn Gly Thr Ile Leu Gln Leu Ala Ile Ser
65                  70                  75                  80

Pro Ser Arg Ala Ala Arg Gln Leu Met Glu Arg Thr Gln Ser Ser Asn
                85                  90                  95

Met Glu Thr Arg Leu Asp Ala Met Lys Glu Leu Ala Lys Leu Ser Ala
            100                 105                 110

Asp Val Thr Phe Ala Thr Glu Phe Ile Asn Met Asp Gly Ile Ile Val
        115                 120                 125

Leu Thr Arg Leu Val Glu Ser Gly Thr Lys Leu Leu Ser His Tyr Ser
    130                 135                 140

Glu Met Leu Ala Phe Thr Leu Thr Ala Phe Leu Glu Leu Met Asp His
145                 150                 155                 160

Gly Ile Val Ser Trp Asp Met Val Ser Ile Thr Phe Ile Lys Gln Ile
                165                 170                 175

Ala Gly Tyr Val Ser Gln Pro Met Val Asp Val Ser Ile Leu Gln Arg
            180                 185                 190

Ser Leu Ala Ile Leu Glu Ser Met Val Leu Asn Ser Gln Ser Leu Tyr
        195                 200                 205

Gln Lys Ile Ala Glu Glu Ile Thr Val Gly Gln Leu Ile Ser His Leu
    210                 215                 220

Gln Val Ser Asn Gln Glu Ile Gln Thr Tyr Ala Ile Ala Leu Ile Asn
225                 230                 235                 240

Ala Leu Phe Leu Lys Ala Pro Glu Asp Lys Arg Gln Asp Met Ala Asn
                245                 250                 255

Ala Phe Ala Gln Lys His Leu Arg Ser Ile Ile Leu Asn His Val Ile
            260                 265                 270

Arg Gly Asn Arg Pro Ile Lys Thr Glu Met Ala His Gln Leu Tyr Val
        275                 280                 285

Leu Gln Val Leu Thr Phe Asn Leu Leu Glu Glu Arg Met Met Thr Lys
    290                 295                 300
```

```
Met Asp Pro Asn Asp Gln Ala Gln Arg Asp Ile Ile Phe Glu Leu Arg
305                 310                 315                 320

Arg Ile Ala Phe Asp Ala Glu Ser Asp Pro Ser Asn Ala Pro Gly Ser
            325                 330                 335

Gly Thr Glu Lys Arg Lys Ala Met Tyr Thr Lys Asp Tyr Lys Met Leu
        340                 345                 350

Gly Phe Thr Asn His Ile Asn Pro Ala Met Asp Phe Thr Gln Thr Pro
            355                 360                 365

Pro Gly Met Leu Ala Leu Asp Asn Met Leu Tyr Leu Ala Lys Val His
    370                 375                 380

Gln Asp Thr Tyr Ile Arg Ile Val Leu Glu Asn Ser Ser Arg Glu Asp
385                 390                 395                 400

Lys His Glu Cys Pro Phe Gly Arg Ser Ala Ile Glu Leu Thr Lys Met
            405                 410                 415

Leu Cys Glu Ile Leu Gln Val Gly Glu Leu Pro Asn Glu Gly Arg Asn
            420                 425                 430

Asp Tyr His Pro Met Phe Phe Thr His Asp Arg Ala Phe Glu Glu Leu
        435                 440                 445

Phe Gly Ile Cys Ile Gln Leu Leu Asn Lys Thr Trp Lys Glu Met Arg
    450                 455                 460

Ala Thr Ala Glu Asp Phe Asn Lys Val Met Gln Val Arg Glu Gln
465                 470                 475                 480

Ile Thr Arg Ala Leu Pro Ser Lys Pro Asn Ser Leu Asp Gln Phe Lys
            485                 490                 495

Ser Lys Leu Arg Ser Leu Ser Tyr Ser Glu Ile Leu Arg Leu Arg Gln
        500                 505                 510

Ser Glu Arg Met Ser Gln Asp Asp Phe Gln Ser Pro Pro Ile Val Glu
    515                 520                 525

Leu Arg Glu Lys Ile Gln Pro Glu Ile Leu Glu Leu Ile Lys Gln Gln
    530                 535                 540

Arg Leu Asn Arg Leu Cys Glu Gly Ser Ser Phe Arg Lys Ile Gly Asn
545                 550                 555                 560

Arg Arg Arg Gln Glu Arg Phe Trp Tyr Cys Arg Leu Ala Leu Asn His
                565                 570                 575

Lys Val Leu His Tyr Gly Asp Leu Asp Asp Asn Pro Gln Gly Glu Val
            580                 585                 590

Thr Phe Glu Ser Leu Gln Glu Lys Ile Pro Val Ala Asp Ile Lys Ala
    595                 600                 605

Ile Val Thr Gly Lys Asp Cys Pro His Met Lys Glu Lys Ser Ala Leu
    610                 615                 620

Lys Gln Asn Lys Glu Val Leu Glu Leu Ala Phe Ser Ile Leu Tyr Asp
625                 630                 635                 640

Pro Asp Glu Thr Leu Asn Phe Ile Ala Pro Asn Lys Tyr Glu Tyr Cys
            645                 650                 655

Ile Trp Ile Asp Gly Leu Ser Ala Leu Leu Gly Lys Asp Met Ser Ser
        660                 665                 670

Glu Leu Thr Lys Ser Asp Leu Asp Thr Leu Leu Ser Met Glu Met Lys
            675                 680                 685

Leu Arg Leu Leu Asp Leu Glu Asn Ile Gln Ile Pro Glu Ala Pro Pro
        690                 695                 700

Pro Ile Pro Lys Glu Pro Ser Ser Tyr Asp Phe Val Tyr His Tyr Gly
705                 710                 715                 720
```

-continued

```
<210> SEQ ID NO 102
<211> LENGTH: 720
<212> TYPE: PRT
<213> ORGANISM: Human

<400> SEQUENCE: 102
```

| | | | | | | | | | | | | | | |
|---|---|---|---|---|---|---|---|---|---|---|---|---|---|---|
Met | Pro | Pro | Pro | Ser | Asp | Ile | Val | Lys | Val | Ala | Ile | Glu | Trp | Pro | Gly
1 | | | | 5 | | | | | 10 | | | | | 15 |

Ala Asn Ala Gln Leu Leu Glu Ile Asp Gln Lys Arg Pro Leu Ala Ser
            20                  25                  30

Ile Ile Lys Glu Val Cys Asp Gly Trp Ser Leu Pro Asn Pro Glu Tyr
            35                  40                  45

Tyr Thr Leu Arg Tyr Ala Asp Gly Pro Gln Leu Tyr Ile Thr Glu Gln
50                  55                  60

Thr Arg Ser Asp Ile Lys Asn Gly Thr Ile Leu Gln Leu Ala Ile Ser
65                  70                  75                  80

Pro Ser Arg Ala Ala Arg Gln Leu Met Glu Arg Thr Gln Ser Ser Asn
            85                  90                  95

Met Glu Thr Arg Leu Asp Ala Met Lys Glu Leu Ala Lys Leu Ser Ala
            100                105              110

Asp Val Thr Phe Ala Thr Glu Phe Ile Asn Met Asp Gly Ile Ile Val
            115                120              125

Leu Thr Arg Leu Val Glu Ser Gly Thr Lys Leu Leu Ser His Tyr Ser
            130                135              140

Glu Met Leu Ala Phe Thr Leu Thr Ala Phe Leu Glu Leu Met Asp His
145                 150                155              160

Gly Ile Val Ser Trp Asp Met Val Ser Ile Thr Phe Ile Lys Gln Ile
            165                170              175

Ala Gly Tyr Val Ser Gln Pro Met Val Asp Val Ser Ile Leu Gln Arg
            180                185              190

Ser Leu Ala Ile Leu Glu Ser Met Val Leu Asn Ser Gln Ser Leu Tyr
            195                200              205

Gln Lys Ile Ala Glu Glu Ile Thr Val Gly Gln Leu Ile Ser His Leu
            210                215              220

Gln Val Ser Asn Gln Glu Ile Gln Thr Tyr Ala Ile Ala Leu Ile Asn
225                 230                235              240

Ala Leu Phe Leu Lys Ala Pro Glu Asp Lys Arg Gln Asp Met Ala Asn
            245                250              255

Ala Phe Ala Gln Lys His Leu Arg Ser Ile Ile Leu Asn His Val Ile
            260                265              270

Arg Gly Asn Arg Pro Ile Lys Thr Glu Met Ala His Gln Leu Tyr Val
            275                280              285

Leu Gln Val Leu Thr Phe Asn Leu Leu Glu Glu Arg Met Met Thr Lys
            290                295              300

Met Asp Pro Asn Asp Gln Ala Gln Arg Asp Ile Ile Phe Glu Leu Arg
305                 310                315              320

Arg Ile Ala Phe Asp Ala Glu Ser Asp Pro Ser Asn Ala Pro Gly Ser
            325                330              335

Gly Thr Glu Lys Arg Lys Ala Met Tyr Thr Lys Asp Tyr Lys Met Leu
            340                345              350

Gly Phe Thr Asn His Ile Asn Pro Ala Met Asp Phe Thr Gln Thr Pro
            355                360              365

Pro Gly Met Leu Ala Leu Asp Asn Met Leu Tyr Leu Ala Lys Val His
            370                375              380

Gln Asp Thr Tyr Ile Arg Ile Val Leu Glu Asn Ser Ser Arg Glu Asp
385                 390                 395                 400

Lys His Glu Cys Pro Phe Gly Arg Ser Ala Ile Glu Leu Thr Lys Met
            405                 410                 415

Leu Cys Glu Ile Leu Gln Val Gly Glu Leu Pro Asn Glu Gly Arg Asn
        420                 425                 430

Asp Tyr His Pro Met Phe Phe Thr His Asp Arg Ala Phe Glu Glu Leu
            435                 440                 445

Phe Gly Ile Cys Ile Gln Leu Leu Asn Lys Thr Trp Lys Glu Met Arg
        450                 455                 460

Ala Thr Ala Glu Asp Phe Asn Lys Val Met Gln Val Val Arg Glu Gln
465                 470                 475                 480

Ile Thr Arg Ala Leu Pro Ser Lys Pro Asn Ser Leu Asp Gln Phe Lys
                485                 490                 495

Ser Lys Leu Arg Ser Leu Ser Tyr Ser Glu Ile Leu Arg Leu Arg Gln
            500                 505                 510

Ser Glu Arg Met Ser Gln Asp Phe Gln Ser Pro Ile Val Glu
            515                 520                 525

Leu Arg Glu Lys Ile Gln Pro Glu Ile Leu Glu Leu Ile Lys Gln Gln
530                 535                 540

Arg Leu Asn Arg Leu Cys Glu Gly Ser Ser Phe Arg Lys Ile Gly Asn
545                 550                 555                 560

Arg Arg Arg Gln Glu Arg Phe Trp Tyr Cys Arg Leu Ala Leu Asn His
                565                 570                 575

Lys Val Leu His Tyr Gly Asp Leu Asp Asp Asn Pro Gln Gly Glu Val
            580                 585                 590

Thr Phe Glu Ser Leu Gln Glu Lys Ile Pro Val Ala Asp Ile Lys Ala
        595                 600                 605

Ile Val Thr Gly Lys Asp Cys Pro His Met Lys Glu Lys Ser Ala Leu
610                 615                 620

Lys Gln Asn Lys Glu Val Leu Glu Leu Ala Phe Ser Ile Leu Tyr Asp
625                 630                 635                 640

Pro Asp Glu Thr Leu Asn Phe Ile Ala Pro Asn Lys Tyr Glu Tyr Cys
                645                 650                 655

Ile Trp Ile Asp Gly Leu Ser Ala Leu Leu Gly Lys Asp Met Ser Ser
            660                 665                 670

Glu Leu Thr Lys Ser Asp Leu Asp Thr Leu Leu Ser Met Glu Met Lys
        675                 680                 685

Leu Arg Leu Leu Asp Leu Glu Asn Ile Gln Ile Pro Glu Ala Pro Pro
        690                 695                 700

Pro Ile Pro Lys Glu Pro Ser Ser Tyr Asp Phe Val Tyr His Tyr Gly
705                 710                 715                 720

<210> SEQ ID NO 103
<211> LENGTH: 718
<212> TYPE: PRT
<213> ORGANISM: Human

<400> SEQUENCE: 103

Met Pro Pro Pro Ser Asp Ile Val Lys Val Ala Ile Glu Trp Pro Gly
1               5                   10                  15

Ala Asn Ala Gln Leu Leu Glu Ile Asp Gln Lys Arg Pro Leu Ala Ser
            20                  25                  30

Ile Ile Lys Glu Val Cys Asp Gly Trp Ser Leu Pro Asn Pro Glu Tyr

```
                35                  40                  45
Tyr Thr Leu Arg Tyr Ala Asp Gly Pro Gln Leu Tyr Ile Thr Glu Gln
 50                  55                  60

Thr Arg Ser Asp Ile Lys Asn Gly Thr Ile Leu Gln Leu Ala Ile Ser
 65                  70                  75                  80

Pro Ser Arg Ala Ala Arg Gln Leu Met Glu Arg Thr Gln Ser Ser Asn
                 85                  90                  95

Met Glu Thr Arg Leu Asp Ala Met Lys Glu Leu Ala Lys Leu Ser Ala
                100                 105                 110

Asp Val Thr Phe Ala Thr Glu Phe Ile Asn Met Asp Gly Ile Ile Val
                115                 120                 125

Leu Thr Arg Leu Val Glu Ser Gly Thr Lys Leu Leu Ser His Glu Met
                130                 135                 140

Leu Ala Phe Thr Leu Thr Ala Phe Leu Glu Leu Met Asp His Gly Ile
145                 150                 155                 160

Val Ser Trp Asp Met Val Ser Ile Thr Phe Ile Lys Gln Ile Ala Gly
                165                 170                 175

Tyr Val Ser Gln Pro Met Val Asp Val Ser Ile Leu Gln Arg Ser Leu
                180                 185                 190

Ala Ile Leu Glu Ser Met Val Leu Asn Ser Gln Ser Leu Tyr Gln Lys
                195                 200                 205

Ile Ala Glu Glu Ile Thr Val Gly Gln Leu Ile Ser His Leu Gln Val
                210                 215                 220

Ser Asn Gln Glu Ile Gln Thr Tyr Ala Ile Ala Leu Ile Asn Ala Leu
225                 230                 235                 240

Phe Leu Lys Ala Pro Glu Asp Lys Arg Gln Asp Met Ala Asn Ala Phe
                245                 250                 255

Ala Gln Lys His Leu Arg Ser Ile Ile Leu Asn His Val Ile Arg Gly
                260                 265                 270

Asn Arg Pro Ile Lys Thr Glu Met Ala His Gln Leu Tyr Val Leu Gln
                275                 280                 285

Val Leu Thr Phe Asn Leu Leu Glu Glu Arg Met Met Thr Lys Met Asp
                290                 295                 300

Pro Asn Asp Gln Ala Gln Arg Asp Ile Ile Phe Glu Leu Arg Arg Ile
305                 310                 315                 320

Ala Phe Asp Ala Glu Ser Asp Pro Ser Asn Ala Pro Gly Ser Gly Thr
                325                 330                 335

Glu Lys Arg Lys Ala Met Tyr Thr Lys Asp Tyr Lys Met Leu Gly Phe
                340                 345                 350

Thr Asn His Ile Asn Pro Ala Met Asp Phe Thr Gln Thr Pro Pro Gly
                355                 360                 365

Met Leu Ala Leu Asp Asn Met Leu Tyr Leu Ala Lys Val His Gln Asp
                370                 375                 380

Thr Tyr Ile Arg Ile Val Leu Glu Asn Ser Ser Arg Glu Asp Lys His
385                 390                 395                 400

Glu Cys Pro Phe Gly Arg Ser Ala Ile Glu Leu Thr Lys Met Leu Cys
                405                 410                 415

Glu Ile Leu Gln Val Gly Glu Leu Pro Asn Glu Gly Arg Asn Asp Tyr
                420                 425                 430

His Pro Met Phe Phe Thr His Asp Arg Ala Phe Glu Glu Leu Phe Gly
                435                 440                 445

Ile Cys Ile Gln Leu Leu Asn Lys Thr Trp Lys Glu Met Arg Ala Thr
                450                 455                 460
```

Ala Glu Asp Phe Asn Lys Val Met Gln Val Val Arg Glu Gln Ile Thr
465                 470                 475                 480

Arg Ala Leu Pro Ser Lys Pro Asn Ser Leu Asp Gln Phe Lys Ser Lys
                485                 490                 495

Leu Arg Ser Leu Ser Tyr Ser Glu Ile Leu Arg Leu Arg Gln Ser Glu
            500                 505                 510

Arg Met Ser Gln Asp Asp Phe Gln Ser Pro Pro Ile Val Glu Leu Arg
        515                 520                 525

Glu Lys Ile Gln Pro Glu Ile Leu Glu Leu Ile Lys Gln Gln Arg Leu
    530                 535                 540

Asn Arg Leu Cys Glu Gly Ser Ser Phe Arg Lys Ile Gly Asn Arg Arg
545                 550                 555                 560

Arg Gln Glu Arg Phe Trp Tyr Cys Arg Leu Ala Leu Asn His Lys Val
                565                 570                 575

Leu His Tyr Gly Asp Leu Asp Asp Asn Pro Gln Gly Glu Val Thr Phe
            580                 585                 590

Glu Ser Leu Gln Glu Lys Ile Pro Val Ala Asp Ile Lys Ala Ile Val
        595                 600                 605

Thr Gly Lys Asp Cys Pro His Met Lys Glu Lys Ser Ala Leu Lys Gln
    610                 615                 620

Asn Lys Glu Val Leu Glu Leu Ala Phe Ser Ile Leu Tyr Asp Pro Asp
625                 630                 635                 640

Glu Thr Leu Asn Phe Ile Ala Pro Asn Lys Tyr Glu Tyr Cys Ile Trp
                645                 650                 655

Ile Asp Gly Leu Ser Ala Leu Leu Gly Lys Asp Met Ser Ser Glu Leu
            660                 665                 670

Thr Lys Ser Asp Leu Asp Thr Leu Leu Ser Met Glu Met Lys Leu Arg
        675                 680                 685

Leu Leu Asp Leu Glu Asn Ile Gln Ile Pro Glu Ala Pro Pro Pro Ile
    690                 695                 700

Pro Lys Glu Pro Ser Ser Tyr Asp Phe Val Tyr His Tyr Gly
705                 710                 715

<210> SEQ ID NO 104
<211> LENGTH: 632
<212> TYPE: PRT
<213> ORGANISM: Human

<400> SEQUENCE: 104

Met Glu Arg Thr Gln Ser Ser Asn Met Glu Thr Arg Leu Asp Ala Met
1               5                   10                  15

Lys Glu Leu Ala Lys Leu Ser Ala Asp Val Thr Phe Ala Thr Glu Phe
            20                  25                  30

Ile Asn Met Asp Gly Ile Ile Val Leu Thr Arg Leu Val Glu Ser Gly
        35                  40                  45

Thr Lys Leu Leu Ser His Tyr Ser Glu Met Leu Ala Phe Thr Leu Thr
    50                  55                  60

Ala Phe Leu Glu Leu Met Asp His Gly Ile Val Ser Trp Asp Met Val
65                  70                  75                  80

Ser Ile Thr Phe Ile Lys Gln Ile Ala Gly Tyr Val Ser Gln Pro Met
                85                  90                  95

Val Asp Val Ser Ile Leu Gln Arg Ser Leu Ala Ile Leu Glu Ser Met
            100                 105                 110

Val Leu Asn Ser Gln Ser Leu Tyr Gln Lys Ile Ala Glu Glu Ile Thr

```
            115                 120                 125
Val Gly Gln Leu Ile Ser His Leu Gln Val Ser Asn Gln Glu Ile Gln
    130                 135                 140

Thr Tyr Ala Ile Ala Leu Ile Asn Ala Leu Phe Leu Lys Ala Pro Glu
145                 150                 155                 160

Asp Lys Arg Gln Asp Met Ala Asn Ala Phe Ala Gln Lys His Leu Arg
                165                 170                 175

Ser Ile Ile Leu Asn His Val Ile Arg Gly Asn Arg Pro Ile Lys Thr
            180                 185                 190

Glu Met Ala His Gln Leu Tyr Val Leu Gln Val Leu Thr Phe Asn Leu
        195                 200                 205

Leu Glu Glu Arg Met Met Thr Lys Met Asp Pro Asn Asp Gln Ala Gln
    210                 215                 220

Arg Asp Ile Ile Phe Glu Leu Arg Arg Ile Ala Phe Asp Ala Glu Ser
225                 230                 235                 240

Asp Pro Ser Asn Ala Pro Gly Ser Gly Thr Glu Lys Arg Lys Ala Met
                245                 250                 255

Tyr Thr Lys Asp Tyr Lys Met Leu Gly Phe Thr Asn His Ile Asn Pro
            260                 265                 270

Ala Met Asp Phe Thr Gln Thr Pro Pro Gly Met Leu Ala Leu Asp Asn
        275                 280                 285

Met Leu Tyr Leu Ala Lys Val His Gln Asp Thr Tyr Ile Arg Ile Val
    290                 295                 300

Leu Glu Asn Ser Ser Arg Glu Asp Lys His Glu Cys Pro Phe Gly Arg
305                 310                 315                 320

Ser Ala Ile Glu Leu Thr Lys Met Leu Cys Glu Ile Leu Gln Val Gly
                325                 330                 335

Glu Leu Pro Asn Glu Gly Arg Asn Asp Tyr His Pro Met Phe Phe Thr
            340                 345                 350

His Asp Arg Ala Phe Glu Glu Leu Phe Gly Ile Cys Ile Gln Leu Leu
        355                 360                 365

Asn Lys Thr Trp Lys Glu Met Arg Ala Thr Ala Glu Asp Phe Asn Lys
    370                 375                 380

Val Met Gln Val Val Arg Glu Gln Ile Thr Arg Ala Leu Pro Ser Lys
385                 390                 395                 400

Pro Asn Ser Leu Asp Gln Phe Lys Ser Lys Leu Arg Ser Leu Ser Tyr
                405                 410                 415

Ser Glu Ile Leu Arg Leu Arg Gln Ser Glu Arg Met Ser Gln Asp Asp
            420                 425                 430

Phe Gln Ser Pro Pro Ile Val Glu Leu Arg Glu Lys Ile Gln Pro Glu
        435                 440                 445

Ile Leu Glu Leu Ile Lys Gln Gln Arg Leu Asn Arg Leu Cys Glu Gly
    450                 455                 460

Ser Ser Phe Arg Lys Ile Gly Asn Arg Arg Gln Glu Arg Phe Trp
465                 470                 475                 480

Tyr Cys Arg Leu Ala Leu Asn His Lys Val Leu His Tyr Gly Asp Leu
                485                 490                 495

Asp Asp Asn Pro Gln Gly Glu Val Thr Phe Glu Ser Leu Gln Glu Lys
            500                 505                 510

Ile Pro Val Ala Asp Ile Lys Ala Ile Val Thr Gly Lys Asp Cys Pro
        515                 520                 525

His Met Lys Glu Lys Ser Ala Leu Lys Gln Asn Lys Glu Val Leu Glu
    530                 535                 540
```

```
Leu Ala Phe Ser Ile Leu Tyr Asp Pro Asp Glu Thr Leu Asn Phe Ile
545                 550                 555                 560

Ala Pro Asn Lys Tyr Glu Tyr Cys Ile Trp Ile Asp Gly Leu Ser Ala
                565                 570                 575

Leu Leu Gly Lys Asp Met Ser Ser Glu Leu Thr Lys Ser Asp Leu Asp
            580                 585                 590

Thr Leu Leu Ser Met Glu Met Lys Leu Arg Leu Leu Asp Leu Glu Asn
        595                 600                 605

Ile Gln Ile Pro Glu Ala Pro Pro Ile Pro Lys Glu Pro Ser Ser
    610                 615                 620

Tyr Asp Phe Val Tyr His Tyr Gly
625                 630

<210> SEQ ID NO 105
<211> LENGTH: 463
<212> TYPE: PRT
<213> ORGANISM: Human

<400> SEQUENCE: 105

Met Ala Ala Leu Arg Ala Leu Cys Gly Phe Arg Gly Val Ala Ala Gln
1               5                   10                  15

Val Leu Arg Pro Gly Ala Gly Val Arg Leu Pro Ile Gln Pro Ser Arg
                20                  25                  30

Gly Val Arg Gln Trp Gln Pro Asp Val Glu Trp Ala Gln Gln Phe Gly
            35                  40                  45

Gly Ala Val Met Tyr Pro Ser Lys Glu Thr Ala His Trp Lys Pro Pro
        50                  55                  60

Pro Trp Asn Asp Val Asp Pro Pro Lys Asp Thr Ile Val Lys Asn Ile
65                  70                  75                  80

Thr Leu Asn Phe Gly Pro Gln His Pro Ala Ala His Gly Val Leu Arg
                85                  90                  95

Leu Val Met Glu Leu Ser Gly Glu Met Val Arg Lys Cys Asp Pro His
                100                 105                 110

Ile Gly Leu Leu His Arg Gly Thr Glu Lys Leu Ile Glu Tyr Lys Thr
            115                 120                 125

Tyr Leu Gln Ala Leu Pro Tyr Phe Asp Arg Leu Asp Tyr Val Ser Met
        130                 135                 140

Met Cys Asn Glu Gln Ala Tyr Ser Leu Ala Val Glu Lys Leu Leu Asn
145                 150                 155                 160

Ile Arg Pro Pro Arg Ala Gln Trp Ile Arg Val Leu Phe Gly Glu
                165                 170                 175

Ile Thr Arg Leu Leu Asn His Ile Met Ala Val Thr Thr His Ala Leu
            180                 185                 190

Asp Leu Gly Ala Met Thr Pro Phe Phe Trp Leu Phe Glu Glu Arg Glu
        195                 200                 205

Lys Met Phe Glu Phe Tyr Glu Arg Val Ser Gly Ala Arg Met His Ala
    210                 215                 220

Ala Tyr Ile Arg Pro Gly Gly Val His Gln Asp Leu Pro Leu Gly Leu
225                 230                 235                 240

Met Asp Asp Ile Tyr Gln Phe Ser Lys Asn Phe Ser Leu Arg Leu Asp
                245                 250                 255

Glu Leu Glu Glu Leu Leu Thr Asn Asn Arg Ile Trp Arg Asn Arg Thr
            260                 265                 270

Ile Asp Ile Gly Val Val Thr Ala Glu Glu Ala Leu Asn Tyr Gly Phe
```

```
                275                 280                 285
Ser Gly Val Met Leu Arg Gly Ser Gly Ile Gln Trp Asp Leu Arg Lys
    290                 295                 300

Thr Gln Pro Tyr Asp Val Tyr Asp Gln Val Glu Phe Asp Val Pro Val
305                 310                 315                 320

Gly Ser Arg Gly Asp Cys Tyr Asp Arg Tyr Leu Cys Arg Val Glu Glu
                325                 330                 335

Met Arg Gln Ser Leu Arg Ile Ile Ala Gln Cys Leu Asn Lys Met Pro
            340                 345                 350

Pro Gly Glu Ile Lys Val Asp Asp Ala Lys Val Ser Pro Pro Lys Arg
        355                 360                 365

Ala Glu Met Lys Thr Ser Met Glu Ser Leu Ile His His Phe Lys Leu
    370                 375                 380

Tyr Thr Glu Gly Tyr Gln Val Pro Pro Gly Ala Thr Tyr Thr Ala Ile
385                 390                 395                 400

Glu Ala Pro Lys Gly Glu Phe Gly Val Tyr Leu Val Ser Asp Gly Ser
                405                 410                 415

Ser Arg Pro Tyr Arg Cys Lys Ile Lys Ala Pro Gly Phe Ala His Leu
            420                 425                 430

Ala Gly Leu Asp Lys Met Ser Lys Gly His Met Leu Ala Asp Val Val
        435                 440                 445

Ala Ile Ile Gly Thr Gln Asp Ile Val Phe Gly Glu Val Asp Arg
    450                 455                 460

<210> SEQ ID NO 106
<211> LENGTH: 463
<212> TYPE: PRT
<213> ORGANISM: Human

<400> SEQUENCE: 106

Met Ala Ala Leu Arg Ala Leu Cys Gly Phe Arg Gly Val Ala Ala Gln
1               5                   10                  15

Val Leu Arg Pro Gly Ala Gly Val Arg Leu Pro Ile Gln Pro Ser Arg
            20                  25                  30

Gly Val Arg Gln Trp Gln Pro Asp Val Glu Trp Ala Gln Gln Phe Gly
        35                  40                  45

Gly Ala Val Met Tyr Pro Ser Lys Glu Thr Ala His Trp Lys Pro Pro
    50                  55                  60

Pro Trp Asn Asp Val Asp Pro Pro Lys Asp Thr Ile Val Lys Asn Ile
65              70                  75                  80

Thr Leu Asn Phe Gly Pro Gln His Pro Ala Ala His Gly Val Leu Arg
                85                  90                  95

Leu Val Met Glu Leu Ser Gly Glu Met Val Arg Lys Cys Asp Pro His
            100                 105                 110

Ile Gly Leu Leu His Arg Gly Thr Glu Lys Leu Ile Glu Tyr Lys Thr
        115                 120                 125

Tyr Leu Gln Ala Leu Pro Tyr Phe Asp Arg Leu Asp Tyr Val Ser Met
    130                 135                 140

Met Cys Asn Glu Gln Ala Tyr Ser Leu Ala Val Glu Lys Leu Leu Asn
145                 150                 155                 160

Ile Arg Pro Pro Pro Arg Ala Gln Trp Ile Arg Val Leu Phe Gly Glu
                165                 170                 175

Ile Thr Arg Leu Leu Asn His Ile Met Ala Val Thr Thr His Ala Leu
            180                 185                 190
```

```
Asp Leu Gly Ala Met Thr Pro Phe Phe Trp Leu Phe Glu Glu Arg Glu
            195                 200                 205

Lys Met Phe Glu Phe Tyr Glu Arg Val Ser Gly Ala Arg Met His Ala
210                 215                 220

Ala Tyr Ile Arg Pro Gly Val His Gln Asp Leu Pro Leu Gly Leu
225                 230                 235                 240

Met Asp Asp Ile Tyr Gln Phe Ser Lys Asn Phe Ser Leu Arg Leu Asp
            245                 250                 255

Glu Leu Glu Glu Leu Leu Thr Asn Asn Arg Ile Trp Arg Asn Arg Thr
260                 265                 270

Ile Asp Ile Gly Val Val Thr Ala Glu Glu Ala Leu Asn Tyr Gly Phe
            275                 280                 285

Ser Gly Val Met Leu Arg Gly Ser Gly Ile Gln Trp Asp Leu Arg Lys
290                 295                 300

Thr Gln Pro Tyr Asp Val Tyr Asp Gln Val Glu Phe Asp Val Pro Val
305                 310                 315                 320

Gly Ser Arg Gly Asp Cys Tyr Asp Arg Tyr Leu Cys Arg Val Glu Glu
            325                 330                 335

Met Arg Gln Ser Leu Arg Ile Ile Ala Gln Cys Leu Asn Lys Met Pro
            340                 345                 350

Pro Gly Glu Ile Lys Val Asp Asp Ala Lys Val Ser Pro Pro Lys Arg
            355                 360                 365

Ala Glu Met Lys Thr Ser Met Glu Ser Leu Ile His His Phe Lys Leu
            370                 375                 380

Tyr Thr Glu Gly Tyr Gln Val Pro Pro Gly Ala Thr Tyr Thr Ala Ile
385                 390                 395                 400

Glu Ala Pro Lys Gly Glu Phe Gly Val Tyr Leu Val Ser Asp Gly Ser
            405                 410                 415

Ser Arg Pro Tyr Arg Cys Lys Ile Lys Ala Pro Gly Phe Ala His Leu
            420                 425                 430

Ala Gly Leu Asp Lys Met Ser Lys Gly His Met Leu Ala Asp Val Val
            435                 440                 445

Ala Ile Ile Gly Thr Gln Asp Ile Val Phe Gly Glu Val Asp Arg
450                 455                 460

<210> SEQ ID NO 107
<211> LENGTH: 693
<212> TYPE: PRT
<213> ORGANISM: Human

<400> SEQUENCE: 107

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Gly Gly Trp
        35                  40                  45

Arg Arg Ala Ala Gly Gly Arg Glu Ala Arg Gly Leu Leu Ala Pro Thr
    50                  55                  60

Pro Asp Ala Pro Arg Pro Ala Ala Leu Ile Val Arg Asp Gln Thr
65                  70                  75                  80

Glu Leu Arg Leu Cys Glu Arg Ser Gly Gln Arg Thr Ala Ser Val Leu
            85                  90                  95

Trp Pro Trp Ile Asn Arg Asn Ala Arg Val Ala Asp Leu Val His Ile
            100                 105                 110
```

```
Leu Thr His Leu Gln Leu Leu Arg Ala Arg Asp Ile Ile Thr Ala Trp
        115                 120                 125

His Pro Pro Ala Pro Leu Pro Ser Pro Gly Thr Thr Ala Pro Arg Pro
        130                 135                 140

Ser Ser Ile Pro Ala Pro Ala Glu Ala Glu Ala Trp Ser Pro Arg Lys
145                 150                 155                 160

Leu Pro Ser Ser Ala Ser Thr Phe Leu Ser Pro Ala Phe Pro Gly Ser
                165                 170                 175

Gln Thr His Ser Gly Pro Glu Leu Gly Leu Val Pro Ser Pro Ala Ser
                180                 185                 190

Leu Trp Pro Pro Pro Ser Pro Ala Pro Ser Ser Thr Lys Pro Gly
        195                 200                 205

Pro Glu Ser Ser Val Ser Leu Leu Gln Gly Ala Arg Pro Phe Pro Phe
        210                 215                 220

Cys Trp Pro Leu Cys Glu Ile Ser Arg Gly Thr His Asn Phe Ser Glu
225                 230                 235                 240

Glu Leu Lys Ile Gly Glu Gly Gly Phe Gly Cys Val Tyr Arg Ala Val
                245                 250                 255

Met Arg Asn Thr Val Tyr Ala Val Lys Arg Leu Lys Glu Asn Ala Asp
        260                 265                 270

Leu Glu Trp Thr Ala Val Lys Gln Ser Phe Leu Thr Glu Val Glu Gln
        275                 280                 285

Leu Ser Arg Phe Arg His Pro Asn Ile Val Asp Phe Ala Gly Tyr Cys
        290                 295                 300

Ala Gln Asn Gly Phe Tyr Cys Leu Val Tyr Gly Phe Leu Pro Asn Gly
305                 310                 315                 320

Ser Leu Glu Asp Arg Leu His Cys Gln Thr Gln Ala Cys Pro Pro Leu
                325                 330                 335

Ser Trp Pro Gln Arg Leu Asp Ile Leu Leu Gly Thr Ala Arg Ala Ile
                340                 345                 350

Gln Phe Leu His Gln Asp Ser Pro Ser Leu Ile His Gly Asp Ile Lys
        355                 360                 365

Ser Ser Asn Val Leu Leu Asp Glu Arg Leu Thr Pro Lys Leu Gly Asp
370                 375                 380

Phe Gly Leu Ala Arg Phe Ser Arg Phe Ala Gly Ser Ser Pro Ser Gln
385                 390                 395                 400

Ser Ser Met Val Ala Arg Thr Gln Thr Val Arg Gly Thr Leu Ala Tyr
                405                 410                 415

Leu Pro Glu Glu Tyr Ile Lys Thr Gly Arg Leu Ala Val Asp Thr Asp
                420                 425                 430

Thr Phe Ser Phe Gly Val Val Val Leu Glu Thr Leu Ala Gly Gln Arg
        435                 440                 445

Ala Val Lys Thr His Gly Ala Arg Thr Lys Tyr Leu Lys Asp Leu Val
450                 455                 460

Glu Glu Glu Ala Glu Glu Ala Gly Val Ala Leu Arg Ser Thr Gln Ser
465                 470                 475                 480

Thr Leu Gln Ala Gly Leu Ala Ala Asp Ala Trp Ala Ala Pro Ile Ala
                485                 490                 495

Met Gln Ile Tyr Lys Lys His Leu Gly Gln Leu Ala Cys Cys Cys Leu
                500                 505                 510

His Arg Arg Ala Lys Arg Pro Pro Met Thr Gln Glu Asn Ser Tyr
        515                 520                 525
```

```
Val Ser Ser Thr Gly Arg Ala His Ser Gly Ala Ala Pro Trp Gln Pro
    530                 535                 540

Leu Ala Ala Pro Ser Gly Ala Ser Ala Gln Ala Ala Glu Gln Leu Gln
545                 550                 555                 560

Arg Gly Pro Asn Gln Pro Val Glu Ser Asp Glu Ser Leu Gly Gly Leu
                565                 570                 575

Ser Ala Ala Leu Arg Ser Trp His Leu Thr Pro Ser Cys Pro Leu Asp
            580                 585                 590

Pro Ala Pro Leu Arg Glu Ala Gly Cys Pro Gln Gly Asp Thr Ala Gly
        595                 600                 605

Glu Ser Ser Trp Gly Ser Gly Pro Gly Ser Arg Pro Thr Ala Val Glu
    610                 615                 620

Gly Leu Ala Leu Gly Ser Ser Ala Ser Ser Ser Glu Pro Pro Gln
625                 630                 635                 640

Ile Ile Ile Asn Pro Ala Arg Gln Lys Met Val Gln Lys Leu Ala Leu
                645                 650                 655

Tyr Glu Asp Gly Ala Leu Asp Ser Leu Gln Leu Leu Ser Ser Ser Ser
            660                 665                 670

Leu Pro Gly Leu Gly Leu Glu Gln Asp Arg Gln Gly Pro Glu Glu Ser
        675                 680                 685

Asp Glu Phe Gln Ser
    690
```

<210> SEQ ID NO 108
<211> LENGTH: 712
<212> TYPE: PRT
<213> ORGANISM: Human

<400> SEQUENCE: 108

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205
```

```
Thr His Asn Phe Ser Glu Glu Leu Lys Ile Gly Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
    370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
        420                 425                 430

Tyr Leu Lys Asp Leu Val Glu Glu Ala Glu Glu Ala Gly Val Ala
    435                 440                 445

Leu Arg Ser Thr Gln Ser Thr Leu Gln Ala Gly Leu Ala Ala Asp Ala
450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                485                 490                 495

Ala Cys Cys Cys Leu His Arg Arg Ala Lys Arg Arg Pro Pro Met Thr
        500                 505                 510

Gln Val Tyr Glu Arg Leu Glu Lys Leu Gln Ala Val Val Ala Gly Val
    515                 520                 525

Pro Gly His Ser Glu Ala Ala Ser Cys Ile Pro Pro Ser Pro Gln Glu
530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
                565                 570                 575

Gln Leu Gln Arg Gly Pro Asn Gln Pro Val Glu Ser Asp Glu Ser Leu
        580                 585                 590

Gly Gly Leu Ser Ala Ala Leu Arg Ser Trp His Leu Thr Pro Ser Cys
    595                 600                 605

Pro Leu Asp Pro Ala Pro Leu Arg Glu Ala Gly Cys Pro Gln Gly Asp
    610                 615                 620
```

```
Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
            645                 650                 655

Pro Pro Gln Ile Ile Ile Asn Pro Ala Arg Gln Lys Met Val Gln Lys
                660                 665                 670

Leu Ala Leu Tyr Glu Asp Gly Ala Leu Asp Ser Leu Gln Leu Leu Ser
                675                 680                 685

Ser Ser Ser Leu Pro Gly Leu Gly Leu Glu Gln Asp Arg Gln Gly Pro
690                 695                 700

Glu Glu Ser Asp Glu Phe Gln Ser
705                 710
```

<210> SEQ ID NO 109
<211> LENGTH: 682
<212> TYPE: PRT
<213> ORGANISM: Human

<400> SEQUENCE: 109

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
                20                  25                  30

Val Met Asp Ala Leu Glu Pro Ala Asp Trp Cys Gln Phe Ala Ala Leu
            35                  40                  45

Ile Val Arg Asp Gln Thr Glu Leu Arg Leu Cys Glu Arg Ser Gly Gln
        50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
                100                 105                 110

Thr Thr Ala Pro Arg Pro Ser Ser Ile Pro Ala Pro Ala Glu Ala Glu
            115                 120                 125

Ala Trp Ser Pro Arg Lys Leu Pro Ser Ser Ala Ser Thr Phe Leu Ser
130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
                180                 185                 190

Ala Arg Pro Phe Pro Phe Cys Trp Pro Leu Cys Glu Ile Ser Arg Gly
            195                 200                 205

Thr His Asn Phe Ser Glu Glu Leu Lys Ile Gly Glu Gly Gly Phe Gly
        210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285
```

```
Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
                340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Leu Glu
                405                 410                 415

Thr Leu Ala Gly Gln Arg Ala Val Lys Thr His Gly Ala Arg Thr Lys
                420                 425                 430

Tyr Leu Lys Asp Leu Val Glu Glu Ala Glu Ala Gly Val Ala
                435                 440                 445

Leu Arg Ser Thr Gln Ser Thr Leu Gln Ala Gly Leu Ala Ala Asp Ala
450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                485                 490                 495

Ala Cys Cys Cys Leu His Arg Arg Ala Lys Arg Arg Pro Pro Met Thr
                500                 505                 510

Gln Glu Asn Ser Tyr Val Ser Ser Thr Gly Arg Ala His Ser Gly Ala
                515                 520                 525

Ala Pro Trp Gln Pro Leu Ala Ala Pro Ser Gly Ala Ser Ala Gln Ala
                530                 535                 540

Ala Glu Gln Leu Gln Arg Gly Pro Asn Gln Pro Val Glu Ser Asp Glu
545                 550                 555                 560

Ser Leu Gly Gly Leu Ser Ala Ala Leu Arg Ser Trp His Leu Thr Pro
                565                 570                 575

Ser Cys Pro Leu Asp Pro Ala Pro Leu Arg Glu Ala Gly Cys Pro Gln
                580                 585                 590

Gly Asp Thr Ala Gly Glu Ser Ser Trp Gly Ser Gly Pro Gly Ser Arg
                595                 600                 605

Pro Thr Ala Val Glu Gly Leu Ala Leu Gly Ser Ser Ala Ser Ser Ser
            610                 615                 620

Ser Glu Pro Pro Gln Ile Ile Ile Asn Pro Ala Arg Gln Lys Met Val
625                 630                 635                 640

Gln Lys Leu Ala Leu Tyr Glu Asp Gly Ala Leu Asp Ser Leu Gln Leu
                645                 650                 655

Leu Ser Ser Ser Ser Leu Pro Gly Leu Gly Leu Glu Gln Asp Arg Gln
                660                 665                 670

Gly Pro Glu Glu Ser Asp Glu Phe Gln Ser
            675                 680
```

<210> SEQ ID NO 110
<211> LENGTH: 633

<212> TYPE: PRT
<213> ORGANISM: Human

<400> SEQUENCE: 110

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
    370                 375                 380

Arg Gly Thr Leu Ala Tyr Leu Pro Glu Glu Tyr Ile Lys Thr Gly Arg
385                 390                 395                 400
```

```
Leu Ala Val Asp Thr Asp Thr Phe Ser Phe Gly Val Val Leu Glu
                405                 410                 415

Thr Leu Ala Gly Gln Arg Ala Val Lys Thr His Gly Ala Arg Thr Lys
            420                 425                 430

Tyr Leu Val Tyr Glu Arg Leu Glu Lys Leu Gln Ala Val Val Ala Gly
        435                 440                 445

Val Pro Gly His Ser Glu Ala Ala Ser Cys Ile Pro Pro Ser Pro Gln
    450                 455                 460

Glu Asn Ser Tyr Val Ser Ser Thr Gly Arg Ala His Ser Gly Ala Ala
465                 470                 475                 480

Pro Trp Gln Pro Leu Ala Ala Pro Ser Gly Ala Ser Ala Gln Ala Ala
                485                 490                 495

Glu Gln Leu Gln Arg Gly Pro Asn Gln Pro Val Glu Ser Asp Glu Ser
            500                 505                 510

Leu Gly Gly Leu Ser Ala Ala Leu Arg Ser Trp His Leu Thr Pro Ser
        515                 520                 525

Cys Pro Leu Asp Pro Ala Pro Leu Arg Glu Ala Gly Cys Pro Gln Gly
    530                 535                 540

Asp Thr Ala Gly Glu Ser Ser Trp Gly Ser Gly Pro Gly Ser Arg Pro
545                 550                 555                 560

Thr Ala Val Glu Gly Leu Ala Leu Gly Ser Ser Ala Ser Ser Ser Ser
                565                 570                 575

Glu Pro Pro Gln Ile Ile Ile Asn Pro Ala Arg Gln Lys Met Val Gln
            580                 585                 590

Lys Leu Ala Leu Tyr Glu Asp Gly Ala Leu Asp Ser Leu Gln Leu Leu
        595                 600                 605

Ser Ser Ser Ser Leu Pro Gly Leu Gly Leu Glu Gln Asp Arg Gln Gly
610                 615                 620

Pro Glu Glu Ser Asp Glu Phe Gln Ser
625                 630

<210> SEQ ID NO 111
<211> LENGTH: 708
<212> TYPE: PRT
<213> ORGANISM: Human

<400> SEQUENCE: 111

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
                20                  25                  30

Val Met Asp Ala Leu Glu Pro Ala Asp Trp Cys Gln Phe Gly Gly Trp
            35                  40                  45

Arg Arg Ala Ala Gly Gly Arg Glu Ala Arg Gly Leu Leu Ala Pro Thr
        50                  55                  60

Pro Asp Ala Pro Arg Pro Ala Ala Leu Ile Val Arg Asp Gln Thr
65                  70                  75                  80

Glu Leu Arg Leu Cys Glu Arg Ser Gly Gln Arg Thr Ala Ser Val Leu
                85                  90                  95

Trp Pro Trp Ile Asn Arg Asn Ala Arg Val Ala Asp Leu Val His Ile
            100                 105                 110

Leu Thr His Leu Gln Leu Leu Arg Ala Arg Asp Ile Ile Thr Ala Trp
        115                 120                 125

His Pro Pro Ala Pro Leu Pro Ser Pro Gly Thr Thr Ala Pro Arg Pro
```

```
              130                 135                 140
Ser Ser Ile Pro Ala Pro Ala Glu Ala Glu Ala Trp Ser Pro Arg Lys
145                 150                 155                 160

Leu Pro Ser Ser Ala Ser Thr Phe Leu Ser Pro Ala Phe Pro Gly Ser
                165                 170                 175

Gln Thr His Ser Gly Pro Glu Leu Gly Leu Val Pro Ser Pro Ala Ser
                180                 185                 190

Leu Trp Pro Pro Pro Ser Pro Ala Pro Ser Ser Thr Lys Pro Gly
            195                 200                 205

Pro Glu Ser Ser Val Ser Leu Leu Gln Gly Ala Arg Pro Phe Pro Phe
        210                 215                 220

Cys Trp Pro Leu Cys Glu Ile Ser Arg Gly Thr His Asn Phe Ser Glu
225                 230                 235                 240

Glu Leu Lys Ile Gly Glu Gly Gly Phe Gly Cys Val Tyr Arg Ala Val
                245                 250                 255

Met Arg Asn Thr Val Tyr Ala Val Lys Arg Leu Lys Glu Asn Ala Asp
                260                 265                 270

Leu Glu Trp Thr Ala Val Lys Gln Ser Phe Leu Thr Glu Val Glu Gln
            275                 280                 285

Leu Ser Arg Phe Arg His Pro Asn Ile Val Asp Phe Ala Gly Tyr Cys
        290                 295                 300

Ala Gln Asn Gly Phe Tyr Cys Leu Val Tyr Gly Phe Leu Pro Asn Gly
305                 310                 315                 320

Ser Leu Glu Asp Arg Leu His Cys Gln Thr Gln Ala Cys Pro Pro Leu
                325                 330                 335

Ser Trp Pro Gln Arg Leu Asp Ile Leu Leu Gly Thr Ala Arg Ala Ile
                340                 345                 350

Gln Phe Leu His Gln Asp Ser Pro Ser Leu Ile His Gly Asp Ile Lys
            355                 360                 365

Ser Ser Asn Val Leu Leu Asp Glu Arg Leu Thr Pro Lys Leu Gly Asp
        370                 375                 380

Phe Gly Leu Ala Arg Phe Ser Arg Phe Ala Gly Ser Ser Pro Ser Gln
385                 390                 395                 400

Ser Ser Met Val Ala Arg Thr Gln Thr Val Arg Gly Thr Leu Ala Tyr
                405                 410                 415

Leu Pro Glu Glu Tyr Ile Lys Thr Gly Arg Leu Ala Val Asp Thr Asp
                420                 425                 430

Thr Phe Ser Phe Gly Val Val Val Leu Glu Thr Leu Ala Gly Gln Arg
            435                 440                 445

Ala Val Lys Thr His Gly Ala Arg Thr Lys Tyr Leu Lys Asp Leu Val
        450                 455                 460

Glu Glu Glu Ala Glu Ala Gly Val Ala Leu Arg Ser Thr Gln Ser
465                 470                 475                 480

Thr Leu Gln Ala Gly Leu Ala Ala Asp Ala Trp Ala Ala Pro Ile Ala
                485                 490                 495

Met Gln Ile Tyr Lys Lys His Leu Asp Pro Arg Pro Gly Pro Cys Pro
                500                 505                 510

Pro Glu Leu Gly Leu Gly Leu Gly Gln Leu Ala Cys Cys Cys Leu His
            515                 520                 525

Arg Arg Ala Lys Arg Pro Pro Met Thr Gln Glu Asn Ser Tyr Val
        530                 535                 540

Ser Ser Thr Gly Arg Ala His Ser Gly Ala Ala Pro Trp Gln Pro Leu
545                 550                 555                 560
```

```
Ala Ala Pro Ser Gly Ala Ser Ala Gln Ala Glu Gln Leu Gln Arg
            565                 570                 575

Gly Pro Asn Gln Pro Val Glu Ser Asp Glu Ser Leu Gly Gly Leu Ser
        580                 585                 590

Ala Ala Leu Arg Ser Trp His Leu Thr Pro Ser Cys Pro Leu Asp Pro
        595                 600                 605

Ala Pro Leu Arg Glu Ala Gly Cys Pro Gln Gly Asp Thr Ala Gly Glu
610                 615                 620

Ser Ser Trp Gly Ser Gly Pro Gly Ser Arg Pro Thr Ala Val Glu Gly
625                 630                 635                 640

Leu Ala Leu Gly Ser Ser Ala Ser Ser Ser Glu Pro Pro Gln Ile
            645                 650                 655

Ile Ile Asn Pro Ala Arg Gln Lys Met Val Gln Lys Leu Ala Leu Tyr
            660                 665                 670

Glu Asp Gly Ala Leu Asp Ser Leu Gln Leu Leu Ser Ser Ser Ser Leu
            675                 680                 685

Pro Gly Leu Gly Leu Glu Gln Asp Arg Gln Gly Pro Glu Glu Ser Asp
            690                 695                 700

Glu Phe Gln Ser
705

<210> SEQ ID NO 112
<211> LENGTH: 140
<212> TYPE: PRT
<213> ORGANISM: Human

<400> SEQUENCE: 112

Met Ala Ala Ile Pro Ser Ser Gly Ser Leu Val Ala Thr His Asp Tyr
1               5                   10                  15

Tyr Arg Arg Arg Leu Gly Ser Thr Ser Ser Asn Ser Ser Cys Ser Ser
            20                  25                  30

Thr Glu Cys Pro Gly Glu Ala Ile Pro His Pro Gly Glu Cys Arg
        35                  40                  45

Ile Ala Pro Phe Ser Pro Arg Ser Ser Arg Ser Trp Gln His Gln Asp
50                  55                  60

Pro Thr Ser Leu Leu Ser Gly Leu Pro Lys Ala Asp Pro Gly His Trp
65                  70                  75                  80

Trp Ala Ser Phe Phe Gly Lys Ser Thr Leu Pro Phe Met Ala Thr
            85                  90                  95

Val Leu Glu Ser Ala Glu His Ser Glu Pro Pro Gln Ala Ser Ser Ser
            100                 105                 110

Met Thr Ala Cys Gly Leu Ala Arg Asp Ala Pro Arg Lys Gln Pro Gly
            115                 120                 125

Gly Gln Ser Ser Thr Ala Ser Ala Gly Pro Pro Ser
            130                 135                 140

<210> SEQ ID NO 113
<211> LENGTH: 70
<212> TYPE: PRT
<213> ORGANISM: Human

<400> SEQUENCE: 113

Met Ala Ala Ile Pro Ser Ser Gly Ser Leu Val Ala Thr His Asp Tyr
1               5                   10                  15

Tyr Arg Arg Arg Leu Gly Ser Thr Ser Ser Asn Ser Ser Cys Ser Ser
            20                  25                  30
```

```
Thr Glu Cys Pro Gly Glu Ala Ile Pro His Pro Pro Gly Leu Pro Lys
            35                  40                  45

Ala Asp Pro Gly His Trp Trp Ala Ser Phe Phe Phe Gly Lys Ser Thr
 50                  55                  60

Leu Pro Pro Pro Thr Leu
 65                  70

<210> SEQ ID NO 114
<211> LENGTH: 114
<212> TYPE: PRT
<213> ORGANISM: Human

<400> SEQUENCE: 114

Met Ala Ala Ile Pro Ser Ser Gly Ser Leu Val Ala Thr His Asp Tyr
  1               5                  10                  15

Tyr Arg Arg Arg Leu Gly Ser Thr Ser Ser Asn Ser Ser Cys Ser Ser
                 20                  25                  30

Thr Glu Cys Pro Gly Glu Ala Ile Pro His Pro Pro Gly Leu Pro Lys
             35                  40                  45

Ala Asp Pro Gly His Trp Trp Ala Ser Phe Phe Phe Gly Lys Ser Thr
 50                  55                  60

Leu Pro Phe Met Ala Thr Val Leu Glu Ser Ala Glu His Ser Glu Pro
 65                  70                  75                  80

Pro Gln Ala Ser Ser Ser Met Thr Ala Cys Gly Leu Ala Arg Asp Ala
                 85                  90                  95

Pro Arg Lys Gln Pro Gly Gly Ser Ser Thr Ala Ser Ala Gly Pro
                100                 105                 110

Pro Ser

<210> SEQ ID NO 115
<211> LENGTH: 400
<212> TYPE: PRT
<213> ORGANISM: Human

<400> SEQUENCE: 115

Met Glu Asp Gly Val Tyr Glu Pro Pro Asp Leu Thr Pro Glu Glu Arg
  1               5                  10                  15

Met Glu Leu Glu Asn Ile Arg Arg Arg Lys Gln Glu Leu Leu Val Glu
                 20                  25                  30

Ile Gln Arg Leu Arg Glu Glu Leu Ser Glu Ala Met Ser Glu Val Glu
             35                  40                  45

Gly Leu Glu Ala Asn Glu Gly Ser Lys Thr Leu Gln Arg Asn Arg Lys
 50                  55                  60

Met Ala Met Gly Arg Lys Lys Phe Asn Met Asp Pro Lys Lys Gly Ile
 65                  70                  75                  80

Gln Phe Leu Val Glu Asn Glu Leu Leu Gln Asn Thr Pro Glu Glu Ile
                 85                  90                  95

Ala Arg Phe Leu Tyr Lys Gly Glu Gly Leu Asn Lys Thr Ala Ile Gly
                100                 105                 110

Asp Tyr Leu Gly Glu Arg Glu Glu Leu Asn Leu Ala Val Leu His Ala
            115                 120                 125

Phe Val Asp Leu His Glu Phe Thr Asp Leu Asn Leu Val Gln Ala Leu
130                 135                 140

Arg Gln Phe Leu Trp Ser Phe Arg Leu Pro Gly Glu Ala Gln Lys Ile
145                 150                 155                 160
```

```
Asp Arg Met Met Glu Ala Phe Ala Gln Arg Tyr Cys Leu Cys Asn Pro
            165                 170                 175

Gly Val Phe Gln Ser Thr Asp Thr Cys Tyr Val Leu Ser Phe Ala Val
            180                 185                 190

Ile Met Leu Asn Thr Ser Leu His Asn Pro Asn Val Arg Asp Lys Pro
            195                 200                 205

Gly Leu Glu Arg Phe Val Ala Met Asn Arg Gly Ile Asn Glu Gly Gly
            210                 215                 220

Asp Leu Pro Glu Glu Leu Arg Asn Leu Tyr Asp Ser Ile Arg Asn
225                 230                 235                 240

Glu Pro Phe Lys Ile Pro Glu Asp Asp Gly Asn Asp Leu Thr His Thr
            245                 250                 255

Phe Phe Asn Pro Asp Arg Glu Gly Trp Leu Leu Lys Leu Gly Arg Gly
            260                 265                 270

Arg Val Lys Thr Trp Lys Arg Trp Phe Ile Leu Thr Asp Asn Cys
            275                 280                 285

Leu Tyr Tyr Phe Glu Tyr Thr Thr Asp Lys Glu Pro Arg Gly Ile Ile
            290                 295                 300

Pro Leu Glu Asn Leu Ser Ile Arg Glu Val Asp Asp Pro Arg Lys Pro
305                 310                 315                 320

Asn Cys Phe Glu Leu Tyr Ile Pro Asn Asn Lys Gly Gln Leu Ile Lys
            325                 330                 335

Ala Cys Lys Thr Glu Ala Asp Gly Arg Val Val Glu Gly Asn His Met
            340                 345                 350

Val Tyr Arg Ile Ser Ala Pro Thr Gln Glu Glu Lys Asp Glu Trp Ile
            355                 360                 365

Lys Ser Ile Gln Ala Ala Val Ser Val Asp Pro Phe Tyr Glu Met Leu
            370                 375                 380

Ala Ala Arg Lys Lys Arg Ile Ser Val Lys Lys Gln Glu Gln Pro
385                 390                 395                 400

<210> SEQ ID NO 116
<211> LENGTH: 399
<212> TYPE: PRT
<213> ORGANISM: Human

<400> SEQUENCE: 116

Met Glu Asp Gly Val Tyr Glu Pro Pro Asp Leu Thr Pro Glu Glu Arg
1               5                   10                  15

Met Glu Leu Glu Asn Ile Arg Arg Arg Lys Gln Glu Leu Leu Val Glu
            20                  25                  30

Ile Gln Arg Leu Arg Glu Glu Leu Ser Glu Ala Met Ser Glu Val Glu
            35                  40                  45

Gly Leu Glu Ala Asn Glu Gly Ser Lys Thr Leu Gln Arg Asn Arg Lys
            50                  55                  60

Met Ala Met Gly Arg Lys Lys Phe Asn Met Asp Pro Lys Lys Gly Ile
65                  70                  75                  80

Gln Phe Leu Val Glu Asn Glu Leu Leu Gln Asn Thr Pro Glu Glu Ile
            85                  90                  95

Ala Arg Phe Leu Tyr Lys Gly Glu Gly Leu Asn Lys Thr Ala Ile Gly
            100                 105                 110

Asp Tyr Leu Gly Glu Arg Glu Glu Leu Asn Leu Ala Val Leu His Ala
            115                 120                 125

Phe Val Asp Leu His Glu Phe Thr Asp Leu Asn Leu Val Gln Ala Leu
            130                 135                 140
```

Arg Gln Phe Leu Trp Ser Phe Arg Leu Pro Gly Glu Ala Gln Lys Ile
145                 150                 155                 160

Asp Arg Met Met Glu Ala Phe Ala Gln Arg Tyr Cys Leu Cys Asn Pro
                165                 170                 175

Gly Val Phe Gln Ser Thr Asp Thr Cys Tyr Val Leu Ser Phe Ala Val
            180                 185                 190

Ile Met Leu Asn Thr Ser Leu His Asn Pro Asn Val Arg Asp Lys Pro
        195                 200                 205

Gly Leu Glu Arg Phe Val Ala Met Asn Arg Gly Ile Asn Glu Gly Gly
    210                 215                 220

Asp Leu Pro Glu Glu Leu Leu Arg Asn Leu Tyr Asp Ser Ile Arg Asn
225                 230                 235                 240

Glu Pro Phe Lys Ile Pro Glu Asp Asp Gly Asn Asp Leu Thr His Thr
                245                 250                 255

Phe Phe Asn Pro Asp Arg Glu Gly Trp Leu Leu Lys Leu Gly Gly Arg
            260                 265                 270

Val Lys Thr Trp Lys Arg Arg Trp Phe Ile Leu Thr Asp Asn Cys Leu
        275                 280                 285

Tyr Tyr Phe Glu Tyr Thr Thr Asp Lys Glu Pro Arg Gly Ile Ile Pro
    290                 295                 300

Leu Glu Asn Leu Ser Ile Arg Glu Val Asp Asp Pro Arg Lys Pro Asn
305                 310                 315                 320

Cys Phe Glu Leu Tyr Ile Pro Asn Asn Lys Gly Gln Leu Ile Lys Ala
                325                 330                 335

Cys Lys Thr Glu Ala Asp Gly Arg Val Val Glu Gly Asn His Met Val
            340                 345                 350

Tyr Arg Ile Ser Ala Pro Thr Gln Glu Glu Lys Asp Glu Trp Ile Lys
        355                 360                 365

Ser Ile Gln Ala Ala Val Ser Val Asp Pro Phe Tyr Glu Met Leu Ala
    370                 375                 380

Ala Arg Lys Lys Arg Ile Ser Val Lys Lys Lys Gln Glu Gln Pro
385                 390                 395

<210> SEQ ID NO 117
<211> LENGTH: 165
<212> TYPE: PRT
<213> ORGANISM: Human

<400> SEQUENCE: 117

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val

```
                115                 120                 125
Phe Gly Lys Val Lys Glu Gly Met Asn Ile Val Glu Ala Met Glu Arg
            130                 135                 140
Phe Gly Ser Arg Asn Gly Lys Thr Ser Lys Lys Ile Thr Ile Ala Asp
145                 150                 155                 160
Cys Gly Gln Leu Glu
                165

<210> SEQ ID NO 118
<211> LENGTH: 44
<212> TYPE: PRT
<213> ORGANISM: Human

<400> SEQUENCE: 118

Thr Ala Glu Glu Ala Ser Ser Glu Ala Cys Ala Gly Pro Ala Thr
1               5                   10                  15

Arg Ser Pro Gly Trp Gly Asp Pro Gly Ile Ser His Arg Asp Cys Cys
                20                  25                  30

Arg Arg Lys Ala Glu Trp Gly Thr Ala Glu Ser Arg
            35                  40

<210> SEQ ID NO 119
<211> LENGTH: 97
<212> TYPE: PRT
<213> ORGANISM: Human

<400> SEQUENCE: 119

Glu Ala Glu Leu Pro Asp Arg Gly Gly Ala Val Gln Val Ser Ser
1               5                   10                  15

Pro Lys His Cys Gly Leu Cys Trp Leu Leu Cys Ser Glu Arg Leu Leu
                20                  25                  30

Leu Pro Gly Val Arg Leu Pro Ala Gln Arg Leu Pro Gly Gly Pro Ser
            35                  40                  45

Pro Leu Pro Asp Pro Gly Leu Pro Thr Ser Leu Leu Ala Ser Ala Thr
    50                  55                  60

Gly His Pro Ser Gly Tyr Ser Pro Gly Asn Ser Val Ser Thr Ser Gly
65                  70                  75                  80

Gln Pro Gln Pro His Pro Trp Arg His Gln Glu Phe Gln Arg Pro Ser
                85                  90                  95

Gly

<210> SEQ ID NO 120
<211> LENGTH: 81
<212> TYPE: PRT
<213> ORGANISM: Human

<400> SEQUENCE: 120

Leu Arg Gly Leu Ala Pro Pro Ser Pro Pro Val Ile Val Arg Arg
1               5                   10                  15

Gly Pro Arg Gly Val Ala Ala Gln Ile Pro Pro Ala Ser Lys Leu Lys
                20                  25                  30

His Gly Gly His Pro Leu Gln Arg Leu Ala Arg Gly His Pro Arg Leu
            35                  40                  45

Leu Pro Ala Pro Pro Gly Phe His Phe Gln Gln Leu Leu Gln Gln
    50                  55                  60

Tyr Arg Val Pro Arg Gly Ser His Ser Pro Pro Arg Ser Pro Gln
65                  70                  75                  80
```

```
Gly

<210> SEQ ID NO 121
<211> LENGTH: 119
<212> TYPE: PRT
<213> ORGANISM: Human

<400> SEQUENCE: 121

Ala Pro Trp Pro Ser Ala Pro Val Pro Ala Thr Arg Asp Arg Ala Pro
1               5                   10                  15

Arg Pro Ala Arg Gly Arg Arg Pro Asp Pro Thr Ser Gln Gln Ala Lys
            20                  25                  30

Ala Trp Arg Pro Ser Pro Pro Ala Ala Arg Ser Trp Pro Pro Thr Thr
        35                  40                  45

Thr Thr Gly Ala Ala Trp Val Pro Leu Pro Ala Thr Ala Pro Ala Ala
    50                  55                  60

Val Pro Ser Ala Pro Gly Lys Pro Phe Pro Thr Pro Gln Val Ser Pro
65                  70                  75                  80

Arg Leu Thr Arg Val Ile Gly Gly Pro Ala Ser Phe Ser Gly Ser Pro
                85                  90                  95

Pro Ser Arg Ser Trp Pro Arg Cys Trp Ser Pro Gln Ser Thr Arg Asn
            100                 105                 110

Leu Pro Arg Pro Pro Ala Ala
            115

<210> SEQ ID NO 122
<211> LENGTH: 29
<212> TYPE: PRT
<213> ORGANISM: Human

<400> SEQUENCE: 122

Trp Thr Cys Ser Pro His Pro Thr Pro Thr Thr Arg Arg Ser Thr Thr
1               5                   10                  15

Ser Arg Ser Ala Ser Trp Ser Ala Arg Cys Ala Ser Thr
            20                  25
```